US012694948B2

(12) United States Patent
Hahm et al.

(10) Patent No.: US 12,694,948 B2
(45) Date of Patent: Jul. 28, 2026

(54) BIOINFORMATICS SYSTEMS, APPARATUSES, AND METHODS FOR PERFORMING SECONDARY AND/OR TERTIARY PROCESSING

(71) Applicant: Illumina, Inc., San Diego, CA (US)

(72) Inventors: Mark David Hahm, San Diego, CA (US); Jacobus de Beer, San Diego, CA (US); Varun Jain, San Diego, CA (US); Rami Mehio, San Diego, CA (US); Eric Ojard, San Diego, CA (US); Michael Ruehle, Fort Worth, TX (US); Amnon Ptashek, San Diego, CA (US); Severine Catreux, San Diego, CA (US); Arun Visvanath, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 1072 days.

(21) Appl. No.: 17/165,828

(22) Filed: Feb. 2, 2021

(65) Prior Publication Data

US 2021/0183468 A1 Jun. 17, 2021

Related U.S. Application Data

(63) Continuation of application No. 15/796,696, filed on Oct. 27, 2017, now abandoned.

(60) Provisional application No. 62/414,637, filed on Oct. 28, 2016.

(51) Int. Cl.
| | |
|---|---|
| *G16B 30/10* | (2019.01) |
| *G16B 20/00* | (2019.01) |
| *G16B 20/20* | (2019.01) |
| *G16B 20/40* | (2019.01) |
| *G16B 30/00* | (2019.01) |
| *G16B 30/20* | (2019.01) |
| *G16B 50/00* | (2019.01) |
| *G16B 50/30* | (2019.01) |
| *G16B 50/40* | (2019.01) |
| *G16B 50/50* | (2019.01) |
| *G06F 21/76* | (2013.01) |

(52) U.S. Cl.
CPC ............. *G16B 30/10* (2019.02); *G16B 20/00* (2019.02); *G16B 20/20* (2019.02); *G16B 20/40* (2019.02); *G16B 30/00* (2019.02); *G16B 30/20* (2019.02); *G16B 50/00* (2019.02); *G16B 50/30* (2019.02); *G16B 50/40* (2019.02); *G16B 50/50* (2019.02); *G06F 21/76* (2013.01)

(58) Field of Classification Search
CPC ........ G16B 30/10; G16B 20/20; G16B 50/30; G16B 50/50; G16B 20/00; G16B 20/40; G16B 30/20; G16B 50/40; G16B 30/00; G16B 50/00
See application file for complete search history.

(56) References Cited

U.S. PATENT DOCUMENTS

| | | | |
|---|---|---|---|
| 5,629,147 | A | 5/1997 | Asgari et al. |
| 5,859,972 | A | 1/1999 | Subramaniam |
| 5,964,072 | A | 10/1999 | Rasmussen |
| 6,112,288 | A | 8/2000 | Ullner |
| 6,253,529 | B1 | 7/2001 | De Boer et al. |
| 6,681,186 | B1 | 1/2004 | Denisov |
| 7,135,701 | B2 | 11/2006 | Amin et al. |
| 7,533,068 | B2 | 5/2009 | Maassen van den Brink et al. |
| 7,680,790 | B2 | 3/2010 | Indeck et al. |
| 7,917,299 | B2 | 3/2011 | Buhler et al. |
| 7,917,302 | B2 | 3/2011 | Rognes |
| 7,948,015 | B2 | 5/2011 | Rothberg |
| 7,969,805 | B2 | 6/2011 | Thom et al. |
| 8,190,548 | B2 | 5/2012 | Choi |
| 8,195,596 | B2 | 6/2012 | Rose et al. |
| 8,209,130 | B1 | 6/2012 | Kennedy et al. |
| 8,217,433 | B1 | 7/2012 | Fife et al. |
| 8,280,640 | B2 | 10/2012 | Levin et al. |
| 8,445,945 | B2 | 5/2013 | Rothberg et al. |

(Continued)

FOREIGN PATENT DOCUMENTS

| | | |
|---|---|---|
| AU | 20144335877 A1 | 5/2016 |
| CN | 103080333 A | 5/2013 |

(Continued)

OTHER PUBLICATIONS

AU Office Action in Australian Appln. No. 201780081073, mailed on Aug. 2, 2023, 3 pages.
CN Office Action in Chinese Appln. No. 201780081073, dated Dec. 5, 2022, 5 pages (with English translation).
EP Office Action in European Appln. No. 17798358.2, dated Feb. 16, 2023, 8 pages.
CA Office Action in Canadian Appln. No. 3,042,239, mailed on Mar. 6, 2024, 4 pages.

(Continued)

*Primary Examiner* — Jerry Lin
(74) *Attorney, Agent, or Firm* — Heslin Rothenberg Farley & Mesiti P.C.

(57) ABSTRACT

Systems, methods, and computer programs for analyzing genetic sequence data is disclosed. In one aspect, the system can include one or more of a first integrated circuit, with each first integrated circuit forming a central processing unit (CPU) that is responsive to one or more software algorithms that are configured to instruct the CPU to perform a first set of genomic processing steps of a sequence analysis pipeline. Additionally, the system can include one or more second integrated circuits, with each second integrated circuit forming a field programmable gate array (FPGA). The FPGA can be configured by firmware to arrange a set of hardwired digital logic circuits to perform a second set of genomic processing stages of the sequence analysis pipeline, the set of hardwired digital logic circuits of each FPGA being arranged as a set of processing engines to perform the second set of genomic processing stages.

15 Claims, 71 Drawing Sheets

(56) References Cited

U.S. PATENT DOCUMENTS

| | | | |
|---|---|---|---|
| 8,524,487 | B2 | 9/2013 | Fife et al. |
| 8,558,288 | B2 | 10/2013 | Rothberg et al. |
| 8,560,282 | B2 | 10/2013 | Macready et al. |
| 8,594,951 | B2 | 11/2013 | Homer |
| 8,620,923 | B1 | 12/2013 | Wormley et al. |
| 8,700,689 | B2 | 4/2014 | Macready et al. |
| 8,738,105 | B2 | 5/2014 | Berkley et al. |
| 8,751,166 | B2 | 6/2014 | Friedlander et al. |
| 8,936,763 | B2 | 1/2015 | Rothberg et al. |
| 9,014,989 | B2 | 4/2015 | McMillen et al. |
| 9,026,574 | B2 | 5/2015 | Macready et al. |
| 9,235,680 | B2 | 1/2016 | Van Rooyen et al. |
| 9,322,872 | B2 | 4/2016 | Hill |
| 9,355,365 | B2 | 5/2016 | Berkley et al. |
| 9,405,876 | B2 | 8/2016 | Macready et al. |
| 9,483,610 | B2 | 11/2016 | Mcmillen et al. |
| 9,576,103 | B2 | 2/2017 | Mcmillen et al. |
| 9,618,474 | B2 | 4/2017 | Van Rooyen et al. |
| 9,679,104 | B2 | 6/2017 | Van Rooyen et al. |
| 9,792,405 | B2 | 10/2017 | Van Rooyen et al. |
| 10,068,183 | B1 | 9/2018 | Van Rooyen et al. |
| 10,119,167 | B2 | 11/2018 | Srinivasan et al. |
| 10,847,251 | B2 | 11/2020 | Van Rooyen et al. |
| 2002/0086161 | A1 | 7/2002 | Smetana et al. |
| 2003/0033279 | A1 | 2/2003 | Gibson et al. |
| 2003/0033501 | A1 | 2/2003 | Cooke |
| 2003/0039362 | A1 | 2/2003 | Califano et al. |
| 2003/0104470 | A1 | 6/2003 | Fors et al. |
| 2004/0024536 | A1 | 2/2004 | Rognes et al. |
| 2004/0059721 | A1 | 3/2004 | Patzer |
| 2004/0098203 | A1 | 5/2004 | Rognes et al. |
| 2004/0126840 | A1 | 7/2004 | Cheng et al. |
| 2004/0142463 | A1 | 7/2004 | Walker et al. |
| 2005/0060195 | A1 | 3/2005 | Bessette |
| 2005/0131649 | A1 | 6/2005 | Larsen et al. |
| 2005/0228595 | A1 | 10/2005 | Cooke et al. |
| 2006/0225165 | A1 | 10/2006 | Maassen et al. |
| 2007/0038381 | A1 | 2/2007 | Melchior et al. |
| 2007/0078897 | A1 | 4/2007 | Hayashi et al. |
| 2007/0088510 | A1 | 4/2007 | Li et al. |
| 2007/0196816 | A1 | 8/2007 | Schwartz |
| 2008/0005024 | A1 | 1/2008 | Kirkwood et al. |
| 2008/0086274 | A1 | 4/2008 | Chamberlain et al. |
| 2008/0176750 | A1 | 7/2008 | Rose et al. |
| 2008/0250016 | A1 | 10/2008 | Farrar et al. |
| 2009/0121215 | A1 | 5/2009 | Choi et al. |
| 2009/0125248 | A1 | 5/2009 | Shams et al. |
| 2009/0171647 | A1 | 7/2009 | Mannava et al. |
| 2009/0253130 | A1 | 10/2009 | Yoo |
| 2010/0077267 | A1 | 3/2010 | Perego et al. |
| 2010/0082805 | A1 | 4/2010 | Orton et al. |
| 2010/0085827 | A1 | 4/2010 | Thom |
| 2010/0169313 | A1 | 7/2010 | Kenedy et al. |
| 2010/0281401 | A1 | 11/2010 | Tebbs et al. |
| 2010/0327847 | A1 | 12/2010 | Leiber et al. |
| 2011/0004413 | A1 | 1/2011 | Carnevali |
| 2011/0093581 | A1 | 4/2011 | Ventatachalm |
| 2011/0184235 | A1 | 7/2011 | Schostek et al. |
| 2011/0227043 | A1 | 9/2011 | Guo |
| 2012/0001615 | A1 | 1/2012 | Levine |
| 2012/0089339 | A1 | 4/2012 | Ganeshalingam et al. |
| 2012/0102041 | A1 | 4/2012 | Park et al. |
| 2012/0109849 | A1 | 5/2012 | Chamberlain |
| 2012/0135394 | A1 | 5/2012 | Kim et al. |
| 2012/0149981 | A1 | 6/2012 | Khait et al. |
| 2012/0214172 | A1 | 8/2012 | Chen et al. |
| 2013/0018599 | A1 | 1/2013 | Peng et al. |
| 2013/0091121 | A1 | 4/2013 | Galinsky |
| 2013/0110407 | A1 | 5/2013 | Baccash et al. |
| 2013/0124100 | A1 | 5/2013 | Drmanac |
| 2013/0144925 | A1 | 6/2013 | Macready |
| 2013/0157870 | A1 | 6/2013 | Pushkarev et al. |
| 2013/0194882 | A1 | 8/2013 | Ishii et al. |
| 2013/0198755 | A1 | 8/2013 | Kim |
| 2013/0204851 | A1 | 8/2013 | Bhola et al. |
| 2013/0245958 | A1 | 9/2013 | Forster et al. |
| 2013/0246460 | A1 | 9/2013 | Maltbie et al. |
| 2013/0254202 | A1 | 9/2013 | Friedlander et al. |
| 2013/0275486 | A1 | 10/2013 | Dickinson et al. |
| 2013/0296175 | A1 | 11/2013 | Rafnar et al. |
| 2013/0297221 | A1 | 11/2013 | Johnson et al. |
| 2013/0307029 | A1 | 11/2013 | Xu et al. |
| 2013/0311106 | A1 | 11/2013 | White et al. |
| 2013/0316331 | A1 | 11/2013 | Isakov |
| 2013/0324417 | A1 | 12/2013 | Kennedy et al. |
| 2013/0332081 | A1 | 12/2013 | Reese et al. |
| 2013/0338012 | A1 | 12/2013 | Sulem et al. |
| 2013/0338934 | A1 | 12/2013 | Asadi et al. |
| 2014/0024537 | A1 | 1/2014 | Rigatti et al. |
| 2014/0033125 | A1 | 1/2014 | Merel et al. |
| 2014/0045705 | A1 | 2/2014 | Bustamante et al. |
| 2014/0046926 | A1 | 2/2014 | Walton |
| 2014/0051588 | A9 | 2/2014 | Drmanac et al. |
| 2014/0081665 | A1 | 3/2014 | Holmes |
| 2014/0093873 | A1 | 4/2014 | Tynan et al. |
| 2014/0114582 | A1 | 4/2014 | Mittelman et al. |
| 2014/0121116 | A1 | 5/2014 | Richards |
| 2014/0164516 | A1 | 6/2014 | Maltbie |
| 2014/0200166 | A1 | 7/2014 | Van Rooyen et al. |
| 2014/0236490 | A1 | 8/2014 | Van Rooyen et al. |
| 2014/0297196 | A1 | 10/2014 | Olson |
| 2014/0304276 | A1 | 10/2014 | Boyce |
| 2014/0309944 | A1 | 10/2014 | Van Rooyen et al. |
| 2014/0310215 | A1 | 10/2014 | Trakadis |
| 2014/0316716 | A1 | 10/2014 | Jiang et al. |
| 2014/0337052 | A1 | 11/2014 | Pellini et al. |
| 2014/0350968 | A1 | 11/2014 | Hahn et al. |
| 2014/0368550 | A1 | 12/2014 | Vaske et al. |
| 2014/0371109 | A1 | 12/2014 | McMillen et al. |
| 2014/0371110 | A1 | 12/2014 | Van Rooyen et al. |
| 2015/0066824 | A1 | 3/2015 | Harris et al. |
| 2015/0123600 | A1 | 5/2015 | Graot et al. |
| 2015/0142334 | A1 | 5/2015 | Mishra et al. |
| 2015/0154406 | A1 | 6/2015 | Naehrig et al. |
| 2015/0211055 | A1 | 7/2015 | Apte et al. |
| 2015/0248525 | A1 | 9/2015 | Ury et al. |
| 2015/0286495 | A1 | 10/2015 | Lee et al. |
| 2015/0310163 | A1 | 10/2015 | Kingsmore et al. |
| 2015/0339437 | A1 | 11/2015 | McMillen et al. |
| 2015/0363550 | A1 | 12/2015 | Green et al. |
| 2016/0046986 | A1 | 2/2016 | Eltoukhy et al. |
| 2016/0092631 | A1 | 3/2016 | Yandell et al. |
| 2016/0140290 | A1 | 5/2016 | Van Rooyen et al. |
| 2016/0171153 | A1 | 6/2016 | Van Rooyen et al. |
| 2016/0178569 | A1 | 6/2016 | Hoffman et al. |
| 2016/0283407 | A1 | 9/2016 | Van Rooyen et al. |
| 2016/0306923 | A1 | 10/2016 | Van Rooyen et al. |
| 2017/0270245 | A1 | 9/2017 | Van Rooyen et al. |
| 2017/0308644 | A1 | 10/2017 | Van Rooyen et al. |
| 2018/0121601 | A1 | 5/2018 | Hahm et al. |
| 2018/0189444 | A1 | 7/2018 | Van Rooyen et al. |
| 2018/0196916 | A1 | 7/2018 | Van Rooyen et al. |
| 2018/0196917 | A1 | 7/2018 | Van Rooyen et al. |
| 2018/0239865 | A1 | 8/2018 | Van Rooyen et al. |
| 2018/0240032 | A1 | 8/2018 | Van Rooyen |
| 2019/0171963 | A1 | 6/2019 | van Rooyen et al. |
| 2021/0193261 | A1 | 6/2021 | Van Rooyen et al. |
| 2022/0230084 | A1 | 7/2022 | Hahm et al. |

FOREIGN PATENT DOCUMENTS

| | | |
|---|---|---|
| CN | 103293209 A | 9/2013 |
| CN | 103336916 A | 10/2013 |
| CN | 105051741 B | 4/2018 |
| EP | 2313523 A2 | 4/2011 |
| EP | 3317440 A1 | 5/2018 |
| JP | 2007108949 A | 4/2007 |
| JP | 2007512808 A | 5/2007 |
| JP | 2016514291 A | 5/2016 |
| KR | 20130027948 A | 3/2013 |
| KR | 20130088512 A | 8/2013 |
| RU | 2282242 C2 | 8/2006 |
| RU | 2012124158 A | 9/2014 |
| RU | 2015144109 A | 4/2017 |

(56) References Cited

FOREIGN PATENT DOCUMENTS

| WO | WO 2002/086161 A1 | 10/2002 |
|----|------|------|
| WO | 2006096324 A2 | 9/2006 |
| WO | 2008022036 A2 | 2/2008 |
| WO | WO 2011/149534 A2 | 12/2011 |
| WO | WO 2012/122546 A2 | 9/2012 |
| WO | WO 2013/128371 A2 | 9/2013 |
| WO | WO 2014/060305 A1 | 4/2014 |
| WO | WO 2014/074246 A1 | 5/2014 |
| WO | WO 2014113736 A1 | 7/2014 |
| WO | WO 2014/121091 A1 | 8/2014 |
| WO | WO 2014/186604 A1 | 11/2014 |
| WO | WO 2015/051006 A2 | 4/2015 |
| WO | WO 2015089333 A1 | 6/2015 |
| WO | WO 2015/100427 A1 | 7/2015 |
| WO | WO 2015123600 A1 | 8/2015 |
| WO | 2015166389 A1 | 11/2015 |
| WO | 2016051429 A1 | 4/2016 |
| WO | WO 2016/061396 A1 | 4/2016 |

OTHER PUBLICATIONS

CN Office Action in Chinese Appln. No. 201780081073.X, dated Jun. 8, 2023, 11 pages (with English translation).

CN Office Action in Chinese Appln. No. 201780081073.X, mailed on Nov. 30, 2023, 11 pages (with English translation).

Dilthey, A. , et al., "Improved genome inference in the MHC using a population reference graph", Nature Genetics 47, 2015, 682-688.

Harris, B. , et al., "A Banded Amith-Waterman FPGA Accelerator For Mercury BLASTP", BECS Technology, Inc, 2007, 5 pages.

Al Jun id et al. "Development of Novel Data Compression Technique for Accelerate DNA Sequence Alignment Based on Smith-Waterman Algorithm." Highlighted. University Technology MARA (UITM). 2009 Third UKSim European Symposium on Computer Modeling and Simulation, 181-186.

Al Junid et al. "Optimization of DNA Sequences Data for Accelerate DNA Sequences Alignment on FPGA." University Technology MARA (UITM). 2010 Fourth Asia International Conference on Mathematical/Analytical Modelling and Computer Simulation, 231-236.

Al Tera Corp, Implementation of the Smith-Waterman Algorithm on a Reconfigurable Supercomputing Platform, White Paper, 18 pgs. Sep. 2007 Ver. 1.

Alachiotis, et al, Accelerating Phylogeny-Aware Short DNA Read Alignment with FPGAs, The Exelixis Lab, (2011) pp. 8, Heidelberg Institute for Theoretical Studies, Heidelberg, Germany.

Angiuoli et al., "Mugsy: fast multiple alignment of closely related whole genomes," Bio informatics (2011) 27 (3): 334-342. First published on line: Dec. 9, 2010. http://bioinformatics.oxfordjournals. org/content/27 /31334 .full. Retrieved May 25, 2016.

Anonymous: "FPGA-accelerated Bioinformatics at #ASHG-Dragen Aligner from Edico Genome." Oct. 20, 2014 (Oct. 20, 2014). XP055360856. Retrieved from the internet: URL:http:// moolog.us/blogs/glob/2014/210/20/fpga-accelerated-bioi nformics-at-ashg-dragenaliqner- from-edico-genome/# [retrieved on Mar. 31, 2017]. 7 pages.

AU Office Action in Australian Appln. No. 2017348382, dated Aug. 19, 2021, 3 pages.

Auwera et al. From FastQ data to high confidence variant calls: the Genome Analysis Toolkit best practices pipeline. HHS Public Access, Published online Oct. 15, 2013, http://www.ncbi.nlm.nih. qov/pmc/articles/PMC4243306/. Retrieved May 25, 2016. 27 pages.

Benkrid et al., A highly parameterized and efficient FPGA-based skeleton for pairwise biological sequence alignment, IEEE Transactions on VLSI Systems, Apr. 2009, pp. 561-570 (1-12), IEEE Educational Activities Dept. Piscataway, NJ.

Benkrid, Khaled, et al. "A High Performance Reconfigurable Core for Motif Searching Using Profile HMM." NASA ESA Conference on Adaptive Hardware and Systems, IEEE, 2008. pp. 285-292.

Buyukkurt et al, Compiler Generated Systolic Arrays for Wavefront Algorithm Acceleration on FPGAs, Sep. 2008, 4 pgs, International Conference on Field Programmable Logic and Applications, Heidelberg, Germany.

Carneiro, Mauricio. "Accelerating Variant Calling." Broad Institute, Intel Genomic Sequencing Pipeline Workshop, Powerpoint Presentation, Mount Sinai, Dec. 10, 2013. 26 pages.

Chang Mau-Chung Frank et al: "The SMEM Seeding Acceleration for DNA Sequence Alignment." 2016 IEEE 24th Annual International Symposium On Fieldprogrammable Custom Computing Machines (FCCM), IEEE, [retrieved on Aug. 16, 2016] May 2, 2016 (May 2, 2016), pp. 32-39.

Chang, et al., Exploring Sequence Alignment Algorithms on FPGA-based Heterogeneous B Architectures, Proceedings IWBBIO, pp. 330-341, 2014, Granada.

Chang, Xin, et al. "FPGA-based Heterogeneous Architecture for Sequence Alignment." (2014) 4 pages.

Chang, Xin, et al. "FPGA-based Heterogeneous Architecture for Sequence Alignment." 4 pages.

Choi, Young-kyu, et al. "A Quantitative Analysis of Microarchitectures of Modern CPU-FPGA Platforms." Design Automation Conference, Jun. 5-9, 2016, DAG '16, Jun. 5-9, 2016. Austin, TX. Conference Presentation. 6 pages.

Chrysanthou et al. "Parallel Accelerators for GlimmerHMM Bioinformatics Algorithm." 2011 Design, Automation & Test in Europe Conference & Exhibition, IEEE, 2011. 6 pages.

Derrien et al. Fast Computation and Applications of Genome Mappability. PLOS One. Published: Jan. 19, 2012. 15 pages. http://journals.plos.org/plosone/article?id=10.1371/journal.pone. 0030377. Retrieved May 25, 2016.

Deutsch, D. "Quantum theory, the Church-Turing principle and the universal quantum computer." Proceedings of the Royal Society of London A 400, pp. 97-117 (1985). Printed in Great Britain.

Dydel, Stefan and Piotr Bala. "Large Scale Protein Sequence Alignment Using FPGA Reprogrammable Logic Devices." Faculty of Mathematics and Computer Science. N. Copernicus University, 1 O pp. 2004, Torun, Poland.J. Becker, M. Platzner, S. Vernalde (Eds.): FPL 2004, LNCS 3203, oo. 23-32, 2004.

Edward B. Fernandez et al. "Multithreaded FPGA Acceleration of DNA Sequence Mapping." University of California Riverside, Riverside and Jacquard Computing Inc. Riverside. 2012 IEEE. 6 pages.

Edward Fernandez et al. PowerPoint presentation on "Multithreaded FPGA Acceleration of DNA Sequence Mapping." UC Riverside, Department of Computer Science and Engineering Jacquard Computing. 2012. 20 pages.

EP Office Action in European Appl. No. 17731690, dated Jan. 4, 2020, 19 pages.

Faes, et al, Scalable Hardware Accelerator for Comparing DNA and Protein Sequences, Infoscale, 2006, pp. 6, ACM, Hong Kong.

Fagin, FPGA and Rapid Prototyping Technology Use in a Special Purpose Computer for Molecular Genetics, Website: http://www. faginfamily.net/barry/Papers/ICCD92.htm, Thayer School of Engineering, Dartmouth, Hanover, NH. (1992). Retrieved Jan. 11, 2017. 6 pages.

Fernandez, W. Najjar, E. Harris, and S. Lonardi. Exploration of Short Reads Genome Mapping in Hardwares. Field Programmable Logic and Applications (FPL), 20th Int. Conf. Milano, Italy, Aug. 2010. 4 pages.

Ferraz, Samuel and Nahri Moreano. "Evaluating Optimization Strategies for HMMer Acceleration on GPU." 2013 International Conference on Parallel and Distributed Systems, IEEE, 2013. pp. 59-68.

Feynman, Richard P. "Simulating Physics with Computers." International Journal of Theoretical Physics, vol. 21, Nos. 617, (1982): pp. 467-488.

Guccione et al, Gene Matching Usina JBits, Xilinx, Inc. San Jose CA (2002), 9 pages.

Hall, Adam. "Short-Read DNA Sequence Alignment with Custom Designed FPGA-based Hardware." Master of Science Thesis. The University of Cambridae, 2007. 186 pages.

Hardcastle and K. Kelly. baySeq: Empirical Bayesian methods for identifying differential expression in sequence count data. Published Aug. 10, 2010, BMC Bioinformatics http://bmcbioinformatics. biomedcentral.com/ articles/10.1186/1471-2105-11-422. Retrieved, May 25, 2016. 16 pages.

(56) References Cited

OTHER PUBLICATIONS

Hasan et al, An Overview of Hardware-Based Acceleration of Biological Sequence Alignment, Computational Biology and Applied Bioinformatics, Sep. 2011, Tech, Rijeka, Croatia, 187-202.

Herbordt, Martin et al., "Single Pass Streaming BLAS on FPGAs", NIH Public Access Author Manuscript, Nov. 2007, Parallel Comput, 25 pages.

Herbordt, Martin, et al., "Single Pass, BLAST-like, Approximate String Matching of FPGAs", Boston University, 2006, 19 pgs, Boston.

Hoang et al., FPGA Implementation of Systolic Sequence Alignment, 1991, 4 pgs NSF Graduate Fellowship.

Hoang, A Systolic Array for the Sequence Alignment Problem, Apr. 1992, 25 pgs, Brown University, Providence, RI.

Hoang, Searching Genetic Databases on Splash 2, FCCM20 Endorsement, 1993, pp. 185-191, Brown University, Providence, RI.

Homer, B. Merriman, and S. Nelson. BFAST: An Alignment Tool for Large Scale Genome Resequencing. PLOS. Mar. 14, 2011. http://journals.plos.org/plosone/article?id=10.1371/journal.pone.0007767. Retrieved May 25, 2016. 11 pages.

Huang, Sitao, et al. "Hardware Acceleration of the Pair-HMM Algorithm for DNA Variant Calling." Proceedings of the 2017 ACMISIGDA International Symposium on Field-Programmable Gate Arrays, Feb. 22-24, 2017, Monterey, California, USA. pp. 275-284.

Hughey, Parallel Hardware For Sequence Comparison And Alignment, Cabios, 1996, pp. 473-479, vol. 12 No. 6, Oxford University Press, CA.

International Search Report and Written Opinion issued in International Application No. PCT/US2017/013057, mailed Apr. 11, 2017 (Apr. 11, 2017). 10 pages.

International Search Report and Written Opinion issued in International Application No. PCT/US2017/036424, mailed Sep. 12, 2017 (Sep. 12, 2017). 12 pages.

International Search Report and Written Opinion issued in International Application No. PCT/US2017/040385, mailed Oct. 27, 2017 (Oct. 27, 2017). 15 pages.

International Search Report and Written Opinion issued in International Application No. PCT/US2017/058890, mailed Feb. 23, 2018 (Feb. 23, 2018). 16 pages.

International Search Report dated Jun. 18, 2014, for PCT application No. PCT/US2014/012144. 2 pages.

Isa, Nazrin M., et. al. "A Novel Efficient FPGA Architecture for HMM ER Acceleration." 2012 International Conference on Reconfigurable Computing and FPGAs (ReConFig), IEEE, 2013. 6 pages.

Isaac TS Li et al. Methodology article, 160-fold acceleration of the Smith-Waterman algorithm using a field programmable gate array (FPGA). Published Jun. 7, 2007. BMC Bioinformatics 2007, 8:185, Institute of Biomaterials and Biomedical Engineering, University of Toronto, Ontario, Canada. 7 pages.

Jacob, Arpith et al. "FPGA-Accelerated seed generation in Mercury BLASTP", Washington University in St. Louis, BECS Technology Inc. (2007). 10 pgs.

Jacob, Arpith, et. al. "Preliminary Results in Accelerating Profile HMM Search on FPGAs." In Proceedings of 6th IEEE International Workshop on High Performance Computational Biology, Mar. 2007. 9 pages.

JP Japanese Office Action in Japanese Appln. No. 2018-564374, dated Oct. 4, 2021, 7 pages (with English translation).

Kasap, Server et al, "Design and Implementation of an FPGA-based Core for Gapped BLAST Sequence Alignment with the Two-Hit Method", Engineering Letters, 16:3 EL 16 3 25, Aug. 12, 2012, 10 pgs, Scotland, UK (2008).

Khaled Benkrid et al. Review Article: "High Performance Biological Pairwise Sequence Alignment: FPGA versus GPU versus Cell BE versus GPP." Hindawi Publishing Corporation. International Journal of Reconfigurable Computing. vol. 2012. (2012). 15 pages. , Institute of Integrated Systems, School of Engineering, The University of Edinburgh, Kings Edinburgh, UK and Electrical and Computer Engineering Department, The University of Arizona, Tucson, AZ.

Lancaster Joseph, "Design and Evaluation of a BLAST Ungapped Extension Accelerator, Master's Thesis", Washington University, Jan. 1, 2006, 79 pgs, Report No. WUCSE-20016-21, 2006 St. Louis.

Lancaster Joseph, et al. "Acceleration of Ungapped Extension in Mercury BLAST", MSP-7th Workshop on Media and Streaming Processors, Nov. 2005, 9 pgs.

Langmead et al. Searching for SNPs with cloud computing. Genome Biology 2009, vol. 10:lss, II: R134, Published: Nov. 20, 2009. 10 pages.

Laven I ER, Dominque. "SAMBA: Systolic Accelerator for Molecular Biological Applications." Research Report RR-2845, INRIA. 22 pgs, Mar. 1996, France.

Lemoine, et al, High Speed Pattern Matching in Genetic Data Base with Reconfigurable Hardware, ISMB-94 Proceedings, 1994, pas 269-275, AAAI (www.aaai.org), France.

Lopresti, Rapid Implementation of a Genetic Sequence Comparator Using Field-Programmable Logic Arrays, Advanced Research in VLSI, 1991, pp. 138-152, UC Santa Cruz, CA.

Madhavan, Advait, et al. "Race Logic: A Hardware Acceleration for Dynamic Programming Algorithms." 2014 ACM/IEEE 41st international Symposium on Computer Architecture (ISCA), IEEE, 2014. 12 pages.

Mahram, FPGA Acceleration of Sequence Analysis Tools in Bioinformatics, Dissertation, 2013, 180 paaes, Boston, MA.

Maxfield. Impulse achieves 16X speed-up of genome analysis on $2,500 FPGA module. EE Times. Jun. 15, 2012. http://www.eetimes.com/ documentasp?doc id=1317288&print=yes. Retrieved Mar. 29, 2016. 4 pages.

McKenna et al. The Genome Analysis Toolkit: A MapReduce framework for analyzing nextgeneration DNA sequencing data. Genome Research. Published in advance Jul. 19, 2010, 20: 1297-1303 http://genome.cshlp.org/ content/20/19/1297.full.html. Retrieved May 25, 2016.

Mikami, et al, Efficient FPGA-based Hardware Algorithms for Approximate String Matching, ITC-CSCC, 2008, pp. 201-204, Hiroshima, JP.

Miller, Neil A. et al. "A 26-hour system of highly sensitive whole genome sequencing for emergency management of genetic diseases." Genome Medicine. vol. 7, No. 100, Sep. 30, 2015 (Sep. 30, 2015). 16 pages.

Moritz, et al, Implementation of a Parallel Algorithm for Protein Pairwise Alignment Using Reconfigurable Computing, Conference date 2006, Published Feb. 12, 2007. pp. 7, Brazilian National Research Council (CNPq), Brazil.

Muriki, Krishna et al., "RC-BLAST: Towards a Portable, Cost-Effective Open Source Hardware Implementation" Supported in part by NSF Grant EIA-9985986, (2005). 8 pgs.

Nawaz, et al., A Parallel FPGA Design of the Smith-Waterman Traceback, Conference date 2010. Published Jan. 6, 2011, pp. 6, ACE Associated Compiler Expert, The Netherlands.

Nawaz, et al, Fast Smith-Waterman hardware implementation, hArtes (IST-035143), (2010) pp. 4, The Morpheus (IST-027342) and Rcosy (DES-6392) Projects.

Nelson, et al, Shepard: A Fast Exact Match Short Read Aligner, Research Report, (2012) pp. 4, Dept. of Electrical and Computer Engineering, Iowa State University, Ames, IA.

Oliver et al. "Multiple Sequence Alignment on an FPGA." IEEE Computer Society. School of Computer Engineering, Nanyang Technological University, Singapore; Project Proteus, School of Engineering, Ngee Ann Polytechnic, Singapore. Proceedings of the 2005 11th International Conference on Parallel and Distributed Systems. (2005). 5 pages.

Oliver, et al, Using Reconfigurable Hardware to Accelerate Multiple Sequence Alignment with ClustalW, Bioinformatics, 2005, pp. 3431-3432, vol. 21 No. 16, Advanced Access Publication, Singapore.

Oliver, Hyper Customized Processors for Bio-Sequence Database Scanning on FPGAs, FPGA, pp. 229-237, 2005 Monterey, CA.

(56) References Cited

OTHER PUBLICATIONS

Olson et al. "Hardware Acceleration of Short Read Mapping." University of Washington, Pico Computing Inc., Fred Hutchinson Cancer Research Center Seattle, WA. 2012. 8 pages.

Olson, Corey Bruce. "An FPGA Acceleration of Short Read Human Genome Mapping." Master II of Science Thesis. University of Washington, 2011. 103 pages.

Peltenburg, Johan, et al. "Maximizing Systolic Array Efficiency to Accelerate the PairHMM Forward Algorithm." 2016 IEEE International Conference on Bioinformatics and Biomedicine (BIBMJ, IEEE) 2016. pp. 758-762.

Raphael, 8. , et al., "A novel method for multiple alignment of sequences with repeated and shuffled elements", Genome Research 14(11 ), Nov. 1, 2004, 2336-2346.

Ren, Shanshan, et al. "FPGA Acceleration of the Pair-HM Ms Forward Algorithm for DNA Sequence Analysis." 2015 IEEE International Conference on Bioinformatics and Biomedicine (BIBM), IEEE, 2015. 6 pages.

Rimmer, A. , et al., "Integrating mapping-, assembly- and haplotype-based approaches for calling variants in clinical sequencing applications", Nature Genetics 46(8), Jul. 13, 2014, 912-918.

Ruffalo, T. LaFramboise, and M. Koyuturk. Comparative analysis of algorithms for next generation sequencing read alignment. Bioinformatics (2011) 27 (20): 2790-2796. First published online: Aug. 19, 2011. https://bioinformatics.oxfordjournals.org/content/27/20/2790.full. Retrieved May 25, 2016.

Sakar, Souradip et al. "Network-on-Chip Hardware Accelerators for Biological Sequence Alignment." IEEE Transactions on Computers, Jan. 2010, vol. 59, No. 1, pp. 29-41, Washington State.

Schatz, B. Langmead, and S. Salzberg. Cloud Computing and the DNA Data Race. HHS Public Access. Published Nat Biotechnol. Jul. 2010; 28(7): 691-693. http://www.ncbi.nlm.nih.gov/pmciarticles/PMC2904649/. Retrieved May 25, 2016.

Schatz, C. Trapnell, A. Delcher, and A. Varshney. High-throughput sequence alignment using Graphics Processing Units. Published Dec. 10, 2007. BMC Bioinformatics, http://bmcbioinformatics. biomedcentral.com/;articles/10.1186/1471-2105-8-474. Retrieved Mav 25, 2016. 13 Paaes.

Schatz. CloudBurst: highly sensitive read mapping with MapReduce. Bioinformatics (2009) 25 (11 ): 1363-1369. First published online: Apr. 8, 2009. http://bioinformatics.oxfordioumals.ora/content/25/11/1363.full. Retrieved Mav 25, 2016.

Scott and Quinn 0. Snell. "Hardware Accelerated Sequence Alignment with Traceback" International Journal of Reconfigurable Computing, vol. 2009, 2009. 10 pages.

Settle, Sean, et al. "High-Performance Dynamic Programming on FPGAs with OpenCL." 2013 IEEE High Performance Extreme Computing Conference {HPEC}, IEEE, 2013. 6 pages.

Sotiriades Euripides, et al. "FPGA based Architecture for DNA Sequence Comparison and Database Search", University of Crete, 2006, 8 pgs, Crete, Greece.

Sotiriades Euripides, et al., "Some Initial Results on Hardware BLAST acceleration with a Reconfigurable; Architecture", University of Crete, 2006, 8 pas, Crete, Greece.

Sun, Yanteng, et al. "Accelerating HM Mer on FPGAs Using Systolic Array Based Architecture." IEEE International Symposium on Parallel & Distributed Processing, IEEE, 2009. 8 pages.

TimeLogic Division, Active Motif Inc., "Accelerated BLAST Performance with Tera-Blast: a comparison of FPGA versus GPU and CPU Blast implementations", Technical Note, May 2013, 5 pages, Version 1.0.

Treangen, T., et al., "Gapped extension for local multiple alignment of interspersed DNA repeats", ISBRA 2008, LNBI 4983, May 7, 2007, 74-86.

Van Court et al., Families of FPGA-Based Algorithms for Approximate String Matching, (2004), 11 pgs, Boston University, ECE Dept., MA.

Wu and Colin K. Watanabe. Sequence analysis: "GMAP: a genomic mapping and alignment program for mRNA and EST sequences."

Publication Feb. 22, 2005. Bioinformatics Original Paper. vol. 21No.92005, pp. 1859-1875. South San Francisco, CA.

Yamaguchi, et al., High Speed Homology Search with FPGAs, Pacific Symposium On Biocomputing 7:271-282 (2002), Japan.

Ying Liu et al. "An FPGA-Based Web Server for High Performance Biological Sequence Alignment." The University of Edinburgh, Edinburgh, UK and The Queen's University of Belfast, Northern Ireland, UK. 2009 NASA/ESA Conference on Adaptive Hardware and Systems. pp. 361-368.

Yu, et al, A Smith-Waterman Systolic Cell, (2003), 10 pgs Dept. of Computer Science, The Chinese University of HonQ KonQ.

Zhang et al. A Practical Comparison of De Novo Genome Assembly Software Tools for Next-Generation Sequencing Technologies. PLOS One. Published: Mar. 14, 2011, http://joumals.plos.org/plosone/article?id=10.1371 / journal.pone.0017915. Retrieved May 25, 2016. 10 pages.

BR Office Action in Brazilian Appln. No. BR122022025392-0, mailed on Aug. 1, 2024, 10 pages (with English translation).

Guo et al., "A systolic array-based FPGA parallel architecture for the BLAST algorithm," International Scholarly Research Notices, Sep. 2012, vol. 2012, 12 pages.

EP Office Action in European Appln. No. 17798358.2, mailed on Mar. 11, 2025, 6 pages.

C. Wang et al., "Heterogeneous Cloud Framework for Big Data Genome Sequencing," IEEE/ACM Transactions on Computational Biology and Bioinformatics, 12(1) (Sep. 12, 2014).

Batista, "A Parallel Strategy for Biological Sequence Alignment in Restricted Memory Space" Journal of Parallel and Distributed Computing, 2008, 68(4):548-561.

Cheever, Fast Fourier transform-based correlation of DNA sequences using complex plane encoding, Bioinformatics, 1991, 7(2), pp. 143-154).

Lee, H., et al.; "Clinical exome sequencing for genetic identification of rare Mendelian disorders"; JAMA 2014; 312(18): 1880-1887.

Vermij, Erik; "Genetic sequence alignment on a supercomputing platform"; Thesis—Master of Science in Computer Engineering, Delft University of Technology 2011; pp. 1-100.

Oliver, T.F., et al.; "Reconfigurable architectures for bio-sequence database scanning on FPGAs"; IEEE Transaction on Circuits and Systems—11: Express Briefs 2005; 52(12): 851-855.

Russell, et al.; "TGAC Unleashes DRAGEN to Accelerate Genomics Workflows"; XP055360847, Retrieved from the Internet: URL: https://www.hpcwire.com/2015/10/28/tgac-unleashes-dragento-accelerate-genomics-workflows/ 2015 [retrieved on Mar. 31, 2017].

Holt, et al.; "MAKER2: An Annotation Pipeline and Genome-Database Management Tool for Second-Generation Genome Projects"; BMC Bioinformatics 2011; 12:491.

Wilke, et al.; "A RESTful API for Accessing Microbial Community Data for MG-Rast"; PLoS Computational Biology 2015; 11(1):e1004008.

Zhang, et al.; "Joint Haplotype Phasing and Genotype Calling of Multiple Individuals Using Haplotype Informative Reads"; Bioinformatics 2013; 29(19):2427-2434.

Mandelker, et al.; "Navigating Highly Homologous Genes In A Molecular Diagnostic Setting: A Resource For Clinical Next-Generation Sequencing"; Genetics in Medicine 2016; 18(12): 1282-1289.

Iqbal, et al.; "De Novo Assembly And Genotyping Of Variants Using Colored De Bruijn Graphs"; Nature Genetics 2012; 44(2): 226-233.

Oliver, Tim; "Integrating FPGA acceleration into HMMer"; Parallel Computing 2008; 34:681-691.

Doddavula, et al.; "Implementation of a Scalable Next Generation Sequencing Business Cloud Platform—An Experience Report"; Presented at the 2011 IEEE 4th International Conference on Cloud Computing, Washington D.C, USA 2011; pp. 598-605.

Wang et al.; "Heterogeneous cloud framework for big data genome sequencing"; IEEE/ACM Transactions on Computational Biology and Bioinformatics 2015; 12(1):166-178.

Batista, et al.; "Early Scheduling on Steroids: Boosting Parallel State Machine Replication"; Journal of Parallel and Distributed Computing 2022; 163:269-282.

(56) References Cited

OTHER PUBLICATIONS

Choi, Young-Kyu, et al.; "A quantitative analysis on microarchitectures of modern CPU-FPGA platforms"; In Proceedings of the 53rd Annual Design Automation Conference (DAC '16). Association for Computing Machinery, New York, NY, USA, Article 109, 1-6; DOI:https://doi.org/10.1145/2897937.2897972 ,(May 6, 2016).

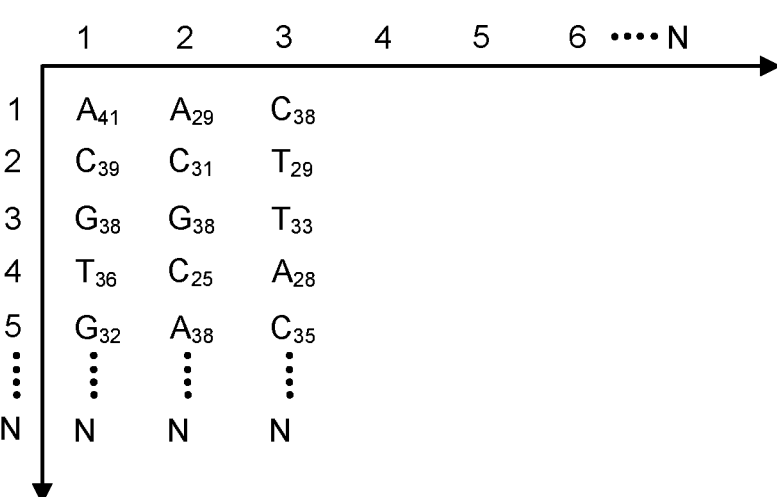
FIG. 1D
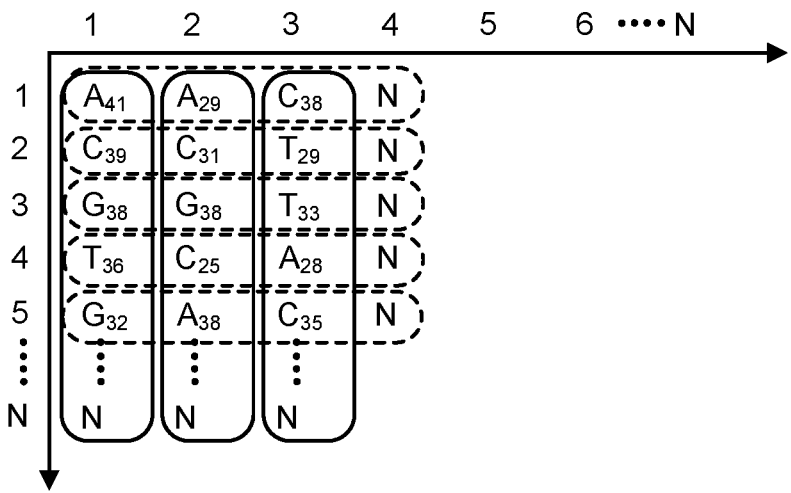
FIG. 1E
| Read 1 | $A_{41}$ | $A_{29}$ | $C_{38}$ | N |
| --- | --- | --- | --- | --- |
| Read 2 | $C_{39}$ | $C_{31}$ | $T_{29}$ | N |
| Read 3 | $G_{38}$ | $G_{38}$ | $T_{33}$ | N |
| Read 4 | $T_{36}$ | $C_{25}$ | $A_{28}$ | N |
| Read 5 | $G_{32}$ | $A_{38}$ | $C_{35}$ | N |
FIG. 1F High-level view of HMM interface structure.

HMM data flow and HW/SW interaction overview.

HMM Cluster Collar connections.

Somewhat high-level view of the major functional blocks within the HMM hardware accelerator.

HMM matrix structure and hardware processing flow example.

Enlarged view of a portion of Figure 8 showing the data flow and dependencies between nearby cells in the HMM M,I, and D state computations.

Computations required for M, I, D state updates.

M,1, and D state update circuits, including effects of simplifying assumptions related to transition probabilities and the effect of sharing some M, I, D adder resources with the final sum operations.

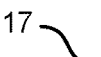
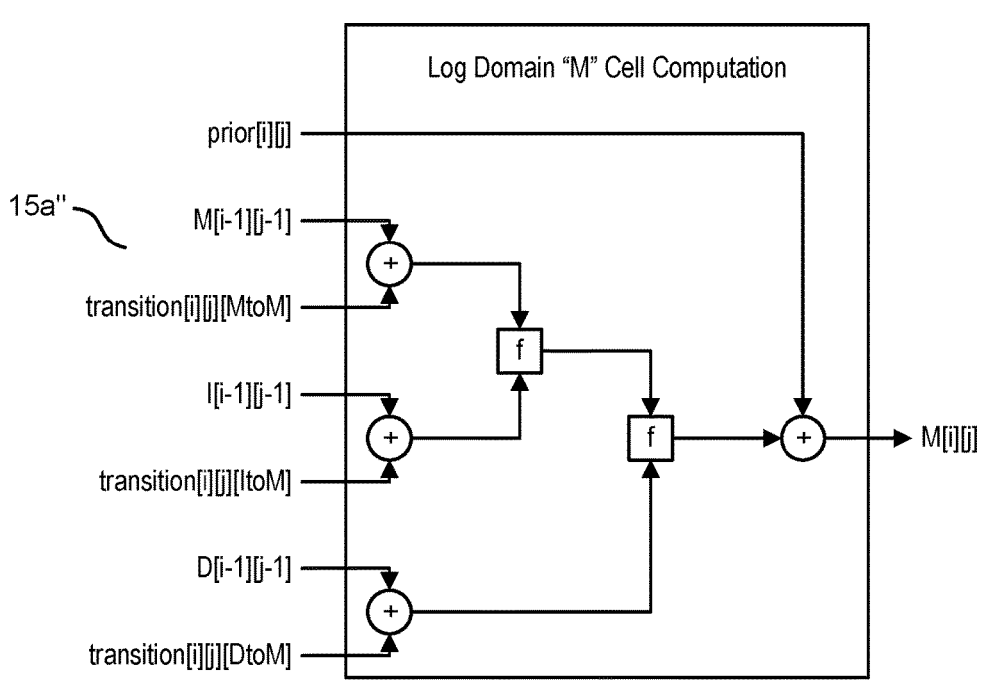
Note:  The "f" function is the approximation to log of addition.  I.e., f(a,b) @ max(a,b) − log₂(1+2^(−|a−b|))
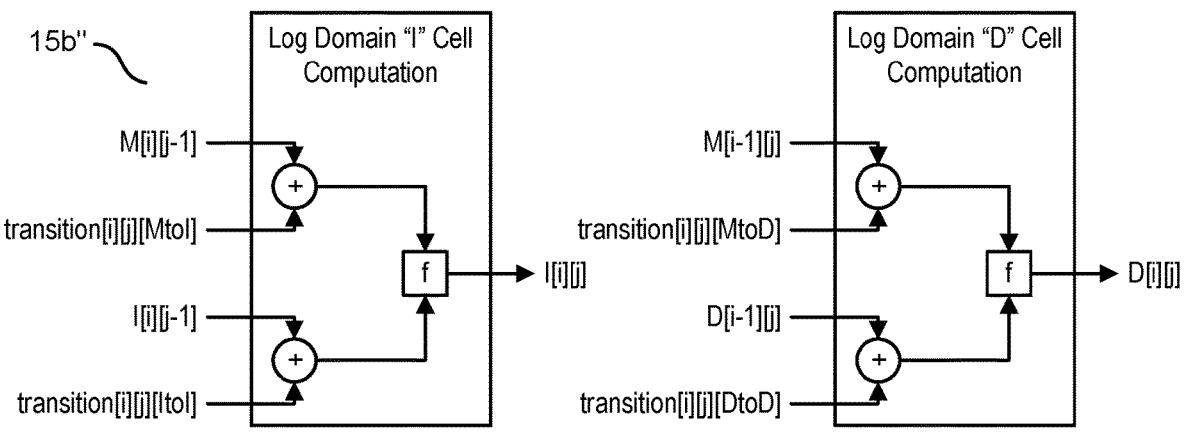
Log domain M, I, D state calculation details.
FIG. 11

HMM state transition diagram showing relation between GOP, GCP and transition probabilities.

HMM Transprobs and priors generation circuit to support the general state transaction diagram of Figure 17.

Simplified HMM state transition diagram showing relation between GOP, GCP and transition probabilities.

HMM transprobs and priors generation circuit to support the simplified state transition diagram of Figure 19.

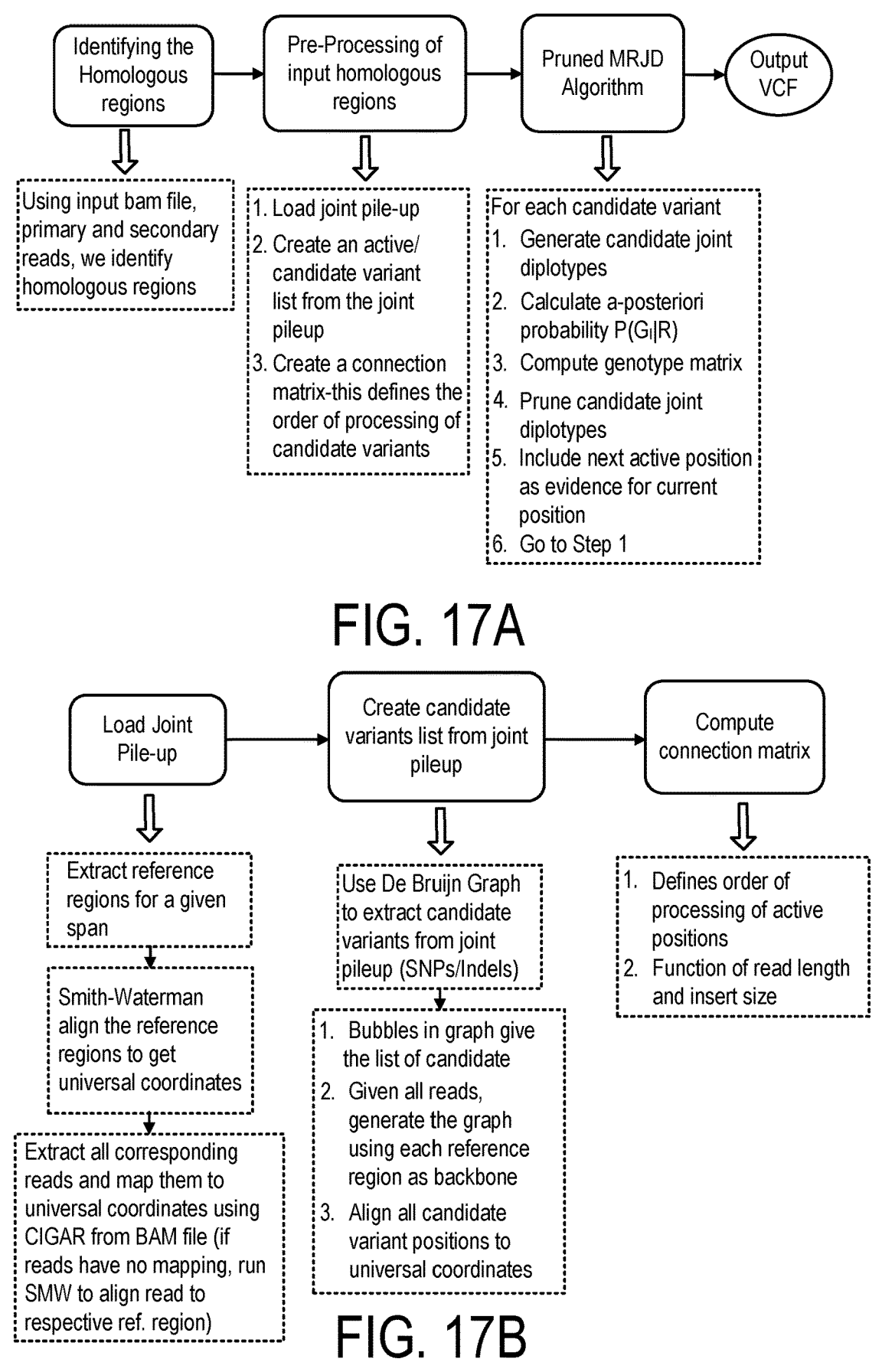

| Identifying the Homologous regions | → | Pre-Processing of input homologous regions | → | Pruned MRJD Algorithm | → | Output VCF |

⇓ (under Identifying the Homologous regions)

Using input bam file, primary and secondary reads, we identify homologous regions ⇓ (under Pre-Processing of input homologous regions)

1. Load joint pile-up
2. Create an active/candidate variant list from the joint pileup
3. Create a connection matrix-this defines the order of processing of candidate variants ⇓ (under Pruned MRJD Algorithm)

For each candidate variant
1. Generate candidate joint diplotypes
2. Calculate a-posteriori probability $P(G_i|R)$
3. Compute genotype matrix
4. Prune candidate joint diplotypes
5. Include next active position as evidence for current position
6. Go to Step 1

FIG. 17A

| Load Joint Pile-up | → | Create candidate variants list from joint pileup | → | Compute connection matrix |

⇓ (under Load Joint Pile-up)

Extract reference regions for a given span

↓

Smith-Waterman align the reference regions to get universal coordinates

↓

Extract all corresponding reads and map them to universal coordinates using CIGAR from BAM file (if reads have no mapping, run SMW to align read to respective ref. region)

⇓ (under Create candidate variants list from joint pileup)

Use De Bruijn Graph to extract candidate variants from joint pileup (SNPs/Indels)

↓

1. Bubbles in graph give the list of candidate
2. Given all reads, generate the graph using each reference region as backbone
3. Align all candidate variant positions to universal coordinates ⇓ (under Compute connection matrix)

1. Defines order of processing of active positions
2. Function of read length and insert size

FIG. 17B

Candidate haplotypes          Bubble Extraction
CGATTCTAAGT                 TTCTAA
CGATTGTAAGT                 TTGTAA

| i | $H_1$=CAT | $H_2$=CAA | $H_3$=CCT | $H_4$=CCA | $H_5$=GAT | $H_6$=GAA | $H_7$=GCT | $H_8$=GCA | CAT GCA / CAT GCA | CAT GCA / CCT GCA |
|---|---|---|---|---|---|---|---|---|---|---|
| 1 | 0.0000 | 0.0033 | 0.0033 | 0.9801 | 0.0000 | 0.0033 | 0.0033 | 0.9801 | 0.4901 | 0.4909 |
| 2 | 0.0000 | 0.0000 | 0.0033 | 0.0033 | 0.0033 | 0.0033 | 0.9801 | 0.9801 | 0.4901 | 0.4909 |
| 3 | 0.0000 | 0.0000 | 0.0033 | 0.0033 | 0.0033 | 0.0033 | 0.9801 | 0.9801 | 0.4901 | 0.4909 |
| 4 | 0.0000 | 0.0000 | 0.0033 | 0.0033 | 0.0033 | 0.0033 | 0.9801 | 0.9801 | 0.4901 | 0.4909 |
| 5 | 0.0000 | 0.0000 | 0.0033 | 0.0033 | 0.0033 | 0.0033 | 0.9801 | 0.9801 | 0.4901 | 0.4909 |
| 6 | 0.0000 | 0.0000 | 0.0033 | 0.0033 | 0.0033 | 0.0033 | 0.9801 | 0.9801 | 0.4901 | 0.4909 |
| 7 | 0.0000 | 0.0033 | 0.0033 | 0.9801 | 0.0000 | 0.0033 | 0.0033 | 0.9801 | 0.4901 | 0.4909 |
| 8 | 0.0000 | 0.0033 | 0.0033 | 0.9801 | 0.0000 | 0.0033 | 0.0033 | 0.9801 | 0.4901 | 0.4909 |
| 9 | 0.0000 | 0.0033 | 0.0033 | 0.9801 | 0.0033 | 0.0033 | 0.0033 | 0.9801 | 0.4901 | 0.4909 |
| 10 | 0.0000 | 0.0000 | 0.0033 | 0.0033 | 0.0000 | 0.0033 | 0.9801 | 0.9801 | 0.4901 | 0.4909 |
| 11 | 0.0000 | 0.0033 | 0.0033 | 0.9801 | 0.0033 | 0.0033 | 0.0033 | 0.9801 | 0.4901 | 0.4909 |
| 12 | 0.0000 | 0.0000 | 0.0033 | 0.0033 | 0.0033 | 0.0033 | 0.9801 | 0.9801 | 0.4901 | 0.4909 |
| 13 | 0.0000 | 0.0000 | 0.0033 | 0.0033 | 0.0033 | 0.0033 | 0.9801 | 0.9801 | 0.4901 | 0.4909 |
| 14 | 0.0000 | 0.9801 | 0.0033 | 0.9801 | 0.0000 | 0.0033 | 0.9801 | 0.9801 | 0.4901 | 0.4909 |
| 15 | 0.0000 | 0.9801 | 0.0033 | 0.0033 | 0.0033 | 0.0033 | 0.0033 | 0.9801 | 0.4901 | 0.4909 |
| 16 | 0.9801 | 0.9801 | 0.0033 | 0.0033 | 0.0033 | 0.0033 | 0.9801 | 0.9801 | 0.4901 | 0.4909 |
| 17 | 0.9801 | 0.0033 | 0.0033 | 0.0033 | 0.0033 | 0.0033 | 0.0000 | 0.0000 | 0.4901 | 0.4909 |
| 18 | 0.9801 | 0.0033 | 0.0033 | 0.0033 | 0.9801 | 0.0033 | 0.0000 | 0.0000 | 0.4901 | 0.2459 |
| 19 | 0.9801 | 0.9801 | 0.0033 | 0.0000 | 0.9801 | 0.0000 | 0.0033 | 0.0000 | 0.4901 | 0.2459 |
| 20 | 0.9801 | 0.0033 | 0.0033 | 0.0000 | 0.0033 | 0.0000 | 0.0000 | 0.0000 | 0.4901 | 0.2459 |
| 21 | 0.9801 | 0.0000 | 0.0033 | 0.0033 | 0.9801 | 0.0000 | 0.0033 | 0.0000 | 0.4901 | 0.2459 |
| 22 | 0.9801 | 0.0033 | 0.0033 | 0.0000 | 0.0033 | 0.0000 | 0.0000 | 0.0000 | 0.4901 | 0.2459 |
| 23 | 0.0033 | 0.0000 | 0.0033 | 0.0000 | 0.0000 | 0.0000 | 0.0033 | 0.0033 | 0.4901 | 0.2459 |
| 24 | 0.0033 | 0.0000 | 0.0033 | 0.0033 | 0.0000 | 0.0000 | 0.9801 | 0.0033 | 0.0033 | 0.2475 |
| 25 | 0.0033 | 0.0033 | 0.9801 | 0.9801 | 0.0033 | 0.0000 | 0.0033 | 0.0033 | 0.0033 | 0.2475 |
| 26 | 0.0033 | 0.0000 | 0.9801 | 0.9801 | 0.0033 | 0.0000 | 0.0033 | 0.0033 | 0.0033 | 0.2475 |
| 27 | 0.0033 | 0.0000 | 0.9801 | 0.0033 | 0.0000 | 0.0000 | 0.9801 | 0.0033 | 0.0033 | 0.2475 |
| 28 | 0.0033 | 0.0000 | 0.9801 | 0.0033 | 0.0033 | 0.0000 | 0.9801 | 0.0033 | 0.0033 | 0.2475 |
| 29 | 0.0033 | 0.0033 | 0.9801 | 0.9801 | 0.0033 | 0.0000 | 0.0033 | 0.0033 | 0.0033 | 0.2475 |
| 30 | 0.0033 | 0.0000 | 0.9801 | 0.0033 | 0.0000 | 0.0000 | 0.9801 | 0.0033 | 0.0033 | 0.2475 |
| 31 | 0.0033 | 0.0000 | 0.9801 | 0.0033 | 0.0033 | 0.0000 | 0.9801 | 0.0033 | 0.0033 | 0.2475 |
| 32 | 0.0033 | 0.0000 | 0.9801 | 0.0033 | 0.0033 | 0.0000 | 0.0033 | 0.0033 | 0.0033 | 0.2475 |
|  |  |  |  |  |  |  |  |  | 3.5e-30 | 2.2e-15 |

FIG. 26

$$G_1^1 = \begin{bmatrix} C & G \\ C & G \end{bmatrix} \qquad P(G_1|R) = 0.99892171 \text{ (phred } 0.00)$$

$$G_2^1 = \begin{bmatrix} G & G \\ C & G \end{bmatrix} \qquad P(G_2|R) = 0.00103398 \text{ (phred } 29.85)$$

$$G_3^1 = \begin{bmatrix} C & G \\ C & C \end{bmatrix} \qquad P(G_3|R) = 0.00003934 \text{ (phred } 44.05)$$

$$G_4^1 = \begin{bmatrix} G & G \\ C & C \end{bmatrix} \qquad P(G_4|R) = 0.00000251 \text{ (phred } 56.00)$$

$$G_5^1 = \begin{bmatrix} G & C \\ G & C \end{bmatrix} \qquad P(G_5|R) = 0.00000126 \text{ (phred } 59.00)$$

$$G_6^1 = \begin{bmatrix} G & G \\ G & C \end{bmatrix} \qquad P(G_6|R) = 0.00000116 \text{ (phred } 59.35)$$

$$G_7^1 = \begin{bmatrix} G & C \\ C & C \end{bmatrix} \qquad P(G_7|R) = 0.00000004 \text{ (phred } 73.55)$$

$$G_8^1 = \begin{bmatrix} G & G \\ G & G \end{bmatrix} \qquad P(G_8|R) = 0.00000000 \text{ (phred } 151.67)$$

$$G_8^1 = \begin{bmatrix} C & C \\ C & C \end{bmatrix} \qquad P(G_9|R) = 0.00000000 \text{ (phred } 225.85)$$

FIG. 28

$$G^2_1 = \begin{bmatrix} CC & GC \\ CA & GC \end{bmatrix} \qquad P(G_1|R) = 0.99799456 \text{ (phred 0.01)}$$

$$G^2_2 = \begin{bmatrix} CA & GC \\ CA & GC \end{bmatrix} \qquad P(G_2|R) = 0.00101673 \text{ (phred 29.93)}$$

$$G^2_3 = \begin{bmatrix} CA & GC \\ CA & CC \end{bmatrix} \qquad P(G_3|R) = 0.00097796 \text{ (phred 30.10)}$$

$$G^2_4 = \begin{bmatrix} CC & GC \\ CA & CC \end{bmatrix} \qquad P(G_4|R) = 0.00000913 \text{ (phred 50.39)}$$

$$G^2_5 = \begin{bmatrix} GC & GC \\ CA & CC \end{bmatrix} \qquad P(G_5|R) = 0.00000125 \text{ (phred 59.02)}$$

$$G^2_6 = \begin{bmatrix} GC & GC \\ CA & GC \end{bmatrix} \qquad P(G_6|R) = 0.00000015 \text{ (phred 68.29)}$$

$$G^2_7 = \begin{bmatrix} GA & GC \\ CA & CC \end{bmatrix} \qquad P(G_7|R) = 0.00000007 \text{ (phred 71.45)}$$

$$G^2_8 = \begin{bmatrix} CC & GC \\ CA & GA \end{bmatrix} \qquad P(G_8|R) = 0.00000007 \text{ (phred 71.45)}$$

$$G^2_9 = \begin{bmatrix} GA & GC \\ CA & GC \end{bmatrix} \qquad P(G_9|R) = 0.00000006 \text{ (phred 72.06)}$$

$$G^2_{10} = \begin{bmatrix} CC & GC \\ CC & CA \end{bmatrix} \qquad P(G_{10}|R) = 0.00000001 \text{ (phred 79.89)}$$

$$G^2_{11} = \begin{bmatrix} GC & CC \\ GC & CA \end{bmatrix} \qquad P(G_{11}|R) = 0.00000000 \text{ (phred 88.51)}$$

$$G^2_{12} = \begin{bmatrix} GC & GC \\ CC & CA \end{bmatrix} \qquad P(G_{12}|R) = 0.00000000 \text{ (phred 88.51)}$$

$$G^2_{13} = \begin{bmatrix} CC & GC \\ CA & CA \end{bmatrix} \qquad P(G_{13}|R) = 0.00000000 \text{ (phred 89.10)}$$

$$G^2_{14} = \begin{bmatrix} GA & GC \\ CC & GC \end{bmatrix} \qquad P(G_{14}|R) = 0.00000000 \text{ (phred 116.35)}$$

$$G^2_{15} = \begin{bmatrix} CA & GC \\ CA & GA \end{bmatrix} \qquad P(G_{15}|R) = 0.00000000 \text{ (phred 120.60)}$$

(candidates 16-70 not shown)

FIG. 29

$$G_1^3 = \begin{bmatrix} CCT & GCA \\ CAT & GCA \end{bmatrix} \qquad P(G_1|R) = 0.99885810 \text{ (phred 0.00)}$$

$$G_2^3 = \begin{bmatrix} CCT & GCT \\ CAT & GCA \end{bmatrix} \qquad P(G_2|R) = 0.00111991 \text{ (phred 29.51)}$$

$$G_3^3 = \begin{bmatrix} CCT & GCA \\ CAT & CCA \end{bmatrix} \qquad P(G_3|R) = 0.00000914 \text{ (phred 50.39)}$$

$$G_4^3 = \begin{bmatrix} CAT & GCT \\ CAT & GCA \end{bmatrix} \qquad P(G_4|R) = 0.00000462 \text{ (phred 53.36)}$$

$$G_5^3 = \begin{bmatrix} CAT & GCA \\ CAT & CCT \end{bmatrix} \qquad P(G_5|R) = 0.00000222 \text{ (phred 56.53)}$$

$$G_6^3 = \begin{bmatrix} CAT & GCT \\ CAT & CCA \end{bmatrix} \qquad P(G_6|R) = 0.00000222 \text{ (phred 56.53)}$$

$$G_7^3 = \begin{bmatrix} CCA & GCT \\ CAT & GCT \end{bmatrix} \qquad P(G_7|R) = 0.00000126 \text{ (phred 59.01)}$$

$$G_8^3 = \begin{bmatrix} GCT & GCA \\ CAT & CCA \end{bmatrix} \qquad P(G_8|R) = 0.00000126 \text{ (phred 59.01)}$$

$$G_9^3 = \begin{bmatrix} CCA & GCT \\ CAT & GCA \end{bmatrix} \qquad P(G_9|R) = 0.00000126 \text{ (phred 59.01)}$$

$$G_{10}^3 = \begin{bmatrix} CCT & GCA \\ CAT & CCT \end{bmatrix} \qquad P(G_{10}|R) = 0.00000001 \text{ (phred 79.89)}$$

$$G_{11}^3 = \begin{bmatrix} CCT & GCT \\ CAT & CCA \end{bmatrix} \qquad P(G_{11}|R) = 0.00000001 \text{ (phred 79.89)}$$

$$G_{12}^3 = \begin{bmatrix} GCT & GCA \\ CAT & CCT \end{bmatrix} \qquad P(G_{12}|R) = 0.00000000 \text{ (phred 88.52)}$$

$$G_{13}^3 = \begin{bmatrix} GCT & GCT \\ CAT & CCA \end{bmatrix} \qquad P(G_{13}|R) = 0.00000000 \text{ (phred 88.52)}$$

$$G_{14}^3 = \begin{bmatrix} CAT & GCT \\ CAA & GCA \end{bmatrix} \qquad P(G_{14}|R) = 0.00000000 \text{ (phred 91.82)}$$

$$G_{15}^3 = \begin{bmatrix} CCT & GCA \\ CAA & GCA \end{bmatrix} \qquad P(G_{15}|R) = 0.00000000 \text{ (phred 94.70)}$$

(candidates 16-65 not shown)

FIG. 30

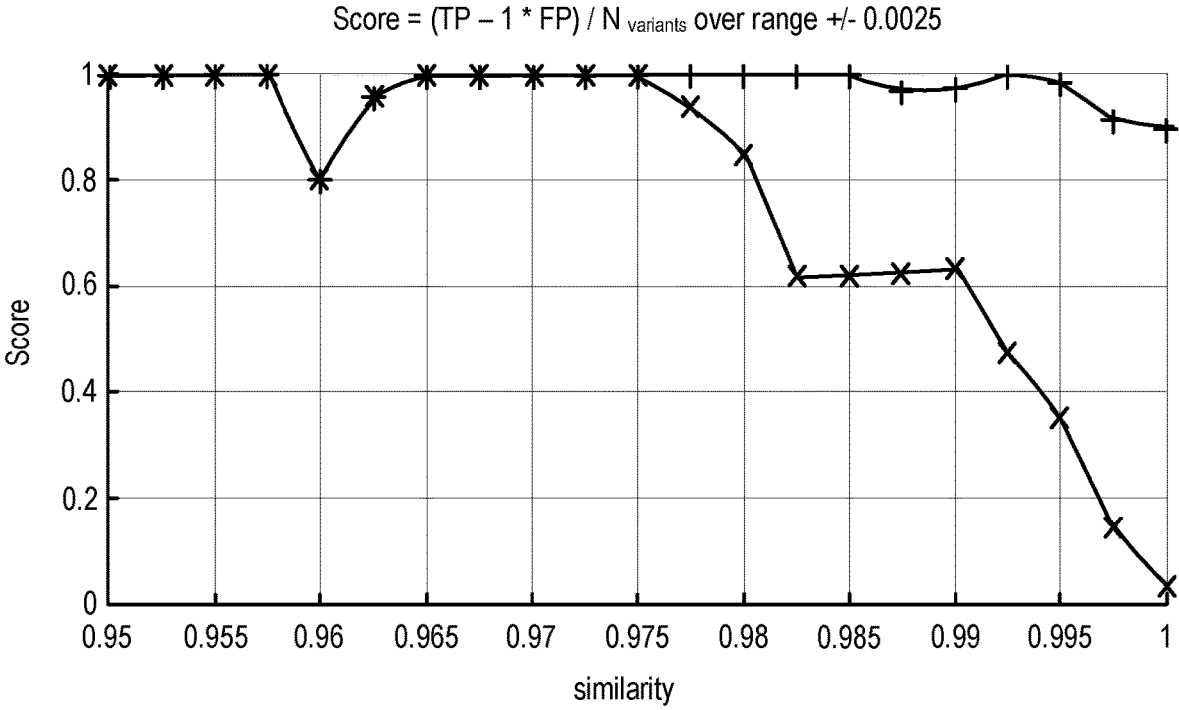
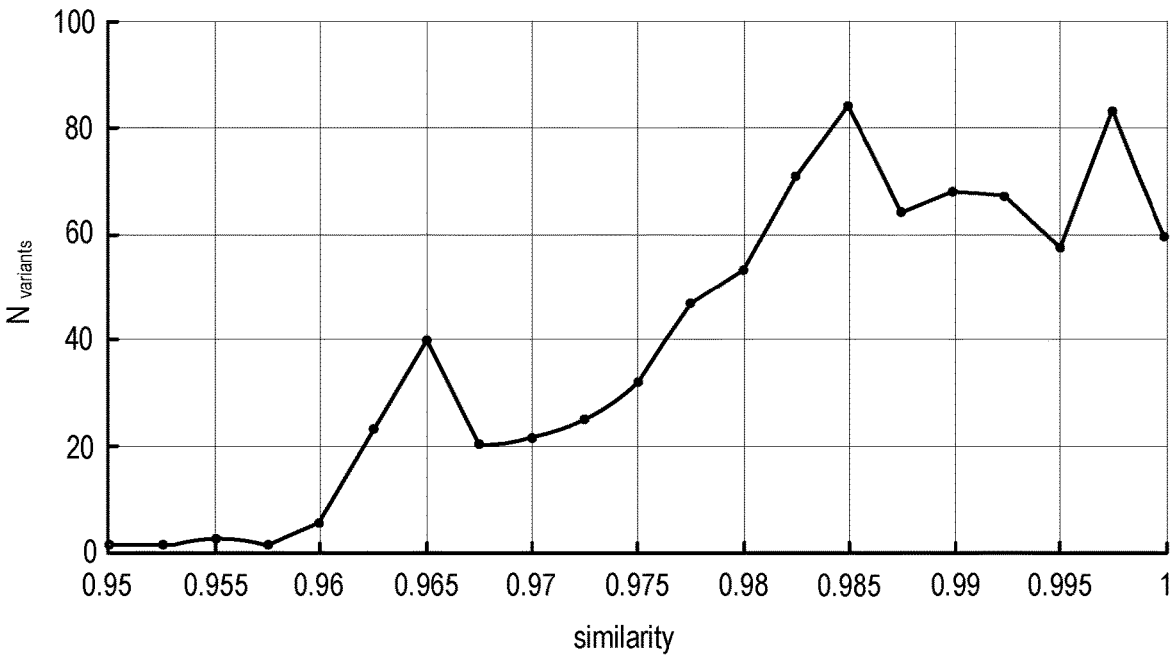
FIG. 32

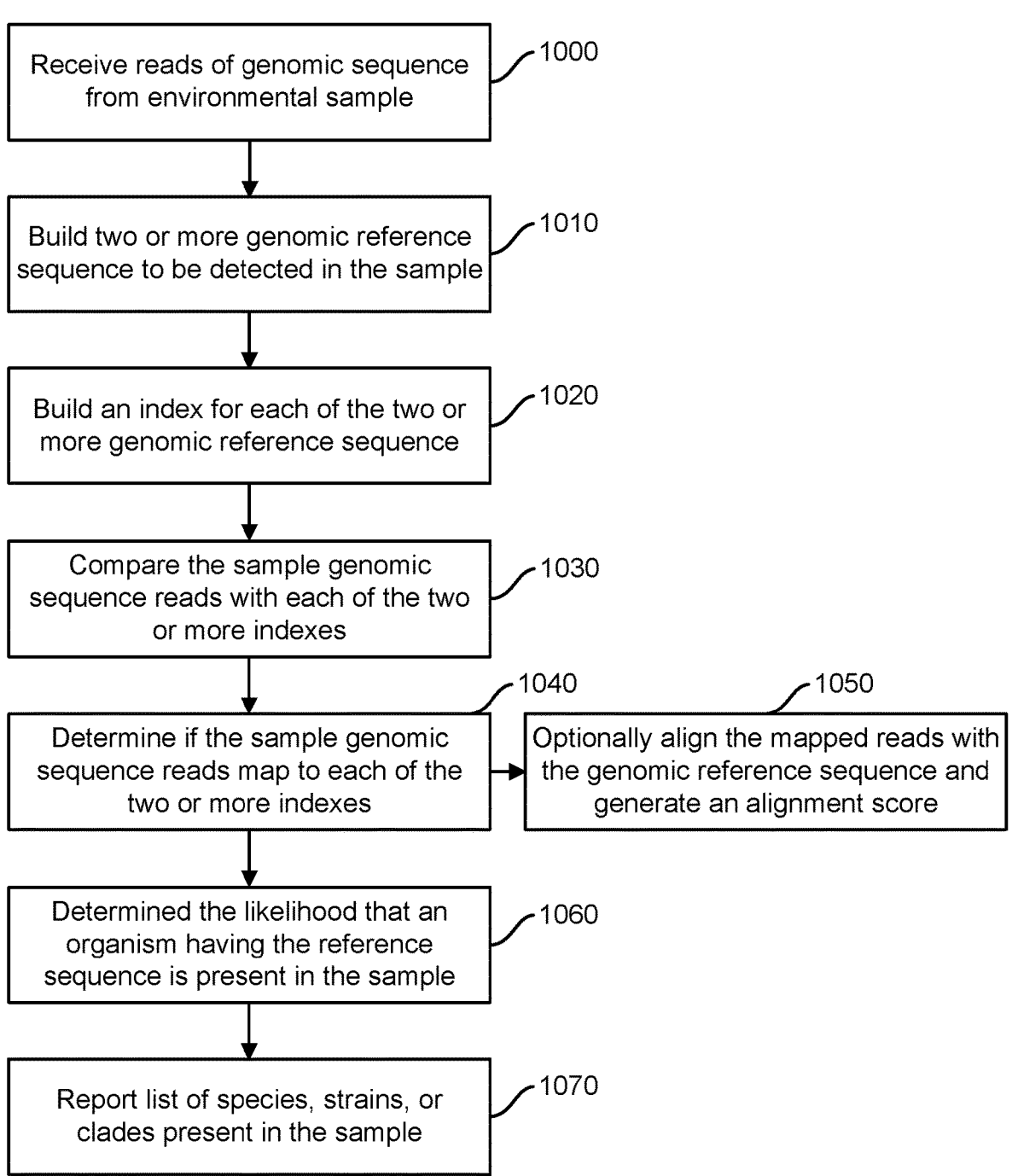

Receive reads of genomic sequence from environmental sample ⟋ 1000

Build two or more genomic reference sequence to be detected in the sample ⟋ 1010

Build an index for each of the two or more genomic reference sequence ⟋ 1020

Compare the sample genomic sequence reads with each of the two or more indexes ⟋ 1030

Determine if the sample genomic sequence reads map to each of the two or more indexes ⟋ 1040

Optionally align the mapped reads with the genomic reference sequence and generate an alignment score ⟋ 1050

Determined the likelihood that an organism having the reference sequence is present in the sample ⟋ 1060

Report list of species, strains, or clades present in the sample ⟋ 1070

FIG. 43B

BIOINFORMATICS SYSTEMS, APPARATUSES, AND METHODS FOR PERFORMING SECONDARY AND/OR TERTIARY PROCESSING

CROSS-REFERENCE TO RELATED APPLICATIONS

This application is a continuation of application Ser. No. 15/796,696, filed Oct. 27, 2017, which claims the benefit U.S. Provisional Application Ser. No. 62/414,637, filed Oct. 28, 2016. The disclosures of the above applications are hereby incorporated by reference in their entirety.

FIELD OF THE DISCLOSURE

The subject matter described herein relates to bioinformatics, and more particularly to systems, apparatuses, and methods for implementing bioinformatic protocols, such as performing one or more functions for analyzing genomic data on an integrated circuit, such as on a hardware processing platform.

BACKGROUND TO THE DISCLOSURE

As described in detail herein, some major computational challenges for high-throughput DNA sequencing analysis is to address the explosive growth in available genomic data, the need for increased accuracy and sensitivity when gathering that data, and the need for fast, efficient, and accurate computational tools when performing analysis on a wide range of sequencing data sets derived from such genomic data.

Keeping pace with such increased sequencing throughput generated by Next Gen Sequencers has typically been manifested as multithreaded software tools that have been executed on ever greater numbers of faster processors in computer clusters with expensive high availability storage that requires substantial power and significant IT support costs. Importantly, future increases in sequencing throughput rates will translate into accelerating real dollar costs for these secondary processing solutions.

The devices, systems, and methods of their use described herein are provided, at least in part, so as to address these and other such challenges.

SUMMARY OF THE DISCLOSURE

The present disclosure is directed to devices, systems, and methods for employing the same in the performance of one or more genomics and/or bioinformatics protocols on data generated through a primary processing procedure, such as on genetic sequence data. For instance, in various aspects, the devices, systems, and methods herein provided are configured for performing secondary and/or tertiary analysis protocols on genetic data, such as data generated by the sequencing of RNA and/or DNA, e.g., by a Next Gen Sequencer ("NGS"). In particular embodiments, one or more secondary and/or tertiary processing pipelines for processing genetic sequence data is provided. Specifically, one or more tertiary processing pipelines for processing genetic sequence data is provided, such as where the pipelines, and/or individual elements thereof, deliver superior sensitivity and improved accuracy on a wider range of sequence derived data than is currently available in the art.

For example, provided herein is a system, such as for executing one or more of a sequence and/or genomic analysis pipeline on genetic sequence data and/or other data derived therefrom. In various embodiments, the system may include one or more of an electronic data source that provides digital signals representing a plurality of reads of genetic and/or genomic data, such as where each of the plurality of reads of genomic data include a sequence of nucleotides. The system may further include a memory, e.g., a DRAM, or a cache, such as for storing one or more of the sequenced reads, one or a plurality of genetic reference sequences, and one or more indices of the one or more genetic reference sequences. The system may additionally include one or more integrated circuits, such as a FPGA, ASIC, or sASIC, and/or a CPU and/or a GPU and/or Quantum Processing Units (QPUs), which integrated circuit, e.g., with respect to the FPGA, ASIC, or sASIC may be formed of a set of hardwired digital logic circuits that are interconnected by a plurality of physical electrical interconnects. The system may additionally include a quantum computing processing unit, for use in implementing one or more of the methods disclosed herein.

In various embodiments, one or more of the plurality of electrical interconnects may include an input to the one or more integrated circuits that may be connected or connectable, e.g., directly, via a suitable wired connection, or indirectly such as via a wireless network connection (for instance, a cloud or hybrid cloud), with the electronic data source. Regardless of a connection with the sequencer, an integrated circuit of the disclosure may be configured for receiving the plurality of reads of genomic data, e.g., directly from the sequencer or from an associated memory. The reads may be digitally encoded in a standard FASTQ or BCL file format. Accordingly, the system may include an integrated circuit having one or more electrical interconnects that may be a physical interconnect that includes a memory interface so as to allow the integrated circuit to access the memory.

Particularly, the hardwired digital logic circuit of the integrated circuit may be arranged as a set of processing engines, such as where each processing engine may be formed of a subset of the hardwired digital logic circuits so as to perform one or more steps in the sequence, genomic, and/or tertiary analysis pipeline, as described herein below, on the plurality of reads of genetic data as well as on other data derived therefrom. For instance, each subset of the hardwired digital logic circuits may be in a wired configuration to perform the one or more steps in the analysis pipeline. Additionally, where the integrated circuit is an FPGA, such steps in the sequence and/or further analysis process may involve the partial reconfiguration of the FPGA during the analysis process.

Particularly, the set of processing engines may include a mapping module, e.g., in a wired configuration, to access, according to at least some of the sequence of nucleotides in a read of the plurality of reads, the index of the one or more genetic reference sequences, from the memory via the memory interface, so as to map the read to one or more segments of the one or more genetic reference sequences based on the index. Additionally, the set of processing engines may include an alignment module in the wired configuration to access the one or more genetic reference sequences from the memory via the memory interface to align the read, e.g., the mapped read, to one or more positions in the one or more segments of the one or more genetic reference sequences, e.g., as received from the mapping module and/or stored in the memory.

Further, the set of processing engines may include a sorting module so as to sort each aligned read according to the one or more positions in the one or more genetic reference sequences. Furthermore, the set of processing engines may include a variant call module, such as for processing the mapped, aligned, and/or sorted reads, such as with respect to a reference genome, to thereby produce an HMM readout and/or variant call file for use with and/or detailing the variations between the sequenced genetic data and the reference genomic reference data. In various instances, one or more of the plurality of physical electrical interconnects may include an output from the integrated circuit for communicating result data from the mapping module and/or the alignment and/or sorting and/or variant call modules.

Particularly, with respect to the mapping module, in various embodiments, a system for executing a mapping analysis pipeline on a plurality of reads of genetic data using an index of genetic reference data is provided. In various instances, the genetic sequence, e.g., read, and/or the genetic reference data may be represented by a sequence of nucleotides, which may be stored in a memory of the system. The mapping module may be included within the integrated circuit and may be formed of a set of pre-configured and/or hardwired digital logic circuits that are interconnected by a plurality of physical electrical interconnects, which physical electrical interconnects may include a memory interface for allowing the integrated circuit to access the memory. In more particular embodiments, the hardwired digital logic circuits may be arranged as a set of processing engines, such as where each processing engine is formed of a subset of the hardwired digital logic circuits to perform one or more steps in the sequence analysis pipeline on the plurality of reads of genomic data.

For instance, in one embodiment, the set of processing engines may include a mapping module in a hardwired configuration, where the mapping module, and/or one or more processing engines thereof is configured for receiving a read of genomic data, such as via one or more of a plurality of physical electrical interconnects, and for extracting a portion of the read in such a manner as to generate a seed therefrom. In such an instance, the read may be represented by a sequence of nucleotides, and the seed may represent a subset of the sequence of nucleotides represented by the read. The mapping module may include or be connectable to a memory that includes one or more of the reads, one or more of the seeds of the reads, at least a portion of one or more of the reference genomes, and/or one or more indexes, such an index built from the one or more reference genomes. In certain instances, a processing engine of the mapping module employ the seed and the index to calculate an address within the index based on the seed.

Once an address has been calculated or otherwise derived and/or stored, such as in an onboard or offboard memory, the address may be accessed in the index in the memory so as to receive a record from the address, such as a record representing position information in the genetic reference sequence. This position information may then be used to determine one or more matching positions from the read to the genetic reference sequence based on the record. Then at least one of the matching positions may be output to the memory via the memory interface.

In another embodiment, a set of the processing engines may include an alignment module, such as in a pre-configured and/or hardwired configuration. In this instance, one or more of the processing engines may be configured to receive one or more of the mapped positions for the read data via one or more of the plurality of physical electrical interconnects. Then the memory (internal or external) may be accessed for each mapped position to retrieve a segment of the reference sequence/genome corresponding to the mapped position. An alignment of the read to each retrieved reference segment may be calculated along with a score for the alignment. Once calculated, at least one best-scoring alignment of the read may be selected and output. In various instances, the alignment module may also implement a dynamic programming algorithm when calculating the alignment, such as one or more of a Smith-Waterman algorithm, e.g., with linear or affine gap scoring, a gapped alignment algorithm, and/or a gapless alignment algorithm. In particular instances, the calculating of the alignment may include first performing a gapless alignment to each reference segment, and based on the gapless alignment results, selecting reference segments with which to further perform gapped alignments.

In various embodiments, a variant call module may be provided for performing improved variant call functions that when implemented in one or both of software and/or hardware configurations generate superior processing speed, better processed result accuracy, and enhanced overall efficiency than the methods, devices, and systems currently known in the art. Specifically, in one aspect, improved methods for performing variant call operations in software and/or in hardware, such as for performing one or more HMM operations on genetic sequence data, are provided. In another aspect, novel devices including an integrated circuit for performing such improved variant call operations, where at least a portion of the variant call operation is implemented in hardware, are provided.

Accordingly, in various instances, the methods disclosed herein may include mapping, by a first subset of hardwired and/or quantum digital logic circuits, a plurality of reads to one or more segments of one or more genetic reference sequences. Additionally, the methods may include accessing, by the integrated and/or quantum circuits, e.g., by one or more of the plurality of physical electrical interconnects, from the memory or a cache associated therewith, one or more of the mapped reads and/or one or more of the genetic reference sequences; and aligning, by a second subset of the hardwired and/or quantum digital logic circuits, the plurality of mapped reads to the one or more segments of the one or more genetic reference sequences.

In various embodiments, the method may additionally include accessing, by the integrated and/or quantum circuit, e.g., by one or more of the plurality of physical electrical interconnects from a memory or a cache associated therewith, the aligned plurality of reads. In such an instance the method may include sorting, by a third subset of the hardwired and/or quantum digital logic circuits, the aligned plurality of reads according to their positions in the one or more genetic reference sequences. In certain instances, the method may further include outputting, such as by one or more of the plurality of physical electrical interconnects of the integrated and/or quantum circuit, result data from the mapping and/or the aligning and/or the sorting, such as where the result data includes positions of the mapped and/or aligned and/or sorted plurality of reads.

In some instances, the method may additionally include using the obtained result data, such as by a further subset of the hardwired and/or quantum digital logic circuits, for the purpose of determining how the mapped, aligned, and/or sorted data, derived from the subject's sequenced genetic sample, differs from a reference sequence, so as to produce a variant call file delineating the genetic differences between the two samples. Accordingly, in various embodiments, the method may further include accessing, by the integrated and/or quantum circuit, e.g., by one or more of the plurality of physical electrical interconnects from a memory or a cache associated therewith, the mapped and/or aligned and/or sorted plurality of reads. In such an instance the method may include performing a variant call function, e.g., an HMM or paired HMM operation, on the accessed reads, by a third or fourth subset of the hardwired and/or quantum digital logic circuits, so as to produce a variant call file detailing how the mapped, aligned, and/or sorted reads vary from that of one or more reference, e.g., haplotype, sequences.

Accordingly, in accordance with particular aspects of the disclosure, presented herein is a compact hardware, e.g., chip based, or quantum accelerated platform for performing secondary and/or tertiary analyses on genetic and/or genomic sequencing data. Particularly, a platform or pipeline of hardwired and/or quantum digital logic circuits that have specifically been designed for performing secondary and/or tertiary genetic analysis, such as on sequenced genetic data, or genomic data derived therefrom, is provided. Particularly, a set of hardwired digital and/or quantum logic circuits, which may be arranged as a set of processing engines, may be provided, such as where the processing engines may be present in a preconfigured and/or hardwired and/or quantum configuration on a processing platform of the disclosure, and may be specifically designed for performing secondary mapping and/or aligning and/or variant call operations related to genetic analysis on DNA and/or RNA data, and/or may be specifically designed for performing other tertiary processing on the results data.

In particular instances, the present devices, systems, and methods of employing the same in the performance of one or more genomics and/or bioinformatics secondary and/or tertiary processing protocols, have been optimized so as to deliver an improvement in processing speed that is orders of magnitude faster than standard secondary processing pipelines that are implemented in software. Additionally, the pipelines and/or components thereof as set forth herein provide better sensitivity and accuracy on a wide range of sequence derived data sets for the purposes of genomics and bioinformatics processing. In various instances, one or more of these operations may be performed on by an integrated circuit that is part of or configured as a general purpose central processing unit and/or a graphics processing unit and/or a quantum processing unit.

For example, genomics and bioinformatics are fields concerned with the application of information technology and computer science to the field of genetics and/or molecular biology. In particular, bioinformatics techniques can be applied to process and analyze various genetic and/or genomic data, such as from an individual, so as to determine qualitative and quantitative information about that data that can then be used by various practitioners in the development of prophylactic, therapeutic, and/or diagnostic methods for preventing, treating, ameliorating, and/or at least identifying diseased states and/or their potential, and thus, improving the safety, quality, and effectiveness of health care on an individualized level. Hence, because of their focus on advancing personalized healthcare, genomics and bioinformatics fields promote individualized healthcare that is proactive, instead of reactive, and this gives the subject in need of treatment the opportunity to become more involved in their own wellness. An advantage of employing the genetics, genomics, and/or bioinformatics technologies disclosed herein is that the qualitative and/or quantitative analyses of molecular biological, e.g., genetic, data can be performed on a broader range of sample sets at a much higher rate of speed and often times more accurately, thus expediting the emergence of a personalized healthcare system. Particularly, in various embodiments, the genomics and/or bioinformatics related tasks may form a genomics pipeline that includes one or more of a micro-array analysis pipeline, a genome, e.g., whole genome analysis pipeline, genotyping analysis pipeline, exome analysis pipeline, epigenome analysis pipeline, metagenome analysis pipeline, microbiome analysis pipeline, genotyping analysis pipeline, including joint genotyping, variants analysis pipelines, including structural variants, somatic variants, and GATK, as well as RNA sequencing and other genetic analyses pipelines.

Accordingly, to make use of these advantages there exists enhanced and more accurate software implementations for performing one or a series of such bioinformatics based analytical techniques, such as for deployment by a general purpose CPU and/or GPU and/or may be implemented in one or more quantum circuits of a quantum processing platform. However, common characteristics of traditionally configured software based bioinformatics methods and systems is that they are labor intensive, take a long time to execute on such general purpose processors, and are prone to errors. Therefore, bioinformatics systems as implemented herein that could perform these algorithms, such as implemented in software by a CPU and/or GPU of quantum processing unit in a less labor and/or processing intensive manner with a greater percentage accuracy would be useful.

Such implementations have been developed and are presented herein, such as where the genomics and/or bioinformatics analyses are performed by optimized software run on a CPU and/or GPU and/or quantum computer in a system that makes use of the genetic sequence data derived by the processing units and/or integrated circuits of the disclosure. Further, it is to be noted that the cost of analyzing, storing, and sharing this raw digital data has far outpaced the cost of producing it. Accordingly, also presented herein are "just in time" storage and/or retrieval methods that optimize the storage of such data in a manner that substitutes the speed of regenerating the data in exchange for the cost of storing such data collectively. Hence, the data generation, analysis, and "just in time" or "JIT" storage methods presented herein solve a key bottleneck that is a long felt but unmet obstacle standing between the ever-growing raw data generation and storage and the real medical insight being sought from it.

Presented herein, therefore, are systems, apparatuses, and methods for implementing genomics and/or bioinformatic protocols or portions thereof, such as for performing one or more functions for analyzing genomic data, for instance, on one or both of an integrated circuit, such as on a hardware processing platform, and a general purpose processor, such as for performing one or more bioanalytic operations in software and/or on firmware. For example, as set forth herein below, in various implementations, an integrated circuit and/or quantum circuit is provided so as to accelerate one or more processes in a primary, secondary, and/or tertiary processing platform. In various instances, the integrated circuit may be employed in performing genetic analytic related tasks, such as mapping, aligning, variant calling, compressing, decompressing, and the like, in an accelerated manner, and as such the integrated circuit may include a hardware accelerated configuration. Additionally, in various instances, an integrated and/or quantum circuit may be provided such as where the circuit is part of a processing unit that is configured for performing one or more genomics and/or bioinformatics protocols on the generated mapped and/or aligned and/or variant called data.

Particularly, in a first embodiment, a first integrated circuit may be formed of an FPGA, ASIC, and/or sASIC that is coupled to or otherwise attached to the motherboard and configured, or in the case of an FPGA may be programmable by firmware to be configured, as a set of hardwired digital logic circuits that are adapted to perform at least a first set of sequence analysis functions in a genomics analysis pipeline, such as where the integrated circuit is configured as described herein above to include one or more digital logic circuits that are arranged as a set of processing engines, which are adapted to perform one or more steps in a mapping, aligning, and/or variant calling operation on the genetic data so as to produce sequence analysis results data. The first integrated circuit may further include an output, e.g., formed of a plurality of physical electrical interconnects, such as for communicating the result data from the mapping and/or the alignment and/or other procedures to the memory.

Additionally, a second integrated and/or quantum circuit may be included, coupled to or otherwise attached to the motherboard, and in communication with the memory via a communications interface. The second integrated and/or quantum circuit may be formed as a central processing unit (CPU) or graphics processing unit (GPU) or quantum processing unit (QPU) that is configured for receiving the mapped and/or aligned and/or variant called sequence analysis result data and may be adapted to be responsive to one or more software algorithms that are configured to instruct the CPU or GPU to perform one or more genomics and/or bioinformatics functions of the genomic analysis pipeline on the mapped, aligned, and/or variant called sequence analysis result data. Specifically, the genomics and/or bioinformatics related tasks may form a genomics analysis pipeline that includes one or more of a micro-array analysis, a genome pipeline, e.g., whole genome analysis pipeline, genotyping analysis pipeline, exome analysis pipeline, epigenome analysis pipeline, metagenome analysis pipeline, microbiome analysis pipeline, genotyping analyses pipelines, including joint genotyping, variants analyses pipelines, including structural variants, somatic variants, and GATK, as well as RNA sequencing analysis pipeline and other genetic analyses pipelines.

For instance, in one embodiment, the CPU and/or GPU and/or QPU of the second integrated circuit may include software that is configured for arranging the genome analysis pipeline for executing a whole genome analysis pipeline, such as a whole genome analysis pipeline that includes one or more of genome-wide variation analysis, whole-exome DNA analysis, whole transcriptome RNA analysis, gene function analysis, protein function analysis, protein binding analysis, quantitative gene analysis, and/or a gene assembly analysis. In certain instances, the whole genome analysis pipeline may be performed for the purposes of one or more of ancestry analysis, personal medical history analysis, disease diagnostics, drug discovery, and/or protein profiling. In a particular instance, the whole genome analysis pipeline is performed for the purposes of oncology analysis. In various instances, the results of this data may be made available, e.g. globally, throughout the system.

In various instances, the CPU and/or GPU and/or a quantum processing unit (QPU) of the second integrated and/or quantum circuit may include software that is configured for arranging the genome analysis pipeline for executing a genotyping analysis, such as a genotyping analysis including joint genotyping. For instance, the joint genotyping analysis may be performed using a Bayesian probability calculation, such as a Bayesian probability calculation that results in an absolute probability that a given determined genotype is a true genotype. In other instances, the software may be configured for performing a metagenome analysis so as to produce metagenome result data that may in turn be employed in the performance of a microbiome analysis.

In certain instances, the first and/or second integrated circuit and/or the memory may be housed on an expansion card, such as a peripheral component interconnect (PCI) card. For instance, in various embodiments, one or more of the integrated circuits may be one or more chips coupled to a PCIe card or otherwise associated with the motherboard. In various instances, the integrated and/or quantum circuit(s) and/or chip(s) may be a component within a sequencer or computer, or server, such as part of a server farm. In particular embodiments, the integrated and/or quantum circuit(s) and/or expansion card(s) and/or computer(s) and/or server(s) may be accessible via the internet, e.g., cloud.

Further, in some instances, the memory may be a volatile random access memory (RAM), e.g., a direct access memory (DRAM). Particularly, in various embodiments, the memory may include at least two memories, such as a first memory that is an HMEM, e.g., for storing the reference haplotype sequence data, and a second memory that is an RMEM, e.g., for storing the read of genomic sequence data. In particular instances, each of the two memories may include a write port and/or a read port, such as where the write port and the read port each accessing a separate clock. Additionally, each of the two memories may include a flip-flop configuration for storing a multiplicity of genetic sequence and/or processing result data.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

BRIEF DESCRIPTION OF THE FIGURES

The accompanying drawings, which are incorporated in and constitute a part of this specification, show certain aspects of the subject matter disclosed herein and, together with the description, help explain some of the principles associated with the disclosed implementations.

FIG. 1D depicts a virtual array of the results of the sequencing performed on the reads of FIGS. 1 and 2, where the reads are set forth in an output column by column order.

FIG. 1E depicts the method by which the transposition of the outcome reads from column by column order to row by row read order may be implemented.

FIG. 1F depicts the transposition of the outcome reads from column by column order, to row by row read order.

FIG. 11 depicts Log domain M, I, D state calculation details.

FIG. 17A presents a method for performing a multi-region joint detection pre-processing procedure.

FIG. 17B presents an exemplary method for computing a connection matrix such as in the pre-processing procedure of FIG. 17A.

FIG. 26 sets forth a probability table in accordance with the disclosed herein.

FIG. 28 represents a selection of candidate solutions for the joint pile up of FIG. 25.

FIG. 29 represents a further selection of candidate solutions for the pile up of FIG. 28, after a pruning function has been performed.

FIG. 30 represents the final candidates of FIG. 28, and their associated probabilities, after the performance of a MRJD function.

FIG. 32 illustrates the same results of FIG. 31 displayed as a function of the sequence similarity of the references.

FIG. 43B provides an exemplary tertiary processing epigenetics analysis for execution by the methods and devices of the system herein.

DETAILED DESCRIPTION OF THE DISCLOSURE

Figure 1A:
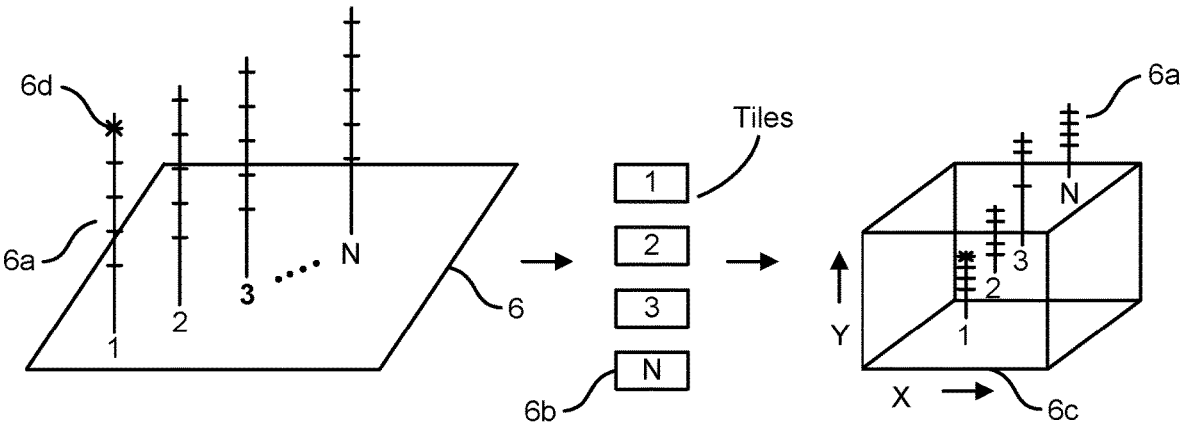
FIG. 1A depicts a sequencing platform with a plurality of genetic samples thereon, a plurality of exemplary tiles are also depicted, as well as a three-dimensional representation of the sequenced reads.

As summarized above, the present disclosure is directed to devices, systems, and methods for employing the same in the performance of one or more genomics and/or bioinformatics protocols, such as a mapping, aligning, sorting, and/or variant call protocol on data generated through a primary processing procedure, such as on genetic sequence data. For instance, in various aspects, the devices, systems, and methods herein provided are configured for performing secondary analysis protocols on genetic data, such as data generated by the sequencing of RNA and/or DNA, e.g., by a Next Gen Sequencer ("NGS"). In particular embodiments, one or more secondary processing pipelines for processing genetic sequence data is provided, such as where the pipelines, and/or individual elements thereof, may be implemented in software, hardware, or a combination thereof in a distributed and/or an optimized fashion so as to deliver superior sensitivity and improved accuracy on a wider range of sequence derived data than is currently available in the art. Additionally, as summarized above, the present disclosure is directed to devices, systems, and methods for employing the same in the performance of one or more genomics and/or bioinformatics tertiary protocols, such as a micro-array analysis protocol, a genome, e.g., whole genome analysis protocol, genotyping analysis protocol, exome analysis protocol, epigenome analysis protocol, metagenome analysis protocol, microbiome analysis protocol, genotyping analysis protocol, including joint genotyping, variants analysis protocols, including structural variants, somatic variants, and GATK, as well as RNA sequencing protocols and other genetic analyses protocols such as on mapped, aligned, and/or other genetic sequence data, such as employing one or more variant call files.

Accordingly, provided herein are software and/or hardware e.g., chip based, accelerated platform analysis technologies for performing secondary and/or tertiary analysis of DNA/RNA sequencing data. More particularly, a platform, or pipeline, of processing engines, such as in a software implemented and/or hardwired configuration, which have specifically been designed for performing secondary genetic analysis, e.g., mapping, aligning, sorting, and/or variant calling; and/or may be specifically designed for performing tertiary genetic analysis, such as a micro-array analysis, a genome, e.g., whole genome analysis, genotyping analysis, exome analysis, epigenome analysis, metagenome analysis, microbiome analysis, genotyping analysis, including joint genotyping analysis, variants analysis, including structural variants analysis, somatic variants analysis, and GATK analysis, as well as RNA sequencing analysis and other genetic analysis, such as with respect to genetic based sequencing data, which may have been generated in an optimized format that delivers an improvement in processing speed that is magnitudes faster than standard pipelines that are implemented in known software alone. Additionally, the pipelines presented herein provide better sensitivity and accuracy on a wide range of sequence derived data sets, such as on nucleic acid or protein derived sequences.

As indicated above, in various instances, it is a goal of bioinformatics processing to determine individual genomes and/or protein sequences of people, which determinations may be used in gene discovery protocols as well as for prophylaxis and/or therapeutic regimes to better enhance the likelihood of each particular person and human kind as a whole. Further, knowledge of an individual's genome and/or protein compellation may be used such as in drug discovery and/or FDA trials to better predict with particularity which, if any, drugs will be likely to work on an individual and/or which would be likely to have deleterious side effects, such as by analyzing the individual's genome and/or a protein profile derived therefrom and comparing the same with predicted biological response from such drug administration.

Such bioinformatics processing usually involves three well defined, but typically separate phases of information processing. The first phase, termed primary processing, involves DNA/RNA sequencing, where a subject's DNA and/or RNA is obtained and subjected to various processes whereby the subject's genetic code is converted to a machine-readable digital code, e.g., a FASTQ file. The second phase, termed secondary processing, involves using the subject's generated digital genetic code for the determination of the individual's genetic makeup, e.g., determining the individual's genomic nucleotide sequence. And the third phase, termed tertiary processing, involves performing one or more analyses on the subject's genetic makeup so as to determine therapeutically useful information therefrom.

Accordingly, once a subject's genetic code is sequenced, such as by a NextGen sequencer, so as to produce a machine readable digital representation of the subject's genetic code, e.g., in a FASTQ and/or BCL file format, it may be useful to further process the digitally encoded genetic sequence data obtained from the sequencer and/or sequencing protocol, such as by subjecting digitally represented data to secondary processing. This secondary processing, for instance, can be used to map and/or align and/or otherwise assemble an entire genomic and/or protein profile of an individual, such as where the individual's entire genetic makeup is determined, for instance, where each and every nucleotide of each and every chromosome is determined in sequential order such that the composition of the individual's entire genome has been identified. In such processing, the genome of the individual may be assembled such as by comparison to a reference genome, such as a reference standard, e.g., one or more genomes obtained from the human genome project or the like, so as to determine how the individual's genetic makeup differs from that of the referent(s). This process is commonly known as variant calling. As the difference between the DNA of any one person to another is 1 in 1,000 base pairs, such a variant calling process can be very labor and time intensive, requiring many steps that may need to be performed one after the other and/or simultaneously, such as in a pipeline, so to analyze the subject's genomic data and determine how that genetic sequence differs from a given reference.

In performing a secondary analysis pipeline, such as for generating a variant call file for a given query sequence of an individual subject; a genetic sample, e.g., DNA, RNA, protein sample, or the like may be obtained, form the subject. The subject's DNA/RNA may then be sequenced, e.g., by a NextGen Sequencer (NGS) and/or a sequencer-on-a-chip technology, e.g., in a primary processing step, so as to produce a multiplicity of read sequence segments ("reads") covering all or a portion of the individual's genome, such as in an oversampled manner. The end product generated by the sequencing device may be a collection of short sequences, e.g., reads, that represent small segments of the subject's genome, e.g., short genetic sequences representing the individual's entire genome. As indicated, typically, the information represented by these reads may be an image file or in a digital format, such as in FASTQ, BCL, or other similar file format.

Particularly, in a typical secondary processing protocol, a subject's genetic makeup is assembled by comparison to a reference genome. This comparison involves the reconstruction of the individual's genome from millions upon millions of short read sequences and/or the comparison of the whole of the individual's DNA to an exemplary DNA sequence model. In a typical secondary processing protocol an image, FASTQ, and/or BCL file is received from the sequencer containing the raw sequenced read data. In order to compare the subject's genome to that of the standard reference genome, it needs to be determined where each of these reads map to the reference genome, such as how each is aligned with respect to one another, and/or how each read can also be sorted by chromosome order so as to determine at what position and in which chromosome each read belongs. One or more of these functions may take place prior to performing a variant call function on the entire full-length sequence, e.g., once assembled. Specifically, once it is determined where in the genome each read belongs, the full length genetic sequence may be determined, and then the differences between the subject's genetic code and that of the referent can be assessed.

For instance, reference based assembly in a typical secondary processing assembly protocol involves the comparison of sequenced genomic DNA/RNA of a subject to that of one or more standards, e.g., known reference sequences. Various mapping, aligning, sorting, and/or variant calling algorithms have been developed to help expedite these processes. These algorithms, therefore, may include some variation of one or more of: mapping, aligning, and/or sorting the millions of reads received from the image, FASTQ, and/or BCL file communicated by the sequencer, to determine where on each chromosome each particular read is located. It is noted that these processes may be implemented in software or hardware, such as by the methods and/or devices described in U.S. Pat. Nos. 9,014,989 and 9,235,680 both assigned to Edico Genome Corporation and incorporated by reference herein in their entireties. Often a common feature behind the functioning of these various algorithms and/or hardware implementations is their use of an index and/or an array to expedite their processing function.

For example, with respect to mapping, a large quantity, e.g., all, of the sequenced reads may be processed to determine the possible locations in the reference genome to which those reads could possibly align. One methodology that can be used for this purpose is to do a direct comparison of the read to the reference genome so as to find all the positions of matching. Another methodology is to employ a prefix or suffix array, or to build out a prefix or suffix tree, for the purpose of mapping the reads to various positions in the reference genome. A typical algorithm useful in performing such a function is a Burrows-Wheeler transform, which is used to map a selection of reads to a reference using a compression formula that compresses repeating sequences of data.

Additionally, an aligning function may be performed to determine out of all the possible locations a given read may map to on a genome, such as in those instances where a read may map to multiple positions in the genome, which is in fact the location from which it actually was derived, such as by being sequenced therefrom by the original sequencing protocol. This function may be performed on a number of the reads, e.g., mapped reads, of the genome and a string of ordered nucleotide bases representing a portion or the entire genetic sequence of the subject's DNA/RNA may be obtained. Along with the ordered genetic sequence a score may be given for each nucleotide in a given position, representing the likelihood that for any given nucleotide position, the nucleotide, e.g., "A", "C", "G", "T" (or "U"), predicted to be in that position is in fact the nucleotide that belongs in that assigned position. Typical algorithms for performing alignment functions include Needleman-Wunsch and Smith-Waterman algorithms. In either case, these algorithms perform sequence alignments between a string of the subject's query genomic sequence and a string of the reference genomic sequence whereby instead of comparing the entire genomic sequences, one with the other, segments of a selection of possible lengths are compared.

Once the reads have been assigned a position, such as relative to the reference genome, which may include identifying to which chromosome the read belongs and/or its offset from the beginning of that chromosome, the reads may be sorted by position. This may enable downstream analyses to take advantage of the oversampling procedures described herein. All of the reads that overlap a given position in the genome will be adjacent to each other after sorting and they can be organized into a pileup and readily examined to determine if the majority of them agree with the reference value or not. If they do not, a variant can be flagged.

For instance, in various embodiments, the methods of the disclosure may include generating a variant call file (VCF) identifying one or more, e.g., all, of the genetic variants in the individual who's DNA/RNA were sequenced, e.g., relevant to one or more reference genomes. For instance, once the actual sample genome is known and compared to the reference genome, the variations between the two can be determined, and a list of all the variations/deviations between the reference genome(s) and the sample genome may be called out, e.g., a variant call file may be produced. Particularly, in one aspect, a variant call file containing all the variations of the subject's genetic sequence to the reference sequence(s) may be generated.

Accordingly, a useful element of the methods and systems disclosed herein is a genomic reference from which mapping, aligning, variant calling, and other such processes of the system may be performed, such as in comparison to a referent. Typically, such maping, aligning, variant calling, and/or the like may be performed with respect to a single human reference, e.g., an "ideal reference" that is a composite of genetic code from a variety of different sources, and as such the typical reference genome doesn't match any single person. Such secondary analysis leverages the fact that most people have a genetic makeup that is very similar to the reference. Hence, although it is not perfect, the typical reference genome is useful in helping to map and align reads to the right place in a person's genome based on their general similarity with the reference.

The typical reference is also useful with respect to forming the pile ups, as discussed herein, of all the reads over their given mapped and/or aligned place(s) in the reference, which pileups thereby allow a greater amount of evidence to be considered when making a variant call at any given position. Particularly, the reference allows one to consider prior probabilities of what particular base at a particular position of a given read should be, as compared to the reference, when determining what that base actually is with respect to the read. Hence, use of a reference allows for the assumption that the identity of any base at any position in the reference is what is the most likely content of that base of the read that is present in the human genome at that position. Accordingly, secondary analysis is usually performed in a manner so as to figure out how any given individual differs from the typical reference.

However, although employing a single reference is useful for determining the identity of any given base pair of a read of a subject, but in some instances, there may be significant differences between a given subject and a typical reference that is used when performing secondary processing of that particular subject's DNA/RNA. Alternatively, there are some places in the typical reference that are problematic for a multiplicity of people, and in certain instances, there are significant differences from the reference that occur commonly in various parts of the population.

For instance, in some instances, there may be individual variants, e.g., single nucleotide polymorphisms (SNPs), which occur in some significant portion of the population, such as 3% or 5% or 10% of the population, or more ten percent of the population. Particularly, in various instances, for any given individual there may be one or more segments of various subjects genome that has been replaced by another sequence of a similar or different length, with different content, of course. Further complicating matters is that this genetic re-arrangement may occur in a single copy of the chromosome. Hence, at one haplotype the subject's DNA may be similar to that of the reference, while at the other haplotype, the subject's DNA may be vastly different from that of the reference.

Consequently, in some places a subject's DNA may be identical to the standard reference, and in some places dramatically different from the standard reference. In some instances, such genetic variations may occur in predictable positions in the genome, and in particular geographical places. In other instances, the variants may occur in a much larger percent of the population, such as 80% of the population. In such an instance, the reference genome may actually show the less common content at a given region of the genome. Hence, in certain instances, there may be large sections of the reference genome, e.g., which might be hundreds or thousands or even millions of basis long, that are significantly different from a large sample set of the population. The outcome, therefore, is that if only the standard reference is employed in performing a secondary analysis process then the accuracy of such secondary analysis, e.g., mapping, aligning, and/or variant calling may not be as accurate is it could be.

It will of course will be better for those whose genome most closely match that of the reference, versus those whose genome has significant variations therefrom. The accuracy of secondary, and consequently, tertiary processing may be improved, therefore, if a reference being employed in the analyses is better fitted to the subject's whose DNA is being processed, such as more closely aligned with that of their family members, ancestry, and the like. There are a multiplicity of methods and/or strategies that may be employed so as to overcome these potential inefficiencies of performing secondary processing using a standard reference genome.

For instance, a first traditional standard, e.g., linear, reference genome may be employed for determining the genomic identity of one strand of a subject's DNA, e.g., one haplotype, and a second traditional, or non-traditional, reference genome may be employed for determining the genomic identity of the other strand of the subject's DNA. Hence, there may be one reference sequence for chromosome one, and another reference sequence for chromosome two, where, in certain instances, the reference sequences may be generated and/or otherwise employed dynamically, e.g., based on auxiliary data, e.g., ancestry, of the subject or person. In such an instance, a first secondary processing procedure, e.g., mapping, alignment, and variant calling procedure, may be performed, e.g., based on a standard reference, and in a second processing procedure, a second reference genome, e.g., one that is ancestry specific, may be employed in the secondary processing procedure(s).

This secondary processing procedure may be performed with respect to the entire genome of the subject, or for one or more identified regions thereof. For example, where a region by region secondary processing procedure is being performed, various genetic markers may be used to identify the regions for more careful processing. Particularly, once a region of variation is determined, for a subject's genome, a given secondary reference may then be employed by the system for the performance of a secondary processing procedure with respect to that one or more segments.

In a manner such as this a plurality of references may be used, where each reference is selected to enhance the accuracy and/or efficiency of the secondary processing procedure being performed. In particular instances, therefore, one cultural reference, e.g., a European or African reference, may be employed for processing a given portion of a subject's DNA, while another cultural reference, e.g., one or more Asian, Indian, South American reference, may be employed for processing another given portion of the subject's DNA. Particularly, a database storing a multiplicity of references, e.g., specific to given populations and/or geographies, may be employed, such that at any given time the system may dynamically switch between what reference is to be employed for determining any given segment of a subject's DNA.

Hence, in a particular use instance, a given long segment of a subject's DNA, e.g., 1 million base pairs, may be analyzed employing a generated or standard European reference, and another long segment of DNA, e.g., 2 million base pairs, may be analyzed by a generated or standard other, e.g., North American, reference. Particularly, a statistical analysis may be performed, e.g., to determine the percentage homology of any given portion of a genome to a particular reference standard, and which of a selection of reference standards is to be employed may be determined based on the outcome of the statistical analysis.

More particularly, the artificial intelligence module, discussed herein below, may be employed to determine the most relevant reference to use for performing secondary analysis on any given region of a subject's DNA, e.g., so as to employ the reference that fits best. In various instances, a plurality of these standards may be mixed and matched in any logical order, so as to produce a combined, e.g., Chimeric, reference, which may be built of segments from a variety of sources.

As indicated, this may be performed in a haploid or diploid manner, such as where the reference is applied to only one copy, e.g., strand, of the DNA, or to both copies of the DNA. This may be complicated by the fact that different strands of DNA of a subject from different sources may have different splicing patterns. These patterns, however, may be used as a map by which to differentially and/or dynamically employ reference genomes. Such splicing patterns may be based on ancestral genetic background. And, in some instances, based on these differential slice patterns, a chimeric reference genome, e.g., including different culturally relevant reference genomes.

Likewise, these references may then be used as a guide for the mapping, aligning, and/or variant calling procedures, such that use of a non-traditional, e.g., other standard or chimeric, reference genome will give a closer match to the actual genome of the user, and therefore will provide for a more accurate mapping, aligning, and/or variant calling of the subject's genomic sequence. Thus, the overall analysis will have a higher probability of accuracy.

As indicated, the reference genome to be employed may be dynamic, and may be built, e.g., on the fly, to specifically, and more closely represent the genome of the subject. For instance, in various instances, the chimeric reference genome may be assembled, such as in a De Bruijn graph format, where variations from the standard reference may be represented by bubbles in the graph, which bubbles may refer to various mapped coordinates in the standard reference. Particularly, a graph based reference may be generated, such that wherever a variation in the reference is to occur, the change from the standard may be represented as a bubble in a graph.

So, where a newly built, e.g., chimeric, reference is used, those regions where the chimeric reference matches with the standard reference, e.g., the backbone, may be represented as a straight line, but where the chimeric reference includes a differential segment, e.g., a branch, this difference may be represented as a bubble in the standard reference, e.g., where the bubble represents the different base pairs from the reference. The bubbles may be any length, and one region of bubbles in the chimeric reference need not be the same length as the other. Hence, once the reference genome is assembled, it may be backtraced and/or otherwise mapped to the traditional reference to track the manner in which the dynamic, e.g., chimeric, reference differs from the traditional reference.

In such an instance, a local assembly reference may be generated so as to accord with the specific ancestry and/or culture of the subject, such as where the bubble regions represent ancestral differences from a standard reference. In a manner such as this, a dynamic reference may be generated where each reference employed is specific to the individual, and consequently, no two references will be alike.

Another manner in which a dynamic reference may be built and/or employed is to build a chimeric reference based on known population variations, e.g., common for the detected ancestry and/or known different segment, where the standard reference is changed in various regions to include known segments of variations, e.g., known ancestral and/or cultural variations, which variations may then be annotated so as to build a map of the chimeric reference. In such an instance, when used, it may be known which reference segment from which source is being used when performing a mapping and/or aligning operation on the subject's DNA and/or for determining how that DNA differs from the reference.

For instance, once it has been determined for a subject, which part of their DNA comes from which part of their ancestry, a reference coherent with that ancestry, over the identified sequence length, may be employed as at least a segment of the chimeric reference. For example, a reference genome may be built based on known variations in human populations, such as based on geography, culture, ancestry, etc., such as where common alleles are known and may be used in producing a chimeric reference.

Specifically, where a sequence includes a plurality of SNPs in a row, a certain part of the population may have a certain order of the combination, and a certain other part of the population may have a different order of the combination, these variations may be represented as either annotations or as bubbles, such as in a De Bruijn graph format. These variations may be representative of different haplotypes of the population, where such common variations from the standard reference may be coded and represented as bubbles or annotations in the reference, e.g., graph, of variable lengths. In such an instance, typical variant callers will not distinguish between these differences, and will not be able to resolve this area of the genome.

However, using the differential reference genome of the system, these regions may be more accurately resolved. In such an instance, it might be more useful to represent these variations as bubble instead of annotations as individual SNPs so that the difference is clear, since the SNPs are near each other or otherwise densely spaced. Hence, there are advantages to having bubbles, even longer bubbles to represent such variations. Consequently, the complete reference need not be non-standard, in some instances, only various segments need be swapped out, e.g., edited and annotated, so as to form the chimeric reference. Specifically, in certain instances, the differential segments need not be absolutely changed, the change may be made optional, e.g., variable, depending on how the system determines which reference code, traditional or variable, in which circumstances, any of which may be implemented in the hardwired configurations disclosed herein.

In such a manner, for any variation in the reference, e.g., at any given nucleotide position, there may be a variation at that position between one nucleotide and another, the absolute determination of which variation depends on which reference is to be employed, and in certain instances, may be determined on the fly, such as during the analysis process. For instance, with respect to one reference genome, such as a dominant reference that matches a large percentage, e.g., 75% of the population, the dominant reference may indicate an "A" at a given position, while a sub-dominant reference, which may match a smaller percentage of the population, e.g. 25%, may differ from the dominant reference by having a "T" at that particular position. Hence, when employing only the dominant reference, a "non-match" may occur, but when using the non-dominant reference, a match may occur. Consequently, employing a plurality of references, or a chimeric reference, may lead to better accuracy.

In various instances, this known variability may simply be flagged or annotated as being a known variation in the population. Specifically, in various instances, these variables may be annotated by one or more flags so as to demarcate regions of variability within the reference. This is especially useful for determining one or more SNPs. However, in various instances, this may lead to another problem, such as where there may be three SNPs in a row, such as an "A" "A" "A", where at each position a known variable may be present and flagged, such as where the first "A" may alternatively be a "C", the second may be "T", and the third variable may alternatively be a "G". In such an instance, these three bases could be flagged as having three independent variables, but in some instances, each variation may not represent an independent SNP, but may actually be a more common haplotype in the population. Hence, the first haplotype may represent an "AAA" sequence, and the second haplotype may represent an "CTG," in which case these variations do not sort randomly, but rather collectively. That is part of the population has an "AAA" haplotype, while another part has a "CTG" haplotype.

In such instances, rather than flag each base individually as a variable, it may be useful to indicate the variation collectively as a "bubble" in the reference graph. Accordingly, in various instances, one or more segments of the genome may from haplotypes that are very similar or even identical to one another. As such, one or more reads in the genome of the subject may correspond to these one or more haplotypes in a primary or secondary assembly. Using a typical reference, such a read covering one of these haplotypes, in a conventional system, will not be mapped or aligned because it matches to too many different positions.

Specifically, in various instances, a read from a subject could correspond or match to one particular haplotype or another or may match to the primary assembly. In various instances, the read may match in all these places substantially equally well. The typical mapper, however, may not be able to resolve this difference. This situation may be overcome by having the mapper simply choose one position over another, in which case the odds of being correct decline with the number of potential matching positions, or it may map to any and all overlapping positions, but this may lead to a decrease in resolution.

Not mapping the sequence leaves viable information unaccounted for. One way to overcome this dilemma is for the system to use alternative references that show regions of variable haplotypes to which known reads containing the variant haplotype configurations may be mapped and aligned. As indicated above, a graph based mapper may be employed to indicate known alternative haplotype variations.

Specifically, in such an instance, the system may be configured to perform an alt aware type analysis. For instance, where various reads from a subject are identical or substantially identical, a branched graph of the reference may be generated to indicate the presence of alternative haplotypes, such as where each haplotype forms a different branch in the graph. The branch, or bubble, may be longer or shorter as is required to meet the length of the haplotype sequence. Additionally, the number of branches may vary based on the number of known variant haplotypes there are, which number may be in the tens, hundreds, or more.

The system, therefore, may be configured such that the mapper will understand that each branch represents a potential alternate haplotype, in comparison to the primary assembly backbone. Another way to overcome this dilemma is for the system to take such substantially identical read sequences and consider them as a "new" chromosome. Specifically, the system may be configured to treat an alternative haplotype, e.g., which alternative has significant difference from the traditionally employed reference, as an entirely new chromosome by which to examine potential candidate sequences.

Such a configuration is useful because it reduces false positives by assuming reads and/or the seeds thereof that don't match the primary reference may in fact align to the alternative haplotype. Particularly, without access to a reference including alternative haplotypes, such sequences may be force fit into a primary reference where they do not actually fit, resulting in a false positive, e.g., for a SNP, being called. However, in various instances, an alternate haplotype may have a sequence that is quite long, and in various instances, may have portions that match the primary reference. This may result in a read that appears to match both the primary and the haplotype reference.

In such a situation the read may not be able to be mapped, or it may simply be randomly assigned to one reference or the other, in which case coverage is reduced by 50%, assuming it has an equal chance of matching either reference, resulting in a lower MAPQ because the two references now become in competition for one another. However, the mapper may be configured so as to be Alt-aware, such as by employing a graph based backbone by which to place both references so as to not be in competition with one another with respect to determining best fit. Consequently, the mapper may be adapted such that it understands that a branch in the chain backbone represents an alternative sequence that is related to, e.g., branched off from, the graph of the primary assembly, as such the two references will not be in competition with one another.

One way to accomplish this functionality is to employ a hash table that is adapted so as to be populated with the substantially similar reads, such as in accordance with the hash table based mapper disclosed above, but in this instance, a virtual, e.g., chimeric, reference may be employed as the index. For instance, known variations, such as known alternate haplotype sequences, may be included within and/or employed as the index, and may be used in the population of the hash table, such as where the identified alternate haplotypes are entered into the hash table, e.g., as a virtual reference index, for seed mapping purposes.

In a manner such as this, matches in those positions may be identified, so as to improve the sensitivity of the system, and allowing reads that would otherwise remain unresolved, e.g., due to alternate haplotypes, to be resolved. Thus, the relationship of substantially identical haplotype reads, which may otherwise map to the primary assembly, but in actuality do not belong there, may be determined. Hence, the mapper may be configured to take responsibility for the sorting and finding of the best match in an alternate haplotype, and then remapping it to its identified, e.g., lift-over, position in the primary assembly graph. Hence, in various instances, the virtual reference may be employed as a graph and/or branch off of the reference, e.g., built upfront into the mapper configuration, and mapping may occur as described above for pre-fix and suffix tree mapping.

These methods provide for enhanced sensitivity and increased accuracy of the system overall, e.g., with respect to mapping and/or aligning, such as by minimizing false positive when substantially identical reads are not mapped, randomly mapped, or mapped to a multiplicity or wrong positions. Accordingly, in various embodiments, as described herein, a dynamic reference based system may be configured so as to employ a multiple graph branch configuration to map multiple substantially identical sequences that often occur non-randomly in a population, such as by employing a population significant and/or chimeric reference genome. And, as population studies increase, and more and more population related data is employed to build chimeric reference genomes, the accuracy of this system will continue to improve. Changes in the building of such graphs and/or tables may be informed by the changes in these population data, such as by accommodating ever increasing branches or bubbles in the graph and/or the number of alternate haplotypes available for consideration.

In various embodiments, a super dynamic reference may be generated, such as where the reference is specializing particularly to a specific community or family or event to the individual subject themselves, such as based on the subject's specific ancestry. Accordingly, in accordance with the methods disclosed herein, the system may be configured for performing a first analysis, employing a standard reference, and may further be configured for performing a second analysis employing a non-standard or modified, e.g., specialized, reference.

For instance, a first pass may be performed with regard to the standard reference, the subject's ancestry may be determined, or other markers, e.g., genetic markers, identified, haplotypic information may be identified, and/or a chimeric reference, e.g., including haplotype information, may be assembled, which chimeric reference may then be used within the system for purposes of mapping and/or aligning, such as when building the hash table.

Specifically, the chimeric assembly can but need not be built from scratch. Rather, identified haplotypes simply be inserted or otherwise substituted within the main reference backbone such as where their branch chain would indicate they be inserted, and this reference may then be inserted into the hash table for hashing. Hence, the chimeric reference may be built it not by completely replacing segments but by substituting segments of specific ancestral references, e.g., lift-over sequences, and listing or flagging them as alternate haplotypes for substitution into the primary reference.

For example, whether a seed of a read maps to a non-chimeric or chimeric, e.g., annotated, reference segment, this information may be included, such as by an appropriate annotation, within the hash table. Particularly, the information to be included within the hash table may indicate that the reference and/or read/seed/Kmer is annotated, that the reference is primary, and/or that one or more alt. haplotypes are included and/or matching, and/or that one or more lift-over groups, e.g., a lift-over seed group, are included, and the like. The actual candidates, therefore, may be in a lift-over group, where each lift-over group may be assigned a score, e.g., of the best representative, and the primary alignment, e.g., MAPQ, of this group may be reported, with respect to the difference in score from the second best group.

Specifically, it is useful to determine how the best lift-over group scored, as well as the distance in score from the second best lift-over group, which if the distance in score is substantial indicates a higher confidence of a correct match, regardless of how close the MAPQ scores are with regard to the sequence(s) in question matching the primary and alt. references. The system, therefore, may be configured to keep track of all of the annotations, to build the hash table, and to implement the hash function, score the results, as well as to map and align the best results, e.g., in a pipeline fashion, and thus, keeping the primary reference as a backbone in building a dynamic reference is an important feature for facilitating the extensive bookkeeping that allows the subsequent functions to work efficiently and with better accuracy.

In a manner such as this, two or more seeds that match each other reasonably well, but do not necessarily match the primary reference, need not be discarded if they match an alt. reference segment. In such an instance, they may be grouped together as alt. seeds.

Accordingly, the hash table may employ one or more of these techniques to recognize the various possible organizational structures of the seeds as well as their positions corresponding to either the ALT haplotype or primary assemblies, may organize them as such (e.g., Alt, Alt, Primary, etc.), and annotate them, e.g., some as being from the alt. and some from the primary assembly, etc., in the organizational structure of the hash table so as to ensure any relevant information they contain is not lost but is useable. In various instances, this information and/or organizational structure may be employed by the mapper and carried over to the aligner.

In manners such as these, one or more of SW, HMM, and/or variant calling may be performed against the primary/chimeric reference, without having to juggle between alternative references and/or competing coordinates thereof, resulting in a more normalized coverage, better sensitivity, and a clear MAPQ. Likewise, the output file may be in any suitable file format, such as a typical BAM and/or SAM file (e.g., an altBAM/SAM file), and/or may be modified to indicate the reference was chimeric and/or which haplotype sequences were implemented in the reference, e.g., an indication may be made for which haplotype was included within the primary reference and where, what coordinates (—such as a lift-over map), and which sequences mapped to the haplotype as compared to the primary reference, and the like. In various instances, it may then be useful to include this seed group as a lift-over position in the chimeric reference.

Specifically, in the context of using a graph based, dynamic reference, as herein disclosed, a more sensitive mapping and/or aligning may be performed resulting in better accuracy, where the graph indicates how the dynamic reference was stitched together and/or how the subject's genetic sequence mapped thereto. Further, as indicated in detail above, this dynamic reference may be implemented in optimized software, such as by performance by a CPU and/or GPU, or may be implemented in hardware, such as by an integrated circuit, e.g., FPGA, ASIC, or the like, of the disclosure.

Hence, in particular embodiments, a platform of technologies for performing genetic analyses are provided where the platform may include the performance of one or more of: mapping, aligning, sorting, local realignment, duplicate marking, base quality score recalibration, variant calling, compression, and/or decompression functions. For instance, in various aspects a pipeline may be provided wherein the pipeline includes performing one or more analytic functions, as described herein, on a genomic sequence of one or more individuals, such as data obtained in an image file and/or a digital, e.g., FASTQ or BCL, file format from an automated sequencer. A typical pipeline to be executed may include one or more of sequencing genetic material, such as a portion or an entire genome, of one or more individual subjects, which genetic material may include DNA, ssDNA, RNA, rRNA, tRNA, and the like, and/or in some instances the genetic material may represent coding or non-coding regions, such as exomes and/or episomes of the DNA. The pipeline may include one or more of performing an image processing procedure, a base calling and/or error correction operation, such as on the digitized genetic data, and/or may include one or more of performing a mapping, an alignment, and/or a sorting function on the genetic data. In certain instances, the pipeline may include performing one or more of a realignment, a deduplication, a base quality or score recalibration, a reduction and/or compression, and/or a decompression on the digitized genetic data. In certain instances the pipeline may include performing a variant calling operation, such as a Hidden Markov Model, on the genetic data.

Accordingly, in certain instances, the implementation of one or more of these platform functions is for the purpose of performing one or more of determining and/or reconstructing a subject's consensus genomic sequence, comparing a subject's genomic sequence to a referent sequence, e.g., a reference or model genetic sequence, determining the manner in which the subject's genomic DNA or RNA differs from a referent, e.g., variant calling, and/or for performing a tertiary analysis on the subject's genomic sequence, such as for genome-wide variation analysis, gene function analysis, protein function analysis, e.g., protein binding analysis, quantitative and/or assembly analysis of genomes and/or transcriptomes, as well as for various diagnostic, and/or a prophylactic and/or therapeutic evaluation analyses.

As indicated above, in one aspect one or more of these platform functions, e.g., mapping, aligning, sorting, realignment, duplicate marking, base quality score recalibration, variant calling, compression, and/or decompression functions is configured for implementation in software. In some aspects, one or more of these platform functions, e.g., mapping, aligning, sorting, local realignment, duplicate marking, base quality score recalibration, decompression, variant calling, compression, and/or decompression functions is configured for implementation in hardware, e.g., firmware. In certain aspects, these genetic analysis technologies may employ improved algorithms that may be implemented by software that is run in a less processing intensive and/or less time-consuming manner and/or with greater percentage accuracy, e.g., the hardware implemented functionality is faster, less processing intensive, and more accurate.

In particular, where the algorithm is to be implemented in a software solution, the algorithm and/or its attendant processes, has been optimized so as to be performed faster and/or with better accuracy for execution by that media. Likewise, where the functions of the algorithm are to be implemented in a hardware solution, e.g., as firmware, the hardware has been designed to perform these functions and/or their attendant processes in an optimized manner so as to be performed faster and/or with better accuracy for execution by that media. Further, where the algorithm is to be implemented in a quantum processing solution, the algorithm and/or its attendant processes, has been optimized so as to be performed faster and/or with better accuracy for execution by that media. These methods, for instance, can be employed such as in an iterative mapping, aligning, sorting, variant calling, and/or tertiary processing procedure. In another instance, systems and methods are provided for implementing the functions of one or more algorithms for the performance of one or more steps for analyzing genomic data in a bioinformatics protocol, as set forth herein, wherein the functions are implemented on a hardware and/or quantum accelerator, which may or may not be coupled with one or more general purpose processors and/or super computers and/or quantum computers.

In one aspect, in various embodiments, once the subject's genome has been reconstructed and/or a VCF has been generated, such data may then be subjected to tertiary processing so as to interpret it, such as for determining what the data means with respect to identifying what diseases this person may or may have the potential for suffer from and/or for determining what treatments or lifestyle changes this subject may want to employ so as to ameliorate and/or prevent a diseased state. For example, the subject's genetic sequence and/or their variant call file may be analyzed to determine clinically relevant genetic markers that indicate the existence or potential for a diseased state and/or the efficacy of a proposed therapeutic or prophylactic regimen may have on the subject. This data may then be used to provide the subject with one or more therapeutic or prophylactic regimens so as to better the subject's quality of life, such as treating and/or preventing a diseased state.

Particularly, once one or more of an individual's genetic variations are determined, such variant call file information can be used to develop medically useful information, which in turn can be used to determine, e.g., using various known statistical analysis models, health related data and/or medical useful information, e.g., for diagnostic purposes, e.g., diagnosing a disease or potential therefore, clinical interpretation (e.g., looking for markers that represent a disease variant), whether the subject should be included or excluded in various clinical trials, and other such purposes. More particularly, in various instances, the generated genomics and/or bioinformatics processed results data may be employed in the performance of one or more genomics and/or bioinformatics tertiary protocols, such as a microarray analysis protocol, a genome, e.g., whole genome analysis protocol, a genotyping analysis protocol, an exome analysis protocol, an epigenome analysis protocol, a metagenome analysis protocol, a microbiome analysis protocol, a genotyping analysis protocol, including joint genotyping, variants analyses protocols, including structural variants, somatic variants, and GATK, as well as RNA sequencing protocols and other genetic analyses protocols.

As there are a finite number of diseased states that are caused by genetic malformations, in tertiary processing variants of a certain type, e.g., those known to be related to the onset of diseased states, can be queried for, such as by determining if one or more genetic based diseased markers are included in the variant call file of the subject. Consequently, in various instances, the methods herein disclosed may involve analyzing, e.g., scanning, the VCF and/or the generated sequence, against a known disease sequence variant, such as in a data base of genomic markers therefore, so as to identify the presence of the genetic marker in the VCF and/or the generated sequence, and if present to make a call as to the presence or potential for a genetically induced diseased state. Since there are a large number of known genetic variations and a large number of individual's suffering from diseases caused by such variations, in some embodiments, the methods disclosed herein may entail the generation of one or more databases linking sequenced data for an entire genome and/or a variant call file pertaining thereto, e.g., such as from an individual or a plurality of individuals, and a diseased state and/or searching the generated databases to determine if a particular subject has a genetic composition that would predispose them to having such diseased state. Such searching may involve a comparison of one entire genome with one or more others, or a fragment of a genome, such as a fragment containing only the variations, to one or more fragments of one or more other genomes such as in a database of reference genomes or fragments thereof.

Therefore, in various instances, a pipeline of the disclosure may include one or more modules, wherein the modules are configured for performing one or more functions, such as an image processing or a base calling and/or error correction operation and/or a mapping and/or an alignment, e.g., a gapped or gapless alignment, and/or a sorting function on genetic data, e.g., sequenced genetic data. And in various instances, the pipeline may include one or more modules, wherein the modules are configured for performing one more of a local realignment, a deduplication, a base quality score recalibration, a variant calling, e.g., HMM, a reduction and/or compression, and/or a decompression on the genetic data. Additionally, the pipeline may include one or more modules, wherein the modules are configured for performing a tertiary analysis protocol, such as micro-array protocols, genome, e.g., whole genome protocols, genotyping protocols, exome protocols, epigenome protocols, metagenome protocols, microbiome protocols, genotyping protocols, including joint genotyping protocols, variants analysis protocols, including structural variants protocols, somatic variants protocols, and GATK protocols, as well as RNA sequencing protocols and other genetic analyses protocols.

Many of these modules may either be performed by software or on hardware, locally or remotely, e.g., via software or hardware, such as on the cloud, e.g., on a remote server and/or server bank, such as a quantum computing cluster. Additionally, many of these modules and/or steps of the pipeline are optional and/or can be arranged in any logical order and/or omitted entirely. For instance, the software and/or hardware disclosed herein may or may not include an image processing and/or a base calling or sequence correction algorithm, such as where there may be a concern that such functions may result in a statistical bias. Consequently, the system may include or may not include the base calling and/or sequence correction function, respectively, dependent on the level of accuracy and/or efficiency desired. And as indicated above, one or more of the pipeline functions may be employed in the generation of a genomic sequence of a subject such as through a reference based genomic reconstruction. Also, as indicated above, in certain instances, the output from the secondary processing pipeline may be a variant call file (VCF, gVCF) indicating a portion or all the variants in a genome or a portion thereof.

For instance, in various embodiments, a Next Generation sequencer, or a sequencer on a chip technology, may be configured to perform a sequencing operation on received genetic data. For instance, as can be seen with respect to FIG. 1A, the genetic data 6a may be coupled to a sequencing platform 6 for insertion into a Next Gen sequencer to be sequenced in an iterative fashion, such that each sequence will be grown by the stepwise addition of one nucleotide after another. Specifically, the sequencing platform 6 may include a number of template nucleotide sequences 6a from the subject that are arranged in a grid like fashion to form tiles 6b on the platform 6, which template sequences 6a are to be sequenced. The platform 6 may be added to a flow cell 6c of the sequencer that is adapted for performing the sequencing reactions.

As the sequencing reactions take place, at each step a nucleotide having a fluorescent tag 6d is added to the platform 6 of the flow cell 6c. If a hybridizing reaction occurs, fluorescence is observed, an image is taken, the image is then processed, and an appropriate base call is made. This is repeated base by base until all of the template sequences, e.g., the entire genome, has been sequenced and converted into reads, thereby producing the read data of the system. Hence, once sequenced, the generated data, e.g., reads, need to be transferred from the sequencing platform into the secondary processing system. For instance, typically, this image data is converted into a BCL and/or FASTQ file that can then be transported into the system.

However, in various instances, this conversion and/or transfer process may be made more efficient. Specifically, presented herein are methods and architectures for expedited BCL conversion into files that can be rapidly processed within the secondary processing system. More specifically, in particular instances, instead of transmitting the raw BCL or FASTQ files, the images produced representing each tile of the sequencing operation may be transferred directly into the system and prepared for mapping and aligning et al. For instance, the tiles may be streamed across a suitably configured PCIe and into the ASIC, FPGA, or QPU, wherein the read data may be extracted therefrom directly, and the reads advanced into the mapping and aligning and/or other processing engines.

Figure 1B:
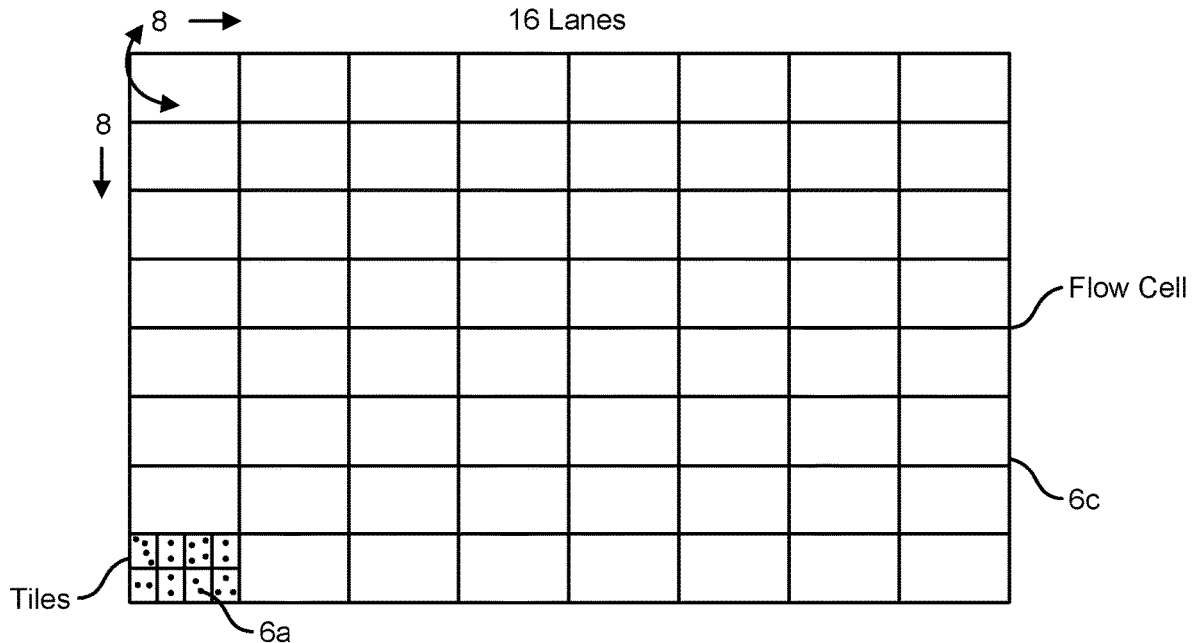
FIG. 1B depicts a representation of a flow cell with the various lanes represented.

Particularly, with respect to the transfer of the data from the tiles obtained by the sequencer to the FPGA/CPU/GPU/QPU, as can be seen with respect to FIG. 1A, the sequencing platform 6 may be imaged as a 3-D cube 6c, within which the growing sequences 6a are generated. Essentially, as can be seen with respect to FIG. 1B, the sequencing platform 6 may be composed of 16 lanes, 8 in the front and 8 in the back, which may be configured to form about 96 tiles 6b. Within each tile 6b are a number of template sequences 6a to be sequenced thereby forming reads, where each read represents the nucleotide sequence for a given region of the genome of a subject, each column represents one file, and as digitally encoded represents 1 byte for every file, with 8 bits per file, such as where 2 bits represents the called base, and the remaining 6 bits represents the quality score.

More particularly, with respect to Next Gen Sequencing, the sequencing is typically performed on glass plates 6 that form flow cells 6c that are entered into the automated sequencer for sequencing. As can be seen with respect to FIG. 1B, a flow cell 6c is a platform 6 composed of 8 vertical columns and 8 horizontal rows (front and back), together which form 16 lanes, where each lane is sufficient for the sequencing of an entire genome. The DNA and/or RNA 6a of a subject to be sequenced is associated within designated positions in between fluidly isolated intersections of the columns and rows of the platform 6 so as to form the tiles 6b, where each tile includes template genetic material 6a to be sequenced. The sequencing platform 6, therefore, includes a number of template nucleotide sequences from the subject, which sequences are arranged in a grid like fashion of tiles on the platform. (See FIG. 1B.) The genetic data 6 is then sequenced in an iterative fashion where each sequence is grown by the stepwise introduction of one nucleotide after another into the flow cell, where each iterative growth step represents a sequencing cycle.

As indicated, an image is captured after each step, and the growing sequence, e.g., of images, form the basis by which the BCL file is generated. As can be seen with respect to FIG. 1C, the reads from the sequencing procedure may form clusters, and it is these clusters that form the theoretical 3-D cube 6c. Accordingly, within this theoretical 3-D cube, each base of each growing nucleotide strand being sequenced will have an x dimension and a y dimension. The image data, or tiles 6b, from this 3-D cube 6c may be extracted and compiled into a two-dimensional map, from which a matrix, as seen in FIG. 1AD may be formed. The matrix is formed of the sequencing cycles, which represent the horizontal axis, and the read identities, which represent the vertical axis. Accordingly, as can be seen with reference to FIG. 1C, the sequenced reads form clusters in the flow cell 6c, which clusters may be defined by a vertical and horizontal axis, cycle by cycle, and the base by base data from each cycle for each read may be inserted into the matrix of FIG. 1D, such as in a streaming and/or pipelined fashion.

Specifically, each cycle represents the potential growth of each read within the flow cell by the addition of one nucleotide, which when sequencing one or several human genomes, may represent the growth of about 1 billion or more reads per lane. The growth of each read, e.g., by the addition of a nucleotide base, is identified by the iterative capturing of images, of the tiles 6b, of the flow cell 6c in between the growth steps. From these images base calls are made, and quality scores determined, and the virtual matrix of FIG. 1D is formed. Accordingly, there will be both a base call and a quality score entered into the matrix, where each tile from each cycle represents a separate file. It is to be noted that where the sequencing is performed on an integrated circuit, sensed electronic data may be substituted for the image data.

For instance, as can be seen with respect to FIG. 1D, the matrix itself will grow iteratively as the images are captured and processed, bases are called, and quality scores are determined for each read, cycle by cycle. This is repeated for each base in the read, for each tile of the flow cell. For example, the cluster of reads. 1C may be numbered and entered into the matrix as the vertical axis. Likewise, the cycle number may be entered as the horizontal axis, and the base call and quality score may then be entered so as to fill out the matrix column by column, row by row. Accordingly, each read will be represented by a number of bases, e.g., about 100 or 150 up to 1000 or more bases per read depending on the sequencer, and there may be up to 10 million or more reads per tile. So, if there are about 100 tiles each having 10 million reads, the matrix would contain about 1 billion reads, which need to be organized and streamed into the secondary processing apparatus.

Figure 1C:
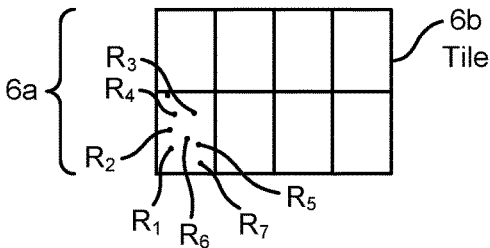
FIG. 1C depicts a lower corner of the flow cell platform of FIG. 1B, showing a constellation of sequenced reads.

Accordingly, such organization is fundamental to rapidly and efficiently processing the data. Hence, in one aspect, presented herein are methods for transposing the data represented by the virtual sequencing matrix in a manner so that the data may be more directly and efficiently streamed into the pipelines of the system herein disclosed. For instance, the generation of the sequencing data, as represented by the star cluster of FIG. 1C, is largely unorganized, which is problematic from a data processing standpoint. Particularly, as the data is generated by the sequencing operation, it is organized as one file per cycle, which means that by the end of the sequencing operation there are millions and millions of files generated, which files are represented in FIG. 1E, by the data in the columns, demarcated by the solid lines.

However, for the purposes of secondary and/or tertiary processing, as disclosed herein, the file data needs to be re-organized into read data, demarcated by the dashed lines of FIG. 1E.

More particularly, in order to more efficiently stream the data generated by the sequencer into the secondary processing data, the data represented by the virtual matrix should be transposed, such as by reorganizing the file data from a column by column basis of tiles per cycle, to a row by row basis identifying the bases of each of the reads. Specifically, the data structure of the generated files forming the matrix, as it is produced by the sequencer, is organized on a cycle by cycle, column by column, basis. By the processes disclosed herein, this data may be transposed, e.g., substantially simultaneously, so as to be represented, as seen within the virtual matrix, on a read by read, row by row basis, where each row represents an individual read, and each read is represented by a sequential number of base calls and quality scores, thereby identifying both the sequence for each read and its confidence. Thus, in a transpose operation as herein described, the data within the memory may be re-organized, e.g., within the virtual matrix, from a column by column basis, representing the input data order, to a row by row basis, representing the output data order, thereby transposing the data order from a vertical to a horizontal organization. Further, although the process may be implemented efficiently in software, it may be made even more efficiently and faster, by being implemented in hardware and/or by a quantum processor.

For instance, in various instances, this transposition process may be accelerated by being implemented in hardware. For example, in one implementation, in a first step, the host software, e.g., of the sequencer, may write input data into the memory, associated with the FPGA, on a column by column basis, e.g., in the input order. Specifically, as the data is generated and stored into an associated memory, the data may be organized into files, cycle by cycle, where the data is saved as separate individual files. This data may be represented by the 3-D cube of FIG. 1A. This generated column organized data may then be queued and/or streamed, e.g., in flight, into the hardware where dedicated processing engines will queue up the column organized data and transpose that data from a column by column, cycle order configuration, to a row by row, read order configuration, in a manner as described herein above, such as by converting the 3-D tile data into a 2-D matrix, whereby the column data may be reorganized into row data, e.g., on a read to read basis. This transposed data may then be stored in the memory in a more strategic order.

Figure 1G:
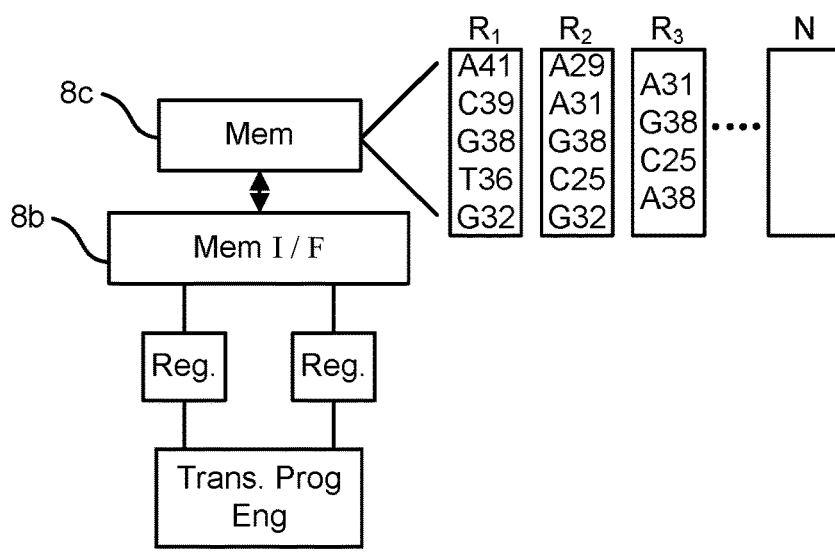
FIG. 1G depicts the system components for performing the transposition.
Figure 1H:
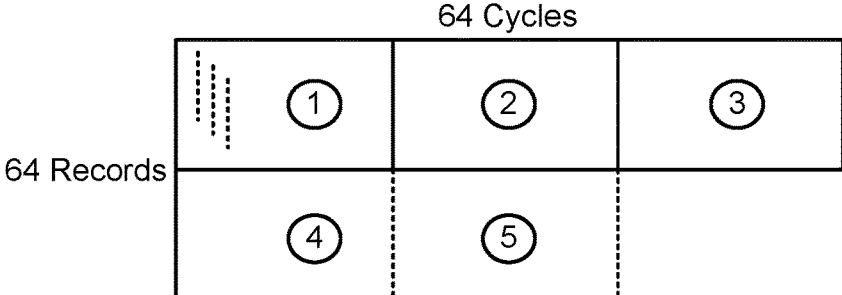
FIG. 1H depicts the transposition order.
Figure 1I:
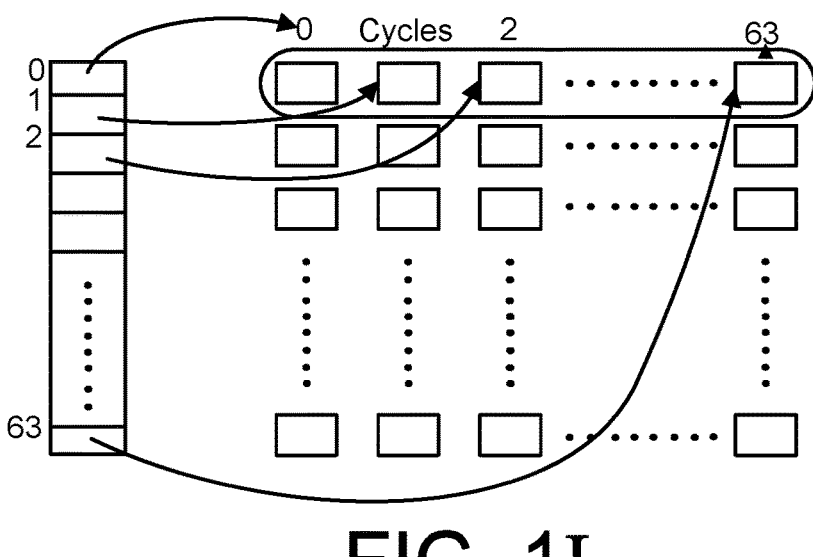
FIG. 1I depicts the architecture for electronically transposing the sequenced data.

For example, the host software may be configured to write input data into the memory associated with the chip, e.g., FPGA, such as in a column-wise input order, and likewise the hardware may be configured to queue the data in a manner so that it is red into the memory in a strategic manner, such as set forth in FIG. 1F. Specifically, the hardware may include an array of registers 8a into which the cycle files may be dispersed and re-organized into individual read data, such as by writing one base from a column into registers that are organized into rows. More specifically, as can be seen with respect to FIG. 1G, the hardware device 1, including the transposition processing engine 8, may include a DRAM port 8a that may queue up the data to be transposed, where the port is operably coupled to a memory interface 8b that is associated with a plurality of registers and/or an external memory 8c, and is configured for handling an increased amount of transactions per cycle, where the queued data is transmitted in bursts.

Particularly, this transposition may take place one data segment at a time, such as where the memory accesses are queued up in such a manner as to take maximal advantage of the DDR transmission rate. For instance, with respect to DRAM, the minimal burst length of the DDR may be, for example, 64 bytes. Accordingly, the column arranged data stored in the host memory may be accessed in a manner such that with each memory access a column worth of corresponding, e.g., 64, bytes of data is obtained. Hence, with one access of the memory a portion of a tile, e.g., representing a corresponding "64" cycles or files, may be accessed, on a column by column basis.

However, as can be seen with respect to FIG. 1F, although the data in the host memory is accessed as column data, when transmitted to the hardware, it may be uploaded into associated smaller memories, e.g., registers, in a different order whereby the data may be converted into bytes, e.g., 64 bytes, of row by row read data, such as in accordance with the minimal burst rate of the DDR, so as to generate a corresponding "64" memory units or blocks per access. This is exemplified by the virtual matrix of FIG. 1D where a number of reads, e.g., 64 reads, are accessed in blocks, and read into memory in segments, as represented by FIG. 1E, such as where each register, or flip-flop, accounts for a particular read, e.g., 64 cycles×64 reads×8 bits per read=32K flip-flops. Specifically, this may be accomplished in various different ways in hardware, such as where the input wiring is organized to match the column ordering, and the output wiring is organized to match the row order. Hence in this configuration, the hardware may be adapted so as to both read and/or write to "64" different addresses per cycle.

More particularly, the hardware may be associated with an array of registers such that each base of a read is directed and written into a single register (or multiple registers in a row) such that when each block is complete, the newly ordered row data may be transmitted to memory as an output, e.g., FASTQ data, in a row by row organization. The FASTQ data may then be accessed by one or more further processing engines of the secondary processing system for further processing, such as by a mapping, aligning, and/or variant calling engine, as described herein. It is to be noted, as described herein, the transpose is performed in small blocks, however, the system may be adapted for the processing of larger blocks as well, as the case may be.

As indicated, once a BCL file has been converted into a FASTQ file, as described above, and/or a BCL or FASTQ file has otherwise been received by the secondary processing platform, a mapping operation may be performed on the received data. Mapping, in general, involves plotting the reads to all the locations in the reference genome to where there is a match. For example, dependent on the size of the read there may be one or a plurality of locations where the read substantially matches a corresponding sequence in the reference genome. Hence, the mapping and/or other functions disclosed herein may be configured for determining where out of all the possible locations one or more reads may match to in the reference genome is actually the true location to where they map.

The output returned from the performance of a mapping function may be a list of possibilities as to where one or more, e.g., each, read maps to one or more reference genomes. For instance, the output for each mapped read may be a list of possible locations the read may be mapped to a matching sequence in the reference genome. In various embodiments, an exact match to the reference for at least a piece, e.g., a seed of the read, if not all of the read may be sought. Accordingly, in various instances, it is not necessary for all portions of all the reads to match exactly to all the portions of the reference genome.

More particularly, in various instances, a mapping module may be provided, such as where the mapping module is configured to perform one or more mapping functions, such as in a hardwired configuration. Specifically, the hardwired mapping module may be configured to perform one or more functions typically performed by one or more algorithms run on a CPU, such as the functions that would typically be implemented in a software based algorithm that produces a prefix and/or suffix tree, a Burrows-Wheeler Transform, and/or runs a hash function, for instance, a hash function that makes use of, or otherwise relies on, a hash-table indexing, such as of a reference, e.g., a reference genome sequence. In such instances, the hash function may be structured so as to implement a strategy, such as an optimized mapping strategy that may be configured to minimize the number of memory accesses, e.g., large-memory random accesses, being performed so as to thereby maximize the utility of the on-board or otherwise associated memory bandwidth, which may fundamentally be constrained such as by space within the chip architecture.

It has been determined where all the possible matches are for the seeds against the reference genome, it must be determined which out of all the possible locations a given read may match to is in fact the correct position to which it aligns. Hence, after mapping there may be a multiplicity of positions that one or more reads appear to match in the reference genome. Consequently, there may be a plurality of seeds that appear to be indicating the exact same thing, e.g., they may match to the exact same position on the reference, if you take into account the position of the seed in the read. The actual alignment, therefore, must be determined for each given read. This determination may be made in several different ways.

In one instance, all the reads may be evaluated so as to determine their correct alignment with respect to the reference genome based on the positions indicated by every seed from the read that returned position information during the mapping, e.g., hash lookup, process. However, in various instances, prior to performing an alignment, a seed chain filtering function may be performed on one or more of the seeds. For instance, in certain instances, the seeds associated with a given read that appear to map to the same general place as against the reference genome may be aggregated into a single chain that references the same general region. All of the seeds associated with one read may be grouped into one or more seed chains such that each seed is a member of only one chain. It is such chain(s) that then cause the read to be aligned to each indicated position in the reference genome.

Specifically, in various instances, all the seeds that have the same supporting evidence indicating that they all belong to the same general location(s) in the reference may be gathered together to form one or more chains. The seeds that group together, therefore, or at least appear as they are going to be near one another in the reference genome, e.g., within a certain band, will be grouped into a chain of seeds, and those that are outside of this band will be made into a different chain of seeds. Once these various seeds have been aggregated into one or more various seed chains, it may be determined which of the chains actually represents the correct chain to be aligned. This may be done, at least in part, by use of a filtering algorithm that is a heuristic designed to eliminate weak seed chains which are highly unlikely to be the correct one.

The outcome from performing one or more of these mapping, filtering, and/or editing functions is a list of reads which includes for each read a list of all the possible locations to where the read may matchup with the reference genome. Hence, a mapping function may be performed so as to quickly determine where the reads of the image file, BCL file, and/or FASTQ file obtained from the sequencer map to the reference genome, e.g., to where in the whole genome the various reads map. However, if there is an error in any of the reads or a genetic variation, you may not get an exact match to the reference and/or there may be several places one or more reads appear to match. It, therefore, must be determined where the various reads actually align with respect to the genome as a whole.

Accordingly, after mapping and/or filtering and/or editing, the location positions for a large number of reads have been determined, where for some of the individual reads a multiplicity of location positions have been determined, and it now needs to be determined which out of all the possible locations is in fact the true or most likely location to which the various reads align. Such aligning may be performed by one or more algorithms, such as a dynamic programming algorithm that matches the mapped reads to the reference genome and runs an alignment function thereon. An exemplary aligning function compares one or more, e.g., all of the reads, to the reference, such as by placing them in a graphical relation to one another, e.g., such as in a table, e.g., a virtual array or matrix, where the sequence of one of the reference genome or the mapped reads is placed on one dimension or axis, e.g., the horizontal axis, and the other is placed on the opposed dimensions or axis, such as the vertical axis. A conceptual scoring wave front is then passed over the array so as to determine the alignment of the reads with the reference genome, such as by computing alignment scores for each cell in the matrix.

The scoring wave front represents one or more, e.g., all, the cells of a matrix, or a portion of those cells, which may be scored independently and/or simultaneously according to the rules of dynamic programming applicable in the alignment algorithm, such as Smith-Waterman, and/or Needleman-Wunsch, and/or related algorithms. Alignment scores may be computed sequentially or in other orders, such as by computing all the scores in the top row from left to right, followed by all the scores in the next row from left to right, etc. In this manner the diagonally sweeping diagonal wave front represents an optimal sequence of batches of scores computed simultaneously or in parallel in a series of wave front steps.

For instance, in one embodiment, a window of the reference genome containing the segment to which a read was mapped may be placed on the horizontal axis, and the read may be positioned on the vertical axis. In a manner such as this an array or matrix is generated, e.g., a virtual matrix, whereby the nucleotide at each position in the read may be compared with the nucleotide at each position in the reference window. As the wave front passes over the array, all potential ways of aligning the read to the reference window are considered, including if changes to one sequence would be required to make the read match the reference sequence, such as by changing one or more nucleotides of the read to other nucleotides, or inserting one or more new nucleotides into one sequence, or deleting one or more nucleotides from one sequence.

An alignment score, representing the extent of the changes that would be required to be made to achieve an exact alignment, is generated, wherein this score and/or other associated data may be stored in the given cells of the array. Each cell of the array corresponds to the possibility that the nucleotide at its position on the read axis aligns to the nucleotide at its position on the reference axis, and the score generated for each cell represents the partial alignment terminating with the cell's positions in the read and the reference window. The highest score generated in any cell represents the best overall alignment of the read to the reference window. In various instances, the alignment may be global, where the entire read must be aligned to some portion of the reference window, such as using a Needleman-Wunsch or similar algorithm; or in other instances, the alignment may be local, where only a portion of the read may be aligned to a portion of the reference window, such as by using a Smith-Waterman or similar algorithm.

Accordingly, in various instances, an alignment function may be performed, such as on the data obtained from the mapping module. Hence, in various instances, an alignment function may form a module, such as an alignment module, that may form part of a system, e.g., a pipeline, that is used, such as in addition with a mapping module, in a process for determining the actual entire genomic sequence, or a portion thereof, of an individual. For instance, the output returned from the performance of the mapping function, such as from a mapping module, e.g., the list of possibilities as to where one or more or all of the reads maps to one or more positions in one or more reference genomes, may be employed by the alignment function so as to determine the actual sequence alignment of the subject's sequenced DNA.

Such an alignment function may at times be useful because, as described above, often times, for a variety of different reasons, the sequenced reads do not always match exactly to the reference genome. For instance, there may be an SNP (single nucleotide polymorphism) in one or more of the reads, e.g., a substitution of one nucleotide for another at a single position; there may be an "indel," insertion or deletion of one or more bases along one or more of the read sequences, which insertion or deletion is not present in the reference genome; and/or there may be a sequencing error (e.g., errors in sample prep and/or sequencer read and/or sequencer output, etc.) causing one or more of these apparent variations. Accordingly, when a read varies from the reference, such as by an SNP or Indel, this may be because the reference differs from the true DNA sequence sampled, or because the read differs from the true DNA sequence sampled. The problem is to figure out how to correctly align the reads to the reference genome given the fact that in all likelihood the two sequences are going to vary from one another in a multiplicity of different ways.

As indicated, typically, an algorithm is used to perform such an alignment function. For example, a Smith-Waterman and/or a Needleman-Wunsch alignment algorithm may be employed to align two or more sequences against one another. In this instance, they may be employed in a manner so as to determine the probabilities that for any given position where the read maps to the reference genome that the mapping is in fact the position from where the read originated. Typically, these algorithms are configured so as to be performed by software, however, in various instances, such as herein presented, one or more of these algorithms can be configured so as to be executed in hardware, as described in greater detail herein below.

In particular, the alignment function operates, at least in part, to align one or more, e.g., all, of the reads to the reference genome despite the presence of one or more portions of mismatches, e.g., SNPs, insertions, deletions, structural artifacts, etc. so as to determine where the reads are likely to fit in the genome correctly. For instance, the one or more reads are compared against the reference genome, and the best possible fit for the read against the genome is determined, while accounting for substitutions and/or Indels and/or structural variants. However, to better determine which of the modified versions of the read best fits against the reference genome, the proposed changes must be accounted for, and as such a scoring function may also be performed.

In view of the above, there are, therefore, at least two goals that may be achieved from performing an alignment function. One is a report of the best alignment, including position in the reference genome and a description of what changes are necessary to make the read match the reference segment at that position, and the other is the alignment quality score. For instance, in various instances, the output from the alignment module may be a Compact Idiosyncratic Gapped Alignment Report, e.g., a CIGAR string, wherein the CIGAR string output is a report detailing all the changes that were made to the reads so as to achieve their best fit alignment, e.g., detailed alignment instructions indicating how the query actually aligns with the reference. Such a CIGAR string readout may be useful in further stages of processing so as to better determine that for the given subject's genomic nucleotide sequence, the predicted variations as compared against a reference genome are in fact true variations, and not just due to machine, software, or human error.

One or more of such alignment procedures may be performed by any suitable alignment algorithm, such as a Needleman-Wunsch alignment algorithm and/or a Smith-Waterman alignment algorithm that may have been modified to accommodate the functionality herein described. In general both of these algorithms and those like them basically perform, in some instances, in a similar manner. For instance, as set forth above, these alignment algorithms typically build the virtual array in a similar manner such that, in various instances, the horizontal top boundary may be configured to represent the genomic reference sequence, which may be laid out across the top row of the array according to its base pair composition. Likewise, the vertical boundary may be configured to represent the sequenced and mapped query sequences that have been positioned in order, downwards along the first column, such that their nucleotide sequence order is generally matched to the nucleotide sequence of the reference to which they mapped. The intervening cells may then be populated with scores as to the probability that the relevant base of the query at a given position, is positioned at that location relative to the reference. In performing this function, a swath may be moved diagonally across the matrix populating scores within the intervening cells and the probability for each base of the query being in the indicated position may be determined.

With respect to a Needleman-Wunsch alignment function, which generates optimal global (or semi-global) alignments, aligning the entire read sequence to some segment of the reference genome, the wave front steering may be configured such that it typically sweeps all the way from the top edge of the alignment matrix to the bottom edge. When the wave front sweep is complete, the maximum score on the bottom edge of the alignment matrix (corresponding to the end of the read) is selected, and the alignment is back-traced to a cell on the top edge of the matrix (corresponding to the beginning of the read). In various of the instances disclosed herein, the reads can be any length long, can be any size, and there need not be extensive read parameters as to how the alignment is performed, e.g., in various instances, the read can be as long as a chromosome. In such an instance, however, the memory size and chromosome length may be limiting factor.

With respect to a Smith-Waterman algorithm, which generates optimal local alignments, aligning the entire read sequence or part of the read sequence to some segment of the reference genome, this algorithm may be configured for finding the best scoring possible based on a full or partial alignment of the read. Hence, in various instances, the wave front-scored band may not extend to the top and/or bottom edges of the alignment matrix, such as if a very long read had only seeds in its middle mapping to the reference genome, but commonly the wave front may still score from top to bottom of the matrix. Local alignment is typically achieved by two adjustments. First, alignment scores are never allowed to fall below zero (or some other floor), and if a cell score otherwise calculated would be negative, a zero score is substituted, representing the start of a new alignment. Second, the maximum alignment score produced in any cell in the matrix, not necessarily along the bottom edge, is used as the terminus of the alignment. The alignment is backtraced from this maximum score up and left through the matrix to a zero score, which is used as the start position of the local alignment, even if it is not on the top row of the matrix.

In view of the above, there are several different possible pathways through the virtual array. In various embodiments, the wave front starts from the upper left corner of the virtual array, and moves downwards towards identifiers of the maximum score. For instance, the results of all possible aligns can be gathered, processed, correlated, and scored to determine the maximum score. When the end of a boundary or the end of the array has been reached and/or a computation leading to the highest score for all of the processed cells is determined (e.g., the overall highest score identified) then a backtrace may be performed so as to find the pathway that was taken to achieve that highest score. For example, a pathway that leads to a predicted maximum score may be identified, and once identified an audit may be performed so as to determine how that maximum score was derived, for instance, by moving backwards following the best score alignment arrows retracing the pathway that led to achieving the identified maximum score, such as calculated by the wave front scoring cells.

Once it has been determined where each read is mapped, and further determined where each read is aligned, e.g., each relevant read has been given a position and a quality score reflecting the probability that the position is the correct alignment, such that the nucleotide sequence for the subject's DNA is known, then the order of the various reads and/or genomic nucleic acid sequence of the subject may be verified, such as by performing a back trace function moving backwards up through the array so as to determine the identity of every nucleic acid in its proper order in the sample genomic sequence. Consequently, in some aspects, the present disclosure is directed to a backtrace function, such as is part of an alignment module that performs both an alignment and a back trace function, such as a module that may be part of a pipeline of modules, such as a pipeline that is directed at taking raw sequence read data, such as form a genomic sample form an individual, and mapping and/or aligning that data, which data may then be sorted.

In the case of affine gap scoring, scoring vector information may be extended, e.g. to 4 bits per scored cell. In addition to the e.g., 2-bit score-choice direction indicator, two 1-bit flags may be added, a vertical extend flag, and a horizontal extend flag. According to the methods of affine gap scoring extensions to Smith-Waterman or Needleman-Wunsch or similar alignment algorithms, for each cell, in addition to the primary alignment score representing the best-scoring alignment terminating in that cell, a 'vertical score' should be generated, corresponding to the maximum alignment score reaching that cell with a final vertical step, and a 'horizontal score' should be generated, corresponding to the maximum alignment score reaching that cell with a final horizontal step; and when computing any of the three scores, a vertical step into the cell may be computed either using the primary score from the cell above minus a gap-open penalty, or using the vertical score from the cell above minus a gap-extend penalty, whichever is greater; and a horizontal step into the cell may be computed either using the primary score from the cell to the left minus a gap-open penalty, or using the horizontal score from the cell to the left minus a gap-extend penalty, whichever is greater. In cases where the vertical score minus a gap extend penalty is selected, the vertical extend flag in the scoring vector should be set, e.g., '1', and otherwise it should be unset, e.g., '0'.

In cases when the horizontal score minus a gap extend penalty is selected, the horizontal extend flag in the scoring vector should be set, e.g. '1', and otherwise it should be unset, e.g. '0'. During backtrace for affine gap scoring, any time backtrace takes a vertical step upward from a given cell, if that cell's scoring vector's vertical extend flag is set, the following backtrace step must also be vertical, regardless of the scoring vector for the cell above. Likewise, any time backtrace takes a horizontal step leftward from a given cell, if that cell's scoring vector's horizontal extend flag is set, the following backtrace step must also be horizontal, regardless of the scoring vector for the cell to the left. Accordingly, such a table of scoring vectors, e.g. 129 bits per row for 64 cells using linear gap scoring, or 257 bits per row for 64 cells using affine gap scoring, with some number NR of rows, is adequate to support backtrace after concluding alignment scoring where the scoring wavefront took NR steps or fewer.

Hence, a method is given for performing incremental backtrace from partial alignment information, e.g., comprising partial scoring vector information for alignment matrix cells scored so far. From a currently completed alignment boundary, e.g., a particular scored wave front position, backtrace is initiated from all cell positions on the boundary. Such backtrace from all boundary cells may be performed sequentially, or advantageously, especially in a hardware implementation, all the backtraces may be performed together. It is not necessary to extract alignment notations, e.g., CIGAR strings, from these multiple backtraces; only to determine what alignment matrix positions they pass through during the backtrace. In an implementation of simultaneous backtrace from a scoring boundary, a number of 1-bit registers may be utilized, corresponding to the number of alignment cells, initialized e.g., all to '1's, representing whether any of the backtraces pass through a corresponding position. For each step of simultaneous backtrace, scoring vectors corresponding to all the current '1's in these registers, e.g. from one row of the scoring vector table, can be examined, to determine a next backtrace step corresponding to each '1' in the registers, leading to a following position for each '1' in the registers, for the next simultaneous backtrace step.

Importantly, it is easily possible for multiple '1's in the registers to merge into common positions, corresponding to multiple of the simultaneous backtraces merging together onto common backtrace paths. Once two or more of the simultaneous backtraces merge together, they remain merged indefinitely, because henceforth they will utilize scoring vector information from the same cell. It has been observed, empirically and for theoretical reasons, that with high probability, all of the simultaneous backtraces merge into a singular backtrace path, in a relatively small number of backtrace steps, which e.g. may be a small multiple, e.g. 8, times the number of scoring cells in the wavefront. For example, with a 64-cell wavefront, with high probability, all backtraces from a given wavefront boundary merge into a single backtrace path within 512 backtrace steps. Alternatively, it is also possible, and not uncommon, for all backtraces to terminate within the number, e.g. 512, of backtrace steps.

Accordingly, the multiple simultaneous backtraces may be performed from a scoring boundary, e.g. a scored wavefront position, far enough back that they all either terminate or merge into a single backtrace path, e.g. in 512 backtrace steps or fewer. If they all merge together into a singular backtrace path, then from the location in the scoring matrix where they merge, or any distance further back along the singular backtrace path, an incremental backtrace from partial alignment information is possible. Further backtrace from the merge point, or any distance further back, is commenced, by normal singular backtrace methods, including recording the corresponding alignment notation, e.g., a partial CIGAR string. This incremental backtrace, and e.g., partial CIGAR string, must be part of any possible final backtrace, and e.g., full CIGAR string, that would result after alignment completes, unless such final backtrace would terminate before reaching the scoring boundary where simultaneous backtrace began, because if it reaches the scoring boundary, it must follow one of the simultaneous backtrace paths, and merge into the singular backtrace path, now incrementally extracted.

Therefore, all scoring vectors for the matrix regions corresponding to the incrementally extracted backtrace, e.g., in all table rows for wave front positions preceding the start of the extracted singular backtrace, may be safely discarded. When the final backtrace is performed from a maximum scoring cell, if it terminates before reaching the scoring boundary (or alternatively, if it terminates before reaching the start of the extracted singular backtrace), the incremental alignment notation, e.g. partial CIGAR string, may be discarded. If the final backtrace continues to the start of the extracted singular backtrace, its alignment notation, e.g., CIGAR string, may then be grafted onto the incremental alignment notation, e.g., partial CIGAR string. Furthermore, in a very long alignment, the process of performing a simultaneous backtrace from a scoring boundary, e.g., scored wave front position, until all backtraces terminate or merge, followed by a singular backtrace with alignment notation extraction, may be repeated multiple times, from various successive scoring boundaries. The incremental alignment notation, e.g. partial CIGAR string, from each successive incremental backtrace may then be grafted onto the accumulated previous alignment notations, unless the new simultaneous backtrace or singular backtrace terminates early, in which case accumulated previous alignment notations may be discarded. The eventual final backtrace likewise grafts its alignment notation onto the most recent accumulated alignment notations, for a complete backtrace description, e.g., CIGAR string.

Accordingly, in this manner, the memory to store scoring vectors may be kept bounded, assuming simultaneous backtraces always merge together in a bounded number of steps, e.g. 512 steps. In rare cases where simultaneous backtraces fail to merge or terminate in the bounded number of steps, various exceptional actions may be taken, including failing the current alignment, or repeating it with a higher bound or with no bound, perhaps by a different or traditional method, such as storing all scoring vectors for the complete alignment, such as in external DRAM. In a variation, it may be reasonable to fail such an alignment, because it is extremely rare, and even rarer that such a failed alignment would have been a best-scoring alignment to be used in alignment reporting.

In various instances, the devices, systems, and their methods of use of the present disclosure may be configured for performing one or more of a full-read gapless and/or gapped alignments that may then be scored so as to determine the appropriate alignment for the reads in the dataset. For instance, in various instances, a gapless alignment procedure may be performed on data to be processed, which gapless alignment procedure may then be followed by one or more of a gapped alignment, and/or by a selective Smith-Waterman alignment procedure. For example, in a first step, a gapless alignment chain may be generated. As described herein, such gapless alignment functions may be performed quickly, such as without the need for accounting for gaps, which after a first step of performing a gapless alignment, may then be followed by then performing a gapped alignment.

For instance, an alignment function may be performed in order to determine how any given nucleotide sequence, e.g., read, aligns to a reference sequence without the need for inserting gaps in one or more of the reads and/or reference. An important part of performing such an alignment function is determining where and how there are mismatches in the sequence in question versus the sequence of the reference genome. However, because of the great homology within the human genome, in theory, any given nucleotide sequence is going to largely match a representative reference sequence. Where there are mismatches, these will likely be due to a single nucleotide polymorphism, which is relatively easy to detect, or they will be due to an insertion or deletion in the sequences in question, which are much more difficult to detect.

Consequently, in performing an alignment function, the majority of the time, the sequence in question is going to match the reference sequence, and where there is a mismatch due to an SNP, this will easily be determined. Hence, a relatively large amount of processing power is not required to perform such analysis. Difficulties arise, however, where there are insertions or deletions in the sequence in question with respect to the reference sequence, because such insertions and deletions amount to gaps in the alignment. Such gaps require a more extensive and complicated processing platform so as to determine the correct alignment. Nevertheless, because there will only be a small percentage of indels, only a relatively smaller percentage of gapped alignment protocols need be performed as compared to the millions of gapless alignments performed. Hence, only a small percentage of all of the gapless alignment functions result in a need for further processing due to the presence of an indel in the sequence, and therefore will need a gapped alignment.

When an indel is indicated in a gapless alignment procedure, only those sequences get passed on to an alignment engine for further processing, such as an alignment engine configured for performing an advanced alignment function, such as a Smith Waterman alignment (SWA). Thus, because either a gapless or a gapped alignment is to be performed, the devices and systems disclosed herein are a much more efficient use of resources. More particularly, in certain embodiments, both a gapless and a gapped alignment may be performed on a given selection of sequences, e.g., one right after the other, then the results are compared for each sequence, and the best result is chosen. Such an arrangement may be implemented, for instance, where an enhancement in accuracy is desired, and an increased amount of time and resources for performing the required processing is acceptable.

Particularly, in various instances, a first alignment step may be performed without engaging a processing intensive Smith Waterman function. Hence, a plurality of gapless alignments may be performed in a less resource intensive, less time-consuming manner, and because less resources are needed less space need be dedicated for such processing on the chip. Thus, more processing may be performed, using less processing elements, requiring less time, therefore, more alignments can be done, and better accuracy can be achieved. More particularly, less chip resource-implementations for performing Smith Waterman alignments need be dedicated using less chip area, as it does not require as much chip area for the processing elements required to perform gapless alignments as it does for performing a gapped alignment. As the chip resource requirements go down, the more processing can be performed in a shorter period of time, and with the more processing that can be performed, the better the accuracy can be achieved.

The output from the alignment module is a SAM (Text) or BAM (e.g., binary version of a SAM) file along with a mapping quality score (MAPA), which quality score reflects the confidence that the predicted and aligned location of the read to the reference is actually where the read is derived. Accordingly, once it has been determined where each read is mapped, and further determined where each read is aligned, e.g., each relevant read has been given a position and a quality score reflecting the probability that the position is the correct alignment, such that the nucleotide sequence for the subject's DNA is known as well as how the subject's DNA differs from that of the reference (e.g., the CIGAR string has been determined), then the various reads representing the genomic nucleic acid sequence of the subject may be sorted by chromosome location, so that the exact location of the read on the chromosomes may be determined. Consequently, in some aspects, the present disclosure is directed to a sorting function, such as may be performed by a sorting module, which sorting module may be part of a pipeline of modules, such as a pipeline that is directed at taking raw sequence read data, such as form a genomic sample form an individual, and mapping and/or aligning that data, which data may then be sorted.

More particularly, once the reads have been assigned a position, such as relative to the reference genome, which may include identifying to which chromosome the read belongs and/or its offset from the beginning of that chromosome, the reads may be sorted by position. Sorting may be useful, such as in downstream analyses, whereby all of the reads that overlap a given position in the genome may be formed into a pile up so as to be adjacent to one another, such as after being processed through the sorting module, whereby it can be readily determined if the majority of the reads agree with the reference value or not. Hence, where the majority of reads do not agree with the reference value a variant call can be flagged. Sorting, therefore, may involve one or more of sorting the reads that align to the relatively same position, such as the same chromosome position, so as to produce a pileup, such that all the reads that cover the same location are physically grouped together; and may further involve analyzing the reads of the pileup to determine where the reads may indicate an actual variant in the genome, as compared to the reference genome, which variant may be distinguishable, such as by the consensus of the pileup, from an error, such as a machine read error or error an error in the sequencing methods which may be exhibited by a small minority of the reads.

Once the data has been obtained there are one or more other modules that may be run so as to clean up the data. For instance, one module that may be included, for example, in a sequence analysis pipeline, such as for determining the genomic sequence of an individual, may be a local realignment module. For example, it is often difficult to determine insertions and deletions that occur at the end of the read. This is because the Smith-Waterman or equivalent alignment process lacks enough context beyond the indel to allow the scoring to detect its presence. Consequently, the actual indel may be reported as one or more SNPs. In such an instance, the accuracy of the predicted location for any given read may be enhanced by performing a local realignment on the mapped and/or aligned and/or sorted read data.

In such instances, pileups may be used to help clarify the proper alignment, such as where a position in question is at the end of any given read, that same position is likely to be at the middle of some other read in the pileup. Accordingly, in performing a local realignment the various reads in a pileup may be analyzed so as to determine if some of the reads in the pile up indicate that there was an insertion or a deletion at a given position where another read does not include the indel, or rather includes a substitution, at that position, then the indel may be inserted, such as into the reference, where it is not present, and the reads in the local pileup that overlap that region may be realigned to see if collectively a better score is achieved then when the insertion and/or deletion was not there. If there is an improvement, the whole set of reads in the pileup may be reviewed and if the score of the overall set has improved then it is clear to make the call that there really was an indel at that position. In a manner such as this, the fact that there is not enough context to more accurately align a read at the end of a chromosome, for any individual read, may be compensated for. Hence, when performing a local realignment, one or more pileups where one or more indels may be positioned are examined, and it is determined if by adding an indel at any given position the overall alignment score may be enhanced.

Another module that may be included, for example, in a sequence analysis pipeline, such as for determining the genomic sequence of an individual, may be a duplicate marking module. For instance, a duplicate marking function may be performed so as to compensate for chemistry errors that may occur during the sequencing phase. For example, as described above, during some sequencing procedures nucleic acid sequences are attached to beads and built up from there using labeled nucleotide bases. Ideally there will be only one read per bead. However, sometimes multiple reads become attached to a single bead and this results in an excessive number of copies of the attached read. This phenomenon is known as read duplication.

After an alignment is performed and the results obtained, and/or a sorting function, local realignment, and/or a de-duplication is performed, a variant call function may be employed on the resultant data. For instance, a typical variant call function or parts thereof may be configured so as to be implemented in a software and/or hardwired configuration, such as on an integrated circuit. Particularly, variant calling is a process that involves positioning all the reads that align to a given location on the reference into groupings such that all overlapping regions from all the various aligned reads form a "pile up." Then the pileup of reads covering a given region of the reference genome are analyzed to determine what the most likely actual content of the sampled individual's DNA/RNA is within that region. This is then repeated, step wise, for every region of the genome. The determined content generates a list of differences termed "variations" or "variants" from the reference genome, each with an associated confidence level along with other metadata.

The most common variants are single nucleotide polymorphisms (SNPs), in which a single base differs from the reference. SNPs occur at about 1 in 1000 positions in a human genome. Next most common are insertions (into the reference) and deletions (from the reference), or "indels" collectively. These are more common at shorter lengths, but can be of any length. Additional complications arise, however, because the collection of sequenced segments ("reads") is random, some regions will have deeper coverage than others. There are also more complex variants that include multi-base substitutions, and combinations of indels and substitutions that can be thought of as length-altering substitutions. Standard software based variant callers have difficulty identifying all of these, and with various limits on variant lengths. More specialized variant callers in both software and/or hardware are needed to identify longer variations, and many varieties of exotic "structural variants" involving large alterations of the chromosomes.

However, variant calling is a difficult procedure to implement in software, and worlds of magnitude more difficult to deploy in hardware. In order to account for and/or detect these types of errors, typical variant callers may perform one or more of the following tasks. For instance, they may come up with a set of hypothesis genotypes (content of the one or two chromosomes at a locus), use Bayesian calculations to estimate the posterior probability that each genotype is the truth given the observed evidence, and report the most likely genotype along with its confidence level. As such variant callers may be simple or complex. Simpler variant callers look only at the column of bases in the aligned read pileup at the precise position of a call being made. More advanced variant callers are "haplotype based callers", which may be configured to take into account context, such as in a window, around the call being made.

A "haplotype" is particular DNA content (nucleotide sequence, list of variants, etc.) in a single common "strand", e.g. one of two diploid strands in a region, and a haplotype based caller considers the Bayesian implications of which differences are linked by appearing in the same read. Accordingly, a variant call protocol, as proposed herein, may implement one or more improved functions such as those performed in a Genome Analysis Tool Kit (GATK) haplotype caller and/or using a Hidden Markov Model (HMM) tool and/or a De Bruijn Graph function, such as where one or more these functions typically employed by a GATK haplotype caller, and/or a HMM tool, and/or a De Bruijn Graph function may be implemented in software and/or in hardware.

More particularly, as implemented herein, various different variant call operations may be configured so as to be performed in software or hardware, and may include one or more of the following steps. For instance, variant call function may include an active region identification, such as for identifying places where multiple reads disagree with the reference, and for generating a window around the identified active region, so that only these regions may be selected for further processing. Additionally, localized haplotype assembly may take place, such as where, for each given active region, all the overlapping reads may be assembled into a "De Bruijn graph" (DBG) matrix. From this DBG, various paths through the matrix may be extracted, where each path constitutes a candidate haplotype, e.g., hypotheses, for what the true DNA sequence may be on at least one strand. Further, haplotype alignment may take place, such as where each extracted haplotype candidate may be aligned, e.g., Smith-Waterman aligned, back to the reference genome, so as to determine what variation(s) from the reference it implies. Furthermore, a read likelihood calculation may be performed, such as where each read may be tested against each haplotype, or hypothesis, to estimate a probability of observing the read assuming the haplotype was the true original DNA sampled.

With respect to these processes, the read likelihood calculation will typically be the most resource intensive and time-consuming operation to be performed, often requiring a pair HMM evaluation. Additionally, the constructing of De Bruijn graphs for each pileup of reads, with associated operations of identifying locally and globally unique K-mers, as described below may also be resource intensive and/or time consuming. Accordingly, in various embodiments, one or more of the various calculations involved in performing one or more of these steps may be configured so as to be implemented in optimized software fashion or hardware, such as for being performed in an accelerated manner by an integrated circuit, as herein described.

As indicated above, in various embodiments, a Haplotype Caller of the disclosure, implemented in software and/or in hardware or a combination thereof may be configured to include one or more of the following operations: Active Region Identification, Localized Haplotype Assembly, Haplotype Alignment, Read Likelihood Calculation, and/or Genotyping. For instance, the devices, systems, and/or methods of the disclosure may be configured to perform one or more of a mapping, aligning, and/or a sorting operation on data obtained from a subject's sequenced DNA/RNA to generate mapped, aligned, and/or sorted results data. This results data may then be cleaned up, such as by performing a de duplication operation on it and/or that data may be communicated to one or more dedicated haplotype caller processing engines for performing a variant call operation, including one or more of the aforementioned steps, on that results data so as to generate a variant call file with respect thereto. Hence, all the reads that have been sequenced and/or been mapped and/or aligned to particular positions in the reference genome may be subjected to further processing so as to determine how the determined sequence differs from a reference sequence at any given point in the reference genome.

Accordingly, in various embodiments, a device, system, and/or method of its use, as herein disclosed, may include a variant or haplotype caller system that is implemented in a software and/or hardwired configuration to perform an active region identification operation on the obtained results data. Active region identification involves identifying and determining places where multiple reads, e.g., in a pile up of reads, disagree with a reference, and further involves generating one or more windows around the disagreements ("active regions") such that the region within the window may be selected for further processing. For example, during a mapping and/or aligning step, identified reads are mapped and/or aligned to the regions in the reference genome where they are expected to have originated in the subject's genetic sequence.

However, as the sequencing is performed in such a manner so as to create an oversampling of sequenced reads for any given region of the genome, at any given position in the reference sequence may be seen a pile up of any and/all of the sequenced reads that line up and align with that region. All of these reads that align and/or overlap in a given region or pile up position may be input into the variant caller system. Hence, for any given read being analyzed, the read may be compared to the reference at its suspected region of overlap, and that read may be compared to the reference to determine if it shows any difference in its sequence from the known sequence of the reference. If the read lines up to the reference, without any insertions or deletions and all the bases are the same, then the alignment is determined to be good.

Hence, for any given mapped and/or aligned read, the read may have bases that are different from the reference, e.g., the read may include one or more SNPs, creating a position where a base is mismatched; and/or the read may have one or more of an insertion and/or deletion, e.g., creating a gap in the alignment. Accordingly, in any of these instances, there will be one or more mismatches that need to be accounted for by further processing. Nevertheless, to save time and increase efficiency, such further processing should be limited to those instances where a perceived mismatch is non-trivial, e.g., a non-noise difference.

In determining the significance of a mismatch, places where multiple reads in a pile up disagree from the reference may be identified as an active region, a window around the active region may then be used to select a locus of disagreement that may then be subjected to further processing. The disagreement, however, should be non-trivial. This may be determined in many ways, for instance, the non-reference probability may be calculated for each locus in question, such as by analyzing base match vs mismatch quality scores, such as above a given threshold deemed to be a sufficiently significant amount of indication from those reads that disagree with the reference in a significant way.

For instance, if 30 of the mapped and/or aligned reads all line up and/or overlap so as to form a pile up at a given position in the reference, e.g., an active region, and only 1 or 2 out of the 30 reads disagrees with the reference, then the minimal threshold for further processing may be deemed to not have been met, and the non-agreeing read(s) can be disregarded in view of the 28 or 29 reads that do agree. However, if 3 or 4, or 5, or 10, or more of the reads in the pile up disagree, then the disagreement may be statistically significant enough to warrant further processing, and an active region around the identified region(s) of difference might be determined. In such an instance, an active region window ascertaining the bases surrounding that difference may be taken to give enhanced context to the region surrounding the difference, and additional processing steps, such as performing a Gaussian distribution and sum of non-reference probabilities distributed across neighboring positions, may be taken to further investigate and process that region to figure out if and active region should be declared and if so what variances from the reference actually are present within that region if any. Therefore, the determining of an active region identifies those regions where extra processing may be needed to clearly determine if a true variance or a read error has occurred.

Particularly, because in many instances it is not desirable to subject every region in a pile up of sequences to further processing, an active region can be identified whereby it is only those regions where extra processing may be needed to clearly determine if a true variance or a read error has occurred that may be determined as needing of further processing. And, as indicated above, it may be the size of the supposed variance that determines the size of the window of the active region. For instance, in various instances, the bounds of the active window may vary from 1 or 2 or about 10 or 20 or even about 25 or about 50 to about 200 or about 300, or about 500 or about 1000 bases long or more, where it is only within the bounds of the active window that further processing is taking place. Of course, the size of the active window can be any suitable length so long as it provides the context to determine the statistical importance of a difference.

Hence, if there are only one or two isolated differences, then the active window may only need to cover one or more to a few dozen bases in the active region so as to have enough context to make a statistical call that an actual variant is present. However, if there is a cluster or a bunch of differences, or if there are indels present for which more context is desired, then the window may be configured so as to be larger. In either instance, it may be desirable to analyze any and all the differences that might occur in clusters, so as to analyze them all in one or more active regions, because to do so can provide supporting information about each individual difference and will save processing time by decreasing the number of active windows engaged. In various instances, the active region boundaries may be determined by active probabilities that pass a given threshold, such as about 0.00001 or about 0.00001 or about 0.0001 or less to about 0.002 or about 0.02 or about 0.2 or more. And if the active region is longer than a given threshold, e.g., about 300-500 bases or 1000 bases or more, then the region can be broken up into sub-regions, such as by sub-regions defined by the locus with the lowest active probability score.

In various instances, after an active region is identified, a localized haplotype assembly procedure may be performed. For instance, in each active region, all the piled up and/or overlapping reads may be assembled into a "De Bruijn Graph" (DBG). A DBG may be a directed graph based on all the reads that overlapped the selected active region, which active region may be about 200 or about 300 to about 400 or about 500 bases long or more, within which active region the presence and/or identity of variants are to be determined. In various instances, as indicated above, the active region can be extended, e.g., by including another about 100 or about 200 or more bases in each direction of the locus in question so as to generate an extended active region, such as where additional context surrounding a difference may be desired. Accordingly, it is from the active region window, extended or not, that all of the reads that have portions that overlap the active region are piled up, e.g., to produce a pileup, the overlapping portions are identified, and the read sequences are threaded into the haplotype caller system and are thereby assembled together in the form of a De Bruin graph, much like the pieces of a puzzle.

For any given active window there will be reads that form a pile up such that en masse the pile up will include a sequence pathway through which the overlapping regions of the various overlapping reads in the pile up covers the entire sequence within the active window. Hence, at any given locus in the active region, there will be a plurality of reads overlapping that locus, albeit any given read may not extend the entire active region. The result of this is that various regions of various reads within a pileup are employed by the DBG in determining whether a variant actually is present or not for any given locus in the sequence within the active region. As it is within the active window that this determination is being made, it is those portions of any given read within the borders of the active window that are considered, and those portions that are outside of the active window may be discarded.

As indicated, it is those sections of the reads that overlap the reference within the active region that are fed into the DBG system. The DBG system then assembles the reads like a puzzle into a graph, and then for each position in the sequence, it is determined based on the collection of overlapping reads for that position, whether there is a match or a mismatch for any given, and if there is a mismatch, what the probability of that mismatch is. For instance, where there are discrete places where segments of the reads in the pile up overlap each other, they may be aligned to one another based on their areas of matching, and from stringing or stitching the matching reads together, as determined by their points of matching, it can be established for each position within that segment, whether and to what extent the reads at any given position match or mismatch each other. Hence, if two or more reads being compiled line up and match each other identically for a while, a graph having a single string will result; however, when the two or more reads come to a point of difference, a branch in the graph will form, and two or more divergent strings will result, until matching between the two or more reads resumes.

Hence, the pathways through the graph are often not a straight line. For instance, where the k-mers of a read varies from the k-mers of the reference and/or the k-mers from one or more overlapping reads, e.g., in the pileup, a "bubble" will be formed in the graph at the point of difference resulting in two divergent strings that will continue along two different path lines until matching between the two sequences resumes. Each vertex may be given a weighted score identifying how many times the respective k-mers overlap in all of the reads in the pileup. Particularly, each pathway extending through the generated graph from one side to the other may be given a count. And where the same k-mers are generated from a multiplicity of reads, e.g., where each k-mer has the same sequence pattern, they may be accounted for in the graph by increasing the count for that pathway where the k-mer overlaps an already existing k-mer pathway. Hence, where the same k-mer is generated from a multiplicity of overlapping reads having the same sequence, the pattern of the pathway between the graph will be repeated over and over again and the count for traversing this pathway through the graph will be increased incrementally in correspondence therewith. In such an instance, the pattern is only recorded for the first instance of the k-mer, and the count is incrementally increased for each k-mer that repeats that pattern. In this mode the various reads in the pile up can be harvested to determine what variations occur and where.

In a manner such as this, a graph matrix may be formed by taking all possible N base k-mers, e.g., 10 base k-mers, which can be generated from each given read by sequentially walking the length of the read in ten base segments, where the beginning of each new ten base segment is offset by one base from the last generated 10 base segment. This procedure may then be repeated by doing the same for every read in the pile up within the active window. The generated k-mers may then be aligned with one another such that areas of identical matching between the generated k-mers are matched to the areas where they overlap, so as to build up a data structure, e.g., graph, that may then be scanned and the percentage of matching and mismatching may be determined. Particularly, the reference and any previously processed k-mers aligned therewith may be scanned with respect to the next generated k-mer to determine if the instant generated k-mer matches and/or overlaps any portion of a previously generated k-mer, and where it is found to match the instant generated k-mer can then be inserted into the graph at the appropriate position.

Once built, the graph can be scanned and it may be determined based on this matching whether any given SNPs and/or indels in the reads with respect to the reference are likely to be an actual variation in the subject's genetic code or the result of a processing or other error. For instance, if all or a significant portion of the k-mers, of all or a significant portion of all of the reads, in a given region include the same SNP and/or indel mismatch, but differ from the reference in the same manner, then it may be determined that there is an actually SNP and/or indel variation in the subject's genome as compared to the reference genome. However, if only a limited number of k-mers from a limited number of reads evidence the artifact, it is likely to be caused by machine and/or processing and/or other error and not indicative of a true variation at the position in question.

As indicated, where there is a suspected variance, a bubble will be formed within the graph. Specifically, where all of the k-mers within all of a given region of reads all match the reference, they will line up in such a manner as to form a linear graph. However, where there is a difference between the bases at a given locus, at that locus of difference that graph will branch. This branching may be at any position within the k-mer, and consequently at that point of difference the 10 base k-mer, including that difference, will diverge from the rest of the k-mers in the graph. In such an instance, a new node, forming a different pathway through the graph will be formed.

Hence, where everything may have been agreeing, e.g., the sequence in the given new k-mer being graphed is matching the sequence to which it aligns in the graph, up to the point of difference the pathway for that k-mer will match the pathway for the graph generally and will be linear, but post the point of difference, a new pathway through the graph will emerge to accommodate the difference represented in the sequence of the newly graphed k-mer. This divergence being represented by a new node within the graph. In such an instance, any new k-mers to be added to the graph that match the newly divergent pathway will increase the count at that node. Hence, for every read that supports the arc, the count will be increased incrementally.

In various of such instances, the k-mer and/or the read it represents will once again start matching, e.g., after the point of divergence, such that there is now a point of convergence where the k-mer begins matching the main pathway through the graph represented by the k-mers of the reference sequence. For instance, naturally after a while the read(s) that support the branched node should rejoin the graph over time. Thus, over time, the k-mers for that read will rejoin the main pathway again. More particularly, for an SNP at a given locus within a read, the k-mer starting at that SNP will diverge from the main graph and will stay separate for about 10 nodes, because there are 10 bases per k-mer that overlap that locus of mismatching between the read and the reference. Hence, for an SNP, at the 11th position, the k-mers covering that locus within the read will rejoin the main pathway as exact matching is resumed. Consequently, it will take ten shifts for the k-mers of a read having an SNP at a given locus to rejoin the main graph represented by the reference sequence.

As indicated above, there is typically one main path or line or backbone that is the reference path, and where there is a divergence a bubble is formed at a node where there is a difference between a read and the backbone graph. Thus, there are some reads that diverge from the backbone and form a bubble, which divergence may be indicative of the presence of a variant. As the graph is processed, bubbles within bubbles within bubbles may be formed along the reference backbone, so that they are stacked up and a plurality of pathways through the graph may be created. In such an instance, there may be a main path represented by the reference backbone, one path of a first divergence, and a further path of a second divergence within the first divergence, all within a given window, each pathway through the graph may represent an actual variation or may be an artifact such as caused by sequencing error, and/or PCR error, and/or a processing error, and the like.

Once such a graph has been produced, it must be determined which pathways through the graph represent actual variations present within the sample genome and which are mere artifacts. Albeit, it is expected that reads containing handling or machine errors will not be supported by the majority of reads in the sample pileup, however, this is not always the case. For instance, errors in PCR processing may typically be the result of a cloning mistake that occurs when preparing the DNA sample, such mistakes tend to result in an insertion and/or a deletion being added to the cloned sequence. Such indel errors may be more consistent among reads, and can wind up with generating multiple reads that have the same error from this mistake in PCR cloning. Consequently, a higher count line for such a point of divergence may result because of such errors.

Hence, once a graph matrix has been formed, with many paths through the graph, the next stage is to traverse and thereby extract all of the paths through the graph, e.g., left to right, e.g., so as to derive one or more candidate haplotypes therefrom. One path will be the reference backbone, but there will be other paths that follow various bubbles along the way. All paths must be traversed and their count tabulated. For instance, if the graph includes a pathway with a two-level bubble in one spot and a three-level bubble in another spot, there will be $(2 \times 3)^6$ paths through that graph. So, each of the paths will individually need to be extracted, which extracted paths are termed as candidate haplotypes. Such candidate haplotypes represent theories for what could really be representative of the subject's actual DNA that was sequenced, and the following processing steps, including one or more of haplotype alignment, read likelihood calculation, and/or genotyping may be employed to test these theories so as to find out the probabilities that anyone and/or each of these theories is correct. The implementation of a De Bruijn graph reconstruction therefore represents a way to reliably extract a good set of hypotheses to test.

For instance, in performing a variant call function, as disclosed herein, an active region identification operation may be implemented, such as for identifying places where multiple reads in a pile up within a given region disagree with a reference, e.g., a standard or chimeric reference, and for generating a window around the identified active region, so that only these regions may be selected for further processing. Additionally, localized haplotype assembly may take place, such as where, for each given active region, all the overlapping reads in the pile up may be assembled into a "De Bruijn graph" (DBG) matrix. From this DBG, various paths through the matrix may be extracted, where each path constitutes a candidate haplotype, e.g., hypotheses, for what the true DNA sequence may be on at least one strand.

Further, haplotype alignment may take place, such as where each extracted haplotype candidate may be aligned, e.g., Smith-Waterman aligned, back to the reference genome, so as to determine what variation(s) from the reference it implies. Furthermore, a read likelihood calculation may be performed, such as where each read may be tested against each haplotype, to estimate a probability of observing the read assuming the haplotype was the true original DNA sampled. Finally, a genotyping operation may be implement, and a variant call file produced.

As indicated above, any or all of these operations may be configured so as to be implemented in an optimized manner in software and/or in hardware, and in various instances, because of the resource intensive and time consuming nature of building a DBG matrix and extracting candidate haplotypes therefrom, and/or because of the resource intensive and time consuming nature of performing a haplotype alignment and/or a read likelihood calculation, which may include the engagement of an Hidden Markov Model (HMM) evaluation, these operations (e.g., localized haplotype assembly, and/or haplotype alignment, and/or read likelihood calculation) or a portion thereof may be configured so as to have one or more functions of their operation implemented in a hardwired form, such as for being performed in an accelerated manner by an integrated circuit as described herein. In various instances, these tasks may be configured to be implemented by one or more quantum circuits such as in a quantum computing device.

Accordingly, in various instances, the devices, systems, and methods for performing the same may be configured so as to perform a haplotype alignment and/or a read likelihood calculation. For instance, as indicated, each extracted haplotype may be aligned, such as Smith-Waterman aligned, back to the reference genome, so as to determine what variation(s) from the reference it implies. In various exemplary instances, scoring may take place, such as in accordance with the following exemplary scoring parameters: a match=20.0; a mismatch=−15.0; a gap open −26.0; and a gap extend=−1.1, other scoring parameters may be used. Accordingly, in this manner, a CIGAR strand may be generated and associated with the haplotype to produce an assembled haplotype, which assembled haplotype may eventually be used to identify variants. Accordingly, in a manner such as this, the likelihood of a given read being associated with a given haplotype may be calculated for all read/haplotype combinations. In such instances, the likelihood may be calculated using a Hidden Markov Model (HMM).

For instance, the various assembled haplotypes may be aligned in accordance with a dynamic programing model similar to a SW alignment. In such an instance, a virtual matrix may be generated such as where the candidate haplotype, e.g., generated by the DBG, may be positioned on one axis of a virtual array, and the read may be positioned on the other axis. The matrix may then be filled out with the scores generated by traversing the extracted paths through the graph and calculating the probabilities that any given path is the true path.

Hence, in such an instance, a difference in this alignment protocol from a typical SW alignment protocol is that with respect to finding the most likely path through the array, a maximum likelihood calculation may be used, such as a calculation performed by an HMM model that is configured to provide the total probability for alignment of the reads to the haplotype. Hence, an actual CIGAR strand alignment, in this instance, need not be produced. Rather all possible alignments are considered and their possibilities are summed. The pair HMM evaluation is resource and time intensive, and thus, implementing its operations within a hardwired configuration within an integrated circuit or via quantum circuits on a quantum computing platform is very advantageous.

For example, each read may be tested against each candidate haplotype, so as to estimate a probability of observing the read assuming the haplotype is the true representative of the original DNA sampled. In various instances, this calculation may be performed by evaluating a "pair hidden Markov model" (HMM), which may be configured to model the various possible ways the haplotype candidate might have been modified, such as by PCR or sequencing errors, and the like, and a variation introduced into the read observed. In such instances, the HMM evaluation may employ a dynamic programming method to calculate the total probability of any series of Markov state transitions arriving at the observed read in view of the possibility that any divergence in the read may be the result of an error model. Accordingly, such HMM calculations may be configured to analyze all the possible SNPs and Indels that could have been introduced into one or more of the reads, such as by amplification and/or sequencing artifacts.

Particularly, paired HMM considers in a virtual matrix all the possible alignments of the read to the reference candidate haplotypes along with a probability associated with each of them, where all probabilities are added up. The sum of all of the probabilities of all the variants along a given path is added up to get one overarching probability for each read. This process is then performed for every pair, for every haplotype, read pair. For example, if there is a six pile up cluster overlapping a given region, e.g., a region of six haplotype candidates, and if the pile up includes about one hundred reads, 600 HMM operations will then need to be performed. More particularly, if there are 6 haplotypes then there are going to be 6 branches through the path and the probability that each one is the correct pathway that matches the subject's actual genetic code for that region must be calculated. Consequently, each pathway for all of the reads may be considered, and the probability for each read that you would arrive at this given haplotype is to be calculated.

The pair Hidden Markov Model is an approximate model for how a true haplotype in the sampled DNA may transform into a possible different detected read. It has been observed that these types of transformations are a combination of SNPs and Indels that have been introduced into the genetic sample set by the PCR process, by one or more of the other sample preparation steps, and/or by an error caused by the sequencing process, and the like. As can be seen with respect to FIG. 2, to account for these types of errors, an underlying 3-state base model may be employed, such as where: (M=alignment match, I=insertion, D=deletion), further where any transition is possible except I<->D.

Figure 2:
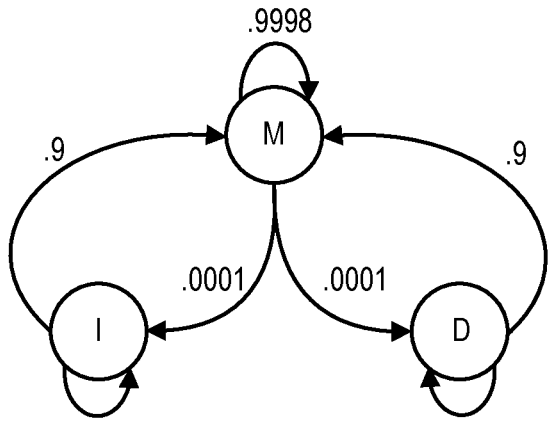
FIG. 2 depicts an HMM 3-state based model illustrating the transition probabilities of going from one state to another.

As can be seen with respect to FIG. 2, the 3-state base model transitions are not in a time sequence, but rather are in a sequence of progression through the candidate haplotype and read sequences, beginning at position 0 in each sequence, where the first base is position 1. A transition to M implies position +1 in both sequences; a transition to I implies position +1 in the read sequence only; and a transition to D implies position +1 in the haplotype sequence only. The same 3-state model may be configured to underlie the Smith-Waterman and/or Needleman-Wunsch alignments, as herein described, as well. Accordingly, such a 3-state model, as set forth herein, may be employed in a SW and/or NW process thereby allowing for affine gap (indel) scoring, in which gap opening (entering the I or D state) is assumed to be less likely than gap extension (remaining in the I or D state). Hence, in this instance, the pair HMM can be seen as alignment, and a CIGAR string may be produced to encode a sequence of the various state transitions.

In various instances, the 3-state base model may be complicated by allowing the transition probabilities to vary by position. For instance, the probabilities of all M transitions may be multiplied by the prior probabilities of observing the next read base given its base quality score, and the corresponding next haplotype base. In such an instance, the base quality scores may translate to a probability of a sequencing SNP error. When the two bases match, the prior probability is taken as one minus this error probability, and when they mismatch, it is taken as the error probability divided by 3, since there are 3 possible SNP results.

The above discussion is regarding an abstract "Markovish" model. In various instances, the maximum-likelihood transition sequence may also be determined, which is termed herein as an alignment, and may be performed using a Needleman-Wunsch or other dynamic programming algorithm. But, in various instances, in performing a variant calling function, as disclosed herein, the maximum likelihood alignment, or any particular alignment, need not be a primary concern. Rather, the total probability may be computed, for instance, by computing the total probability of observing the read given the haplotype, which is the sum of the probabilities of all possible transition paths through the graph, from read position zero at any haplotype position, to the read end position, at any haplotype position, each component path probability being simply the product of the various constituent transition probabilities.

Finding the sum of pathway probabilities may also be performed by employing a virtual array and using a dynamic programming algorithm, as described herein, such that in each cell of a (0 . . . N)×(0 . . . M) matrix, there are three probability values calculated, corresponding to M, D, and I transition states. (Or equivalently, there are 3 matrices.) The top row (read position zero) of the matrix may be initialized to probability 1.0 in the D states, and 0.0 in the I and M states; and the rest of the left column (haplotype position zero) may be initialized to all zeros. (In software, the initial D probabilities may be set near the double-precision max value, e.g. 2^1020, so as to avoid underflow, but this factor may be normalized out later.)

This 3-to-1 computation dependency restricts the order that cells may be computed. They can be computed left to right in each row, progressing through rows from top to bottom, or top to bottom in each column, progressing rightward. Additionally, they may be computed in anti-diagonal wavefronts, where the next step is to compute all cells (n,m) where n+m equals the incremented step number. This wavefront order has the advantage that all cells in the anti-diagonal may be computed independently of each other. The bottom row of the matrix then, at the final read position, may be configured to represent the completed alignments. In such an instance, the Haplotype Caller will work by summing the I and M probabilities of all bottom row cells. In various embodiments, the system may be set up so that no D transitions are permitted within the bottom row, or a D transition probability of 0.0 may be used there, so as to avoid double counting.

As described herein, in various instances, each HMM evaluation may operate on a sequence pair, such as on a candidate haplotype and a read pair. For instance, within a given active region, each of a set of haplotypes may be HMM-evaluated vs. each of a set of reads. In such an instance, the software and/or hardware input bandwidth may be reduced and/or minimized by transferring the set of reads and the set of haplotypes once, and letting the software and/or hardware generate the N×M pair operations. In certain instances, a Smith-Waterman evaluator may be configured to queue up individual HMM operations, each with its own copy of read and haplotype data. A Smith-Waterman (SW) alignment module may be configured to run the pair HMM calculation in linear space or may operate in log probability space. This is useful to keep precision across the huge range of probability values with fixed-point values. However, in other instances, floating point operations may be used.

There are three parallel multiplications (e.g., additions in log space), then two serial additions (~5-6 stage approximation pipelines), then an additional multiplication. In such an instance, the full pipeline may be about L=12-16 cycles long. The I & D calculations may be about half the length. The pipeline may be fed a multiplicity of input probabilities, such as 2 or 3 or 5 or 7 or more input probabilities each cycle, such as from one or more already computed neighboring cells (M and/or D from the left, M and/or I from above, and/or M and/or I and/or D from above-left). It may also include one or more haplotype bases, and/or one or more read bases such as with associated parameters, e.g., pre-processed parameters, each cycle. It outputs the M & I & D result set for one cell each cycle, after fall-through latency.

As indicated above, in performing a variant call function, as disclosed herein, a De Bruijn Graph may be formulated, and when all of the reads in a pile up are identical, the DBG will be linear. However, where there are differences, the graph will form "bubbles" that are indicative of regions of differences resulting in multiple paths diverging from matching the reference alignment and then later re-joining in matching alignment. From this DBG, various paths may be extracted, which form candidate haplotypes, e.g., hypotheses for what the true DNA sequence may be on at least one strand, which hypotheses may be tested by performing an HMM, or modified HMM, operation on the data. Further still, a genotyping function may be employed such as where the possible diploid combinations of the candidate haplotypes may be formed, and for each of them, a conditional probability of observing the entire read pileup may be calculated. These results may then be fed into a Bayesian formula module to calculate an absolute probability that each genotype is the truth, given the entire read pileup observed.

Hence, in accordance with the devices, systems, and methods of their use described herein, in various instances, a genotyping operation may be performed, which genotyping operation may be configured so as to be implemented in an optimized manner in software and/or in hardware and/or by a quantum processing unit. For instance, the possible diploid combinations of the candidate haplotypes may be formed, and for each combination, a conditional probability of observing the entire read pileup may be calculated, such as by using the constituent probabilities of observing each read given each haplotype from the pair HMM evaluation. The results of these calculations feed into a Bayesian formula so as to calculate an absolute probability that each genotype is the truth, given the entire read pileup observed.

Accordingly, in various aspects, the present disclosure is directed to a system for performing a haplotype or variant call operation on generated and/or supplied data so as to produce a variant call file with respect thereto. Specifically, as described herein above, in particular instances, a variant call file may be a digital or other such file that encodes the difference between one sequence and another, such as the difference between a sample sequence and a reference sequence. Specifically, in various instances, the variant call file may be a text file that sets forth or otherwise details the genetic and/or structural variations in a person's genetic makeup as compared to one or more reference genomes.

For instance, a haplotype is a set of genetic, e.g., DNA and/or RNA, variations, such as polymorphisms that reside in a person's chromosomes and as such may be passed on to offspring and thereby inherited together. Particularly, a haplotype can refer to a combination of alleles, e.g., one of a plurality of alternative forms of a gene such as may arise by mutation, which allelic variations are typically found at the same place on a chromosome. Hence, in determining the identity of a person's genome it is important to know which form of various different possible alleles a specific person's genetic sequence codes for. In particular instances, a haplotype may refer to one or more, e.g., a set, of nucleotide polymorphisms (e.g., SNPs) that may be found at the same position on the same chromosome.

Typically, in various embodiments, in order to determine the genotype, e.g., allelic haplotypes, for a subject, as described herein and above, a software based algorithm may be engaged, such as an algorithm employing a haplotype call program, e.g., GATK, for simultaneously determining SNPs and/or insertions and/or deletions, e.g., indels, in an individual's genetic sequence. In particular, the algorithm may involve one or more haplotype assembly protocols such as for local de-novo assembly of a haplotype in one or more active regions of the genetic sequence being processed. Such processing typically involves the deployment of a processing function called a Hidden Markov Model (HMM) that is a stochastic and/or statistical model used to exemplify randomly changing systems such as where it is assumed that future states within the system depend only on the present state and not on the sequence of events that precedes it.

In such instances, the system being modeled bears the characteristics or is otherwise assumed to be a Markov process with unobserved (hidden) states. In particular instances, the model may involve a simple dynamic Bayesian network. Particularly, with respect to determining genetic variation, in its simplest form, there is one of four possibilities for the identity of any given base in a sequence being processed, such as when comparing a segment of a reference sequence, e.g., a hypothetical haplotype, and that of a subject's DNA or RNA, e.g., a read derived from a sequencer. However, in order to determine such variation, in a first instance, a subject's DNA/RNA must be sequenced, e.g., via a Next Gen Sequencer ("NGS"), to produce a readout or "reads" that identify the subject's genetic code.

Next, once the subject's genome has been sequenced to produce one or more reads, the various reads, representative of the subject's DNA and/or RNA need to be mapped and/or aligned, as herein described above in great detail. The next step in the process then is to determine how the genes of the subject that have just been determined, e.g., having been mapped and/or aligned, vary from that of a prototypical reference sequence. In performing such analysis, therefore, it is assumed that the read potentially representing a given gene of a subject is a representation of the prototypical haplotype albeit with various SNPs and/or indels that are to presently be determined.

Specifically, in particular aspects, devices, systems, and/or methods for practicing the same, such as for performing a haplotype and/or variant call function, such as deploying an HMM function, for instance, in an accelerated haplotype caller is provided. In various instances, in order to overcome these and other such various problems known in the art, the HMM accelerator herein presented may be configured to be operated in a manner so as to be implemented in software, implemented in hardware, or a combination of being implemented and/or otherwise controlled in part by software and/or in part by hardware and/or may include quantum computing implementations. For instance, in a particular aspect, the disclosure is directed to a method by which data pertaining to the DNA and/or RNA sequence identity of a subject and/or how the subject's genetic information may differ from that of a reference genome may be determined.

In such an instance, the method may be performed by the implementation of a haplotype or variant call function, such as employing an HMM protocol. Particularly, the HMM function may be performed in hardware, software, or via one or more quantum circuits, such as on an accelerated device, in accordance with a method described herein. In such an instance, the HMM accelerator may be configured to receive and process the sequenced, mapped, and/or aligned data, to process the same, e.g., to produce a variant call file, as well as to transmit the processed data back throughout the system. Accordingly, the method may include deploying a system where data may be sent from a processor, such as a software-controlled CPU or GPU or even a QPU, to a haplotype caller implementing an accelerated HMM, which haplotype caller may be deployed on a microprocessor chip, such as an FPGA, ASIC, or structured ASIC or implemented by one or more quantum circuits. The method may further include the steps for processing the data to produce HMM result data, which results may then be fed back to the CPU and/or GPU and/or QPU.

Figure 3A:
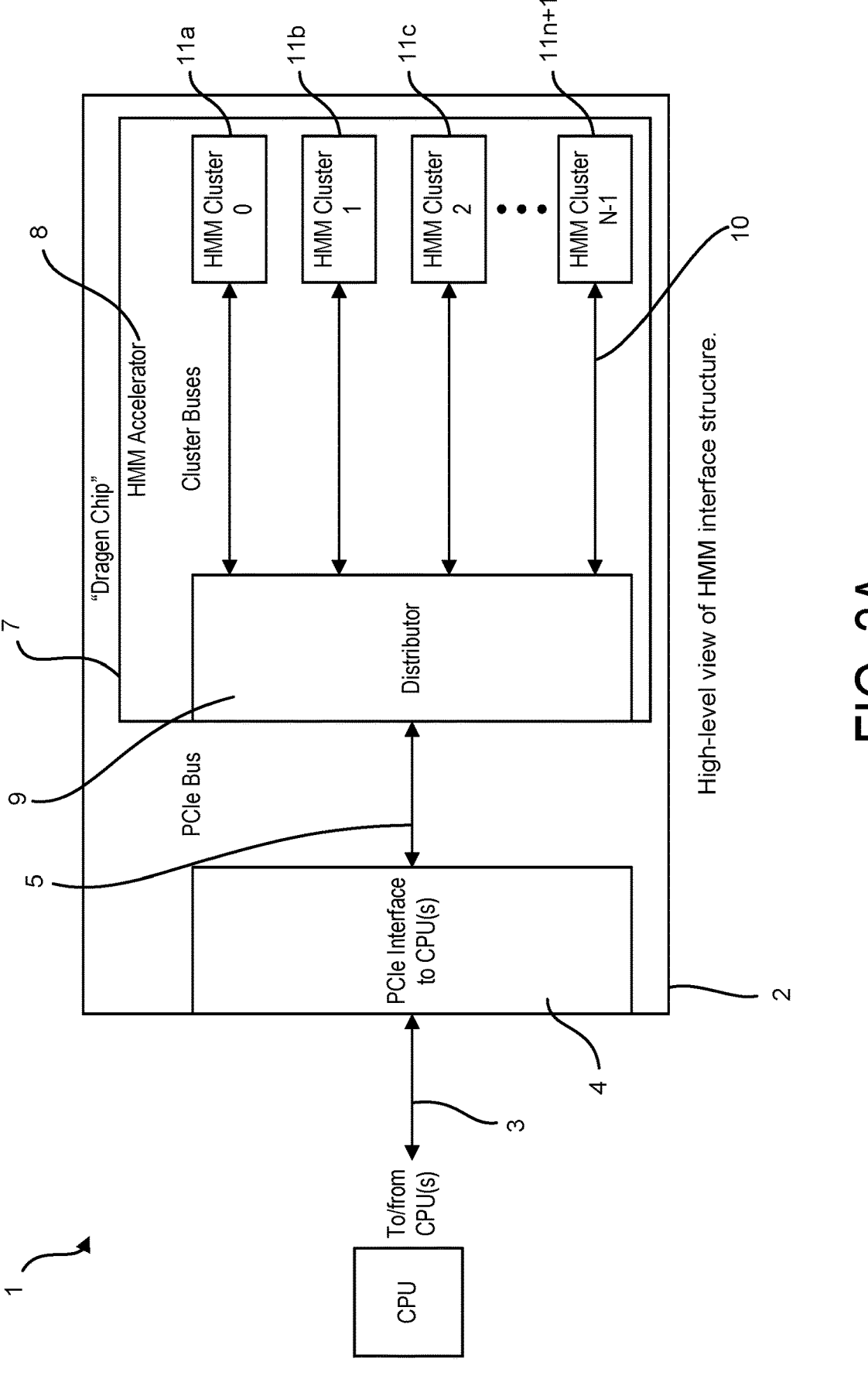
FIG. 3A depicts a high-level view of an integrated circuit of the disclosure including a HMM interface structure.

Particularly, in one embodiment, as can be seen with respect to FIG. 3A, a bioinformatics pipeline system including an HMM accelerator is provided. For instance, in one instance, the bioinformatics pipeline system may be configured as a variant call system 1. The system is illustrated as being implemented in hardware, but may also be implemented via one or more quantum circuits, such as of a quantum computing platform. Specifically, FIG. 3A provides a high-level view of an HMM interface structure. In particular embodiments, the variant call system 1 is configured to accelerate at least a portion of a variant call operation, such as an HMM operation. Hence, in various instances, the HMM system may be referenced herein as a part of the VC system 1. The system 1 includes a server having one or more more central processing units (CPU/GPU/QPU) 1000 configured for performing one or more routines related to the sequencing and/or processing of genetic information, such as for comparing a sequenced genetic sequence to one or more reference sequences.

Additionally, the system 1 includes a peripheral device 2, such as an expansion card, that includes a microchip 7, such as an FPGA, ASIC, or sASIC. In some instances, one or more quantum circuits may be provided and configured for performing the various operations set forth herein. It is also to be noted that the term ASIC may refer equally to a structured ASIC (sASIC), where appropriate. The peripheral device 2 includes an interconnect 3 and a bus interface 4, such as a parallel or serial bus, which connects the CPU/GPU/QPU 1000 with the chip 7. For instance, the device 2 may comprise a peripheral component interconnect, such as a PCI, PCI-X, PCIe, or QPI (quick path interconnect), and may include a bus interface 4, that is adapted to operably and/or communicably connect the CPU/GPU/QPU 1000 to the peripheral device 2, such as for low latency, high data transfer rates. Accordingly, in particular instances, the interface may be a peripheral component interconnect express (PCIe) 4 that is associated with the microchip 7, which microchip includes an HMM accelerator 8. For example, in particular instances, the HMM accelerator 8 is configured for performing an accelerated HMM function, such as where the HMM function, in certain embodiments, may at least partially be implemented in the hardware of the FPGA, AISC, or sASIC or via one or more suitably configured quantum circuits.

Specifically, FIG. 3A presents a high-level figure of an HMM accelerator 8 having an exemplary organization of one or more engines 13, such as a plurality of processing engines $13a$-$13_{m+1}$, for performing one or more processes of a variant call function, such as including an HMM task. Accordingly, the HMM accelerator 8 may be composed of a data distributor 9, e.g., CentCom, and one or a multiplicity of processing clusters $11$-$11_{n+1}$ that may be organized as or otherwise include one or more instances 13, such as where each instance may be configured as a processing engine, such as a small engine $13a$-$13_{m+1}$. For instance, the distributor 9 may be configured for receiving data, such as from the CPU/GPU/QPU 1000, and distributing or otherwise transferring that data to one or more of the multiplicity of HMM processing clusters 11.

Particularly, in certain embodiments, the distributor 9 may be positioned logically between the on-board PCIe interface 4 and the HMM accelerator module 8, such as where the interface 4 communicates with the distributor 9 such as over an interconnect or other suitably configured bus 5, e.g., PCIe bus. The distributor module 9 may be adapted for communicating with one or more HMM accelerator clusters 11 such as over one or more cluster buses 10. For instance, the HMM accelerator module 8 may be configured as or otherwise include an array of clusters $11a$-$11_{n+1}$, such as where each HMM cluster 11 may be configured as or otherwise includes a cluster hub 11 and/or may include one or more instances 13, which instance may be configured as a processing engine 13 that is adapted for performing one or more operations on data received thereby. Accordingly, in various embodiments, each cluster 11 may be formed as or otherwise include a cluster hub $11a$-$11n$+i, where each of the hubs may be operably associated with multiple HMM accelerator engine instances $13a$-$13_{m+1}$, such as where each cluster hub 11 may be configured for directing data to a plurality of the processing engines $13a$-$13_{m+1}$ within the cluster 11.

In various instances, the HMM accelerator 8 is configured for comparing each base of a subject's sequenced genetic code, such as in read format, with the various known or generated candidate haplotypes of a reference sequence and determining the probability that any given base at a position being considered either matches or doesn't match the relevant haplotype, e.g., the read includes an SNP, an insertion, or a deletion, thereby resulting in a variation of the base at the position being considered. Particularly, in various embodiments, the HMM accelerator 8 is configured to assign transition probabilities for the sequence of the bases of the read going between each of these states, Match ("M"), Insert ("I"), or Delete ("D") as set forth in FIG. 2 and as described in greater detail herein below.

More particularly, dependent on the configuration, the HMM acceleration function may be implemented in either software, such as by the CPU/GPU/QPU 1000 and/or microchip 7, and/or may be implemented in hardware and may be present within the microchip 7, such as positioned on the peripheral expansion card or board 2. In various embodiments, this functionality may be implemented partially as software, e.g., run by the CPU/GPU/QPU 1000, and partially as hardware, implemented on the chip 7 or via one or more quantum processing circuits. Accordingly, in various embodiments, the chip 7 may be present on the motherboard of the CPU/GPU/QPU 1000, or it may be part of the peripheral device 2, or both. Consequently, the HMM accelerator module 8 may include or otherwise be associated with various interfaces, e.g., 3, 5, 10, and/or 12 so as to allow the efficient transfer of data to and from the processing engines 13.

Accordingly, as can be seen with respect to FIGS. 2 and 3, in various embodiments, a microchip 7 configured for performing a variant, e.g., haplotype, call function is provided. The microchip 7 may be associated with a CPU/GPU/QPU 1000 such as directly coupled therewith, e.g., included on the motherboard of a computer, or indirectly coupled thereto, such as being included as part of a peripheral device 2 that is operably coupled to the CPU/GPU/QPU 1000, such as via one or more interconnects, e.g., 3, 4, 5, 10, and/or 12. In this instance, the microchip 7 is present on the peripheral device 2. It is to be understood that although configured as a microchip, the accelerator could also be configured as one or more quantum circuits of a quantum processing unit, wherein the quantum circuits are configured as one or more processing engines for performing one or more of the functions disclosed herein.

Hence, the peripheral device 2 may include a parallel or serial expansion bus 4 such as for connecting the peripheral device 2 to the central processing unit (CPU/GPU/QPU) 1000 of a computer and/or server, such as via an interface 3, e.g., DMA. In particular instances, the peripheral device 2 and/or serial expansion bus 4 may be a Peripheral Component Interconnect express (PCIe) that is configured to communicate with or otherwise include the microchip 7, such as via connection 5. As described herein, the microchip 7 may at least partially be configured as or may otherwise include an HMM accelerator 8. The HMM accelerator 8 may be configured as part of the microchip 7, e.g., as hardwired and/or as code to be run in association therewith, and is configured for performing a variant call function, such as for performing one or more operations of a Hidden Markov Model, on data supplied to the microchip 7 by the CPU/GPU/QPU 1000, such as over the PCIe interface 4. Likewise, once one or more variant call functions have been performed, e.g., one or more HMM operations run, the results thereof may be transferred from the HMM accelerator 8 of the chip 7 over the bus 4 to the CPU/GPU/QPU 1000, such as via connection 3.

For instance, in particular instances, a CPU/GPU/QPU 1000 for processing and/or transferring information and/or executing instructions is provided along with a microchip 7 that is at least partially configured as an HMM accelerator 8. The CPU/GPU/QPU 1000 communicates with the microchip 7 over an interface 5 that is adapted to facilitate the communication between the CPU/GPU/QPU 1000 and the HMM accelerator 8 of the microchip 7 and therefore may communicably connect the CPU/GPU/QPU 1000 to the HMM accelerator 8 that is part of the microchip 7. To facilitate these functions, the microchip 7 includes a distributor module 9, which may be a CentCom, that is configured for transferring data to a multiplicity of HMM engines 13, e.g., via one or more clusters 11, where each engine 13 is configured for receiving and processing the data, such as by running an HMM protocol thereon, computing final values, outputting the results thereof, and repeating the same. In various instances, the performance of an HMM protocol may include determining one or more transition probabilities, as described herein below. Particularly, each HMM engine 13 may be configured for performing a job such as including one or more of the generating and/or evaluating of an HMM virtual matrix to produce and output a final sum value with respect thereto, which final sum expresses the probable likelihood that the called base matches or is different from a corresponding base in a hypothetical haplotype sequence, as described herein below.

Figure 3B:
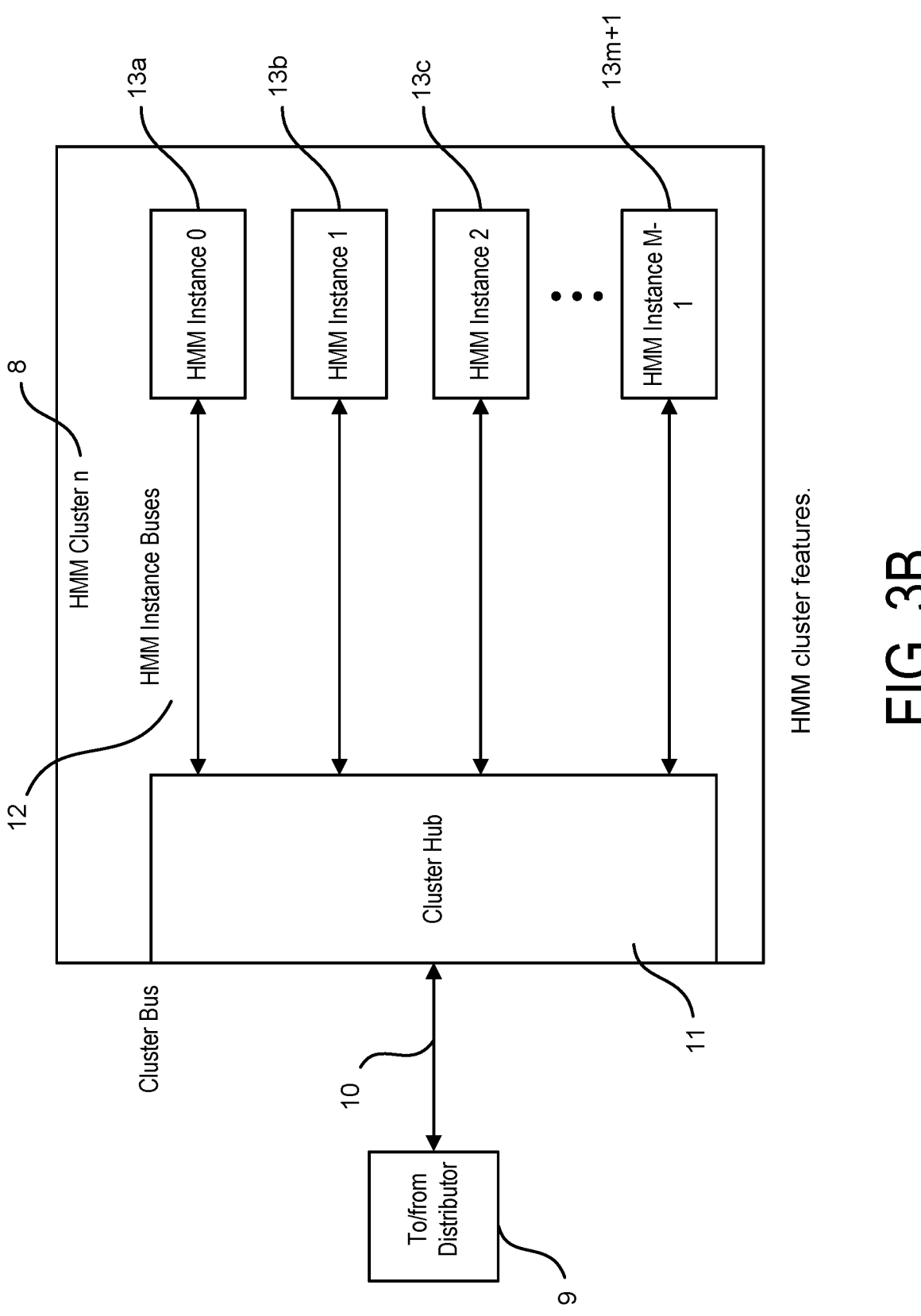
FIG. 3B depicts the integrated circuit of FIG. 3A, showing an HMM cluster features in greater detail.

FIG. 3B presents a detailed depiction of the HMM cluster 11 of FIG. 3A. In various embodiments, each HMM cluster 11 includes one or more HMM instances 13. One or a number of clusters may be provided, such as desired in accordance with the amount of resources provided, such as on the chip or quantum computing processor. Particularly, a HMM cluster may be provided, where the cluster is configured as a cluster hub 11. The cluster hub 11 takes the data pertaining to one or more jobs 20 from the distributor 9, and is further communicably connected to one or more, e.g., a plurality of, HMM instances 13, such as via one or more HMM instance busses 12, to which the cluster hub 11 transmits the job data 20.

The bandwidth for the transfer of data throughout the system may be relatively low bandwidth process, and once a job 20 is received, the system 1 may be configured for completing the job, such as without having to go off chip 7 for memory. In various embodiments, one job 20a is sent to one processing engine 13a at any given time, but several jobs 20a-n may be distributed by the cluster hub 11 to several different processing engines 13a-13$_{m+1}$, such as where each of the processing engines 13 will be working on a single job 20, e.g., a single comparison between one or more reads and one or more haplotype sequences, in parallel and at high speeds.

As described below, the performance of such a job 20 may typically involve the generation of a virtual matrix whereby the subject's "read" sequences may be compared to one or more, e.g., two, hypothetical haplotype sequences, so as to determine the differences there between. In such instances, a single job 20 may involve the processing of one or more matrices having a multiplicity of cells therein that need to be processed for each comparison being made, such as on a base by base basis. As the human genome is about 3 billion base pairs, there may be on the order of 1 to 2 billion different jobs to be performed when analyzing a 30× oversampling of a human genome (which is equitable to about 20 trillion cells in the matrices of all associated HMM jobs).

Accordingly, as described herein, each HMM instance 13 may be adapted so as to perform an HMM protocol, e.g., the generating and processing of an HMM matrix, on sequence data, such as data received thereby from the CPU/GPU/QPU 1000. For example, as explained above, in sequencing a subject's genetic material, such as DNA or RNA, the DNA/RNA is broken down into segments, such as up to about 100 bases in length. The identity of these 100 base segments are then determined, such as by an automated sequencer, and "read" into a FASTQ text based file or other format that stores both each base identity of the read along with a Phred quality score (e.g., typically a number between 0 and 63 in log scale, where a score of 0 indicates the least amount of confidence that the called base is correct, with scores between 20 to 45 generally being acceptable as relatively accurate).

Particularly, as indicated above, a Phred quality score is a quality indicator that measures the quality of the identification of the nucleobase identities generated by the sequencing processor, e.g., by the automated DNA/RNA sequencer. Hence, each read base includes its own quality, e.g., Phred, score based on what the sequencer evaluated the quality of that specific identification to be. The Phred represents the confidence with which the sequencer estimates that it got the called base identity correct. This Phred score is then used by the implemented HMM module 8, as described in detail below, to further determine the accuracy of each called base in the read as compared to the haplotype to which it has been mapped and/or aligned, such as by determining its Match, Insertion, and/or Deletion transition probabilities, e.g., in and out of the Match state. It is to be noted that in various embodiments, the system 1 may modify or otherwise adjust the initial Phred score prior to the performance of an HMM protocol thereon, such as by taking into account neighboring bases/scores and/or fragments of neighboring DNA and allowing such factors to influence the Phred score of the base, e.g., cell, under examination.

In such instances, as can be seen with respect to FIGS. 3A and 3B, the system 1, e.g., computer/quantum software, may determine and identify various active regions 500$n$ within the sequenced genome that may be explored and/or otherwise subjected to further processing as herein described, which may be broken down into jobs 20$n$ that may be parallelized amongst the various cores and available threads 1007 throughout the system 1. For instance, such active regions 500 may be identified as being sources of variation between the sequenced and reference genomes. Particularly, the CPU/GPU/QPU 1000 may have multiple threads 1007 running, identifying active regions 500$a$, 500$b$, and 500$c$, compiling and aggregating various different jobs 20$_n$ to be worked on, e.g., via a suitably configured aggregator 1008, based on the active region(s) 500$a$-$c$ currently being examined. Any suitable number of threads 1007 may be employed so as to allow the system 1 to run at maximum efficiency, e.g., the more threads present the less active time spent waiting.

Once identified, compiled, and/or aggregated, the threads 1007/1008 will then transfer the active jobs 20 to the data distributor 9, e.g., CentCom, of the HMM module 8, such as via PCIe interface 4, e.g., in a fire and forget manner, and will then move on to a different process while waiting for the HMM 8 to send the output data back so as to be matched back up to the corresponding active region 500 to which it maps and/or aligns. The data distributor 9 will then distribute the jobs 20 to the various different HMM clusters 11, such as on a job-by-job manner. If everything is running efficiently, this may be on a first in first out format, but such does not need to be the case. For instance, in various embodiments, raw jobs data and processed job results data may be sent through and across the system as they become available.

Figure 4:
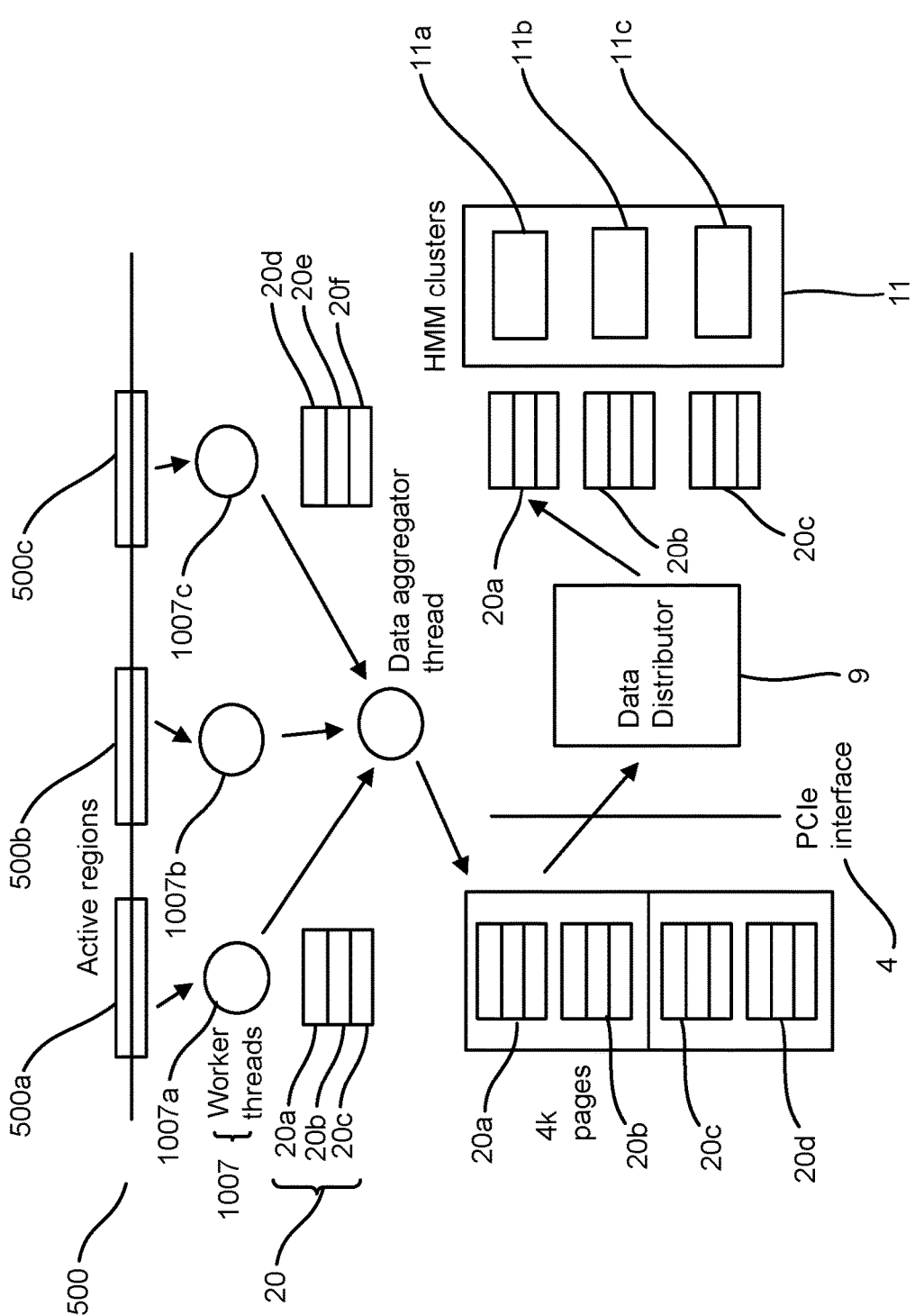
FIG. 4 depicts an overview of HMM related data flow throughout the system including both software and hardware interactions.

Particularly, as can be seen with respect to FIGS. 2, 3, and 4, the various job data 20 may be aggregated into 4K byte pages of data, which may be sent via the PCIe 4 to and through the CentCom 9 and on to the processing engines 13, e.g., via the clusters 11. The amount of data being sent may be more or less than 4K bytes, but will typically include about 100 HMM jobs per 4K (e.g., 1024) page of data. Particularly, these data then get digested by the data distributor 9 and are fed to each cluster 11, such as where one 4K page is sent to one cluster 11. However, such need not be the case as any given job 20 may be sent to any given cluster 11, based on the clusters that become available and when.

Accordingly, the cluster 11 approach as presented here efficiently distributes incoming data to the processing engines 13 at high-speed. Specifically, as data arrives at the PCIe interface 4 from the CPU/GPU/QPU 1000, e.g., over DMA connection 3, the received data may then be sent over the PCIe bus 5 to the CentCom distributor 9 of the variant caller microchip 7. The distributor 9 then sends the data to one or more HMM processing clusters 11, such as over one or more cluster dedicated buses 10, which cluster 11 may then transmit the data to one or more processing instances 13, e.g., via one or more instance buses 12, such as for processing. In this instance, the PCIe interface 4 is adapted to provide data through the peripheral expansion bus 5, distributor 9, and/or cluster 10 and/or instance 12 busses at a rapid rate, such as at a rate that can keep one or more, e.g., all, of the HMM accelerator instances 13$_{a\text{-}(m+1)}$ within one or more, e.g., all, of the HMM clusters 11$_{a(n+1)}$ busy, such as over a prolonged period of time, e.g., full time, during the period over which the system 1 is being run, the jobs 20 are being processed, and whilst also keeping up with the output of the processed HMM data that is to be sent back to one or more CPUs 1000, over the PCIe interface 4.

For instance, any inefficiency in the interfaces 3, 5, 10, and/or 12 that leads to idle time for one or more of the HMM accelerator instances 13 may directly add to the overall processing time of the system 1. Particularly, when analyzing a human genome, there may be on the order of two or more billion different jobs 20 that need to be distributed to the various HMM clusters 11 and processed over the course of a time period, such as under 1 hour, under 45 minutes, under 30 minutes under 30 minutes including 15 minutes, 10 minutes, 5 minutes, or less.

Accordingly, FIG. 4 sets forth an overview of an exemplary data flow throughout the software and/or hardware of the system 1, as described generally above. As can be seen with respect to FIG. 4, the system 1 may be configured in part to transfer data, such as between the PCIe interface 4 and the distributor 9, e.g., CentCom, such as over the PCIe bus 5. Additionally, the system 1 may further be configured in part to transfer the received data, such as between the distributor 9 and the one or more HMM clusters 11, such as over the one or more cluster buses 10. Hence, in various embodiments, the HMM accelerator 8 may include one or more clusters 11, such as one or more clusters 11 configured for performing one or more processes of an HMM function. In such an instance, there is an interface, such as a cluster bus 10, that connects the CentCom 9 to the HMM cluster 11.

Figure 5:
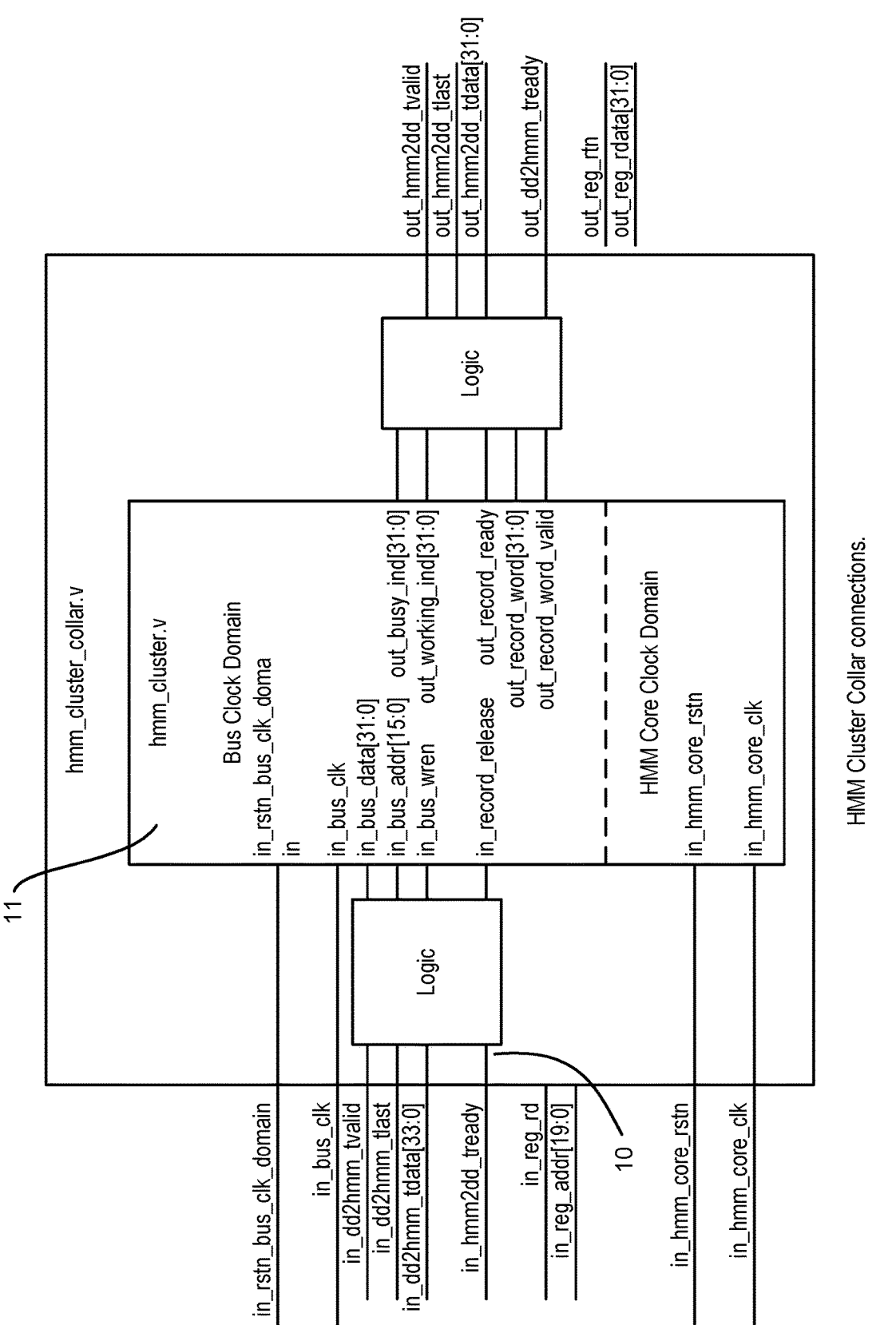
FIG. 5 depicts exemplary HMM cluster collar connections.

For instance, FIG. 5 is a high-level diagram depicting the interface in to and out of the HMM module 8, such as into and out of a cluster module. As can be seen with respect to FIG. 6, each HMM cluster 11 may be configured to communicate with, e.g., receive data from and/or send final result data, e.g., sum data, to the CentCom data distributor 9 through a dedicated cluster bus 10. Particularly, any suitable interface or bus 5 may be provided so long as it allows the PCIe interface 4 to communicate with the data distributor 9. More particularly, the bus 5 may be an interconnect that includes the interpretation logic useful in talking to the data distributor 9, which interpretation logic may be configured to accommodate any protocol employed to provide this functionality. Specifically, in various instances, the interconnect may be configured as a PCIe bus 5.

Additionally, the cluster 11 may be configured such that single or multiple clock domains may be employed therein, and hence, one or more clocks may be present within the cluster 11. In particular instances, multiple clock domains may be provided. For example, a slower clock may be provided, such as for communications, e.g., to and from the cluster 11. Additionally, a faster, e.g., a high speed, clock may be provided which may be employed by the HMM instances 13 for use in performing the various state calculations described herein.

Figure 6:
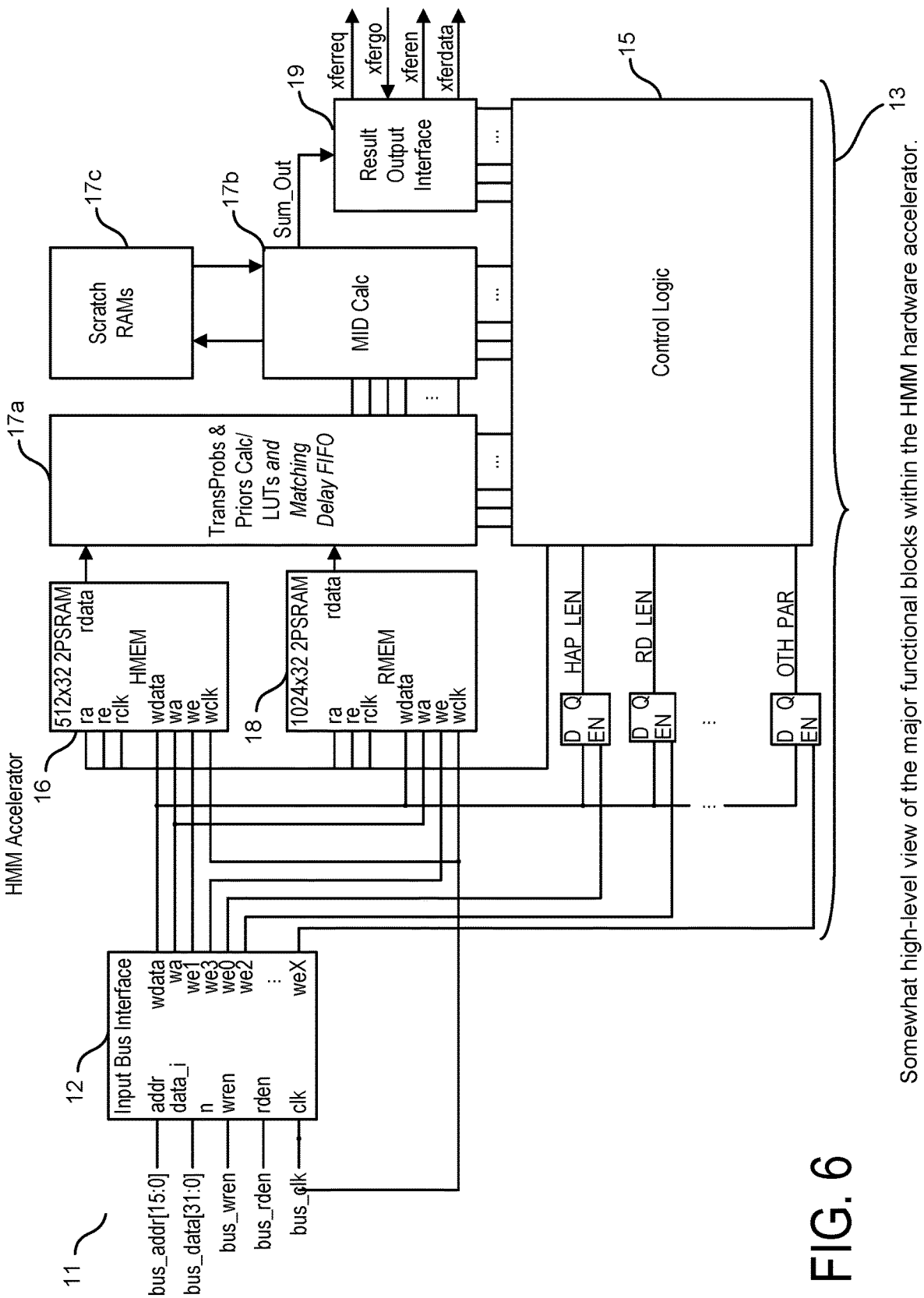
FIG. 6 depicts a high-level view of the major functional blocks within an exemplary HMM hardware accelerator.

Particularly, in various embodiments, as can be seen with respect to FIG. 6, the system 1 may be set up such that, in a first instance, as the data distributor 9 leverages the existing CentCom IP, a collar, such as a gasket, may be provided, where the gasket is configured for translating signals to and from the CentCom interface 5 from and to the HMM cluster interface or bus 10. For instance, an HMM cluster bus 10 may communicably and/or operably connect the CPU/GPU 1000 to the various clusters 11 of the HMM accelerator module 8. Hence, as can be seen with respect to FIG. 6, structured write and/or read data for each haplotype and/or for each read may be sent throughout the system 1.

Following a job 20 being input into the HMM engine, an HMM engine 13 may typically start either: a) immediately, if it is IDLE, or b) after it has completed its currently assigned task. It is to be noted that each HMM accelerator engine 13 can handle ping and pong inputs (e.g., can be working on one data set while the other is being loaded), thus minimizing downtime between jobs. Additionally, the HMM cluster collar 11 may be configured to automatically take the input job 20 sent by the data distributor 9 and assign it to one of the HMM engine instances 13 in the cluster 11 that can receive a new job. There need not be a control on the software side that can select a specific HMM engine instance 13 for a specific job 20. However, in various instances, the software can be configured to control such instances.

Accordingly, in view of the above, the system 1 may be streamlined when transferring the results data back to the CPU/GPU/QPU, and because of this efficiency there is not much data that needs to go back to the CPU/GPU/QPU to achieve the usefulness of the results. This allows the system to achieve about a 30 minute or less, such as about a 25 or about a 20 minute or less, for instance, about a 18 or about a 15 minute or less, including about a 10 or about a 7 minute or less, even about a 5 or about a 3 minute or less variant call operation, dependent on the system configuration.

FIG. 6 presents a high-level view of various functional blocks within an exemplary HMM engine 13 within a hardware accelerator 8, on the FPGA or ASIC 7. Specifically, within the hardware HMM accelerator 8 there are multiple clusters 11, and within each cluster 11 there are multiple engines 13. FIG. 6 presents a single instance of an HMM engine 13. As can be seen with respect to FIG. 6, the engine 13 may include an instance bus interface 12, a plurality of memories, e.g., an HMEM 16 and an RMEM 18, various other components 17, HMM control logic 15, as well as a result output interface 19. Particularly, on the engine side, the HMM instance bus 12 is operably connected to the memories, HMEM 16 and RMEM 18, and may include interface logic that communicates with the cluster hub 11, which hub is in communications with the distributor 9, which in turn is communicating with the PCIe interface 4 that communicates with the variant call software being run by the CPU/GPU and/or server 1000. The HMM instance bus 12, therefore, receives the data from the CPU 1000 and loads it into one or more of the memories, e.g., the HMEM and RMEM. This configuration may also be implemented in one or more quantum circuits and adapted accordingly.

In these instances, enough memory space should be allocated such that at least one or two or more haplotypes, e.g., two haplotypes, may be loaded, e.g., in the HMEM 16, per given read sequence that is loaded, e.g., into the RMEM 18, which when multiple haplotypes are loaded results in an easing of the burden on the PCIe bus 5 bandwidth. In particular instances, two haplotypes and two read sequences may be loaded into their respective memories, which would allow the four sequences to be processed together in all relevant combinations. In other instances four, or eight, or sixteen sequences, e.g., pairs of sequences, may be loaded, and in like manner be processed in combination, such as to further ease the bandwidth when desired.

Additionally, enough memory may be reserved such that a ping-pong structure may be implemented therein such that once the memories are loaded with a new job 20a, such as on the ping side of the memory, a new job signal is indicated, and the control logic 15 may begin processing the new job 20a, such as by generating the matrix and performing the requisite calculations, as described herein and below. Accordingly, this leaves the pong side of the memory available so as to be loaded up with another job 20b, which may be loaded therein while the first job 20a is being processed, such that as the first job 20a is finished, the second job 20b may immediately begin to be processed by the control logic 15.

In such an instance, the matrix for job 20b may be preprocessed so that there is virtually no down time, e.g., one or two clock cycles, from the ending of processing of the first job 20a, and the beginning of processing of the second job 20b. Hence, when utilizing both the ping and pong side of the memory structures, the HMEM 16 may typically store 4 haplotype sequences, e.g., two a piece, and the RMEM 18 may typically store 2 read sequences. This ping-pong configuration is useful because it simply requires a little extra memory space, but allows for a doubling of the throughput of the engine 13.

During and/or after processing the memories 16, 18 feed into the transition probabilities calculator and lookup table (LUT) block 17a, which is configured for calculating various information related to "Priors" data, as explained below, which in turn feeds the Prior results data into the M, I, and D state calculator block 17b, for use when calculating transition probabilities. One or more scratch RAMs 17c may also be included, such as for holding the M, I, and D states at the boundary of the swath, e.g., the values of the bottom row of the processing swath, which as indicated, in various instances, may be any suitable amount of cells, e.g., about 10 cells, in length so as to be commensurate with the length of the swath 35.

Additionally, a separate results output interface block 19 may be included so that when the sums are finished they, e.g., a 4 32-bit word, can immediately be transmitted back to the variant call software of the CPU/GPU/QPU 1000. It is to be noted that this configuration may be adapted so that the system 1, specifically the M, I, and D calculator 17b is not held up waiting for the output interface 19 to clear, e.g., so long as it does not take as long to clear the results as it does to perform the job 20. Hence, in this configuration, there may be three pipeline steps functioning in concert to make an overall systems pipeline, such as loading the memory, performing the MID calculations, and outputting the results. Further, it is noted that any given HMM engine 13 is one of many with their own output interface 19, however they may share a common interface 10 back to the data distributor 9. Hence, the cluster hub 11 will include management capabilities to manage the transfer ("xfer") of information through the HMM accelerator 8 so as to avoid collisions.

Accordingly, the following details the processes being performed within each module of the HMM engines 13 as it receives the haplotype and read sequence data, processes it, and outputs results data pertaining to the same, as generally outlined above. Specifically, the high-bandwidth computations in the HMM engine 13, within the HMM cluster 11, are directed to computing and/or updating the match (M), insert (I), and delete (D) state values, which are employed in determining whether the particular read being examined matches the haplotype reference as well as the extent of the same, as described above.

Particularly, the read along with the Phred score and GOP value for each base in the read is transmitted to the cluster 11 from the distributor 9 and is thereby assigned to a particular processing engine 13 for processing. These data are then used by the M, I, and D calculator 17 of the processing engine 13 to determine whether the called base in the read is more or less likely to be correct and/or to be a match to its respective base in the haplotype, or to be the product of a variation, e.g., an insert or deletion; and/or if there is a variation, whether such variation is the likely result of a true variability in the haplotype or rather an artifact of an error in the sequence generating and/or mapping and/or aligning systems.

As indicated above, a part of such analysis includes the MID calculator 17 determining the transition probabilities from one base to another in the read going from one M, I, or D state to another in comparison to the reference, such as from a matching state to another matching state, or a matching state to either an insertion state or to a deletion state. In making such determinations each of the associated transition probabilities is determined and considered when evaluating whether any observed variation between the read and the reference is a true variation and not just some machine or processing error. For these purposes, the Phred score for each base being considered is useful in determining the transition probabilities in and out of the match state, such as going from a match state to an insert or deletion, e.g., a gapped, state in the comparison. Likewise, the transition probabilities of continuing a gapped state or going from a gapped state, e.g., an insert or deletion state, back to a match state are also determined. In particular instances, the probabilities in or out of the delete or insert state, e.g., exiting a gap continuation state, may be a fixed value, and may be referenced herein as the gap continuation probability or penalty. Nevertheless, in various instances, such gap continuation penalties may be floating and therefore subject to change dependent on the accuracy demands of the system configuration.

Figure 7:
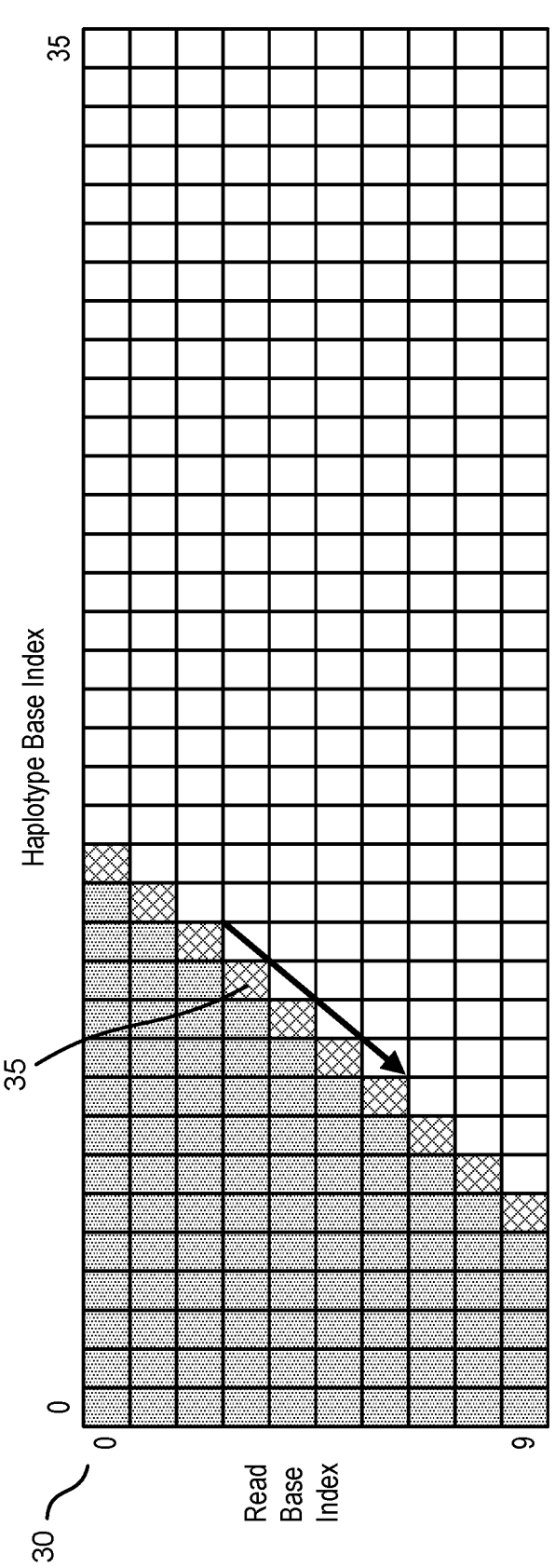
FIG. 7 depicts an exemplary HMM matrix structure and hardware processing flow.
Figure 8:
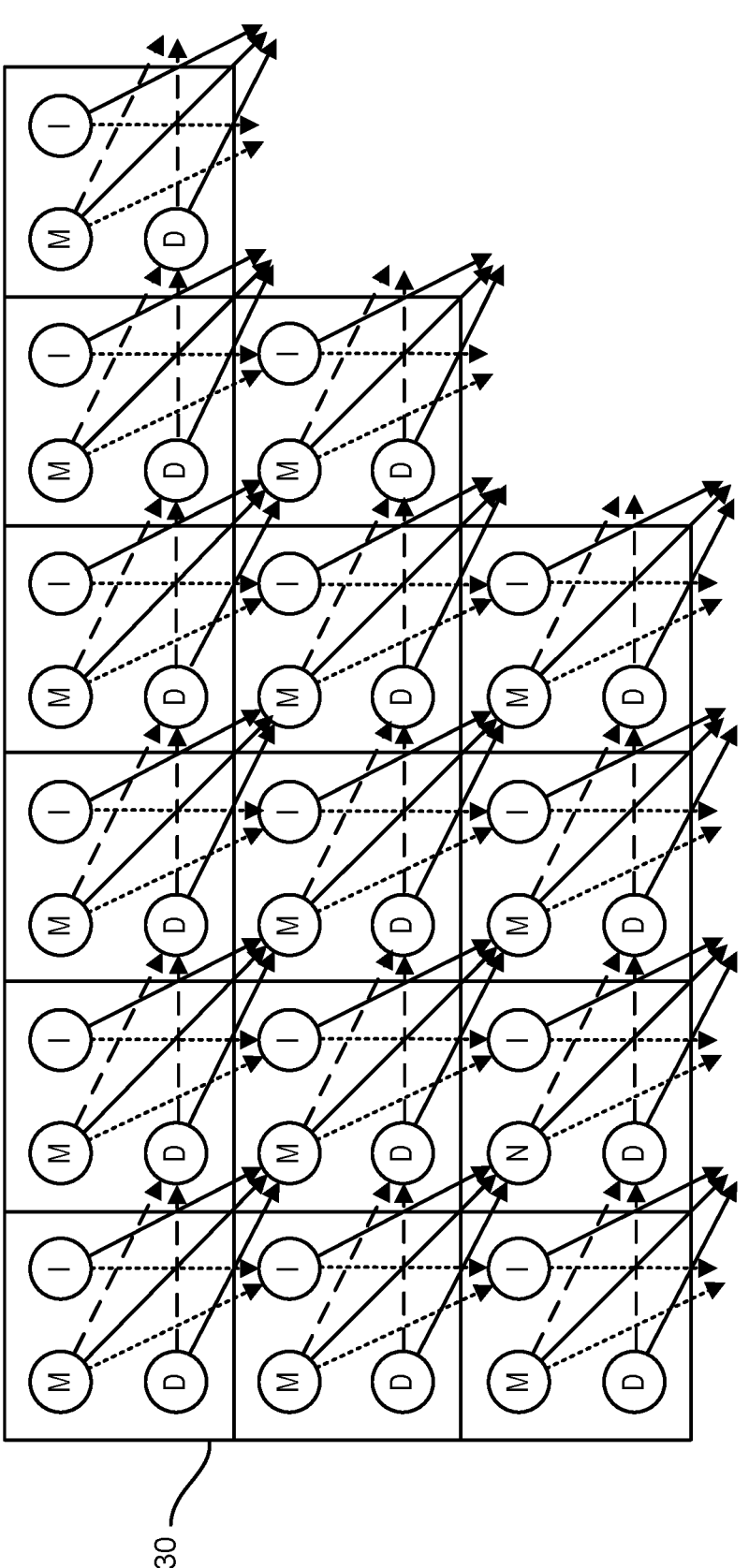
FIG. 8 depicts an enlarged view of a portion of FIG. 2 showing the data flow and dependencies between nearby cells in the HMM M, I, and D state computations within the matrix.

Accordingly, as depicted with respect to FIGS. 7 and 8 each of the M, I, and D state values are computed for each possible read and haplotype base pairing. In such an instance, a virtual matrix 30 of cells containing the read sequence being evaluated on one axis of the matrix and the associated haplotype sequence on the other axis may be formed, such as where each cell in the matrix represents a base position in the read and haplotype reference. Hence, if the read and haplotype sequences are each 100 bases in length, the matrix 30 will include 100 by 100 cells, a given portion of which may need to be processed in order to determine the likelihood and/or extent to which this particular read matches up with this particular reference. Hence, once virtually formed, the matrix 30 may then be used to determine the various state transitions that take place when moving from one base in the read sequence to another and comparing the same to that of the haplotype sequence, such as depicted in FIGS. 7 and 8. Specifically, the processing engine 13 is configured such that a multiplicity of cells may be processed in parallel and/or sequential fashion when traversing the matrix with the control logic 15. For instance, as depicted in FIG. 7, a virtual processing swath 35 is propagated and moves across and down the matrix 30, such as from left to right, processing the individual cells of the matrix 30 down the right to left diagonal.

More specifically, as can be seen with respect to FIG. 7, each individual virtual cell within the matrix 30 includes an M, I, and D state value that needs to be calculated so as to assess the nature of the identity of the called base, and as depicted in FIG. 7 the data dependencies for each cell in this process may clearly be seen. Hence, for determining a given M state of a present cell being processed, the Match, Insert, and Delete states of the cell diagonally above the present cell need to be pushed into the present cell and used in the calculation of the M state of the cell presently being calculated (e.g., thus, the diagonal downwards, forwards progression through the matrix is indicative of matching).

However, for determining the I state, only the Match and Insert states for the cell directly above the present cell need be pushed into the present cell being processed (thus, the vertical downwards "gapped" progression when continuing in an insertion state). Likewise, for determining the D state, only the Match and Delete states for the cell directly left of the present cell need be pushed into the present cell (thus, the horizontal cross-wards "gapped" progression when continuing in a deletion state). As can be seen with respect to FIG. 7, after computation of cell 1 (the shaded cell in the top most row) begins, the processing of cell 2 (the shaded cell in the second row) can also begin, without waiting for any results from cell 1, because there is no data dependencies between this cell in row 2 and the cell of row 1 where processing begins. This forms a reverse diagonal 35 where processing proceeds downwards and to the left, as shown by the arrow. This reverse diagonal 35 processing approach increases the processing efficiency and throughput of the overall system. Likewise, the data generated in cell 1, can immediately be pushed forward to the cell down and forward to the right of the top most cell 1, thereby advancing the swath 35 forward.

For instance, FIG. 7 depicts an exemplary HMM matrix structure 35 showing the hardware processing flow. The matrix 35 includes the haplotype base index, e.g., containing 36 bases, positioned to run along the top edge of the horizontal axis, and further includes the base read index, e.g., 10 bases, positioned to fall along the side edge of the vertical axis in such a manner to from a structure of cells where a selection of the cells may be populated with an M, I, and D probability state, and the transition probabilities of transitioning from the present state to a neighboring state. In such an instance, as described in greater detail above, a move from a match state to a match state results in a forwards diagonal progression through the matrix 30, while moving from a match state to an insertion state results in a vertical downwards progressing gap, and a move from a match state to a deletion state results in a horizontal progressing gap. Hence, as depicted in FIG. 8, for a given cell, when determining the match, insert, and delete states for each cell, the match, insert, and delete probabilities of its three adjoining cells are employed.

The downwards arrow in FIG. 7 represents the parallel and sequential nature of the processing engine(s) that are configured so as to produce a processing swath or wave 35 that moves progressively along the virtual matrix in accordance with the data dependencies, see FIGS. 7 and 8, for determining the M, I, and D states for each particular cell in the structure 30. Accordingly, in certain instances, it may be desirable to calculate the identities of each cell in a downwards and diagonal manner, as explained above, rather than simply calculating each cell along a vertical or horizontal axis exclusively, although this can be done if desired. This is due to the increased wait time, e.g., latency, that would be required when processing the virtual cells of the matrix 35 individually and sequentially along the vertical or horizontal axis alone, such as via the hardware configuration.

For instance, in such an instance, when moving linearly and sequentially through the virtual matrix 30, such as in a row by row or column by column manner, in order to process each new cell the state computations of each preceding cell would have to be completed, thereby increasing latency time overall. However, when propagating the M, I, D probabilities of each new cell in a downwards and diagonal fashion, the system 1 does not have to wait for the processing of its preceding cell, e.g., of row one, to complete before beginning the processing of an adjoining cell in row two of the matrix. This allows for parallel and sequential processing of cells in a diagonal arrangement to occur, and further allows the various computational delays of the pipeline associated with the M, I, and D state calculations to be hidden. Accordingly, as the swath 35 moves across the matrix 30 from left to right, the computational processing moves diagonally downwards, e.g., towards the left (as shown by the arrow in FIG. 7). This configuration may be particularly useful for hardware and/or quantum circuit implementations, such as where the memory and/or clock-by-clock latency are a primary concern.

In these configurations, the actual value output from each cell of an HMM engine 13, e.g., after having calculated the entire matrix 30, may be a bottom row (e.g., Row 35 of FIG. 16) containing M, I, and D states, where the M and I states may be summed (the D states may be ignored at this point having already fulfilled their function in processing the calculations above), so as to produce a final sum value that may be a single probability that estimates, for each read and haplotype index, the probability of observing the read, e.g., assuming the haplotype was the true original DNA sampled.

Particularly, the outcome of the processing of the matrix 30, e.g., of FIG. 7, may be a single value representing the probability that the read is an actual representation of that haplotype. This probability is a value between 0 and 1 and is formed by summing all of the M and I states from the bottom row of cells in the HMM matrix 30. Essentially, what is being assessed is the possibility that something could have gone wrong in the sequencer, or associated DNA preparation methods prior to sequencing, so as to incorrectly produce a mismatch, insertion, or deletion into the read that is not actually present within the subject's genetic sequence. In such an instance, the read is not a true reflection of the subject's actual DNA.

Hence, accounting for such production errors, it can be determined what any given read actually represents with respect to the haplotype, and thereby allows the system to better determine how the subject's genetic sequence, e.g., en masse, may differ from that of a reference sequence. For instance, many haplotypes may be run against many read sequences, generating scores for all of them, and determining based on which matches have the best scores, what the actual genomic sequence identity of the individual is and/or how it truly varies from a reference genome.

More particularly, FIG. 8 depicts an enlarged view of a portion of the HMM state matrix 30 from FIG. 7. As shown in FIG. 8, given the internal composition of each cell in the matrix 30, as well as the structure of the matrix as a whole, the M, I, and D state probability for any given "new" cell being calculated is dependent on the M, I, and D states of several of its surrounding neighbors that have already been calculated. Particularly, as shown in greater detail with respect to FIGS. 1 and 16, in an exemplary configuration, there may be an approximately a 0.9998 probability of going from a match state to another match state, and there may be only a 0.0001 probability (gap open penalty) of going from a match state to either an insertion or a deletion, e.g., gapped, state. Further, when in either a gapped insertion or gapped deletion state there may be only a 0.1 probability (gap extension or continuation penalty) of staying in that gapped state, while there is a 0.9 probability of returning to a match state. It is to be noted that according to this model, all of the probabilities in to or out of a given state should sum to one. Particularly, the processing of the matrix 30 revolves around calculating the transition probabilities, accounting for the various gap open or gap continuation penalties and a final sum is calculated.

Figure 16:
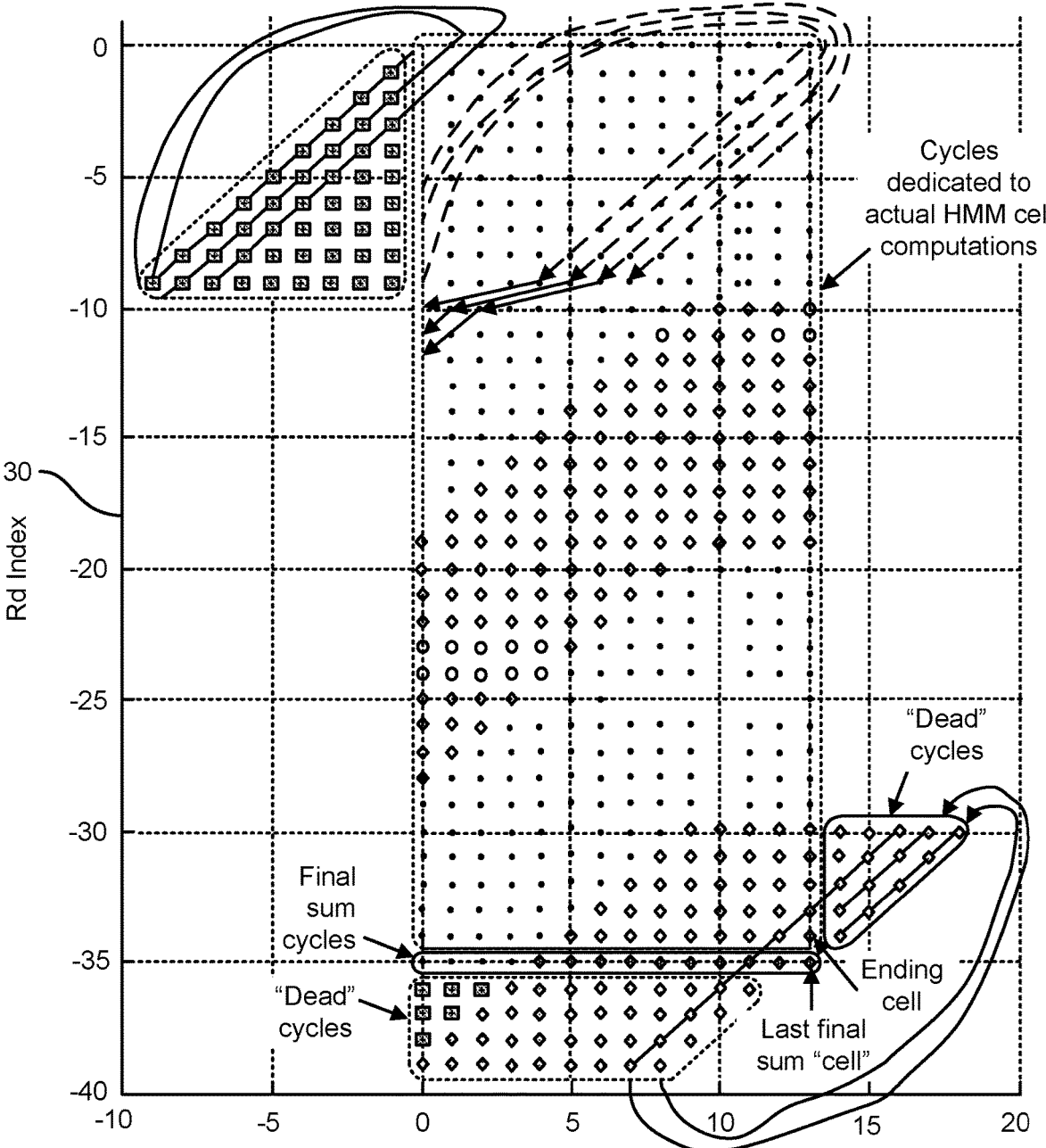
FIG. 16 depicts an exemplary theoretical HMM matrix and illustrates how such an HMM matrix may be traversed.

Hence, these calculated state transition probabilities are derived mainly from the directly adjoining cells in the matrix 30, such as from the cells that are immediately to the left of, the top of, and diagonally up and left of that given cell presently being calculated, as seen in FIGS. 8 and 16. Additionally, the state transition probabilities may in part be derived from the "Phred" quality score that accompanies each read base. These transition probabilities, therefore, are useful in computing the M, I, and D state values for that particular cell, and likewise for any associated new cell being calculated. It is to be noted that as described herein, the gap open and gap continuation penalties may be fixed values, however, in various instances, the gap open and gap continuation penalties may be variable and therefore programmable within the system, albeit by employing additional hardware resources dedicated to determining such variable transition probability calculations. Such instances may be useful where greater accuracy is desired. Nevertheless, when such values are assumed to be constant, smaller resource usage and/or chip size may be achieved, leading to greater processing speed, as explained below.

Accordingly, there is a multiplicity of calculations and/or other mathematical computations, such as multiplications and/or additions, which are involved in deriving each new M, I, and D state value. In such an instance, such as for calculating maximum throughput, the primitive mathematical computations involved in each M, I, and D transition state calculation may be pipelined. Such pipelining may be configured in a way that the corresponding clock frequencies are high, but where the pipeline depth may be non-trivial. Further, such a pipeline may be configured to have a finite depth, and in such instances it may take more than one clock cycle to complete the operations.

For instance, these computations may be run at high speeds inside the processor 7, such as at about 300 MHz. This may be achieved such as by pipelining the FPGA or ASIC heavily with registers so little mathematical computation occurs between each flip-flop. This pipeline structure results in multiple cycles of latency in going from the input of the match state to the output, but given the reverse diagonal computing structure, set forth in FIG. 7 above, these latencies may be hidden over the entire HMM matrix 30, such as where each cell represents one clock cycle.

Hence, the number of M, I, and D state calculations may be limited. In such an instance, the processing engine 13 may be configured in such a manner that a grouping, e.g., swath 35, of cells in a number of rows of the matrix 30 may be processed as a group (such as in a down-and-left-diagonal fashion as illustrated by the arrow in FIG. 7) before proceeding to the processing of a second swath below, e.g., where the second swath contains the same number of cells in rows to be processed as the first. In a manner such as this, a hardware implementation of an accelerator 8, as described herein, may be adapted so as to make the overall system more efficient, as described above.

Figure 9:
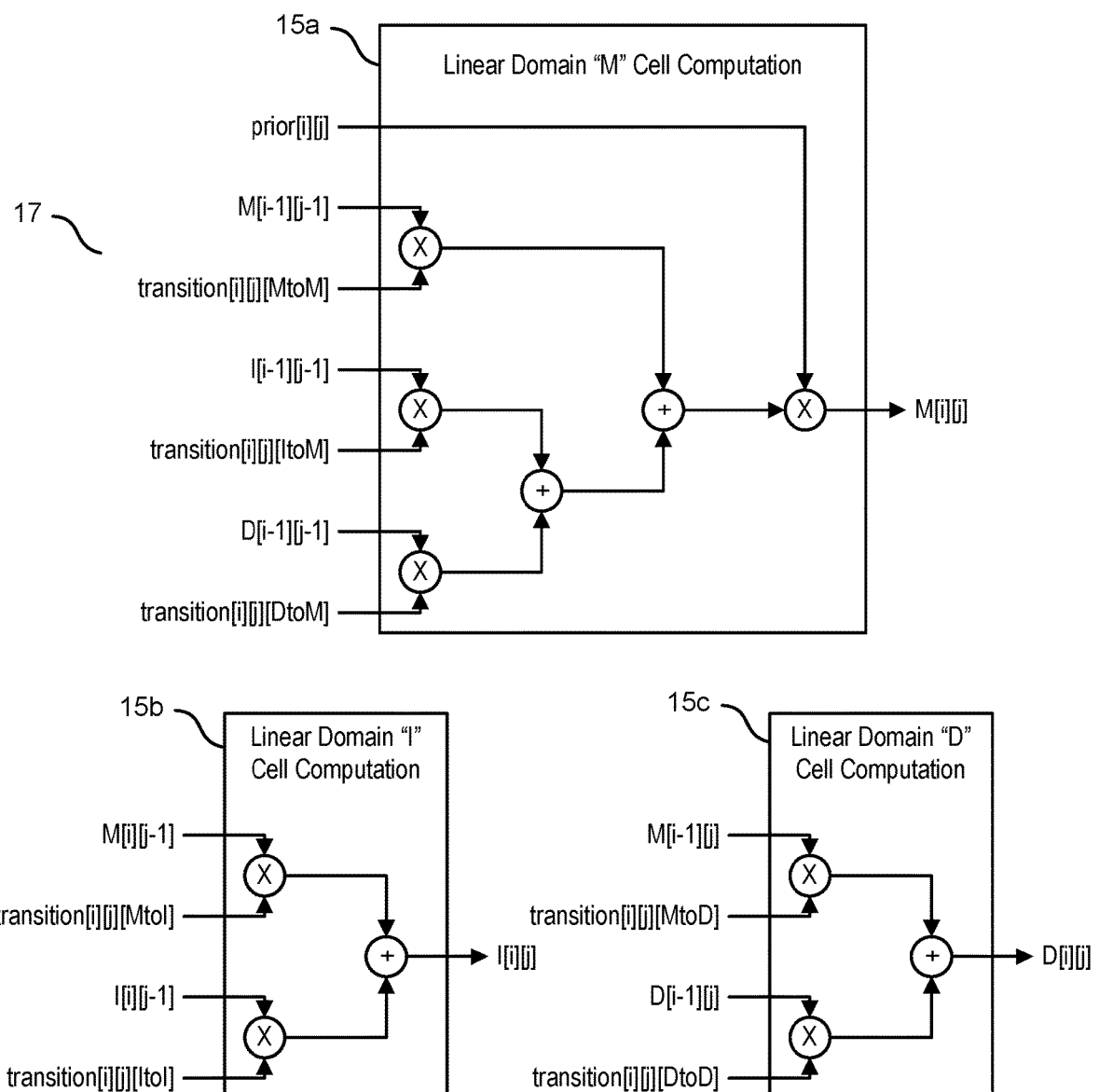
FIG. 9 depicts exemplary computations useful for M, I, D state updates.

Particularly, FIG. 9 sets forth an exemplary computational structure for performing the various state processing calculations herein described. More particularly, FIG. 9 sets forth three dedicated logic blocks 17 of the processing engine 13 for computing the state computations involved in generating each M, I, and D state value for each particular cell, or grouping of cells, being processed in the HMM matrix 30. These logic blocks may be implemented in hardware, but in some instances, may be implemented in software, such as for being performed by one or more quantum circuits.

As can be seen with respect to FIG. 9, the match state computation 15*a* is more involved than either of the insert 15*b* or deletion 15*c* computations, this is because in calculating the match state 15*a* of the present cell being processed, all of the previous match, insert, and delete states of the adjoining cells along with various other, e.g., prior, data are included in the present match computation, whereas only the match and either the insert and delete states are included in their respective calculations. Hence, as can be seen with respect to FIG. 9, in calculating a match state, three state multipliers, as well as two adders, and a final multiplier, which accounts for the prior, e.g., Phred, data are included. However, for calculating the I or D state, only two multipliers and one adder are included. It is noted that in hardware, multipliers are more resource intensive than adders.

Accordingly, to various extents, the M, I, and D state values for processing each new cell in the HMM matrix uses the knowledge or pre-computation of the following values, such as the "previous" M, I, and D state values from left, above, and/or diagonally left and above of the currently-being-computed cell in the HMM matrix. Additionally, such values representing the prior information, or "priors", may at least in part be based on the "Phred" quality score, and whether the read base and the reference base at a given cell in the matrix 30 match or are different. Such information is particularly useful when determining a match state. Specifically, as can be seen with respect to FIG. 9, in such instances, there are basically seven "transition probabilities" (M-to-M, I-to-M, D-to-M, I-to-I, M-to-I, D-to-D, and M-to-D) that indicate and/or estimate the probability of seeing a gap open, e.g., of seeing a transition from a match state to an insert or delete state; seeing a gap close; e.g., going from an insert or delete state back to a match state; and seeing the next state continuing in the same state as the previous state, e.g., Match-to-Match, Insert-to-Insert, Delete-to-Delete.

The state values (e.g., in any cell to be processed in the HMM matrix 30), Priors, and transition probabilities are all values in the range of [0,1]. Additionally, there are also known starting conditions for cells that are on the left or top edge of the HMM matrix. As can be seen from the logic 15*a* of FIG. 9, there are four multiplication and two addition computations that may be employed in the particular M state calculation being determined for any given cell being processed. Likewise, as can be seen from the logic of 15*b* and 15*c* there are two multiplications and one addition involved for each I state and each D state calculation, respectively. Collectively, along with the priors multiplier this sums to a total of eight multiplications and four addition operations for the M, I, and D state calculations associated with each single cell in the HMM matrix 8 to be processed.

The final sum output of the computation of the matrix, e.g., for a single job of comparing one read to one or two haplotypes, is the summation of the final M and I states across the entire bottom row of the matrix, which is the final sum value that is output from the HMM accelerator 8 and delivered to the CPU/GPU/QPU. This final summed value represents how well the read matches the haplotype(s). The value is a probability, e.g., of less than one, for a single job that may then be compared to the output resulting from another job such as form the same active region 500. It is noted that there are on the order of 20 trillion HMM cells to evaluate in a "typical" human genome at 30X coverage, where these 20 trillion HMM cells are spread across about 1 to 2 billion HMM matrices of all associated HMM jobs.

The results of such calculations may then be compared one against the other so as to determine, in a more precise manner, how the genetic sequence of a subject differs, e.g., on a base by base comparison, from that of one or more reference genomes. For the final sum calculation, the adders already employed for calculating the M, I, and/or D states of the individual cells may be re-deployed so as to compute the final sum value, such as by including a mux into a selection of the re-deployed adders thereby including one last additional row, e.g., with respect to calculation time, to the matrix so as to calculate this final sum, which if the read length is 100 bases amounts to about a 1% overhead. In alternative embodiments, dedicated hardware resources can be used for performing such calculations. In various instances, the logic for the adders for the M and D state calculations may be deployed for calculating the final sum, which D state adder may be efficiently deployed since it is not otherwise being used in the final processing leading to the summing values.

In certain instances, these calculations and relevant processes may be configured so as to correspond to the output of a given sequencing platform, such as including an ensemble of sequencers, which as a collective may be capable of outputting (on average) a new human genome at 30× coverage every 28 minutes (though they come out of the sequencer ensemble in groups of about 150 genomes every three days). In such an instance, when the present mapping, aligning, and variant calling operations are configured to fit within such a sequencing platform of processing technologies, a portion of the 28 minutes (e.g., about 10 minutes) it takes for the sequencing cluster to sequence a genome, may be used by a suitably configured mapper and/or aligner, as herein described, so as to take the image/BCL/FASTQ file results from the sequencer, such as streaming real-time, e.g., on the fly, and perform the steps of mapping and/or aligning the genome, e.g., post-sequencer processing.

This leaves about 18 minutes of the sequencing time period for performing the variant calling step, of which the HMM operation is the main computational component, such as prior to the nucleotide sequencer sequencing the next genome, such as over the next 28 minutes, where during the sequencing process, generated data may be streamed, such as substantially real-time into the present system, such as via the cloud, for instance, for processing to begin on the fly. Accordingly, in such instances, 18 minutes may be budgeted to computing the 20 trillion HMM cells that need to be processed in accordance with the processing of a genome, such as where each of the HMM cells to be processed includes about twelve mathematical operations (e.g., eight multiplications and/or four addition operations). Such a throughput allows for the following computational dynamics (20 trillion HMM cells)×(12 math ops per cell)/(18 minutes×60 seconds/minute), which is about 222 billion operations per second of sustained throughput.

Figure 10:
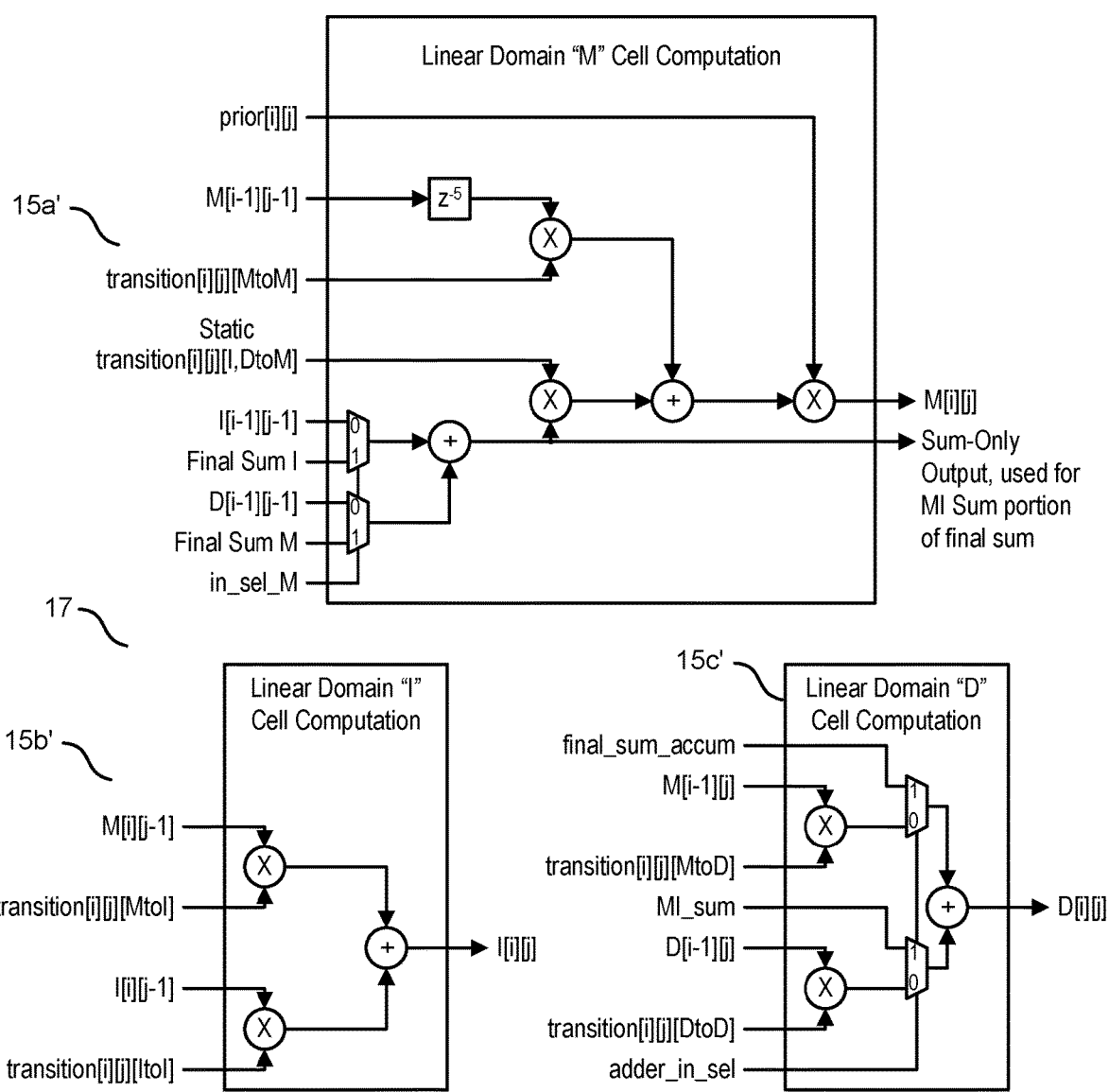
FIG. 10 depicts M, I, and D state update circuits, including the effects of simplifying assumptions of FIG. 9 related to transition probabilities and the effect of sharing some M, I, D adder resources with the final sum operations.

FIG. 10 sets forth the logic blocks 17 of the processing engine of FIG. 9 including exemplary M, I, and D state update circuits that present a simplification of the circuit provided in FIG. 9. The system may be configured so as to not be memory-limited, so a single HMM engine instance 13

(e.g., that computes all of the single cells in the HMM matrix 30 at a rate of one cell per clock cycle, on average, plus overheads) may be replicated multiple times (at least 65-70 times to make the throughput efficient, as described above). Nevertheless, to minimize the size of the hardware, e.g., the size of the chip 2 and/or its associated resource usage, and/or in a further effort to include as many HMM engine instances 13 on the chip 2 as desirable and/or possible, simplifications may be made with regard to the logic blocks 15a'-c' of the processing instance 13 for computing one or more of the transition probabilities to be calculated.

In particular, it may be assumed that the gap open penalty (GOP) and gap continuation penalty (GCP), as described above, such as for inserts and deletes are the same and are known prior to chip configuration. This simplification implies that the I-to-M and D-to-M transition probabilities are identical. In such an instance, one or more of the multipliers, e.g., set forth in FIG. 9, may be eliminated, such as by pre-adding I and D states before multiplying by a common Indel-to-M transition probability. For instance, in various instances, if the I and D state calculations are assumed to be the same, then the state calculations per cell can be simplified as presented in FIG. 10. Particularly, if the I and D state values are the same, then the I state and the D state may be added and then that sum may be multiplied by a single value, thereby saving a multiply. This may be done because, as seen with respect to FIG. 10, the gap continuation and/or close penalties for the I and D states are the same. However, as indicated above, the system can be configured to calculate different values for both the I and D transition state probabilities, and in such an instance, this simplification would not be employed.

Additionally, in a further simplification, rather than dedicate chip or other computing resources configured specifically to perform the final sum operation at the bottom of the HMM matrix, the present HMM accelerator 8 may be configured so as to effectively append one or more additional rows to the HMM matrix 30, with respect to computational time, e.g., overhead, it takes to perform the calculation, and may also be configured to "borrow" one or more adders from the M-state 15a and D-state 15c computation logic such as by MUXing in the final sum values to the existing adders as needed, so as to perform the actual final summing calculation. In such an instance, the final logic, including the M logic 15a, I logic 15b, and D logic 15c blocks, which blocks together form part of the HMM MID instance 17, may include 7 multipliers and 4 adders along with the various MUXing involved.

Accordingly, FIG. 10 sets forth the M, I, and D state update circuits 15a', 15b', and 15c' including the effects of simplifying assumptions related to transition probabilities, as well as the effect of sharing various M, I, and/or D resources, e.g., adder resources, for the final sum operations. A delay block may also be added to the M-state path in the M-state computation block, as shown in FIG. 10. This delay may be added to compensate for delays in the actual hardware implementations of the multiply and addition operations, and/or to simplify the control logic, e.g., 15.

As shown in FIGS. 9 and 10, these respective multipliers and/or adders may be floating point multipliers and adders. However, in various instances, as can be seen with respect to FIG. 11, a log domain configuration may be implemented where in such configuration all of the multiplies turn into adds. FIG. 11 presents what log domain calculation would look like if all the multipliers turned into adders, e.g., 15a", 15b", and 15c", such as occurs when employing a log domain computational configuration. Particularly, all of the multiplier logic turns into an adder, but the adder itself turns into or otherwise includes a function where the function such as: $f(a,b)=max(a,b)-\log 2(1+2^{(-[a-b])})$, such as where the log portion of the equation may be maintained within a LUT whose depth and physical size is determined by the precision required.

Given the typical read and haplotype sequence lengths as well as the values typically seen for read quality (Phred) scores and for the related transition probabilities, the dynamic range requirements on the internal HMM state values may be quite severe. For instance, when implementing the HMM module in software, various of the HMM jobs 20 may result in underruns, such as when implemented on single-precision (32-bit) floating-point state values. This implies a dynamic range that is greater than 80 powers of 10, thereby requiring the variant call software to bump up to double-precision (64-bit) floating point state values. However, full 64-bit double-precision floating-point representation may, in various instances, have some negative implications, such as if compact, high-speed hardware is to be implemented, both storage and compute pipeline resource requirements will need to be increased, thereby occupying greater chip space, and/or slowing timing. In such instances, a fixed-point-only linear-domain number representation may be implemented. Nevertheless, the dynamic range demands on the state values, in this embodiment, make the bit widths involved in certain circumstances less than desirable. Accordingly, in such instances, fixed-point-only log-domain number representation may be implemented, as described herein.

In such a scheme, as can be seen with respect to FIG. 11, instead of representing the actual state value in memory and computations, the −log-base−2 of the number may be represented. This may have several advantages, including employing multiply operations in linear space that translate into add operations in log space; and/or this log domain representation of numbers inherently supports wider dynamic range with only small increases in the number of integer bits. These log-domain M, I, D state update calculations are set forth in FIGS. 11 and 12.

As can be seen when comparing the logic 17 configuration of FIG. 11 with that of FIG. 9, the multiply operations go away in the log-domain. Rather, they are replaced by add operations, and the add operations are morphed into a function that can be expressed as a max operation followed by a correction factor addition, e.g., via a LUT, where the correction factor is a function of the difference between the two values being summed in the log-domain. Such a correction factor can be either computed or generated from the look-up-table. Whether a correction factor computation or look-up-table implementation is more efficient to be used depends on the required precision (bit width) on the difference between the sum values. In particular instances, therefore, the number of log-domain bits for state representation can be in the neighborhood of 8 to 12 integer bits plus 6 to 24 fractional bits, depending on the level of quality desired for any given implementation. This implies somewhere between 14 and 36 bits total for log-domain state value representation. Further, it has been determined that there are log-domain fixed-point representations that can provide acceptable quality and acceptable hardware size and speed.

In various instances, one read sequence is typically processed for each HMM job 20, which as indicated may include a comparison against one or two haplotype sequences, or more. And like above for the haplotype memory, a ping-pong structure may also be used in the read sequence memory 18 to allow various software implemented functions the ability to write new HMM job information 20*b* while a current job 20*a* is still being processed by the HMM engine instance 13. Hence, a read sequence storage requirement may be for a single 1024×32 two-port memory (such as one port for write, one port for read, and/or separate clocks for write and read ports).

Particularly, as described above, in various instances, the architecture employed by the system 1 is configured such that in determining whether a given base in a sequenced sample genome matches that of a corresponding base in one or more reference genomes, a virtual matrix is formed, wherein the reference genome is theoretically set across a horizontal axis, while the sequenced reads, representing the sample genome, is theoretically set in descending fashion down the vertical axis. Consequently, in performing an HMM calculation, the HMM processing engine 13, as herein described, is configured to traverse this virtual HMM matrix. Such processing can be depicted as in FIG. 7, as a swath 35 moving diagonally down and across the virtual array performing the various HMM calculations for each cell of the virtual array, as seen in FIG. 8.

More particularly, this theoretical traversal involves processing a first grouping of rows of cells 35*a* from the matrix 30 in its entirety, such as for all haplotype and read bases within the grouping, before proceeding down to the next grouping of rows 35*b* (e.g., the next group of read bases). In such an instance, the M, I, and D state values for the first grouping are stored at the bottom edge of that initial grouping of rows so that these M, I, and D state values can then be used to feed the top row of the next grouping (swath) down in the matrix 30. In various instances, the system 1 may be configured to allow up to 1008 length haplotypes and/or reads in the HMM accelerator 8, and since the numerical representation employs W-bits for each state, this implies a 1008 word×W-bit memory for M, I, and D state storage.

Accordingly, as indicated, such memory could be either a single-port or double-port memory. Additionally, a cluster-level, scratch pad memory, e.g., for storing the results of the swath boundary, may also be provided. For instance, in accordance with the disclosure above, the memories discussed already are configured for a per-engine-instance 13 basis. In particular HMM implementations, multiple engine instances 13*a*-$_{(n+1)}$ may be grouped into a cluster 11 that is serviced by a single connection, e.g., PCIe bus 5, to the PCIe interface 4 and DMA 3 via CentCom 9. Multiple clusters 11*a*-$_{(n+1)}$ can be instantiated so as to more efficiently utilize PCIe bandwidth using the existing CentCom 9 functionality.

Hence, in a typical configuration, somewhere between 16 and 64 engines 13$_m$ are instantiated within a cluster 11$_n$, and one to four clusters might be instantiated in a typical FPGA/ASIC implementation of the HMM 8 (e.g., depending on whether it is a dedicated HMM FPGA image or whether the HMM has to share FPGA real estate with the sequencer/mapper/aligner and/or other modules, as herein disclosed). In particular instances, there may be a small amount of memory used at the cluster-level 11 in the HMM hardware. This memory may be used as an elastic First In First Out ("FIFO") to capture output data from the HMM engine instances 13 in the cluster and pass it on to CentCom 9 for further transmittal back to the software of the CPU 1000 via the DMA 3 and PCIe 4. In theory, this FIFO could be very small (on the order of two 32-bit words), as data are typically passed on to CentCom 9 almost immediately after arriving in the FIFO. However, to absorb potential disrupts in the output data path, the size of this FIFO may be made parametrizable. In particular instances, the FIFO may be used with a depth of 512 words. Thus, the cluster-level storage requirements may be a single 512×32 two-port memory (separate read and write ports, same clock domain).

Figure 12A:
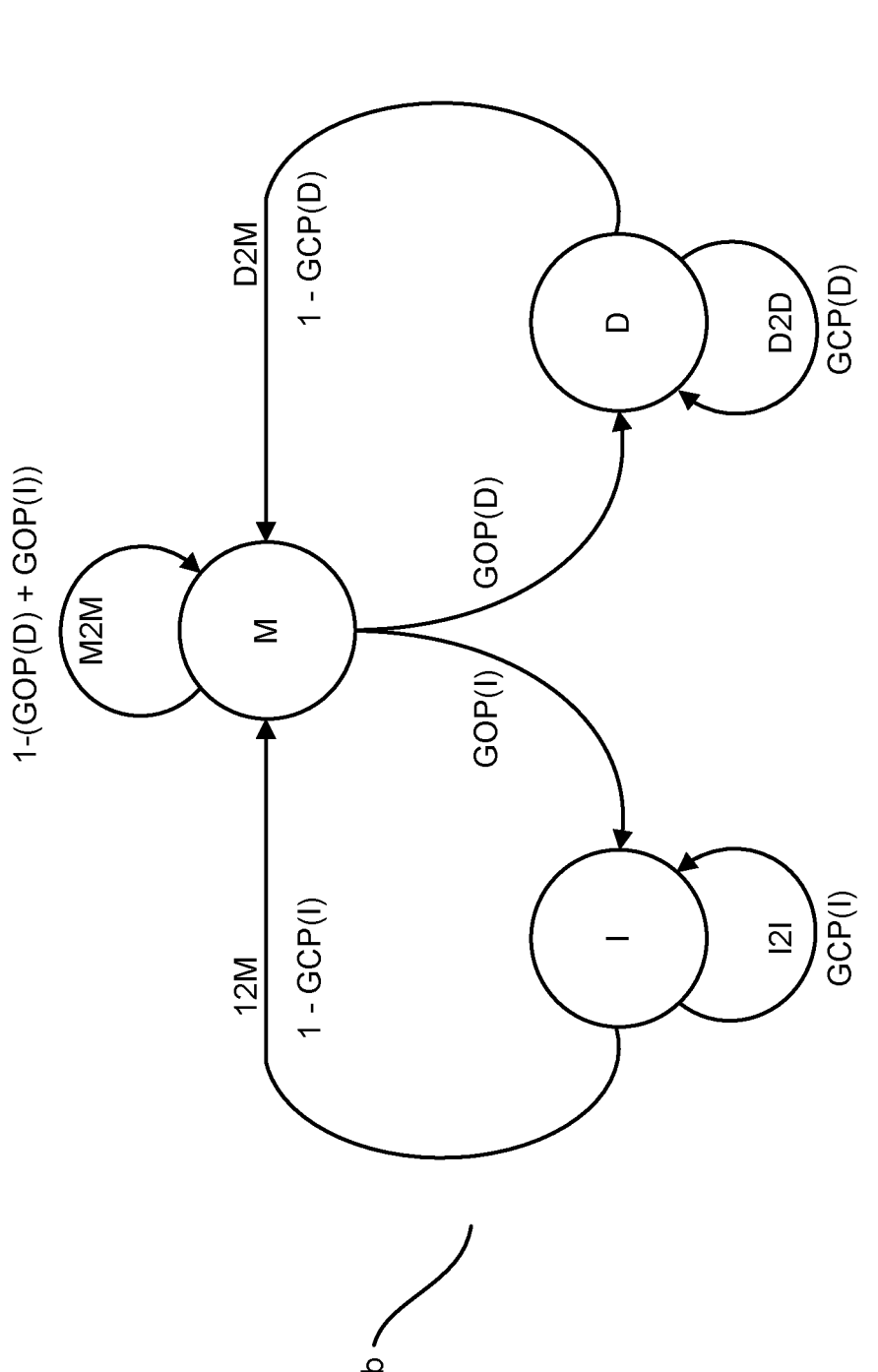
FIG. 12A depicts an HMM state transition diagram showing the relation between GOP, GCP and transition probabilities.

FIG. 12A sets forth the various HMM state transitions 17b depicting the relationship between Gap Open Penalties (GOP), Gap Close Penalties (GCP), and transition probabilities involved in determining whether and how well a given read sequence matches a particular haplotype sequence. In performing such an analysis, the HMM engine 13 includes at least three logic blocks 17b, such as a logic block for determining a match state 15a, a logic block for determining an insert state 15b, and a logic block for determining a delete state 15c. These M, I, and D state calculation logic 17 when appropriately configured function efficiently to avoid high-bandwidth bottlenecks, such as of the HMM computational flow. However, once the M, I, D core computation architecture is determined, other system enhancements may also be configured and implemented so as to avoid the development of other bottlenecks within the system.

Particularly, the system 1 may be configured so as to maximize the process of efficiently feeding information from the computing core 1000 to the variant caller module 2 and back again, so as not to produce other bottlenecks that would limit overall throughput. One such block that feeds the HMM core M, I, D state computation logic 17 is the transition probabilities and priors calculation block. For instance, as can be seen with respect to FIG. 9, each clock cycle employs the presentation of seven transition probabilities and one Prior at the input to the M, I, D state computation block 15a. However, after the simplifications that result in the architecture of FIG. 10, only four unique transition probabilities and one Prior are employed for each clock cycle at the input of the M, I, D state computation block. Accordingly, in various instances, these calculations may be simplified and the resulting values generated. Thus, increasing throughput, efficiency, and reducing the possibility of a bottleneck forming at this stage in the process.

Additionally, as described above, the Priors are values generated via the read quality, e.g., Phred score, of the particular base being investigated and whether, or not, that base matches the hypothesis haplotype base for the current cell being evaluated in the virtual HMM matrix 30. The relationship can be described via the equations bellow: First, the read Phred in question may be expressed as a probability=$10^{\wedge}(-(\text{read Phred}/10))$. Then the Prior can be computed based on whether the read base matches the hypothesis haplotype base: If the read base and hypothesis haplotype base match: Prior=1−read Phred expressed as a probability. Otherwise: Prior=(read Phred expressed as probability)/3. The divide-by-three operation in this last equation reflects the fact that there are only four possible bases (A, C, G, T). Hence, if the read and haplotype base did not match, then it must be one of the three remaining possible bases that does match, and each of the three possibilities is modeled as being equally likely.

The per-read-base Phred scores are delivered to the HMM hardware accelerator 8 as 6-bit values. The equations to derive the Priors, then, have 64 possible outcomes for the "match" case and an additional 64 possible outcomes for the "don't match" case. This may be efficiently implemented in the hardware as a 128 word look-up-table, where the address into the look-up-table is a 7-bit quantity formed by concatenating the Phred value with a single bit that indicates whether, or not, the read base matches the hypothesis haplotype base.

Further, with respect to determining the match to insert and/or match to delete probabilities, in various implemen-tations of the architecture for the HMM hardware accelerator 8, separate gap open penalties (GOP) can be specified for the Match-to-Insert state transition, and the Match-to-Delete state transition, as indicated above. This equates to the M2I and M2D values in the state transition diagram of FIG. 12A being different. As the GOP values are delivered to the HMM hardware accelerator 8 as 6-bit Phred-like values, the gap open transition probabilities can be computed in accordance with the following equations: M2I transition probability=$10^{\wedge}(-(\text{read GOP(I)}/10))$ and M2D transition probability=$10^{\wedge}(-(\text{read GOP(D)}/10))$. Similar to the Priors derivation in hardware, a simple 64 word look-up-table can be used to derive the M2I and M2D values. If GOP(I) and GOP(D) are inputted to the HMM hardware 8 as potentially different values, then two such look-up-tables (or one resource-shared look-up-table, potentially clocked at twice the frequency of the rest of the circuit) may be utilized.

Furthermore, with respect to determining match to match transition probabilities, in various instances, the match-to-match transition probability may be calculated as: M2M transition probability=1−(M2I transition probability+M2D transition probability). If the M2I and M2D transition prob-abilities can be configured to be less than or equal to a value of ½, then in various embodiments the equation above can be implemented in hardware in a manner so as to increase overall efficiency and throughput, such as by reworking the equation to be: M2M transition probability=(0.5−M2I tran-sition probability)+(0.5−M2D transition probability). This rewriting of the equation allows M2M to be derived using two 64 element look-up-tables followed by an adder, where the look-up-tables store the results.

Further still, with respect to determining the Insert to Insert and/or Delete to Delete transition probabilities, the I2I and D2D transition probabilities are functions of the gap continuation probability (GCP) values inputted to the HMM hardware accelerator 8. In various instances, these GCP values may be 6-bit Phred-like values given on a per-read-base basis. The I2I and D2D values may then be derived as shown: I2I transition probability=$10^{\wedge}(-(\text{read GCP(I)}/10))$, and D2D transition probability=$10^{\wedge}(-(\text{read GCP(D)}/10))$. Similar to some of the other transition probabilities dis-cussed above, the I2I and D2D values may be efficiently implemented in hardware, and may include two look-up-tables (or one resource-shared look-up-table), such as hav-ing the same form and contents as the Match-to-Indel look-up-tables discussed previously. That is, each look-up-table may have 64 words.

Additionally, with respect to determining the Inset and/or Delete to Match probabilities, the I2M and D2M transition probabilities are functions of the gap continuation probabil-ity (GCP) values and may be computed as: I2M transition probability=1−I2I transition probability, and D2M transition probability=1−D2D transition probability, where the I2I and D2D transition probabilities may be derived as discussed above. A simple subtract operation to implement the equa-tions above may be more expensive in hardware resources than simply implementing another 64 word look-up-table and using two copies of it to implement the I2M and D2M derivations. In such instances, each look-up-table may have 64 words. Of course, in all relevant embodiments, simple or complex subtract operations may be formed with the suit-ably configured hardware.

Figure 13:
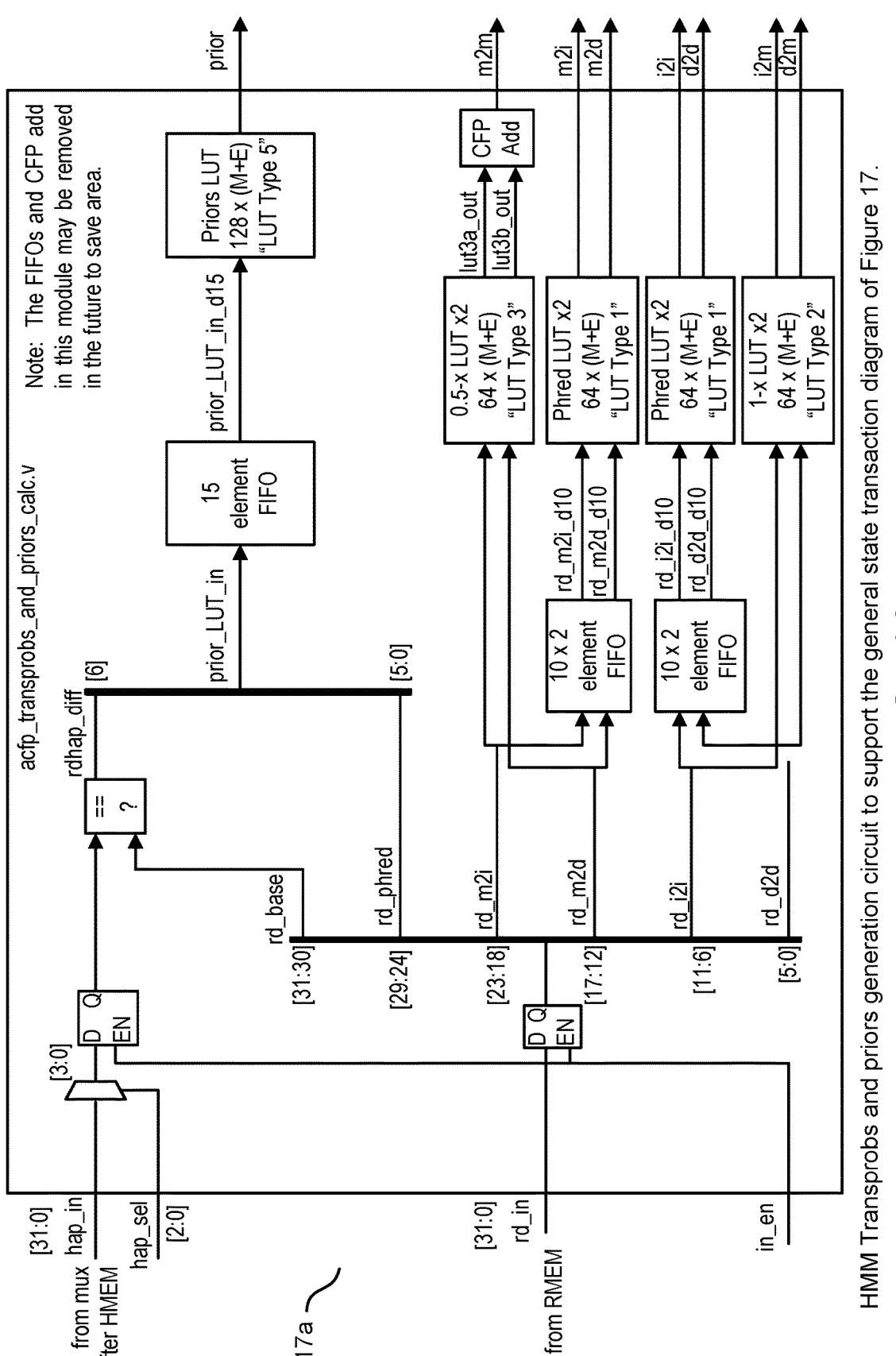
FIG. 13 depicts an HMM Transprobs and Priors generation circuit to support the general state transition diagram of FIG. 12.

FIG. 13 provides the circuitry 17a for a simplified calcu-lation for HMM transition probabilities and Priors, as described above, which supports the general state transition diagram of FIG. 12A. As can be seen with respect to FIG. 13, in various instances, a simple HMM hardware accelerator architecture 17*a* is presented, which accelerator may be configured to include separate GOP values for Insert and Delete transitions, and/or there may be separate GCP values for Insert and Delete transitions. In such an instance, the cost of generating the seven unique transition probabilities and one Prior each clock cycle may be configured as set forth below: eight 64 word look-up-tables, one 128 word look-up-table, and one adder.

Further, in various instances, the hardware 2, as presented herein, may be configured so as to fit as many HMM engine instances 13 as possible onto the given chip target (such as on an FPGA, sASIC, or ASIC). In such an instance, the cost to implement the transition probabilities and priors generation logic 17*a* can be substantially reduced relative to the costs as provided by the below configurations. Firstly, rather than supporting a more general version of the state transitions, such as set forth in FIG. 13, e.g., where there may be separate values for GOP(I) and GOP(D), rather, in various instances, it may be assumed that the GOP values for insert and delete transitions are the same for a given base. This results in several simplifications to the hardware, as indicated above.

In such instances, only one 64 word look-up-table may be employed so as to generate a single M2Indel value, replacing both the M2I and M2D transition probability values, whereas two tables are typically employed in the more general case. Likewise, only one 64 word look-up-table may be used to generate the M2M transition probability value, whereas two tables and an add may typically be employed in the general case, as M2M may now be calculated as 1−2×M2Indel.

Secondly, the assumption may be made that the sequencer-dependent GCP value for both insert and delete are the same AND that this value does not change over the course of an HMM job 20. This means that: a single Indel2Indel transition probability may be calculated instead of separate I2I and D2D values, using one 64 word look-up-table instead of two tables; and single Indel2Match transition probability may be calculated instead of separate I2M and D2M values, using one 64 word look-up-table instead of two tables.

Additionally, a further simplifying assumption can be made that assumes the Inset2Insert and Delete2Delete (I2I and D2D) and Insert2Match and Delete2Match (I2M and D2M) values are not only identical between insert and delete transitions, but may be static for the particular HMM job 20. Thus, the four look-up-tables associated in the more general architecture with I2I, D2D, I2M, and D2M transition probabilities can be eliminated altogether. In various of these instances, the static Indel2Indel and Indel2Match probabilities could be made to be entered via software or via an RTL parameter (and so would be bitstream programmable in an FPGA). In certain instances, these values may be made bitstream-programmable, and in certain instances, a training mode may be implemented employing a training sequence so as to further refine transition probability accuracy for a given sequencer run or genome analysis.

Figure 14:
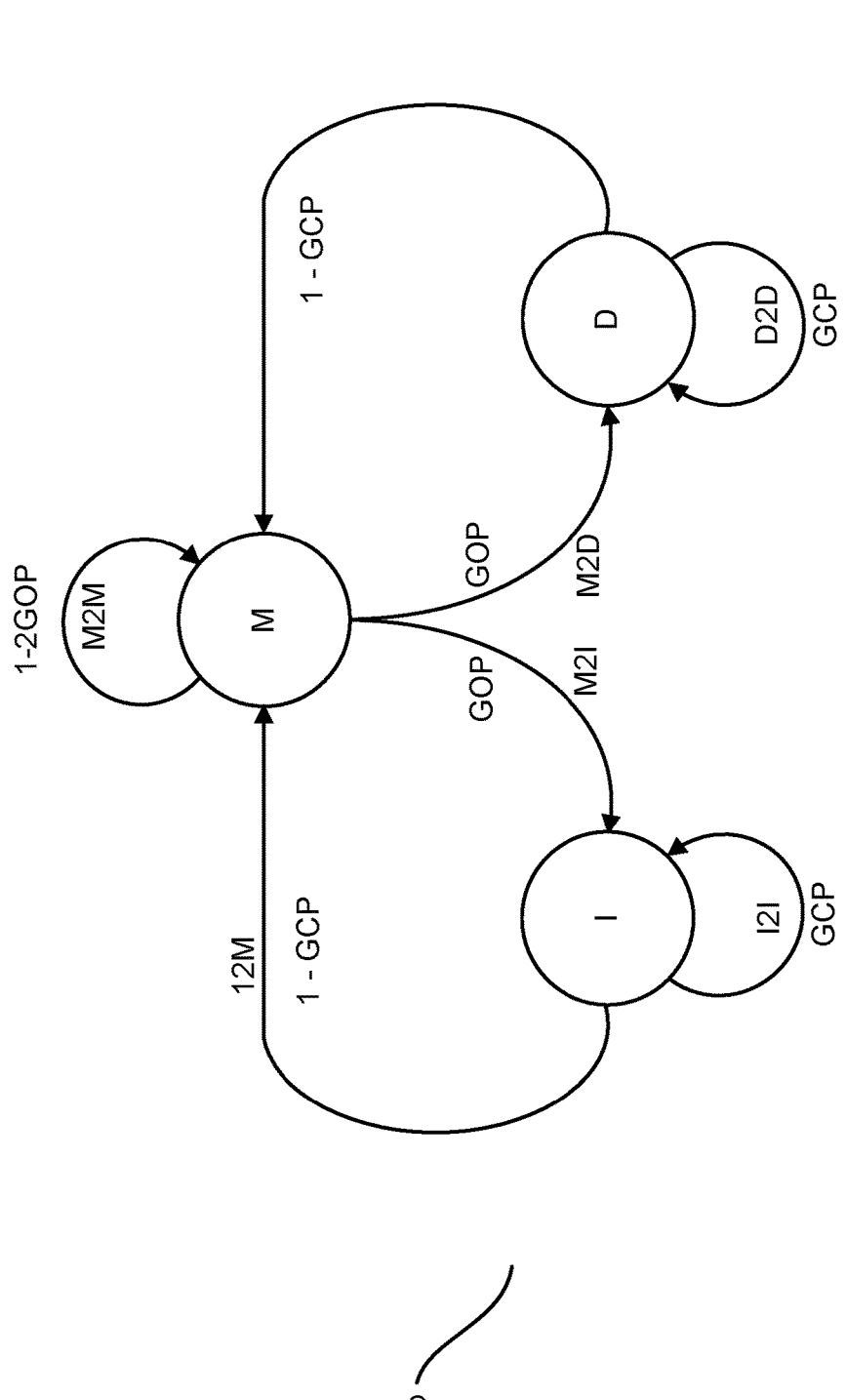
FIG. 14 depicts a simplified HMM state transition diagram showing the relation between GOP, GCP and transition probabilities.

FIG. 14 sets forth what the new state transition 17*b* diagram may look like when implementing these various simplifying assumptions. Specifically, FIG. 14 sets forth the simplified HMM state transition diagram depicting the relationship between GOP, GCP, and transition probabilities with the simplifications set forth above.

Figure 15:
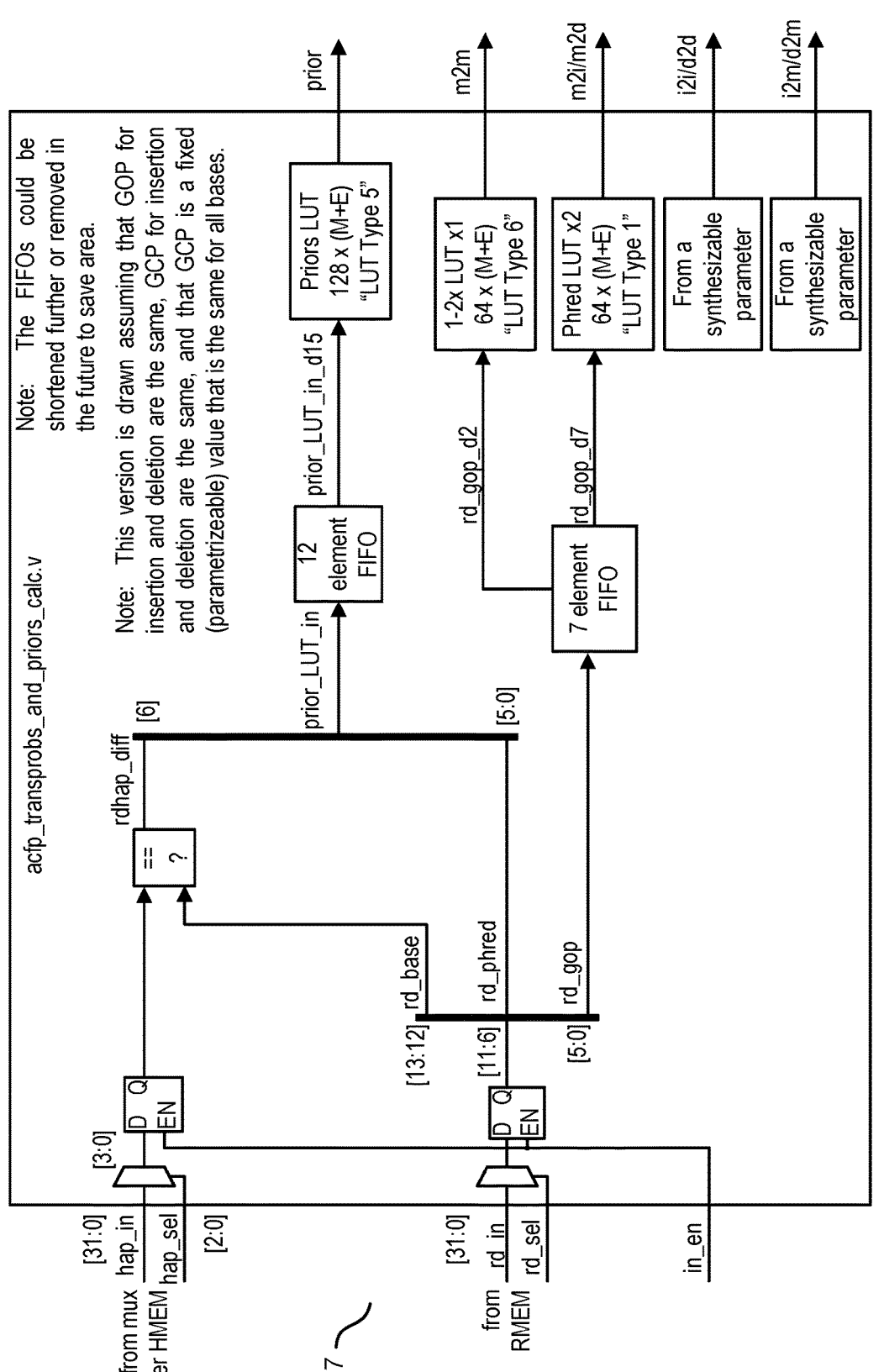
FIG. 15 depicts a HMM Transprobs and Priors generation circuit to support the simplified state transition.

Likewise, FIG. 15 sets forth the circuitry 17*a,b* for the HMM transition probabilities and priors generation, which supports the simplified state transition diagram of FIG. 14. As seen with respect to FIG. 15, a circuit realization of that state transition diagram is provided. Thus, in various instances, for the HMM hardware accelerator 8, the cost of generating the transition probabilities and one Prior each clock cycle reduces to: Two 64 word look-up-tables, and One 128 word look-up-table.

Figure 12B:
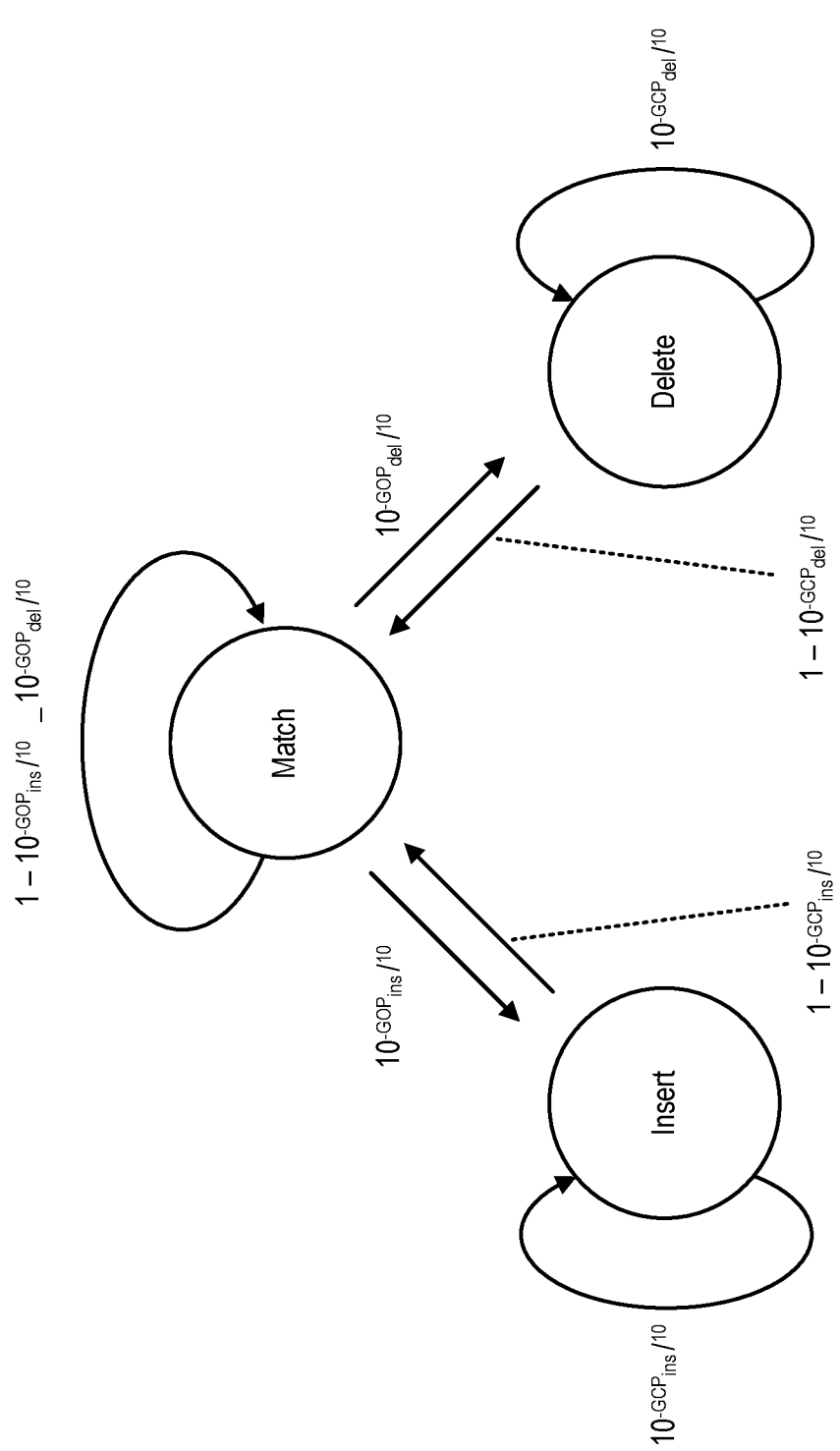
FIG. 12B depicts a particular embodiment of an exemplary HMM state transition diagram showing the relation between GOP, GCP and transition probabilities.
Figure 12C:
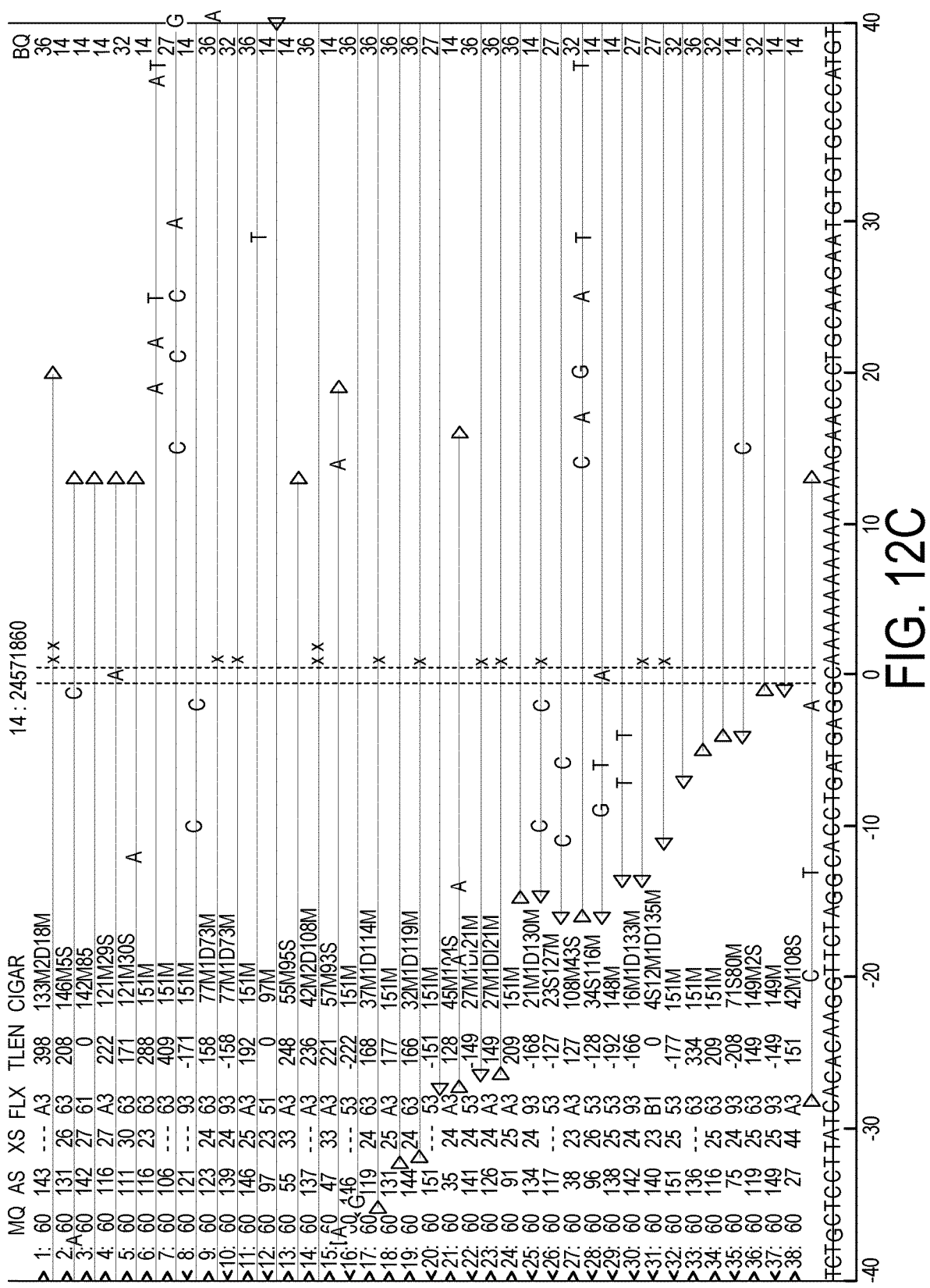
FIG. 12C depicts a pileup of a region in the genome evidencing short tandem repeats (STR).
Figure 12D:
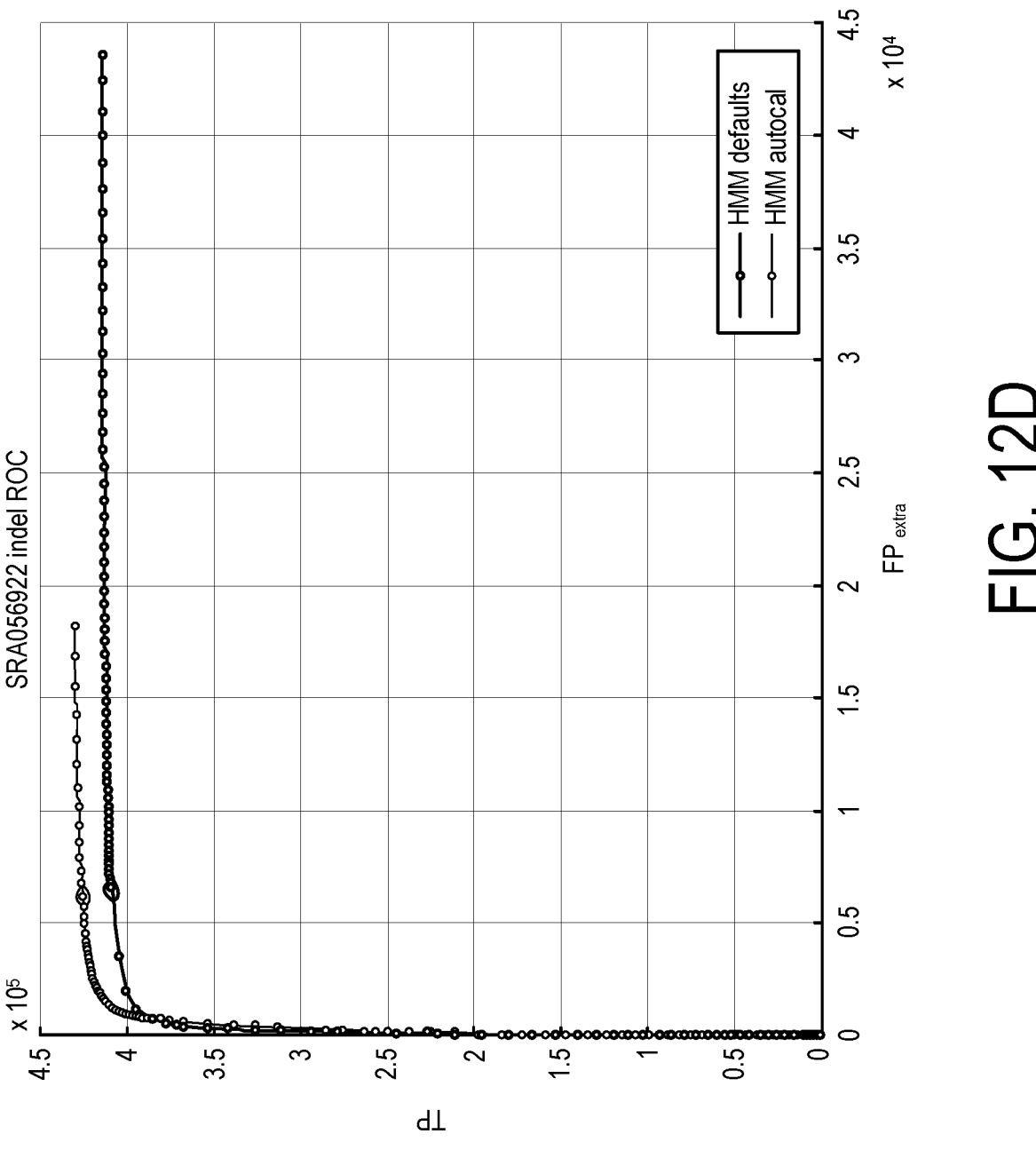
FIG. 12D depicts an area under the curve graph expressing indels within a given region.

Accordingly, as can be seen with reference to the above discussion as well as FIGS. 12B-12D, one of the challenges in variant calling is distinguishing indel errors from true variants. To do so, a variant caller may be configured to employ a Hidden Markov Model (HMM), as disclosed herein, which models the statistical behavior of indel errors, as part of the probability calculation. As can be seen with respect to FIG. 12B, the HMM may have input parameters $GOP_{ins}$, $GCP_{ins}$, $GOP_{del}$, $GCP_{del}$, where GOP and GCP stand for the Gap Open Penalty and Gap Continuation Penalty, respectively, and the subscripts indicate insertion and deletion. FIG. 12B, illustrates that the HMM parameters may depend on the context of the read and/or the haplotype being processed, this is because indel errors are more likely in the presence of short tandem repeats (STRs), and in such an instance, the error probability may depend on both the period and the length of the STR. The error process may differ significantly from one dataset to another, depending on factors such as PCR amplification, and/or other sources of error. For accurate detection, it is useful to use HMM parameters that accurately model the error process. However, where the variant caller is configured to use fixed parameters or predetermined functions, this may fail to accurately model the error process, resulting in poor detection performance.

Accordingly, in such an instance, such errors may be corrected for, such as through an auto-calibration process disclosed herein. Particularly, presented herein is an HMM Auto-Calibration addresses such problems, for instance, by estimating the PCR parameters directly from the dataset being processed. This operation may be performed after mapping & alignment and prior to variant calling, with or without knowledge of the ground truth and with or without using external databases of known mutations. In such an instance, the parameters depend on both the STR period and the repeat length.

For a given STR period and length, a set of N loci with the desired period and length, the pileups of reads mapped to those loci may be examined, counting the indels observed at each locus to estimate the parameters of interest. Particularly, the HMM parameters to be estimated include one or more of $GOP_{ins}$, $GCP_{ins}$, $GOP_{del}$, $GCP_{del}$ as well as the variant probabilities $$\alpha_l^{het} \text{ and } \alpha_l^{hom},$$

which represent the probability of an indel variant of length l, where positive values of l indicate insertions of l bases and negative values indicate deletions of |l| bases, and the superscript indicates whether the variant is heterozygous or homozygous. In various instances, it may be assumed that the underlying organism is diploid, but it is noted that this can be generalized to non-diploid organisms. Note also that for a single locus with limited coverage depth, it is often difficult to determine whether the indels are due to errors or a true variant, and such pileups may not be particularly helpful for estimating the HMM parameters.

For example, as can be seen with respect to FIG. 12C, a pileup is presented wherein 11 out of 38 reads contain deletions. Specifically, FIG. 12C presents an STR locus with multiple deletions in the pileup. In this instance, the STR has a period of 1 base and a length of 14 bases. It is difficult to determine from this pileup alone whether these deletions are errors or evidence of a true variant. However, by considering a sufficient number of loci, it's possible to accurately estimate the parameters of interest. This may be done by finding the parameters that maximize the probability of producing the set of N observed pileups. Even pileups that seem completely unhelpful in isolation, in this instance, can play an important role when analyzed in conjunction with other pileups.

A straightforward way to estimate the parameters of interest is to use the HMM module to calculate the joint probability of the observed pileups, sweeping the HMM parameters and choosing those that maximize the total probability. However, the computational complexity of doing so may be prohibitive, both because of the complexity of the HMM operation and because of the number of independent parameters to sweep. Accordingly, presented herein is a simplified method based on counting the number of indels of each length at each locus, without need using HMM. In such an instance, a qualifying read may be defined as one with a high-confidence alignment spanning the STR with a minimum number of flanking bases on each side. Accordingly, the appropriate calculations may be set forth as follows.

Let $k_{l,i}$ be the number of qualifying reads containing an indel of length l bases (relative to the reference) aligned at locus i, where positive values of l indicate insertions and negative values indicate deletions, and l=0 indicates the absence of an indel. Let $\Psi$ be an approximation of the probability of making the observations $(n_i, k_{l,i})$, i=1□N given the parameters $$GOP_{ins}, GCP_{ins}, GOP_{del}, GCP_{del}, \alpha_l^{het} \text{ and } \alpha_l^{hom}:$$

$$\Psi = \prod_{i=1\square n}\left[\left(1 - \sum_{l \neq 0}\alpha_l^{het} - \sum_{l \neq 0}\alpha_l^{hom}\right)\prod_m p_m^{k_{m,i}} + \right.$$

$$\left. \sum_{l \neq 0}\alpha_l^{hom}\prod_m p_{m-l}^{k_{m,i}} + \sum_{l \neq 0}\alpha_l^{het}\prod_m \left(\frac{p_m + p_{m-l}}{2}\right)^{k_{m,i}}\right]$$

where:

$$p_m = \begin{cases} \lambda 10^{-(GOP_{del}+(|m|-1)GCP_{del})/10}\left(1 - 10^{-GCP_{del}/10}\right) & m < 0 \\ (\lambda + m)10^{-(GOP_{ins}+(|m|-1)GCP_{ins})/10}\left(1 - 10^{-GCP_{ins}/10}\right) & m > 0 \\ 1 - \sum_{m \neq 0} p_m & m = 0 \end{cases}$$

and $\lambda$ is the STR length measured in bases. In general, our HMM auto-calibration procedure consists of tabulating the values of $k_{l,i}$ and then finding the values of $$GOP_{ins}, GCP_{ins}, GOP_{del}, GCP_{del}, \alpha_l^{het} \text{ and } \alpha_l^{hom}$$

that maximize $\Psi$. This operation is performed for each STR period and length.

In practice, the number of independent parameters above can be problematic, both because there may be insufficient data to train a large number of parameters, and because searching over a large number of dimensions can be difficult or impractical. Fortunately, it is easy to reduce the number of independent parameters and still get good performance.

In one embodiment, the following assumptions may be made:

$$GOP_{ins} = GOP_{del}$$

$$GCP_{ins} = GCP_{del}$$

$$\alpha_l^{het} = 2\alpha_l^{hom}$$

$$\alpha_l^{het} = \alpha_0^{het}\left(\frac{\alpha_1^{het}}{\alpha_0^{het}}\right)^{|l|}$$

This reduces the number of independent variables to 4.

In another embodiment, these calculations may further be simplified by disregarding the length of the indels. In this embodiment, $k_i$ represents the number of qualifying reads with an indel (of any length) aligned at locus i and $n_i$ indicates the total number of qualifying reads at locus i. It may be assumed that GCP is user-specified (by default, GCP=10/$\omega$, where $\omega$ is the period of the STR), and $\alpha_{het}$ and $\alpha_{hom}$ indicate the probability of indel variants of any non-zero length. The calculation may then be defined as:

$$\Psi = \prod_{i \in I_r}\left[(1 - \alpha_{het} - \alpha_{hom})p^{k_i}(1 - p)^{n_i - k_i} + \alpha_{het}\left(\frac{1}{2}\right)^{n_i} + \alpha_{hom}\,\partial(n_i, k_i)\right]$$

where $$p = 2\lambda 10^{-(GOP+(\omega-1)GCP)/10}(1 - 10^{-GCP/10})$$

$\omega$ is the period of the STR.

$$\partial(n_i, k_i) = \begin{cases} 1 & \text{if } n_i = k_i \\ 0 & \text{if } n_i \neq k_i \end{cases}$$

$$\alpha_{het} = 2\alpha_{hom}$$

This reduces the number of independent variable to 2, which can be easily performed by exhaustive search. It is noted that the expression for $\Psi$ may be an approximate expression that discounts or ignores the possibility that a locus may contain a mixture of indel variants and indel errors (which may cancel an indel variant). This approximation may be employed in instances where it has little impact on the accuracy of the result.

In various instances, STRs with a period ranging from 1 to 8 and lengths ranging from 1 to 20 whole periods may be considered. In such an instance, each STR in the genome may be classified according to the period for which it has the greatest repeat length, breaking ties toward shorter periods. A target quantity of 2K to 4K STR loci of each period/length combination may be sampled pseudo-randomly from the genomic regions covered by the aligned reads.

When fewer than 4K STR loci are available in a given period/length class, all covered STRs may be considered, even though this quantity is much smaller than 2K for combinations of long period and high repeat length. In such an instance, each STR period/length class failing to meet a minimum sample count of N≥50 may be merged with other STR classes (e.g., merging with STRs with the same period but smaller repeat length) prior to maximum-likelihood parameter estimation. For each period and repeat length, a maximum-likelihood parameter estimation may be performed as described above, sweeping the parameters GOP and $\alpha_{het}$ over a 2-dimensional grid of integers on a phred scale. For each period, start with the lowest repeat length, where the GOP should be monotonically non-increasing with increasing repeat length, An increase in GOP may be an indication of insufficient data. If an increase in GOP is observed, the class may be merged with the previous (shorter repeat-length) class.

This method of indel error model estimation is applicable to diploid germline DNA-seq, given a sample covering at the equivalent of human whole-exome (tens of millions of locus nucleotides) at substantial coverage depth (say 10× or deeper). Modification for other ploidy is straightforward. Substantially smaller samples, such as amplicon panels, lack enough STR loci to calibrate the model across important period/length combinations; but variant calling on small samples could use a model estimated from a larger dataset with similar PCR and sequencing protocols. This method remains valid for whole-exome or whole-genome tumor samples, because although somatic variants violate the 50%/100% allele frequency assumptions, there are too few real ones to disturb model parameter estimation. It also should be applicable to RNA-seq data, provided a sensitive spliced aligner is employed, and STR loci interrupted by alignment introns may be ignored.

FIG. 12D shows the indel ROC for a dataset SRA056922 (a human whole genome dataset). It can be seen that this HMM auto-calibration provides a large gain in indel sensitivity. For this dataset, the best f-measure increases from 0.9113 to 0.9319.

As set forth above, the engine control logic 15 is configured for generating the virtual matrix and/or traversing the matrix so as to reach the edge of the swath, e.g., via high-level engine state machines, where result data may be finally summed, e.g., via final sum control logic 19, and stored, e.g., via put/get logic. Accordingly, as can be seen with respect to FIG. 16, in various embodiments, a method for producing and/or traversing an HMM cell matrix 30 is provided. Specifically, FIG. 16 sets forth an example of how the HMM accelerator control logic 15 goes about traversing the virtual cells in the HMM matrix. For instance, assuming for exemplary purposes, a 5 clock cycle latency for each multiply and each add operation, the worst-case latency through the M, I, D state update calculations would be the 20 clock cycles it would take to propagate through the M update calculation. There are half as many operations in the I and D state update calculations, implying a 10 clock cycle latency for those operations.

These latency implications of the M, I, and D compute operations can be understood with respect to FIG. 16, which sets forth various examples of the cell-to-cell data dependencies. In such instances, the M and D state information of a given cell feed the D state computations of the cell in the HMM matrix that is immediately to the right (e.g., having the same read base as the given cell, but having the next haplotype base). Likewise, the M and I state information for the given cell feed the I state computations of the cell in the HMM matrix that is immediately below (e.g., having the same haplotype base as the give cell, but having the next read base). So, in particular instances, the M, I, and D states of a given cell feed the D and I state computations of cells in the next diagonal of the HMM cell matrix, as described above.

Similarly, the M, I, and D states of a given cell feed the M state computation of the cell that is to the right one and down one (e.g., having both the next haplotype base AND the next read base). This cell is actually two diagonals away from the cell that feeds it (whereas, the I and D state calculations rely on states from a cell that is one diagonal away). This quality of the I and D state calculations relying on cells one diagonal away, while the M state calculations rely on cells two diagonals away, has a beneficial result for hardware design.

Particularly, given these configurations, I and D state calculations may be adapted to take half as long (e.g., 10 cycles) as the M state calculations (e.g., 20 cycles). Hence, if M state calculations are started 10 cycles before I and D state calculations for the same cell, then the M, I, and D state computations for a cell in the HMM matrix 30 will all complete at the same time. Additionally, if the matrix 30 is traversed in a diagonal fashion, such as having a swath 35 of about 10 cells each within it (e.g., that spans ten read bases), then: The M and D states produced by a given cell at (hap, rd) coordinates (i, j) can be used by cell (i+1, j) D state calculations as soon as they are all the way through the compute pipeline of the cell at (i, j).

The M and I states produced by a given cell at (hap, rd) coordinates (i, j) can be used by cell (i, j+1) I state calculations one clock cycle after they are all the way through the compute pipeline of the cell at (i, j). Likewise, the M, I and D states produced by a given cell at (hap, rd) coordinates (i, j) can be used by cell (i+1, j+1) M state calculations one clock cycle after they are all the way through the compute pipeline of the cell at (i, j). Taken together, the above points establish that very little dedicated storage is needed for the M, I, and D states along the diagonal of the swath path that spans the swath length, e.g., of ten reads. In such an instance, just the registers required to delay cell (i, j) M, I, and D state values one clock cycle for use in cell (i+1, j+1) M calculations and cell (i, j+1) I calculations by one clock cycle). Moreover, there is somewhat of a virtuous cycle here as the M state computations for a given cell are begun 10 clock cycles before the I and D state calculations for that same cell, natively outputting the new M, I, and D states for any given cell simultaneously.

In view of the above, and as can be seen with respect to FIG. 16, the HMM accelerator control logic 15 may be configured to process the data within each of the cells of the virtual matrix 30 in a manner so as to traverse the matrix. Particularly, in various embodiments, operations start at cell (0,0), with M state calculations beginning 10 clock cycles before I and D state calculations begin. The next cell to traverse should be cell (1,0). However, there is a ten cycle latency after the start of I and D calculations before the results from cell (0,0) will be available. The hardware, therefore, inserts nine "dead" cycles into the compute pipeline. These are shown as the cells with haplotype index less than zero in FIG. 16.

After completing the dead cycle that has an effective cell position in the matrix of (−9,−9), the M, I, and D state values for cell (0,0) are available. These (e.g., the M and D state outputs of cell (0,0)) may now be used straight away to start the D state computations of cell (0,1). One clock cycle later, the M, I, and D state values from cell (0,0) may be used to begin the I state computations of cell (0,1) and the M state computations of cell (1,1).

The next cell to be traversed may be cell (2,0). However, there is a ten cycle latency after the start of I and D calculations before the results from cell (1,0) will be available. The hardware, therefore, inserts eight dead cycles into the compute pipeline. These are shown as the cells with haplotype index less than zero, as in FIG. 16 along the same diagonal as cells (1,0) and (0,1). After completing the dead cycle that has an effective cell position in the matrix of (−8, −9), the M, I, and D state values for cell (1,0) are available. These (e.g., the M and D state outputs of cell (1,0)) are now used straight away to start the D state computations of cell (2,0).

One clock cycle later, the M, I, and D state values from cell (1,0) may be used to begin the I state computations of cell (1,1) and the M state computations of cell (2,1). The M and D state values from cell (0,1) may then be used at that same time to start the D state calculations of cell (1,1). One clock cycle later, the M, I, and D state values from cell (0,1) are used to begin the I state computations of cell (0,2) and the M state computations of cell (1,2).

Now, the next cell to traverse may be cell (3,0). However, there is a ten-cycle latency after the start of I and D calculations before the results from cell (2,0) will be available. The hardware, therefore, inserts seven dead cycles into the compute pipeline. These are again shown as the cells with haplotype index less than zero in FIG. 16 along the same diagonal as cells (2,0), (1,1), and (0,2). After completing the dead cycle that has an effective cell position in the matrix of (−7,−9), the M, I, and D state values for cell (2,0) are available. These (e.g., the M and D state outputs of cell (2,0)) are now used straight away to start the D state computations of cell (3,0). And, so, computation for another ten cells in the diagonal begins.

Such processing may continue until the end of the last full diagonal in the swath 35a, which, in this example (that has a read length of 35 and haplotype length of 14), will occur after the diagonal that begins with the cell at (hap, rd) coordinates of (13,0) is completed. After the cell (4,9) in FIG. 16 is traversed, the next cell to traverse should be cell (13,1). However, there is a ten-cycle latency after the start of the I and D calculations before the results from cell (12,1) will be available.

The hardware may be configured, therefore, to start operations associated with the first cell in the next swath 35b, such as at coordinates (0, 10). Following the processing of cell (0, 10), then cell (13, 1) can be traversed. The whole diagonal of cells beginning with cell (13, 1) is then traversed until cell (5, 9) is reached. Likewise, after the cell (5, 9) is traversed, the next cell to traverse should be cell (13, 2). However, as before there may be a ten-cycle latency after the start of I and D calculations before the results from cell (12, 2) will be available. Hence, the hardware may be configured to start operations associated with the first cell in the second diagonal of the next swath 35b, such as at coordinates (1, 10), followed by cell (0, 11).

Following the processing of cell (0, 11), the cell (13, 2) can be traversed, in accordance with the methods disclosed above. The whole diagonal 35 of cells beginning with cell (13,2) is then traversed until cell (6, 9) is reached. Additionally, after the cell (6, 9) is traversed, the next cell to be traversed should be cell (13, 3). However, here again there may be a ten-cycle latency period after the start of the I and D calculations before the results from cell (12, 3) will be available. The hardware, therefore, may be configured to start operations associated with the first cell in the third diagonal of the next swath 35c, such as at coordinates (2, 10), followed by cells (1, 11) and (0, 12), and likewise.

This continues as indicated, in accordance with the above until the last cell in the first swath 35a (the cell at (hap, rd) coordinates (13, 9)) is traversed, at which point the logic can be fully dedicated to traversing diagonals in the second swath 35b, starting with the cell at (9, 10). The pattern outlined above repeats for as many swaths of 10 reads as necessary, until the bottom swath 35c (those cells in this example that are associated with read bases having index 30, or greater) is reached.

In the bottom swath 35, more dead cells may be inserted, as shown in FIG. 16 as cells with read indices greater than 35 and with haplotype indices greater than 13. Additionally, in the final swath 35c, an additional row of cells may effectively be added. These cells are indicated at line 35 in FIG. 16, and relate to a dedicated clock cycle in each diagonal of the final swath where the final sum operations are occurring. In these cycles, the M and I states of the cell immediately above are added together, and that result is itself summed with a running final sum (that is initialized to zero at the left edge of the HMM matrix 30).

Taking the discussion above as context, and in view of FIG. 16, it is possible to see that, for this example of read length of 35 and haplotype length of 14, there are 102 dead cycles, 14 cycles associated with final sum operations, and 20 cycles of pipeline latency, for a total of 102+14+20=146 cycles of overhead. It can also be seen that, for any HMM job 20 with a read length greater than 10, the dead cycles in the upper left corner of FIG. 16 are independent of read length. It can also be seen that the dead cycles at the bottom and bottom right portion of FIG. 16 are dependent on read length, with fewest dead cycles for reads having mod(read length, 10)=9 and most dead cycles for mod(read length, 10)=0. It can further be seen that the overhead cycles become smaller as a total percentage of HMM matrix 30 evaluation cycles as the haplotype lengths increase (bigger matrix, partially fixed number of overhead cycles) or as the read lengths increase (note: this refers to the percentage of overhead associated with the final sum row in the matrix being reduced as read length—row-count—increases). Using such histogram data from representative whole human genome runs, it has been determined that traversing the HMM matrix in the manner described above results in less than 10% overhead for the whole genome processing.

Further methods may be employed to reduce the amount of overhead cycles including: Having dedicated logic for the final sum operations rather than sharing adders with the M and D state calculation logic. This eliminates one row of the HMM matrix 30. Using dead cycles to begin HMM matrix operations for the next HMM job in the queue.

Each grouping of ten rows of the HMM matrix 30 constitutes a "swath" 35 in the HMM accelerator function. It is noted that the length of the swath may be increased or decreased so as to meet the efficiency and/or throughput demands of the system. Hence, the swatch length may be about five rows or less to about fifty rows or more, such as about ten rows to about forty-five rows, for instance, about fifteen or about twenty rows to about forty rows or about thirty-five rows, including about twenty five rows to about thirty rows of cells in length.

With the exceptions noted in the section, above, related to harvesting cycles that would otherwise be dead cycles at the right edge of the matrix of FIG. 16, the HMM matrix may be processed one swath at a time. As can be seen with respect to FIG. 16, the states of the cells in the bottom row of each swath 35a feed the state computation logic in the top row of the next swath 35b. Consequently, there may be a need to store (put) and retrieve (get) the state information for those cells in the bottom row, or edge, of each swath.

The logic to do this may include one or more of the following: when the M, I, and D state computations for a cell in the HMM matrix 30 complete for a cell with mod(read index, 10)=9, save the result to the M, I, D state storage memory. When M and I state computations (e.g., where D state computations do not require information from cells above them in the matrix) for a cell in the HMM matrix 30 begin for a cell with mod(read index, 10)=0, retrieve the previously saved M, I, and D state information from the appropriate place in the M, I, D state storage memory. Note in these instances that M, I, and D state values that feed row 0 (the top row) M and I state calculations in the HMM matrix 30 are simply a predetermined constant value and do not need to be recalled from memory, as is true for the M and D state values that feed column 0 (the left column) D state calculations.

As noted above, the HMM accelerator may or may not include a dedicated summing resource in the HMM hardware accelerator such that exist simply for the purpose of the final sum operations. However, in particular instances, as described herein, an additional row may be added to the bottom of the HMM matrix 30, and the clock cycles associated with this extra row may be used for final summing operations. For instance, the sum itself may be achieved by borrowing (e.g., as per FIG. 13) an adder from the M state computation logic to do the M+I operation, and further by borrowing an adder from the D state computation logic to add the newly formed M+I sum to the running final sum accumulation value. In such an instance, the control logic to activate the final sum operation may kick in whenever the read index that guides the HMM traversing operation is equal to the length of the inputted read sequence for the job. These operations can be seen at line 34 toward the bottom of the sample HMM matrix 30 of FIG. 16.

Hence, as can be seen above, in one implementation, the variant caller may make use of the mapper and/or aligner engines to determine the likelihood as to where various reads originated, such as with respect to a given location, e.g., chromosomal location. In such instances, the variant caller may be configured to detect the underlying sequence at that location, such as independently of other regions not immediately adjacent to it, such as by implementing the HMM operations set forth herein above. This is particularly useful and works well when the region of interest does not resemble any other region of the genome over the span of a single read (or a pair of reads for paired-end sequencing). However, a significant fraction of the human genome does not meet this criterion, which can make variant calling, e.g., the process of reconstructing a subject's genome from the reads that an NGS produces, challenging.

Particularly, though DNA sequencing has improved dramatically, variant calling remains a difficult problem, largely due to the genome's redundant structure. As disclosed herein, however, the complexities presented by the genome's redundancy may be overcome, at least in part, from a perspective driven by short read data. More particularly, the devices, systems, and methods of employing the same as disclosed herein may be configured in such a manner so as to focus on Homologous or Similar regions that may otherwise have been characterized by low variant calling accuracy. In certain instances, such low variant calling accuracy may stem from difficulties observed in read mapping and alignments with respect to homologous regions that typically may result in very low read MAPQs. Accordingly, presented herein are strategic implementations that accurately call variants (SNPs, Indels, and the like) in homologous regions, such as by jointly considering the information present in these homologous regions.

For instance, many regions of the genome are homologous, e.g., they have near-identical copies located elsewhere in the genome, e.g., in multiple locations, and as a result, the true source location of a read may be subject to considerable uncertainty. Specifically, if a group of reads is mapped with low confidence, e.g., due to apparent homology, a typical variant caller may ignore and not process the reads, even though they may contain useful information. In other instances, if a read is mis-mapped (e.g., the primary alignment is not the true source of the read), detection errors may result. More specifically, previously implemented short-read sequencing technologies have been susceptible to these problems, and conventional detection methods often leaves large regions of the genome in the dark.

In some instances, long-read sequencing can be employed to mitigate these problems, but it typically has much higher cost and/or higher error rates, takes longer, and/or suffers from other shortcomings. Therefore, in various instances, it may be beneficial to perform a multi-region joint detection operation as herein described. For instance, instead of considering each region in isolation and/or instead of performing and analyzing long read sequencing, multi-region joint detection (MRJD) methodologies may be employed, such as where the MRJD protocol considers multiple, e.g., all, locations from which a group of reads may have originated, and attempts to detect the underlying sequences together, e.g., jointly, using all available information, which may be regardless of low or abnormal confidence and/or certainty scores.

For example, for a diploid organism with statistically uniform coverage, a brute force Bayesian calculation, as described above, may be performed in a variant call analysis. However, in a brute force MLRD computation, the complexity of the calculation grows rapidly with the number of regions N, and the number of candidate haplotypes K to be considered. Particularly, to consider all combinations of candidate haplotypes, the number of candidate solutions for which to calculate probabilities may often times be exponential. For instance, as described in greater detail below, in a brute force implementation, the number of candidate haplotypes includes the number of active positions, which if a graph-assembly technique is used to generate the list of candidate haplotypes in a variant call operation, such as in the building of a De Brujin graph as disclosed herein, then the number of active positions is the number of independent "bubbles" in the graph. Hence, such a brute-force calculation can be prohibitively expensive to implement, and as such brute force Bayesian calculations can be prohibitively complex.

Accordingly, in one aspect, as set forth in FIG. 17A, a method to reduce the complexity of such brute force calculations is herein provided. For instance, as disclosed above, though the speed and accuracy of DNA/RNA sequencing has improved dramatically, especially with respect to the methods disclosed herein, variant calling, e.g., the process of reconstructing a subject's genome from the reads a sequencer produces, remains a difficult problem, largely due to the genome's redundant structure. The devices, systems, and methods disclosed herein therefore are configured to reduce the complexities presented by the genome's redundancy from a perspective driven by short read data in contrast to long read sequencing. In particular, provided herein are methods for performing very long read detection that accounts for homologous and/or similar regions of the genome that are usually characterized by low variant calling accuracy without necessarily having to perform long read sequencing.

For instance, in one embodiment, a system and method for performing multi region joint detection is provided. Specifically, in a first instance, a general variant calling operation may be performed such as employing the methods disclosed herein. Particularly, a general variant caller may employ a reference genome sequence, which reference genome presents all the bases in a model genome. This reference forms the backbone of an analysis by which a subject's genome is compared to a reference genome. For instance, as discussed above, employing a Next Gen sequencer, a subject's genome may be broken down into subsequences, e.g., reads, typically about 100-1,000 bases each, which reads may be mapped and aligned to the reference, much like putting a jigsaw puzzle together.

Once the subject's genome has been mapped and/or aligned, using this reference genome in comparison to the subject's actual genome, it may be determined to what extent, and how the subject's genome differs from the reference genome, e.g., on a base by base basis. Particularly, in comparing the subject's genome to one or more reference genomes, such as on a base by base basis, the analysis moves iteratively along the sequences comparing the one with the other(s) to determine if they agree or disagree. Accordingly, each base within the sequences represents a position to be called, such as represented by position A in FIG. 18A.

Specifically, for every position A of the reference to be called with respect to the subject's genome, a pile up of sequences, e.g., reads, will be mapped and aligned in such a manner that a large sample set of reads may all overlap one another at any given position A. Particularly, this oversampling can include a number of reads, e.g., from one to a hundred or more, where each of the reads in the pileup have nucleotides overlapping the region being called. The calling of these reads from base to base, therefore, involves the formation of a processing window that slides along the sequences making calls, where the length of the window, e.g., the number of bases under examination at any given time, forms the active region of determination, as described above. Hence, the window represents the active region of bases in the sample being called, where the calling involves comparing each base at a given position, e.g., A, in all of the reads of the pile up within the active region, where the identity of the base at that position in the number of pile up of reads, provides evidence for the true identity of the base at that position being called.

For this purpose, based on the relevant MAPQ confidence score derived for each read segment, it may be generally determined, within a certain confidence score, that the mapping and aligning was performed accurately. However, the question still remains, no matter how slight, as to whether or not the mapping and aligning of the reads is accurate, or if one or more of the reads really belong to someplace else. Accordingly, in one aspect, provided herein are devices and methods for improving the confidence in performing variant calling.

Particularly, in various instances, the variant caller can be configured to perform one or more multi-region joint detection operations, as herein described, which may be employed to give greater confidence in the achievable results. For instance, in such an instance, the variant caller may be configured to analyze the various regions in the genome so as to determine particular regions that appear to be similar. For example, as can be seen with respect to FIG. 18A, there may be a reference region A, and a reference region B, where the referenced sequences are very similar to one another, e.g., but with a few regions of dissimilar base pair matching, such as where example Ref A has an "A," and example Ref B has a "T", but outside of these few dissimilates, everyplace else within the region in question may appear to match. Because of the extent of similarities, these two regions, e.g., Ref A and Ref B, will typically be considered homologous, or paralogous, regions.

As depicted, the two reference regions A and B are 99% similar. There may be other regions, e.g., Ref's C and D, which are relatively similar, e.g., about 93% similar, but as compared to the 99% similarity between reference regions A and B, the reference regions C and D would not be considered homologous, or at least would have a lessor chance of actually being homologous. In such an instance, the variant calling procedures may be able to adequately call out the differences between reference regions C and D, but may, in certain instances, have difficulties calling out the differences between the highly homologous regions of reference regions A and B, e.g., because of their high homology. Particularly, because of the extent of the dissimilarity between reference sequences A and B to reference sequences C and D, it would not be expected that reads that map and align to either Ref Seq A or B, would mistakenly be mapped to Ref Seq C or D. However, it might be expected that reads that map and align to Ref Seq A may be mis-mapped to Ref Seq B.

Given the extent of the homology, mis-mapping between regions A and B may be quite likely. Accordingly, to increase accuracy it may be desirable for the system to be able to distinguish and/or account for the difference between homologous regions, such as when performing a mapping, aligning, and/or variant calling procedure. Specifically, when generating a pile up of reads that map and align to a region within Ref A, and generating a pile up of reads that map and align to a region within Ref B, any of the reads may in fact be mis-mapped to the wrong place, and as such, to effectuate better accuracy, when performing the variant calling operations disclosed herein, these homologous regions, and the reads mapped and aligned thereto, should be considered together, such as in a joint detection protocol, e.g., a multi-region joint detection protocol, as described herein.

Accordingly, presented herein, are devices, systems, as well as the methods of their use, which are directed to multi-region joint detection (MRJD), such as where a plurality, e.g., all, of the reads from the various pileups of the various identified homologous regions are considered together, such as where instead of making a single call for each location, a joint call is made for all locations that appear to be homologous. Making such joint calls is advantageous because before attempting to make a call for each reference individually, it would first have to be determined to which region, of which reference, the various reads in question actually map and align, and that is inherently uncertain, and the very problem being solved by the proposed joint detection. Hence, because the regions of the two references are so similar, it is very difficult to determine which reads map to which regions. However, if these regions are called jointly, it is not necessary to make an upfront decision about which homologous reads map to which reference region. Therefore, when making a joint call, the assumption may be made that any reads in a pileup of a region on one reference, e.g., A, that is homologous to another region on a second reference, e.g., B, could belong to either Ref. A or Ref. B.

Consequently, where desired, an MRJD protocol may be implemented on addition to the variant call algorithm implemented in the devices, systems, and methods herein. For instance, in one iteration, a variant call algorithm takes the evidence presented in the mapped and/or aligned reads for a given region in the sample and reference genomes, analyzes the possibility that what appears to be in the sample's genome is in fact present, based on a comparison with the reference genome, and makes a decision given the evidence as to how the sample actually differs from the reference, e.g., given this evidence the variant caller algorithm determines the most likely answer of what's different between the read and the reference. However, MRJD is a further algorithm that may be implemented along with the VC algorithm, where the MRJD is configured to help the variant caller to more accurately determine if an observed difference, e.g., in the subject's read, is in fact a true deviation from the reference.

Figure 18A:
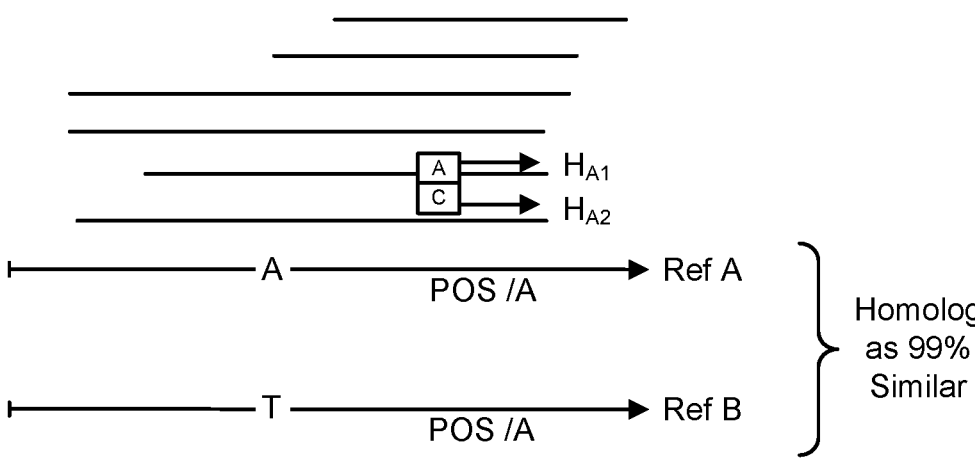
FIG. 18A depicts an exemplary event between two homologous sequenced regions in a pileup of reads.

Accordingly, the first step in an MJRD analysis involves the identification of homologous regions, based on a percentage of correspondence between the sequence in a plurality of regions of one or more references, e.g., Ref. A and Ref. B, and the pileup sequences in one or more regions of the subject's reads. Particularly, Ref. A and Ref. B may actually be diploid forms of the same genetic material, such as where there are two copies of a given region of the chromosome. Hence, where diploid references are being analyzed, at various positions Ref A may have one particular nucleotide, and at that same position in Ref. B, another nucleotide may be present. In this example, Ref. A and Ref. B, are homozygous at position A for "A". However, as can be seen in FIG. 18A, the DNA of the subject is heterozygous at this position A, such as where with respect to the reads of the pile up of Ref. A, one allele of the subject's chromosome has an "A", but the other allele has a "C", yet with respect to Ref. B, another copy of the subject's chromosome has an "A" for both alleles at position A. This also becomes more complicated, where the sample being analyzed contains a mutation, e.g., at one of those naturally occurring variable positions, such as a heterozygous SNP at position A (not shown).

Figure 18B:
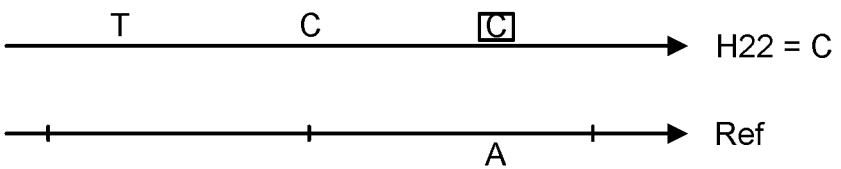
FIG. 18B depicts the constructed reads of FIG. 18A, demarcating nucleotide difference between the two sequences.

As can be seen with respect to Ref. A of FIG. 18B, at position A, the subject's sample may include reads that indicate there is heterozygosity at position A, such as where some of the reads include a "C" at this position, and some of the reads indicate an "A" at this position (e.g., $Haplotype_{a1}$="A", $H_{a2}$="C"); while with respect to Ref. B, the reads at position A indicate homozygosity, such as where all the reads in the pileup have an "A" at that position (e.g., $H_{b1}$="A", $H_{b2}$="A"). However, MRJD overcomes these difficulties by making a joint call simultaneously, by analyzing all of the reads that get mapped to both regions of the reference, while considering the possibility that any one of the reads may be in the wrong location.

After the various homologous regions are identified, the next step is to determine the correspondence between the homologous reference regions, and then, with respect to MRJD, the mapper and/or aligners determination as to where the various applicable reads are "supposed to map" between the two homologous regions may be discarded, and rather, all of the reads in any of the pileups in these homologous regions may be considered collectively together, knowing that any of these reads may belong to any of the homologous regions being compared. Hence, the calculations for determining these joint calls, as set forth in detail below, considers the possibility that any of these reads came from any of the homologous reference regions, and, where applicable, from either haplotype of either of the reference regions.

It is to be noted, although the preceding was with reference to multiple regions of homology within a reference, the same analysis may be applied for single region detection as well. For instance, as can be seen with respect to FIG. 18B, even for a single region, for any given region, there may be two separate haplotypes present, e.g., $H_1$ and $H_2$, that the subjects genetic sample may have for a particular region, and because they are haplotypes, they are likely to be very similar to one another. Consequently, if these positions are analyzed one in isolation of the other, it may be hard to determine if there are true variations being considered. Thus, the calculations being performed with respect to homologous regions are useful for non-homologous regions as well, because any specific region is likely to be diploid, e.g., having both a first haplotype ($H_1$) and a second haplotype ($H_2$), and so being analyzing the regions jointly will enhance the accuracy of the system. Likewise, for a two-reference region, e.g., a homologous region, as described above, what is being called is an $H_{A1}$ and $H_{A2}$ for the first region, and an $H_{A1}$ and $H_{A2}$ for the second region (which is equivalent two strands for each chromosome and two regions for each strand=4 diploidtypes, generally.

Accordingly, MRJD may be employed to determine an initial answer, with respect to one or more, e.g., all, homologous regions, and then single region detection may be applied back to one or more, e.g., all, single or non-homologous regions, e.g., employing the same basic analysis, and thus, better accuracy may be achieved. Hence, single region non-joint detection may also be performed. For instance, with respect to single region detection, for the candidate haplotypes, $H_{A1}$, in current iterations the reference region may be about 300-500 base pairs long, and on top of the reference a graph, e.g., a De Bruijn graph, as set forth in FIG. 18C, is built, such as from K-mers from the reads, where any location that differs from the reference forms a divergent pathway or "bubble" in the graph, from which haplotypes are extracted, where each extracted haplotype, e.g., divergent pathway, forms a potential hypothesis for what might be on one of the two strands of the chromosomes at a particular location of the active region under examination.

Figure 18C:
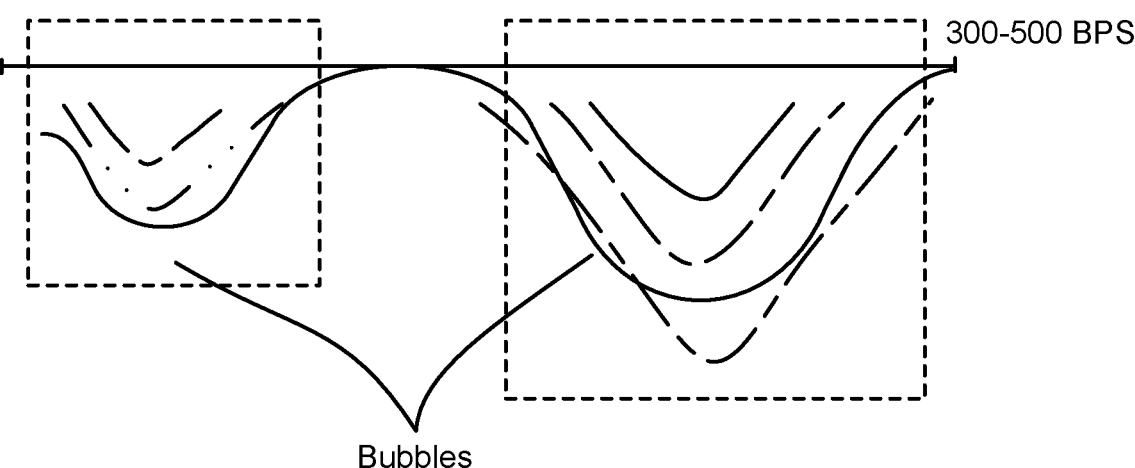
FIG. 18C depicts various bubbles of a De Brujin graph that may be used in performing an accelerated variant call operation.

However, if there are a lot of divergent pathways, e.g., a lot of bubbles through the graph are formed, as seen with respect to FIG. 18C, and a large number of haplotypes are extracted, then a maximum cutoff may be introduced to keep the calculations manageable. The cutoff can be at any statistically significant number, such as 35, 50, 100, 125-128, 150, 175, 200, or more, etc. Nevertheless, in certain instances, substantially a greater number, e.g., all, of the haplotypes may be considered.

In such an instance, instead of extracting complete source to sink haplotypes from start to finish, e.g., from the beginning of the sequence to the end, only the sequences associated with the individual bubbles need be extracted, e.g., only the bubbles need to be aligned to the reference. Accordingly, the bubbles are extracted from the DBG, the sequences aligned to the reference, and from these alignments, specific SNPs, insertions, deletions, and the like may be determined, with respect as to why the sequences of the various bubbles differ from the reference. Hence, in this regard, all of the different hypothetical haplotypes for analysis may be derived from mixing and matching the sequences pertaining to all of the various bubbles in different combinations. In a manner such as this, all of the haplotypes to be extracted do not need to be enumerated. These methods for performing multi-region joint detection, are described in greater detail herein below.

Further, abstractly, even though all of these candidate haplotypes may be tested, a growing the tree algorithm may be performed where the graph being produced begins to look like a growing tree. For instance, a branching tree graph of joint haplotypes/diplotypes may be built in such a manner that as the tree grows, the underlying algorithm functions to both grow and prune the tree at the same time as more and more calculations are made, and it becomes apparent that various different candidate hypotheses are simply too improbable. Hence, as the tree grows and is pruned, not all of the hypothesized haplotypes need to be calculated.

Specifically, with respect to the growing of the tree function, when there is disagreement between two references, or between the references and the reads, as to what base is present at given positions being resolved, it must be determined which base actually belongs in which position, and in view of such disagreements it must be determined which differences may be caused by SNPs, Indels, or the like, versus which are machine errors. Accordingly, when growing the tree, e.g., extracting bubbles from the De Bruijn graph, such as via SW or NW aligning, and positioning them within the emerging tree graph, each bubble to be extracted becomes an event in the tree graph, which represents possible SNPs, Indels, and/or other differences from the reference. See FIG. 18C.

Particularly, in a DBG, the bubbles represent mismatches from the reference, e.g., representative of Indels (which bases have been added or deleted), SNPs (which bases are different), and the like. Consequently, as the bubbles are aligned to the reference(s), the various differences between the two are categorized as events, and a list of the various events, e.g., bubbles, is generated, Therefore, the determination then becomes: what combination of the possible events, e.g., of possible SNPs and Indels, has led to the actual variations in the subject's genetic sequence, e.g., is the truth in each of the actual various haplotypes, e.g., 4, based on probability. More particularly, any one candidate, e.g., joint diplotype candidate, forming a root Go (representing events for a given segment) may have 4 haplotypes, and each of the four haplotypes will form an identified subset of the events.

Figure 18D:
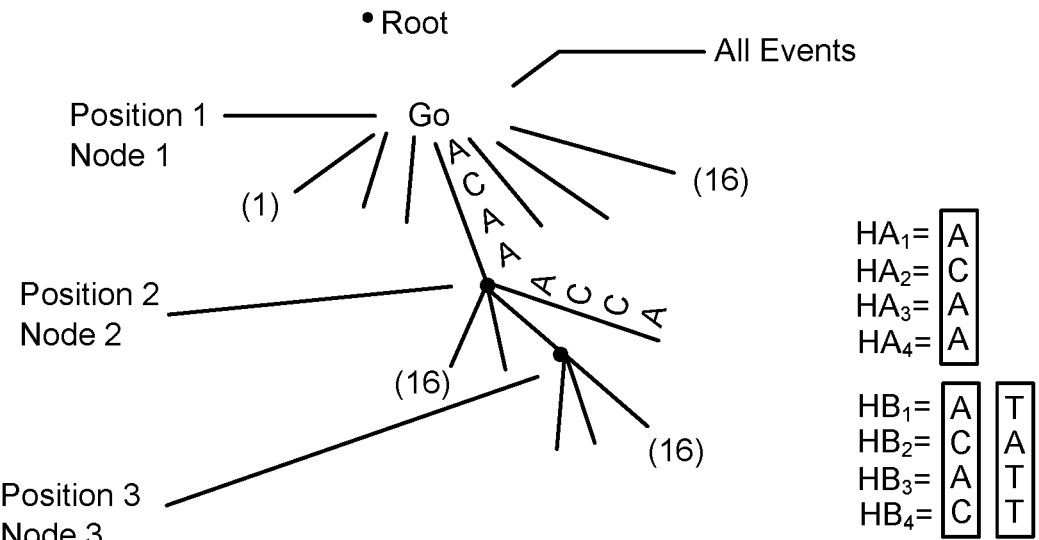
FIG. 18D depicts a representation of a pruning the tree function as described herein.

However, as can be seen with respect to FIG. 18D, when performing a growing and/or pruning of the tree function, a full list of the entire subset of all combinations of events can be, but need not be, determined all at once. Instead, the determination begins at a single position Go, e.g., one event, and the tree is grown from there one event at a time, which through the pruning function, may leave various low probability events unresolved. Hence, with respect to a growing the tree function, as can be seen with respect to FIG. 18D, the calculation begins with determining the haplotypes, e.g., $H_{A1}$, $H_{A2}$, $H_{B1}$, $H_{B2}$ (for a diploid organism), where the initial haplotypes are considered to all be unresolved with respect to their respective references, e.g., Ref. A and Ref. B, basically with none of the events present.

Figure 18E:
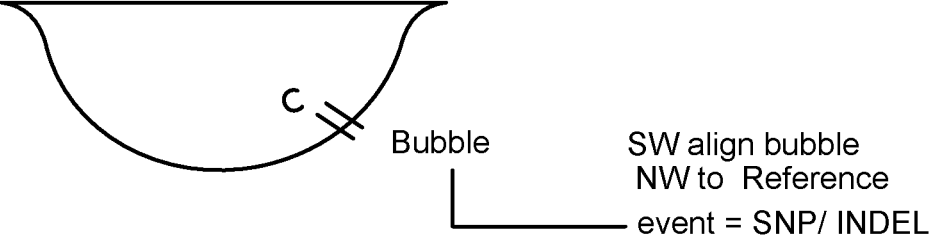
FIG. 18E depicts one of the bubbles of FIG. 18C.

Accordingly, the initial starting point is with the root of the tree being Go, and the joint diplotype having all events unresolved. Then a particular event, e.g., an initial bubble, is selected as the origin for determination, whereby the initial event is to be resolved for all of the haplotypes, where the event may be a first point of divergence from the reference, such as with respect to the potential presence of an SNP or Indel at position one. As exemplified in FIG. 18E, at position one, there is an event or bubble, such as an SNP, where a "C" has been substituted for an "A", such that the reference has an "A" at position one, but the read in question has a "C". In such an instance, since for this position in the pileup there are 4 haplotypes, and each may have either an "A", as in the reference, or the event "C", there are potentially $2^4=16$ possibilities for resolving this position. Hence, the calculation moves immediately from the root to 16 branches, representing the potential resolutions for the event at position one.

Therefore, as can be seen with respect to FIG. 18D, all of the potential sequences for all of the four haplotypes may be set forth, e.g., $H_{A1}$, $H_{A2}$, $H_{B1}$, $H_{B2}$, where at position one there is either the "A", as in accordance with the reference, or event "C", indicating the presence of an SNP, for that one event, where the event "C" is determined by the examining the various bubble pathways through the graph. So, for each branch or child node, each branch may differ based on the likelihood of the base at position one according to or diverging from the reference, while the rest of the events remain unresolved. This process then will be repeated for each branch node, and for each base within the variation bubbles, so as to resolve all events for all haplotypes. Hence, the probabilities may be recalculated for observing any particular read given the various potential haplotypes.

Particularly, for each node, there may be four haplotypes, and each haplotype may be compared against each read in the pileup. For instance, in one embodiment, the SW, NW, and/or HMM engine, analyzes each node and considers each of the four haplotypes for each node. Consequently, generating each node activates the SW and/or HMM engine to analyze that node by considering all of the haplotypes, e.g., 4, for that node in comparison for each of the reads, where the SW and/or HMM engine considers one haplotype for one read for each of the haplotypes and each of the reads for all of the viable nodes.

Hence, if for exemplary purposes of this example, it is the case that there is a heterozygous SNP "C" for the one region of one haplotype, e.g., one strand of one chromosome has a "C", but all of the other bases at this position for the other strands do not, e.g., they all match the reference "A", then it would be expected that all of the reads in the pile up support this finding, such as by having a majority of "A"s at position one, and a minority, e.g., about ¼, of the reads having a "C" at position one, for the true node. Thus, if any later observable reads at a different node, show a multiplicity of "Cs" at position one, then that node will be unlikely to be the true node, e.g., will have a low probability, because there will not be enough reads with Cs at this position in the pileup to make their occurrence likely. Specifically, it will be more probable that the existence of a "C" at this position in the reads in question is evidence of a sequencing or other scientific error, rather than being a true haplotype candidate. Consequently, if certain nodes end up having small probabilities, as compared to the true node, it is because they are not supported by a majority of the reads, e.g., in the pileup, and thus, these nodes may be pruned off, thereby discarding the nodes of low probabilities, but in a manner that preserves the true node(s).

Accordingly, once the event one position has been determined, the next event position may be determined, and the processes herein described may then be repeated for that new position with respect to any of the surviving nodes that have not heretofore been pruned. Particularly, event two may be selected from the existing available nodes, and that event can serve as the $G_1$ root for determining the likely identity of the base at position two, such as by once again defining the new haplotypes, e.g., 4, as well as their various branches, e.g., 16, explaining the possible variations with respect to position 2. Hence, through repeating this same process, event 2 may now be resolved. Therefore, as can be seen with respect to FIG. 18D, once position 1 has been determined, a new node for position 2 may be selected, and its 16 potential haplotype candidates may be considered. In such an instance, the candidates for each of $H_{A1}$, $H_{A2}$, $H_{B1}$, $H_{B2}$ may be determined, but in this instance, since position 1 has already been resolved, with respect to determining the nucleotide identify for each of the haplotypes at position 1, it is position 2, that will now be resolved, for each of the haplotypes at position 2, as set forth in FIG. 18D, showing the resolution of position 2.

Once this process is finished, once all of the events have been processed and resolved, e.g., including all children nodes and children of children nodes that have not been pruned, then the nodes of the tree that have not been pruned may be examined, and it may be determined based on the probability scores, which tree represents the joint diplotype, e.g., which sequence has the highest probability of being true. Therefore, in this manner, because of the pruning function, the entire tree does not need to be built, e.g., most of the tree will end up being pruned as the analysis continues, so the overall amount of calculations is greatly reduced over non-pruning functions, albeit substantially more than performing non-joint diplotype calling, e.g., single region calling. Accordingly, the present analytics modules are able to determine and resolve two or more regions of high homology with a high degree of accuracy, e.g., employing joint diplotype analysis, where traditional methods are simply not capable of resolving such regions at all, e.g., because of false positives and irresolution.

Particularly, various variant caller implementations may be configured to simply not perform an analysis on regions of high homology. The present iterations overcome these and other such problems in the field. More particularly, the present devices, systems, and their methods of use may be configured so as to consider a greater proportion, e.g., all of the haplotypes, despite the occurrence of regions of high homology. Of course, the speed of these calculations may further be increased, by not performing certain calculations where it can be determined that the results of such calculations have a low probability of being true, such as by implementing a pruning function, as herein described.

A benefit of these configurations, e.g., joint-diplotype resolution and pruning, is that now the size of the active region window, e.g., of bases being analyzed, may be increased from about a few hundred of bases being processed to a few thousands, or even tens or hundreds of thousands of bases can be processed together, such as in one contiguous active region. This increase in size of the active window of analysis allows for more evidence to be considered when determining the identity of any particular nucleotide at any given position, thereby allowing for a greater context within which a more accurate determination of the identity of the nucleotide may be made. Likewise, a greater context allows for supporting evidence to better be chained together when comparing one or more reads covering one or more regions having one or more deviations from the reference. Hence, in such a manner, one event can be connected to another event, which itself may be connected to another event, etc., and from these connections a more accurate call with respect to a given particular event presently under consideration may be made, thereby allowing evidence from farther away, e.g., hundreds to thousands of bases or more away, to be informative in making a present variant call (despite the fact that any given read is only typically hundreds of bases long), thereby further making the processes herein much more accurate.

Particularly, in a manner such as this, the active region can further be made to include thousands, to tens of thousands, even hundreds of thousands of bases or more, and consequently, the method of forming a De Bruijn graph by extracting all of the haplotypes can be avoided, as only a limited number of haplotypes, those with bubbles that may be viable, need be explored, and even of those that are viable, once it becomes clear they are no longer viable they may be pruned, and for those that remain viable, chaining may be employed so as to improve the accuracy of the eventual variant calls being made. This is all made possible by quantum and/or Hardware computing. It may also be performed in software by a CPU or a GPU, but it will be slower.

It is to be noted that with respect to the above examples, it is the probability of the input data, e.g., the reads, that are being determined, given these haplotype theories produced by the De Bruijn graph. However, it may also be useful to employ Bayes theorem, such as for determining the probability of reads given a joint diplotype, down to the opposite probability of determining from the theory of a joint diplotype a best fit given the reads and the evidence assessed. Accordingly, as can be seen with respect to FIG. 18C, from the generated De Bruijn graph, once multi-region joint detection, and/or pruning has occurred, a set of potential haplotypes will result, and then these haplotypes will be tested against the actual reads of the subject. Specifically, each horizontal cross section represents a haplotype, e.g., B1, that may then be subjected to another HMM protocol so as to be tested against the reads so as to determine the probability of a particular read given the haplotype B1.

However, in certain instances, the haplotype, e.g., B1, may not yet be fully determined, but HMM may still be useful to be performed, and in such an instance, a modified HMM calculation, e.g., a partially determined (PD)-HMM operation, discussed below, may be performed where the haplotype is allowed to have undetermined variants, e.g., SNPs and/or indels, in it that have yet to be determined, and as such, the calculation is similar to calculating the best possible probability for an achievable answer given any combination of variants in the unresolved positions. Therefore, this further facilitates the iterative growing of the tree function, where the actual growing of the tree, e.g., the performing of PD-HMM operations, need not be restricted to only those calculations where all the possible variants are known. Hence, in this manner, a number of PD-HMM calculations may be performed, in an iterative fashion, to grow the tree of nodes, despite the fact there are still un-determined regions of unknown possible events in particular candidate haplotypes, and where it becomes possible to trim the tree, PD-HMM resources may be shifted, fluidly, from calculating pruned nodes so as to process only those possibilities that have the greatest probability for successful characterizing the true genotype.

Accordingly, when determining the probability of a specific base actually being present at any one position, the identity of the base at that position may be determined based on the identity at that position on each region of each chromosome, e.g., each haplotype, that represents a viable candidate. Hence, for any candidate, what is being determined is the identity of the given base at the position in question in each of the four haplotypes simultaneously. Particularly, what is being determined is the probability of observing the reads of each of the pileups given the determined likelihood. Specifically, each candidate represents a joint diplotpye, and so being each candidate includes about four haplotypes, which may be set forth in the following equation as G=genotype, where G=the four haplotypes of a single diploid region of a chromosome of the genome e.g., a joint diplotype. In such an instance, what is to be calculated is the probability of actually observing each of the identified candidate read bases of the sequences in the pileups assuming that they are in fact the truth. This initial determination may be performed by an HMM haplotype calculation, as set forth herein above.

For instance, for a candidate "Joint Diploidtype"=4 Haplotypes: (Region A: $H_{A1}H_{A2}$, and Region B: $H_{B1}H_{B2}$)=G→P (R/G) as determined by an $$HMM \text{ (Error Model)} = \prod P(r/G) = \frac{P(r/HA1) + \dots + P(r/Hn)}{n}$$

Hence, if it is assumed that the specific haplotype Hai is the true sequence in this region, and the read came from there, then what are the odds that this read sequence Hai was actually observed. Accordingly, the HMM calculator functions to determine, assuming that the Hai haplotype is the truth, what is the likelihood of actually observing the given read sequence in question.

Specifically, if the read actually matches the haplotype, this will be a very high probability, of course. However, if the particular read in question does not match the haplotype, then any deviation from there should be explainable by a scientific error, such as a sequencing or sequencing machinery error, and not an actual variation. Hence, the HMM calculation is a function of the error models. Specifically, it asks what is the probability of the necessary combination of errors that would have had to occur so as to observe the particular reads being analyzed. Consequently, in this model not only one region is being considered, but a multiplicity of positions at a multiplicity of regions at a multiplicity of strands are being considered simultaneously (e.g., instead of considering at most possibly two haplotypes at one region, now what is being considered is simultaneously the possibility of four haplotypes for any given position at any given region, simultaneously, using all of the reads data from all of the regions in question. These processes, e.g., pruning the tree, multi-region joint detection, and PD-HMM, will now be described in greater detail.

Specifically, as can be seen with respect to FIGS. 17 and 18, a high-level processing chain is provided, such as where the processing chain may include one or more of the following steps: Identifying and inputting homologous regions, performing pre-processing of the input homologous regions, performing a pruned very long read (VLRD) or multi region joint detection (MJRD),S and outputting a variant call file. Particularly with respect to identifying homologous regions, a mapped, aligned, and/or sorted SAM and/or BAM file, e.g., a CRAM, may be used as the primary input to a multi-region joint detection processing engine implementing an MRJD algorithm, as described herein. The MJRD processing engine may be part of an integrated circuit such as a CPU and/or GPU and/or Quantum computing platform, running software, e.g., a quantum algorithm, or implemented within an FPGA, ASIC, or the like. For instance, the above disclosed mapper and/or aligner may be used to generate a CRAM file, e.g., with settings to output N secondary alignments for each read along with the primary alignments. These primary and secondary reads may then be used to identify a list of homologous regions, which homologous regions may be computed based on a user defined similarity threshold between the N regions of the reference genome. This list of identified homologous regions may then be fed to the pre-processing stage of a suitably configured MRJD module.

Accordingly, in the pre-processing stage, for every set of homologous regions, a joint-pileup may first be generated such as by using the primary alignments from one or more, e.g., every, region in the set. See, for instance, FIG. 19. Using this joint pileup, a list of active/candidate variant positions (SNPS/INDELs) may then be generated whereby each of these candidate variants may be processed and evaluated by the MRJD pre-processing engine(s). To reduce computation complexity, a connection matrix may be computed that may be used to define the order of processing of the candidate variants.

In such implementations, the multi-region joint detection algorithm evaluates each identified candidate variant based on the processing order defined in the generated connection matrix. Firstly, one or more candidate joint diplotypes $(G_i)$ may be generated and given a candidate variant. Next, the a-posteriori probabilities of each of the joint diplotypes $(P(G_i|R))$ may be calculated. From these a-posteriori probabilities a genotype matrix may be computed. Next, N diplotypes with the lowest a-posteriori probabilities may be pruned so as to reduce the computational complexity of the calculations. Then the next candidate variant that provides evidence for the current candidate variant being evaluated may be included and the above process repeated. Having included information such as from one or more, e.g., all, the candidate variants from one or more, e.g., all, regions in the homologous region set for the current variant, a variant call may be made from the final genotyping matrix. Each of the active positions, therefore, may all be evaluated in the manner above thereby resulting in a final VCF file.

Particularly, as can be seen with respect to FIG. 17B, a MJRD preprocessing step may be implemented, such as including one or more of the following steps or blocks: The identified and assembled joint pile-up is loaded, a candidate variant list is then created from the assembled joint pile up, and a connection matrix is computed. Particularly, in various instances, a preprocessing methodology may be performed, such as prior to performing one or more variant call operations, such as a multiple read joint detection operation. Such operations may include one or more preprocessing blocks, including: steps pertaining to the loading of joint pile-ups, generating a list of variant candidates from the joint pileups, and computing a connection matrix. Each of the blocks and potential steps associated therewith will now be discussed in greater detail.

Specifically, a first joint pile up pre-processing block may be included in the analysis procedure. For example, various reference regions for an identified span may be extracted, such as from the mapped and/or aligned reads. Particularly, using the list of homologous regions, a joint pileup for each set of homologous regions may be generated. Next, a user-defined span may be used to extract the N reference regions corresponding to N homologous regions within a set. Subsequently, one or more, e.g., all, of the reference regions may be aligned, such as by using a Smith-Waterman alignment, which may be used to generate a universal coordinate system of all the bases in the N reference regions. Further, all the primary reads corresponding to each region may then be extracted from the input SAM or BAM file and be mapped to the universal coordinates. This mapping may be done, as described herein, such as by using the alignment information (CIGAR) present in a CRAM file for each read. In the scenario where some reads pairs were not previously mapped, the reads may be mapped and/or aligned, e.g., Smith-Waterman aligned, to its respective reference region.

Figure 19:
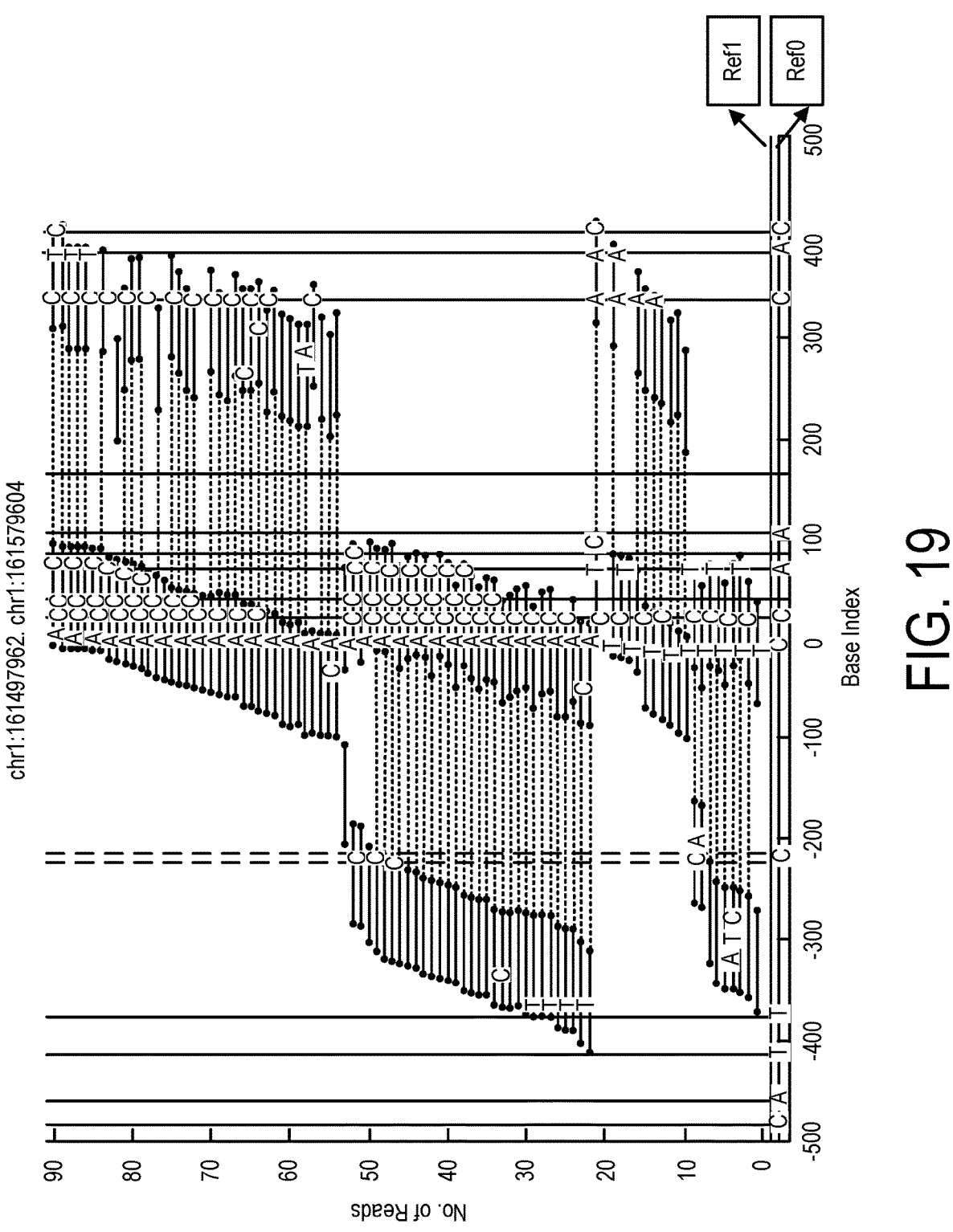
FIG. 19 is a graphical representation of the exemplary pileup pursuant to the connection matrix of FIG. 17.

More particularly, once a joint pile up has been generated and loaded, see for instance, FIG. 19, a candidate variant list may be created, such as from the joint pile up. For instance, a De Bruijn graph (DBG) or other assembly graph may be produced so as to extract various candidate variants (SNPs/

Indels) that may be identified from the joint pileup. Once the DBG is produced the various bubbles in the graph can be mined so as to derive a list of variant candidates.

Particularly, given all the reads, a graph may be generated using each reference region as a backbone. All of the identified candidate variant positions can then be aligned to universal coordinates. A connection matrix may then be computed, where the matrix defines the order of processing of the active positions, which may be a function of the read length and/or insert size. As referenced herein, FIG. 19 shows an example of a joint pileup of two homologous regions in chromosome 1. Although this pileup is with reference to two homologous regions of chromosome 1, this is for exemplary purposes only as the production of the pileup process may be used for any and all homologous regions regardless of chromosome.

Figure 20:
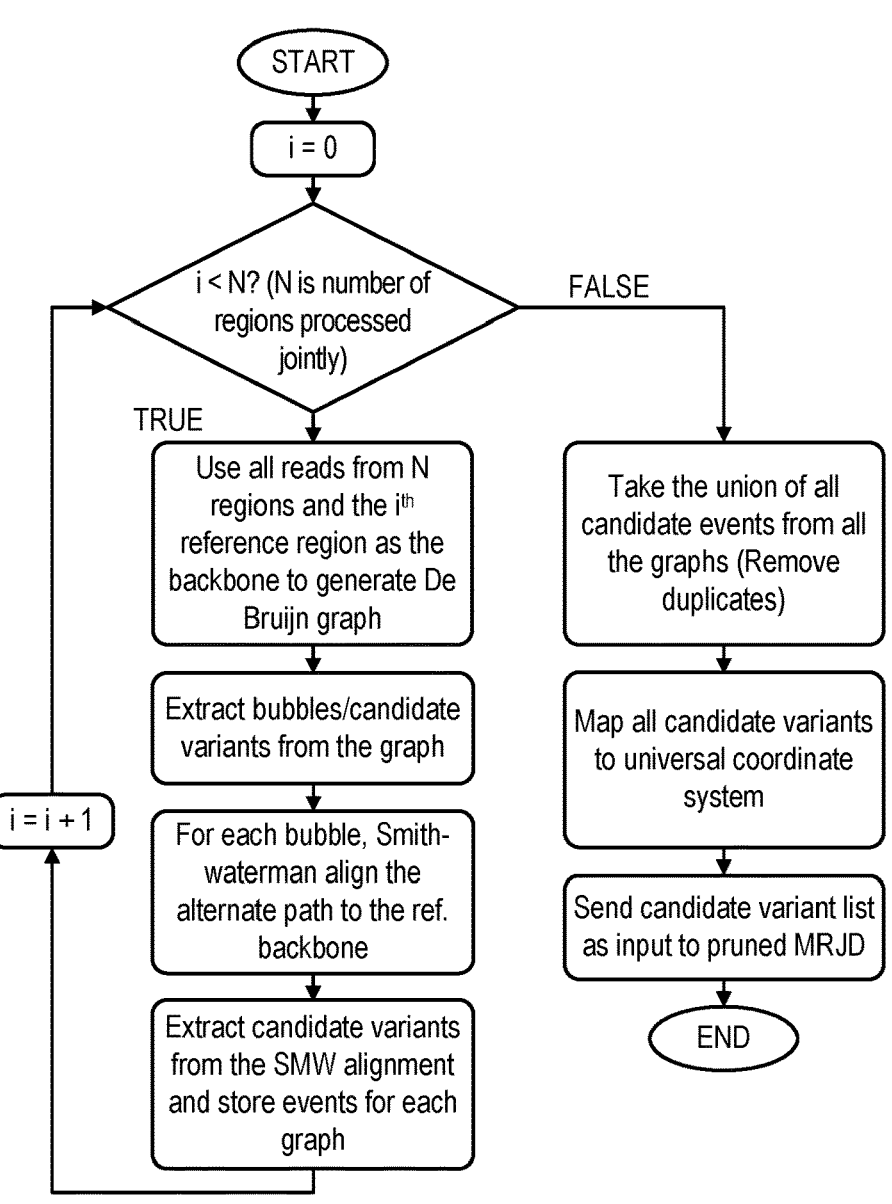
FIG. 20 is a processing matrix for performing the pre-processing procedure of FIGS. 17A and B.

As can be seen with respect to FIG. 20, a candidate variant list may be created as follows. First, a joint pileup may be formed and a De Bruijn graph (DBG) or other assembly graph may be constructed, in accordance with the methods disclosed herein. The DBG may then be used to extract the candidate variants from the joint pileups. The construction of the DBG is performed in such a manner as to generate bubbles, indicating variations, representing alternate pathways through the graph where each alternate path is a candidate haplotypes. See, for instance, FIGS. 20 and 21.

Accordingly, the various bubbles in the graph represent the list of candidate variant haplotype positions. Hence, given all of the reads, the DBG may be generated using each reference region as a backbone. Then all of the candidate variant positions can be aligned to universal coordinates. Specifically, FIG. 20 illustrates a flow chart setting forth the process of generating a DBG and using the same to produce candidate haplotypes. More specifically, the De Bruijn graph may be employed in order to create the candidate variant list of SNPs and INDELs. Given that there are N regions that are being jointly processed by MRJD, N de-bruijn graphs may be constructed. In such an instance, every graph may use one reference region as a backbone and all of the reads corresponding to the N regions.

For instance, in one methodological implementation, after the DBG is constructed, the candidate haplotypes may be extracted from the De Bruijn graph based on the candidate events. However, when employing an MRJD pre-processing protocol, as described herein, N regions may be jointly processed, such as where the length of the regions can be a few thousand bases or more, and the number of haplotypes to be extracted can grow exponentially very quickly. Accordingly, in order to reduce the computational complexity, instead of extracting entire haplotypes, only the bubbles need be extracted from the graphs that are representative of the candidate variants.

Figure 21:
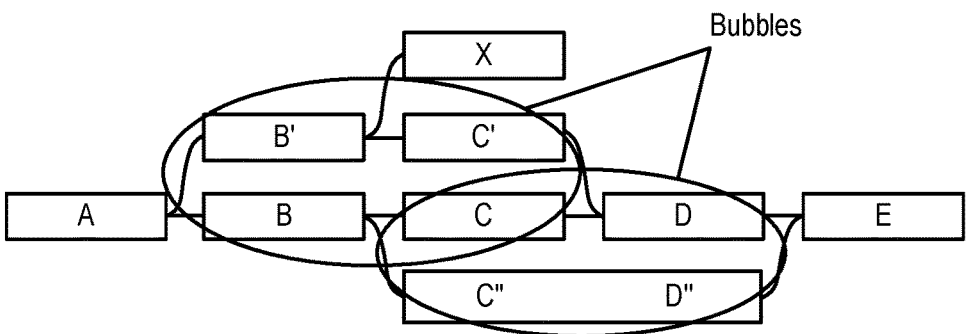
FIG. 21 is an example of a bubble formation in a De Brujin graph in accordance with the methods of FIG. 20.

An example of bubble structures formed in a De Bruijn graph is shown in FIG. 21. A number of regions to be processed jointly are identified. This determines one of two processing pathways that may be followed. If joint regions are identified all the reads may be used to form a DBG. Bubbles showing possible variants may be extracted so as to identify the various candidate haplotypes. Specifically, for each bubble a SW alignment may be performed on the alternate paths to the reference backbone. From this the candidate variants may be extracted and the events from each graph may be stored.

Figure 22:
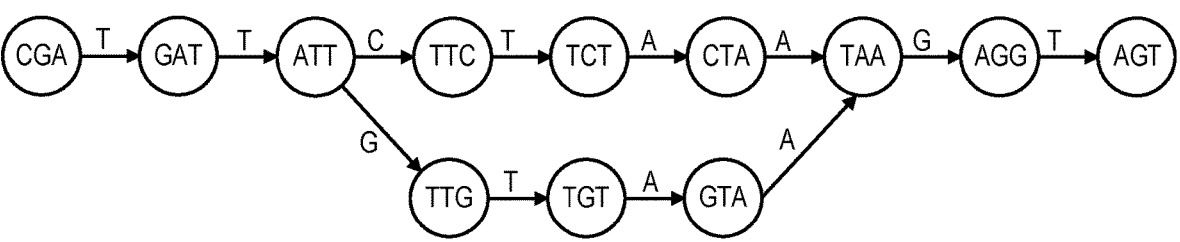
FIG. 22 is an example of a variant pathway through an exemplary De Brujin graph.

However, in other instances, once the first process has been performed, so as to generate one or more DBGs, and/or i is now equal to 0, then the union of all candidate events from all of the DBGs may be generated, where any duplicates may be removed. In such an instance, all candidate variants may be mapped, such as to a universal coordinate system, so as to produce the candidate list, and the candidate variant list may be sent as an input to a pruning module, such as the MJRD module. An example of only performing bubble extraction, instead of extracting the entire haplotypes, is shown in FIG. 22. In this instance, it is only the bubble region showing possible variants that is extracted and processed, as described herein.

Specifically, once the representative bubbles have been extracted, the global alignment, e.g., Smith-Waterman alignment, of the bubble path and the corresponding reference backbone may be performed to get the candidate variant(s) and its position in the reference. This may be done for all extracted bubbles in all of the De Bruijn graphs. Next, the union of all the extracted candidate variants may be taken from the N graphs, the duplicate candidates, if any, may be removed, and the unique candidate variant positions may be mapped to the universal coordinate system obtained from the joint pile-up. This results in a final list of candidate variant positions for the N regions that may act as an input to a "Pruned" MRJD algorithm.

Figure 23:
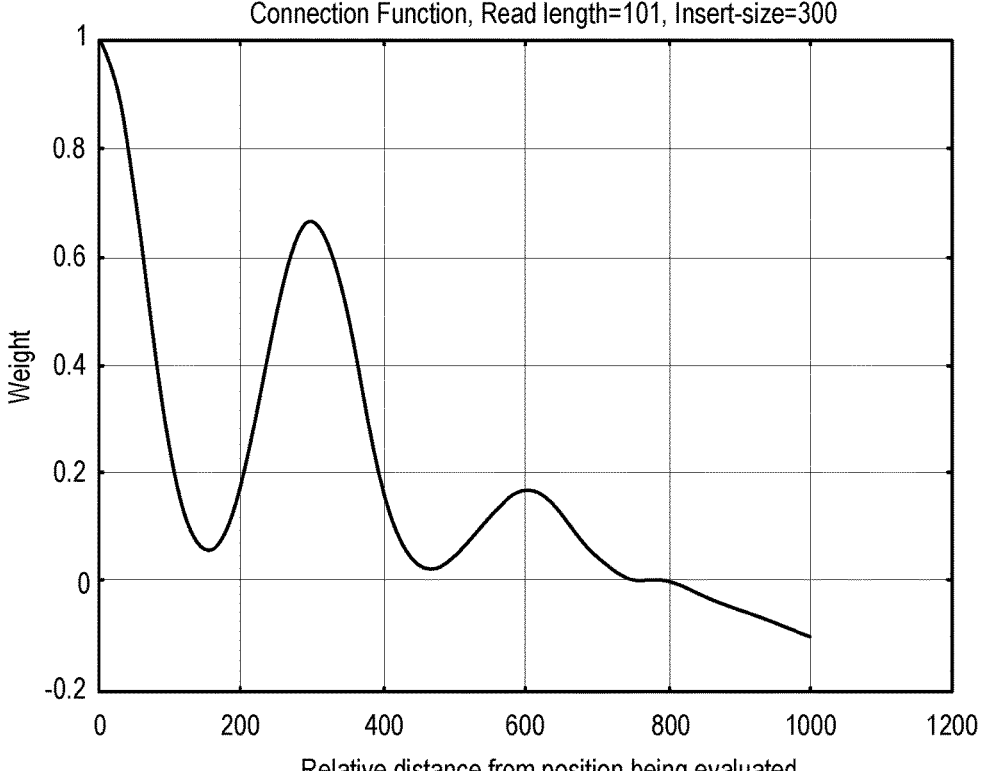
FIG. 23 is a graphical representation of an exemplary sorting function.

In particular preprocessing blocks, as described herein above, a connection matrix may be computed. For instance, a connection matrix may be used to define the order of processing of active, e.g., candidate, positions, such as a function of read length and insert size. For example, to further reduce computational complexity, a connection matrix may be computed so as to define the order of processing of identified candidate variants that are obtained from the De Bruijn graph. This matrix may be constructed and employed in conjunction with or as a sorting function to determine which candidate variants to process first. This connection matrix, therefore, may be a function of the mean read length and the insert size of the paired-end reads. Accordingly, for a given candidate variant, other candidate variant positions that are at integral multiples of the insert size or within the read length have higher weights compared to the candidate variants at other positions. This is because these candidate variants are more likely to provide evidence for the current variant being evaluated. An exemplary sorting function, as implemented herein, is shown in FIG. 23 for mean read length of 101 and insert-size of 300.

Figure 24:
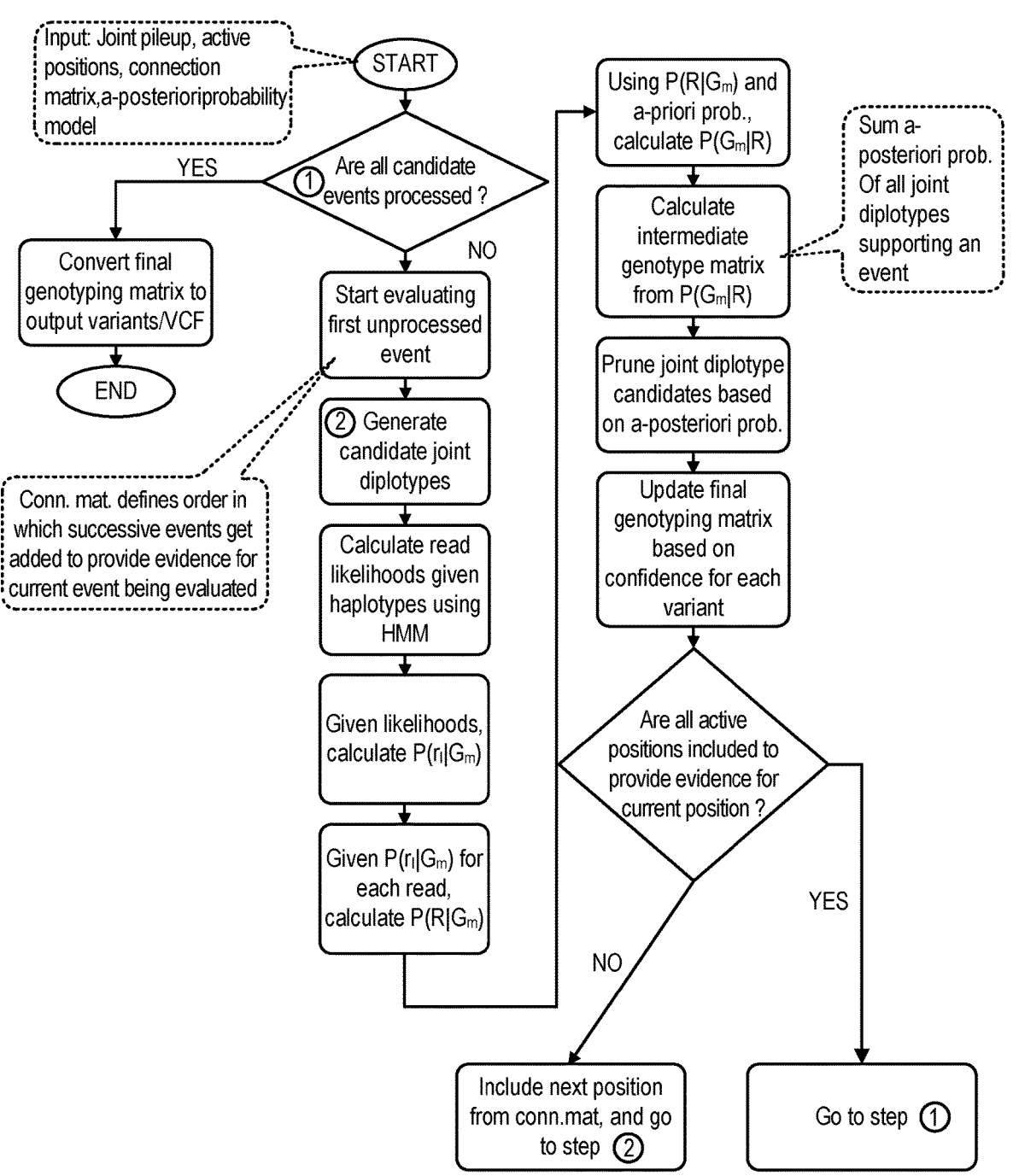
FIG. 24 is another example of a processing matrix for a pruned multi-region joint detection procedure.

With respect to a MJRD pruning function, exemplary steps of a pruned MRJD algorithm, as referenced above, is set forth in FIG. 24. For instance, the input to the MRJD platform and algorithm is the joint pileup of N regions, e.g., all the candidate variants (SNPs/INDELs), the a-priori probabilities based on a mutation model, and the connection matrix. Accordingly, the input into the pruned MRJD processing platform may be the joint pile-up, the identified active positions, the generated connection matrix, and the a-posteriori probability model, and/or the results thereof.

Next, each candidate variant in the list can be processed and other variants can be successively added as evidence for a current candidate being processed using the connection matrix. Accordingly, given the current candidate variant and any supporting candidates, candidate joint diplotypes may be generated. For instance, a joint diplotype is a set of 2N haplotypes, where N is the number of regions being jointly processed. The number of candidate joint diplotypes M is a function of the number of regions being jointly processed, number of active/candidate variants being considered, and the number of phases. An example for generating joint diplotypes is shown below.

For: P=1, Number of active/candidate variant positions being considered;

N=2, Number of regions being jointly processed;

M=$2^{2 \cdot N \cdot P}$=$2^4$=16 candidate joint-diplotypes

Hence, for a single candidate active position, given all the reads and both the reference regions, let the two haplotypes be 'A' and 'G'.

Unique haplotypes='A' and 'G'

Candidate Diplotypes='AA', 'AG', 'GA' and 'GG', (4 candidates for 1 region).

$$\text{Candidate Joint Diplotypes} = \begin{matrix} \text{'AAAA', 'AAAG', 'AAGA', 'AAGG'} \\ \text{'AGAA', 'AGAG', 'AGGA', 'AGGG'} \\ \text{'GAAA', 'GAAG', 'GAGA', 'GAGG'} \\ \text{'GGAA', 'GGAG', 'GGGA', 'GGGG'} \end{matrix}$$

Accordingly, using the candidate joint diplotypes, the read likelihoods can be calculated given a haplotype for each haplotype in every candidate joint diplotype set. This may be done using a HMM algorithm, as described herein. However, in doing so the HMM algorithm may be modified from its standard use case so as to allow for candidate variants (SNPs/INDELs) in the haplotype, which have not yet been processed, to be considered. Subsequently, the read likelihoods can be calculated given a joint diplotype $(P(n|G_m))$ using the results from the modified HMM. This may be done using the formula below.

For the case of 2-region joint detection:

$G_m=[\vartheta_{11,m}, \vartheta_{12,m}, \vartheta_{21,m}, \vartheta_{22,m}]$, wherein $\vartheta_{ij,m}$, i is the region and j is the phase $$P(r_i \mid G_m) = \frac{P(ri|\vartheta 11, m) + P(ri|\vartheta 12, m) + P(ri|\vartheta 21, m) + P(ri|\vartheta 22, m)}{4}$$

$P(R|G_m)=\Pi_i \, P(ri|Gm)$. Given $P(r_i|G_m)$, it is straightforward to calculate $P(R|G_m)$ for all the reads. Next, using Bayes' formula, the a-posteriori probability $(P(G_i|R))$ may be computed from $P(R|G_i)$ and the a-priori probabilities $(P(G_i))$.

$P(G_i|R)=P(R|G_i)P(G_i)/\Sigma_k P(R|Gk)P(Gk)$.

Further, an intermediate genotype matrix may be calculated for each region given the a-posteriori probabilities for all the candidate joint diplotypes. For each event combination in the genotype matrix the a-posteriori probabilities of all joint diplotypes supporting that event may be summed up. At this point, the genotype matrix may be considered as "intermediate" because not all the candidate variants supporting the current candidate have been included. However, as seen earlier, the number of joint diplotype candidates grows exponentially with the number of candidate variant positions and number of regions. This in-turn exponentially increases the computation required to calculate the a-posteriori probabilities. Therefore, in order to reduce the computational complexity, at this stage, the number of joint diplotypes based on the a-posteriori probabilities may be pruned so that the number of joint diplotypes to keep may be user defined and programmable. Finally, the final genotype matrix may be updated based on a user-defined confidence metric of variants which is computed using the intermediate genotype matrix. The various steps of these processes are set forth in the process flow diagram of FIG. 24.

The process above may be repeated until all the candidate variants are included as evidence for the current candidates being processed using the connection matrix. Once all of the candidates have been included, the processing of the current candidate is done. Other stopping criteria for processing candidate variants are also possible. For example, the process may be stopped when the confidence has stopped increasing as more candidate's variants are added. This analysis, as exemplified in FIG. 24, may be restarted and repeated in the same manner for all other candidate variants in the list thereby resulting in a final variant call file at the output of MRJD. Accordingly, instead of considering each region in isolation, a Multi-Region Joint Detection protocol, as described herein, may be employed so as to consider all locations from which a group of reads may have originated as it attempts to detect the underlying sequences jointly using all available information.

Accordingly, for Multi-Region Joint Detection, an exemplary MRJD protocol may employ one or more of the following equations in accordance with the methods disclosed herein. Specifically, instead of considering each region to be assessed in isolation, MRJD considers a plurality of locations from which a group of reads may have been originated and attempts to detect the underlying sequences jointly, such as by using as much as, e.g., all, the available information that is useful. For instance, in one exemplary embodiment:

Let N be the number of regions to be jointly processed. And let $H_k$ be a candidate haplotype, k=1 . . . K, each of which may include various SNPs, insertions and/or deletions relative to a reference sequence. Each haplotype $H_k$ represents a single region along a single strand (or "phase", e.g., maternal or paternal), and they need not be contiguous (e.g., they may include gaps or "don't care" sequences).

Let $G_m$ be a candidate solution for both phases $\Phi$=1,2 (for a diploid organism) and all regions n=1 . . . N:

$$G_m = \begin{bmatrix} Gm, 1, 1 & \ldots & Gm, 1, N \\ Gm, 2, 1 & \ldots & Gm, 2, N \end{bmatrix}$$

where each element $G_{m,\Phi,n}$ is a haplotype chosen from the set of candidates $\{H_1 \ldots H_k\}$.

First, the probability of each read may be calculated for each candidate haplotype $P(r_i|H_k)$, for example, by using a Hidden Markov Model (HMM), as discussed herein above. In the case of datasets with paired reads, $r_i$ indicates the pair $\{r_{i,1}, r_{i,2}\}$, and $P(r_i|H_k)=P(r_{i,1}|H_k) \, P(r_{i,2}|H_k)$. In the case of datasets with linked reads (e.g., barcoded reads), $r_i$ indicates the group of reads $\{r_{i,1} \ldots r_{i,NL}\}$ that came from the same long molecule, and $$P(r_i \mid H_k) = \prod_{n=1}^{NL} P(ri, n \mid Hk).$$

Next, for each candidate solution $G_m$, m=1 . . . M, we calculate the conditional probability of each read $$P(r_i \mid G_m) = \frac{1}{2N} \sum_{n=1}^{N}$$

$$\sum_{\Phi=1}^{2} P(ri \mid Gm, \Phi, n)$$

and conditional probability of the entire pileup $$R = \{r_1 \ \ldots \ r_{NR}\}: P(R \mid G_m) = \prod\nolimits_{i=1}^{NR} P(ri \mid Gm).$$

Next, the a-posteriori probability is calculated of each candidate solution given the observed pileup:

$$P(G_m \mid R) = P(R \mid Gm)P(Gm)/\sum\nolimits_{i=1}^{M} P(R \mid Gi)P(Gi)$$

where $P(G_m)$ indicates the a-priori probability of the candidate solution, which is set forth in detail here below.

Finally, the relative probability of every candidate variant $V_j$ is calculated $$\frac{P(Vj \mid R)}{P(ref \mid R)} = \sum\nolimits_{n|Gm=>vj} P(Gm \mid R)/\sum\nolimits_{m|Gm=>ref} P(Gm \mid R),$$

such as where $G_m \rightarrow V_j$ indicates that $G_m$ supports variant $V_j$, and $G_m \rightarrow$ref indicates that $G_m$ supports the reference. In a VCF file, this may be reported as a quality score on a phred scale:

$$QUAL(V_j) = -10\log_{10}\frac{P(Vj \mid R)}{P(ref \mid R)}.$$

Figure 25:
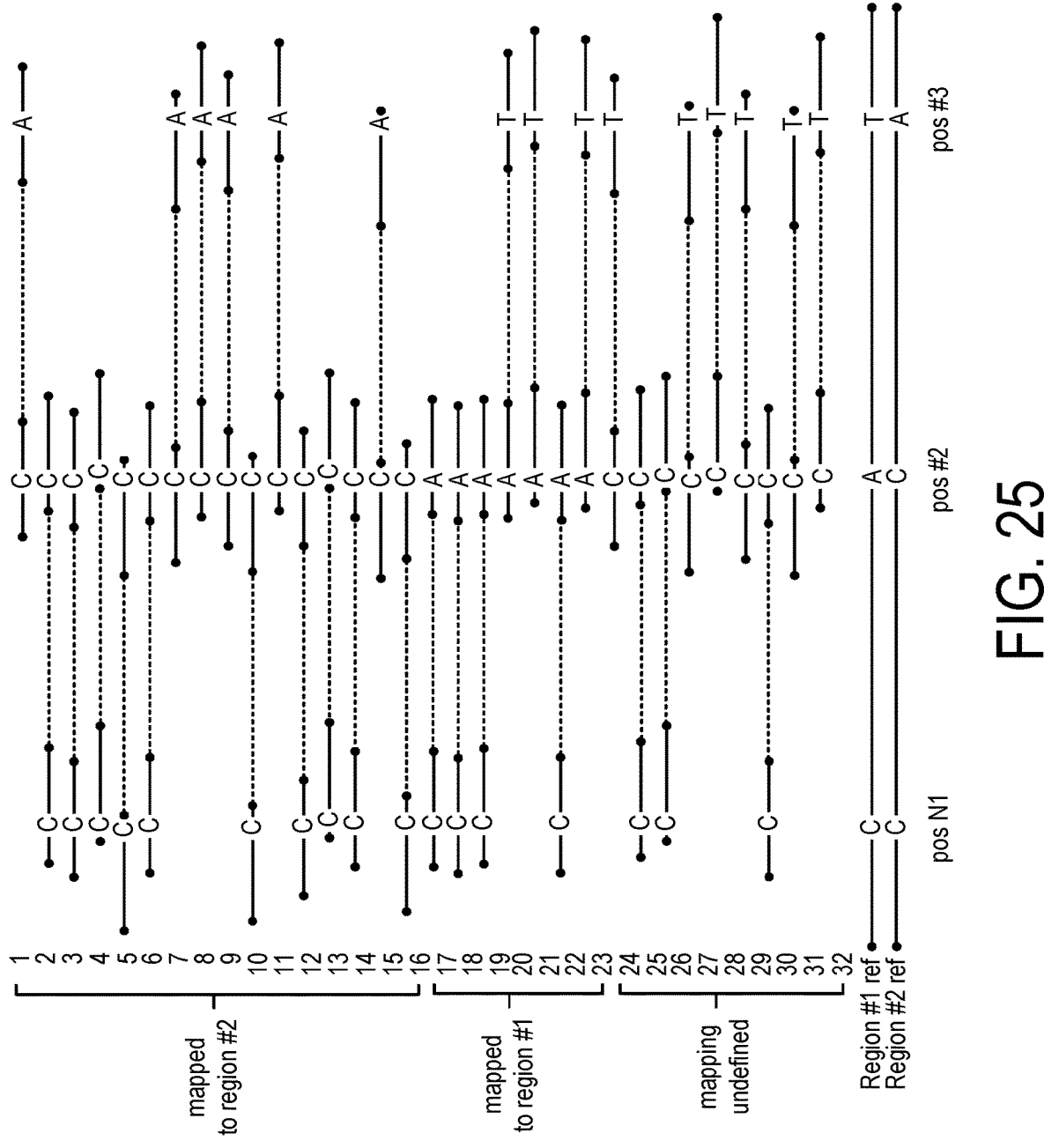
FIG. 25 illustrates a joint pileup of paired reads for two regions.

An exemplary process for performing various variant calling operations is set forth herein with respect to FIG. 25 where a conventional and MRJD detection process are compared. Specifically, FIG. 25 illustrates a joint pileup of paired reads for two regions whose reference sequences differ by only 3 bases over the range of interest. All the reads are known to come from either region #1 or region #2, but it is not known with certainty from which region any individual read originated. Note, as described above, that the bases are only shown for the positions where the two references differ, e.g., bubble regions, or where the reads differ from the reference. These regions are referred to as the active positions. All other positions can be ignored, as they don't affect the calculation.

Accordingly, as can be seen with respect to FIG. 25, in a conventional detector, the read pairs 1-16 would be mapped to region #2, and these alone would be used for variant calling in region #2. All of these reads match the reference for region #2, so no variants would be called. Likewise, read pairs 17-23 would be mapped to region #1, and these alone would be used for variant calling in region #1. As can be seen, all of these reads match the reference for region #1, so no variants will be called. However, read pairs 24-32 map equally well to region #1 and region #2 (each has a one-base difference to ref #1 and to ref #2), so the mapping is indeterminate, and a typical variant caller would simply ignore these reads. As such, a conventional variant caller would make no variant calls for either region, as seen in FIG. 25.

However, with MRJD, FIG. 25 illustrates that the result is completely different than that received employing conventional methods. The relevant calculations are set forth below. In this instance N=2 regions. Additionally, there are three positions, each with 2 candidate bases (one can safely ignore bases whose count is sufficiently low, and in this example the count is zero on all but 2 bases in each position). If all combinations are considered, this will yield $K=2^3=8$ candidate haplotypes: $H_1$=CAT, $H_2$=CAA, $H_3$=CCT, $H_4$=CCA, $H_5$=GAT, $H_6$=GAA, $H_7$=GCT, $H_8$=GCA.

In a brute-force calculation where all combinations of all candidate haplotypes are considered, the number of candidate solutions is $M=K^{2N}=8^{2.2}=4096$, and $P(G_m/R)$ may be calculated for each candidate solution $G_m$. The following illustrates this calculation for two candidate solutions:

$$G_{m1} = \begin{bmatrix} CAT & GCA \\ CAT & GCA \end{bmatrix}, G_{m2} = \begin{bmatrix} CAT & GCA \\ CCT & GCA \end{bmatrix}$$

Where $G_{m1}$ has no variants (this is the solution found by a conventional detector), and $G_{m2}$ has a single heterozygous SNP A$\rightarrow$C in position #2 of region #1.

The probability $P(r_i|H_k)$ depends on various factors including the base quality and other parameters of the HMM. It may be assumed that only base call errors are present and all base call errors are equally likely, so $P(r_i|H_k)$ $=(1-p_e)^{Np(i)-Ne(i)}(p_e/3)^{Ne(i)}$, where $p_e$ is the probability of a base call error, $N_p(i)$ is the number of active base position(s) overlapped by read i, and $N_e(i)$ is the number of errors for read i, assuming haplotype $H_k$. Accordingly, it may be assumed that $p_e=0.01$, which corresponds to a base quality of phred 20. The table set forth in FIG. 26 shows $P(r_i|H_k)$, for all read pairs and all candidate haplotypes. The two far right columns show $P(r_i|G_{m1})$ and $P(r_i|G_{m2})$, with the product at the bottom. FIG. 26 shows that $P(R|G_{m1})=3.5^{-30}$ and $P(R|G_{m2})=2.2^{-15}$, a difference of 15 orders of magnitude in favor of $G_{m2}$.

The a-posteriori probabilities $P(G_m|R)$ depend on the a-priori probabilities $P(G_m)$. To complete this example, a simple independent identically distributed (IID) model may be assumed, such that the a-priori probability of a candidate solution with Nv variants is $(1-p_v)^{N.Np-Nv}(p_v/9)^{Nv}$, where $N_p$ is the number of active positions (3 in this case) and Pv is the probability of a variant, assumed to be 0.01 in this example. This yields $P(G_{m1})=7.22e-13$, and $P(G_{m2})=0.500$. It is noted that $G_{m2}$ is heterozygous over region #1, and all heterozygous pairs of haplotypes have a mirror-image representation with the same probability (obtained by simply swapping the phases). In this case, the sum of the probabilities for $G_{m2}$ and its mirror image sum to 1.000. Calculating probabilities of individual variants, a heterozygous A$\rightarrow$C SNP at position #2 of region #1, with quality score of phred 50.4 can be seen.

Accordingly, as can be seen, there is an immense computational complexity for performing a brute force variant calling operation, which complexity can be reduced by performing multiple region joint detection, as described herein. For instance, the complexity of the above calculations grows rapidly with the number of regions N and the number of candidate haplotypes K. To consider all combinations of candidate haplotypes, the number of candidate solutions for which to calculate probabilities is $M=K^{2N}$. In a brute force implementation, the number of candidate haplotypes is $K=2^{Np}$, where $N_p$ is the number of active positions (e.g., as exemplified above, if graph-assembly techniques are used to generate the list of candidate haplotypes, then Np is the number of independent bubbles in the graph). Hence, a mere brute-force calculation can be prohibitively expensive to implement. For example, if N=3 and Np=10, the number of candidate solutions is $M=2^{3.2.10}=2^{60}=10^{18}$. However, in practice, it's not uncommon to have values of $N_p$ much higher than this.

Consequently, because a brute force Bayesian calculation can be prohibitively complex, the following description sets forth further methods for reducing the complexity of such calculations. For instance, in a first step of another embodiment, starting with a small number of positions $$N_p^j$$

(or even a single position $$N_p^j = 1),$$

the Bayesian calculation may be performed over those positions. At the end of the calculation, the candidates whose probability falls below a predefined threshold may be eliminated, such as in a pruning of the tree function, as described above. In such an instance, the threshold may be adaptive.

Figure 27:
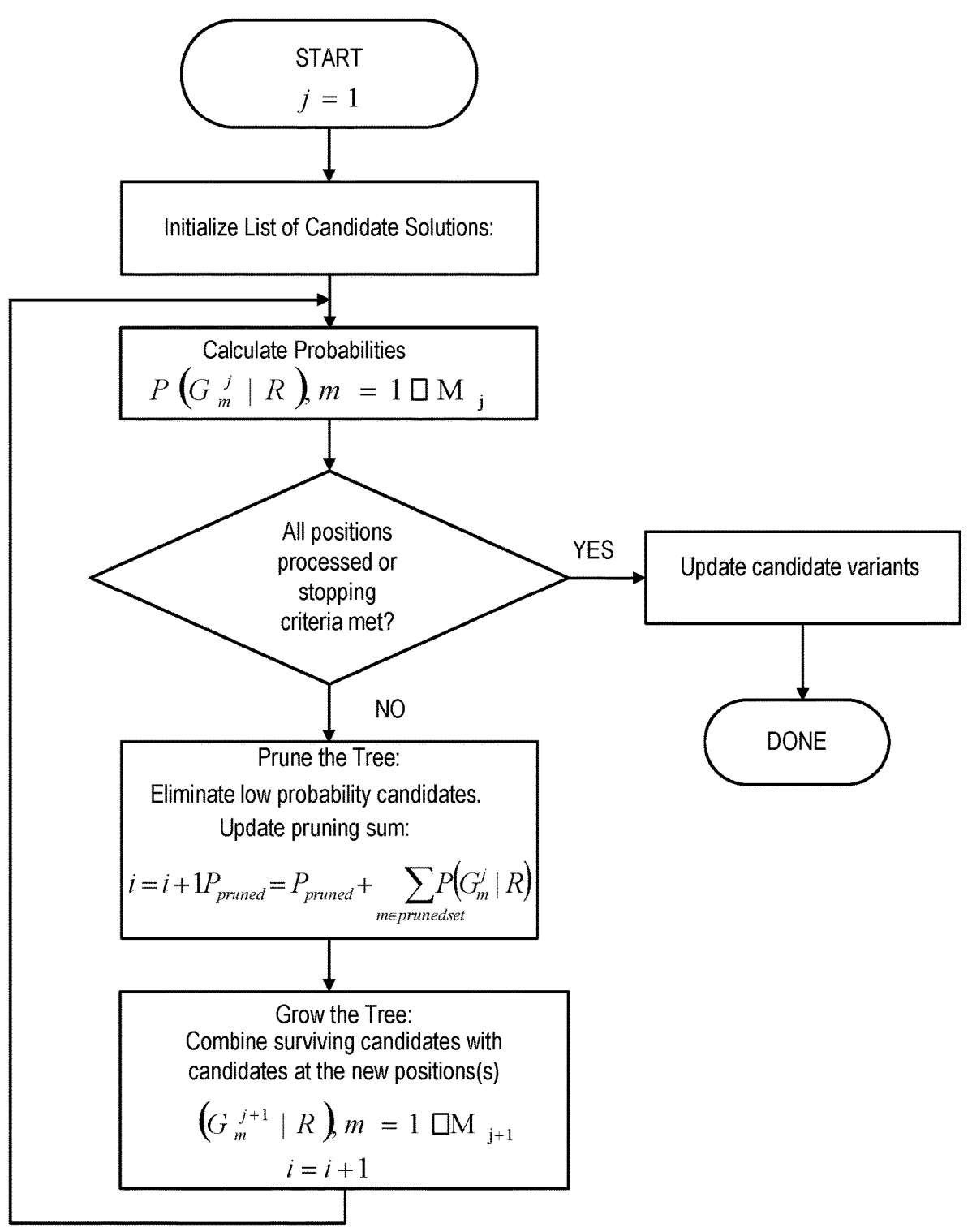
FIG. 27 is a further example of a processing matrix for a multi-region joint detection procedure.

Next, in a second step, the number of positions $$N_p^j$$

may be increased by a small number $\Delta N_p$ (such as one:

$$N_p^{j+1} = N_p^j + \Delta N_P),$$

and the surviving candidates can be combined with one or more, e.g., all, possible candidates at the new position(s), such as in a growing the tree function. These steps of (1) performing the Bayesian calculation, (2) pruning the tree, and (3) growing the tree, may then be repeated, e.g., sequentially, until a stopping criteria is met. The threshold history may then be used to determine the confidence of the result (e.g., the probability that the true solution was or was not found). This process is illustrated in the flow chart set forth in FIG. 27.

It is to be understood that there are a variety of possible variations to this approach. For instance, as indicated, the pruning threshold may be adaptive, such as based on the number of surviving candidates. For instance, a simple implementation may set the threshold to keep the number of candidates below a fixed number, while a more sophisticated implementation may set the threshold based on a cost-benefit analysis of including additional candidates. Further, a simple stopping criteria may be that a result has been found with a sufficient level of confidence, or that the confidence on the initial position has stopped increasing as more positions are added. Further still, a more sophisticated implementation may perform some type of cost-benefit analysis of continuing to add more positions. Additionally, as can be seen with respect to FIG. 27, the order in which new positions are added may depend on several criteria, such as the distance to the initial position(s) or how highly connected these positions are to the already-included positions (e.g., the amount of overlap with the paired reads).

A useful feature of this algorithm is that the probability that the true solution wasn't found can be quantified. For instance, a useful estimate is obtained by simply summing the probabilities of all pruned branches at each step:

$$P_{pruned} = P_{pruned} + \sum\nolimits_{m \varepsilon pruned\,set} P\!\left(G_m^j \mid R\right).$$

Such an estimate is useful for calculating the confidence of the resulting variant calls:

$$\frac{P(vj \mid R)}{P(ref \mid R)} =$$

$$\sum\nolimits_{m \mid Gm => vj} P(Gm \mid R) + Ppruned / \sum\nolimits_{m \mid Gm => ref} P(Gm \mid R) + Ppruned.$$

Good confidence estimates are essential for producing good Receiver Operating Characteristic (ROC) curves. This is a key advantage of this pruning method over other ad hoc complexity reductions.

Returning to the example pileup of FIG. 25, and starting from the left-most position (position #1) and working toward the right one base position at a time, using a pruning threshold of phred 60 on each iteration: Let $$\left\{ G_m^j, m = 1 \ldots M_j \right\}$$

represent the candidate solutions on the j-th iteration. FIG. 28 shows the candidate solutions on the first iteration, representing all combinations of bases C and G, listed in order of decreasing probability. For any solution with equivalent mirror-image representations (obtained by swapping the phases), only a single representation is shown here. The probabilities for all candidate solutions can be calculated, and those probabilities beyond the pruning threshold (indicated by the solid line in the FIG. 28) can be dropped. As can be seen with respect to FIG. 28, as a result of the pruning methods disclosed herein, six candidates survive.

Next, as can be seen with respect to FIG. 29, the tree can be grown by finding all combinations of the surviving candidates from iteration #1 and candidate bases (C and A) in the position #2. A partial list of the new candidates is shown in FIG. 29, again shown in order of decreasing probability. Again, the probabilities can be calculated and compared to the pruning threshold, and in this instance 5 candidates survive.

Finally, all combinations of the surviving candidates from iteration #2 and the candidate bases in position #3 (A and T) can be determined. The final candidates and their associated probabilities are shown in FIG. 30. Accordingly, when calculating the probabilities of individual variants, it is determined that a heterozygous A→C SNP at position #2 of region #1, with quality score of phred 50.4, which is the same result found in the brute-force calculation. In this example, pruning had no significant effect on the end result, but in general pruning may affect the calculation, often resulting in a more confidence score.

There are many possible variations to the implementations of this approach, which may affect the performance and complexity of the system, and different variations may be appropriate for different scenarios. For instance, there can be variations in deciding which regions to include. For example, prior to running a Multi-Region Joint Detection (MRJD), the variant caller may be configured to determine whether a given active region should be processed individually or jointly with other regions, and if jointly, it may then determine which regions to include. In other instances, some implementations may rely on a list of secondary alignments provided by the mapper so as to inform or otherwise make this decision. Other implementations may use a database of homologous regions, computed offline, such as based on a search of the reference genome.

Accordingly, a useful step in such operations is in deciding which positions to include. For instance, it is to be noted that various regions of interest may not be self-contained and/or isolated from adjacent regions. Hence, information in the pileup can influence the probability of bases separated by far more than the total read length (e.g., the paired read length or long molecule length). As such, it must be decided which positions to include in the MRJD calculation, and the number of positions is not unconstrained (even with pruning). For example, some implementations may process overlapping blocks of positions and update the results for a subset of the positions based on the confidence levels at those positions, or the completeness of the evidence at those positions (e.g., positions near the middle of the block typically have more complete evidence than those near the edge).

Another determining factor may be the order in which new positions may be added. For instance, for pruned MRJD, the order of adding new positions may affect performance. For example, some implementations may add new positions based on the distance to the already-included positions, or the degree of connectivity with these positions (e.g., the number of reads overlapping both positions). Additionally, there are also many variations on how pruning may be performed. In the example set forth above, the pruning was based on a fixed probability threshold, but in general the pruning threshold may be adaptive or based on the number of surviving candidates. For instance, a simple implementation may set the threshold to keep the number of candidates below a fixed number, while a more sophisticated implementation may set the threshold based on a cost-benefit analysis of including additional candidates.

Various implementations may perform pruning based on probabilities $P(R|G_m)$ instead of the a-priori probabilities $P(G_m|R)$. This has the advantage of allowing the elimination of equivalent mirror-image representations across regions (in addition to phases). This advantage is at least partially offset by the disadvantage of not pruning out candidates with very low a-priori probabilities, which in various instances may be beneficial. As such, a useful solution may depend on the scenario. If pruning is done, such as based on the $P(R|G_m)$, then the Bayesian calculation would be performed once after the final iteration.

Further in the example above, the process was stopped after processing all base positions in the pileup shown, but other stopping criteria are also possible. For instance, if only a subset of the base positions (e.g. when processing overlapping blocks) is being solved for, the process may stop when the result for the subset has been found with a sufficient level of confidence, or when the confidence has stopped increasing as more positions are added. A more sophisticated implementation, however, may perform some type of cost-benefit analysis, weighing the computational cost against the potential value of adding more positions.

A-priori probabilities may also be useful. For instance, in the examples above, a simple IID model was used, but other models may also be used. For example, it is to be noted that clusters of variants are more common than would be predicted by an IID model. It is also to be noted that variants are more likely to occur at positions where the references differ. Therefore, incorporating such knowledge into the a-priori probabilities $P(G_m)$ can improve the detection performance and yield better ROC curves. Particularly, it is to be noted that the a-priori probabilities for homologous regions are not well-understood in the genomics community, and this knowledge is still evolving. As such, some implementations may update the a-priori models as better information becomes available. This may be done automatically as more results are produced. Such updates may be based on other biological samples or other regions of the genome for the same sample, which learnings can be applied to the methods herein to further promote a more rapid and accurate analysis.

Accordingly, in some instance, an iterative MJRD process may be implemented. Specifically, the methodology described herein can be extended to allow message passing between related regions so as to further reduce the complexity and/or increase the detection performance of the system. For instance, the output of the calculation at one location can be used as an input a-priori probability for the calculation at a nearby location. Additionally, some implementations may use a combination of pruning and iterating to achieve the desired performance/complexity tradeoff.

Further, sample preparation may be implemented to optimize the MRJD process. For instance, for paired-end sequencing, it may be useful to have a tight distribution on the insertion size when using conventional detection. However, in various instances, introducing variation in the insertion size could significantly improve the performance for MRJD. For example, the sample may be prepared to intentionally introduce a bimodal distribution, a multi-modal distribution, or bell-curve-like distribution with a higher variance than would typically be implemented for conventional detection.

Figure 31:
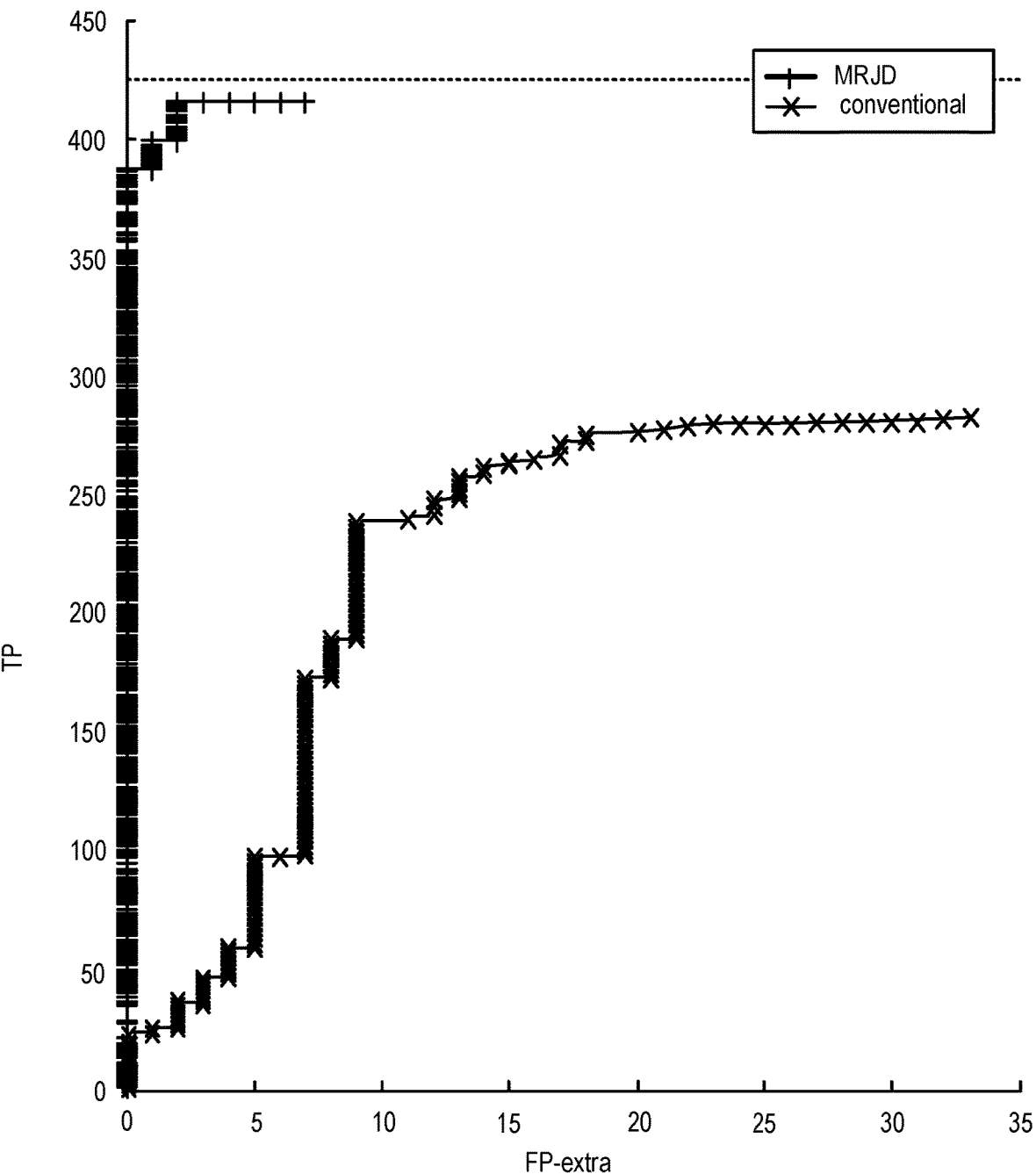
FIG. 31 illustrates the ROC curves for MRJD and a conventional detector.

FIG. 31 illustrates the ROC curves for MRJD and a conventional detector for human sample NA12878 over selected regions of the genome with a single homologous copy, such that N=2, with varying degrees of reference sequence similarity. This dataset used paired-end sequencing with a read length of 101 and a mean insertion size of approx. 400. As can be seen with respect to FIG. 31, MRJD offers dramatically improved sensitivity and specificity over these regions than conventional detection methods. FIG. 32 illustrates the same results displayed as a function of the sequence similarity of the references, measured over a window of 1000 bases (e.g. if the references differ by 10 bases out of 1000, then the similarity is 99.0 percent). For this dataset, it may be seen that conventional detection starts to perform badly at a sequence similarity −0.98, while MRJD performs quite well up to 0.995 and even beyond.

Additionally, in various instances, this methodology may be extended to allow message passing between related regions to further reduce the complexity and/or increase the detection performance. For instance, the output of the calculation at one location can be used as an input a-priori probability for the calculation at a nearby location, and in some implementations may use a combination of pruning and iterating to achieve the desired performance/complexity tradeoff. In particular instances, as indicated above, prior to running multi-region joint detection, the variant caller may determine whether a given active region should be processed individually or jointly with other regions. Additionally, as indicated above, some implementations may rely on a list of secondary alignments provided by the mapper to make such a decision. Other implementations may use a database of homologous regions, computed offline based on a search of the reference genome.

In view of the above, a Pair-Determined Hidden Markov Model (PD-HMM may be implemented in a manner so as to take advantage of the benefits of MRJD. For instance, MRJD can separately estimate the probability of observing a portion or all of the reads given each possible joint diplotype, which comprises one haplotype per ploidy per homologous reference region, e.g., for two homologous regions in diploid chromosomes, each joint diplotype will include four haplotypes. In such instances, all or a portion of the possible haplotypes may be considered, such as by being constructed, for instance, by modifying each reference region with every possible subset of all the variants for which there is nontrivial evidence. However, for long homologous reference regions, the number of possible variants is large, so the number of haplotypes (combinations of variants) becomes exponentially large, and the number of joint diplotypes (combinations of haplotypes) may be astronomical.

Consequently, to keep MRJD calculations tractable, it may not be useful to test all possible joint diplotypes. Rather, in some instances, the system may be configured in such a manner that only a small subset of "most likely" joint diplotypes is tested. These "most likely" joint diplotypes may be determined by incrementally constructing a tree of partially-determined joint diplotypes. In such an instance, each node of the tree may be a partially determined joint diplotype that includes a partially determined haplotype per ploidy per homologous reference region. In this instance, a partially determined haplotype may include a reference region modified by a partially determined subset of the possible variants. Accordingly, a partially determined subset of the possible variants may include an indication, for each possible variant, of one of three states: that the variant is determined and present, or the variant is determined and absent, or the variant is not yet determined, e.g., it may be present or absent. At the root of the tree, all variants are undetermined in all haplotypes; tree nodes branching successively further from the root have successively more variants determined as present or absent in each haplotype of each node's joint diplotype.

Further, in the context of this joint diplotype tree, as described above, the amount of MRJD calculations is kept limited and tractable by trimming branches of the tree in which all joint diplotype nodes are unlikely, e.g., moderately to extremely unlikely, relative to other more likely branches or nodes. Accordingly, such trimming may be performed on branches at nodes that are still only partially determined; e.g., several or many variants are still not determined as present or absent from the haplotypes of a trimmed node's joint diplotype. Thus, in such an instance, it is useful to be able to estimate or bound the likelihood of observing each read assuming the truth of a partially determined haplotype. A modified pair hidden Markov model (pHMM) calculation, denoted "PD-HMM" for "partially determined pair hidden Markov model" is useful to estimate the probability $P(R|H)$ of observing read R assuming the true haplotype H* is consistent with partially determined haplotype H. Consistent in this context means that some specific true haplotype H* agrees with partially determined haplotype H with respect to all variants whose presence or absence are determined in H, but for variants undetermined in H, H* may agree with the reference sequence either modified or unmodified by each undetermined variant.

Note that it is not generally adequate to run an ordinary pHMM calculation for some shorter sub-haplotype of H chosen to encompass only determined variant positions. It is generally important to build the joint diplotype tree with undetermined variants being resolved in an efficient order, which is generally quite different than their geometric order, so that a partially determined haplotype H will typically have many undetermined variant positions interleaved with determined ones. To properly consider PCR indel errors, it is useful to use a pHMM-like calculation spanning through all determined variants and significant radius around them, which may not be compatible with attempts to avoid undetermined variant positions.

Accordingly, the inputs to PD-HMM may include the called nucleotide sequence of read R, the base quality scores (e.g., phred scale) of the called nucleotides of R, a baseline haplotype H0, and a list of undetermined variants (edits) from H0. The undetermined variants may include single-base substitutions (SNPs), multiple-base substitutions (MNPs), insertions, and deletions. Advantageously, it may be adequate to support undetermined SNPs and deletions. An undetermined MNP may be imperfectly but adequately represented as multiple independent SNPs. An undetermined insertion may be represented by first editing the insertion into the baseline haplotype, then indicating the corresponding undetermined deletion which would undo that insertion.

Restrictions may be placed on the undetermined deletions, to facilitate hardware engine implementation with limited state memory and logic, such as that no two undetermined deletions may overlap (delete the same baseline haplotype bases). If a partially determined haplotype must be tested with undetermined variants violating such restrictions, this may be resolved by converting one or more undetermined variants into determined variants in a larger number of PD-HMM operations, covering cases with those variants present or absent. For example, if two undetermined deletions A and B violate by overlapping each other in baseline haplotype H0, then deletion B may be edited into H0 to yield HOB, and two PD-HMM operations may be performed using undetermined deletion A only, one for baseline haplotype H0, and the other for baseline haplotype HOB, and the maximum probability output of the two PD-HMM operations may be retained.

The result of a PD-HMM operation may be an estimate of the maximum P(R|H*) among all haplotypes H* that can be formed by editing H0 with any subset of the undetermined variants. The maximization may be done locally, contributing to the pHMM-like dynamic programming in a given cell as if an adjacent undetermined variant is present or absent from the haplotype, whichever scores better, e.g., contributes the greater partial probability. Such local maximization during dynamic programming may result in larger estimates of the maximum P(R|H*) than true maximization over individual pure H* haplotypes, but the difference is generally inconsequential.

Undetermined SNPs may be incorporated into PD-HMM by allowing one or more matching nucleotide values to be specified for each haplotype position. For example, if base 30 of H0 is 'C' and an undetermined SNP replaces this 'C' with a CT, then the PD-HMM operation's haplotype may indicate position 30 as matching both bases 'C' and 'T'. In the usual pHMM dynamic programming, any transition to an 'M' state results in multiplying the path probability by the probability of a correct base call (if the haplotype position matches the read position) or by the probability of a specific base call error (if the haplotype position mismatches the read position); for PD-HMM this is modified by using the correct-call probability if the read position matches either possible haplotype base (e.g. 'C' or 'T'), and the base-call-error probability otherwise.

Undetermined haplotype deletions may be incorporated into PD-HMM by flagging optionally-deleted haplotype positions, and modifying the dynamic programming of pHMM to allow alignment paths to skip horizontally across undetermined deletion haplotype segments without probability loss. This may be done in various manners, but with the common property that probability values in M, I, and/or D states can transmit horizontally (along the haplotype axis) over the span of an undetermined deletion without being reduced by ordinary gap-open or gap-extend probabilities.

In one particular embodiment, haplotype positions where undetermined deletions begin are flagged "F1", and positions where undetermined deletions end are flagged "F2". In addition to the M, I, and D "states" (partial probability representations) for each cell of the HMM matrix (haplotype horizontal/read vertical), each PD-HMM cell may further include BM, BI, and BD "bypass" states. In F1-flagged haplotype columns, BM, BI, and BD states receive values copied from M, I, and D states of the cell to the left, respectively. In non-F2-flagged haplotype columns, particularly columns starting with an F1 flagged column end extending into the interior of an undetermined deletion, BM, BI, and BD states transmit their values to BM, BI, and BD states of the cell to the right, respectively. In F2-flagged haplotype columns, in place of M, I, and D states used to calculate states of adjacent cells, the maximum of M and BM is used, and the maximum of I and BI is used, and the maximum of D and BD is used, respectively. This is exemplified in an F2 column as multiplexed selection of signals from M and BM, from I and BI, and from D and BD registers.

Note that although BM, BI, and DB state registers may be represented in F1 through F2 columns, and maximizing M/BM, $1$/BI, and D/BD multiplexers may be shown in an F2 column, these components may be present for all cell calculations, enabling an undetermined deletion to be handled in any position, and enabling multiple undetermined deletions with corresponding F1 and F2 flags throughout the haplotype. Note also that F1 and F2 flags may be in the same column, for the case of a single-base undetermined deletion. It is further to be noted that the PD-HMM matrix of cells may be depicted as a schematic representation of the logical M, I, D, BM, BI, and BD state calculations, but in a hardware implementation, a smaller number of cell calculating logic elements may be present, and pipelined appropriately to calculate M, D, I, BM, BI, and BD state values at high clock frequencies, and the matrix cells may be calculated with various degrees of hardware parallelism, in various orders consistent with the inherent logical dependencies of the PD-HMM calculation.

Thus, in this embodiment, the pHMM state values in one column may be immediately left of an undetermined deletion which may be captured and transmitted rightward, unchanged, to the rightmost column of this undetermined deletion, where they substitute into pHMM calculations whenever they beat normal-path scores. Where these maxima are chosen, the "bypass" state values BM, BI, and BD represent the local dynamic programming results where the undetermined deletion is taken to be present, while "normal" state values M, I, and D represent the local dynamic programming results where the undetermined deletion is taken to be absent.

In another embodiment, a single bypass state may be used, such as a BM state receiving from an M state in F1 flagged columns, or receiving a sum of M, D, and/or I states. In another embodiment, rather than using "bypass" states, gap-open and/or gap-extend penalties are eliminated within columns of undetermined deletions. In another embodiment, bypass states contribute additively to dynamic programming rightward of undetermined deletions, rather than local maximization being used. In a further embodiment, more or fewer or differently defined or differently located haplotype position flags are used to trigger bypass or similar behavior, such as a single flag indicating membership in an undetermined deletion. In an additional embodiment, two or more overlapping undetermined deletions may participate, such as with the use of additional flags and/or bypass states. Additionally, undetermined insertions in the haplotype are supported, rather than, or in addition to, undetermined deletions. Likewise, undetermined insertions and/or deletions on the read axis are supported, rather than or in addition to undetermined deletions and/or insertions on the haplotype axis. In another embodiment, undetermined multiple-nucleotide substitutions are supported as atomic variants (all present or all absent). In a further embodiment, undetermined length-varying substitutions are supported as atomic variants. In another embodiment, undetermined variants are penalized with fixed or configurable probability or score adjustments.

This PD-HMM calculation may be implemented as a hardware engine, such as in FPGA or ASIC technology, by extension of a hardware engine architecture for "ordinary" pHMM calculation or may be implemented by one or more quantum circuits in a quantum computing platform. In addition to an engine pipeline logic to calculate, transmit, and store M, I, and D state values for various or successive cells, parallel pipeline logic can be constructed to calculate, transmit, and store BM, BI, and BD state values, as described herein and above. Memory resources and ports for storage and retrieval of M, I, and D state values can be accompanied by similar or wider or deeper memory resources and ports for storage and retrieval of BM, BI, and BD state values. Flags such as F1 and F2 may be stored in memories along with associated haplotype bases.

Multiple matching nucleotides for e.g. undetermined SNP haplotype positions may be encoded in any manner, such as using a vector of one bit per possible nucleotide value. Cell calculation dependencies in the pHMM matrix are unchanged in PD-HMM, so order and pipelining of multiple cell calculations can remain the same for PD-HMM. However, the latency in time and/or clock cycles for complete cell calculation increases somewhat for PD-HMM, due to the requirement to compare "normal" and "bypass" state values and select the larger ones. Accordingly, it may be advantageous to include one or more extra pipeline stages for PD-HMM cell calculation, resulting in additional clock cycles of latency. Additionally, it may further be advantageous to widen each "swath" of cells calculated by one or more rows, to keep the longer pipeline filled without dependency issues.

This PD-HMM calculation tracks twice as many state values (BM, BI, and BD, in addition to M, I, and D), as an ordinary pHMM calculation, and may require about twice the hardware resources for an equivalent throughput engine embodiment. However, a PD-HMM engine has exponential speed and efficiency advantages for increasing numbers of undetermined variants, versus an ordinary pHMM engine run once for each haplotype representing a distinct combination of the undetermined variants being present or absent. For example, if a partially determined haplotype has 30 undetermined variants, each of which may be independently present or absent, there are $2^{30}$, or more than 1 billion, distinct specific haplotypes that pHMM would otherwise need to process.

Accordingly, these and other such operations herein disclosed may be performed so as to better understand and accurately predict what happened to the subject's genome such that the reads varied in relation to reference. For instance, even though the occurrence of mutations may be random, there are instances wherein the likelihood of their occurrence appears to be potentially predictable to some extent. Particularly, in some instances when mutations occur, they may occur in certain defined locations and in certain forms. More particularly, mutations, if they occur, will occur on one allele or another or both, and will have a tendency to occur in certain locations over others, such as at the ends of the chromosomes. Consequently, this and other associated information may be used to develop mutation models, which may be generated and employed to better assess the likely presence of a mutation in one or more regions of the genome. For instance, by taking account of various a priori knowledge, e.g., one or more mutation models, when performing genomic variation analyses, better and more accurate genomic analysis results may be obtained, such as with more accurate demarcations of genetic mutation.

Such mutation models may give an account for the frequency and/or location of various known mutations and/or mutations that appear to happen in conjunction with one another or otherwise non-randomly. For instance, it has been determined that toward the ends of a given chromosome variations occur more predominantly. Thus, known models of mutations can be generated, stored in a database herein, and used by the system to make a better prediction of the presence of one or more variations within the genomic data being analyzed. Additionally, a machine learning process, as described in greater detail herein below, may also be implemented such that the various results data derived by the analyses performed herein may be analyzed and used to better inform the system as to when to make a specific variance call, such as in accordance with the machine learning principles disclosed herein. Specifically, machine learning may be implemented on the collective data sets, especially with respect to the variations determined, and this learning may be used to better generate more comprehensive mutation models that in turn may be employed to make more accurate variance determinations.

Hence, the system may be configured to observe all the various variation data, mine that data for various correlations, and where correlations are found, such information may be used to better weight and therefore more accurately determine the presence of other variations in other genome samples, such as on an ongoing basis. Accordingly, in a manner such as this, the system, especially the variant calling mechanism, may constantly be updated with respect to the learned variant correlation data so as to make better variant calls moving forward, so as to get better and more accurate results data.

Specifically, telemetry may be employed to update the growing mutation model so as to achieve better analysis in the system. This may be of particular usefulness when analyzing samples that are in some way connected with one another, such as from being within the same geographical population, and/or may be used to determine which reference genome out of a multiplicity of reference genomes may be a better reference genome by which a particular sample is to be analyzed. Further, in various instances, the mutation model and/or telemetry may be employed so as to better select the reference genome to be employed in the system processes, and thereby enhance the accuracy and efficiency of the results of the system. Particularly, where a plurality of reference genomes may be employed in one or more of the analyses herein, a particular reference genome may be selected for use over the others such as by applying a mutation model so at select the most appropriate reference genome to apply.

It is to be noted that when performing secondary analysis, the fundamental structure for each region of the genome being mapped and aligned may include one or more underlying genes. Accordingly, in various instances, this understanding of the underlying genes and/or the functions of the proteins they code for may be informative when performing secondary analysis. Particularly, tertiary indications and/or results may be useful in the secondary analysis protocols being run by the present system, such as in a process of biological contextually sensitive mutation model. More particularly, since DNA codes for genes, which genes code for proteins, information about such proteins that result in mutations and/or abhorrent functions can be used to inform the mutation models being employed in the performance of secondary and/or tertiary analyses on the subject's genome.

For example, tertiary analysis, such as on a sample set of genes coding for mutated proteins, may be informative when performing secondary analysis of genomic regions known to code for such mutations. Hence, as set forth above, various tertiary processing results may be used to inform and/or update the mutation models used herein for achieving better accuracy and efficiency when performing the various secondary analysis operations disclosed herein. Specifically, information about mutated proteins, e.g., contextual tertiary analysis, can be used to update the mutation model when performing secondary analysis of those regions known to code for the proteins and/or to potentially include such mutations Accordingly, in view of the above, for embodiments involving FPGA-accelerated mapping, alignment, sorting, and/or variant calling applications, one or more of these functions may be implemented in one or both of software and hardware (HW) processing components, such as software running on a traditional CPU, GPU, QPU, and/or firmware such as may be embodied in an FPGA, ASIC, sASIC, and the like. In such instances, the CPU and FPGA need to be able to communicate so as to pass results from one step on one device, e.g., the CPU or FPGA, to be processed in a next step on the other device. For instance, where a mapping function is run, the building of large data structures, such as an index of the reference, may be implemented by the CPU, where the running of a hash function with respect thereto may be implemented by the FPGA. In such an instance, the CPU may build the data structure, store it in an associated memory, such as a DRAM, which memory may then be accessed by the processing engines running on the FPGA.

For instance, in some embodiments, communications between the CPU and the FPGA may be implemented by any suitable interconnect such as a peripheral bus, such as a PCIe bus, USB, or a networking interface such as Ethernet. However, a PCIe bus may be a comparatively loose integration between the CPU and FPGA, whereby transmission latencies between the two may be relatively high. Accordingly, although one device e.g., (the CPU or FPGA) may access the memory attached to the other device (e.g., by a DMA transfer), the memory region(s) accessed are non-cacheable, because there is no facility to maintain cache coherency between the two devices. As a consequence, transmissions between the CPU and FPGA are constrained to occur between large, high-level processing steps, and a large amount of input and output must be queued up between the devices so they don't slow each other down waiting for high latency operations. This slows down the various processing operations disclosed herein. Furthermore, when the FPGA accesses non-cacheable CPU memory, the full load of such access is imposed on the CPU's external memory interfaces, which are bandwidth-limited compared to its internal cache interfaces.

Accordingly, because of such loose CPU/FPGA integrations, it is generally necessary to have "centralized" software control over the FPGA interface. In such instances, the various software threads may be processing various data units, but when these threads generate work for the FPGA engine to perform, the work must be aggregated in "central" buffers, such as either by a single aggregator software thread, or by multiple threads locking aggregation access via semaphores, with transmission of aggregated work via DMA packets managed by a central software module, such as a kernel-space driver. Hence, as results are produced by the HW engines, the reverse process occurs, with a software driver receiving DMA packets from the HW, and a de-aggregator thread distributing results to the various waiting software worker threads. However, this centralized software control of communication with HW FPGA logic is cumbersome and expensive in resource usage, reduces the efficiency of software threading and HW/software communication, limits the practical HW/software communication bandwidth, and dramatically increases its latency.

Figure 33A:
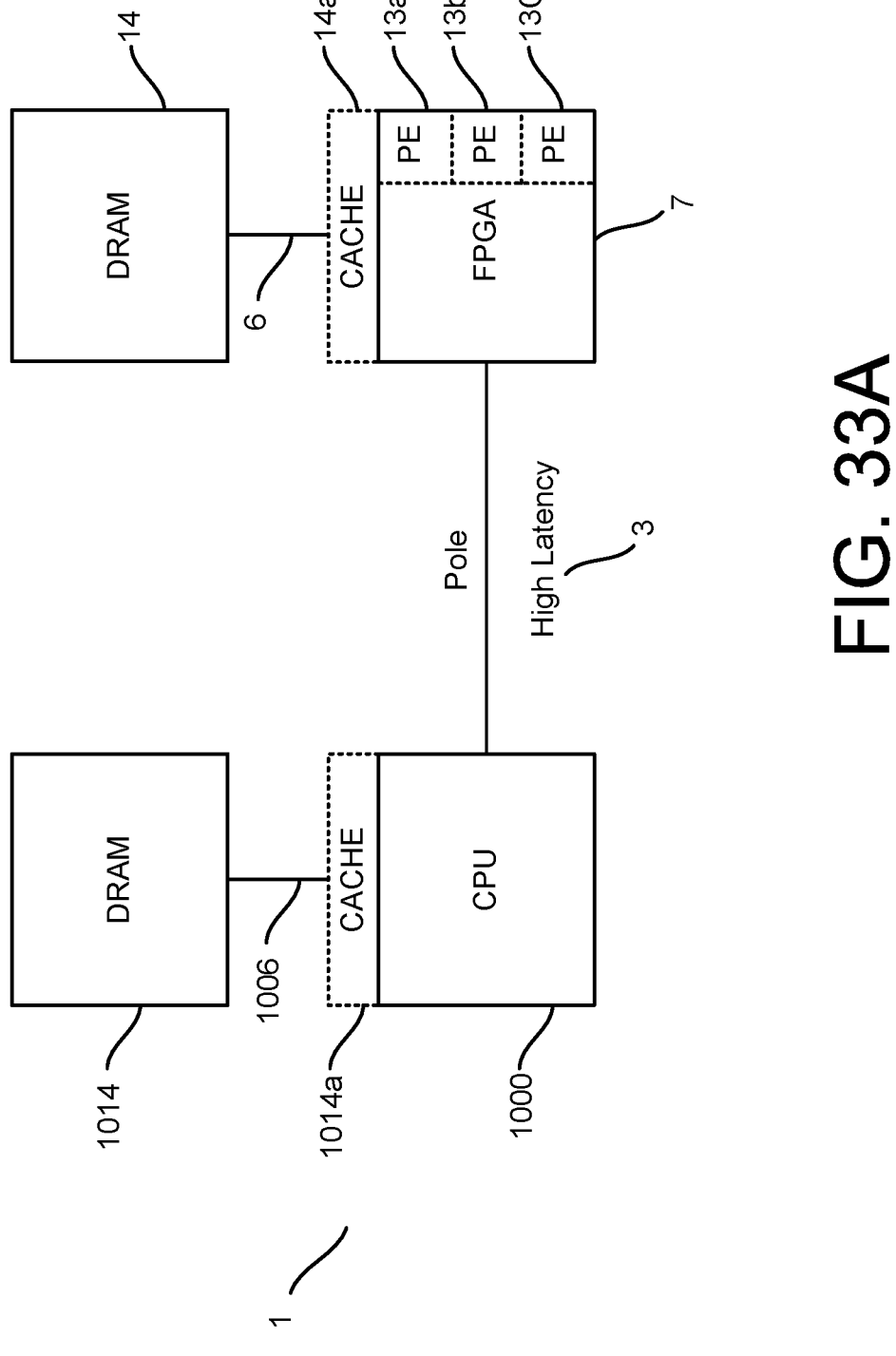
FIG. 33A depicts an exemplary architecture illustrating a loose coupling between a CPU and an FPGA of the disclosure.

Additionally, as can be seen with respect to FIG. 33A, a loose integration between the CPU 1000 and FPGA 7 may require each device to have its own dedicated external memory, such as DRAMs 1014, 14. As depicted in FIG. 33A, the CPU(s) 1000 has its own DRAM 1014 on the system motherboard, such as DDR3 or DDR4 DIMMs, while the FPGA 7 has its own dedicated DRAMs 14, such as four 8 GB SODIMMs, that may be directly connected to the FPGA 7 via one or more DDR3 busses 6, such as a high latency PCIe bus. Likewise, the CPU 1000 may be communicably coupled to its own DRAM 1014, such as by a suitably configured bus 1006. As indicated above, the FPGA 7 may be configured to include one or more processing engines 13, which processing engines may be configured for performing one or more functions in a bioinformatics pipeline as herein described, such as where the FPGA 7 includes a mapping engine 13a, an alignment engine 13b, and a variant call engine 13c. Other engines as described herein may also be included. In various embodiments, one or both of the CPU may be configured so as to include a cache 1014a, 14a respectively, that is capable of storing data, such as result data that is transferred thereto by one or more of the various components of the system, such as one or more memories and/or processing engines.

Many of the operations disclosed herein, to be performed by the FPGA 7 for genomic processing, require large memory accesses for the performance of the underlying operations. Specifically, due to the large data units involved, e.g. 3+ billion nucleotide reference genomes, 100+ billion nucleotides of sequencer read data, etc., the FPGA 7 may need to access the host memory 1014 a large number of times such as for accessing an index, such as a 30 GB hash table or other reference genome index, such as for the purpose of mapping the seeds from a sequenced DNA/RNA query to a 3 Gbp reference genome, and/or for fetching candidate segments, e.g., from the reference genome, to align against.

Accordingly, in various implementations of the system herein disclosed, many rapid random memory accesses may need to occur by one or more of the hardwired processing engines 13, such as in the performance of a mapping, aligning, and/or variant calling operation. However, it may be prohibitively impractical for the FPGA 7 to make so many small random accesses over the peripheral bus 3 or other networking link to the memory 1014 attached to the host CPU 1000. For instance, in such instances, latencies of return data can be very high, bus efficiency can be very low, e.g., for such small random accesses, and the burden on the CPU external memory interface 1006 may be prohibitively great.

Additionally, as a result of each device needing its own dedicated external memory, the typical form factor of the full CPU 1000+FPGA 7 platform is forced to be larger than may be desirable, e.g., for some applications. In such instances, in addition to a standard system motherboard for one or more CPUs 1000 and supporting chips 7 and memories, 1014 and/or 14, room is needed on the board for a large FPGA package (which may even need to be larger so as to have enough pins for several external memory busses) and several memory modules, 1014, 14. Standard motherboards, however, do not include these components, nor would they easily have room for them, so a practical embodiment may be configured to utilize an expansion card 2, containing the FPGA 7, its memory 14, and other supporting components, such as power supply, e.g. connected to the PCIe expansion slot on the CPU motherboard. To have room for the expansion card 2, the system may be fabricated to be in a large enough chassis, such as a 1U or 2U or larger rack-mount server.

Figure 33B:
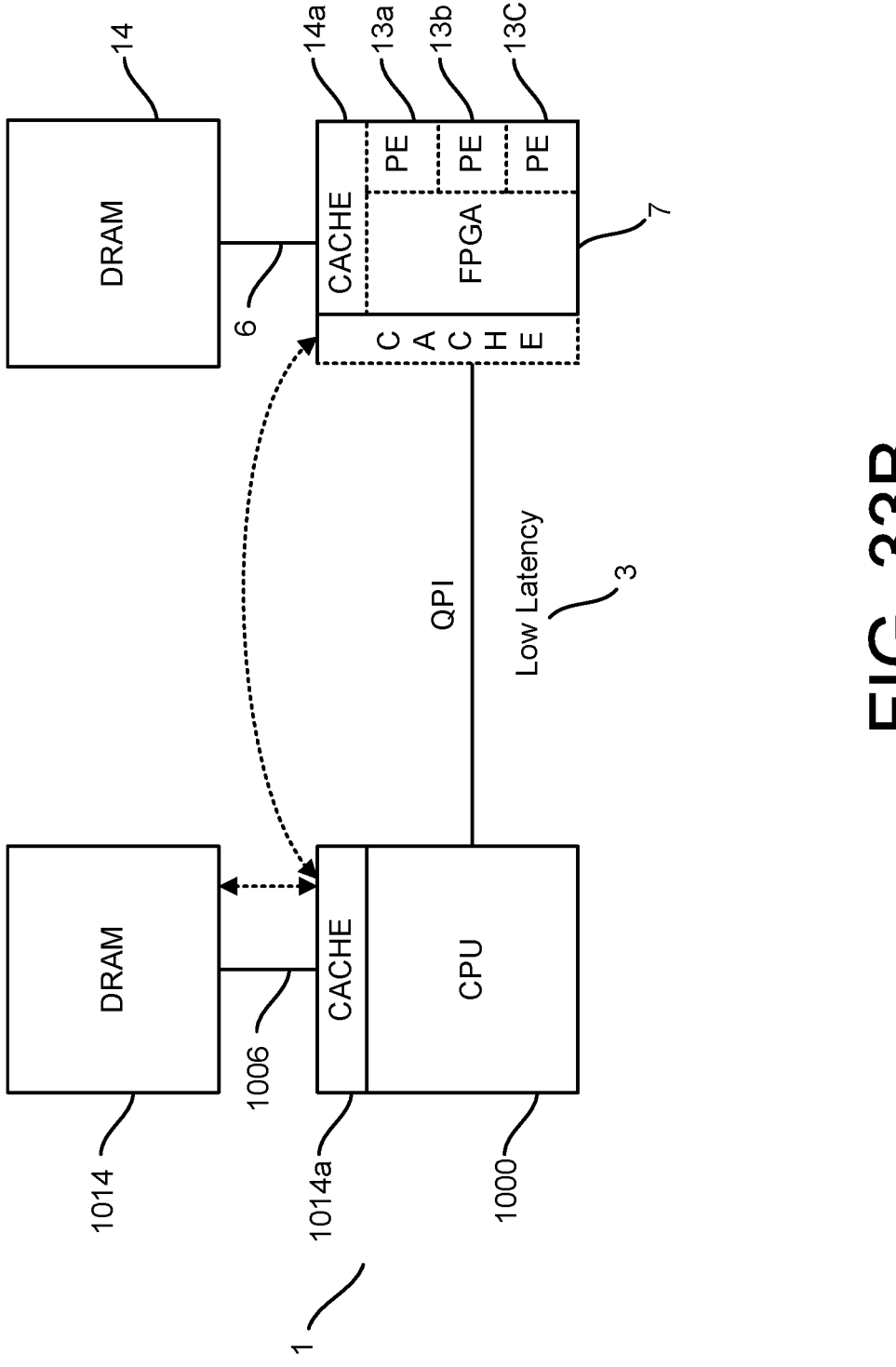
FIG. 33B depicts an exemplary architecture illustrating a tight coupling between a CPU and an FPGA of the disclosure.

In view of the above, in various instances, as can be seen with respect to FIG. 33B, to overcome these factors, it may be desirable to configure the CPU 1000 to be in a tight coupling arrangement with the FPGA 7. Particularly, in various instances, the FPGA 7 may be tightly coupled to the CPU 1000, such as by a low latency interconnect 3, such as a quick path interconnect (QPI). Specifically, to establish a tighter CPU+FPGA integration, the two devices may be connected by any suitable low latency interface, such as a "processor interconnect" or similar, such as INTELS® Quick Path Interconnect (QPI) or HyperTransport (HT).

Accordingly, as seen with respect to FIG. 33B, a system 1 is provided wherein the system includes both a CPU 1000 and a processor, such as an FPGA 7, wherein both devices are associated with one or more memory modules. For instance, as depicted, the CPU 1000 may be coupled, such as via a suitably configured bus 1006, to a DRAM 1014, and likewise, the FPGA 7 is communicably coupled to an associated memory 14 via a DDR3 bus 6. However, in this instance, instead of being coupled to one another such as by a typical high latency interconnect, e.g., PCIe interface, the CPU 1000 is coupled to the FPGA 7 by a low latency, hyper transport interconnect 3, such as a QPI. In such an instance, due to the inherent low latency nature of such interconnects, the associated memories 1014, 14 of the CPU 1000 and the FPGA 7 are readily accessible to one another. Additionally, in various instances, due to this tight coupling configuration, one or more cashes 1114a/14a associated with the devices may be configured so as to be coherent with respect to one another.

Some key properties of such a tightly coupled CPU/FPGA interconnect include a high bandwidth, e.g., 12.8 GB/s; low latency, e.g., 100-300 ns; an adapted protocol designed for allowing efficient remote memory accesses, and efficient small memory transfers, e.g., on the order of 64 bytes or less; and a supported protocol and CPU integration for cache access and cache coherency. In such instances, a natural interconnect for use for such tight integration with a given CPU 1000 may be its native CPU-to-CPU interconnect 1003, which may be employed herein to enable multiple cores and multiple CPUs to operate in parallel in a shared memory 1014 space, thereby allowing the accessing of each other's cache stacks and external memory in a cache-coherent manner.

Figures 34A, 34B:
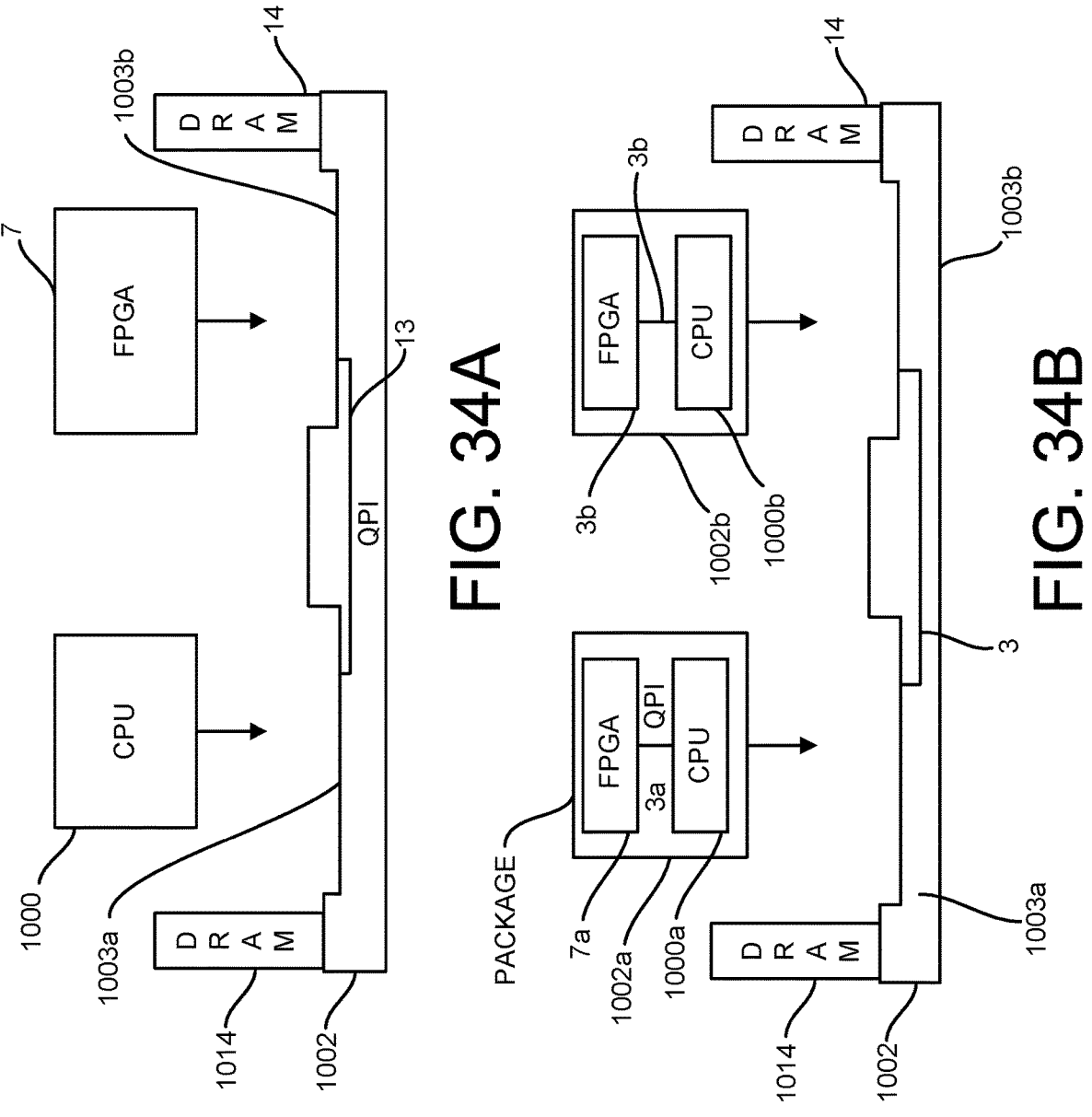
FIG. 34A depicts a direct coupling of a CPU and a FPGA of the disclosure.
FIG. 34B depicts an alternative embodiment of the direct coupling of a CPU and a FPGA of FIG. 34A.

Accordingly, as can be seen with respect to FIGS. 34A and 34B, a board 2 may be provided, such as where the board may be configured to receive one or more CPUs 1000, such as via a plurality of interconnects 1003, such as native CPU-CPU interconnects 1003a and 1003b. However, in this instance, as depicted in FIG. 34A, a CPU 1000 is configured so as to be coupled to the interconnect 1003a, but rather than another CPU being coupled therewith via interconnect 1003b, an FPGA 7 of the disclosure is configured so as to be coupled therewith. Additionally, the system 1 is configured such that the CPU 1000 may be coupled to the associated FPGA 7, such as by a low latency, tight coupling interconnect 3. In such instances, each memory 1014, 14 associated with the respective devices 1000, 7 may be made so as to accessible to each other, such as in a high-bandwidth, cache coherent manner.

Likewise, as can be seen with respect to FIG. 34B, the system can also be configured so as to receive packages 1002a and/or 1002b, such as where each of the packages include one or more CPUs 1000a, 1000b that are tightly coupled, e.g., via low latency interconnects 3a and 3b, to one or more FPGAs 7a, 7b, such as where given the system architecture, each package 2a and 2b may be coupled one with the other such as via a tight coupling interconnect 3. Further, as can be seen with respect to FIG. 35, in various instances, a package 1002a may be provided, wherein the package 1002a includes a CPU 1000 that has been fabricated in such a manner so as to be closely coupled with an integrated circuit such as an FPGA 7. In such an instance, because of the close coupling of the CPU 1000 and the FPGA 7, the system may be constructed such that they are able to directly share a cache 1014a in a manner that is consistent, coherent, and readily accessible by either device, such as with respect to the data stored therein.

Hence, in such instances, the FPGA 7, and or package 2a/2b, can, in effect, masquerade as another CPU, and thereby operate in a cache-coherent shared-memory environment with one or more CPUs, just as multiple CPUs would on a multi-socket motherboard 1002, or multiple CPU cores would within a multi-core CPU device. With such an FPGA/CPU interconnect, the FPGA 7 can efficiently share CPU memory 1014, rather than having its own dedicated external memory 14, which may or may not be included or accessed. Thus, in such a configuration, rapid, short, random accesses are supported efficiently by the interconnect 3, such as with low latency. This makes it practical and efficient for the various processing engines 13 in the FPGA 7 to access large data structures in CPU memory 1000.

Figure 37:
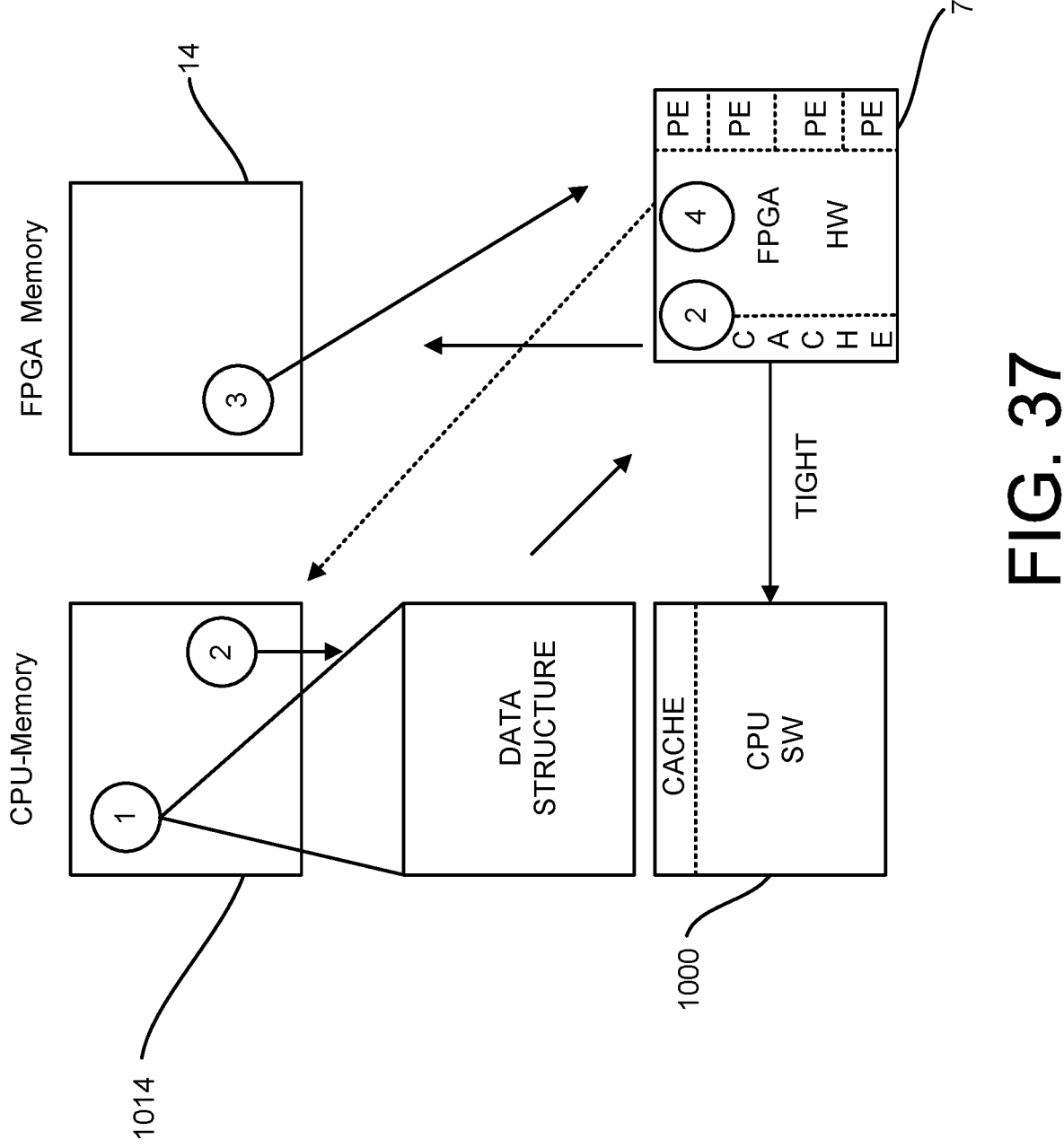
FIG. 37 illustrates an exemplary method of data transfer throughout the system.

For instance, as can be seen with respect to FIG. 37, a system for performing one or more of the methods disclosed herein is provided, such as where the method includes one or more steps for performing the functions of the disclosure, such as one or more mapping and/or aligning and/or variant calling function, as described herein, in a shared manner. Particularly, in one step (1) a data structure may be generated or otherwise provided, such as by an NGS and/or CPU 1000, which data structure may then be stored in an associated memory (2), such as a DRAM 1014. The data structure may be any data structure, such as with respect to those described herein, but in this instance, may be a plurality of reads of sequenced data and/or a reference genome and/or an index of the reference genome, such as for the performance of mapping and/or aligning and/or variant calling functions.

In a second step (2), such as with respect to mapping and/or aligning, etc. functions, an FPGA 7 associated with the CPU 1000, such as by a tight coupling interface 3, may access the CPU associated memory 1014, so as to perform one or more actions with respect to the stored sequenced reads, reference genome(s), and/or an index thereof. Particularly, in a step (3), e.g., in an exemplary mapping operation, the FPGA 7 may access the data structure, e.g., the sequenced reads and/or reference sequences, so as to produce one or more seeds there from, such as where the data structure includes one or more reads and/or genome reference sequences. In such an instance, the seeds, e.g., or the reference and/or read sequences may be employed for the purposes of performing a hash function with respect thereto, such as to produce one or more reads that have been mapped to one or more positions with respect to the reference genome.

In a further step (3), the mapped result data may be stored, e.g., in either the host memory 1014 or in an associated DRAM 14. Additionally, once the data has been mapped, the FPGA 7, or a processing engine 13 thereof, may be reconfigured, e.g., partially re-configured, as an alignment engine, which may then access the stored mapped data structure so as to perform an aligning function thereon, so as to produce one or more reads that have been aligned to the reference genome. In an additional step (4), the host CPU may then access the mapped and/or aligned data so as to perform one or more functions thereon, such as for the production of a De Brujin Graph ("DBG"), which DBG may then be stored in its associated memory. Likewise, in one or more additional steps, the FPGA 7 may once again access the host CPU memory 1014 so as to access the DBG and perform an HMM analysis thereon so as to produce one or more variant call files.

In particular instances, the CPU 1000 and/or FPGA 7 may have one or more memory cache's which due to the tight coupling of the interface between the two devices will allow the separate caches to be coherent, such as with respect to the transitionary data, e.g., results data, stored thereon, such as results from the performance of one or more functions herein. In a manner such as this, data may be shared substantially seamlessly between the tightly coupled devices, thereby allowing a pipeline of functions to be weaved together such as in a bioinformatics pipeline. Thus, in such an instance, it may no longer be necessary for the FPGA 7 to have its own dedicated external memory 14 attached, and hence, due to such a tight coupling configuration, the stored reads, the reference genome, and/or reference genomic index, as herein described, may be intensively shared, e.g., in a cache coherent manner, such as for read mapping and alignment, and other genomic data processing operations.

Figure 38:
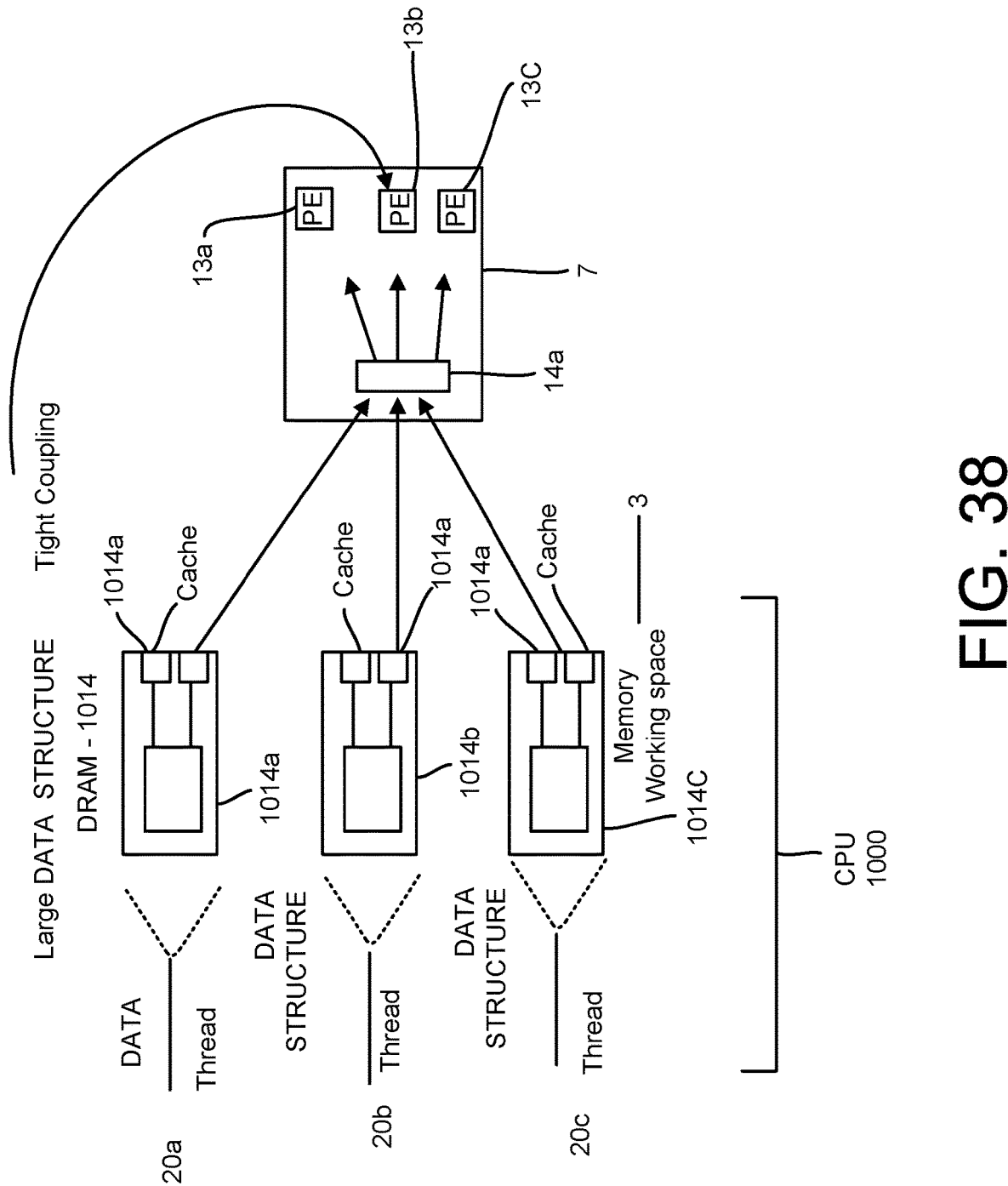
FIG. 38 depicts the embodiment of FIG. 36 in greater detail.

Additionally, as can be seen with respect to FIG. 38, the low latency and cache coherency configurations, as well as other component configurations discussed herein, allow smaller, lower-level operations to be performed in one device (e.g., in a CPU or FPGA), before handing back a data structure or processing thread 20 to the other device, such as for further processing. For example, in one instance, a CPU thread 20a, may be configured to que up large amounts of work for the FPGA hardware logic 13 to process, and the same or another thread 20b, may be configured to then process the large queue of results data generated thereby, such as at a substantially later time. However, in various instances, it may be more efficient, as presented herein, for a single CPU thread 20 to make a blocking "function call" to a coupled FPGA hardware engine 13, which CPU may be set to resume software execution as soon as the hardware function of the FPGA is completed. Hence, rather than packaging up data structures in packets to stream by DMA 14 into the FPGA 7, and unpacking results when they return, a software thread 20 could simply provide a memory pointer to the FPGA engine 13, which could access and modify the shared memory 1014/14 in place, in a cache-coherent manner.

Particularly, given the relationship between the structures provided herein, the granularity of the software/hardware cooperation can be much finer, with much smaller, lower level operations being allocated so as to be performed by various hardware engines 13, such as function calls from various allocated software threads 20. For example, in a loose CPU/FPGA interconnect platform, for efficient acceleration of DNA/RNA read mapping, alignment, and/or variant calling, a full mapping/aligning/variant calling pipeline may be constructed as one or more software and/or FPGA engines, with unmapped and unaligned reads being streamed from software to hardware, and the fully mapped and aligned reads streamed from the hardware back to the software, where the process may be repeated, such as for variant calling. With respect to the configurations herein described, this can be very fast. However, in various instances, such a system may suffer from limitations of flexibility, complexity, and/or programmability, such because the whole map/align and/or variant call pipeline is implemented in hardware circuitry, which although reconfigurable in an FPGA, is generally much less flexible and programmable than software, and may therefore be limited to less algorithmic complexity.

By contrast, using a tight CPU/FPGA interconnect, such as a QPI or other interconnect in the configurations disclosed herein, several resource expensive discrete operations, such as seed generation and/or mapping, rescue scanning, gapless alignment, gapped, e.g., Smith-Waterman, alignment, etc., can be implemented as distinct separately accessible hardware engines 13, e.g., see FIG. 38, and the overall mapping/alignment and/or variant call algorithms can be implemented in software, with low-level acceleration calls to the FPGA for the specific expensive processing steps. This framework allows full software programmability, outside the specific acceleration calls, and enables greater algorithmic complexity and flexibility, than standard hardware implemented operations.

Furthermore, in such a framework of software execution accelerated by discrete low-level FPGA hardware acceleration calls, hardware acceleration functions may more easily be shared for multiple purposes. For instance, when hardware engines 13 form large, monolithic pipelines, the individual pipeline subcomponents may generally be specialized to their environment, and interconnected only within one pipeline, which unless tightly coupled may not generally be accessible for any purpose. But many genomic data processing operations, such as Smith-Waterman alignment, gapless alignment, De Bruijn or assembly graph construction, and other such operations, can be used in various higher level parent algorithms. For example, as described herein, Smith-Waterman alignment may be used in DNA/RNA read mapping and aligning, such as with respect to a reference genome, but may also be configured so as to be used by haplotype-based variant callers, to align candidate haplotypes to a reference genome, or to each other, or to sequenced reads, such as in a HMM analysis and/or variant call function. Hence, exposing various discrete low-level hardware acceleration functions via general software function calls may enable the same acceleration logic, e.g., 13, to be leveraged throughout a genomic data processing application, such as in the performance of both alignment and variant calling, e.g. HMM, operations.

It is also practical, with tight CPU/FPGA interconnection, to have distributed rather than centralized CPU 1000 software control over communication with the various FPGA hardware engines 13 described herein. In widespread practices of multi-threaded, multi-core, and multi-CPU software design, many software threads and processes communicate and cooperate seamlessly, without any central software modules, drivers, or threads to manage intercommunication. In such a format, this is practical because of the cache-coherent shared memory, which is visible to all threads in all cores in all of the CPUs; while physically, coherent memory sharing between the cores and CPUs occurs by intercommunication over the processor interconnect, e.g., QPI or HT.

Figure 36:
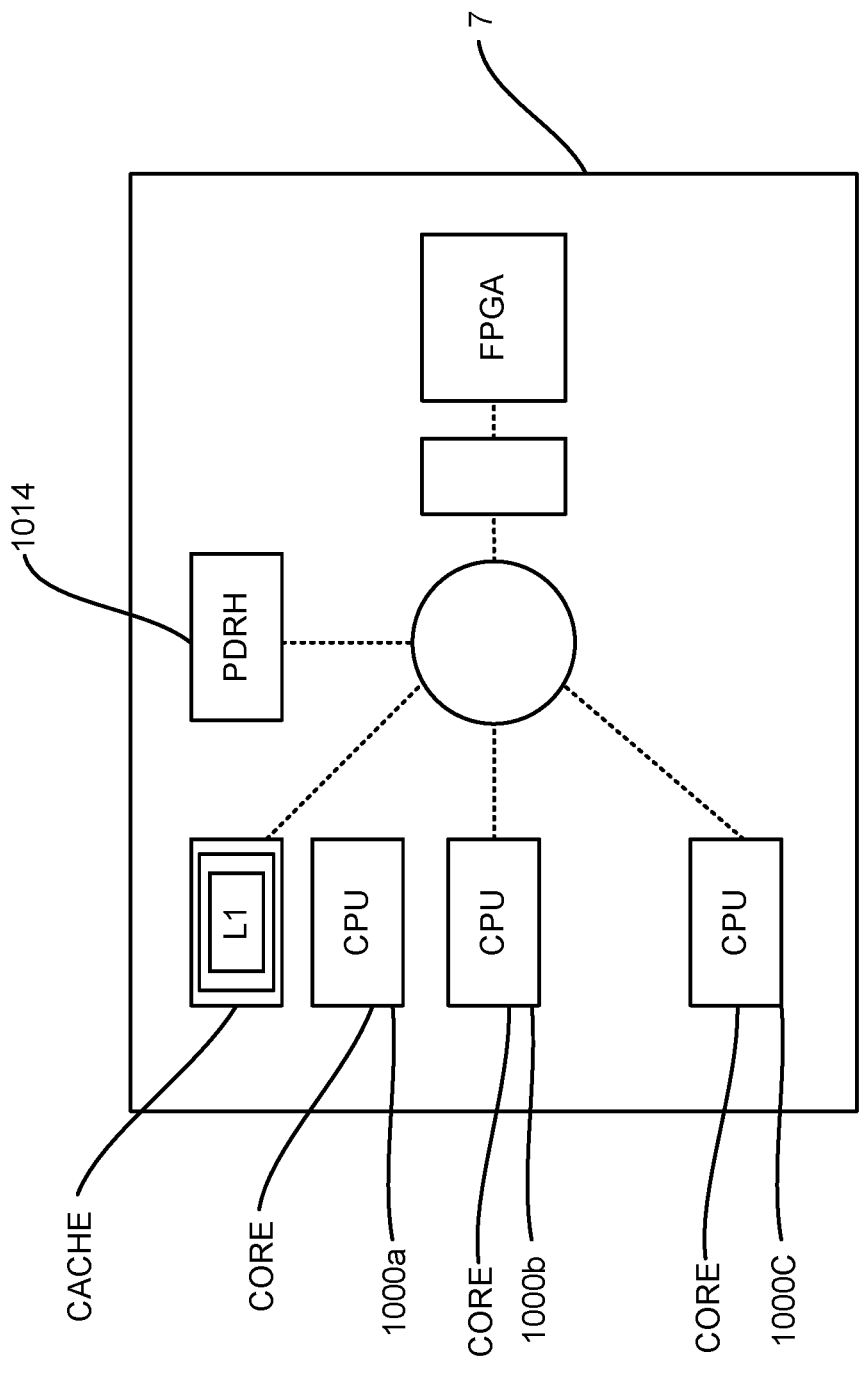
FIG. 36 illustrates a core of CPUs sharing one or more memories and/or caches, wherein the CPUs are configured for communicating with one or more FPGAs that may also include a shared or common memory or caches.

In a similar manner, as can be seen with respect to FIGS. 36-38, the systems provided herein may have a number of CPUs and/or FPGAs that may be in a tight CPU/FPGA interconnect configuration that incorporates a multiplicity of threads, e.g., 20*a*, *b*, *c*, and a multiplicity of processes running on one or the multiple cores and/or CPUs, e.g., 1000*a*, 100*b*, and 1000*c*. As such, the system components are configured for communicating and cooperating in a distributed manner with one another, e.g., between the various different CPU and/or FPGA hardware acceleration engines, such as by the use of cache-coherent memory sharing between the various CPU(s) and FPGA(s). For instance, as can be seen with respect to FIG. 36, a multiplicity of CPU cores 1000*a*, 1000*b*, and 1000*c* can be coupled together in such a manner as to share one or more memories, e.g., DRAMs 1014, and/or one or more caches having one or more layers, e.g., L1, L2, L3, etc., or levels associated therewith. Likewise, with respect to FIG. 38, in another embodiment, a single CPU 1000 may be configured to include multiple cores 1000*a*, 1000*b*, and 1000*c* that can be coupled together in such a manner so as to share one or more memories, e.g., DRAMs 1014, and/or one or more caches, 1014*a*, having one or more layers or levels associated therewith.

Hence, in either embodiment, data to be passed from one or more software threads 20 from one or more CPU cores 1000 to a hardware engine 13, e.g., of an FPGA, or vice versa, may be continuously and/or seamlessly updated in the shared memory 1014, or a cache and/or layer thereof, which is visible to each device. Additionally, requests to process data in the shared memory 1014, or notification of results updated therein, can be signaled between the software and/or hardware, such as over a suitably configured bus, e.g., DDR4 bus, such as in queues that may be implemented within the shared memory itself. Standard software mechanisms for control, transfer, and data protection, such as semaphores, mutexes, and atomic integers, can also be implemented similarly for software/hardware coordination.

Consequently, in some embodiments, as exemplified in FIG. 36, with no need for the FPGA 7 to have its own dedicated memory 14, or other external resources, due to cache coherent memory-sharing over a tight CPU/FPGA interconnect, it becomes much more practical to package the FPGA 7 more compactly and natively within traditional CPU 1000 motherboards, without the use of expansion cards. See, for example FIGS. 34A and 34B and FIG. 35. Several packaging alternatives are available. Specifically, an FPGA 7 may be installed onto a multi-CPU motherboard in a CPU socket, as shown in FIGS. 34A and 34B, such as by use of an appropriate interposer, such as a small PC board 2, or alternative wire-bond packaging of the FPGA die within the CPU chip package 2*a*, where the CPU socket pins are appropriately routed to the FPGA pins, and include power and ground connections, a processer interconnect 3 (QPI, HT, etc.), and other system connections. Accordingly, an FPGA die and CPU die may be included in the same multi-chip package (MCP) with the necessary connections, including power, ground, and CPU/FPGA interconnect, made within the package 2*a*. Inter-die connections may be made by die-to-die wire-bonding, or by connection to a common substrate or interposer, or by bonded pads or through-silicon vias between stacked dice.

Figure 35:
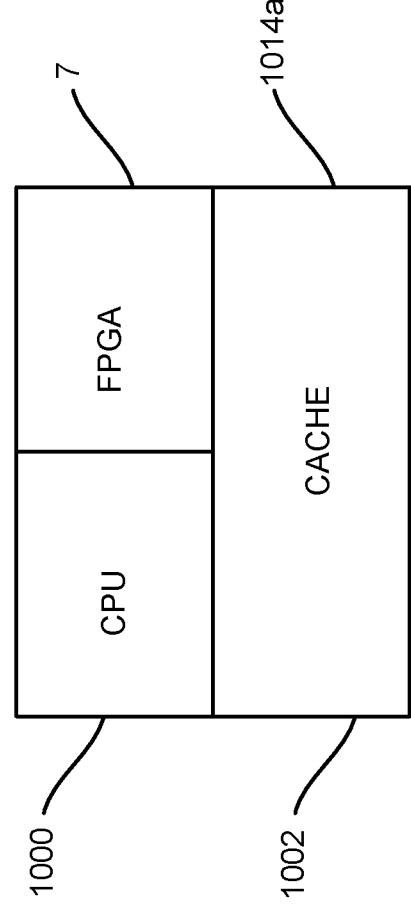
FIG. 35 depicts an embodiment of a package of a combined CPU and FPGA, where the two devices share a common memory and/or cache.

Additionally, in various implementations, FPGA and CPU cores may be fabricated on a single die, see FIG. 35, using a system-on-a-chip (SOC) methodology. In any of these cases, custom logic, e.g., 17, may be instantiated inside the FPGA 7 to both communicate over the CPU/FPGA interconnect 3, e.g., by properly dedicated protocols, and to service, convert, and/or route memory access requests from internal FPGA engines 13 to the CPU/FPGA interconnect 3, via appropriate protocols, to the shared memory 1014*a*. Additionally, some or all of this logic may be hardened into custom silicon, to avoid using up FPGA logic real estate for this purpose, such as where the hardened logic may reside on the CPU die, and/or the FPGA die, or a separate die. Also, in any of these cases, power supply and heat dissipation requirements may be appropriately achieved, such as within a single package (MCP or SOC). Further, the FPGA size and CPU core count may be selected to stay within a safe power envelope, and/or dynamic methods (clock frequency management, clock gating, core disabling, power islands, etc.) may be used to regulate power consumption according to changing the CPU and/or the FPGA computation demands.

All of these packaging options share several advantages. The tightly-integrated CPU/FPGA platform becomes compatible with standard motherboards and/or system chassis, of a variety of sizes. If the FPGA is installed via an interposer in a CPU socket, see FIGS. 34A and 34B, then at least a dual-socket motherboard 1002 may be employed. In others instances, a quad-socket motherboard may be employed so as to allow 3 CPUs+1 FPGA, 2 CPUs+2 FPGAs, or 1 CPU+3 FPGAs, etc. configurations to be implemented. If each FPGA resides in the same chip package as a CPU (either MCP or SOC), then a single-socket motherboard may be employed, potentially in a very small chassis (although a dual socket motherboard is depicted); this also scales upward very well, e.g. 4 FPGAs and 4 multi-core CPUs on a 4-socket server motherboard, which nevertheless could operate in a compact chassis, such as a 1U rack-mount server.

Accordingly, in various instances, therefore, there may be no need for an expansion card to be installed so as to integrate the CPU and FPGA acceleration, because the FPGA 7 may be integrated in to the CPU socket 1003. This implementation avoids the extra space and power requirements of an expansion card, and avoids various additional failure points expansion cards sometimes have with respect to relatively low-reliability components. Furthermore, standard CPU cooling solutions (head sinks, heat pipes, and/or fans), which are efficient yet low-cost since they are manufactured in high volumes, can be applied to FPGAs or CPU/FPGA packages in CPU sockets, whereas cooling for expansion cards can be expensive and inefficient.

Likewise, an FPGA/interposer and/or CPU/FPGA package may include the full power supply of a CPU socket, e.g.

150 W, whereas a standard expansion card may be power limited, e.g. 25 W or 75 W from the PCIe bus. In various instances, for genomic data processing applications, all these packaging options may facilitate easy installation of a tightly-integrated CPU+FPGA compute platform, such as within a DNA sequencer. For instance, typical modern "next-generation" DNA sequencers contain the sequencing apparatus (sample and reagent storage, fluidics tubing and control, sensor arrays, primary image and/or signal processing) within a chassis that also contains a standard or custom server motherboard, wired to the sequencing apparatus for sequencing control and data acquisition. A tightly-integrated CPU+FPGA platform, as herein described, may be achieved in such a sequencer such as by simply installing one or more FPGA/interposer and/or FPGA/CPU packages in CPU sockets of its existing motherboard, or alternatively by installing a new motherboard with both CPU(s) and FPGA(s), e.g., tightly coupled, as herein disclosed. Further, all of these packaging options may be configured to facilitate easy deployment of the tightly-integrated CPU+FPGA platform such as into a cloud accessible and/or datacenter server rack, which include compact/dense servers with very high reliability/availability.

Hence, in accordance with the teachings herein, there are many processing stages for data from DNA (or RNA) sequencing to mapping and aligning to sorting and/or deduplicating to variant calling, which can vary depending on the primary and/or secondary and/or tertiary processing technologies employed and their applications. Such processing steps may include one or more of: signal processing on electrical measurements from a sequencer, an image processing on optical measurements from the sequencer, base calling using processed signal or image data to determine the most likely nucleotide sequence and confidence scores, filtering sequenced reads with low quality or polyclonal clusters, detecting and trimming adapters, key sequences, barcodes, and low quality read ends, as well as De novo sequence assembly, generating and/or utilizing De Bruijn graphs and/or sequence graphs, e.g., De Bruijn and sequence graph construction, editing, trimming, cleanup, repair, coloring, annotation, comparison, transformation, splitting, splicing, analysis, subgraph selection, traversal, iteration, recursion, searching, filtering, import, export, including mapping reads to a reference genome, aligning reads to candidate mapping locations in the reference genome, local assembly of reads mapped to a reference region, sorting reads by aligned position, marking and/or removing duplicate reads, including PCR or optical duplicates, re-alignment of multiple overlapping reads for indel consistency, base quality score recalibration, variant calling (single sample or joint), structural variant analysis, copy number variant analysis, somatic variant calling (e.g., tumor sample only, matched tumor/normal, or tumor/unmatched normal, etc.), RNA splice junction detection, RNA alternative splicing analysis, RNA transcript assembly, RNA transcript expression analysis, RNA differential expression analysis, RNA variant calling, DNA/RNA difference analysis, DNA methylation analysis and calling, variant quality score recalibration, variant filtering, variant annotation from known variant databases, sample contamination detection and estimation, phenotype prediction, disease testing, treatment response prediction, custom treatment design, ancestry and mutation history analysis, population DNA analysis, genetic marker identification, encoding genomic data into standard formats and/or compression files (e.g. FASTA, FASTQ, SAM, BAM, VCF, BCF), decoding genomic data from standard formats, querying, selecting or filtering genomic data subsets, general compression and decompression for genomic files (gzip, BAM compression), specialized compression and decompression for genomic data (CRAM), genomic data encryption and decryption, statistics calculation, comparison, and presentation from genomic data, genomic result data comparison, accuracy analysis and reporting, genomic file storage, archival, retrieval, backup, recovery, and transmission, as well as genomic database construction, querying, access management, data extraction, and the like.

All of these operations can be quite slow and expensive when implemented on traditional compute platforms. The sluggishness of such exclusively software implemented operations may be due in part to the complexity of the algorithms, but is typically due to the very large input and output datasets that results in high latency with respect to moving the data. The devices and systems disclosed herein overcome these problems, in part due to the configuration of the various hardware processing engines, acceleration by the various hardware implementations, and/or in part due to the CPU/FPGA tight coupling configurations. Accordingly, as can be seen with respect to FIG. 39, one or more, e.g., all of these operations, may be accelerated by cooperation of CPUs 1000 and FPGAs 7, such as in a distributed processing model, as described herein. For instance, in some cases (encryption, general compression, read mapping, and/or alignment), a whole operational function may be substantially or entirely implemented in custom FPGA logic (such as by hardware design methodology, e.g. RTL), such as where the CPU software mostly serves the function of compiling large data packets for preprocessing via worker threads 20, such as aggregating the data into various jobs to be processed by one or more hardware implemented processing engines, and feeding the various data inputs, such as in a first in first out format, to one or more of the FPGA engine(s) 13, and/or receives results therefrom.

Figure 39:
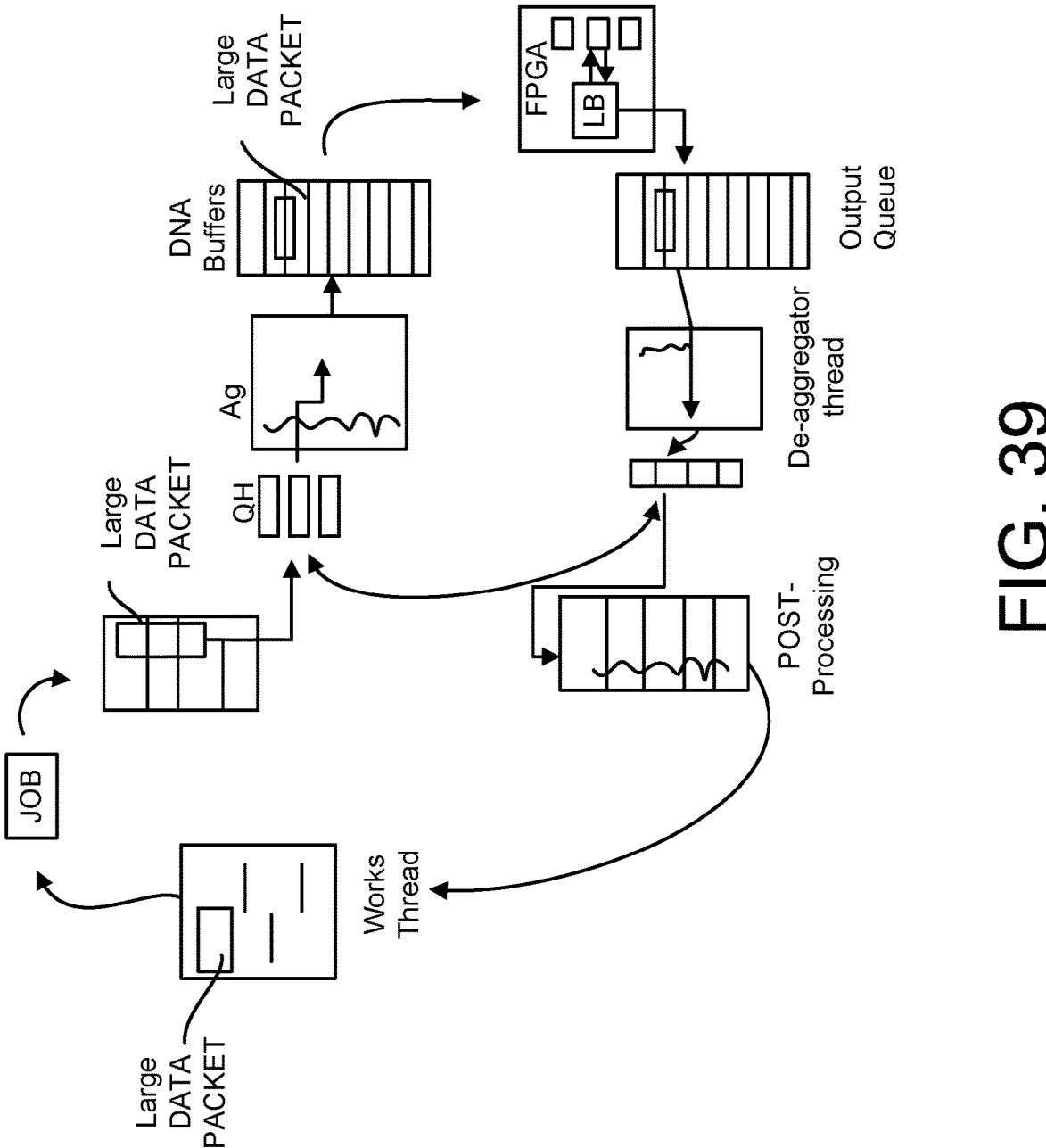
FIG. 39 depicts an exemplary method for the processing of one or more jobs of a system of the disclosure.

For instance, as can be seen with respect to FIG. 39, in various embodiments, a worker thread generates various packets of job data that may be compiled and/or streamed into larger job packets that may be queued up and/or further aggregated in preparation for transfer, e.g., via a DDR3 to the FPGA 7, such as over a high bandwidth, low latency, point to point interconnect protocol, e.g., QPI 3. In particular instances, the data may be buffered in accordance with the particular data sets being transferred to the FPGA. Once the packaged data is received by the FPGA 7, such as in a cache coherent manner, it may be processed and sent to one or more specialized clusters 11 whereby it may further be directed to one or more sets of processing engines for processing thereby in accordance with one or more of the pipeline operations herein described.

Once processed, results data may then be sent back to the cluster and queued up for being sent back over the tight coupling point to point interconnect to the CPU for post processing. In certain embodiments, the data may be sent to a de-aggregator thread prior to post processing. Once post processing has occurred, the data may be sent back to the initial worker thread 20 that may be waiting on the data. Such distributed processing is particularly beneficial for the functions herein disclosed above. Particularly, these functions are distinguishable by the facts that their algorithmic complexity (although having a very high net computational burden) are pretty limited, and they each may be configured so as to have a fairly uniform compute cost across their various sub-operations.

However, in various cases, rather than processing the data in large packets, smaller sub-routines or discrete function protocols or elements may be performed, such as pertaining to one or more functions of a pipeline, rather than performing the entire processing functions for that pipeline on that data. Hence, a useful strategy may be to identify one or more critical compute-intensive sub-functions in any given operation, and then implement that sub-function in custom FPGA logic (hardware acceleration), such as for the intensive sub-function(s), while implementing the balance of the operation, and ideally much or most of the algorithmic complexity, in software to run on CPUs/GPUs/QPUs, as described herein, such as with respect to FIG. 39.

Generally, it is typical of many genomic data processing operations that a small percentage of the algorithmic complexity accounts for a large percentage of the overall computing load. For instance, as a typical example, 20% of the algorithmic complexity for the performance of a given function may account for 90% of the compute load, while the remaining 80% of the algorithmic complexity may only account for 10% of the compute load. Hence, in various instances, the system components herein described may be configured so as to implement the high, e.g., 20% or more, complexity portion so as to be run very efficiently in custom FPGA logic, which may be a tractable and maintainable in a hardware design, and thus, may be configured for executing this in FPGA; which in turn may reduce the CPU compute load by 90%, thereby enabling 10× overall acceleration. Other typical examples may be even more extreme, such as where 10% of the algorithmic complexity may account for 98% of the compute load, in which case applying FPGA acceleration, as herein described, to the 10% complexity portion be even easier, but may also enable up to 50× net acceleration. In various instances, where extreme accelerated processing is desired, one or more of these functions may be performed by a quantum processing unit.

However, such a "piecemeal" or distributed processing acceleration approaches may be more practical when implemented in a tightly integrated CPU/GPU+FPGA platform, rather than on a loosely integrated CPU/GPU+FPGA platform. Particularly, in a loosely integrated platform, the portion, e.g., the functions, to be implemented in FPGA logic may be selected so as to minimize the size of the input data to the FPGA engine(s), and to minimize the output data from the FPGA engine(s), such as for each data unit processed, and additionally may be configured so as to keep the software/hardware boundary tolerant of high latencies. In such instances, the boundary between the hardware and software portions may be forced, e.g., on the loosely-integrated platform, to be drawn through certain low-bandwidth/high-latency cut-points, which divisions may not otherwise be desirable when optimizing the partitioning of the algorithmic complexity and computational loads. This may often result either in enlarging the boundaries of the hardware portion, encompassing an undesirably large portion of the algorithmic complexity in the hardwired format, or in shrinking the boundaries of the hardware portion, undesirably excluding portions with dense compute load.

By contrast, on a tightly integrated CPU/GPU+FPGA platform, due to the cache-coherent shared memory and the high-bandwidth/low-latency CPU/GPU/FPGA interconnect, the low-complexity/high-compute-load portions of a genomic data processing operation can be selected very precisely for implementation in custom FPGA logic (e.g., via the hardware engine(s) described herein), with optimized software/hardware boundaries. In such an instance, even if a data unit is large at the desired software/hardware boundary, it can still be efficiently handed off to an FPGA hardware engine for processing, just by passing a pointer to the particular data unit. Particularly, in such an instance, as per FIG. 33B, the hardware engine 13 of the FPGA 7, may not need to access every element of the data unit stored within the DRAM 1014; rather, it can access the necessary elements, e.g., within the cache 1014a, with efficient small accesses over the low-latency interconnect 3' serviced by the CPU/GPU cache, thereby consuming less aggregate bandwidth than if the entire data unit had to be accessed and/or transferred to the FPGA 7, such as by DMA of the DRAM 1014, over a loose interconnect 3, as per FIG. 33A.

In such instances, the hardware engine 13 can annotate processing results into the data unit in-place in CPU/GPU memory 1014, without streaming an entire copy of the data unit by DMA to CPU/GPU memory. Even if the desired software/hardware boundary is not appropriate for a software thread 20 to make a high-latency, non-blocking queued handoff to the hardware engine 13, it can potentially make a blocking function call to the hardware engine 13, sleeping for a short latency until the hardware engine completes, the latency being dramatically reduced by the cache-coherent shared memory, the low-latency/high-bandwidth interconnect, and the distributed software/hardware coordination model, as in FIG. 33B.

In particular instances, because the specific algorithms and requirements of signal/image processing and base calling vary from one sequencer technology to another, and because the quantity of raw data from the sequencer's sensor is typically gargantuan (this being reduced to enormous after signal/image processing, and to merely huge after base calling), such signal/image processing and base calling may be efficiently performed within the sequencer itself, or on a nearby compute server connected by a high bandwidth transmission channel to the sequencer. However, DNA sequencers have been achieving increasingly high throughputs, at a rate of increase exceeding Moore's Law, such that existing Central Processing Unit ("CPU") and/or Graphics Processing Unit "GPU" based signal/image processing and base calling, when implemented individually and alone, have become increasingly inadequate to the task. Nevertheless, since a tightly integrated CPU+FPGA and/or a GPU+FPGA and/or a GPU/CPU+FPGA platform can be configured to be compact and easily instantiated within such a sequencer, e.g., as CPU and/or GPU and/or FPGA chip positioned on the sequencer's motherboard, or easily installed in a server adjacent to the sequencer, or a cloud-based server system accessible remotely from the sequencer, such a sequencer may be an ideal platform to offer the massive compute acceleration offered by the custom FPGA/ASIC hardware engines described herein.

For instance, the system provided herein may be configured so as to perform primary, secondary, and/or tertiary processing, or portions thereof so as to be implemented by an accelerated CPU, GPU, and/or FPGA; a CPU+FPGA; a GPU+FPGA; a GPU/CPU+FPGA; QPU; CPU/QPU; GPU/QPU; CPU and/or GPU and/or QPU+FPGA platform. Further, such accelerated platforms, e.g., including one or more FPGA and/or QPU hardware engines, are useful for implementation in cloud-based systems, as described herein. For example, signal/image processing, base calling, mapping, aligning, sorting, de-duplicating, and/or variant calling algorithms, or portions thereof, generally require large amounts of floating point and/or fixed-point math, notably additions and multiplications. These functions can also be configured so as to be performed by one or more quantum processing circuits such as to be implemented in a quantum processing platform.

Particularly, large modern FPGAs/quantum circuits contain thousands of high-speed multiplication and addition resources. More particularly, these circuits may include custom engines that may be implemented on or by them, which custom engines may be configured to perform parallel arithmetic operations at rates far exceeding the capabilities of simple general CPUs. Likewise, simple GPUs, have more comparable parallel arithmetic resources. However, GPUs often have awkward architectural limitations and programming restrictions that may prevent them from being fully utilized. Accordingly, these FPGA and/or quantum processing and/or GPU arithmetic resources can be wired up or otherwise configured by design to operate in exactly the designed manner with near 100% efficiency, such as for performing the calculations necessary to execute the functions herein. Accordingly, GPU cards may be added to expansion slots on a motherboard with a tightly integrated CPU and/or FPGA, thereby allowing all three processor types to cooperate, although the GPU may still cooperate with all of its own limitations and the limitations of loose integration.

More particularly, in various instances, with respect to Graphics Processing Units (GPUs), a GPU can be configured so as to implement one or more of the functions, as herein described, so as to accelerate the processing speed of the underlying calculations necessary for preforming that function, in whole or in part. More particularly, a GPU may be configured to perform one or more tasks in a mapping, aligning, sorting, de-duplicating, and/or variant calling protocol, such as to accelerate one or more of the computations, e.g., the large amounts of floating point and/or fixed-point math, such as additions and multiplications involved therein, so as to work in conjunction with a server's CPU and/or FPGA to accelerate the application and processing performance and shorten the computational cycles required for performing such functions. Cloud servers, as herein described, with GPU/CPU/FPGA cards may be configured so as to easily handle compute-intensive tasks and deliver a smoother user experience when leveraged for virtualization. Such compute-intensive tasks can also be offloaded to the cloud, such as to be performed by a quantum processing unit.

Accordingly, if a tightly integrated CPU+FPGA or GPU+FPGA and/or CPU/GPU/FPGA with shared memory platform is employed within a sequencer, or attached or cloud based server, such as for signal/image processing, base calling, mapping, aligning, sorting, de-duplicating, and/or variant calling functions, there may be an advantage achieved such as in an incremental development process. For instance, initially, a limited portion of the compute load, such as a dynamic programming function for base calling, mapping, aligning, sorting, de-duplicating, and/or variant calling may be implemented in one or more FPGA engines, where as other work may be done in the CPU and/or GPU expansion cards. However, the tight CPU/GPU/FPGA integration and shared memory model, herein presented, may be further configured, later, so as to make it easy to incrementally select additional compute-intensive functions for GPU, FPGA, and/or quantum acceleration, which may then be implemented as processing engines, and various of their functions may be offloaded for execution into the FPGA(s) and/or in some instances may be offloaded onto the cloud, e.g., for performance by a QPU, thereby accelerating signal/image/base calling/mapping/aligning/variant processing. Such incremental advances can be implemented as needed to keep up with the increasing throughput of various primary and/or secondary and/or tertiary processing technologies.

Hence, read mapping and alignment, e.g., of one or more reads to a reference genome, as well as sorting, de-duplicating, and/or variant calling may be benefited from such GPU and/or FPGA and/or QPU acceleration. Specifically, mapping and alignment and/or variant calling, or portions thereof, may be implemented partially or entirely as custom FPGA logic, such as with the "to be mapped and/or aligned and/or variant called" reads streaming from the CPU/GPU memory into the FPGA map/align/variant calling engines, and mapped and/or aligned and/or variant called read records streaming back out, which may further be streamed back on-board, such as in the performance of sorting and/or variant calling. This type of FPGA acceleration works on a loosely-integrated CPU/GPU+FPGA platform, and in the configurations described herein may be extremely fast. Nevertheless, there are some additional advantages that may be gained by moving to a tightly-integrated CPU/GPU/QPU+ FPGA platform.

Accordingly, with respect to mapping and aligning and variant calling, in some embodiments, a shared advantage of a tightly-integrated CPU/GPU+FPGA and/or quantum processing platform, as described herein, is that the map/align/ variant calling acceleration, e.g., hardware acceleration, can be efficiently split into several discrete compute-intensive operations, such as seed generation and/or mapping, seed chain formation, paired end rescue scans, gapless alignment, and gapped alignment (Smith-Waterman or Needleman-Wunsch), De Bruijn graph formation, performing a HMM computation, and the like, such as where the CPU and/or GPU and/or quantum computing software performs lighter (but not necessarily less complex) tasks, and may make acceleration calls to discrete hardware and/or other quantum computing engines as needed. Such a model may be less efficient in a typical loosely-integrated CPU/GPU+FPGA platform, e.g., due to large amounts of data to transfer back and forth between steps and high latencies, but may be more efficient in a tightly-integrated CPU+FPGA, GPU+FPGA, and/or quantum computing platform with cache-coherent shared memory, high-bandwidth/low-latency interconnect, and distributed software/hardware coordination model. Additionally, such as with respect to variant calling, both Hidden Markov model (HMM) and/or dynamic programming (DP) algorithms, including Viterbi and forward algorithms, may be implemented in association with a base calling/mapping/aligning/sorting/de-duplicating operation, such as to compute the most likely original sequence explaining the observed sensor measurements, in a configuration so as to be well suited to the parallel cellular layout of FPGAs and quantum circuits described herein.

Specifically, an efficient utilization of hardware and/or software resources in a distributed processing configuration can result from reducing hardware and/or quantum computing acceleration to discrete compute-intensive functions. In such instances, several of the functions disclosed herein may be performed in a monolithic pure-hardware engine so as to be less compute intensive, but may nevertheless still be algorithmically complex, and therefore may consume large quantities of physical FPGA resources (lookup-tables, flip-flops, block-RAMs, etc.). In such instances, moving a portion or all of various discrete functions to software could take up available CPU cycles, in return for relinquishing substantial amounts of FPGA area. In certain of these instances, the freed FPGA area can be used for establishing greater parallelism for the compute intensive map/align/ variant call sub-functions, thus increasing acceleration, or for other genomic acceleration functions. Such benefits may also be achieved by implementing compute intensive functions in one or more dedicated quantum circuits for implementation by a quantum computing platform.

Hence, in various embodiments, the algorithmic complexity of the one or more functions disclosed herein may be somewhat lessened by being configured in a pure hardware or pure quantum computing implementation. However, some operations, such as comparing pairs of candidate alignments for paired-end reads, and/or performing subtle mapping quality (MAPQ) estimations, represent very low compute loads, and thus could benefit from more complex and accurate processing in CPU/GPU and/or quantum computing software. Hence, in general, reducing the hardware processing to specific compute-intensive operations would allow more complex and accurate algorithms to be employed in the CPU/GPU portions.

Furthermore, in various embodiments, the whole or a part of the map/align/sorting/de-duplicating/variant calling operations, disclosed herein, could be configured in such a manner that the more algorithmically complex computations may be employed at high levels in hardware and/or via one or more quantum circuits, such as where the called compute-intensive hardware and/or quantum functions are configured to be performed in a dynamic or iterative order. Particularly, a monolithic pure-hardware/quantum processing design may be implemented in a manner so as to function more efficiently as a linear pipeline. For example, if during processing one Smith-Waterman alignment displayed evidence of the true alignment path escaping the scoring band, e.g., swath as described above, another Smith-Waterman alignment could be called to correct this. Hence, these configurations could essentially reduce the FPGA hardware/quantum acceleration to discrete functions, such as a form of procedural abstraction, which would allow higher level complexity to be built easily on top of it.

Additionally, in various instances, flexibility within the map/align/variant calling algorithms and features thereof may be improved by reducing hardware and/or quantum acceleration to discrete compute-intensive functions, and configuring the system so as to perform other, e.g., less intensive parts, in the software of the CPU and/or GPU. For instance, although hardware algorithms can be modified and reconfigured in FPGAs, generally such changes to the hardware designs, e.g., via firmware, may require several times as much design effort as similar changes to software code. In such instances, the compute-intensive portions of mapping and alignment and sorting and de-duplicating, and/or variant calling, such as seed mapping, seed chain formation, paired end rescue scans, gapless alignment, gapped alignment, and HMM, which are relatively well-defined, are thus stable functions and do not require frequent algorithmic changes. These functions, therefore, may be suitably optimized in hardware, whereas other functions, which could be executed by CPU/GPU software, are more appropriate for incremental improvement of algorithms, which is significantly easier in software. However, once fully developed could be implemented in hardware. One or more of these functions may also be configured so as to be implemented in one or more quantum circuits of a quantum processing machine.

Accordingly, in various instances, variant calling (with respect to DNA or RNA, single sample or joint, germline or somatic, etc.) may also benefit from FPGA and/or quantum acceleration, such as with respect to its various compute intensive functions. For instance, haplotype-based callers, which call bases on evidence derived from a context provided within a window around a potential variant, as described above, is often the most compute-intensive operation. These operations include comparing a candidate haplotype (e.g., a single-strand nucleotide sequence representing a theory of the true sequence of at least one of the sampled strands at the genome locus in question) to each sequencer read, such as to estimate a conditional probability of observing the read given the truth of the haplotype.

Such an operation may be performed via one or more of an MRJD, Pair Hidden Markov Model (pair-HMM), and/or a Pair-Determined Hidden Markov Model (PD-HMM) calculation that sums the probabilities of possible combinations of errors in sequencing or sample preparation (PCR, etc.) by a dynamic programming algorithm. Hence, with respect thereto, the system can be configured such that a pair-HMM or PD-HMM calculation may be accelerated by one or more, e.g., parallel, FPGA hardware or quantum processing engines, whereas the CPU/GPU/QPU software may be configured so as to execute the remainder of the parent haplotype-based variant calling algorithm, either in a loosely-integrated or tightly-integrated CPU+FPGA, or GPU+FPGA or CPU and/or GPU+FPGA and/or QPU platform. For instance, in a loose integration, software threads may construct and prepare a De Bruijn and/or assembly graph from the reads overlapping a chosen active region (a window or contiguous subset of the reference genome), extract candidate haplotypes from the graph, and queue up haplotype-read pairs for DMA transfer to FPGA hardware engines, such as for pair-HMM or PD-HMM comparison. The same or other software threads can then receive the pair-HMM results queued and DMA-transferred back from the FPGA into the CPU/GPU memory, and perform genotyping and Bayesian probability calculations to make final variant calls. Of course, one or more of these functions can be configured so as to be run on one or more quantum computing platforms.

For instance, as can be seen with respect to FIG. 38, the CPU/GPU 1000 may include one or more, e.g., a plurality, of threads 20a, 20b, and 20c, which may each have access to an associated DRAM 1014, which DRAM has work space 1014a, 1014b, and 1014c, within which each thread 20a, 20b, and 20c, may have access, respectively, so as to perform one or more operations on one or more data structures, such as large data structures. These memory portions and their data structures may be accessed, such as via respective cache portions 1014a', such as by one or more processing engines 13a, 13b, 13c of the FPGA 7, which processing engines may access the referenced data structures such as in the performance of one or more of the operations herein described, such as for mapping, aligning, sorting, and/or variant calling. Because of the high bandwidth, tight coupling interconnect 3, data pertaining to the data structures and/or related to the processing results may be shared substantially seamlessly between the CPU and/or GPU and/or QPU and/or the associated FPGA, such as in a cache coherent manner, so as to optimize processing efficiency.

Accordingly, in one aspect, as herein disclosed, a system may be provided wherein the system is configured for sharing memory resources amongst its component parts, such as in relation to performing some computational tasks or sub-functions via software, such as run by a CPU and/or GPU and/or QPU, and performing other computational tasks or sub functions via firmware, such as via the hardware of an associated chip, such as an FPGA and/or ASIC or structured ASIC. This may be achieved in a number of different ways, such as by a direct loose or tight coupling between the CPU/GPU/QPU and the chip, e.g., FPGA. Such configurations may be particularly useful when distributing operations related to the processing of large data structures, as herein described, that have large functions or sub-functions to be used and accessed by both the CPU and/or GPU and/or QPU and the integrated circuit. Particularly, in various embodiments, when processing data through a genomics pipeline, as herein described, such as to accelerate overall processing function, timing, and efficiency, a number of different operations may be run on the data, which operations may involve both software and hardware processing components.

Consequently, data may need to be shared and/or otherwise communicated, between the software component running on the CPU and/or GPU and/or the QPU and the hardware component embodied in the chip, e.g., an FPGA or ASIC. Accordingly, one or more of the various steps in the processing pipeline, or a portion thereof, may be performed by one device, e.g., the CPU/GPU/QPU, and one or more of the various steps may be performed by the other device, e.g., the FPGA or ASIC. In such an instance, the CPU and the FPGA need to be communicably coupled, such as by a point to point interconnect, in such a manner to allow the efficient transmission of such data, which coupling may involve the shared use of memory resources. To achieve such distribution of tasks and the sharing of information for the performance of such tasks, the CPU and/or GPU and/or QPU may be loosely or tightly coupled to each other and/or to an FPGA, or other chip set, and a workflow management system may be included so as to distribute the workload efficiently.

Hence, in particular embodiments, a genomics analysis platform is provided. For instance, the platform may include a motherboard, a memory, and plurality of integrated circuits, such as forming one or more of a CPU/GPU/QPU, a mapping module, an alignment module, a sorting module, and/or a variant call module. Specifically, in particular embodiments, the platform may include a first integrated circuit, such as an integrated circuit forming a central processing unit (CPU) and/or a graphics processing unit (GPU) that is responsive to one or more software algorithms that are configured to instruct the CPU/GPU to perform one or more sets of genomics analysis functions, as described herein, such as where the CPU/GPU includes a first set of physical electronic interconnects to connect with the motherboard. In other embodiments, a quantum processing unit is provided, wherein the QPU includes one or more quantum circuits that are configured for performing one or more of the functions disclosed herein. In various instances, a memory is provided where the memory may also be attached to the motherboard and may further be electronically connected with the CPU and/or GPU and/or QPU, such as via at least a portion of the first set of physical electronic interconnects. In such instances, the memory may be configured for storing a plurality of reads of genomic data, and/or at least one or more genetic reference sequences, and/or an index, e.g., such as a hash table, of the one or more genetic reference sequences.

Additionally, the platform may include one or more of a second integrated circuit(s), such as where each second integrated circuit forms a field programmable gate array (FPGA) or ASIC, or structured ASIC having a second set of physical electronic interconnects to connect with the CPU and the memory, such as via a point-to-point interconnect protocol. In such an instance, the FPGA (or structured ASIC) may be programmable by firmware to configure a set of hardwired digital logic circuits that are interconnected by a plurality of physical interconnects to perform a second set of genomics analysis functions, e.g., mapping, aligning, sorting, de-duplicating, variant calling, e.g., an HMM function, etc. Particularly, the hardwired digital logic circuits of the FPGA may be arranged as a set of processing engines to perform one or more pre-configured steps in a sequence analysis pipeline of the genomics analysis platform, such as where the set(s) of processing engines include one or more of a mapping and/or aligning and/or sorting and/or de-duplicating and/or variant calling module, which modules may be formed of the separate or the same subsets of processing engines.

For instance, with respect to variant calling, a pair-HMM or PD-HMM calculation is one of the most compute-intensive steps of a haplotype-based variant calling protocol. Hence, variant calling speed may be greatly improved by accelerating this step in one or more FPGA or quantum processing engines, as herein described. However, there may be additional benefit in accelerating other compute-intensive steps in additional FPGA and/or QP engines, to achieve a greater speed-up of variant calling, or a portion thereof, or reduce CPU/GPU load and the number of CPU/GPU cores required, or both, as seen with respect to FIG. 38.

Additional compute-intensive functions, with respect to variant calling, that may be implemented in FPGA and/or quantum processing engines include: callable-region detection, where reference genome regions covered by adequate depth and/or quality of aligned reads are selected for processing; active-region detection, where reference genome loci with nontrivial evidence of possible variants are identified, and windows of sufficient context around these loci are selected as active regions for further processing; De-Bruijn or other assembly graph construction, where reads overlapping an active region and/or K-mers from those reads are assembled into a graph; assembly graph preparation, such as trimming low-coverage or low-quality paths, repairing dangling head and tail paths by joining them onto a reference backbone in the graph, transformation from K-mer to sequence representation of the graph, merging similar branches and otherwise simplifying the graph; extracting candidate haplotypes from the assembly graph; as well as aligning candidate haplotypes to the reference genome, such as by Smith-Waterman alignment, e.g., to determine variants (SNPs and/or indels) from the reference represented by each haplotype, and synchronize its nucleotide positions with the reference.

All of these functions may be implemented as high-performance hardware engines within the FPGA, and/or by one or more quantum circuits of a quantum computing platform. However, calling such a variety of hardware acceleration functions from many integration points in the variant calling software may become inefficient on a loosely-coupled CPU/GPU/QPU+FPGA platform, and therefore a tightly-integrated CPU/GPU/QPU+FPGA platform may be desirable. For instance, various stepwise processing methods such as: constructing, preparing, and extracting haplotypes from a De Bruijn graph, or other assembly graph, could strongly benefit from a tightly-integrated CPU/GPU/QPU+FPGA platform. Additionally, assembly graphs are large and complex data structures, and passing them repeatedly between the CPU and/or GPU and the FPGA could become resource expensive and inhibit significant acceleration.

Hence, an ideal model for such graph processing, employing a tightly-integrated CPU/GPU/QPU and/or FPGA platform, is to retain such graphs in cache-coherent shared memory for alternating processing by CPU and/or GPU and/or QPU software and FPGA hardware functions. In such an instance, a software thread processing a given graph may iteratively command various compute-intensive graph processing steps by a hardware engine, and then the software could inspect the results and determine the next steps between the hardware calls, such as exemplified in the process of FIG. 39. This processing model, may be controlled by a suitably configured workflow management system, and/or may be configured to correspond to software paradigms such as a data-structure API or an object-oriented method interface, but with compute intensive functions being accelerated by custom hardware and/or quantum processing engines, which is made practical by being implemented on a tightly-integrated CPU and/or GPU and/or QPU+FPGA platform, with cache-coherent shared memory and high-bandwidth/low-latency CPU/GPU/QPU/FPGA interconnects.

Accordingly, in addition to mapping and aligning sequenced reads to a reference genome, reads may be assembled "de novo," e.g., without a reference genome, such as by detecting apparent overlap between reads, e.g., in a pileup, where they fully or mostly agree, and joining them into longer sequences, contigs, scaffolds, or graphs. This assembly may also be done locally, such as using all reads determined to map to a given chromosome or portion thereof. Assembly in this manner may also incorporate a reference genome, or segment of one, into the assembled structure.

In such an instance, due to the complexity of joining together read sequences that do not completely agree, a graph structure may be employed, such as where overlapping reads may agree on a single sequence in one segment, but branch into multiple sequences in an adjacent segment, as explained above. Such an assembly graph, therefore, may be a sequence graph, where each edge or node represents one nucleotide or a sequence of nucleotides that is considered to adjoin contiguously to the sequences in connected edges or nodes. In particular instances, such an assembly graph may be a k-mer graph, where each node represents a k-mer, or nucleotide sequence of (typically) fixed length k, and where connected nodes are considered to overlap each other in longer observed sequences, typically overlapping by k–1 nucleotides. In various methods there may be one or more transformations performed between one or more sequence graphs and k-mer graphs.

Although assembly graphs are employed in haplotype-based variant calling, and some of the graph processing methods employed are similar, there are important differences. De novo assembly graphs are generally much larger, and employ longer k-mers. Whereas variant-calling assembly graphs are constrained to be fairly structured and relatively simple, such as having no cycles and flowing source-to-sink along a reference sequence backbone, de novo assembly graphs tend to be more unstructured and complex, with cycles, dangling paths, and other anomalies not only permitted, but subjected to special analysis. De novo assembly graph coloring is sometimes employed, assigning "colors" to nodes and edges signifying, for example, which biological sample they came from, or matching a reference sequence. Hence, a wider variety of graph analysis and processing functions need to be employed for de novo assembly graphs, often iteratively or recursively, and especially due to the size and complexity of de novo assembly graphs, processing functions tend to be extremely compute intensive.

Hence, as set forth above, an ideal model for such graph processing, on a tightly-integrated CPU/GPU/QPU+FPGA platform, is to retain such graphs in cache-coherent shared memory for alternating processing between the CPU/GPU/QPU software and FPGA hardware functions. In such an instance, a software thread processing a given graph may iteratively command various compute-intensive graph processing steps to be performed by a hardware engine, and then inspect the results to thereby determine the next steps to be performed by the hardware, such as by making appropriate hardware calls. Like above, this processing model, is greatly benefitted by implementation on a tightly-integrated CPU+FPGA platform, with cache-coherent shared memory and high-bandwidth/low-latency CPU/FPGA interconnect.

Additionally, as described herein below, tertiary analysis includes genomic processing that may follow graph assembly and/or variant calling, which in clinical applications may include variant annotation, phenotype prediction, disease testing, and/or treatment response prediction, as described herein. Reasons it is beneficial to perform tertiary analysis on such a tightly-integrated CPU/GPU/QPU+FPGA platform are that such a platform configuration enables efficient acceleration of primary and/or secondary processing, which are very compute intensive, and it is ideal to continue with tertiary analysis on the same platform, for convenience and reduced turnaround time, and to minimize transmission and copying of large genomic data files. Hence, either a loosely or tightly-integrated CPU/GPU/QPU+FPGA platform is a good choice, but a tightly coupled platform may include additional benefits because tertiary analysis steps and methods vary widely from one application to another, and in any case where compute-intensive steps slow down tertiary analysis, custom FPGA acceleration of those steps can be implemented in an optimized fashion.

For instance, a particular benefit to tertiary analysis on a tightly-integrated CPU/GPU/QPU and/or FPGA platform is the ability to re-analyze the genomic data iteratively, leveraging the CPU/GPU/QPU and/or FPGA acceleration of secondary processing, in response to partial or intermediate tertiary results, which may benefit additionally from the tight integration configuration. For example, after tertiary analysis detects a possible phenotype or disease, but with limited confidence as to whether the detection is true or false, focused secondary re-analysis may be performed with extremely high effort on the particular reads and reference regions impacting the detection, thus improving the accuracy and confidence of relevant variant calls, and in turn improving the confidence in the detection call. Additionally, if tertiary analysis determines information about the ancestry or structural variant genotypes of the analyzed individual, secondary analysis may be repeated using a different or modified reference genome, which is more appropriate for the specific individual, thus enhancing the accuracy of variant calls and improving the accuracy of further tertiary analysis steps.

However, if tertiary analysis is done on a CPU-only platform after primary and secondary processing (possibly accelerated on a separate platform), then re-analysis with secondary processing tools is likely to be too slow to be useful on the tertiary analysis platform itself, and the alternative is transmission to a faster platform, which is also prohibitively slow. Thus, in the absence of any form of hardware or quantum acceleration on the tertiary analysis platform, primary and secondary processing must generally be completed before tertiary analysis begins, without the possibility of easy re-analysis or iterative secondary analysis and/or pipelining of analytic functions. But on an FPGA and/or quantum-accelerated platform, and especially a tightly-integrated CPU and/or GPU and/or QPU and/or FPGA platform where secondary processing is maximally efficient, iterative analysis becomes practical and useful.

Accordingly, as indicated above, the modules herein disclosed may be implemented in the hardware of the chip, such as by being hardwired therein, and in such instances their implementation may be such that their functioning may take place at a faster speed, with greater accuracy, as compared to when implemented in software, such as where there are minimal instructions to be fetched, read, and/or executed. Additionally, in various instances, the functions to be performed by one or more of these modules may be distributed such that various of the functions may be configured so as to be implemented by the host CPU and/or GPU and/or QPU software, whereas in other instances, various other functions may be performed by the hardware of an associated FPGA, such as where the two or more devices perform their respective functions with one another such as in a seamless fashion. For such purposes, the CPU, GPU, QPU, and/or FPGA or ASIC or Structured ASIC may be tightly coupled, such as via a low latency, high bandwidth interconnect, such as a QPI, CCVI, CAPI, and the like. Accordingly, in some instances, the high computationally intensive functions to be performed by one or more of these modules may be performed by a quantum processor implemented by one or more quantum circuits.

Hence, given the unique hardware and/or quantum processing implementation, the modules of the disclosure may function directly in accordance with their operational parameters, such as without needing to fetch, read, and/or execute instructions, such as when implemented solely in CPU software. Additionally, memory requirements and processing times may be further reduced, such as where the communications within chip is via files, e.g., stored locally in the FPGA/CPU/GPU/QPU cache, such as a cache coherent manner, rather than through extensive accessing an external memory. Of course, in some instances, the chip and/or card may be sized so as to include more memory, such as more on board memory, so as to enhance parallel processing capabilities, thereby resulting in even faster processing speeds. For instance, in certain embodiments, a chip of the disclosure may include an embedded DRAM, so that the chip does not have to rely on external memory, which would therefore result in a further increase in processing speed, such as where a Burrows-Wheeler algorithm or De Brujin Graph may be employed, instead of a hash table and hash function, which may in various instances, rely on external, e.g., host memory. In such instances, the running of a portion or an entire pipeline can be accomplished in 6 or 10 or 12 or 15 or 20 minutes or less, such as from start to finish.

As indicated above, there are various different points where any given module can be positioned on the hardware, or be positioned remotely therefrom, such as on a server accessible on the cloud. Where a given module is positioned on the chip, e.g., hardwired into the chip, its function may be performed by the hardware, however, where desired, the module may be positioned remotely from the chip, at which point the platform may include the necessary instrumentality for sending the relevant data to a remote location, such as a server, e.g., quantum server, accessible via the cloud, so that the particular module's functionality may be engaged for further processing of the data, in accordance with the user selected desired protocols. Accordingly, part of the platform may include a web-based interface for the performance of one or more tasks pursuant to the functioning of one or more of the modules disclosed herein. For instance, where mapping, alignment, and/or sorting are all modules that may occur on the chip, in various instances, one or more of local realignment, duplicate marking, base quality core recalibration, and/or variant calling may take place on the cloud.

Particularly, once the genetic data has been generated and/or processed, e.g., in one or more primary and/or secondary processing protocols, such as by being mapped, aligned, and/or sorted, such as to produce one or more variant call files, for instance, to determine how the genetic sequence data from a subject differs from one or more reference sequences, a further aspect of the disclosure may be directed to performing one or more other analytical functions on the generated and/or processed genetic data such as for further, e.g., tertiary, processing, as depicted in FIG. 40. For example, the system may be configured for further processing of the generated and/or secondarily processed data, such as by running it through one or more tertiary processing pipelines 700, such as one or more of a micro-array analysis pipeline, a genome, e.g., whole genome analysis pipeline, genotyping analysis pipeline, exome analysis pipeline, epigenome analysis pipeline, metagenome analysis pipeline, microbiome analysis pipeline, genotyping analysis pipeline, including joint genotyping, variants analyses pipeline, including structural variants pipelines, somatic variants pipelines, and GATK and/or MuTect2 pipelines, as well as RNA sequencing pipelines and other genetic analyses pipelines.

Additionally, in various instances, an additional layer of processing 800 may be provided, such as for disease diagnostics, therapeutic treatment, and/or prophylactic prevention, such as including NIPT, NICU, Cancer, LDT, AgBio, and other such disease diagnostics, prophylaxis, and/or treatments employing the data generated by one or more of the present primary and/or secondary and/or tertiary pipelines. For example, particular bioanalytic pipelines include genome pipelines, epigenome pipelines, metagenome pipelines, genotyping pipelines, variants, e.g., GATK/MuTect2 pipelines, and other such pipelines. Hence, the devices and methods herein disclosed may be used to generate genetic sequence data, which data may then be used to generate one or more variant call files and/or other associated data that may further be subject to the execution of other tertiary processing pipelines in accordance with the devices and methods disclosed herein, such as for particular and/or general disease diagnostics as well as for prophylactic and/or therapeutic treatment and/or developmental modalities. See, for instance, FIGS. 41B, C and 43.

As described above, the methods and/or systems herein presented may include the generating and/or the otherwise acquiring of genetic sequence data. Such data may be generated or otherwise acquired from any suitable source, such as by a NGS or "sequencer on a chip technology." Once generated and/or acquired, the methods and systems herein may include subjecting the data to further processing such as by one or more secondary processing protocols 600. The secondary processing protocols may include one or more of mapping, aligning, and sorting of the generated genetic sequence data, such as to produce one or more variant call files, for example, so as to determine how the genetic sequence data from a subject differs from one or more reference sequences or genomes. A further aspect of the disclosure may be directed to performing one or more other analytical functions on the generated and/or processed genetic data, e.g., secondary result data, such as for additional processing, e.g., tertiary processing 700/800, which processing may be performed on or in association with the same chip or chipset as that hosting the aforementioned sequencer technology.

Accordingly, in a first instance, such as with respect to the generation, acquisition, and/or transmission of genetic sequence data, as set forth in FIGS. 37-41, such data may be produced either locally or remotely and/or the results thereof may then be directly processed, such as by a local computing resource 100, or may be transmitted to a remote location, such as to a remote computing resource 300, for further processing, e.g. for secondary and/or tertiary processing, see FIG. 42. For instance, the generated genetic sequence data may be processed locally, and directly, such as where the sequencing and secondary processing functionalities are housed on the same chipset and/or within the same device on-site 10. Likewise, the generated genetic sequence data may be processed locally, and indirectly, such as where the sequencing and secondary processing functionalities occur separately by distinct apparatuses that share the same facility or location but may be separated by a space albeit communicably connected, such as via a local network 10. In a further instance, the genetic sequence data may be derived remotely, such as by a remote NGS, and the resultant data may be transmitted over a cloud based network 30/50 to an off-site remote location 300, such as separated geographically from the sequencer.

Figure 40A:
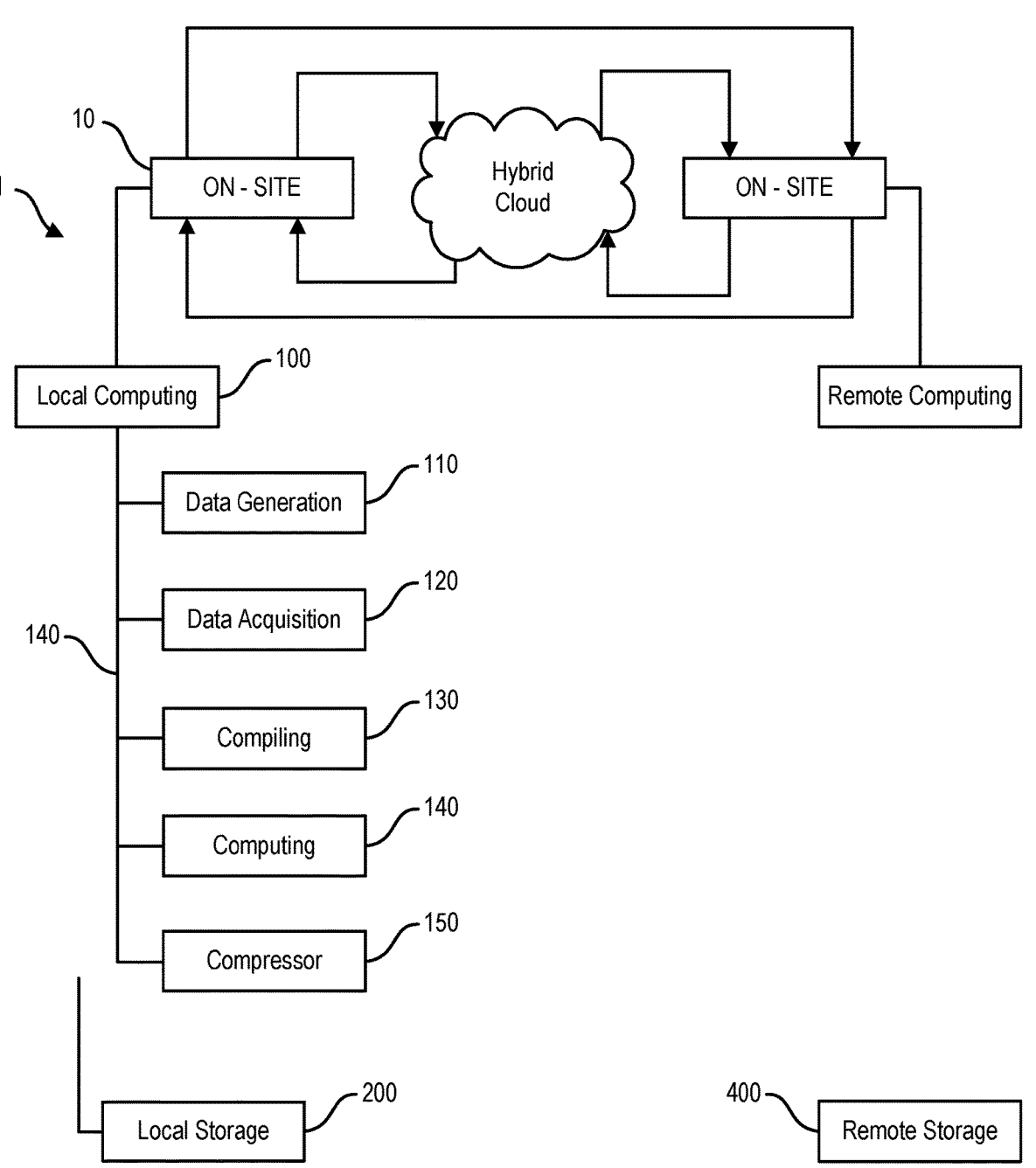
FIG. 40A depicts a block diagram for a genomic infrastructure for onsite and/or cloud based genomics processing and analysis.

Specifically, as illustrated in FIG. 40A, in various embodiments, a data generation apparatus, e.g., nucleotide sequencer 110, may be provided on site, such as where the sequencer is a "sequencer on a chip" or a NGS, wherein the sequencer is associated with a local computing resource 100 either directly or indirectly such as by a local network connection 10/30. The local computing resource 100 may include or otherwise be associated with one or more of a data generation 110 and/or a data acquisition 120 mechanism(s). Such mechanisms may be any mechanism configured for either generating and/or otherwise acquiring data, such as analog, digital, and/or electromagnetic data related to one or more genetic sequences of a subject or group of subjects, such as where the genetic sequence data is in a BCL or FASTQ file format.

For example, such a data generating mechanism 110 may be a primary processor such as a sequencer, such as a NGS, a sequencer on a chip, or other like mechanism for generating genetic sequence information. Further, such data acquisition mechanisms 120 may be any mechanism configured for receiving data, such as generated genetic sequence information; and/or together with the data generator 110 and/or computing resource 100 is capable of subjecting the same to one or more secondary processing protocols, such as a secondary processing pipeline apparatus configured for running a mapper, aligner, sorter, and/or variant caller protocol on the generated and/or acquired sequence data as herein described. In various instances, the data generating 110 and/or data acquisition 120 apparatuses may be networked together such as over a local network 10, such as for local storage 200; or may be networked together over a local and/or cloud based network 30, such as for transmitting and/or receiving data, such as digital data related to the primary and/or secondary processing of genetic sequence information, such as to or from a remote location, such as for remote processing 300 and/or storage 400. In various embodiments, one or more of these components may be communicably coupled together by a hybrid network as herein described.

The local computing resource 100 may also include or otherwise be associated with a compiler 130 and/or a processor 140, such as a compiler 130 configured for compiling the generated and/or acquired data and/or data associated therewith, and a processor 140 configured for processing the generated and/or acquired and/or compiled data and/or controlling the system 1 and its components, as herein described, such as for performing primary, secondary, and/or tertiary processing. For instance, any suitable compiler may be employed, however, in certain instances, further efficiencies may be achieved not only by implementing a tight-coupling configuration, such as discussed above, for the efficient and coherent transfer of data between system components, but may further be achieved by implementing a just-in-time (JIT) computer language compiler configuration. Further, in certain instances, the processor 140 may include a workflow management system for controlling the functioning of the various system components with respect to generated, received, and/or data to be processed through the various stages of the platform pipelines.

Specifically, as used herein just-in-time (JIT) refers to a device, system, and/or method for converting acquired and/or generated file formats from one form to another. In a broad usage structure, the JIT system disclosed herein may include a compiler 130, or other computing architecture, e.g., a processing program, that may be implemented in a manner so as to convert various code from one form into another. For instance, in one implementation, a JIT compiler may function to convert bytecode, or other program code that contains instructions that must be interpreted, into instructions that can be sent directly to an associated processor 140 for near immediate execution, such as without the need for interpretation of the instructions by the particular machine language. Particularly, after a coding program, e.g., a Java program, has been written, the source language statements may be compiled by the compiler, e.g., Java compiler, into bytecode, rather than compiled into code that contains instructions that match any given particular hardware platform's processing language. This bytecode compiling action, therefore, is platform-independent code that can be sent to any platform and run on that platform regardless of its underlying processor. Hence, a suitable compiler may be a compiler that is configured so as to compile the bytecode into platform-specific executable code that may then be executed immediately. In this instance, the JIT compiler may function to immediately convert one file format into another, such as "on the fly".

Hence, a suitably configured compiler, as herein described, is capable of overcoming various deficiencies in the art. Specifically, past compiling programs that were written in a specific language had to be recompiled and/or re-written dependent on each specific computer platform on which it was to be implemented. In the present compiling system, the compiler may be configured so as to only have to write and compile a program once, and once written in a particular form, may be converted into one or more other forms nearly immediately. More specifically, the compiler 130 may be a JIT, or in another similar dynamic translation compiler format, which is capable of writing instructions in a platform agnostic language that does not have to be recompiled and/or re-written dependent on the specific computer platform on which it is implemented. For instance, in a particular use model, the compiler may be configured for interpreting compiled bytecode, and/or other coded instructions, into instructions that are understandable by a given particular processor for the conversion of one file format into another, regardless of computing platform. Principally, the JIT system herein is capable of receiving one genetic file, such as representing a genetic code, for example, where the file is a BCL or FASTQ file, e.g., generated from a genetic sequencer, and rapidly converting it into another form, such as into a SAM, BAM, and/or CRAM file, such as by using the methods disclosed herein.

Particularly, in various instances, the system herein disclosed may include a first and/or a second compiler 130_a_ and 130_b_, such as a virtual compiling machine, that handles one or a plurality of bytecode instruction conversions at a time.

For instance, using a Java type just-in-time compiler, or other suitably configured second compiler, within the present system platform, will allow for the compiling of instructions into bytecode that may then be converted into the particular system code, e.g., as though the program had been compiled initially on that platform. Accordingly, once the code has been compiled and/or (re-)compiled, such as by the JIT compiler(s) 130, it will run more quickly in the computer processor 140. Hence, in various embodiments, just-in-time (JIT) compilation, or other dynamic translation compilation, may be configured so as to be performed during execution of a given program, e.g., at run time, rather than prior to execution. In such an instance, this may include the step(s) of translation to machine code or translation into another format, which may then be executed directly, thereby allowing for one or more of ahead-of-time compilation (AOT) and/or interpretation.

More particularly, as implemented within the present system, a typical genome sequencing dataflow generally produces data in one or more file formats, derived from one or more computing platforms, such as in a BCL, FASTQ, SAM, BAM, CRAM, and/or VCF file format, or their equivalents. For instance, a typical DNA sequencer 110, e.g., an NGS, produces raw signals representing called bases that are designated herein as reads, such as in a BCL and/or FASTQ file, which may optionally be further processed, e.g., enhanced image processing, and/or compressed 150. Likewise, the reads of the generated BCL/FASTQ files may then be further processed within the system, as herein described, so as to produce mapping and/or alignment data, which produced data, e.g., of the mapped and aligned reads, may be in a SAM or BAM file format, or alternatively a CRAM file format. Further, the SAM or BAM file may then be processed, such as through a variant calling procedure, so as to produce a variant call file, such as a VCF file or gVCF file. Accordingly, all of these produced BCL, FASTQ, SAM, BAM, CRAM, and/or VCF files, once produced are (extremely) large files that all need to be stored such as in system memory architecture locally 200 or remotely 400. The storage of any one of these files is expensive. The storage of all of these file formats is extremely expensive.

As indicated, just-in-time (JIT) or other dual compiling or dynamic translation compilation analysis, may be configured and deployed herein so as to reduce such high storage costs. For instance, a JIT analysis scheme may be implemented herein so as to store data in only one format (e.g., a compressed FASTQ or BAM, etc., file format), while providing access to one or more file formats (e.g., BCL, FASTQ, SAM, BAM, CRAM, and/or VCF, etc.). This rapid file conversion process may be effectuated by rapidly processing the genomic data utilizing the herein disclosed respective hardware and/or quantum acceleration platforms, e.g., such as for mapping, aligning, sorting, and/or variant calling (or component functions thereof, such as de-duplicating, HMM and Smith-Waterman, compression and decompression, and the like), in hardware engines on an integrated circuit, such as an FPGA, or by a quantum processor. Hence, by implementing JIT or similar analysis along with such acceleration, the genomic data can be processed in a manner so as to generate desired file formats on the fly, at speeds comparable to normal file access. Thus, considerable storage savings may be realized by JIT-like processing with little or no loss of access speed.

Particularly, two general options are useful for the underlying storage of the genomic data produced herein so as to be accessible for JIT-like processing, these include the storage of unaligned reads (e.g., that may include compressed FASTQ, or unaligned compressed SAM, BAM, or CRAM files), and the storage of aligned reads (e.g., that may include compressed BAM or CRAM files). However, since the accelerated processing disclosed herein allows any of the referenced file formats to be derived rapidly, e.g., on the fly, the underlying file format for storage may be selected so as to achieve the smallest compressed file size, thereby decreasing the expense of storage. Hence, because of the comparatively smaller file size for unprocessed, e.g., raw un-aligned, read data, there is an advantage to storing unaligned reads so that the data fields are minimized. Likewise, there is an advantage to storing the processed and compressed data, such as in a CRAM file format.

More particularly, in view of the rapid processing speeds achievable by the devices, systems, and methods of their use disclosed herein, in many instances, there may be no need to store mapped and/or alignment information for each and every read, because this information may be rapidly derived upon need, such as on the fly. Further, although a compressed FASTQ (e.g. FASTQ.gz) file format is commonly used for storage of genetic sequence data, such unaligned read data may be stored in more advanced compressed formats as well, such as post mapping and/or aligning in SAM, BAM, or CRAM files, which may further reduce the file size, such as by use of compact binary representation and/or more targeted compression methods. Hence, these file formats may be compressed prior to storage, be decompressed after storage, and processed rapidly, such as on the fly, so as to convert one file format from another.

An advantage to storing aligned reads is that much or all of each read's sequence content can be omitted. Specifically, system efficiency can be enhanced and storage space saved by only storing the differences between the read sequences and the selected reference genome, such as at indicated variant alignment positions of the read. More specifically, since differences from the reference are usually sparse, the aligned position and list of differences can often be more compactly stored than the original read sequence. Therefore, in various instances, the storage of an aligned read format, e.g., when storing data related to the differences of aligned reads, may be preferable to the storage of unaligned read data. In such an instance, if an aligned read and/or variant call format is used as the underlying storage format, such as in a JIT procedure, other formats, such as a SAM, BAM, and/or CRAM, compressed file formats, may also be used.

Along with the aligned and/or unaligned read file data to be stored, a wide variety of other data, such as metadata derived from the various computations determined herein, may also be stored. Such computated data may include read mapped, alignment and/or subsequent processing data, such as alignment scores, mapping confidence, edit distance from the reference, etc. In certain instances, such metadata and/or other extra information need not be retained in the underlying storage for JIT analysis, such as in those instances where it can be reproduced on the fly, such as by the accelerated data processing herein described.

With respect to metadata, this data may be a small file that instructs the system as to how to go backwards or forwards from one file format into conversion to another file format. Hence, the metadata file allows the system to create a bit-compatible version of any other file type. For instance, proceeding forward from an originating data file, the system need only access and implement the instructions of the metadata. Along with rapid file format conversion, JIT also enables rapid compression and/or decompression and/or storage, such as in a genomics dropbox memory cache.

As discussed in greater detail below, once sequence data is generated 110, it may be stored locally 200, and/or may be made accessible for storage remotely, such as in a cloud accessible dropbox-like memory cache 400. For example, once in the genomic dropbox, the data may appear as accessible on the cloud 50, and may then be further processed, e.g., substantially immediately. This is particularly useful when there is a plurality of mapping/aligning/sorting/variant calling systems 100/300, such as with one on either side of the cloud 50 interface facilitating the automatic uploading and processing of the data, which can be further processed such as using the JIT technology herein described.

For instance, an underlying storage format for JIT compiling and/or processing may contain only minimal data fields, such as read name, base quality scores, alignment position, and/or orientation in the reference, and a list of differences from the reference, such as where each field may be compressed in an optimal manner for its data type. Various other metadata may be included and/or otherwise associated with the storage file. In such an instance, the underlying storage for JIT analysis may be in a local file system 200, such as on hard disk drives and solid state drives, or a network storage resource such as a NAS or object or Dropbox like storage system 400. Particularly, when various file formats, such as BCL, FASTQ, SAM, BAM, CRAM, VCF, etc., have been produced for a genomic dataset, which may be submitted for JIT processing and/or storage, the JIT or other similar compiling and/or analysis system may be configured so as to convert the data to a single underlying storage format for storage. Additional data, such as metadata and/or other information (which may be small) necessary to reproduce all other desired formats by accelerated genomic data processing, may also be associated with the file and stored. Such additional information may include one or more of: a list of file formats to be reproduced, data processing commands to reproduce each format, unique ID (e.g., URL or MD5/SHA hash) of reference genome, various parameter settings, such as for mapping, alignment, sorting, variant calling, and/or any other processing, as described herein, randomization seeds for processing steps, e.g., utilizing pseudo-randomization, to deterministically reproduce the same results, user Interface, and the like.

In various instances, the data to be stored and/or retrieved in a JIT or similar dynamic translation processing and/or analysis system may be presented to the user, or other applications, in a variety of manners. For instance, one option is to have the JIT analysis storage in a standard or custom "JIT object" file format, such as for storage and/or retrieval as a SAM, BAM, CRAM, or other custom file format, and provide user tools to rapidly convert the JIT object into the desired format (e.g., in a local temporary storage 200) using the accelerated processing disclosed herein. Another option is to present the appearance of multiple file formats, such as BCL, FASTQ, SAM, BAM, CRAM, VCF, etc. to the user, and the user applications, in such a manner that the file system access to various file formats utilizes a JIT procedure, thus only one file type needs be saved, and from these file type, all other files can be generated on the fly. A further option is to make user tools that otherwise accept specific file formats (BCL, FASTQ, SAM, BAM, CRAM, VCF, etc.) that are able to be presented as a JIT object instead, and may automatically call for JIT analysis to obtain the data in the desired data format, e.g., BCL, FASTQ, SAM, BAM, CRAM, VCF, etc. automatically when called.

Accordingly, JIT procedures are useful for providing access to multiple file formats, e.g., BCL, FASTQ, SAM, BAM, CRAM, VCF, and the like, from a single file format by rapidly processing the underlying stored compressed file format. Additionally, JIT remains useful even if only a single file format is to be accessed, because compression is still achieved relative to storing the accessed format directly. In such an instance, the underlying file storage format may be different than the accessed file format, and/or may contain less metadata, and/or may be compressed more efficiently than the accessed format. Further, in such an instance, as discussed above, the file is compressed prior to storage, and decompressed upon retrieval, e.g., automatically.

In various instances, the methods of JIT analysis, as provided herein, may also be used for transmission of genomic data, over the internet or another network, to minimize transmission time and lessen consumed network bandwidth. Particularly, in one storage application, a single compressed underlying file format may be stored, and/or one or more formats may be accessed via decompression and/or accelerated genomic data processing. Similarly, in the transmission application, only a single compressed underlying file format need be transmitted, e.g., from a source network node to a destination network node, such as where the underlying format may be chosen primarily for smallest compressed file size, and/or where all desired file formats may be generated at the destination node by or for genomic data processing, such as on the fly. In this manner, only one compressed data file format need be used for storage and/or transfer, from which file format the other various file formats may be derived.

Accordingly, in view of FIG. 40A, hardware and/or quantum accelerated genomic data processing, as herein described, may be utilized in (or by) both the source network node, to generate and/or compress the underlying format for transmission, and the destination network node, to decompress and/or generate other desired file formats by accelerated genomic data processing. Nevertheless, JIT or other dynamic translation analysis continues to be useful in the transmission application even if only one of the source node or the destination node utilizes hardware and/or quantum accelerated genomic data processing. For example, a data server that sends large amounts of genomic data may utilize hardware and/or quantum accelerated genomic data processing so as to generate the compressed underlying format for transmission to various destinations. In such instances, each destination may use slower software genomic data processing to generate other desired data formats. Hence, although the speed advantage of JIT analysis is lessened at the destination node, transmission time, and network utilization are still usefully reduced, and the source node is able to service many such transmissions efficiently due to its corresponding hardware and/or quantum accelerated genomic data processing apparatus.

Further, in another example, a data server that receives uploads of large amounts of genomic data, e.g., from various sources, may utilize hardware and/or quantum accelerated genomic data processing and/or storage, while the various source nodes may use slower software run on a CPU/GPU to generate the compressed underlying file format for transmission. Alternatively, hardware and/or quantum accelerated genomic data processing may be utilized by one or more intermediate network nodes, such as a gateway server, between the source and destination nodes, to transmit and/or receive genomic data in a compressed underlying file format, according to the JIT or other dynamic translation analysis methods, thus gaining the benefits of reduced transmission time and network utilization without overburdening the said intermediate network nodes with excessive software processing.

Hence, as can be seen with respect to FIG. 40A, in certain instances, the local computing resource 100 may include a compiler 130, such as a JIT compiler, and may further include a compressor unit 150 that is configured for compressing data, such as generated and/or acquired primary and/or secondary processed data (or tertiary data), which data may be compressed, such as prior to transfer over a local 10 and/or cloud 30 and/or hybrid cloud based 50 network, such as in a JIT analysis procedure, and which may be decompressed subsequent to transfer and/or prior to use.

As described above, in various instances, the system may include a first integrated and/or quantum circuit 100 such as for performing a mapping, aligning, sorting, and/or variant calling operation, so as to generate one or more of mapped, aligned, sorted, de-duplicated, and/or variant called results data. Additionally, the system may include a further integrated and/or quantum circuit 300 such as for employing the results data in the performance of one or more genomics and/or bioinformatics pipeline analyses, such as for tertiary processing. For instance, the result data generated by the first integrated and/or quantum circuit 100 may be used, e.g., by the first or a second integrated and/or quantum circuit 300, in the performance of a further genomics and/or bioinformatics pipeline processing procedure. Specifically, secondary processing of genomics data may be performed by a first hardware and/or quantum accelerated processor 100 so as to produce results data, and tertiary processing may be performed on that results data, such as where the further processing is performed by a CPU and/or GPU and/or QPU 300 that is operatively coupled to the first integrated circuit. In such an instance, the second circuit 300 may be configured for performing tertiary processing of the genomics variation data produced by the first circuit 100. Accordingly, the results data derived from the first integrated server acts as an analysis engine driving the further processing steps described herein with reference to tertiary processing, such as by the second integrated and/or quantum processing circuit 300.

However, the data generated in each of these primary and/or secondary and/or tertiary process steps may be immense, requiring very high resource and/or memory costs such as for storage, either locally 200 or remotely 400. For instance, in a first primary processing step, generated nucleic acid sequence data 110, such as in a BCL and/or FASTQ file format, may be received 120, such as from an NGS 110. Regardless of the file format of this sequence data, the data may be employed in a secondary processing protocol as described herein. The ability to receive and process primary sequence data directly from an NGS, such as in a BCL and/or FASTQ file format, is very useful. Particularly, instead of converting the sequence data file from the NGS, e.g., BCL, to a FASTQ file, the file may be directly received from the NGS, e.g., as a BCL file, and may be processed, such as by being received and converted by the JIT system, e.g., on the fly, into a FASTQ file that may then be processed, as described herein, such as to produce a mapped, aligned, sorted, deduped, and/or variant called results data that may then be compressed, such as into a SAM, BAM, and/or CRAM file, and/or may be subjected to further processing, such as by one or more of the disclosed genomics tertiary processing pipelines.

Accordingly, such data once produced needs to be stored in some manner. However, such storage is not only resource intensive, it is also costly. Specifically, in a typical genomics protocol, the sequenced data once generated is stored as a large FASTQ file. Then, once processed such as by being subjected to a mapping and/or aligning protocol, a BAM file is created, which file is also typically stored, increasing the expense of genomic data storage, such as by having to store both a FASTQ and a BAM file. Further, once the BAM file is processed, such as by being subjected to variant calling protocol, a VCF file is produced, which VCF also typically needs to be stored. In such an instance, in order to adequately provide and make use of the generated genetic data, all three of the FASTQ, BAM, and VCF files may need to be stored, either locally 200 or remotely 400. Additionally, the original BCL file may also be stored. Such storage is inefficient as well as being memory resource intensive and expensive.

However, the computational power of the hardware and/or quantum processing architectures implemented herein, along with the JIT compilation, compression, and storage, greatly ameliorates these inefficiencies, resource costs, and expenses. For instance, in view of the methods implemented and the processing speeds achieved by the present accelerated integrated circuits, such as for the conversion of a BCL file to a FASTQ file, and then the conversion of a FASTQ file to a SAM or BAM file, and then the conversion of a BAM file to a CRAM and/or VCF file, and back again, the present system greatly reduces the number of computing resources and/or file sizes needed for the efficient processing and/or storage of such data. The benefits of these systems and methods are further enhanced by the fact that only one file format, e.g., a BCL, FASTQ, SAM, BAM, CRAM, and/or VCF, need be stored, from which all the other file formats may be derived and processed. Particularly, only one file format needs to be saved and from such file any of the other file formats may be generated rapidly, e.g., on the fly, in accordance with the methods disclosed herein, such as in a just in time, or JIT, compiling format.

For example, in accordance with typical prior methods, a large amount of computing resources, e.g., server farms and large memory banks, is needed for the processing and storage of FASTQ files being generated by a NGS sequencer. Particularly, in a typical instance, once the NGS produces the large FASTQ file, the server farm would then be employed to receive and convert the FASTQ file to a BAM and/or CRAM file, which processing may take up to a day or more. However, once produced, the BAM file itself must then be stored, requiring further time and resources. Likewise, the BAM or CRAM file may be processed in such a manner to generate a VCF, which may also take up another day or more, and which file will also need to be stored, thereby incurring further resource costs and expenses. More particularly, in a typical instance, the FASTQ file for a human genome consumes about 90 GB of storage, per file. Likewise, a typical human genome BAM file may consume about 160 GB. The VCF file may also need to be stored, albeit such files are quite smaller than the FASTQ and/or BAM files. SAM and CRAM files may also be generated throughout the secondary processing procedures, and these too may need to be stored.

Prior to the technologies provided herein, it has been computationally intensive to go from one step to another, e.g., from one file format to another, and hence, all of the data for these file formats would typically have to be stored. This is in part due to the fact that if a user ever wanted to go back and regenerate one or more of the files, it would require a large amount of computing resources and time to re-do the processes involved in regenerate the various files thereby incurring a high monetary expense. Further, where these files are compressed before storage, such compression may take from about 2 to about 5 to about 10 or more hours, with about the same amount of time required for decompression, prior to reuse. Because of these high expenses, typical users would not compress such files prior to storage, and would also typically store all two, three or more file formats, e.g., BCL, FASTQ, BAM, VCF, incurring increased costs over increased time.

Accordingly, the JIT protocols employed herein make use of the accelerated processing speeds achieved by the present hardware and/or quantum accelerators, so as to realize enhanced efficiency, at reduced time and costs both for processing as well as for storage. Instead of storing 2, 3, or more copies of the same general data in different file formats, only one file format needs to be stored, and on the fly, any of the other file types can be regenerated, such as using the accelerated processing platforms discussed herein. Particularly, from storing a FASTQ file, the present devices and systems make it easy to go backwards to a BCL file, or forwards to a BAM file, and then further to a VCF, such as in under 30 minutes, such as within 20 minutes, or about within 15 or 10 minutes, or less.

Hence, using the pipelines and the speed of processing offered by the hardwired/quantum processing engines herein disclosed, only a single file format need be stored, while the other file formats may easily and rapidly be generated therefrom. So instead of needing to store all three file formats, a single file format need be stored from which any other file format may be regenerated such as on the fly, just in time for the further processing steps desired by the user. Consequently, the system may be configured for ease of use such that if a user simply interacts with a graphical user interface, such as presented at an associated display of the device, e.g., the user clicks on the FASTQ, BAM, VCF, etc. button presented in the GUI, the desired file format may be presented, while in the background, one or more of the processing engines of the system may be performing the accelerated processing steps necessary for regenerating the requested file in the requested file format from the stored file.

Typically, one or more of a compressed version of a BCL, FASTQ, SAM, BAM, CRAM, and/or VCF file will be saved, along with a small metafile that includes all of the configurations of how the system was run to create the compressed and/or stored file. Such metafile data details how the particular file format, e.g., FASTQ and/or BAM file, was generated and/or what steps would be necessary for going backwards or forwards so as to generate any of the other file formats. This process is described in greater detail herein below. In a manner such as this the process can proceed forwards or be reversed going backwards using the configuration stored in the metafile. This can be about an 80% or more reduction in storage and economic cost if the computing function is bundled with the storage functions.

Accordingly, in view of the above and as can be seen with respect to FIG. 40A, a cloud based server system for data analytics and storage is provided. For instance, using a cloud accessible server system, as disclosed herein, a user may connect with a storage device, such as for the storage of input data. For example, a remote user may access the system so as to input genomics and/or bioinformatics data into the system, such as for storage and/or the processing thereof. Particularly, a remote user of the system, e.g., using local computing resource 100, may access the system 1 so as to upload genomic data, e.g., such as one or more sequenced genomes of one or more individuals. As described in detail below, the system may include a user interface, e.g., accessing a suitably configured API, which will allow a user to access the BioIT platform so as to upload data to be processed, control the parameters of the processing, and/or download output, e.g., results data, from the platform.

Specifically, the system may include an API, e.g., an S3 or "S3-like" object that allows access to one or more memories of the system, for the storage 400 and/or receipt of stored files. For instance, a cloud accessible API object may be present, such as where the API is configurable so as to store data files in the cloud 50, such as into one or more storage buckets 500, e.g., an S3 bucket. Accordingly, the system may be configured so as to allow a user to have access to remotely stored files, e.g., via an S3 or S3-like API, such as by accessing the API via a cloud based interface on a personal computing device.

Such an API therefore may be configured for allowing access to the cloud 50 to thereby connect the user with one or more of the cloud based servers 300 disclosed herein, such as to upload and/or download a given stored file, e.g., so as to make files accessible between the cloud server 300 and the local hard drive 100. This may be useful, for instance, to allow a remote user to provide, access data, and/or download data, on or from the server 300, and further to run one or more applications and/or calculations on that data, either locally 100 or on the server 300, and then to call the API to send the transformed data back to or from the cloud 50, e.g., for storage 200 and/or further processing. This is specifically useful for the retrieval, analyses, and storage of genomics data.

However, typical cloud based storage of data, e.g., "S3" storage, is expensive. This expense is increased when storing the large amounts of data associated with the fields of genomics and bioinformatics, where such costs often become prohibitive. Additionally, the time required to record, upload, and/or download the data for use, e.g., either locally 100 or remotely 300, and/or for storage 400 also makes such expensive cloud based storage solutions less attractive. The present solutions disclosed herein overcome these and other such needs.

Particularly, instead of going through a typical "S3" or other typical cloud based object API, presented herein, is an alternative S3-compatible API, which may be implemented so as to reduce the speed of transmission and/or the cost of storage of data. In such an instance, when a user wants to store a file, instead of going through a typical cloud based, e.g., S3, API, the alternative service API system, e.g., the proprietary S3 compatible API disclosed herein, will launch a compute instance, e.g., a CPU and/or FPGA instance of the system, which will function to compress the file, will generate a metadata index with respect to indicating what the data is and/or how the file was generated, etc., and will then store the compressed file via an S3 Compatible storage-like bucket 400. Accordingly, presented herein is a cloud-based 50 service that employs a compute instance 300, which may be launched by an alternative API, so as to compresses data before storage 400, and/or decompress data upon retrieval. In such an instance, what is stored, therefore, is not the actual file, but rather what is stored is a compressed version of the original file.

Specifically, in such instance, the initial file may be in a first format, which may be loaded into the system via the proprietary S3 compatible API, which receives the file, e.g., an F1 file, and may then perform a compute function on the file, and/or then compresses the file, such as via a suitably configured CPU/GPU/QPU/FPGA processing engine 300, which then prepares the compressed file for storage, as a compressed, e.g., a compressed F1 file. However, when the compressed and stored file needs to be retrieved, it may then be decompressed, which decompressed file may then be returned to the user. The advantage of this accelerated compression and decompression system is that the storage 400 of the compressed file means an incredible savings in storage costs, which advantage is made possible by the computing and/or compressing functionalities achieved by the systems disclosed herein.

Hence, because of the rapid and efficient computing and/or compressing functionalities achieved by the present systems, the user need not even know that the file is being compressed before storage, and subsequently decompressed post storage and presented at the user's interface. Particularly, the system functions so rapidly and efficiently that the user need not be aware of the multiplicity of compression, computation, and/or decompression steps that take place when storing and/or retrieving the requested data, to the user, this all appears seamless and timely. However, the fact that the present storage system will cost less and be more efficient than previous storage systems will be apparent.

Accordingly, in view of the above, object-based storage services are provided herein, wherein the storage services can be offered at lower costs, by combining a compute and/or compress instance along with a storage functionality. In such an instance, the typical storage costs can be substituted for computing costs, which are offered at a much lower level, because, as set forth herein, the computing costs may be implemented in an accelerated fashion such as by an FPGA and/or quantum computing platform 300, as described herein. Hence, the accelerated platforms disclosed herein can be configured as a rapid and efficient storage and retrieval system that allows for the rapid compressed storage of data that may be both compressed and stored as well as rapidly decompressed and retrieved at much lower costs and with greater efficiency and speed. This is particularly useful with respect to genomics data storage 400, and is compatible with the Just In Time processing functionalities disclosed herein, above. Therefore, in accordance with the devices, systems, and methods disclosed herein is an object storage service that may be provided, wherein the storage service implements a rapid compression functionality, such as genomics specific compression so as to store genomics processing results data.

More particularly, as can be seen with respect to FIG. 40A, in one exemplary implementation, the BioIT systems provided herein may be configured such that a pipeline server system 300, e.g., a portion thereof, receives the request at the API, e.g., S3 compatible API, which is operably connected to a database 400 that is adapted for associating the initial (F1) file with the compressed version of the (CF1) file, e.g., based on the coupled metadata. Likewise, once the original CF1 files are decompressed and processed, the resulting results data (F2) files may then be compressed and stored as a CF2 file. Accordingly, when retrieval of the file is desired from the database 400, the server 300 has an API that has already associated the original file with the compressed file via appropriately configured metadata, hence, when retrieval is requested, a work flow management controller (WMS) of the system will launch the compute instance 300, which will launch the appropriate compute instance so as to perform any necessary computations and/or decompress the file for further processing, transmission, and/or presentation to the requesting user 100.

Hence, in various embodiments, an exemplary method may include one or more steps, in any logical order: 1) The request comes in through the API, e.g., S3 compatible API, 2) API communicates with the WMS, 3) the WMS populates the database and initiates the compute instance(s), 4) the compute instance(s) performs the requisite compression on the F1 file, and generates the characteristic metadata and/or other relevant file associations (X), e.g., to produce a CF1 X1 file, 4) thereby preparing the data for storage 400. This process may then be repeated for F2, F3, Fn files, e.g., other processed information, so that the WMS knows how the compressed file was generated, as well as where and how it was stored. It is to be noted that a unique feature of this system is that several different users 100 may be allowed to access the stored data 400 substantially simultaneously. For instance, the compression systems and methods disclosed herein are useful in conjunction with the BioT platforms disclosed herein, whereby at any time during the processing process the results data may be compressed and stored in accordance with the methods herein, and accessible to others, with the right permissions.

With respect to performing genomic analysis, a user 100 may access the system 300 herein, e.g., via a genomic analysis API such as an S3 or S3 compatible API, upload genomic data, such as in a BCL and/or FASTQ file or other file format, and thereby request the performance of one or genomics operations, such as a mapping, aligning, sorting, de-duplicating, variant calling, and/or other operations. The system 300 receives the request at a workflow manager API, the workflow manager system then assesses the incoming requests, indexes the jobs, forms a queue, allocates the resources, e.g., instance allocation, and generates the pipeline flow. Accordingly, when a request comes in and is preprocessed and queued, an instance allocator, e.g., API, will then spin up the various job specific instances, described in greater detail herein below, in accordance with the work projects. Hence, once the jobs are indexed, queued, and/or stored in an appropriate database 400, the workflow manager will then pull the data from storage 400, e.g., S3 or S3 compatible storage, cycle up an appropriate instance, which retrieves the file, and runs the appropriate processes on the data to perform one or more of the requested jobs.

Additionally, where a plurality of jobs are requested to be performed on the data, requiring the performance of a plurality of instances, then once the first instance has performed its operations, the results data may be compressed and stored, such as in an appropriate memory instance, e.g., a first data base, such as an elastic or flexible storage device, so as to wait while the further pipeline instance(s) is spun up and retrieves the results data for further processing, such as in accordance with the systems and methods disclosed herein above. Further, as new requests come in and/or current jobs are being run, the workflow management system will constantly be updating the queue so as to allocate jobs to the appropriate instances, via an instance allocator API, so as to keep the data flowing through the system and the processes of the system running efficiently.

Likewise, the system 300 may constantly be taking the results data and storing the data 200/400, e.g., in a first or a second database, prior to further processing and/or transmission, such as transmission back to the original requestor 100 or a designated party. In certain instances, the results data may be compressed, as disclosed herein, prior to storage 400 and/or transmission. Further, as indicated above, the generated results data files when compressed may include appropriate meta data and/or other associated data, where in the results data may designated differently as it flows through the system, such as going from an F1 file to an F1C file to an F2 file, to an F2C, file, and so on, as the data is processed and moves through the platform pipeline e.g., as directed by a file associations API.

Accordingly, because of the proprietary dedicated APIs, as disclosed herein, the system may have a common backbone to which other services may be coupled and/or additional resources, e.g., instances, may be brought online so as to make sure all of the pipeline operations run smoothly and efficiently. Likewise, when desired the compressed and stored results data files may be called, whereby the workflow manager will spin up the appropriate compute and/or decompress database instance to decompress the results data for presentation to the requester. It is noted that in various instances, the specified compute and compress instance, as well as the specified compute and decompress instance, may be a single or multiple instances, and may be implemented as a CPU, FPGA, or a tightly coupled CPU/FPGA, tightly coupled CPU/CPU, or tightly coupled FPGA/FPGA. In certain instances, one or more of these and the other instances disclosed herein may be implemented as a quantum processing unit.

Accordingly, in view of the disclosures herein, in one aspect, a device for performing one or more of a multiplicity of functions in performing genomics sequence analysis operations is provided. For instance, once the data has been received, e.g., by a remote user 100, and/or stored 400 within the cloud based system, the input data may be accessed by the WMS, and may be prepared for further processing, e.g., for secondary analysis, the results thereof may then be transmitted back to the local user 100, e.g., after being compressed, stored 400, and/or subjected to additional processing, e.g., tertiary processing by the system server 300.

In certain instances, the secondary processing steps disclosed herein, in particular implementations, may be performed by a local computing resource 100, and may be implemented by software and/or hardware, such as by being executed by a box-top computing resource 200, where the computing resource 200 includes a core of CPUs, such as from about 4 to about 14 to about 24 or more CPU cores, and may further include one or more FPGAs. The local box-top computing resource 100 may be configured to access a large storage block 200, such as 120 GBs of RAM memory, which access may be directly, such as by being directly coupled therewith, or indirectly, such as by being communicably coupled therewith over a local cloud based network 30.

Specifically, within a local system, data may be transmitted to or from the memory 200 via suitably configured SSD drives that are adapted for writing processing jobs data to, e.g., genomics jobs to be processed, and reading processed results data from the memory 200. In various embodiments, the local computing resource 100 may be communicably coupled to a sequencer 110 from where a BCL and/or FASTQ file may be obtained e.g., from the sequencer, and written to the SSD drivers, directly such as through a suitably configured interconnect. The local computing resource 100 may then perform one or more secondary processing operations on the data. For instance, in one embodiment, the local computing resource is a LINUX® server having 24 CPUs, which CPUs may be coupled to a suitably configurable FPGA that is adapted for performing one or more of the secondary processing operations disclosed herein.

Hence, in particular instances, the local computing device 100 may be a "work bench" computing solution having a BioIT chip set that is configured for performing one or more of secondary and/or tertiary processing on genetics data. For instance, as disclosed herein, the computing resource 100 may be associated with a PCIe card that is inserted into the computing device so as to thereby be associated with the one or more internal CPUs, GPUs, QPU cores and/or associated memories. Particularly, the components of the computing device 100 including the processing units, associated memories, and/or associated PCIe card(s), having one or more FPGA/ASIC chipsets therein, may be in communication with one another, all of which may be provided within a housing, such as in a box set manner that is typical within the art. More particularly, the box set may be configured for work-bench use, or in various instances, it may be configured and provided and/or usable within a remotely accessible server rack. In other embodiments, the CPU/FPGA/Memory chip sets and/or associated interconnect express card(s) can be associated within a Next Gen sequencing device so as to form one unit there with.

Accordingly, in one particular instance, a desktop box set may include a plurality of CPUs/GPUs/QPUs coupled to one or more FPGAs, such as 4 CPUs/GPUs, or 8, or 12, 16, 20, 22, or 24 CPUs, or more, which may be coupled to 1, or 2, or 3, or more FPGAs, such as within a single housing. Specifically, in one particular instance, a box set computing resource is provided wherein the computing resource includes 24 CPU cores, a reconfigurable FPGA, a database, e.g., 128×8 RAM, one or more SSDs, such as where the FPGA is adapted to be at least partially reconfigurable between operations, such as between performing mapping and aligning. Hence, in such an instance, BCL and/or FASTQ files generated by the sequencing apparatus 110 may be read into the CPU and/or transferred into the FPGA, for processing, and the results data thereof may be read back to the associated CPU via the SSD drives. Consequently, in this embodiment, the local computing system 100 may be configured to offload various high-compute functionalities to an associated FPGA, thereby enhancing speed, accuracy, and efficiency of bioinformatics processing. However, although a desktop box set solution 100 is useful, e.g., at a local facility, it may not be suitable for being accessed by a plurality of users that may be located remotely from the box set.

Particularly, in various instances, a cloud-based server solution 50 may be provided, such as where the server 300 may be accessible remotely. Accordingly, in particular instances, one or more of the integrated circuits (CPU, FPGA, QPU) disclosed herein may be provided and configured for being accessed via a cloud 50 based interface. Hence, in particular instances, a work bench box set computing resource, as described above, may be provided where the box set configuration is adapted so as to be portable to the cloud and accessible remotely. However, such a configuration may not be sufficient for handling a large of amount of traffic from remote users. Accordingly, in other cases, one or more of the integrated circuits disclosed herein may be configured as a server based solution 300 configurable as part of a server rack, such as where the server accessible system is configured specifically for being accessed remotely, such as via the cloud 50.

For instance, in one embodiment, a computing resource, or local server 100, having one or more, e.g., a multiplicity, of CPU and/or GPU and/or QPU cores, and associated memories, may be provided in conjunction with one or more of the FPGAs/ASICs disclosed herein. Particularly, as indicated above, in one implementation, a desktop box set may be provided, wherein the box set includes an 18 to 20 to 24 or more CPU/GPU core box set having SSDs, 128×8 RAM, and one or more BioIT FPGA/ASIC circuits, and further includes a suitably configured communications module having transmitters, receivers, antennae, as well as WIFI, Bluetooth, and/or cellular communications capabilities that are adapted in a manner so as to allow the box set to be accessible remotely. In this implementation, such as where a single FPGA is provided, the FPGA(s) may be adapted for being reconfigured, such as partially reconfigured, between one or more of the various steps of the genomics analysis pipeline.

However, in other instances, a server system is provided and may include up to about 20 to 24 to 30 to 34 to 36 or more CPU/GPU cores and about 972 GB of RAM, or more, which may be associated with one or more, such as about two or four or about six or about eight or more FPGAs, which FPGAs may be configurable as herein described. For instance, in one implementation, the one or more FPGAs may be adapted for being reconfigured, such as partially reconfigured, between one or more of the various steps of the genomics analysis pipeline. However, in various other implementations, a set of dedicated FPGAs may be provided, such as where each FPGA is dedicated for performing a specific BioIT operation, such as mapping, aligning, variant calling, etc., thereby obviating the reconfiguration step.

Accordingly, in various instances, one or more FPGAs may be provided, such as where the FPGA(s) are adapted so as to be reconfigurable between various pipeline operations. However, in other instances, one or more of the FPGAs may be configured so as to be dedicated to performing one or more functions without the need to be partially or fully configured. For instance, the FPGAs provided herein may be configured so as to be dedicated to performing one or more computationally intensive operations in the BioIT pipeline, such as where one FPGA is provided and dedicated to performing a mapping operation, and another FPGA is provided and configured for performing an alignment operation, although, in some instances, a single FPGA may be provided and configured for being at least partially reconfigured between performing both a mapping and an alignment operation.

Additionally, other operations in the pipeline that may also be performed by reconfigurable or dedicated FPGAs may include performing a BCL conversion/transposition operation, a Smith-Waterman operation, an HMM operation, a local realignment operation, and/or various other variant calling operations. Likewise, various of the pipeline operations may be configured for being performed by one or more of the associated CPUs/GPUs/QPUs of the system. Such operations may be one or more less computationally intensive operations of the pipeline, such as for preforming a sorting, deduplication, and other variant calling operations. Hence, the overarching system may be configured for performing a combination of operations part by CPU/GPU/QPU, and part by hardware, such as by an FPGA/ASIC of the system.

Figure 40B:
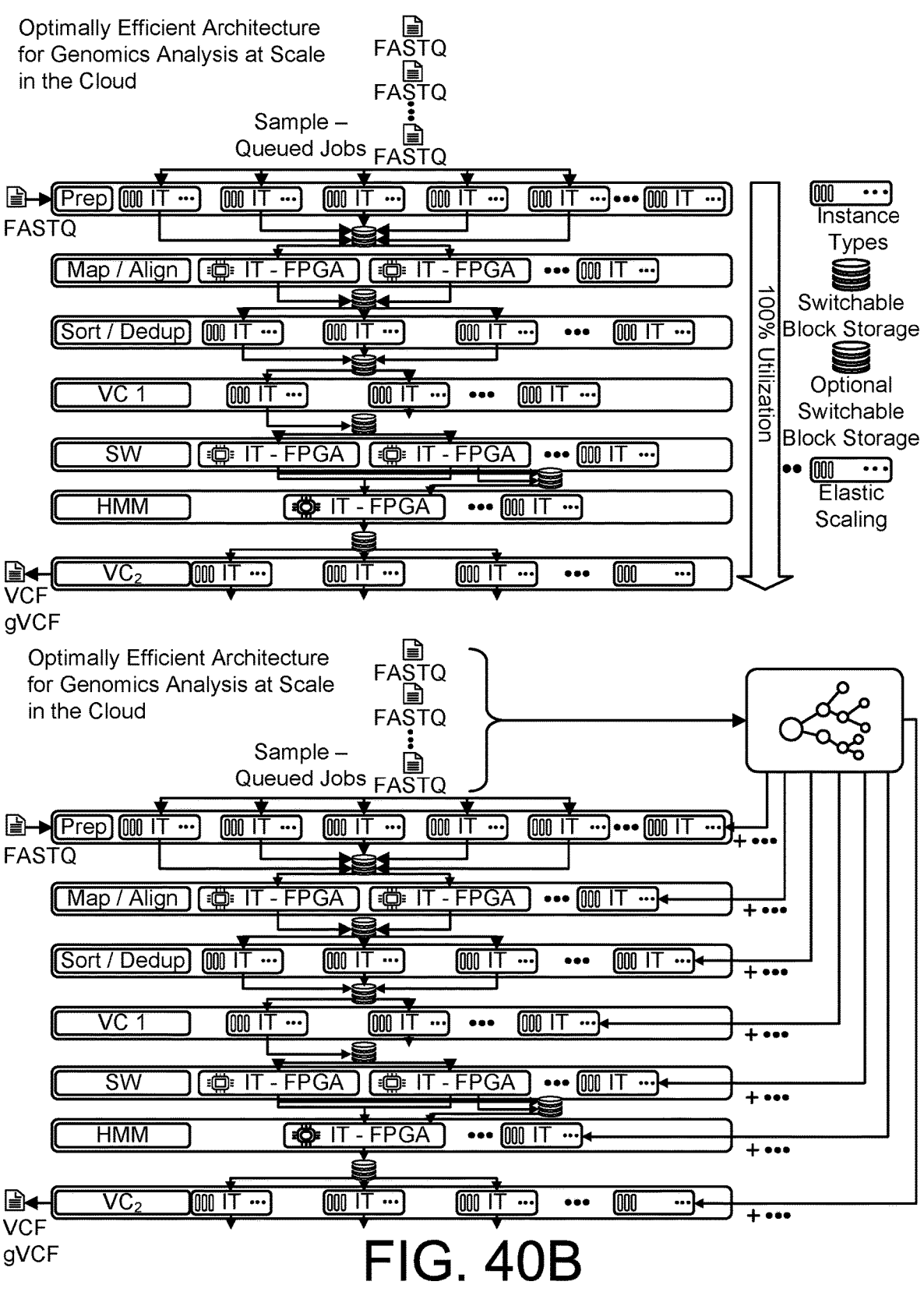
FIG. 40B depicts a block diagram of a cloud-based genomics processing platform for performing the BioIT analysis disclosed herein.

Accordingly, as can be seen with respect to FIG. 40B, in various implementations of the cloud based system 50, the system may include a plurality of computing resources, including a plurality of instances, and/or levels of instances, such as where the instances and/or layers of instances are configured for performing one or more of the BioIT pipeline of operations disclosed herein. For instance, various CPU/GPU/QPU and/or hardwired integrated circuit instances may be provided for performing dedicated functions of the genomic pipeline analysis provided herein. For example, various FPGA instances may be provided for performing dedicated genomic analysis operations, such as an FPGA instance for performing mapping, another for performing aligning, another for performing local realignment and/or other Smith-Waterman operations, another for performing HMM operations, and the like.

Likewise, various CPU/GPU/QPU instances may be provided for performing dedicated genomic analysis operations, such as CPU/GPU/QPU instance for performing signal processing, sorting, de-duplication, compression, various variant calling operations, and the like. In such instances, an associated memory or memories may be provided, such as between the various computation steps of the pipeline, for receiving results data as it is computed, compiled, and processed throughout the system, such as between the various CPU and/or FPGA instances and/or layers thereof. Further, it is to be noted that the size of the various CPU and/or FPGA instances may vary dependent on the computational needs of the cloud based system, and may range from small to medium to large to very large, and the number of CPU/GPU/QPU and FPGA/ASIC instances may vary likewise.

Additionally, as can be seen with respect to FIG. 40B, the system may further include a workflow manager that is configured for scheduling and directing the movement of data throughout the system and from one instance to another and/or from one memory to another. In some cases, the memory may be a plurality of memories that are dedicated memories that are instance specific, and in other cases the memory may be one or more memories that are configured to be elastic and therefore capable of being switched from one instance to another, such as a switchable elastic block storage memory. In yet other instances, the memory may be instance non-specific and therefore capable of being communicably coupled to a plurality of instances, such as for elastic file storage.

Further, the workflow manager may be a dedicated instance itself such as a CPU/GPU/QPU core that is dedicated and/or configured for determining what jobs need to be performed, and when and what resources will be utilized in the performance of those jobs, as well as for queuing up the jobs and directing them from resource to resource, e.g., instance to instance. The workflow manager may include or may otherwise be configured as a load estimator and/or form an elastic control node that is a dedicated instance that may be run by a processor, e.g. a CPU/GPU/QPU core. In various instances, the workflow manager may have a database connected to it, which may be configured for managing all the jobs that need to be, are being, or have been processed. Hence, the WMS manager may be configured for detecting and managing how data flows throughout the system, determining how to allocate system resources, and when to bring more resources online.

As indicated above, in certain instances, both a work bench and/or server based solution may be provided where the computing device includes a plurality of X CPU core servers having a size Y that may be configured to feed into one or more FPGAs with a size of Z, where X, Y, and Z are numbers that may vary depending on the processing needs of the system, but should be selected and/or otherwise configured for being optimized, e.g., 10, 14, 18, 20, 24, 30, etc. For instance, typical system configurations are optimized for performing the BioIT operations of the system herein described. Specifically, certain system configurations have been optimized so as to maximize the flow of data from various CPU/GPU/QPU instances to various integrated circuits, such as FPGAs, of the system, where the size of the CPU and/or FPGA may vary in relation to one another based on the processing needs of the system. For example, one or more of the CPU and/or FPGA may have a size that is relatively small, medium, large, extra-large, or extra-extra-large. More specifically, the system architecture may be configured in such a manner that the CPU/FPGA hardware are sized and configured to run in an optimally efficient manner so as to keep both instance platforms busy during all run times, such as where the CPUs outnumber the FPGA(s) 4 to 1, 8 to 1, 16 to 1, 32 to 1, 64 to 2, etc.

Hence, although it is generally good to have large FPGA capabilities, however, it may not be efficient to have a high capacity FPGA to process data, if there is not enough data needing to be processed being fed into the system. In such an instance, only a single or a partial FPGA may be implemented. Particularly, in an ideal arrangement, the workflow management system directs the flow of data to identified CPUs and/or FPGAs that are configured in such a manner as to keep the system and its components computing full time. For instance, in one exemplary configuration, one or more, e.g., 2, 3, or 4 or more CPU/GPU/QPU cores may be configured to feed data into a small, medium, large, extra-large FPGA, or a portion thereof. Specifically, in one embodiment, a CPU specific instance may be provided, such as for performing one or more of the BioIT processing operations disclosed herein, such as where the CPU instance is cloud accessible and includes up to 4, 8, 16, 24, 30, 36 CPU cores, which cores may or may not be configured for being operably coupled to a portion of one or more FPGAs.

For example, a cloud accessible server rack 300 may be provided wherein the server includes a CPU core instance having about 4 CPU cores to about 16 to about 24 CPU cores that are operably connectable to an FPGA instance. For instance, an FPGA instance may be provided, such as where an average size of an FPGA is X, and the included FPGA may be of a size of about ⅛x, X, 2.5× up to 8×, or even about 16×, or more. In various instances, additional CPU/GPU/QPU cores and/or FPGAs may be included, and/or provided as a combined instance, such as where there is a large amount of data to process, and where the number of CPU cores is selected so as to keep the FPGA(s) full time busy. Hence, the ratio of the CPUs to FPGA(s) may be proportioned by being combined in a manner to optimize data flow, and thus, the system may be configured so as to be elastically scaled up or down as needs be, e.g., to minimize expense while optimizing utilization based on workflow.

However, where the CPU(s) do not generate enough work to keep the FPGA busy and/or fully utilized, the configuration will be less than ideal. Provided herein, therefore, is a flexible architecture of one or more instances, which may be directly coupled together, or capable of being coupled together, in a manner that is adapted such that the CPU/FPGA software/hardware are run efficiently so as to ensure the present CPUs/GPUs/QPUs optimally feed the available FPGA(s), and/or a portion thereof, in such a manner to keep both instance platforms busy during all run times. Pursuantly, allowing such a system to be accessible from the cloud will ensure a plurality of data being provided to the system so as to be queued up by the workflow manager and directed to the specific CPU/FPGA resources that are configured and capable of receiving and processing the data in an optimally efficient manner.

For instance, in some configurations, cloud accessible instances may include a plurality of numbers and sizes of CPUs/GPUs/QPUs, and additionally, there may be cloud accessible instances that include a plurality of numbers and sizes of FPGAs (or ASICs) and/or QPUs. There may even be instances that have a combination of these instances. However, in various iterations, the provided CPU/GPU/QPU and/or FPGA/QPU and/or mixed instances, may have too many of one instance and/or to less of the other instance for efficiently running the present BioIT pipeline processing platforms disclosed herein. Accordingly, herein presented, are systems and architectures, flexible combinations of the same, and/or methods for implementing them for the efficient formation and use of a bioinformatics and/or genomics processing platform of pipelines, such as is made accessible via the cloud 50.

In such systems, the number and configurations of the selected CPU(s)/GPUs/QPUs may be selected and configured to process the less computationally intensive operations, and the number and configurations of FPGA(s) and/or QPUs may be adapted for handling the computationally intensive tasks, such as where the data is seamlessly passed back and forth between the CPU/GPU/QPU and FPGA/QPU instances. Additionally, one or more memories may be provided for the storing of data, e.g., results data, between the various steps of the procedures and/or between the various different instance types, thereby avoiding substantial period of instance latency. Specifically, during mapping and aligning, very little of the CPU/GPU is utilized, because of the intensive nature of the computations, these tasks are configured for being performed by the hardware implementations. Likewise, during variant calling, the tasks may be split in such a way as to be roughly fairly distributed between the CPU/FPGA instances in their tasks, such as where Smith-Waterman and HMM operations may be performed by the hardware, and various other operations may be performed by software run on one or more CPU/GPU/QPU instances.

Accordingly, the architectural parameters set forth herein are not necessarily limited to one-set architecture, but rather the system is configured so as to have more flexibility for organizing its implementations, and relying on the workflow manager to determine what instances are active when, how, and for how long, and directing which computations are performed on which instances. For instance, the number of CPUs and/or FPGAs to be brought online, and operationally coupled together, should be selected and configured in such a manner that the activated CPUs and FPGAs, as well as their attendant software/hardware, are kept optimally busy. Particularly, the number of CPUs, and their functioning, should be configured so as to keep the number of FPGAs, or a portion thereof, full time busy, such that the CPUs are optimally and efficiently feeding the FPGA(s) so as to keep both instances and their component parts running proficiently.

Hence, in this manner, the work flow management controller of the system may be configured for accessing the workflow and organizing and dividing it in such a manner that the tasks that may be more optimally performed by the CPUs/GPUs/QPUs are directed to the number of CPUs necessary so as to optimally perform those operations, and that the tasks that may be more optimally performed by the FPGA(s)/ASICs/QPUs are directed to the number of FPGAs necessary so as to optimally perform those operations. An elastic and/or an efficient memory may further be included for efficiently transmitting the results data of these operations from one instance to another. In this manner, a combination of machines and memories may be configured and combined so as to be optimally scaled based on the extent of the work to be performed, and the optimal configuration and usage of the instances so as to best perform that work efficiently and more cost effectively.

Specifically, the cloud based architectures set forth herein shows that various known deficiencies in previous architectural offerings may cause inefficiencies that can be overcome by flexibly allowing more CPU/GPU/QPU core instances to access various different hardware instances, e.g., of FPGAs, or portions thereof, that have been organized in a more intentional manner so to be able to dedicate the right instance to performing the appropriate functions so as to be optimized by being implemented in that format. For instance, the system may be configured such that there is a greater proportion of available CPU/GPU instances that may be accessible remotely so as to be full time busy producing results data that can be optimally fed into the available FPGA/QPU instance(s) so as to keep the selected FPGA instance(s) full time busy. Therefore, it is desirable to provide a structured architecture that is as efficient as possible and is full time busy. It is to be noted that configurations where too few CPUs feed into too many FPGAs such that one or more of the FPGAs are being underutilized is not efficient and should be avoided.

In one implementation, as can be seen with respect to FIG. 40B, the architecture can be configured so as to virtually include several different layers or levels, such as a first level having a first number of X CPU cores, e.g., from 4 to about 30 CPU cores, and a second level having from 1 to 12 or more FPGA instances, where the size of the FPGAs may range from small to medium to large, etc. A third level of CPU cores and/or a fourth level of further FPGAs, and so on, may also be included. Hence, there are many available instances in the cloud based server 300, such as instances that simply include CPUs or GPUs and/or instances that include FPGAs and/or combinations of them, such as in one or more levels described herein. Accordingly, in a manner such as this, the architecture may be flexibly or elastically organized so that the most intensive, specific computing functions are performed by the hardware instances or QPUs, and those functions that can be run through the CPUs, are directed to the appropriate CPU/GPU at the appropriate level for general processing purposes, and where necessary the number of CPU/FPGA instances may be increased or decreased within the system as needs be.

For example, the architecture can be elastically sized to both minimize system expense while at the same time maximizing optimal utilization. Specifically, the architecture may be configured to maximize efficiency and reduce latency by combining the various instances on various different virtual levels. Particularly, a plurality, e.g., a significant and/or all, of the Level 1 CPU/GPU instances can be configured to feed into the various Level 2 FPGA instances that have been specifically configured to perform specific functions, such as a mapping FPGA and an aligning FPGA. In a further level, one or more additional (or the same as Level I) CPUs may be provided, such as for performing a sorting and/or de-duplicating operations and/or various variant calling operations. Further still, one or more additional layers of FPGAs may be configured for performing a Needleman-Wunsch, Smith-Waterman, an HMM, variant calling operation, and the like. Hence, the first level CPUs can be engaged to form an initial level of a genomics analysis, such as for performing general processing steps, including the queuing up and preparing of data for further pipeline analysis, which data once processed by one or a multiplicity of CPUs, can be fed into one or more further levels of dedicated FPGA instances, such as where the FPGA instance is configured for performing intensive computing functions.

In this manner, in a particular implementation, the CPU/GPU instances in the pipeline route their data, once prepared, to the one or two mapping and aligning Level 2 FPGA instances. Once the mapping has been performed the result data may be stored in a memory and/or then fed into an aligning instance, where aligning may be performed, e.g., by at least one dedicated Level 2 FPGA instance. Likewise, the processed mapped and aligned data may then be stored in a memory and/or directed to a Level 3 CPU instance for further processing, which may be the same Level 1 or a different instance, such as for performing a less processing intense genomics analysis function, such as for performing a sorting function. Additionally, once the Level 3 CPUs have performed their processing, the resultant data may then be forwarded either back up to other Level 2 instances of the FPGAs, or to a Level 4 FPGA instance, such as for further genomics processing intense functions, such as for performing a Needleman-Wunsch (NW), Smith-Waterman (SW) processing function, e.g., at a NW or SW dedicated FPGA instance. Likewise, once the SW analysis has been performed, such as by an SW dedicated FPGA, then the processed data may be sent to one or more associated memories and/or further down the processing pipeline, such as to another, e.g., Level 4 or 5, or back up to Level 1 or 3, CPU and/or FPGA instance, such as for performing HMM and/or Variant Calling analysis, such as in a dedicated FPGA and/or further layer of CPU processing core.

In a manner such as this latency and efficiency issues can be overcome by combining the various different instances, on one or more different levels, so as to provide a pipeline platform for genomics processing. Such a configuration may involve more than a scaling and/or combining instances, the instances may be configured so that they specialize in performing dedicated functions. In such an instance, the Mapping FPGA instance only performs mapping, and likewise the aligning FPGA instance only performs aligning, and so on, rather than a single instance performing end-to-end processing of the pipeline. Albeit, in other configurations, one or more of the FPGAs may be at least partially reconfigured, such as between performing pipeline tasks. For instance, in certain embodiments, as the genomics analyses to be performed herein is a multi-step process, the code of on FPGA may be configured so as to be changed halfway through processing process, such as when the FPGA completes the mapping operation, it may be reconfigured so as to perform one or more of aligning, variant calling, Smith-Waterman, HMM, and the like.

Hence, the pipeline manager, e.g., workflow management system, may function to manage the queue of genomic processing requests being formulated by the Level I CPU instances so as to be broken down into discrete jobs, aggregated, and be routed to the appropriate job specific CPU and then to the job specific FPGA instances for further processing, such as for mapping and/or aligning, e.g., at Level 2, which mapped and aligned data once processed can be sent backwards or forwards to the next level of CPU/FPGA processing of the results data, such as for the performance of various steps in the variant calling module.

For instance, the variant calling function may be divided into a plurality of operations, which can be performed in software, then forwarded to Smith-Waterman and/or HMM processing in one or more FPGA hardware instances, and then may be sent to a CPU for continued variant calling operations, such as where the entire platform is elastically and/or efficiently sized and implemented to minimize cost of the expensive FPGA instances, while maximizing utilization, minimizing latency, and therefore optimizing operations. Accordingly, in this manner, less hardware instances are needed because of their pure processing capabilities and hardwired specificity, and therefore, the number of FPGAs to the number of CPUs may be minimized, and their use, e.g., of the FPGAs, may be maximized, and therefore, the system optimized so as to keep all instances full time busy. Such a configuration is optimally designed for genomics processing analysis, especially for mapping, aligning, and variant calling.

An additional structural element that may be included, e.g., as an attachment, to the pipeline architecture, disclosed herein, is one or more elastic and/or efficient memory modules, which may be configured to function for providing block storage of the data, e.g., results data, as it is transitioned throughout the pipeline. Accordingly, one or more Elastic Block Data Storage (EBDS) and/or one or more efficient (flexible) block data storage modules may be inserted between one or more of the processing levels, e.g., between the different instances and/or instance levels. In such an instance, the storage device may be configured such that as data gets processed and results obtained, the processed results may be directed to the storage device for storage prior to being routed to the next level of processing, such as by a dedicated FPGA processing module. The same storage device may be employed between all instances, or instance levels, or a multiplicity of storage devices may be employed between the various instances and/or instance levels, such as for storing and/or compiling and/or for queuing of results data. Accordingly, one or more memories may be provided in such a manner that the various instances of the system may be coupled to and/or have access to the same memory so as to be able to see and access the same or similar files. Hence, one or more elastic memories (memories capable of being coupled to a plurality of instances sequentially) and/or efficient memories (memories capable of being coupled to a plurality of instances simultaneously) may be present whereby the various instances of the system are configured to read and write to the same or similar memory.

For instance, in one exemplary embodiment with respect to configurations employing such elastic memories, prior to sending data directly from one instance and/or one level of processing to another, the data may be routed to an EBDS, or other memory device or structure, e.g., an efficient memory block, for storage and thereafter routed to the appropriate hardwired-processing module. Specifically, a block storage module may be attached to a node for memory storage where data can be written to the BSD for storage at one level, and the BSD may be flipped to another node for routing the stored data to the next processing level. In this manner, one or more, e.g., multiple, BDS modules may be included in the pipeline and configured for being flipped from one node to another so as to participate in the transitioning of data throughout the pipeline.

Further, as indicated above, a more flexible File Storage Device may be employed, such as a device that is capable of being coupled to one or more instances concurrently, such as without having to be switched from one to the other. In a manner such as this, the system may be elastically scaled at each level of the system, such as where at each level there may be a different number of nodes for processing the data at that level, and once processed the results data can be written to one or more associated EBDS devices that may then be switched to the next level of the system so as to make the stored data available to the next level of processors for the performance of their specific tasks at that level.

Accordingly, there are many steps in the processing pipeline, e.g., at its attendant nodes, as data is prepared for processing, e.g., preprocessing, which data once it is prepared is directed to an appropriate processing instance at one level where results data may be generated, then the result data may be stored, e.g., within an EDS device, queued and prepared for the next stage of processing by being flipped to the next node of instances and routed to the next instance for processing by the next order of FPGA and/or CPU processing instances, where further results data may be generated, and again once generated the results data may be directed either back to the same or forward to the next level of EDS for storage prior to being advanced to the next stage of processing.

Particularly, in one specific implementation, flow through the pipeline may look like the following: CPU (e.g., a 4 CPU core, or C4 instance): data prepared (queued and/or stored); FPGA (e.g. a 2XL FPGA—⅛ of a full server, or an F1 instance): Mapping, temporary storage; FPGA (e.g. a 2XL FPGA—⅛ of a full server, or an F1 instance): aligning, temporary storage; CPU: sorting, temporary storage; CPU: de-duplication, temporary storage; CPU: variant calling 1, temporary storage; FPGA (e.g., an F1 or a 16XL, or F2 instance): Smith-Waterman, temporary storage; FPGA (e.g. F1 or F2 instance): HMM, temporary storage; CPU: variant calling 2, temporary storage; CPU: VCGF, temporary storage, and so on. Additionally, a work flow management system may be included to control and/or direct the flow of data through the system, such as where the WMS may be implemented in a CPU core, such as a 4 core CPU, or C4 instance. It is noted, one or more of these steps may be performed in any logical order and may be implemented by any suitably configured resource such as implemented in software and/or hardware, in various different combinations. And it is to be noted that any of these operations may be performed on one or more CPU instances and one or more FPGA instances on one or more theoretical levels of processing, such as to form the BioIT processing described herein.

As indicated, a work flow manager may be included, such as where the WMS is implemented in one or more CPU cores. Hence, in various instances, the WMS may have a database operationally coupled to it. In such an instance, the database includes the various operations or jobs to be queued, pending jobs, as well as the history of all jobs previously or currently to be performed. As such, the WMS monitors the system and database to identify any new jobs to be performed. Consequently, when a pending job is identified, the WMS initiates a new analysis protocol on the data and farms it out to the appropriate instance node(s). Accordingly, the workflow manager keeps track of and knows where all the input files are, either stored, being processed, or to be stored, and therefore, directs and instructs the instances of the various processing nodes to access respective files at a given location, to begin reading files, to begin implementing processing instructions, and where to write results data. And, hence, the WMS directs the systems as to the passing results data to down line processing nodes. The WMS also determines when new instance needs to be fired up and brought online so as to allow for the dynamic scaling of each step or level of processing. Hence, the WMS identifies, organizes, and directs discrete jobs that have to be performed at each level, and further directs the results data being written to the memory to be stored, and once one job is completed, another node fires up, reads the next job, and performs the next iterative operation.

In a manner such as this, the input jobs may be spread across a lot of different instances, which instances can be scaled, e.g., independently or collectively, by including less or more and more instances. These instances may be employed to build nodes so as to more efficiently balance the use of resources, where such instances may comprise a partial or full instance. The workflow manager may also direct and/or control the use of one or more memories, such as in between the processing steps disclosed herein. The various instances may also include complimentary programming so as to allow them to communicate with each other and/or the various memories, so as to virtualize the server. The WMS may also include a load estimator so as to elastically control the usage of the nodes.

Further, with respect to the use of memories, one or more EBDS, or other suitably configured data and/or file storage devices, may be attached to one or more of the various nodes, e.g., between the various levels of instances, such as for temporary storage between the various different processing steps. Hence, the storage device may be a single storage device configured for being coupled to all of the various instances, e.g., an efficient memory block, such as elastic file storage, or may be multiple storage devices, such as one storage device per instance or instance type that is switchable between instances, e.g., elastic block storage device. Accordingly, in a manner such as this, each level of processing instances and/or memory may be elastically scaled on an as needed basis, such as between each of the different nodes or levels of nodes, such as for processing one or several genomes.

In view of the architecture herein, one or a multiplicity of genomes may be introduced into the system for processing, such as from one or more lanes of a flow cell of a Next Gen Sequencer, as indicated in FIG. 1. Specifically, providing a cloud based server system 300, as herein described, will allow a multiplicity of jobs to be piled up and/or queued for processing, which jobs may be processed by the various different instances of the system simultaneously or sequentially. Hence, the pipeline may be configured to support a multiplicity of jobs being processed by a virtual matrix of processors that are coupled to suitably configured memory devices so as to facilitate the efficient processing and data from one instance to another. Further, as indicated, a single memory device may be provided, where the memory device is configured for being coupled to a plurality of different instance, e.g., at the same time. In other instances, the memory device may be an elastic type memory device that may be configured for being coupled to a first instance, e.g., at a single time, and then being reconfigured and/or otherwise decoupled from the first instance, and switched to a second instance.

As such, in one implementation, one or more elastic block storage devices may be included and the system may be configured so as to include a switching control mechanism. For instance, a switch controller may be included and configured so as to control the functioning of such memory devices as they switch from one instance to another. This configuration may be arranged so as to allow the transfer of data through the pipeline of dedicated processors, thereby increasing the efficiency of the system, e.g., among all of the instances, such as by flowing the data through the system, allowing each level to be scaled independently and to bring processors online as needed to efficiently scale.

Additionally, the workflow management system algorithm may be configured so as to determine the number of jobs, the number of resources to process those jobs, the order of processing, and directs the flow of the data from one node to another by the flipping or switching of one or more flexible switching devices, and where needed can bring additional resources online to handle an increase in workflow. It is to be noted that this configuration may be adapted so as to avoid the copying of data from one instance to the next to the next, which is inefficient and takes up too much time. Rather, by flipping the elastic storage from one set of instances to another, e.g., pulling it from one node and attaching to a second node, can greatly enhance the efficiency of the system. Further, in various instances, instead of employing EBSD, one or more elastic file storage devices, e.g., single memory devices capable of being coupled to a multiplicity of instances without needing to be flipped from one to another, may be employed, so as to further enhance the transmission of data between instances, making the system even more efficiency. Additionally, it is to be noted, as indicated earlier herein, in another configuration the CPUs of the architecture can be directly to one another. Likewise, the various FPGAs may be directly coupled together. And, as indicated above, the CPUs can be directly coupled to the FPGAs, such as where such coupling is via a tight coupling interface as described above.

Accordingly, with respect to user storage and accessing of the generated results data, from a system wide perspective, all of the generated results data need not be stored. For instance, the generated results data will typically be in a particular file format, e.g., a BCL, FASTQ, SAM, BAM, CRAM, VCF file. However, each one of these files is extensive and the storage of all of them would consume a lot of memory thereby incurring a lot of expense. Nevertheless, an advantage of the present devices, systems, and methods herein, all of these files need not be stored. Rather, given the rapid processing speeds and/or the rapid compression and decompression rates achievable by the components and methods of the system, only a single file format, e.g., a compressed file format, need be stored, such as in the cloud based database 400. Specifically, only a single data file format need be stored, from which file format, implementing the devices and methods of the system, all other file formats may be derived. And, because of the rapid compression and decompression rates achieved by the system, it is typically a compressed file, e.g., a CRAM file.

Particularly, as can be seen with respect to FIG. 40A, in one implementation, a user of a local computing resource 100 may upload data, such as genomics data, e.g., a BCL and/or FASTQ file, into the system via the cloud 50 for receipt by the cloud based computing resource, e.g., server 300. The server 300 will then either temporarily store the data 400, or will begin processing the data in accordance with the jobs request by the user 100. When processing the input data, the computing resource 300 will thereby generate results data, such as in a SAM or BAM and/or VCF file. The system may then store one or more of these files, or it may compress one or more of these files and store those. However, in order to lower cost and more efficiently make use of the resources, the system may store a single, e.g., compressed, file, from which file all other file formats may be generated, such as by using the devices and methods herein disclosed. Accordingly, the system is configured for generating data files, e.g., results data, which may be stored on a server 300 associated database 400 that is accessible via the cloud 50, in a manner that is cost effective.

Accordingly, using a local computing resource 100, a user of the system may log on and access the cloud 50 based server 300, may upload data to the server 300 or database 400, and may request one or more jobs be performed on that data. The system 300 will then perform the requested jobs and store the results data in database 400. As noted, in particular instances, the system 300 will store the generated results data in a single file format, such as a CRAM file. Further, with the click of a button, the user can access the stored file, and with another click of a button, all of the other file formats may then be made accessible. For instance, in accordance with the methods disclosed herein, given the systems rapid processing capabilities, which would then be processed and generated behind the scene, e.g., on the fly, thus cutting down on both processing time and burden as well as storage costs, such as where the computing and the storage functions are bundled together.

Particularly, there are two parts of this efficient and rapid storage process that are enabled by the speed of performing the accelerated operations herein disclosed. More particularly, because the various processing operations of mapping, aligning, sorting, de-duplicating, and/or variant calling, may be implemented in a hardwired and/or quantum processing configuration, the production of results data, in one or more file formats, may be achieved rapidly. Additionally, because of the close coupling architectures disclosed herein, a seamless compression and storing of the results data, e.g., in a FASTQ, SAM, BAM, CRAM, VCF file format, is further achieved.

Further still, because of the accelerated processing provided by the devices of the system, and because of their seamless integration with the associated storage devices, the data that results from the processing operations of the system, which data is to be stored, may be both efficiently compressed prior to storage and decompressed subsequent to storage. Such efficiencies thereby lower storage costs and/or the penalties related to decompression of files before use. Accordingly, because of these advantages, the system may be configured so as to enable seamless compression and storing of only a single file type, with on-the-fly regeneration of any of the other file types, as needed or requested by the user. For instance, a BAM file, or a compressed SAM or CRAM file associated therewith, may be stored, and from that file the others may be generated, e.g., in a forward or a reverse direction, such as to reproduce a VCF or FASTQ or BCL file, respectively.

For instance, in one embodiment, a FASTQ file may originally be input into the system, or otherwise generated, and stored. In such an instance, when going in the forward direction, a checksum of the file may be taken. Likewise, once result data is produced, when going backward, another checksum may be generated. These checksums may then be used to ensure that any further file formats to be generated and/or recreated by the system, in the forward or reverse direction, match identically to one another and/or their compressed file formats. In a manner such as this it may be ensured that all of the necessary data is stored, in as efficient as manner as possible, and the WMS knows exactly where the data is stored, in what file format it is stored in, what the original file format was in, and from this data the system can regenerate any file format in an identical manner going forwards or backwards between file formats (once the template is originally generated).

Hence, the speed advantage of the "just in time" compiling is enabled in part by the hardware and/or quantum implemented generation of the relevant files, such as in generating a BAM file from a previously generated FASTQ file. Particularly, compressed BAM files, including SAM and CRAM files, are not typically stored within a database because of the increased time it takes prior to processing to decompress the compressed stored file. However, the JIT system allows this to be done without substantial penalties. More particularly, implementing the devices and processes disclosed herein, not only can generated sequence data be compressed and decompressed rapidly, e.g., almost instantaneously, it may also be stored efficiently. Additionally, from the stored file, in whatever file format it is stored, any of the other file formats may be regenerated in mere moments.

Figure 40C:
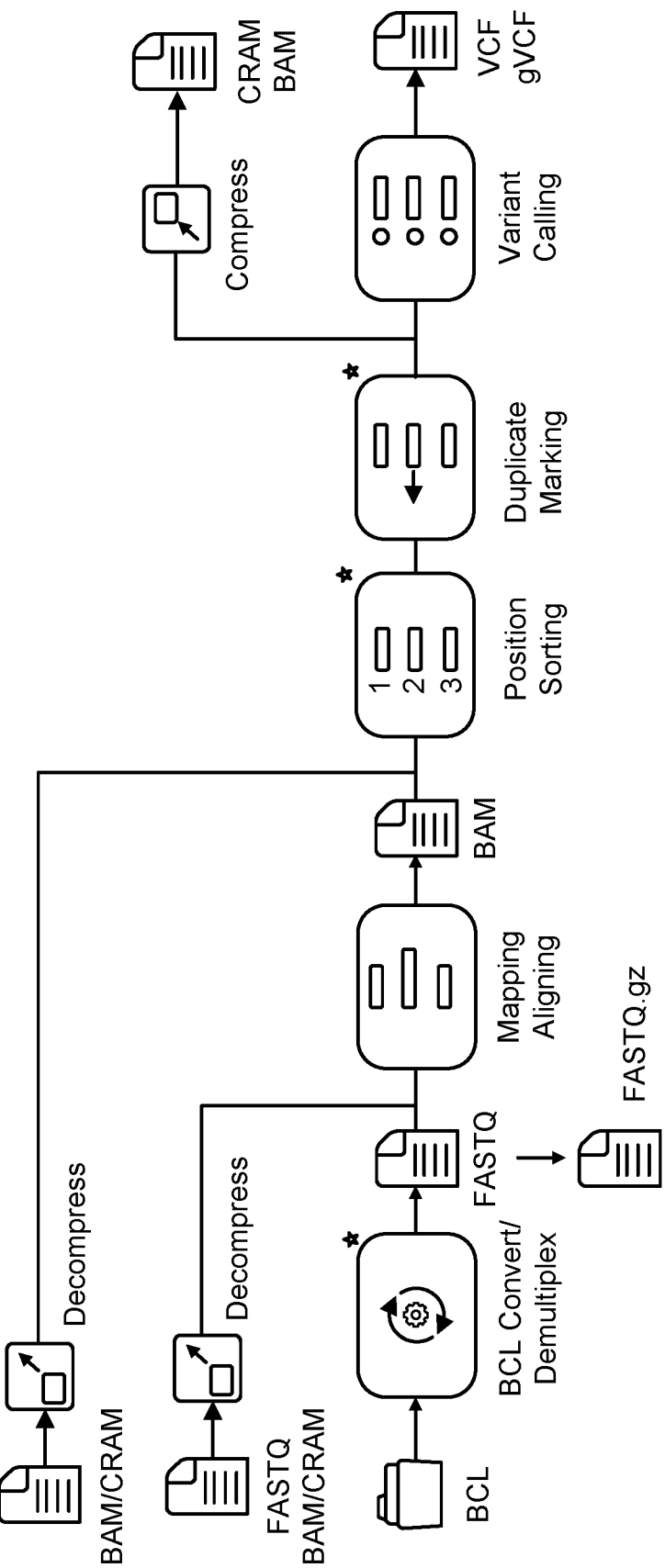
FIG. 40C depicts a block diagram for an exemplary genomic processing and analysis pipeline.

Hence, as can be seen with reference to FIG. 40C, when the accelerated hardware and/or quantum processing performs various secondary processing procedures, such as mapping and aligning, sorting, de-duplicating, and variant calling, a further step of compression may also be performed, such as in an all in one process, prior to storage in the compressed form. Then when the user desires to analyze or otherwise use the compressed data, the file may be retrieved, decompressed, and/or converted from one file format to another, and/or be analyzed, such as by the JIT engine(s) being loaded into the hardwired processor, or configured within the quantum processor, and subjecting the compressed file to one or more procedures of the JIT pipeline.

Accordingly, in various instances, where the system includes an associated FPGA, the FPGA can be fully or partially reconfigured, and/or a quantum processing engine may be organized, so as to perform a JIT procedure. Particularly, the JIT module can be loaded into the system and/or configured as one or more engines, which engines may include one or more compression engines 150 that are configured for working in the background. Hence, when a given file format is called, the JIT-like system may perform the necessary operations on the requested data so as to produce a file in the requested format. These operations may include compression and/or decompression as well as conversion so as to derive the requested data in the identified file format.

For instance, when genetic data is generated, it is usually produced in a raw data format, such as a BCL file, which then may get converted into a FASTQ file, e.g., by the NGS that generates the data. However, with the present system, the raw data files, such as in BCL or other raw file format, may be streamed or otherwise transmitted into the JIT module, which can then convert the data into a FASTQ file and/or into another file format. For example, once a FASTQ file is generated, the FASTQ file may then be processed, as disclosed herein, and a corresponding BAM file may be generated. And likewise, from the BAM file a corresponding VCF may be generated. Additionally, SAM and CRAM files may also be generated during appropriate steps. Each one of these steps may be performed very rapidly, especially once the appropriate file format has once been generated. Hence, once the BCL file is received, e.g., straight from the sequencer, the BCL can be converted into a FASTQ file or be directly converted into a SAM, BAM, CRAM, and/or VCF file, such as by a hardware and/or quantum implemented mapping/aligning/sorting/variant calling procedure.

For example, in one use model, on a typical sequencing instrument, a large number of different subject's genomes may be loaded into individual lanes of a single sequencing instrument to be run in parallel. Consequently, at the end of the run, a large number of diverse BCL files, derived from all the different lanes and representing the whole genomes of each of the different subjects, are generated in a multiplex complex. Accordingly, these multiplexed BCL files may then be de-multiplexed, and respective FASTQ files may be generated representing the genetic code for each individual subject. For instance, if in one sequencing run N BCL files are generated, these files will need to be de-multiplexed, layered, and stitched together for each subject. This stitching is a complex process where each subject's genetic material is converted to BCL files, which may then be converted to a FASTQ file or used directly for mapping, aligning, and/or sorting, variant calling, and the like. This process may be automated so as to greatly speed up the various steps of the process.

Further, as can be seen with respect to FIG. 40A, once this data has been generated 110, and therefore needs to be stored, e.g., in which ever file format is selected, the data may be stored in a password protected and/or encrypted memory cache, such as in a dedicated genomics dropbox-like memory 400. Accordingly, as the generated and/or processed genetic data comes off of the sequencer, the data may be processed and/or stored and made available to other users on other systems, such as in a dropbox-like cache 400. In such an instance, the automated bioinformatics analysis pipeline system may then access the data in the cache and automatically begin processing it. For example, the system may include a management system, e.g., a workflow management system 151, having a controller, such as a microprocessor or other intelligence, e.g., artificial intelligence, that manages the retrieving of the BCL and/or FASTQ files, e.g., from the memory cache, and then directs the processing of that information, so as to generate a BAM, CRAM, SAM, and/or VCF, thereby automatically generating and outputting the various processing results and/or storing the same in the dropbox memory 400.

A unique benefit of JIT processing, as implemented within this use model, is that JIT allows the various genetic files produced to be compressed, e.g., prior to data storage, and to be decompressed rapidly prior to usage. Hence, JIT processing can compile and/or compress and/or store the data as it is coming off the sequencer, where such storage is in a secure genomic dropbox memory cache. This genomic dropbox cache 400 may be a cloud 50 accessible memory cache that is configured for the storing of genomics data received from one or more automated sequencers 110, such as where the sequencer(s) are located remotely from the memory cache 400.

Particularly, once the sequence data has been generated 110, e.g., by a remote NGS, it may be compressed 150 for transmission and/or storage 400, so as to reduce the amount of data that is being uploaded to and stored in the cloud 50. Such uploading, transmission, and storage may be performed rapidly because of the data compression 150 that takes place in the system, such as prior to transmission. Additionally, once uploaded and stored in the cloud based memory cache 400, the data may then be retrieved, locally 100 or remotely 300, so as to be processed in accordance with the devices, systems, and methods of the BioIT pipeline disclosed herein, so as to generate a mapping, aligning, sorting, and/or variant call file, such as a SAM, BAM, and/or CRAM file, which may then be stored, along with a metafile that sets forth the information as to how the generated file, e.g., SAM, BAM, CRAM, etc. file, was produced.

Hence, when taken together with the metadata, the compressed SAM, BAM, and/or CRAM file may then be processed to produce any of the other file formats, such as FASTQ and/or VCF files. Accordingly, as discussed above, on the fly, JIT can be used to regenerate the FASTQ file or VCF from the compressed BAM file and vice versa. The BCL file can also be regenerated in like manner. It is to be noted that SAM and CRAM files can likewise be compressed and/or stored and can be used to produce one or more of the other file formats. For instance, a CRAM file, which can be un-CRAMed, can be used to produce a variant call file, and likewise for the SAM file. Hence, only the SAM, BAM and/or CRAM file need be saved and from these files, the other file formats, e.g., VCF, FASTQ, BCL files, can be reproduced.

Accordingly, as can be seen with respect to FIG. 40A, a mapping and/or aligning and/or sorting and/or variant calling instrument 110, e.g., a work bench computer, may be on-site 100 and/or another second corresponding instrument 300 may be located remotely and made accessible in the cloud 50. This configuration, along with the devices and methods disclosed herein, is adapted to enable a user to rapidly perform a BioIT analysis "in the cloud", as herein disclosed, so as to produce results data. The results data may then be processed so as to be compressed, and once compressed, the data may be configured for transmittal, e.g., back to the local computing resource 100, or may be stored in the cloud 400, and made accessible via a cloud based interface by the local computing resource 100. In such an instance, the compressed data may be a SAM, BAM, CRAM, and/or VCF file.

Specifically, the second computing resource 300 may be another work-bench solution, or it may be a server configured resource, such as where the computing resource is accessible via the cloud 50, and is configured for performing mapping and/or aligning and/or sorting and/or variant calling instrument. In such an instance, a user may requests the cloud-based server 300 perform one or more BioIT jobs on uploaded data, e.g., BCL and/or FASTQ data. In this instance, the server 300 will then access the stored and/or compressed file(s) and may process the data so as to rapidly process that data and generate one or more results data, which data may then be compressed and/or stored. Additionally, from the results data file one or more BCL, FASTQ, SAM, BAM, VCF, or other file formats may be generated, e.g., on the fly, using JIT processing. This configuration thereby alleviates the typical transfer speed bottleneck.

Hence, in various embodiments, the system 1 may include, a first mapping and/or aligning and/or sorting and/or variant calling instrument 100, which may be positioned locally 100, such as for local data production, compression 150, and/or storage 200; and a second instrument 300 may be positioned remotely and associated in the cloud 50, whereby the second instrument 300 is configured for receiving the generated and compressed data and storing it, e.g., via an associated storage device 400. Once stored, the data may be accessed decompression and conversion of the stored files into one or more of the other file formats.

Therefore, in one implementation of the system, data e.g., raw sequence data such as in a BCL or FASTQ file format, which is generated by a data generating apparatus, e.g., a sequencer 110, may be uploaded and stored in the cloud 50, such as in an associated genomics dropbox-like memory cache 400. This data may then be accessed directly by the first mapping and/or aligning and/or sorting and/or variant calling instrument 100, as described herein, or may be accessed indirectly by the server resource 300, which may then process the sequence data to produce mapped, aligned, sorted, and/or variant results data.

Accordingly, in various embodiments, one or more of the storage devices herein disclosed may be configured so as to be accessible, with the appropriate permissions, via the cloud. For instance, various of the results data of the system may be compressed and/or stored in a memory, or other suitably configured database, where the database is configured as a genomics dropbox cache 400, such as where various results data may be stored in a SAM, BAM, CRAM and/or VCF file, which may be accessible remotely. Specifically, it is to be noted that, with respect to FIG. 40A, a local instrument 100 may be provided, where the local instrument may be associated with the sequencing instrument 110 itself, or it may be remote therefrom but and associated with the sequencing instrument 110 via a local cloud 30, and the local instrument 100 may further be associated with a local storage facility 200 or remote memory cache 400, such as where the remote memory cache is configured as the genomics dropbox. Further, in various instance, a second mapping and/or aligning and/or sorting and/or variant calling instrument 300, e.g., a cloud based instrument, with the proper authorities, may also be connected with the genomics dropbox 400, so as to access the files, e.g., compressed files, stored thereby the local computing resource 100, and may then decompress those files to make the results available for further, e.g., secondary or tertiary, processing.

Accordingly, in various instances, the system may be streamlined such that as data is generated and comes off of the sequencer 110, such as in raw data format, it may either be immediately uploaded into the cloud 50 and stored in a genomics dropbox 400, or it may be transmitted to a BioIT processing system 300 for further processing and/or compression prior to being uploaded and stored 400. Once stored within the memory cache 400, the system may then immediately queue up the data for retrieval, compression, decompression, and/or for further processing such as by another associated BioIT processing apparatus 300, which when processed into results data may then be compressed and/or stored 400 for further use later. At this point, a tertiary processing pipeline may be initiated whereby the stored results data from secondary processing may be decompressed and used such as for tertiary analysis, in accordance with the methods disclosed herein.

Hence, in various embodiments, the system may be pipelined such that all of the data that comes off of the sequencer 110 may either be compressed, e.g., by a local computing resource 100, prior to transfer and/or storage 200, or the data may be transferred directly into the genomics dropbox folder for storage 400. Once received thereby, the stored data may then substantially immediately be queued for retrieval and compression and/or decompression, such as by a remote computing resource 300. After being decompressed the data may substantially immediately be available for processing such as for mapping, aligning, sorting, and/or variant calling to produce secondarily processed results data that may then be re-compressed for storage. Afterward, the compressed secondary results data may then be accessed, e.g., in the genomics dropbox 400, be decompressed, and/or be used in one or more tertiary processing procedures. As the data may be compressed when stored and substantially immediately decompressed when retrieved, it is available for use by many different systems and in many different bioanalytical protocols at different times, simply by accessing the dropbox storage cache 400.

Therefore, in such manners as these, the BioIT platform pipelines presented herein may be configured so as to offer incredible flexibility of data generation and/or analysis, and are adapted to handle the input of particular forms of genetic data in multiple formats so as to process the data and produce output formats that are compatible for various downstream analysis. Accordingly, as can be seen with respect to FIG. 40C, presented herein are devices, systems, and methods for performing genetic sequencing analysis, which may include one or more of the following steps: First, a file input is received, the input may be in one or more of a FASTQ or BCL or other form of genetic sequence file format, such as in a compressed file format, which file may then be decompressed, and/or processed through a number of steps disclosed herein so as to generate a VCF/gVCF, which file may then be compressed and/or stored and/or transmitted. Such compression and/or decompression may occur at any suitable stage throughout the process.

For instance, once a BCL file is received, it may be subjected to a pipeline of analyses, such as in a sequential manner as disclosed herein. For example, once received, the BCL file may be converted and/or de-multiplexed such as into a FASTQ and/or FASTQgz file format, which file may be sent to a mapping and/or aligning module, e.g., of a sever 300, so as to be mapped and/or aligned in accordance with the apparatuses and their methods of use described herein. Additionally, in various instances, the mapped and aligned data, such as in a SAM or BAM file format, may be position sorted and/or any duplications can be marked and removed. The files may then be compressed, such as to produce a CRAM file, e.g., for transmission and/or storage, or may be forwarded to a variant calling, e.g., HMM, module, to be processed so as to produce a variant call file, VCF or gVCF.

Figure 40D:
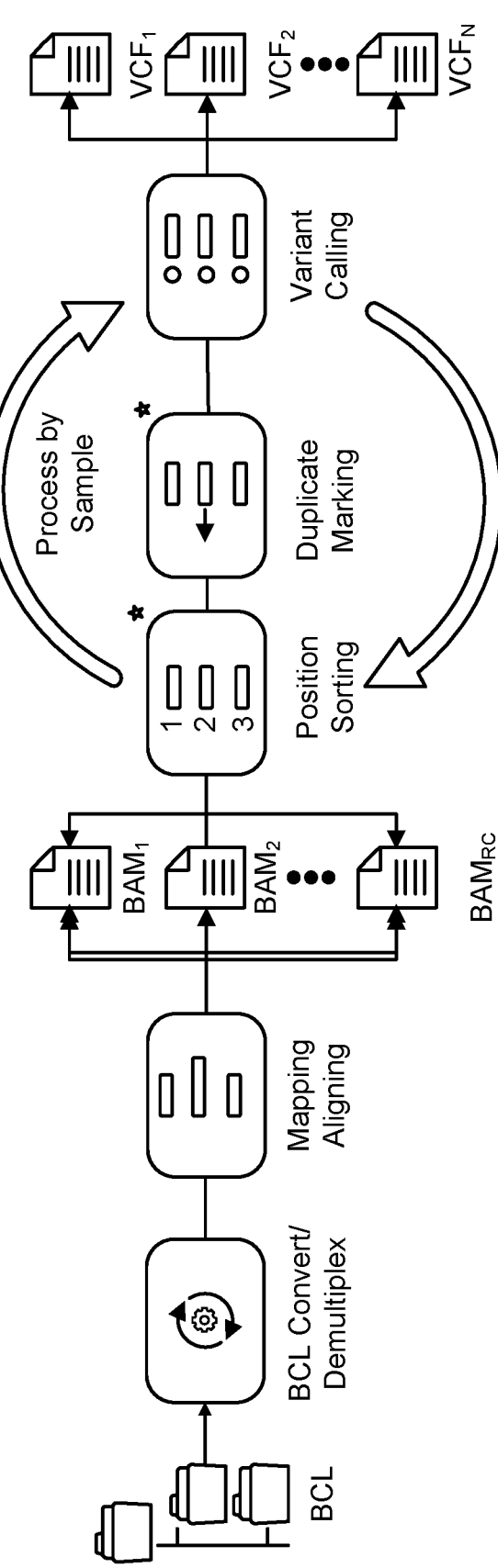
FIG. 40D depicts a block diagram for an exemplary genomic processing and analysis pipeline.

More specifically, as can be seen with respect to FIGS. 40C and 40D, in certain instances, the file to be received by the system may be streamed or otherwise transferred to the system directly from the sequencing apparatus, e.g., NGS 110, and as such the transferred file may be in a BCL file format. Where the received file is in a BCL file format it may be converted, and/or otherwise de-multiplexed, into a FASTQ file for processing by the system, or the BCL file may be processed directly. For instance, the platform pipeline processors can be configured to receive BCL data that is streamed directly from the sequencer, as described with respect to FIG. 1, or it may receive data in a FASTQ file format. However, receiving the sequence data directly as it is streamed off of the sequencer is useful because it enables the data to go directly from raw sequencing data to being directly processed, e.g., into one or more of a SAM, BAM, and/or VCF/gVCF for output.

Accordingly, once the BCL and/or the FASTQ file is received, e.g., by a computing resource 100 and/or 300, it may be mapped and/or aligned by the computing resource, which mapping and/or aligning may be performed on single end or paired end reads. For instance, once received, the sequence data may be compiled into reads, for analysis, such as with read lengths that may range from about 10 or about 20, such as 26, or 50, or 100, or 150 bp or less up to about 1K, or about 2.5K, or about 5K, even about 10K bp or more. Likewise, once mapped and/or aligned the sequence may then be sorted, such as position sorted, such as through binning by reference range and/or sorting of the bins by reference position. Further, the sequence data may be processed via duplicate marking, such as based on the starting position and CIGAR string, so as to generate a high quality duplicate report, and any marked duplicates may be removed at this point. Consequently, a mapped and aligned SAM file may be generated, which may be compressed so as to form a BAM/CRAM file, such as for storage and/or further processing. Furthermore, once the BAM/CRAM file has been retrieved, the mapped and/or aligned sequence data may be forwarded to a variant calling module of the system, such as a haplotype variant caller with reassembly, which in some instances, may employ one or more of a Smith-Waterman Alignment and/or Hidden Markov Model that may be implemented in a combination of software and/or hardware, so as to generate a VCF.

Hence, as seen in FIG. 40D, the system and/or one or more of its components may be configured so as to be able to convert BCL data to FASTQ or SAM/BAM/CRAM data formats, which may then be sent throughout the system for further processing and/or data reconstruction. For instance, once the BCL data is received and/or converted into a FASTQ file and de-multiplexed and/or deduped, the data may then be forwarded to one or more of the pipeline modules disclosed herein, such as for mapping and/or aligning, which dependent on the number of samples being processed will result in the production of one or more, e.g., several, SAM/BAM files. These files may then be sorted, de-duped, and forwarded to a variant calling module, so as to produce one or more VCF files. These steps may be repeated for greater context and accuracy. For example, once the sequence data is mapped or aligned, e.g., to produce a SAM file, the SAM file may then be compressed into one or more BAM files, which may then be transmitted to a VCF engine so as to be converted throughout the processing of the system to a VCF/gVCF, which may then be compressed into a CRAM file. Consequently, the files to be output along the system may be a Gzip and/or CRAM file.

Particularly, as can be seen with respect to FIGS. 40C and 40D, one or more of the files, once generated may be compressed and/or transferred from one system component to another, e.g., from a local 100 to a remote resource 300, and once received may then be decompressed, e.g., if previously compressed, or converted/de-multiplexed. More particularly, once a BCL file is received, either by a local 100 or remote 300 resource, it may be converted into a FASTQ file that may then be processed by the integrated circuit(s) of the system, so as to be mapped and/or aligned, or may be transmitted to a remote resource 300 for such processing. Once mapped and/or aligned, the resulting sequence data, e.g., in a SAM file format, may be processed further such as by being compressed one or more times, e.g., into a BAM/CRAM file, which data may then be processed by position sorting, duplicate marking, and/or variant calling, the results of which, e.g., in a VCF format, may then be compressed once more and/or stored and/or transmitted, such as from a remote resource 300 to local 100 resource.

More particularly, the system may be adapted so as to process BCL data directly, thereby eliminating a FASTQ file conversion step. Likewise, the BCL data may be fed directly to the pipeline to produce a unique output VCF file per sample. Intermediate SAM/BAM/CRAM files can also be generated on demand. The system, therefore, may be configured for receiving and/or transmitting one or more data files, such as a BCL or FASTQ data file containing sequence information, and processing the same so as to produce a data file that has been compressed, such as a SAM/BAM/CRAM data file.

Figure 41A:
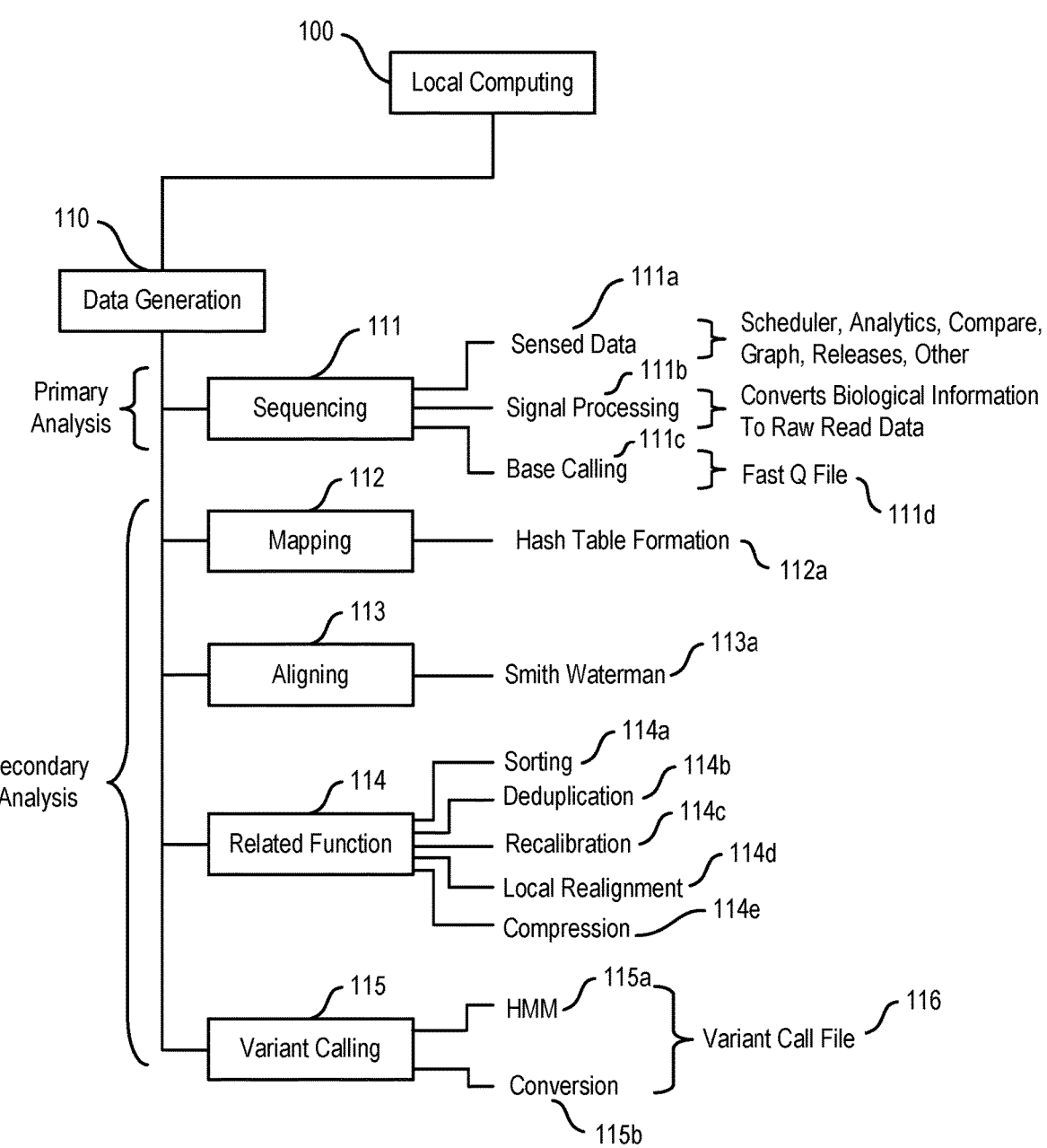
FIG. 41A depicts a block diagram of a local and/or cloud based computing function of FIG. 40A for a genomic infrastructure for onsite and/or cloud based genomics processing and analysis.

Accordingly, as can be seen with respect to FIG. 41A, a user may want to access the compressed file and convert it to an original version of the generated BCL 111c and/or FASTQ file 111d, such as for subjecting the data to further, e.g., more advanced, signal processing 111b, such as for error correction. Alternatively, the user may access the raw sequence data, e.g., in a BCL or FASTQ file format 111, and subject that data to further processing, such as for mapping 112 and/or aligning 113 and/or other related functions 114/115. For instance, the results data from these procedures may then be compressed and/or stored and/or subjected to further processing 114, such as for sorting 114a, de-duplication 114b, recalibration 114c, local realignment 114d, and/or compression/decompression 114e. The same or another user may then want to access the compressed form of the mapped and/or aligned results data and then run another analysis on the data, such as to produce one or more variant calls 115, e.g., via HMM, Smith-Waterman, Conversion, etc., which may then be compressed and/or stored. An additional user of the system may then access the compressed VCF file 116, decompress it, and subject the data to one or more tertiary processing protocols.

Further, a user may want to do a pipeline compare. The mapping/aligning/sorting/variant calling is useful for pre-forming various genomic analysis. For instance, if a further DNA or RNA analysis, or some other kind of analysis, is afterward desired, a user may want to run the data through another pipeline, and hence having access to the regenerated original data file is very useful. Likewise, this process may be useful such as where a different SAM/BAM/CRAM file may be desired to be created, or recreated, such as where there is a new or different reference genome generated, and hence it may be desired to re-do the mapping and aligning to the new reference genome.

Storing the compressed SAM/BAM/CRAM files is further useful because it allows a user of the system 1 to take advantage of the fact that a reference genome forms the backbone of the results data. In such an instance, it is not the data that agrees with the reference that is important, but rather how the data disagrees with the reference. Hence, only that data that disagrees with the reference is essential for storage. Consequently, the system 1 can take advantage of this fact by storing only what is important and/or useful to the users of the system. Thus, the entire genomic file (showing agreement and disagreement with the reference), or a sub-portion of it (showing only agreement or disagreement with the reference), may be configured for being compressed and stored. It may be seen, therefore, that as only the differences and/or variations between the reference and the genome being examined are the most useful to examine, in various embodiments, only these differences need be stored, as anything that is the same as the reference need not be reviewed again. Accordingly, since any given genome differs only slightly from a reference, e.g., 99% of human genomes are typically identical, after the BAM file is created, it is only the variations between the reference genome that need be reviewed and/or saved.

Figure 41B:
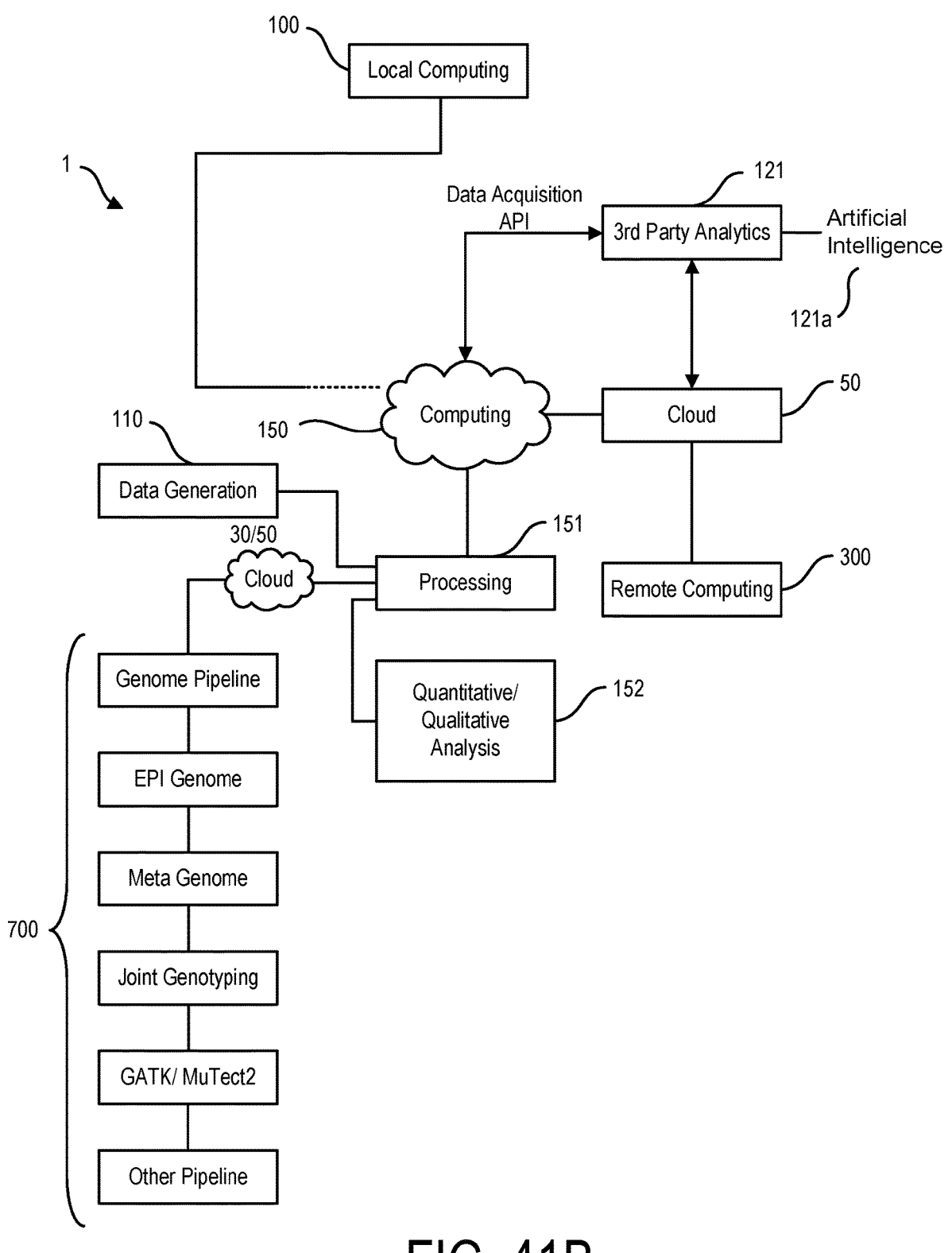
FIG. 41B depicts the block diagram of FIG. 41A illustrating greater detail regarding the computing function for a genomic infrastructure for onsite and/or cloud based genomics processing and analysis.

Additionally, as can be seen with respect to FIG. 41B, another useful component of a cloud accessible system 1, provided herein, is a workflow management controller 151, which may be used to automate the system flow. Such system animation may include utilizing the various system componentry to access data, either locally 100 or remotely 300, as and/or where it becomes available and then substantially automatically subjecting the data to further processing steps, such with respect to the BioIT pipelines disclosed herein. Accordingly, the workflow management controller 151 is a core automation technology for directing the various pipelines of the system, e.g., 111, 112, 113, 114, and/or 115, and in various instances may employ an artificial intelligence component 121a.

For instance, the system 1 may include an artificial intelligence (A/I) module, as described in greater detail herein below, that is configured to analyze the various data of the system, and in response thereto to communicate its findings with the workflow management system 151. Particular, in various instances, the A/I module may be configured for analyzing the various genomic data presented to the system, as well as the results data that is generated by the processing of that data, so as to identify and determine various relationships between that data and/or with any other data that may be entered into the system. More particularly, the A/I module may be configured for analyzing various genomic data in correspondence with a plurality of other factors, so as to determine any relationship, e.g., effect based relationships, between the various factors, e.g., data points, which may be informative as to the effects of the considered factors on the determined genomic data, e.g., variance data, and vice-versa.

Specifically, as described in greater detail below, the A/I module may be configured to correlate the genomics data of a subject generated by the system with any electronic medical records, for that subject or others, so as to determine any relationships between them and/or any other relevant factors and/or data. Accordingly, such other data that may be used by the system in determining any relevant effects and/or relationships that these factors may have on a subject and/or their genomic data and/or health include: NIPT data, NICU data, Cancer related data, LDT data, Environmental and/or Ag Bio data, and/or other such data. For instance, further data to be analyzed may be derived by such other factors as environmental data, clad data, microbiom data, methylation data, structural data, e.g., chimeric or mate read data, germline variants data, allele data, RNA data, and other such data related to a subject's genetic material. Hence, the A/I module may be used to link various related data flowing through the system to the variants determined in the genome of one or more subjects along with one or more other possible related effect based factors.

Particularly, the A/I engine may be configured to be run on a CPU/GPU/QPU, and/or it may be configured to be run as an accelerated AI engine, which may be implemented in an FPGA and/or Quantum Processing Unit. Specifically, the AI engine may be associated with one or more, e.g., all, of the various databases of the system, so as to allow the AI engine to explore and process the various data flowing through the system. Additionally, where a subject whose genome is being processed gives the appropriate authorization to access both genomic and patient record data, the system is then configured for correlating the various data sets one with the other, and may further mine the data to determine various significant correspondences, associations, and or relationships.

More specifically, the A/I module may be configured so as to implement a machine learning protocol with respect to the input data. For instance, the genomics data of a plurality of subjects that is generated from the analyses being performed herein may be stored in a database. Likewise, with the appropriate authorizations and authentications, the Electronic Medical/Health Records (EMR), for the subject's whose genomic DNA has been processed, may be obtained, and may likewise be stored in the database. As described in greater detail below, the processing engine(s) may be configured to analyze the subject's genomic data, as well as their EMR data, so as to determine any correlations between the two. These correlations will then be explored, observed relationships strengthened, and the results thereof may be used to more effectively and more efficiently perform the various functions of the system.

For example, the AI processing engine may access the genomic data of the subject, in correlation with the known diseases or conditions of those subjects, and from this analysis, the AI module may learn to perform predictive correlations based on that data, so as to become more and more capable of predicting the presence of disease and/or other similar conditions in other individuals. Particularly, by determining such correlations between the genomes of others with their EMR, e.g., with respect to the presence of disease markers, the A/I module may learn to identify such correlations, e.g., system determined disease markers, in the genomes of others, thereby being able to predict the possibility of a disease or other identifiable conditions. More particularly, by analyzing a subject's genome in comparison to known or determined genetic disease markers, and/or by determining variance in the subject's genome, and/or further, by determining a potential relationship between the genomic data and the subject's health condition, e.g., EMR, the A/I module may be able draw conclusions not only for the subject being sampled, but for others who may be sampled in the future. This can be done, e.g., in a systematic manner, on a subject by subject basis, or may be done within populations and/or within geographically distinct locations.

More particularly, with respect to the present systems, a pileup of reads is produced. The pileup may overlap regions known to have a higher probability of a significant variance. Accordingly, the system on one hand will analyze the pileup to determine the presence of variance, while at the same time, based on its previous findings, will already know the likelihood that a variance should or should not be there, e.g., it will have an initial prediction as to what the answer should be. Whether or not the expected variance is or is not there will be informative when analyzing that region of the genomes of others. For instance, this may be one data point in a sum of data points being used by the system to make better variant calls, and/or better associating those variants with one or more disease states or other health conditions.

For example, in an exemplary learning protocol, the A/I analysis may include taking an electronic image of a pileup of one or more regions in a genome, such as for those regions suspected of coding for one or more health conditions, and associating that image with the known variance calls from other pileups, such as where those variance may be known or not known to be related to disease states. This may be done again and again with the system learning to process the information, make the appropriate associations, and make the correct calls quicker and quicker, and with greater accuracy. Once this has been performed for various, e.g., all, of the known regions of the genome suspected of causing disease, the same may be repeated for the rest of the genome, e.g., until the whole genome has been reviewed. Likewise, this may be repeated again and again for a plurality of sample genomes, over and over, so as to train the system, e.g., the variant caller, so as to make more accurate calls, sooner, and with greater efficiency, and/or to allow the tertiary processing module to better identify unhealthy conditions.

Accordingly, the system receives many inputs with known answers, performs the analysis and computes the answer, and thereby learns from the process, e.g., renders an image of a pileup, with respect to one genome, and then learns to make a call based on another genome, sooner and sooner, as it is more readily determined that future pileups resemble the previously captured images that are known to be related to unhealthy conditions. Thus, the system may be configured so as to learn to make predictions as to the presence of variants, e.g., based on pattern recognitions, ad/or predicting the relationship between the presence of those variance with one or more medical conditions.

More specifically, the more the system performs partial or whole genome analyses, and determines the relationship between variations and various conditions, e.g., in a plurality of samples, the better at making predictions, e.g., based on partial or whole genome images of pileups, the system becomes. This is useful when predicting diseased states based on images of pileups and/or other read analysis, and may include the building of a correlation between one or more of the EMR (including phenotypic data), the pileup image, and/or known variants (genotypic data) and/or disease states or conditions, e.g., from which the predictions may be made. In various instances, the system may include a transcription function, so as to be able to transcribe any of the physical notes that may be a part of the subject's medical record, so as to include that data within the associations.

In one use model, a subject may have a mobile tracker and/or sensor, such as mobile phone or other computing device, which may be configured for both tracking the location of the subject as well as for sensing the environmental and/or physiological conditions of the user at that location. Other sensed data may also be collected. For instance, the mobile computing device may include a GPS tracker, and/or its location may be determined by triangulation by cellular towers, and may further be configured for transmitting its collected data, e.g., via cellular, WIFI, Bluetooth, or other suitably configured communications protocol. Hence, the mobile device may track and categorize environmental data pertaining to the geographical locations, environmental conditions, physiological status, and other sensed data of the subject owner of the mobile computer encounters in their daily life. The collected location, environmental, physiological, health data, and/or other associated data, e.g., ZNA data, may then be transmitted, e.g., regularly and periodically, to one or more of the system databases herein, wherein the collected ZNA data may be correlated with the subject's patient history, e.g., EMR records, and/or their genomic data, as determined by the system herein.

Likewise, in various instances, one or more of these data may be forwarded from the ZNA collection and analysis platform, to a central repository, e.g., at a government facility, so as to be analyzed on a greater, e.g., nationwide, scale, such as in accordance with the Artificial Intelligence disclosed herein. For instance, the database, e.g., governmental controlled database, may have recorded environmental data to which the environmental data of the subject may be compared. For example, in one exemplary instance, a NICU test may be performed on a mother, a father, and their child, and then throughout the lives of the three, their environmental and genomic and medical record data may be continually collected and correlated with one another and/or on or more models, such as over the lifespan of the individuals, especially with respect to the onset of mutations, such as due to environmentally impactful factors. This data collection may be performed over the life of the individual, and may be performed on a family as whole basis, so as to better build a data collection database and to better predict the effects of such factors on genetic variation, and vice versa.

Accordingly, the workflow management controller 151 allows the system 1 to receive inputs from one or more sources, such as one or multiple sequencing instruments, e.g., 110*a*, 110*b*, 110*c*, etc., and multiple inputs from a single sequencing instrument 110, where the data being received represents the genomes of multiple subjects. In such instances, the workflow management controller 151 not only keeps track of all of the incoming data, but it also efficiently organizes and facilitates the secondary and/or tertiary processing of the received data. Accordingly, the workflow management controller 151 allows the system 1 to seamlessly connect to both small and large sequencing centers, where all kinds of genetic material may be coming through one or more sequencing instruments 110 at the same time, all of which may be transferred into the system 1, such as over the cloud 50.

More specifically, as can be seen with respect to FIG. 41A, in various instances, one or a multiplicity of samples may be received within the system 1, and hence the system 1 may be configured for receiving and efficiently processing the samples, either sequentially or in parallel, such as in a multi sample processing regime. Accordingly, to streamline and/or automate multi sample processing, the system may be controlled by a comprehensive Workflow Management System (WMS) or LIMS (laboratory information management system) 151. The WMS 151 enables users to easily schedule multiple workflow runs for any pipeline, as well as to adjust or accelerate NGS analysis algorithms, platform pipelines, and their attendant applications.

In such an instance, each run sequence may have a bar code on it indicating the type of sequence it is, the file format, and/or what processing steps have been performed, and what processing steps need to be performed. For instance, the bar code may include a manifest indicating "this is a genome run, of subject X, in file format Y, so this data has to go through pipeline Z," or likewise may indicate "this is A's result data that needs to go in this reporting system." Accordingly, as the data is received, processed, and transmitted through the system, the bar codes and results will get loaded into the workflow management system 151, such as LIMS (laboratory information management system). LIMS, in this instance, may be a standard tool that is employed for the management of laboratories, or it may be a specifically designed tool used for managing process flow.

In any instance, the workflow management controller 151 tracks a bar-coded sample from when it arrives in a given site, e.g., for storage and/or processing, until the results are sent out to the user. Particularly, the workflow management controller 151 is configured to track all data as it flows through the system end-to-end. More particularly, as the sample comes in, the bar code associated with the sample is read, and based on that reading the system determines what the requested work flows are, and prepares the sample for processing. Such processing may be simple, such as being run through a single genome pipeline, or it may be more complex, such as by being run through multiple, e.g., five pipelines, that need to be stitched together. In one particular model the generated or received data may be run through the system to produce processed data, the processed data may then be run through a GATK equivalent module, the results may be compared, and then the sample may be transmitted to another pipeline for further, e.g., tertiary processing 700. See FIG. 41B.

Hence, the system as a whole can be run in accordance with several different processing pipelines. In fact, many of the system processes can be interconnected, where the workflow manager 151 is notified or otherwise determines that a new job is pending, quantifies the job matrices, identifies available resources for performing the required analyses, loads the job into the system, receives the data coming in, e.g., off the sequencer 110, loads it in, and then processes it. Particularly, once the workflow is set up, it can be saved, and then a modified bar code gets assigned to that workflow, and the automated process takes place in accordance with the directives of the workflow.

Prior to the present automated workflow management system 151, it would take a number of Bioinformaticians a long period of time to configure and set up the system, and its component parts, and it would then require further time for actually running the analysis. To make matters more complicated, the system would have to be reconfigured prior to receiving the next sample to analyze, requiring even more time to reconfigure the system for analyzing the new sample set. With the technology disclosed herein the system can be entirely automated. The present system, particularly, is configured so as to automatically receive multiple samples, map them to multiple different workflows and pipelines, and run them on the same or multiple different system cards.

Accordingly, the workflow management system 151 reads the job requirements of the bar codes, allocates resources for performing the jobs, e.g., regardless of location, updates the sample barcode, and directs the samples to the allocated resources, e.g., processing units, for processing. Hence, it is the workflow manager 151 that determines the secondary 600 and/or tertiary 700 analyses protocols that will be run on the received samples. These processing units are resources that are available for delineating and performing the operations allocated to each data set. Particularly, the work flow controller 151 controls the various operations associated with receiving and reading the sample, determining jobs, allocating resources for the performance of those jobs, e.g., secondary processing, connecting all system components, and advancing the sample set through the system from component to component. The controller 151, therefore, acts to manage the overall system from start to finish, e.g., from sample receipt to VCF generation, and/or through to tertiary processing, see FIG. 41B.

Figure 41C:
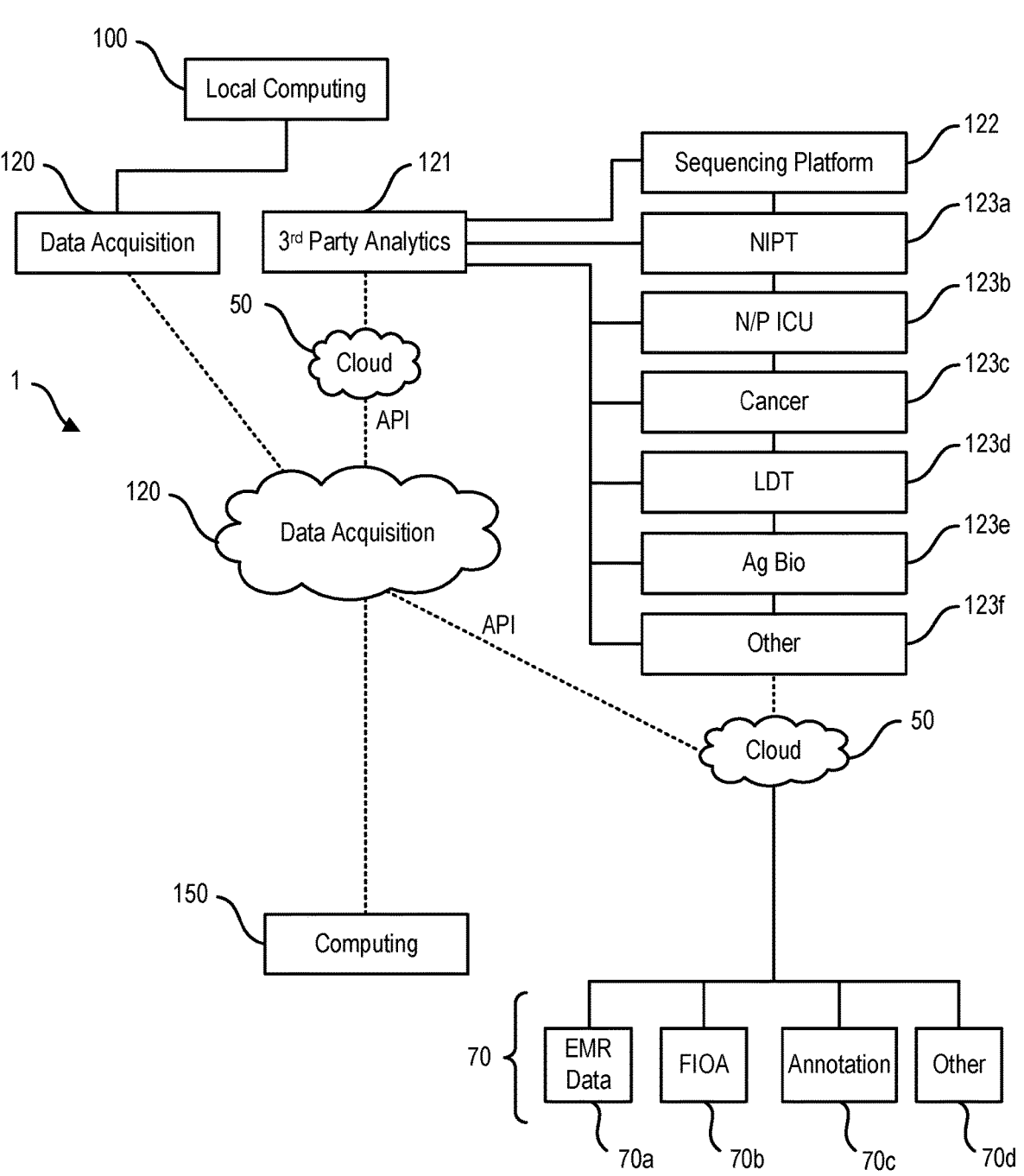
FIG. 41C depicts the block diagram of FIG. 40 illustrating greater detail regarding the 3rd-Party analytics function for a genomic infrastructure for onsite and/or cloud based genomics processing and analysis.

In additional instances, as can be seen with respect to FIG. 41C, the system 1 may include a further tier of processing modules 800, such as configured for rendering additional processing, e.g., of the secondary and/or tertiary processing results data, such as for diagnosis, disease and/or therapeutic discovery, and/or prophylaxis thereof. For instance, in various instances, an additional layer of processing 800 may be provided, such as for disease diagnostics, therapeutic treatment, and/or prophylactic prevention 70, such as including NIPT 123a, NICU 123b, Cancer 123c, LDT 123d, AgBio 123e, and other such disease diagnostics, prophylaxis, and/or treatments employing the data generated by one or more of the present primary and/or secondary and/or tertiary pipelines.

Accordingly, herein presented is a system 1 for producing and using a local 30 and/or global hybrid 50 cloud network. For instance, presently, the local cloud 30 is used primarily for private storage, such as at a remote storage location 400. In such an instance, the computing of data is performed locally 100 by a local computing resource 140, and where storage needs are extensive, the local cloud 30 may be accessed so as to store the data generated by the local computing resource 140, such as by use of a remote private storage resource 400. Hence, generated data is typically managed wholly on site locally 100. In other embodiments, data may be generated, computed, and managed completely offsite by securely connecting to a remote computing resource 300 via a private cloud interface 30.

Particularly, in a general implementation of a bioinformatics analysis platform, the local computing 140 and/or storage 200 functions are maintained locally on site 100. However, where storage needs exceed local storage capacity, the data may be uploaded via a local cloud access 30 so as to be stored privately off site 400. Further, where there is a need for stored data 400 to be made available to other remote users, such data may be transferred and made available via a global cloud 50 interface for remote storage 400 thereby, but for global access. In such an instance, where the computing resources 140 required for performance of the computing functions are minimal, but the storage requirements extensive, the computing function 140 may be maintained locally 100, while the storage function 400 may be maintained remotely, e.g., for either private or global access, with the fully processed data being transferred back and forth between the local processing function 140, such as for local processing only, and the storage function 400, such as for the remote storage 400 of the processed data, such as by employing the JIT protocols disclosed herein above.

For instance, this may be exemplified with respect to the sequencing function 110, such as with a typical NGS, where the data generation and/or computing resource 100 is configured for performing the functions required for the sequencing of the genetic material so as to produce genetic sequenced data, e.g., reads, which data is produced onsite 100 and/or transferred onsite locally 30. These reads, once generated, such as by the onsite NGS, may then be transferred, e.g., as a BCL or FASTQ file, over the cloud network 30, such as for storage 400 at a remote location 300 in a manner so as to be recalled from the cloud 30 when necessary, such as for further processing. For example, once the sequence data has been generated and stored, e.g., 400, the data may then be recalled, e.g. for local usage, such as for the performance of one or more of secondary 600 and/or tertiary 700 processing functions, that is at a location remote from the storage facility 400, e.g., locally 100. In such an instance, the local storage resource 200 serves merely as a storage cache where data is placed while waiting transfer to or from the cloud 30/50, such as to or from the remote storage facility 400.

Likewise, where the computing function is extensive, such as requiring one or more remote computing servers or computing cluster cores 300 for processing the data, and where the storage demands for storing the processed data 200 are relatively minimal, as compared to the computing resources 300 required to process the data, the data to be processed may be sent, such as over the cloud 30, so as to be processed by a remote computing resource 300, which resource may include one or more cores or clusters of computing resources, e.g., one or more super computing resources. In such an instance, once the data has been processed by the cloud based computer core 300, the processed data may then be transferred over the cloud network 30 so as to be stored locally 200 and made readily available for use by the local computing resource 140, such as for local analysis and/or diagnostics. Of course, the remotely generated data 300 may also be stored remotely 400.

This may further be exemplified with respect to a typical secondary processing function 600, such as where the pre-processed sequenced data, e.g., read data, is stored locally 200, and is accessed, such as by the local computing resource 100, and transmitted over the cloud internet 30 to a remote computing facility 300 so as to be further processed thereby, e.g., in a secondary 600 or tertiary 700 processing function, to obtain processed results data that may then be sent back to the local facility 100 for storage 200 thereby. This may be the case where a local practitioner generates sequenced read data using a local data generating resource 110, e.g., automated sequencer, so as to produce a BCL or FASTQ file, and then sends that data over the network 50 to a remote computing facility 300, which then runs one or more functions on that data, such as a Burrows-Wheeler transform or Needlemen-Wunsch and/or Smith-Waterman alignment function on that sequence data, so as to generate results data, e.g., in a SAM file format, that may then be compressed and transmitted over the internet 30/50, e.g., as a BAM file, to the local computing resource 100 so as to be examined thereby in one or more local administered processing protocols, such as for producing a VCF, which may then be stored locally 200. In various instances the data may also be stored remotely 400.

What is needed, however, is a seamless integration between the engagement between local 100 and remote 300 computer processing as well as between local 200 and remote 400 storage, such as in the hybrid cloud 50 based system presented herein. In such an instance, the system can be configured such that local 100 and remote 300 computing resources are configured so as to run seamlessly together, such that data to be processed thereby can be allocated real time to either the local 200 or the remote 300 computing resource without paying an extensive penalty due to transfer rate and/or in operational efficiency. This may be the case, for instance, where the software and/or hardware and/or quantum processing to be deployed or otherwise run by the computing resources 100 and 300 are configured so as to correspond to one another and/or are the same or functionally similar, e.g., the hardware and/or software is configured in the same manner so as to run the same algorithms in the same manner on the generated and/or received data.

For instance, as can be seen with respect to FIG. 41A a local computing resource 100 may be configured for generating or for receiving generated data, and therefore may include a data generating mechanism 110, such as for primary data generation and/or analysis 500, e.g., so as to produce a BCL and/or a FASTQ sequence file. This data generating mechanism 110 may be or may be associated with a local computer 100, as described herein throughout, having a processor 140 that may be configured to run one or more software applications and/or may be hardwired so as to perform one or more algorithms such as in a wired configuration on the generated and/or acquired data. For example, the data generating mechanism 110 may be configured for one or more of generating data, such as sequencing data 111. In various embodiments, the generated data may be sensed data 111*a*, such as data that is detectable as a change in voltage, ion concentration, electromagnetic radiation, and the like; and/or the data generating mechanism 110 may be configured for generating and/or processing signal, e.g., analog or digital signal data, such as data representing one or more nucleotide identities in a sequence or chain of associated nucleotides. In such an instance, the data generating mechanism 110, e.g., sequencer 111, may further be configured for performing preliminarily processing on the generated data so as for signal processing 111*b* or to perform one or more base call operations 111*c*, such as on the data so as to produce sequence identity data, e.g., a BCL and/or FASTQ file 111*d*.

It is to be noted that in this instance, the produced data 111 may be generated locally and directly, such as by a local data generating 110 and/or computing resource 140, e.g., an NGS or sequencer on a chip. Alternatively, the data may be produced locally and indirectly, e.g., by a remote computing and/or generating resource, such as a remote NGS. The data 111, e.g., in BCL and/or FASTQ file format, once produced may then be transferred indirectly over the local cloud 30 to the local computing resource 100 such as for secondary processing 140 and/or storage thereby in a local storage resource 200, such as while awaiting further local processing 140. In such an instance, where the data generation resource is remote from the local processing 100 and/or storage 200 resources, the corresponding resources may be configured such that the remote and/or local storage, remote and local processing, and/or communicating protocols employed by each resource may be adapted to smoothly and/or seamlessly integrate with one another, e.g., by running the same, similar, and/or equivalent software and/or by having the same, similar, and/or equivalent hardware configurations, and/or employing the same communications and/or transfer protocols, which, in some instances, may have been implemented at the time of manufacture or later thereto.

Specifically, in one implementation, these functions may be implemented in a hardwired configuration such as where the sequencing function and the secondary processing function are maintained upon the same or associated chip or chipset, e.g., such as where the sequencer and secondary processor are directly interconnected on a chip, as herein described. In other implementations, these functions may be implemented on two or more separate devices via software, e.g., on a quantum processor, CPU, or GPU that has been optimized to allow the two remote devices to communicate seamlessly with one another. In other implementations, a combination of optimized hardware and software implementations for performing the recited functions may also be employed.

More specifically, the same configurations may be implemented with respect to the performance of the mapping, aligning, sorting, variant calling, and/or other functions that may be deployed by the local 100 and/or remote 300 computing resources. For example, the local computing 100 and/or remote 300 resources may include software and/or hardware configured for performing one or more secondary 600 tiers of processing functions 112-115, and/or or tertiary tiers 700/800 of processing functions, on locally and/or remotely generated data, such as genetic sequence data, in a manner that the processing and results thereof may be seamlessly shared with one another and/or stored thereby. Particularly, the local computing function 100 and/or the remote computing function 300 may be configured for generating and/or receiving primary data, such as genetic sequence data, e.g., in a BCL and/or a FASTQ file format, and running one or more secondary 600 and/or tertiary 700 processing protocols on that generated and/or acquired data. In such an instance, one or more of these protocols may be implemented in a software, hardware, or combinational format, such as run on a quantum processor, a CPU, and/or a GPU. For instance, the data generating 110 and/or the local 100 and/or the remote 300 processing resource may be configured for performing one or more of a mapping operation 112, an alignment operation 113, variant calling 115, or other related function 114 on the acquired or generated data in software and/or in hardware.

Accordingly, in various embodiments, the data generating resource, such as the sequencer 111, e.g., NGS or sequencer on a chip, whether implemented in software and/or in hardware, or a combination of the same, may further be configured to include an initial tier of processors 500 such as a scheduler, various analytics, comparers, graphers, releasers, and the like, so as to assist the data generator 111, e.g., sequencer, in converting biological information into raw read data, such as in a BCL or FASTQ file format 111*d*. Further, the local computing 100 resource, whether implemented in software and/or in hardware, or a combination of the same, may further be configured to include a further tier of processors 600 such as may include a mapping engine 112, or may otherwise include programming for running a mapping algorithm on the genetic sequence data, such as for performing a Burrows-Wheeler transform and/or other algorithms for building a hash table and/or running a hash function 112*a* on said data, such as for hash seed mapping, so as to generate mapped sequence data. Further still, the local computing 100 resource whether implemented in software and/or in hardware, or a combination of the same, may further be configured to include an initial tier of processors 600 such as may also include an alignment engine 113, as herein described, or may otherwise include programming for running an alignment algorithm on the genetic sequence data, e.g., mapped sequenced data, such as for performing a gapped and/or gapless Smith-Waterman alignment, and/or Needleman-Wunsch, or other like scoring algorithm 113*a* on said data, so as to generate aligned sequence data.

The local computing 100 and/or data generating resource 110 may also be configured to include one or more other modules 114, whether implemented in software and/or in hardware, or a combination of the same, which may be adapted to perform one or more other processing functions on the genetic sequence data, such as on the mapped and/or aligned sequence data. Thus, the one or more other modules may include a suitably configured engine 114, or otherwise include programming, for running the one or more other processing functions such as a sorting 114*a*, de-duplication 114*b*, recalibration 114*c*, local realignment 114*d*, duplicate marking 114*f*, Base Quality Score Recalibration 114*g* function(s) and/or a compression function (such as to produce a SAM, Reduced BAM, and/or a CRAM compression and/or decompression file) 114*e*, in accordance with the methods herein described. In various instances, one or more of these processing functions may be configured as one or more pipelines of the system 1.

Likewise, the system 1 may be configured to include a module 115, whether implemented in software and/or in hardware, or a combination of the same, which may be adapted for processing the data, e.g., the sequenced, mapped, aligned, and/or sorted data in a manner such as to produce a variant call file 116. Particularly, the system 1 may include a variant call module 115 for running one or more variant call functions, such as a Hidden Markov Model (HMM) and/or GATK function 115*a* such as in a wired configuration and/or via one or more software applications, e.g., either locally or remotely, and/or a converter 115*b* for the same. In various instances, this module may be configured as one or more pipelines of the system 1.

In particular embodiments, as set forth in FIG. 41B, the system 1 may include a local computing function 100 that may be configured for employing a computer processing resource 150 for performing one or more further processing functions on data, e.g., BCL and/or FASTQ data, generated by the system data generator 110 or acquired by the system acquisition mechanism 120 (as described herein), such as by being transferred thereto, for instance, by a third party 121, such as via a cloud 30 or hybrid cloud network 50. For example, a third-party analyzer 121 may deploy a remote computing resource 300 so as to generate relevant data in need of further processing, such as genetic sequence data or the like, which data may be communicated to the system 1 over the network 30/50 so as to be further processed. This may be useful, for instance, where the remote computing resource 300 is a NGS, configured for taking raw biological data and converting it to a digital representation thereof, such as in the form of one or more FASTQ files containing reads of genetic sequence data; and where further processing is desired, such as to determine how the generated sequence of an individual differs from that of one or more reference sequences, as herein described, and/or it is desired to subject the results thereof to furthered, e.g., tertiary, processing.

In such an instance, the system 1 may be adapted so as to allow one or more parties, e.g., a primary and/or secondary and/or third party user, to access the associated local processing resources 100, and/or a suitably configured remote processing resource 300 associated therewith, in a manner so as to allow the user to perform one or more quantitative and/or qualitative processing functions 152 on the generated and/or acquired data. For instance, in one configuration, the system 1 may include, e.g., in addition to primary 500 and/or secondary 600 processing pipelines, a third tier of processing modules 700/800, which processing modules may be configured for performing one or more processing functions on the generated and/or acquired primary and/or secondary processed data.

Particularly, in one embodiment, the system 1 may be configured for generating and/or receiving processed genetic sequence data 111 that has been either remotely or locally mapped 112, aligned 113, sorted 114a, and/or further processed 114 so as to generate a variant call file 116, which variant call file may then be subjected to further processing such as within the system 1, such as in response to a second and/or third party analytics requests 121. More particularly, the system 1 may be configured to receive processing requests from a third party 121, and further be configured for performing such requested secondary 600 and/or tertiary processing 700/800 on the generated and/or acquired data. Specifically, the system 1 may be configured for producing and/or acquiring genetic sequence data 111, may be configured for taking that genetic sequence data and mapping 112, aligning 113, and/or sorting 114a it and processing it to produce one or more variant call files (VCFs) 116, and additionally the system 1 may be configured for performing a tertiary processing function 700/800 on the data, e.g., with respect to the one or more VCFs generated or received by the system 1.

Particularly, the system 1 may be configured so as to perform any form of tertiary processing 700 on the generated and/or acquired data, such as by subjecting it to one or more pipeline processing functions 700 such as to generate genome, e.g., whole genome, data 122a, epigenome data 122b, metagenome data 122c, and the like, including genotyping, e.g., joint genotyping, data 122d, variants analyses data, including GATK 122e and/or MuTect2 122f analysis data, among other potential data analytic pipelines, such as a micro-array analysis pipeline, exome analysis pipeline, microbiome analysis pipeline, RNA sequencing pipelines, and other genetic analyses pipelines. Further, the system 1 may be configured for performing an additional tier of processing 800 on the generated and/or processed data, such as including one or more of non-invasive prenatal testing (NIPT) 123a, N/P ICU 123b, cancer related diagnostics and/or therapeutic modalities 123c, various laboratory developed tests (LDT) 123d, agricultural biological (Ag Bio) applications 123e, or other such health care related 123f processing function. See FIG. 41C.

Hence, in various embodiments, where a primary user may access and/or configure the system 1 and its various components directly, such as through direct access therewith, such as through the local computing resource 100, as presented herein, the system 1 may also be adapted for being accessed by a secondary party, such as is connected to the system 1 via a local network or intranet connection 10 so as to configure and run the system 1 within the local environment. Additionally, in certain embodiments, the system may be adapted for being accessed and/or configured by a third party 121, such as over an associated hybrid-cloud network 50 connecting the third party 121 to the system 1, such as through an application program interface (API), accessible as through one or more graphical user interface (GUI) components. Such a GUI may be configured to allow the third-party user to access the system 1, and using the API to configure the various components of the system, the modules, associated pipelines, and other associated data generating and/or processing functionalities so as to run only those system components necessary and/or useful to the third party and/or requested or desired to be run thereby.

Accordingly, in various instances, the system 1 as herein presented may be adapted so as to be configurable by a primary, secondary, or tertiary user of the system. In such an instance, the system 1 may be adapted to allow the user to configure the system 1 and thereby to arrange its components in such a manner as to deploy one, all, or a selection of the analytical system resources, e.g., 152, to be run on data that is either generated, acquired, or otherwise transferred to the system, e.g., by the primary, secondary, or third party user, such that the system 1 runs only those portions of the system necessary or useful for running the analytics requested by the user to obtain the desired results thereof. For example, for these and other such purposes, an API may be included within the system 1 wherein the API is configured so as to include or otherwise be operably associated with a graphical user interface (GUI) including an operable menu and/or a related list of system function calls from which the user can select and/or otherwise make so as to configure and operate the system and its components as desired.

In such an instance, the GUI menu and/or system function calls may direct the user selectable operations of one or more of a first tier of operations 600 including: sequencing 111, mapping 112, aligning 113, sorting 114a, variant calling 115, and/or other associated functions 114 in accordance with the teachings herein, such as with relation to the primary and/or secondary processing functions herein described. Further, where desired the GUI menu and/or system function calls may direct the operations of one or more of a second tier of operations 700 including: a genome, e.g., whole genome, analysis pipeline 122a, epigenome pipeline 122b, metagenome pipeline 122c, a genotyping, e.g., joint, genotyping pipeline 122d, variants pipelines, e.g., GATK 122e and/or MuTect2 122f analysis pipelines, including structural variants pipelines, as well as other tertiary analyses pipelines, such as a micro-array analysis pipeline, exome analysis pipeline, microbiome analysis pipeline, RNA sequencing pipelines, and other genetic analyses pipelines. Furthermore, where desired the GUI menu and system function calls may direct the user selectable operations of one or more of a third tier of operations 800 including: non-invasive prenatal testing (NIPT) 123a, N/P ICU 123b, cancer related diagnostics and/or therapeutic modalities 123c, various laboratory developed tests (LDT) 123d, agricultural biological (Ag Bio) applications 123e, or other such health care related 123f processing functions.

Accordingly, the menu and system function calls may include one or more primary, secondary, and/or tertiary processing functions, so as to allow the system and/or its component parts to be configured such as with respect to performing one or more data analysis pipelines as selected and configured by the user. In such an instance, the local computing resource 100 may be configured to correspond to and/or mirror the remote computing resource 300, and/or likewise the local storage resource 200 may be configured to correspond and/or mirror the remote storage resource 400 so that the various components of the system may be run and/or the data generated thereby may be stored either locally or remotely in a seamless distributed manner as chosen by the use of the system 1. Additionally, in particular embodiments, the system 1 may be made accessible to third parties, for running proprietary analysis protocols 121a on the generated and/or processed data, such as by running through an artificial intelligence interface designed to find correlations there between.

The system 1 may be configured so as to perform any form of tertiary processing on the generated and/or acquired data. Hence, in various embodiments, a primary, secondary, or tertiary user may access and/or configure any level of the system 1 and its various components either directly, such as through direct access with the computing resource 100, indirectly, such as via a local network connection 30, or over an associated hybrid-cloud network 50 connecting the party to the system 1, such as through an appropriately configured API having the appropriate permissions. In such an instance, the system components may be presented as a menu, such as a GUI selectable menu, where the user can select from all the various processing and storage options desired to be run on the user presented data. Further, in various instances, the user may upload their own system protocols so as to be adopted and run by the system so as to process various data in a manner designed and selected for by the user. In such an instance, the GUI and associated API will allow the user to access the system 1 and using the API add to and configure the various components of the system, the modules, associated pipelines, and other associated data generating and/or processing functionalities so as to run only those system components necessary and/or useful to the party and/or requested or desired to be run thereby.

With respect to FIG. 41C, one or more of the above demarcated modules, and their respective functions and/or associated resources, may be configured for being performed remotely, such as by a remote computing resource 300, and further be adapted to be transmitted to the system 1, such as in a seamless transfer protocol over a global cloud based internet connection 50, such as via a suitably configured data acquisition mechanism 120. Accordingly, in such an instance, a local computing resource 100 may include a data acquisition mechanism 120, such as configured for transmitting and/or receiving such acquired data and/or associated information.

For instance, the system 1 may include a data acquisition mechanism 120 that is configured in a manner so as to allow the continued processing and/or storage of data to take place in a seamless and steady manner, such as over a cloud based network 50 where the processing functions are distributed both locally 100 and/or remotely 300. Likewise, where one or more of the results of such processing may be stored locally 200 and/or remotely 400, such that the system seamlessly allocates to which local or remote resource a given job is to be sent for processing and/or storage regardless of where the resource is physically positioned. Such distributed processing, transferring, and acquisition may include one or more of sequencing 111, mapping 112, aligning 113, sorting 114a, duplicate marking 114c, deduplication, recalibration 114d, local realignment 114e, Base Quality Score Recalibration 114f function(s) and/or a compression function 114g, as well as a variant call function 116, as herein described. Where stored locally 200 or remotely 400, the processed data, in whatever state it is in in the process may be made available to either the local 100 or remote processing 300 resources, such as for further processing prior to re-transmission and/or re-storage.

Specifically, the system 1 may be configured for producing and/or acquiring genetic sequence data 111, may be configured for taking that genetic sequence data and processing it locally 140, or transferring the data over a suitably configured cloud 30 or hybrid cloud 50 network such as to a remote processing facility for remote processing 300. Further, once processed the system 1 may be configured for storing the processed data remotely 400 or transferring it back for local storage 200. Accordingly, the system 1 may be configured for either local or remote generation and/or processing of data, such as where the generation and/or processing steps may be from a first tier of primary and/or secondary processing functions 600, which tier may include one or more of: sequencing 111, mapping 112, aligning 113, and/or sorting 114a so as to produce one or more variant call files (VCFs) 116.

Further, the system 1 may be configured for either local or remote generation and/or processing of data, such as where the generation and/or processing steps may be from a second tier of tertiary processing functions 700, which tier may include one or more of generating and/or acquiring data pursuant to a genome pipeline 122a, epigenome pipeline 122b, metagenome pipeline 122c, a genotyping pipeline 122d, variants, e.g., GATK 122e and/or MuTect2, analysis 122f pipeline, as well as other tertiary analyses pipelines, such as a micro-array analysis pipeline, a microbiome analysis pipeline, an exome analysis pipeline, as well as RNA sequencing pipelines and other genetic analyses pipelines. Additionally, the system 1 may be configured for either local or remote generation and/or processing of data, such as where the generation and/or processing steps may be from a third tier of tertiary processing functions 800, which tier may include one or more of generating and/or acquiring data related to and including: non-invasive prenatal testing (NIPT) 123a, N/P ICU 123b, cancer related diagnostics and/or therapeutic modalities 123c, various laboratory developed tests (LDT) 123d, agricultural biological (Ag Bio) applications 123e, or other such health care related 123f processing functions.

In particular embodiments, as set forth in FIG. 41C, the system 1 may further be configured for allowing one or more parties to access the system and transfer information to or from the associated local processing 100 and/or remote 300 processing resources as well as to store information either locally 200 or remotely 400 in a manner that allows the user to choose what information get processed and/or stored where on the system 1. In such an instance, a user can not only decide what primary, secondary, and/or tertiary processing functions get performed on generated and/or acquired data, but also how those resources get deployed, and/or where the results of such processing gets stored. For instance, in one configuration, the user may select whether data is generated either locally or remotely, or a combination thereof, whether it is subjected to secondary processing, and if so, which modules of secondary processing it is subjected to, and/or which resource runs which of those processes, and further may determine whether the then generated or acquired data is further subjected to tertiary processing, and if so, which modules and/or which tiers of tertiary processing it is subjected to, and/or which resource runs which of those processes, and likewise, where the results of those processes are stored for each step of the operations.

Particularly, in one embodiment, the user may configure the system 1 of FIG. 41A so that the generating of genetic sequence data 111 takes place remotely, such as by an NGS, but the secondary processing 600 of the data occurs locally 100. In such an instance, the user can then determine which of the secondary processing functions occur locally 100, such as by selecting the processing functions, such as mapping 112, aligning 113, sorting 111, and/or producing a VCF 116, from a menu of available processing options. The user may then select whether the locally processed data is subjected to tertiary processing, and if so which modules are activated so as to further process the data, and whether such tertiary processing occurs locally 100 or remotely 300. Likewise, the user can select various options for the various tiers of tertiary processing options, and where any generated and/or acquired data is to be stored, either locally 200 or remotely 400, at any given step or time of operation.

More particularly, a primary user may configure the system to receive processing requests from a third party, where the third party may configure the system for performing such requested primary, secondary, and/or tertiary processing on generated and/or acquired data. Specifically, the user or second and/or third party may configure the system 1 for producing and/or acquiring genetic sequence data, either locally 100 or remotely 200. Additionally, the user may configure the system 1 for taking that genetic sequence data and mapping, aligning, and/or sorting it, either locally or remotely, so as to produce one or more variant call files (VCFs). Additionally, the user may configure the system for performing a tertiary processing function on the data, e.g., with respect to the one or more VCFs, either locally or remotely.

More particular still, the user or other party may configure the system 1 so as to perform any form of tertiary processing on the generated and/or acquired data, and where that processing is to occur in the system. Hence, in various embodiments, the first, second, and/or third party 121 user may access and/or configure the system 1 and its various components directly such as by directly accessing the local computing function 100, via a local network connection 30, or over an associated hybrid-cloud network 50 connecting the party 121 to the system 1, such as through an application program interface (API), accessible as through one or more graphical user interface (GUI) components. In such an instance, the third party user may access the system 1 and use the API to configure the various components of the system, the modules, associated pipelines, and other associated data generating and/or processing functionalities so as to run only those system components necessary and/or useful to the third party and/or requested or desired to be run thereby, and further allocate which computing resources will provide the requested processing, and where the results data will be stored.

Accordingly, in various instances, the system 1 may be configurable by a primary, secondary, or tertiary user of the system who can configure the system 1 so as to arrange its components in such a manner as to deploy one, all, or a selection of the analytical system resources to be run on data that the user either directly generates, causes to be generated by the system 1, or causes to be transferred to the system 1, such as over a network associated therewith, such as via the data acquisition mechanism 120. In such a manner, the system 1 is configurable so as to only run those portions of the system necessary or useful for the analytics desired and/or requested by the requesting party. For example, for these and other such purposes, an API may be included wherein the API is configured so as to include a GUI operable menu and/or a related list of system function calls that from which the user can select so as to configure and operate the system as desired.

Additionally, in particular embodiments, the system 1 may be made accessible to a primary user and/or third parties, such as governmental regulators, such as the Federal Drug Administration (FDA) 70b, or allow primary users and/or third parties to collate, compile, and/or access a data base of genetic information derived or otherwise acquired and/or compiled by the system 1 so as to form an electronic medical records (EMR) database 70a and/or to allow governmental access and/or oversight of the system, such as the FDA for Drug Development Evaluation. The system 1 may also be set up to conglomerate, compile, and/or annotate the data 70c and/or allow other high level users access thereto.

Accordingly, the system 1, and or its components, may be configured for being accessed by a remote user, such as a primary user or third party, and therefore, one or more of the computer resources 100 and/or 300 may include a user interface, and/or may further include a display device having a graphic user interface for allowing a potential user of the system to access the system so as to transmit sample data for entry into one or more of the BioIT pipelines disclosed herein, and/or for receiving results data therefrom. The GUI or other interface may be configured for allowing the user to manage the system components, e.g., via a suitably configured web portal, and to track sample processing progress, regardless of whether the computing resources to be engaged are available locally 100 or remotely 300. Accordingly, the GUI may list a set of jobs that may be performed, e.g., mapping 112, aligning 113, etc., and/or a set of resources for performing the jobs, and the user may self-select which jobs they want to run and by which resources. Hence, in an instance such as this, each individual user may build thereon a unique, or may use a predetermined, analysis workflow, such as by clicking on, dragging, or otherwise selecting the particular work projects they desire to be run.

For instance, in one use model, a dashboard is presented with a GUI interface that may include a plurality of icons representing the various processes that may be implemented and run on the system. In such an instance, a user can click on or drag the selected work process icons into a workflow interface, so as to build a desired workflow process, which once built may be saved and used to establish the control instructions for the sample set barcodes. Once the desired work projects have been selected, the work flow management controller 151 may configure the desired workflow processes (e.g., secondary analysis), and then identify and select the resources for performing the selected analysis.

Once the workflow analysis process begins, the dashboard may be viewed so as to track progress through the system. For example, the dashboard may indicate how much data is running through the system, what processes are being run on the data, how much has been accomplished, how much processing remains, what workflows have been completed, and which still need to be accessed, the latest projects to be run, and which runs have been completed. Essentially, full access to everything that's running on the system, or a sub-portion thereof, may be provided to the desktop.

Further, in various instances, the desktop may include various different user interfaces that may be accessible via one or more tabs. For instance, one tab for accessing the system controls may be a "local resources 100 tab," which when selected allows a user to select control functions that are capable of being implemented locally. Another tab may be configured for accessing "cloud resources 300," which when selected allows a user to select other control functions that are capable of being implemented remotely. Accordingly, in interacting with the dashboard, a user can select which resources to perform which tasks, and as such can increase or decrease resource usage as required so as to meet the project requirements.

Hence, as the computational complexity increases, and/or increased speed is desired, the user (or the system itself, e.g., WMS 151) can bring more and more resources online, as needed, such as by the mere click of a button, instructing the workflow manager to bring additional local 100 and/or cloud based 300 resources online, as needed to complete the task within the desired timeframe. In this manner, although the system is automated and/or controlled by the workflow manager controller 151, a user of the system can still set the control parameters, and when needed can bring cloud based resources 300 on line. Accordingly, the controller 151 can expand to the cloud 50/300 as needed to bring on line additional processing and/or storage resources 400.

In various instances, the desktop interface may be configured as a mobile application or "app" that is accessible via a mobile device and/or desktop computer. Consequently, in one aspect, a genomics market place, or cohort, may be provided so as to allow a plurality of users to collaborate in one or more research projects, so as to form an electronic cohort market place that is accessible via the dashboard app, e.g., a web based browser interface. As such, the system may provide an online forum for performing collaborative research and/or a market place for developing various analytical tools for analyzing genetic data, which system may be accessible directly via the system interface, or via the app, to allow remote control of the system by a user.

Figure 42A:
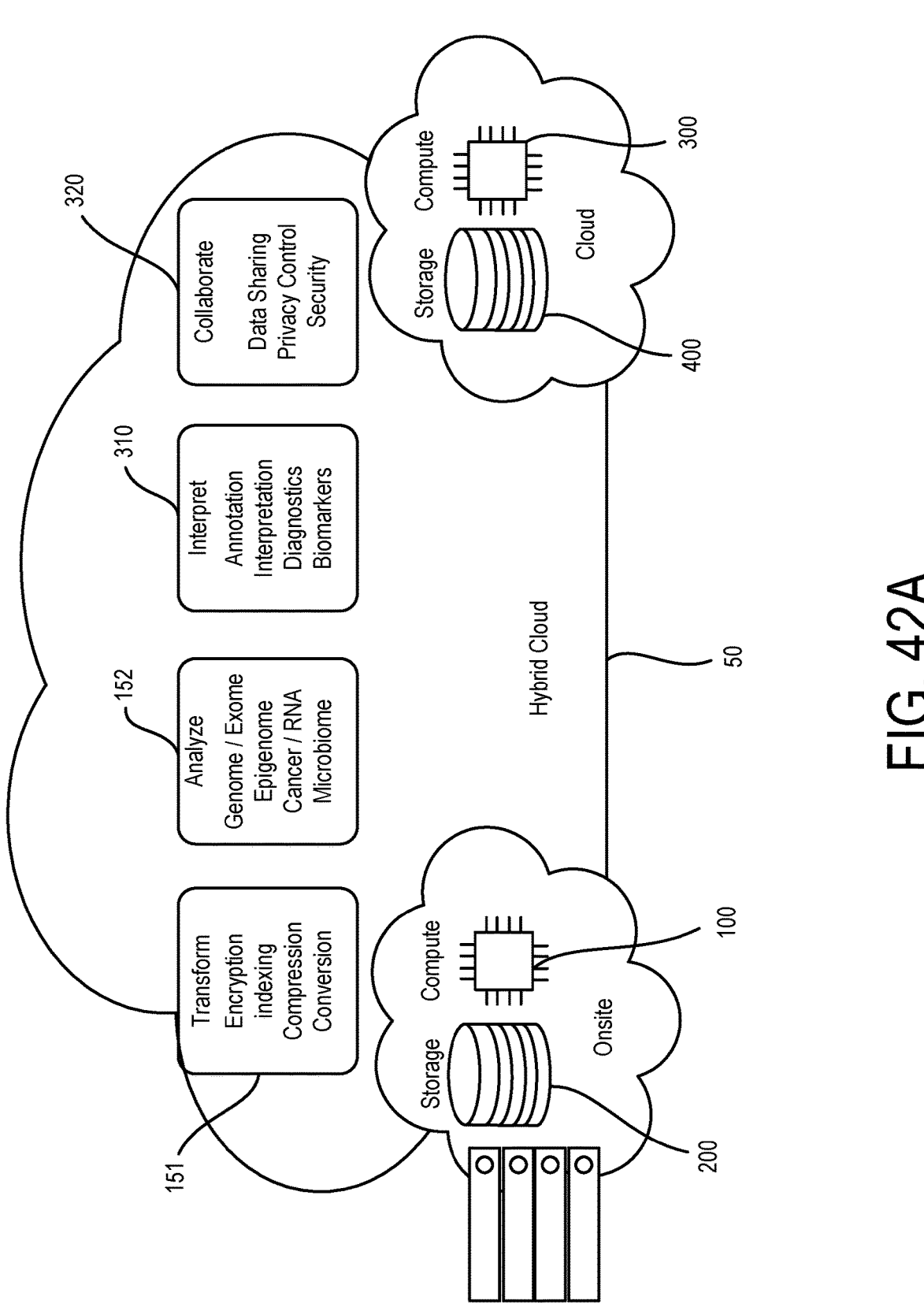
FIG. 42A depicts a block diagram illustrating a hybrid cloud configuration.

Accordingly, in various embodiments, as can be seen with respect to FIG. 42A, a hybrid cloud 50 is provided wherein the hybrid cloud is configured for connecting a local computing 100 and/or storage resource 200 with a remote computing 300 and/or storage 400 resource, such as where the local and remote resources are separated one from the other distally, spatially, geographically, and the like. In such an instance, the local and distal resources may be configured for communicating with one another in a manner so as to share information, such as digital data, seamlessly between the two. Particularly, the local resources may be configured for performing one or more types of processing on the data, such as prior to transmission across the hybrid network 50, and the remote resources may be configured for performing one or more types of further processing of the data.

For instance, in one particular configuration, the system 1 may be configured such that a generating and/or analyzing function 152 is configured for being performed locally 100 by a local computing resource, such as for the purpose of performing a primary and/or secondary processing function, so as to generate and/or process genetic sequence data, as herein described. Additionally, in various embodiments, the local resources may be configured for performing one or more tertiary processing functions on the data, such as one or more of genome, exome, and/or epigenome analysis, or a cancer, microbiome, and/or other DNA/RNA processing analysis. Further, where such processed data is meant to be transferred, such as to a remote computing 300 and/or storage 400 resource, the data may be transformed such as by a suitably configured transformer, which transformer may be configured for indexing, converting, compressing, and/or encrypting the data, such as prior to transfer over the hybrid network 50.

In particular instances, such as where the generated and processed data is transferred to a remote computing resource, e.g., server 300, for further processing, such processing may be of a global nature and may include receiving data from a plurality of local computing resources 100, collating such pluralities of data, annotating the data, and comparing the same, such as to interpret the data, determine trends thereof, analyzing the same for various biomarkers, and aiding in the development of diagnostics, therapeutics, and/or prophylactics. Accordingly, in various instances, the remote computing resource 300 may be configured as a data processing hub, such as where data from a variety of sources may be transferred, processed, and/or stored while waiting to be transformed and/or transferred, such as by being accessed by the local computing resource 100. More particularly, the remote processing hub 300 may be configured for receiving data from a plurality of resources 100, processing the same, and distributing the processed data back to the variety of local resources 100 so as to allow for collaboration amongst researchers and/or resources 100. Such collaboration may include various data sharing protocols, and may additionally include preparing the data to be transferred, such as by allowing a user of the system 1 to select amongst various security protocols and/or privacy settings so as to control how the data will be prepared for transfer.

Figure 42B:
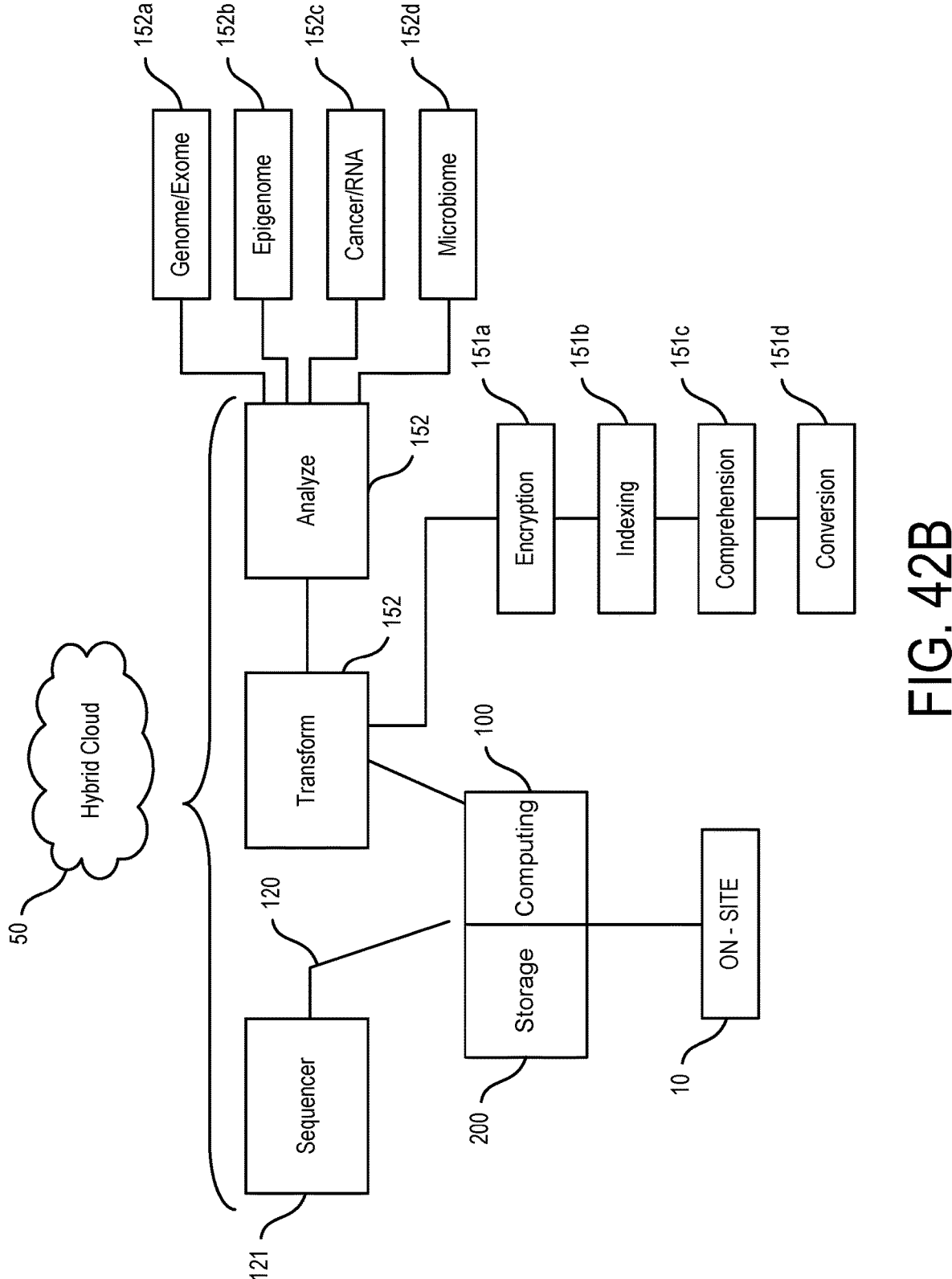
FIG. 42B depicts the block diagram of FIG. 42A in greater detail, illustrating a hybrid cloud configuration.

In one particular instance, as presented in FIG. 42B, a local computing 100 and/or storage 200 resource is provided, such as on-site at a user's location. The computing resource 100 and/or storage 200 resource may be coupled to a data generating resource 121, such as an NGS or sequencer on a chip, as herein described, such as over a direct or an intranet connection 10, where the sequencer 121 is configured for generating genetic sequencing data, such as BCL and/or FASTQ files. For instance, the sequencer 121 may be part of and/or housed in the same apparatus as that of the computing resource 100 and/or storage unit 200, so as to have a direct communicable and/or operable connection therewith, or the sequencer 121 and computing resource 100 and/or storage resource 200 may be part of separate apparatuses from one another, but housed in the same facility, and thus connected over a cabled or intranet 10 connection. In some instances, the sequencer 121 may be housed in a separate facility than that of the computing 100 and/or storage 200 resource and thus may be connected over an internet 30 or hybrid cloud connection 50.

In such instances, the genetic sequence data may be processed 100 and stored locally 200, prior to being transformed, by a suitably configured transformer, or the generated sequence data may be transmitted directly to one or more of the transformer and/or analyzer 152, such as over a suitably configured local connection 10, intranet 30, or hybrid cloud connection 50, as described above such as prior to being processed locally. Particularly, like the data generating resource 121, the transformer 151 and/or analyzer 152 may be part of and/or housed in the same apparatus as that of the computing resource 100 and/or storage unit 200, so as to have a direct communicable and/or operable connection therewith, or the transformer and/or analyzer 152 and computing resource 100 and/or storage resource 200 may be part of separate apparatuses from one another, but housed in the same facility, and thus connected over a cabled or intranet 10 connection. In some instances, the transformer 151 and/or analyzer 152 may be housed in a separate facility than that of the computing 100 and/or storage 200 resource and thus may be connected over an internet 30 or hybrid cloud connection 50.

For instance, the transformer may be configured for preparing the data to be transmitted either prior to analysis or post analysis, such as by a suitably configured computing resource 100 and/or analyzer 152. For instance, the analyzer 152 may perform a secondary and/or tertiary processing function on the data, as herein described, such as for analyzing the generated sequence data with respect to determining its genomic and/or exomic characteristics 152a, its epigenomic features 152b, any various DNA and/or RNA markers of interests and/or indicators of cancer 152c, and its relationships to one or more microbiomes 152d, as well as one or more other secondary and/or tertiary processes as described herein.

As indicated, the generated and/or processed data may be transformed, such as by a suitably configured transformer such as prior to transmission throughout the system 1 from one component thereof to another, such as over a direct, local 10, internet 30, or hybrid cloud 50 connection. Such transformation may include one or more of conversion 151d, such as where the data is converted from one form to another; comprehension 151c, including the coding, decoding, and/or otherwise taking data from an incomprehensible form and transforming it to a comprehensible form, or from one comprehensible form to another; indexing 151b, such as including compiling and/or collating the generated data from one or more resources, and making it locatable and/or searchable, such as via a generated index; and/or encryption 151a, such as creating a lockable and unlockable, password protected dataset, such as prior to transmission over an internet 30 and/or hybrid cloud 50.

Figure 42C:
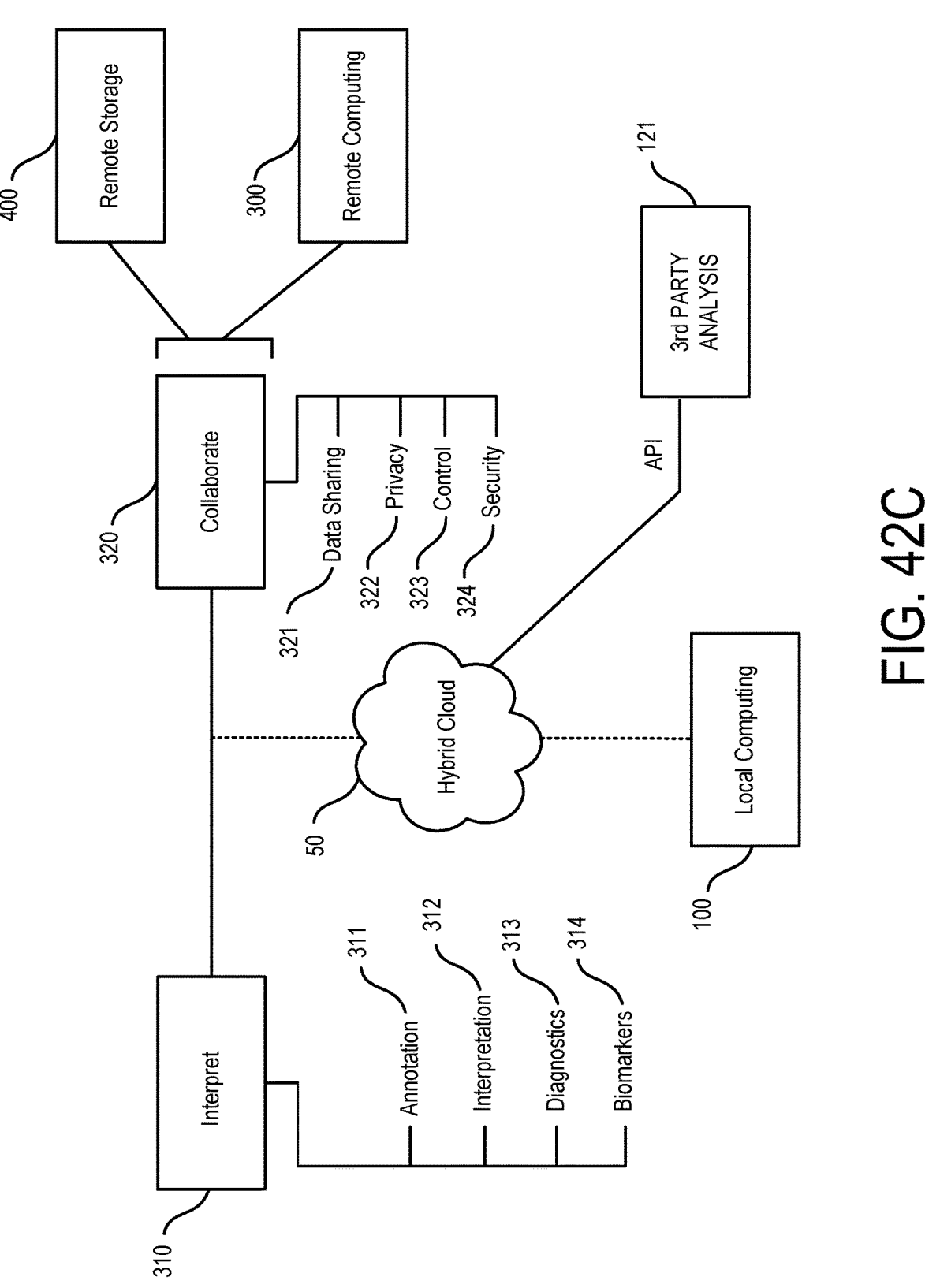
FIG. 42C depicts the block diagram of FIG. 42A in greater detail, illustrating a hybrid cloud configuration.

Hence, as can be seen with respect to FIG. 42C, in these and/other such instances, the hybrid cloud 50 may be configured for allowing seamless and protected transmission of data throughout the components of the system, such as where the hybrid cloud 50 is adapted to allow the various users of the system to configure its component parts and/or the system itself so as to meet the research, diagnostic, therapeutic and/or prophylactic discovery and/or development needs of the user. Particularly, the hybrid cloud 50 and/or the various components of the system 1 may be operably connected with compatible and/or corresponding API interfaces that are adapted to allow a user to remotely configure the various components of the system 1 so as to deploy the resources desired in the manner desired, and further to do so either locally, remotely, or a combination of the same, such as based on the demands of the system and the particulars of the analyses being performed, all the while being enabled to communicate in a secured, encryptable environment.

In particular instances, the system 1 may include a processing architecture 310, such as an interpreter, that is configured for performing an interpreting function 310. The interpreter 310 may perform one or a series of analytic functions on generated data, such as annotation 311, interpretation 312, diagnostics 313, and/or a detection and/or an analysis function for determining the presence of one or more biomarkers, such as in the genetic data. The interpreter 313 may be part of or separate from the local computing resource 100, such as where the interpreter 310 is coupled to the computing resource 100 via a cloud interface, such as a hybrid cloud 50.

Further an additional processing architecture 320 may be included, such as where the architecture 320 is configured as a collaborator. The collaborator 320 may be configured for performing one or more functions directed to ensuring the security and/or privacy of data to be transmitted. For instance, the collaborator may be configured for securing the data sharing process 321, for ensuring the privacy of transmission 322, setting control parameters 323, and/or for initiating a security protocol 324. The collaborator 313 is configured for allowing for the sharing of data, such as for facilitating the collaboration of processing, as such the collaborator 320 may be part of or separate from the local computing resource 100, such as where the collaborator 320 is coupled to the computing resource 100 via a cloud interface, such as a hybrid cloud 50. The interpreter 310, collaborator 320, and/or the local computing resource 100 may further be coupled to a remote computing resource 300, such as for enhancing system efficiency by offloading computing 300 and/or storage 400 functions into the cloud 50. In various instance, the system 1 may be configured for allowing secure third party analysis 121 to take place, such as where the third party can connect with and engage the system such as through a suitably configured API.

As can be seen with respect to FIG. 43, the system 1 may be a multi-tiered and/or multiplexed bioanalytical processing platform that includes layers of data generating and/or data processing units each having one or more processing pipelines that may be deployed in a systematic and concurrent or sequential manner so as to process genetic information from its primary processing stage to a secondary and/or tertiary processing stage. Particularly, presented herein are devices configured for performing bioanalysis in one or more of hardware and/or software and/or quantum processing implementations, as well as methods of their use, and systems including the same. For instance, in one embodiment, a genomics processing platform may be provided and configured as a multiplicity of integrated circuits, which integrated circuits may be adapted as, or otherwise be included within, one or more of a central or graphics processing unit, such as a general purpose CPU and/or GPU, a hardwired implementation, and/or a quantum processing unit. Particularly, in various embodiments, one or more pipelines of the genomics processing platform may be configured by one or more integrated and/or quantum circuits of a quantum processing unit.

Accordingly, the platforms herein presented may be configured so as to harnesses the tremendous power of optimized software and/or hardware and/or quantum processing implementations for the performance of the various genetic sequencing and/or secondary and/or tertiary processing functions, herein disclosed, which may be run on one or more integrated circuits. Such integrated circuits may be seamlessly coupled together and may further be seamlessly coupled to various other integrated circuits, e.g., CPUs and/or GPUs and/or QPUs, of the system that are configured for running the various software and/or hardwired based applications of tertiary bioanlytical functions.

Particularly, in various embodiments, these processes may be performed by optimized software run on a CPU, GPU, and/or QPU, and/or may be implemented as a firmware configured integrated circuit, e.g., an FPGA, which may be part of the same device or separate devices that may be positioned on the same motherboard, different PCIe cards within the same device, separate devices in the same facility, and/or located at different facilities. Accordingly, the one or more processing units and/or integrated circuits may be directly coupled together, e.g., tightly, such as by being physically incorporated into the same mother board, or separate mother boards positioned within the same housing and/or otherwise coupled together, or they may be positioned on separate motherboards or pCIE cards that are capable of communicating with one another remotely, such as wirelessly and/or via a networked interface, such as via a local cloud 30, and in various embodiments the one or more processing units and/or integrated circuits may be positioned geographically remotely from one another but communicable via a hybrid cloud 50. In particular instances, the integrated circuit(s) forming or being a part of the CPU, GPU, and/or QPU, which integrated circuit(s) may be arranged as and/or be a part of the secondary and/or tertiary analytics platform, may be configured so as to form one or more pipelines of analyses where the various data generated may be fed into and out of, back and forth between, the various processing units and/or integrated circuits, such as in a seamless and/or streaming fashion, so as to allow for the rapid transmission of data between the multiplicity of integrated circuit, and more particularly to expedite the analyses herein.

For instance, in some instances, the various devices for use in accordance with the methods disclosed herein may include, or otherwise be associated with, one or more sequencing devices, for performing a sequencing protocol, which sequencing protocol may be performed by software run on a remote sequencer, such as by a Next Gen sequencer, e.g., Illumina's HiSeq Ten, located in a core sequencing facility, such as made accessible via a cloud based interface. In other instances, the sequencing may be performed in a hardwired configuration run on a sequencing chip, such as implemented by Thermo Fisher's Ion Torrent, or other sequencer a chip technologies, where sequencing is performed by use of a semiconductor technology that delivers benchtop next gen sequencing, and/or by an integrated circuit configured as, or to otherwise include, a field effect transistor employing a graphene channel layer. In such instances, where the sequencing is performed by one or more integrated circuits configured as, or to include, a semiconducting sequencing microchip, the chip(s) may be positioned remotely from the one or more other processing units and/or integrated circuits disclosed herein, which may be configured for performing secondary and/or tertiary analytics on the sequenced data. Alternatively, the chips and/or processing units may be positioned relatively close to one another so as to be directly coupled together, or at least within the same general proximity of one another, such as within the same facility. In this and other such instances, a sequencing and/or BioIT analytics pipeline may be formed such that the raw sequencing data generated by the sequencer may be rapidly communicated, e.g., streamed, to the other analytic components of the pipeline for direct analysis, such as in a streaming manner.

Further, once the raw sequencing data (e.g., BCL data) or read data (e.g., FASTQ data) is produced by the sequencing instrument, this data may be transmitted to, and be received by, an integrated circuit configured for performing various bioanalytic functions on genetic and/or protein sequences, such as with respect to analyzing the generated and/or received DNA, RNA, and/or protein sequence data. This sequence analysis may involve the comparing of a generated or received nucleic acid or protein sequence to one or more databases of known sequences, such as for performing secondary analysis on the received data, and/or in some instances, for performing disease diagnostics, such as where the database of known sequences for performing the comparison may be a database containing morphologically distinct and/or abhorrent sequence data, that is data of genetic samples pertaining to or believed to pertain to one or more diseased states.

Accordingly, in various instances, once isolated and sequenced, the genetic, e.g., DNA and/or RNA, data may be subjected to secondary analysis, which may be performed on the received data, such as for the performance of mapping, aligning, sorting, variant calling, and/or the like, so as to generate mapped and/or aligned data that may then be used to derive one or more VCF detailing the difference between the mapped and/or aligned genetic sequence and a reference sequence. Particularly, once secondary processing has occurred, the genetic information may then be passed onto one or more tertiary processing modules of the system, such as for further processing thereby, such as to derive therapeutically and/or prophylactic results. More particularly, after variant calling, the mapper/aligner/variant caller may output a standard VCF file that is ready for and may be communicated to an additional integrated circuit for performing tertiary analysis, such as analyses related to genome, e.g., whole genome, analysis, genotyping, e.g., joint genotyping, analysis, micro-array analysis, exome analysis, microbiome analysis, an epigenome analysis, a metagenome analysis, a joint genotyping analysis, a variance analysis, e.g., a GATK analysis, structural variants analysis, somatic variants analysis, and the like, as well as an RNA-sequencing or other genomics analysis.

Hence, the bioanalytic, e.g., the BioIT, platform herein presented may include highly optimized algorithms for mapping, aligning, sorting, duplicate marking, haplotype variant calling, compression and/or decompression, such as in a software, hardwired, and/or a quantum processing configuration. For example, although one or more of these functions may be configured to be performed entirely or partially in a hardwired configuration, in particular instances, the secondary and/or tertiary processing platform may be configured for running one or more software and/or quantum processing applications, such as one or more programs directed at performing one or more bioanalytics functions, such as one or more of the functions disclosed herein below. Particularly, the sequenced and/or mapped and/or aligned and/or other processed data may then be further processed by one or more other highly optimized algorithms for one or more of whole genome analysis, genotyping analysis, microarray analysis, exome analysis, microbiome analysis, epigenome analysis, metagenome analysis, joint genotyping, and/or a variant, e.g., GATK analysis, such as implemented by software being run on a general purpose CPU and/or GPU and/or QPU, albeit in certain instances one or more of these functions may at least partially implemented in hardware.

Accordingly, as can be seen with reference to FIG. 43, in various embodiments, the multiplexed bioanalytical processing platforms are configured for performing one or more of primary, secondary, and/or tertiary processing. For example, the primary processing stage produces genetic sequence data, such as in one or more BCL and/or FASTQ files for transfer into the system 1. Once within the system 1 the sequenced genetic data, including any associated metadata, may be advanced to a secondary processing stage 600, so as to produce one or more variant call files. Hence, the system may also be configured to take the one or more variant call files along with any associated metadata, and/or or other associated processed data, and in one or more tertiary processing stages, may perform one or more other operations thereon, such as for the purposes of performing one or more diagnostics and/or prophylactic and/or therapeutic procedures there with.

Particularly, an analysis of the data may be initiated, e.g., in response to a user request 120, e.g., made from a remote computing resource 100, and/or in response to data submitted by the third party 121, and/or data automatically retrieved from a local 200 and/or remote 400 storage facility. Such further processing may include a first tier of processing wherein various pipeline run protocols 700 are configured to perform analytics on the determined genetic, e.g., variation, data of one or more subjects. For instance, a first tier of tertiary processing units may include a genomics processing platform that is configured to perform genome, epigenome, metagenome, genotyping, and/or various variant analysis, and/or other bioinformatics based analysis. Additionally, in a second tertiary processing tier, various disease diagnostic, research, and/or analysis protocols 800 may be performed, which analysis may include one or more of NIPT, NICU, cancer, LDT, biological, AgBio applications and the like.

The system 1 may further be adapted so as to receive and/or transmit various data 900 related to the procedures and processes herein disclosed such as related to electronic medical records (EMR) data, Federal Drug Administration testing and/or structuring data, data relevant to annotation, and the like. Such data may be useful so as to allow a user to make and/or allow access to generated medical, diagnostic, therapeutic, and/or prophylactic modalities developed through use of the system 1 and/or made accessible thereby. Accordingly, in various instances, the devices, methods, and systems presented herein allow for the secure performance of genetic and bioanalytic analysis, as well as for the secure transfer of the results thereof, in a forum that may be easily usable for downstream processing. Additionally, in various instances, the devices, methods, and systems presented herein allow for the secure transmission of data into the system, such as from one or more health monitoring and/or data storage facilities and/or from a government agency, such as the FDA or NIH. For example, the system may be configured for securely receiving EMR/PHR data, such as may be transmitted from a health care and/or storage facility for use in accordance with the methods disclosed herein, such for the performance of genetic and bioanalytic analysis, as well as for the secure transfer of the results thereof, in a forum that may be easily usable for downstream processing.

Particularly, the first tertiary processing tier 700 may include one or more genomics processing platforms, such as for performing genetics analysis, such as on mapped and/or aligned data, e.g., in a SAM or BAM file format, and/or for processing variant data, such as in a VCF format. For instance, the first tertiary processing platform may include one or more of a genome pipeline, epigenome pipeline, a metagenome pipeline, a joint genotyping pipeline, as well as one/or more variant analysis pipelines, including: a GATK pipeline, structural variant pipeline, somatic variant calling pipeline, and in some instances, may include an RNA-sequencing analysis pipeline. One or more other genomic analysis pipelines may also be included.

More specifically, with reference to FIG. 43, in various instances, the multi-tiered and/or multiplexed bioanalytical processing platform includes a further layer of data generation and/or processing units. For instance, in certain instances, the bioanalytical processing platform incorporates one or more processing pipelines, in one or more of software and/or hardware implementations, that are directed to performing one or more tertiary processing protocols. For example, in particular instances, a platform of tertiary processing pipelines 700 may include one or more of a genome pipeline, an epigenome pipeline, a metagenome pipeline, a joint genotyping pipeline, a variance pipeline, such as a GATK pipeline, and/or other pipelines, such as an RNA pipeline. Additionally, a second layer of the tertiary processing analyses platform may include a number of processing pipelines, such as one or more of a micro-array analysis pipeline, a genome, e.g., whole genome analysis pipeline, genotyping analysis pipeline, exome analysis pipeline, epigenome analysis pipeline, metagenome analysis pipeline, microbiome analysis pipeline, genotyping analysis pipeline, including joint genotyping, variants analyses pipeline, including structural variants pipelines, somatic variants pipelines, and GATK and/or MuTect2 pipelines, as well as RNA sequencing pipelines and other genetic analyses pipelines.

Accordingly, in one embodiment, the multi-tiered bioanalytical processing platform includes a metagenomics pipeline. For instance, a metagenomics pipeline may be included, such as for the performance of one or more environmental genomics processes. Particularly, in various embodiments, the metagenomics analysis may be configured for determining if a group of organisms evolved from a common ancestor, such as a species or other clade. More particularly, in various embodiments, an environmental sample containing a multiplicity of living and/or dead organisms within it may be obtained, from which the DNA/RNA present may be isolated, sequenced, and processed via, one or more of the processing platforms herein, so as to identify the particular species present and/or one or more other genomic factors relevant thereto. Such "environmental" samples may include a multiplicity of human microbiomes (e.g. related to the microorganisms that are found in association with both healthy and diseased humans, including microorganisms found in the skin, blood, sputum, stool samples) as well as external environmental agents.

There is a plurality of methods for deriving the sequenced genetic samples for performing metagenomic processing. A first method includes a targeted 16S ribosomal RNA cloning and/or gene sequencing protocol. For instance, 16S ribosomal RNA is highly variable across species (or even strains of one species). Accordingly, this RNA may be isolated and sequenced to produce a genetic profile of bio-diversity that is derived from naturally occurring biological samples, which may be used to inform the A/I or other databases of the system. However, a problem with such sequencing is that a large amount of microbial biodiversity may be missed simply due to the manner by which it has been cultivated.

Accordingly, a second method includes a shotgun and/or PCR directed protocol that may be used to generate samples of a plurality, e.g., all, genes from all biological agents of the sampled communities, which once sequenced may reveal the genetic diversity of microscopic life. Specifically, in the shotgun sequencing method, an aggregate reference sequence may be generated, e.g., from many (e.g., tens of thousands) of reference genomes of different species. However, the aggregate size of this many reference genomes is huge. Hence, it is advantageous to select one or more distinctive sub-sequences from each reference genome so as to build the aggregate reference sequence.

For instance, such a subsequence may range from several hundred bases to several thousand bases long, which ideally are unique sequences not occurring in other species (or strains). These subsequences may then be aggregated so as to construct the reference sequences. Accordingly, once isolated, sequenced, mapped and aligned, these metagenomic sequences can be compared against partial or full reference genomes for many species, and genetic biodiversity can be determined.

Hence, metagenomics offers a powerful lens for viewing the microbial world that can revolutionize our understanding of the living world. Consequently, in either of these instances, when there is a significant presence of an organisms DNA present in a sample, that species can be identified as being within that environment. Ideally, in a manner such as this, species not common to other species generally present in that environment may be identified. Specifically, when coverage of all species is normalized for the obtained environmental samples, genetic diversity of all species present can be determined and can be compared against the entire coverage, such as by comparing a portion of a particular organism's DNA to that of the generated biologically diverse reference genetic sequence.

The significance of these analyses can be determined by Bayesian methods, such as by estimating the probability of observing the sequenced reads of a particular organism, assuming a given species is or is not present. Bayesian probability methods are directed to describing the probability of an event, based on conditions that might be related to that event. For example, if one is interested in determining the presence of cancer in a subject, and if the subject's age is known, and if is determined that cancer is an age related disease, then, using Bayes' theorem, information about the subject's age can be used to more accurately assess the probability of cancer.

Specifically, with the Bayesian probability interpretation the theorem expresses how a subjective degree of belief can rationally change to account for the observed evidence. Bayes' theorem is stated mathematically as the following equation: $P(A/B)=P(B/A) \ P(A)/P(B)$ where A and B are events and $P(B) \neq 0$. $P(A)$ and $P(B)$ are the probabilities of observing A and B without regard to each other. $P(A|B)$, a conditional probability, is the probability of observing event A given that B is true. $P(B|A)$ is the probability of observing event B given that A is true.

Accordingly, one or more steps for performing a Bayesian Probability analyses in this context may include one or more of: Presence calls can be made for clades at various taxonomic levels: kingdom, phylum, class, order, family, genus, species, and/or strain. However, this is complicated by the fact that DNA tends to be increasingly similar between organisms sharing lower taxonomic levels. Additionally, often times a sample may match a reference genome from multiple species within a higher taxonomic level (or multiple strains of one species), and hence, in many instances, only a more general clade (such as a genus or family) can be called present unambiguously, rather than a specific species or strain. Nevertheless, the devices, systems, and methods of using the same disclosed herein can be employed to overcome these and other such difficulties.

Specifically, in one embodiment, a method for determining the presence of two or more species or clades of organisms from a sample is provided. For instance, in a first step, reads of genomic sequence data may be obtained from a sample, such as where the reads may be in a FASTQ or BCL format. Mapping of the genomic sequence may be performed so to map the reads to multiple genomic reference sequences. In this instance, the genomic reference sequences may be a whole genome, or may be a partial genome in order to reduce the amount of data required for each species, strain, or clade. However, using larger portions of a genome will increase the sensitivity of detection, and each reference sequence used should be selected to represent each species, strain, or clade that will be distinct from one another.

For this purpose, all or a portion of the genomic sequence from the 16S ribosome of each species or clade may be used. In this manner, two or more genomic reference sequences of species, strains, or clades of organisms suspected to be in the sample, may be built so as to detect members of these groups in the sample. Once built, an index for each of the genomic reference sequences may also be built. The indexes may be a hash table or a tree index, such as a prefix or suffix tree index. Once the index has been built, the sample genomic sequence reads may be compared with each of the two or more indexes. Then it may be determined if the sample genomic sequence reads map to each of the indexes.

Likewise, the reads of the genomic sequence may also be aligned to the genomic reference sequence(s) to which they are mapped. This will generate an alignment score, in accordance with the methods herein, which may be used in analyzing the probability that a read indicates the presence or absence of a species or clade of organism in the sample. Specifically, the mapping and/or aligning may be accomplished by the present software and/or hardware modules, as described herein. In some embodiments, the mapped and aligned data may then be communicated to the computing resource 100/300 for further analysis and processing.

For instance, the mapped and/or aligned genomic sequence reads may be analyzed to determine the likelihood that an organism having the genomic reference sequence is present in the sample. Likewise, a list of species, strains, or clades that are determined to be present in the environmental sample may be reported. In certain embodiments, the list may be reported with a confidence metric (e.g. P-value) so as to indicate the statistical confidence of the evaluation. The entire list of species, strains, or clades of organisms analyzed may also be reported, along with an indication of which species, strains, or clades were present, and a confidence metric. It is to be noted that although described with respect to the analysis of microbiomes, various of the techniques and procedures disclosed herein may be employed in the analysis of all other tertiary processing protocols, where appropriate.

Figure 43A:
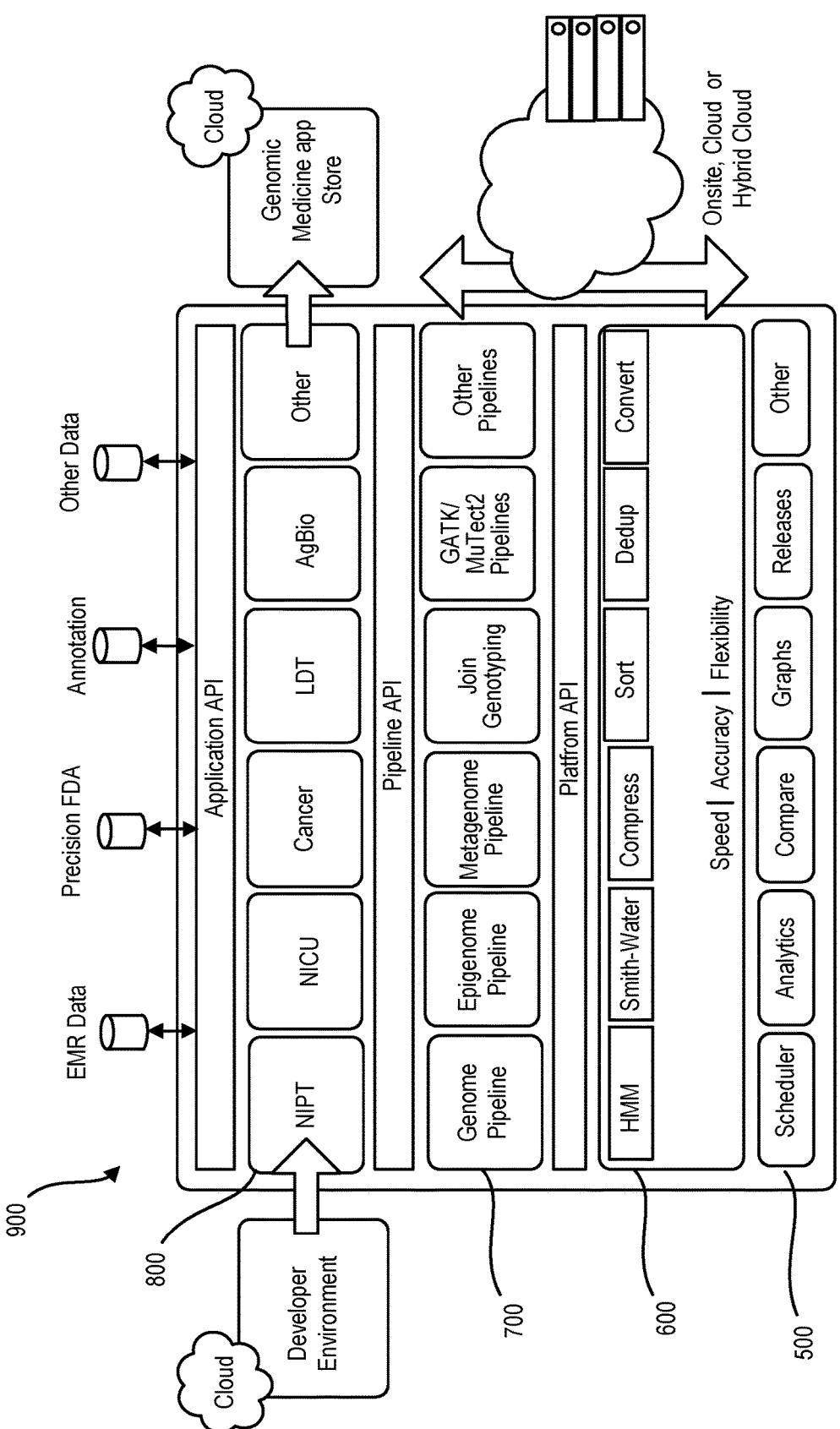
FIG. 43A depicts a block diagram illustrating a primary, secondary, and/or tertiary analysis pipeline as presented herein.
Figure 43C:
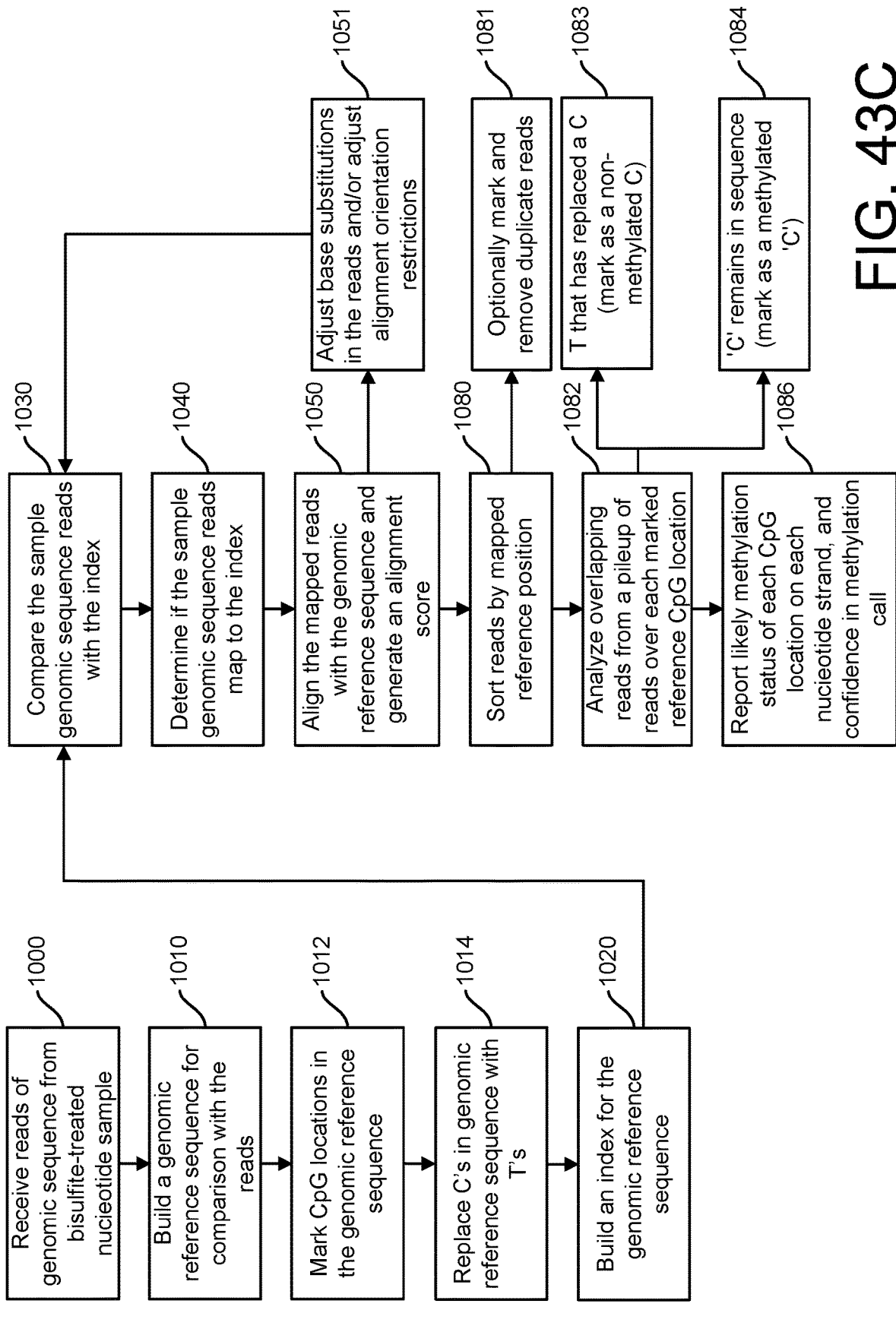
FIG. 43C provides an exemplary tertiary processing methylation analysis for execution by the methods and devices of the system herein.

For Instance, FIG. 43B sets forth an exemplary implementation of a method for performing environmental analysis, such as of microbiomes within an environmental sample. For example, in a first instance, an environmental sample may be obtained, and the various genetic material may be isolated therefrom. The various genetic material may then be processed and sequenced, such as via a suitably configured NGS.

Consequently, in a first step 1000, once the various genetic material has been sequenced, e.g., by an NGS, it may be transmitted to the system 1 disclosed herein. In step 1010, one, two, or more genomic reference sequences of interest, e.g., to be detected within the sample, may be built. At step 1020, an index for each of the one, two, or more genomic reference sequences may be built. Further, at step 1030, the obtained sequenced reads of the genomic sample may then be compared to the one, two, or more indexes, such as via a suitably configured mapping module. At step 1040, then it may be determined if the genomic sample of sequenced reads map to each of the two or more indexes.

At this point, if desired, at step 1050, the mapped reads may be aligned with the genomic reference sequences to generate an alignment and/or an alignment score. Accordingly, once the obtained genetic materials within the sample are mapped and/or aligned, at step 1060, the likelihood that a given organism having the reference sequence is present within the sample may be determined. And once processed a list of species, strains, and/or clades that are present in the sample may be identified and/or reported.

The tertiary processing platform disclosed herein may also include an epigenomic pipeline. Particularly, epigenetics studies the genetic effects not encoded in the DNA sequence of an organism. The term also refers to the changes themselves: functionally relevant changes to the genome that do not involve a change in the nucleotide sequence. Nevertheless, epigenetic changes are stably heritable phenotypes that result from changes in a chromosome that does not alter the DNA sequence. These alterations may or may not be heritable. Particularly, epigenetic changes modify the activation of certain genes, but not the genetic code sequence of DNA. It is the microstructure (not code) of DNA itself or the associated chromatin proteins may be modified, causing activation or silencing.

The epigenome is involved in regulating gene expression, development, tissue differentiation, and suppression of transposable elements. Unlike the underlying genome that is largely static within an individual, the epigenome can be dynamically altered by environmental conditions. The field is analogous to genomics and proteomics, which are the study of the genome and proteome of a cell. Additionally, epigenomics involves the study of the complete set of epigenetic modifications on the genetic material of a cell, known as the epigenome consisting of a record of the chemical changes to the DNA and histone proteins of an organism. These changes can be passed down to an organism's offspring via transgenerational epigenetic inheritance. Changes to the epigenome can result in changes to the structure of chromatin and changes to the function of the genome.

This epigenetic mechanism enables differentiated cells in a multicellular organism to express only the genes that are necessary for their own activity. Epigenetic changes are preserved when cells divide. Particularly, most epigenetic changes only occur within the course of one individual organism's lifetime. However, if gene inactivation occurs in a sperm or egg cell that results in fertilization, then some epigenetic changes can be transferred to the next generation. Several types of epigenetic inheritance systems may play a role in what has become known as cell memory. For instance, various covalent modifications of either DNA (e.g., cytosine methylation and hydroxymethylation) or of histone proteins (e.g. lysine acetylation, lysine and arginine methylation, serine and threonine phosphorylation, and lysine ubiquitination and sumoylation) may play central roles in many types of epigenetic inheritance. Because the phenotype of a cell or individual is affected by which of its genes are transcribed, heritable transcription states can give rise to epigenetic effects. Such effects on cellular and physiological phenotypic traits may result from external or environmental factors that switch genes on and off and affect how cells express genes.

For instance, DNA damage can cause epigenetic changes. DNA damage is very frequent. These damages are largely repaired, but at the site of a DNA repair, epigenetic changes can remain. In particular, a double strand break in DNA can initiate unprogrammed epigenetic gene silencing both by causing DNA methylation as well as by promoting silencing types of histone modifications (chromatin remodeling). Other examples of mechanisms that produce such changes are DNA methylation and histone modification, each of which alters how genes are expressed without altering the underlying DNA sequence. Nucleosome remodeling has also been found to cause epigenetic silencing of DNA repair. Further, DNA damaging chemicals, can also cause considerable hypomethylation of DNA, such as through the activation of oxidative stress pathways. Additionally, gene expression can be controlled through the action of repressor proteins that attach to silencer regions of the DNA.

These epigenetic changes may last through cell divisions for the duration of the cell's life, and may also last for multiple generations even though they do not involve changes in the underlying DNA sequence of the organism; instead, non-genetic factors cause the organism's genes to behave (or "express themselves") differently. One example of an epigenetic change in eukaryotic biology is the process of cellular differentiation. During morphogenesis, totipotent stem cells become the various pluripotent cell lines of the embryo, which in turn become fully differentiated cells. In other words, as a single fertilized egg cell—the zygote— continues to divide, the resulting daughter cells change into all the different cell types in an organism, including neurons, muscle cells, epithelium, endothelium of blood vessels, etc., by activating some genes while inhibiting the expression of others.

There are several layers of regulation of gene expression. One way that genes are regulated is through the remodeling of chromatin. Chromatin is the complex of DNA and the histone proteins with which it associates. If the way that DNA is wrapped around the histones changes, gene expression can change as well. A first way is post translational modification of the amino acids that make up histone proteins. Histone proteins are made up of long chains of amino acids. If the amino acids that are in the chain are changed, the shape of the histone might be modified. DNA is not completely unwound during replication. It is possible, then, that the modified histones may be carried into each new copy of the DNA. Once there, these histones may act as templates, initiating the surrounding new histones to be shaped in the new manner. By altering the shape of the histones around them, these modified histones would ensure that a lineage-specific transcription program is maintained after cell division.

The second way is the addition of methyl groups to the DNA, mostly at CpG sites, to convert cytosine to 5-methylcytosine. 5-Methylcytosine performs much like a regular cytosine, pairing with a guanine in double-stranded DNA. However, some areas of the genome are methylated more heavily than others, and highly methylated areas tend to be less transcriptionally active, through a mechanism not fully understood. Methylation of cytosines can also persist from the germ line of one of the parents into the zygote, marking the chromosome as being inherited from one parent or the other (genetic imprinting). Although histone modifications occur throughout the entire sequence, the unstructured N-termini of histones (called histone tails) are particularly highly modified. These modifications include acetylation, methylation, ubiquitylation, phosphorylation, sumoylation, ribosylation and citrullination.

Accordingly, DNA methylation is the presence of methyl groups on some DNA nucleotides, especially 'C' bases followed by 'G's, or "CpG" dinucleotides. Methylation in promotor regions tends to suppress gene expression. Methylation analysis is the process of detecting which 'C' bases are methylated in a given sample genome. Bisulfite sequencing (MethylC-seq) is the most common method of detecting methylation using whole-genome sequencing, where unmethylated cytosine ('C') bases are chemically converted to uracil ('U') bases, which become thymine (T) bases after PCR amplification. Methylated 'C' bases resist conversion.

Accordingly, in accordance with the devices and methods disclosed herein, detection of modifications of DNA molecules, where the modifications do not affect the DNA sequence, but do affect gene expression, are provided herein, such as by performing one or more mapping and/or aligning operations on epigenetic genetic material. In such methods, the obtained reads may be mapped and aligned to the reference genome in a manner allowing converted 'T' bases to align to reference 'C' positions, and 'C' bases may be replaced with 'T's in the reference sequence, prior to mapping/alignment. This allows for accurate mapping and alignment of the reads, which have bisulfite converted C's (now T's), thus revealing the non-bisulfite converted (methylated) C's in the genomic sequence reads. For reverse-complemented alignments, the complementary substitutions may be used, e.g., 'G's may be replaced with 'A's.

Likewise, the reference index (e.g. hash table) builder and the mapper/aligner may be modified to perform these substitutions automatically for MethylC-seq usage. Alternatively, the mapper/aligner may be modified to allow the forward alignment of read 'T's to reference 'C's, and the reverse-complemented alignment of read 'A's to reference 'G's. The methods disclosed herein improve accuracy, and prevent erroneous forward alignment of read 'C's to reference 'T's, or erroneous reverse-complemented alignment of read 'G's to reference 'A's.

Additionally, provided herein are methods for determining the methylation state of cytosine bases in genomic sequence reads. For instance, in a first step, reads of genomic sequence from bisulfite-treated nucleotide samples may be obtained. Particularly, one or more modified sequencing protocols may be employed so as to generate the reads for secondary processing, in these regards. Specifically, one or more of: whole genome bisulfate sequencing; reduced representation bisulfate sequencing; methylated DNA immunoprecipitation sequencing, and methylation-sensitive restriction enzyme sequencing may be used to identify DNA methylation across portions of the genome, at varying levels of resolution down to basepair level. Further, chromatin accessibility may be accessed, for instance, where DNase I hypersensitivity site sequencing may be performed, such as where the DNase I enzyme may be used to find open or accessible regions in the genome. Further, RNA-sequencing and expression arrays may be used to identify expression levels or protein coding genes. Particularly, smRNA-sequencing may be used to identify expression of small noncoding RNA, primarily miRNAs.

Consequently, once sequenced to produce reads, a genomic reference sequence may be built for comparison with the reads. CpG locations in the genomic reference sequence may then be marked. Further, the genomic reference sequence may be preprocessed by replacing C's in genomic with T's. An index for the genomic reference sequence may be built. And once the index has been built the sample genomic sequence reads may be compared with the index, and it may be determined if the sample epi-genomic sequence reads map to the index.

Further, the mapped reads may be aligned with the genomic reference sequence so as to generate an alignment score. In certain embodiments, base substitutions may be made in the read sequence, and the read may be re-compared and re-aligned with the index. In some embodiments, an alignment orientation restriction may be utilized during mapping and/or alignment of a read, such that only forward alignments may be permitted with C to T replacements in the read and genomic sequence reference, and only reverse-complement alignments are permitted with G to A replacements, in the read and genomic sequence reference.

These mapping and aligning procedures may be accomplished by the various software and/or hardware modules described herein. In some embodiments, the mapped and aligned data may then be communicated to a CPU/GPU/ QPU for further analysis and processing. For instance, the mapped and aligned reads may be sorted by their mapped reference position. In some embodiments, duplicate reads may be marked and removed. Overlapping reads from a pileup of reads may be analyzed over each marked reference CpG location. In such an instance, A thymine (T) that has replaced a cytosine (C) indicates a non-methylated cytosine and is marked as such. And a cytosine that remains in the read sequence may be marked as a methylated cytosine. Reverse-complemented alignments of CpG locations may also be marked as methylated or non-methylated. For example, a guanine (G) that has replaced an adenine (A) is marked as the reverse-complement of a non-methylated cytosine (C), while a guanine (G) that remains in the read sequence is marked as the reverse complement of a methylated cytosine (C). The likely methylation status of each CpG location on each nucleotide strand may be reported, and an associated confidence metric (e.g. p-value) in the methylation call may be made. In some embodiments, the methylation status of the marked CpG locations may also be indicated for each chromosome of a diploid pair of chromosomes.

With respect to histone modification, histone modification includes various naturally occurring chemical modifications of the histone proteins that DNA wraps around, resulting in the DNA wrapping more or less tightly. Loosely wrapped DNA, for instance, is associated with higher rates of gene expression. Such histone modifications may be determined by Chromatin Immunoprecipitation Sequencing (ChIP-Seq), which may be used to identify genome wide patterns of histone modifications, such as by using antibodies against the modifications. Further, ChIP-seq is a method that may be employed so as to isolate and sequence DNA that is tightly bound to histones (or other selected proteins). After ChIP-seq has been performed, the sample may be prepared, the DNA isolated and sequenced, and the sequenced DNA may then be mapped/aligned to a reference genome as disclosed herein, and the mapped coverage may be used to infer the level of histone binding at various loci in the genome. Additionally provided herein are methods of analyzing ChIP-derived nucleotide sequences, which is similar to the methods described below for analyzing structural variants.

Of special note is that epigenetics is useful in cancer research and diagnostics. For instance, human tumors undergo a major disruption of DNA methylation and histone modification patterns. In fact the aberrant epigenetic landscape of the cancer cell is characterized by a global genomic hypomethylation, CpG island promoter hypermethylation of tumor suppressor genes, an altered histone code for critical genes, and a global loss of monoacetylated and trimethylated histone H4. Accordingly, the methods disclosed herein may be used for the purposes of cancer research and/or diagnostics.

Further, the methods herein disclosed may be useful for generating one or more epigenomic databases and/or reference genomes. For example, the methods herein disclosed, e.g., employing an A/I learning protocol of the system, may be useful for generating a human reference of epigenomes, such as from normal, healthy individuals across a large variety of cell lines, primary cells, and/or primary tissues. Such data produced may then be used to enhance the mapping and/or aligning protocols disclosed herein. Furthermore, once a database of epigenomic differences has been generated, the database may be mined, e.g., by the A/I module so as to better characterize and determine relevant factors that occur in various disease states, such as cancer, dementia, Alzheimer's disease, and other neurological conditions.

Accordingly, in various instances, an epigenomics analysis may be performed, such as to identify one or more or the entire set of epigenetic modifications that have taken place on the genetic material of a cell. Particularly, employing the methods disclosed herein, the epigenome of an organism, and/or the cells thereof, may be determined, so as to catalog and/or record of the chemical changes to the DNA and histone proteins of the cells of the organism. For example, an exemplary epigenomic analysis is set forth herein in FIG. 43C.

For instance, in a first step, a genomic sample may be obtained from an organism, and the genetic material isolated therefrom and sequenced. Hence, once sequenced, at step 1000, the sequenced reads of the sample may be transmitted into and received by the system 1. In this instance, the reads may be derived from a bisulfate-treated nucleotide sample. Likewise, at step 1010, a genomic reference of sequences, e.g., for the organism, may be built such as for performing a comparison of the epigenomic sample reads. At step 1012, any various CpG locations in the genomic reference sequence(s) may be identified.

Once identified, at 1014, the "C's" of the CpG locations, in the reference, may be replaced with "Ts," and at step 1020, an index for the modified genomic reference sequence may be generated. Once the index for the modified reference is generated, at step 1030, the genomic sequence reads of the sample may be compared with the index, and at step 1040 it may be determined if the genomic sequence reads of the sample map to the index, such as by being mapped in accordance with the methods and apparatuses disclosed herein. The mapped reads may then be aligned with the genomic reference sequence, and an alignment score may be generated, such as by performing one or more alignment operations, as discussed herein.

At this point, one of a couple of various analyses may be performed. For instance, at step 1051, if greater context is desired, the base substitutions in the reads, as processed above, and/or the alignment orientation, and/or parameter restrictions may be adjusted, and the comparison steps 1030-1050 may be repeated. This process itself may be repeated as desired until a sufficient level of context is achieved. Accordingly, once a sufficient level of context has been achieved, the mapped and/or aligned reads, at step 1080, may be sorted, such as in the processes disclosed herein, by the mapped/aligned reference position. And at step 1081, any duplicate reads may be marked and/or removed.

Further, at step 1082, the reads from the pileup of reads overlapping each marked reference CpG location may be analyzed. Where a "T" has been replaced with a "C", it may be marked as a non-methylated "C", at step 1083; and where a "C" remains in the sequence, at step 1084, the "C" may be marked as a methylated "C". Finally, at step 1086, a determination and/or report on the likely methylation status of each of the CpG location on each nucleotide strand, and a confidence in the methylation call, may also be made.

Additionally, provided herein, are methods for analyzing genomic material where part of the genetic material may have, or may otherwise be associated with, a structural variant. Particularly, a structural variation is a variation in the structure of an organism's chromosome. Structural variations involve many kinds of variations in the genome of a species, including microscopic and submicroscopic types, such as deletions, duplications, copy-number variants, insertions, inversions, and translocations. Many structural variants are associated with genetic diseases. In fact, about 13% of the human genome is defined as structurally variant in the normal population, and there are at least 240 genes that exist as homozygous deletion polymorphisms in human populations. Such structural variations can comprise millions of nucleotides of heterogeneity within every genome, and are likely to make an important contribution to human disease susceptibility.

Copy-number variation is a large category of structural variation, which includes insertions, deletions, and duplications. There are several inversions known that are related to human disease. For instance, recurrent 400 kb inversion in factor VIII gene is a common cause of haemophilia A, and smaller inversions affecting idunorate 2-sulphatase will cause Hunter syndrome. More examples include Angelman syndrome and Sotos syndrome. The most common type of complex structural variation are non-tandem duplications, where sequence is duplicated and inserted in inverted or direct orientation into another part of the genome. Other classes of complex structural variant include deletion-inversion-deletions, duplication-inversion-duplications, and tandem duplications with nested deletions. There are also cryptic translocations and segmental uniparental disomy (UPD).

However, the detection of abnormal DNA structures is problematic and beyond the scope of variant calling heretofore known. Such structural variants that are problematic to detect include those having: large insertions and deletions (e.g., beyond the 50-100 bp indel size); duplications, and other copy-number variations (CNVs); inversions and translocations, and aneuploidy (abnormal chromosome copy counts: monosomy, disomy, trisomy, etc.). In certain instances disclosed herein, identified copy-number variations may be tested on subjects who do not have genetic diseases, such as by using quantitative SNP genotyping.

Structural variation detection generally begins with performing a mapping and an aligning operation as using the devices and methods disclosed herein. For instance, the reads of the genomic sample to be analyzed may be mapped and aligned to a reference genome, such as in a protocol that supports chimeric alignments. Specifically, some structural variants (e.g. CNVs and aneuploidy) can be detected by analysis of relative mapped coverage. However, other structural variants (e.g., large indels, inversions, translocations) can be detected by analysis of clipped and chimeric alignments.

Specifically, each structural variant involves one or more "break" positions, where the read does not map to the reference genome, such as where the geometry changes between the sample and the reference. In such an instance, the pileup may be configured such that the reads therein that slightly overlap the structural variant breaks may be clipped at the break, and the reads substantially overlapping the structural variant breaks may be chimerically aligned, e.g., with two portions of a read mapped to different reference locations. However, read pairs overlapping structural variant breaks may be inconsistently aligned, with the two mate reads mapped to widely different reference locations, and/or with abnormal relative orientation of mate reads. Such obstacles may be overcome by the methods disclosed herein.

For instance, in certain instances, data pertaining to known structural variants may be used to better determine the sequence of a structural variant. For example, a database having a list of the structural variations in human genome may be compiled, e.g., with an emphasis on CNVs, and such data may be used in determining the sequence of particular variants, such as in a suitably configured weighting protocol. Particularly, where a structural variant is known, its "inner" and "outer" coordinates may be employed as a minimal and maximum range of sequence that may be affected by the structural variation. Additionally, known insertion, loss, gain, inversion, LOH, everted, transchr and UPD variations may be classified and fed into the knowledge base of the present system.

In various instances, the determination of a structural variant may be performed by a CPU/GPU/QPU running suitably configured software, such as employing previously determined sequencing data, and in other instances, structural variant analyses may be performed such as in the hardware disclosed herein. Accordingly, in particular instances, a method for analyzing genomic sequences for structural variants is provided. For instance, in a first step, genomic sequence reads may be received from a nucleotide sample. In certain instances, the sequenced reads may have been derived from paired end or mate pair protocols for detecting structural variants. Next an index for the genomic reference sequence may be built, such as where the index may be a hash table or a tree, such as a prefix or suffix tree.

Once the index has been built, the sample genomic sequence reads may be compared with the index so as to determine if the sample genomic sequence reads map to the index. If so, the sample genomic sequence reads may then be aligned to the genomic reference sequence to which they are mapped, and an alignment score may be determined.

As indicated above, the mapping and aligning may be accomplished by the hardware module as described herein. In some embodiments, the mapped and aligned data may then be communicated to an associated CPU/GPU/QPU for further analysis and processing. The reads may be sorted by mapped reference position, and duplicate reads may be marked and deleted. Chimeric reads and/or unusual relative alignments of two mate reads may be determined, and possible structural variants may be determined based on any detected chimeric reads and/or unusual relative alignments (e.g. large indel, an inversion, or a translocation). Likewise, posterior probabilities of each possible structural variant may be calculated. In some embodiments, structural variant haplotypes may be determined, such as by using HMM analysis of the chimeric reads and/or the unusual relative alignments. For example, pair HMM may be used for such a determination. The pair HMM may be accomplished using the hardware module.

Figure 43D:
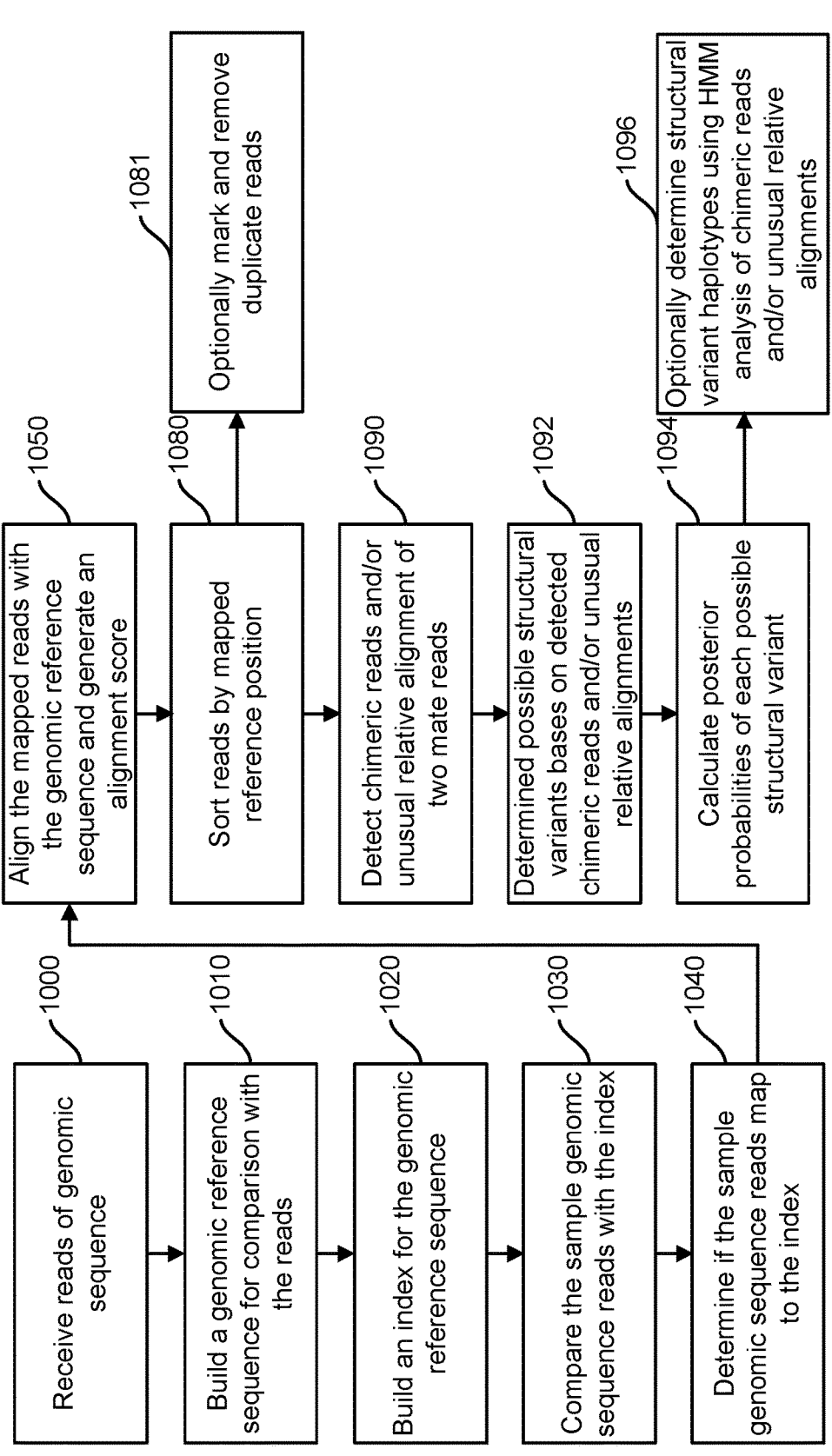
FIG. 43D provides an exemplary tertiary processing structural variants analysis for execution by the methods and devices of the system herein.

Accordingly, in various instance, as can be seen with respect to FIG. 43D, a method for determining variations in the structure of an organism's chromosomes is presented. For instance, in accordance with the methods disclosed herein, at step 1000, reads of genomic sequence data may be received. At step 1010 one or more genomic reference sequences may be built, so as to perform a comparison between the reads and the reference sequence(s). Specifically, at step 1010 a genomic reference sequence may be built so as to allow the received reads to be compared against the generated reference. More specifically, for these purposes, at step 1020 an index for the genomic reference sequence may be generated, for example, at step 1020 a hash table or prefix/suffix tree may be generated. Hence, at step 1030, the reads of the sample genomic sequence may be compared with the generated index, such as in accordance with the software and/or hardware implementations disclosed herein.

If, at step 1040, it is determined that the reads of the sample genomic sequence map to the index, then at step 1050, the mapped reads may be aligned with the genomic reference sequence, and an alignment score may be generated. At step 1080, the sample reads may be sorted by their mapped reference positions. At this point, at step 1081, duplicate reads may be marked and removed. Further, at step 1090 chimeric reads and/or unusual relative alignments, e.g., of two mate reads, may be detected, and at 1092 possible structural variants may be determined, such as based on the detected chimeric reads and/or unusual relative alignments. Furthermore, posterior probabilities of each possible structural variant may be calculated, and, optionally, at step 1096, structural variant haplotypes may be determined, such as by using HMM analysis, as described herein, of the chimeric reads and/or unusual relative alignments.

Further, the devices, systems, and methods disclosed herein may be employed for the processing of RNA sequences. Particularly, herein presented are methods for analyzing RNA-sequence reads, such as employing a spliced mapping and alignment protocol (e.g., with a suitably configured RNA mapper/aligner). For instance, in one embodiment, a transcriptome pipeline may be provided, such as for ultra-rapid RNA-sequence data analysis. Particularly, this pipeline may be configured to perform secondary analysis on RNA transcripts, such as with respect to reference-only alignment as well as annotation-assisted alignment.

Accordingly, in a first method, raw read data, e.g., in a BCL and/or FASTQ file format, may be produced by a sequencing instrument, and may be input into the system, where mapping, aligning, and variant calling may be performed. However, in various instances, one or more gene annotations files (GTF) may be input into the system, such as to guide the spliced alignments, e.g., a splice junction LUT may be built and used. For instance, alignment accuracy and splice junction tables may be employed. Consequently, a 2-phase alignment may be performed, such as where in a first detection phase novel splice junctions may employed, which may then be used to guide a second pass mapping/aligning phase. After variant calling, the system will output a standard VCF file ready for tertiary analysis.

Particularly, once an input file is received, spliced mapping and aligning may be performed, such as on both single and paired read ends. As indicated, configurable junction filters may be employed to give a single junction output. Position sorting may be performed, which may include binning by the reference range, and then the sorting of the bins by reference position, and duplicate marking may take place, such as based on the starting position and CIGAR string so as to achieve a high quality duplicate report, whereby any duplicates may be removed. Haplotype variant calling may then be performed, e.g., using a SW and HMM processing engine, and assembly may be performed.

Additionally, the devices, systems, and methods disclosed herein may be employed for performing somatic variant calling. For instance, a somatic variant calling protocol may be employed so as to detect variants that may occur in cancer cells. Particularly, genomic samples for somatic calling may be obtained from single or multiple tumor biopsies, or from blood. Optionally, a "normal" (non-tumor) sample may also obtained, such as for comparison during variant calling, e.g., where the somatic variants will occur in the tumor cells but not in the cells of the normal sample. The DNA/RNA form the sample(s) may be isolated and sequenced, such as by a Next Gen sequencer. The sequenced data, e.g., from each sample, may then be transmitted into the secondary processing platform, and the reads may be mapped and aligned. Further, the reads may be subjected to a plurality of variant calling procedures, including processing by one or both of SW and pair HMM engines.

However, the system should be configured so as to be able to detect low variant allele frequencies, such as 3% to 10% (or higher). More particularly, a genotyping probability model may be employed, where the model is configured to allow arbitrary allele frequencies. One method for allowing this is to assign each variant genotype allele frequencies corresponding to the observed allele frequencies in the overlapping reads. For instance, if 10% of overlapping reads exhibit a certain variant, a genotype can be tested consisting of 90% reference allele and 10% alternate allele. For tumor/normal dual samples, the posterior probability that a variant is present in the tumor sample but not the normal sample can be estimated.

Further, the somatic variant caller pipeline may be configured to provide information on tumor heterogeneity, e.g., that a series of distinct mutation events occurred, such as where one or more sections of a tumor with different genotypes (a subclone) has been identified. Such subclone information may be derived from a determination of variant allele frequencies and distributions thereof, and/or by explicitly calling variants differentially among multiple tumor samples.

Accordingly, methods for detecting sequence variants of cancer cells from a sample are provided. In a first step, genomic sequence reads from a nucleotide sample may be obtained from cancerous and/or normal cells. The sequence reads may be from paired end or mate pair protocols similar to that for detecting structural variants. An index for the genomic reference sequence may be built, such as where the index may be a hash table or a tree, such as a prefix or suffix tree. The sample genomic sequence reads, e.g., of the tumor and/or of the normal sample, may be compared with the index, and it may be determined if the sample genomic sequence reads map to the index.

The sample genomic sequence reads may then be aligned to the genomic reference sequence to which they are mapped, and an alignment score may be generated. The mapping and aligning may be accomplished by a software and/or hardware module, as described herein. In some embodiments, the mapped and aligned data may then be communicated to a CPU/GPU/QPU for further analysis and processing. The reads may be sorted by mapped reference position, and any duplicate reads may be marked and deleted. Variants may be detected using a Bayesian analysis that is modified to expect arbitrary variant allele frequencies, and to detect and report possible low allele frequencies (e.g. 3% to 10%).

In some embodiments, germline variants may be detected in both non-cancerous and cancerous samples, and somatic variants may be detected in only the cancerous samples. For example, the germline and somatic mutations may be distinguished by relative frequency. Posterior probabilities may be calculated of each possible cancer variant, and in some embodiments, structural variant haplotypes may be determined using HMM analysis of the chimeric reads and/or the unusual relative alignments. For example, pair HMM may be used for such a determination. The pair HMM may be accomplished using hardware modules as described herein.

Figure 43E:
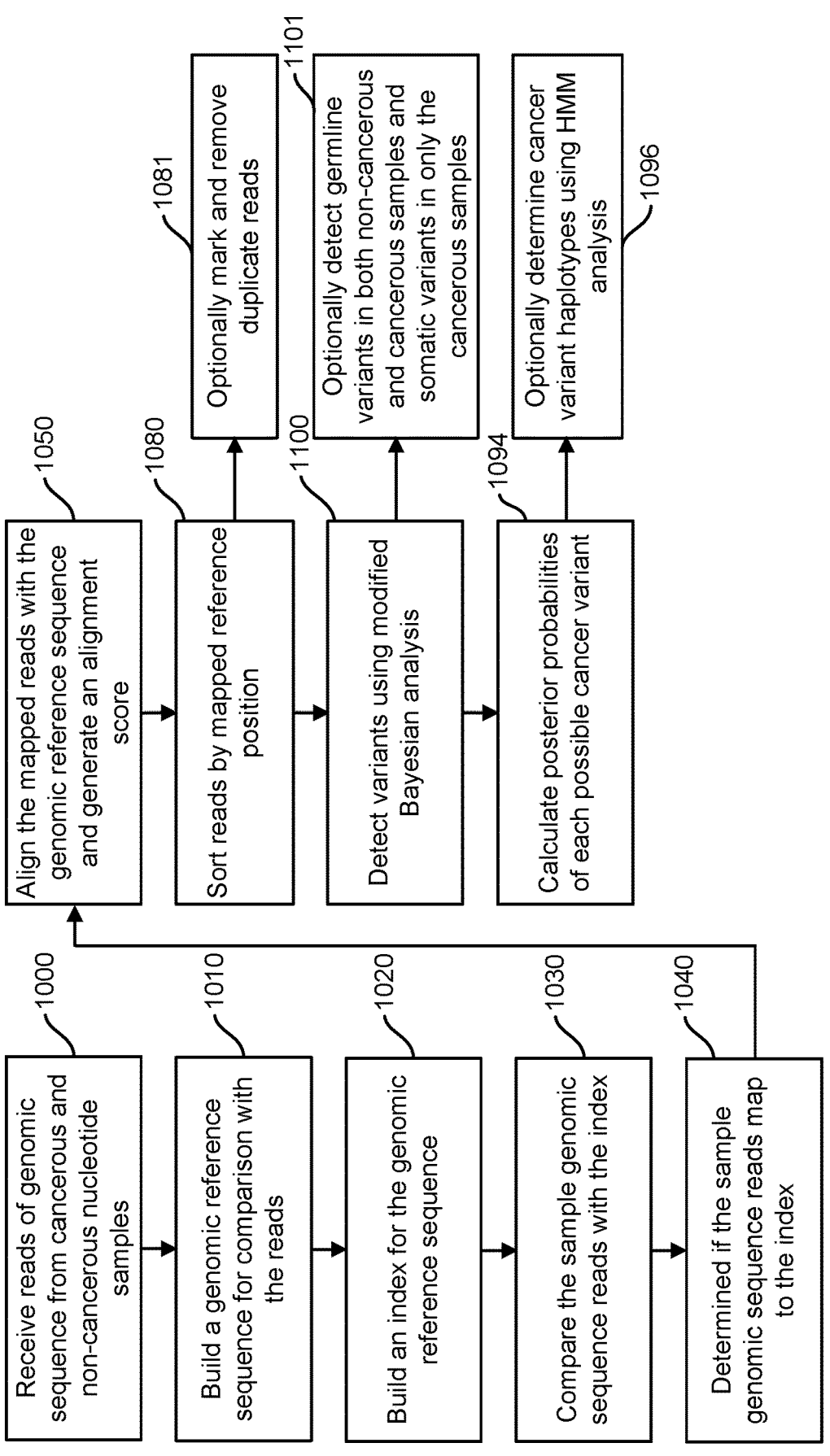
FIG. 43E provides an exemplary tertiary cohort processing analysis for execution by the methods and devices of the system herein.

Accordingly, in various embodiments, a somatic variant calling procedure, as exemplified, in FIG. 43E, may be performed, such as to calculate the probability that a variant is a cancer variant. For instance, at step 1000 reads of genomic sequence samples may be generated, e.g., via sequencing of an NGS, and/or be received, e.g., via transmission over a suitably configured cloud based network system, such as from one or both of cancerous and non-cancerous genetic samples. At step 1010 a genomic reference sequence may be generated such as for comparison of the reads, at step 1020 an index may be built from the genomic reference sequence, and at step 1030 the sample genomic sequence may be compared with the index, such as employing the software and/or hardware implementations disclosed herein, so as to map the genomic sequence reads to the index, at step at 1040. Further, at step 1050, the mapped reads may be aligned with the genomic reference sequence to generate an alignment score. The mapped and/or aligned reads may then be sorted with respect to the reference position, at 1080, and optionally, at 1081 any duplicate reads may be marked and removed.

Additionally, once the reads have been mapped and/or aligned and/or sorted and/or de-duped, then at step 1100 variants may be detected, such as by employing a Bayesian analysis, and at 1101 germline variants in both non-cancerous and cancerous samples as well as somatic variants therein may optionally be detected. Likewise, at step 1094, posterior probabilities of each possible cancer variant may be calculated. Further, at step 1096, cancer variant haplotypes may optionally be determined, such as by implementing an HMM analysis in software and/or in hardware as disclosed herein.

Furthermore, the devices, systems, and methods disclosed herein may be configured for performing a joint genotyping operation. Particularly, a joint genotyping operation may be employed so as to improve variant calling accuracy, such as by jointly considering reads from a cohort of multiple subjects. For instance, in various instances, genomic variations may be highly correlated in certain populations, e.g., where certain variants are common to a plurality of subjects. In such instances, the sensitivity and specificity of variant calling can be improved by jointly considering the evidence for each variant from multiple DNA (or RNA) samples. Specifically, sensitivity may be improved because weak evidence for a variant in one subject can be enhanced by evidence for the same variant in other samples. More specifically, sensitivity may be improved because moderate evidence for a false-positive variant can be tempered by absence of evidence for the same variant in other samples. Generally, the more samples participating in joint genotyping, the more accurate the variant calls can be for any given subject.

Joint genotyping involves the estimation of posterior probabilities for various subsets of all the subjects having a given variant, using prior probabilities that express the observed correlations in genetic variation. In various instances, joint genotyping may be performed in a single variant-calling pass, where aligned reads from multiple samples are examined by the variant caller. This is usually only practical for small numbers of samples, because when dozens, hundreds, or thousands of samples are involved, the total data size becomes impractical to rapidly access and manipulate.

Alternatively, joint genotyping can be done by first performing variant calling separately for each sample, then merging the results with a joint genotyping tool, which updates the variant probabilities for each subject using the joint information. This method uses additional output from each single-sample variant calling pass so as to better measure areas of weak evidence for variants and/or in regions where no variant would be called without joint processing. Whereas the VCF format is commonly used to represent called variants from single-sample variant calling, a special gVCF format may be used to represent first-stage variant (and non-variant) calls in preparation for merging. The gVCF format includes records for locations, and/or blocks of multiple locations, where most likely no variant is present, so this information can be merged with other gVCF calls or non-calls at the same locations to yield improved joint genotype calls for each subject.

Accordingly, the joint genotyping pipeline may be configured to call variants from multiple samples faster and with greater accuracy. Additionally, the joint genotyping pipeline may further be configured to supports pedigree as well as population variant calling from a cohort of samples. For instance, the pipeline may be configured to handle up to 10, 15, 20, 25, even 50 or more samples at one time. In various instances, a population calling configuration may be adapted to handle sample sizes of many thousands at once. Further, a combination of speed and hierarchical grouping of multiple samples provides a computationally efficient analysis solution for joint genotyping. Additionally, the sequencing of the samples for joint genotyping may be performed within the same flow cell of a Next Gen sequencer thereby allowing the system to simultaneously map/align multi-sample inputs thereby speeding up the overall process of joint calling, such as where the BCL data may be fed directly to the pipeline to produce unique gVCF files for each sample.

Therefore, provided herein is a method for improving variant calling accuracy by jointly considering reads from a cohort of multiple subjects. In a first step, reads of genomic sequence from two or more samples are received. A genomic reference sequence for comparison with the reads is built, and from the genomic reference sequence an index is generated. The genomic sequence reads of each sample are then compared with the index, and it is determined if the genomic sequence reads of each sample map to the index.

The mapped reads may then be aligned with the genomic reference sequence and an alignment score may be generated. The reads may be sorted by mapped reference position, and duplicate reads may be marked and/or removed. Additionally, overlapping reads from the pileup of reads may then be analyzed to determine if a majority of reads agree with the reference genomic sequence. Posterior probabilities of each possible variant are calculated, and the variant call data from all samples may be merged so as to enhance the variant call accuracy for each individual sample. This can enhance the variant calling accuracy (e.g., the sensitivity and specificity) for each sample, and may be accomplished as a processing step after all of the samples have undergone variant calling analysis, or it may be accomplished cumulatively, after each of the samples undergoes variant calling analysis. The likelihood of non-reference alleles in regions where no variant is called may then be determined, and the determined likelihood of non-reference alleles in the regions where no variant is called may be reported.

Figure 43F:
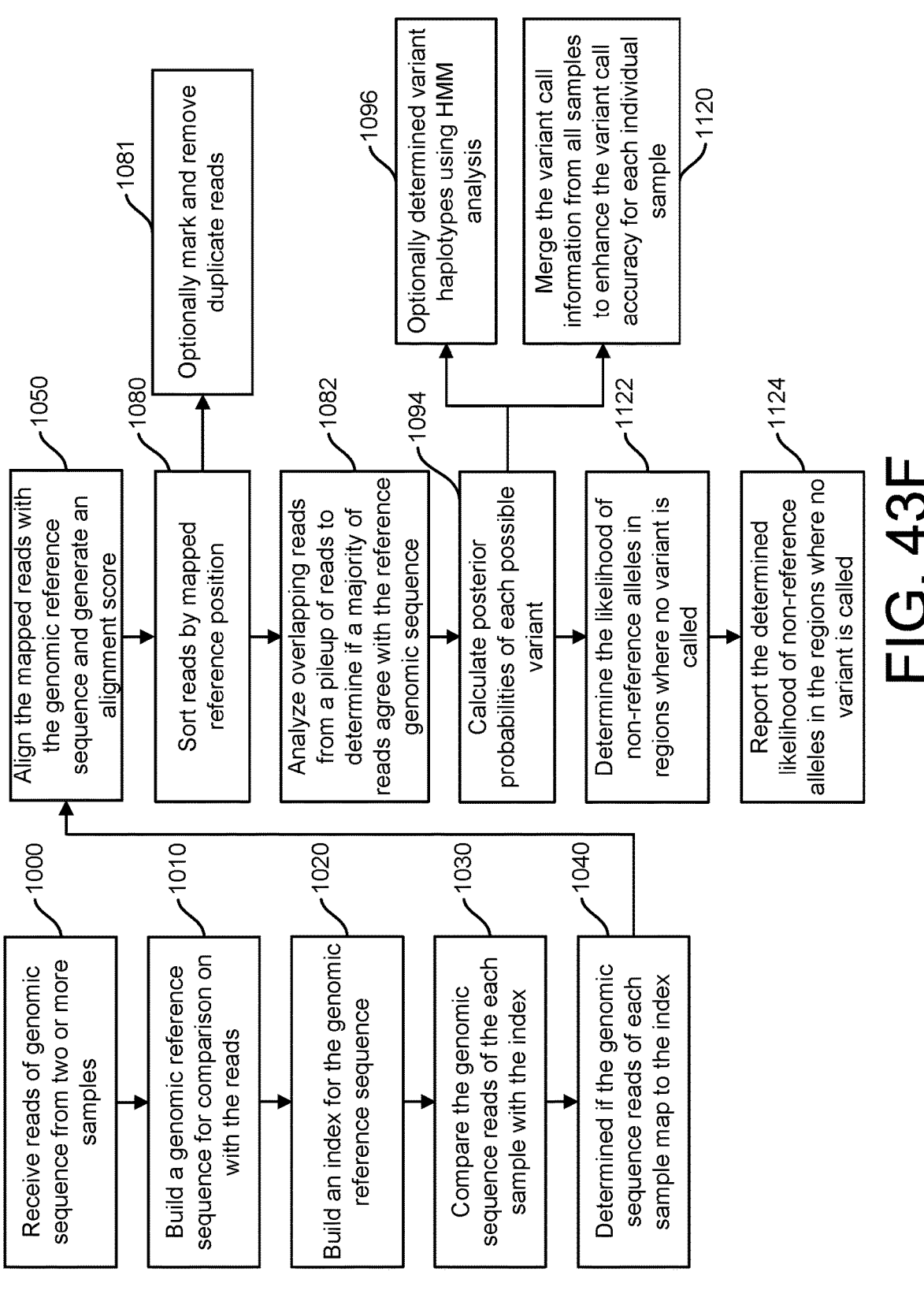
FIG. 43F provides an exemplary joint genotyping tertiary processing analysis for execution by the methods and devices of the system herein.

Accordingly, in various embodiments, a somatic variant calling procedure, as exemplified, in FIG. 43F, may be performed, such as to calculate the probability that a variant is a cancer variant. For instance, at step 1000 reads of genomic sequence samples may be generated, e.g., via sequencing of an NGS, and/or be received, e.g., via transmission over a suitably configured cloud based network system, such as from one or both of cancerous and non-cancerous genetic samples. At step 1010 a genomic reference sequence may be generated such as for comparison of the reads, at step 1020 an index may be built from the genomic reference sequence, and at step 1030 the sample genomic sequence may be compared with the index, such as employing the software and/or hardware implementations disclosed herein, so as to map the genomic sequence reads to the index, at step at 1040. Further, at step 1050, the mapped reads may be aligned with the genomic reference sequence to generate an alignment score. The mapped and/or aligned reads may then be sorted with respect to the reference position, at 1080, and optionally, at 1081 any duplicate reads may be marked and removed.

Likewise, at 1082, overlapping reads from a pileup of reads may be analyzed to determine if one or more, e.g., a majority of the reads, agree with the reference genomic sequence(s), and at step 1094, posterior probabilities of each possible variant may be calculated. At this point, at step 1096, variant haplotypes may be determined, if desired, such as by performing an HMM analysis, and/or at step 1120, the variant call data, e.g., from all samples, may optionally be merged so as to enhance the variant call accuracy for each individual sample. Further, at step 1122, the likelihood of non-reference alleles, e.g., in regions where no variant is called may be determined and reported.

Additionally, as can be seen with reference to FIG. 43, in one aspect, an online app store is provided to allow users to develop, sell, and use genomics tools that can be incorporated into the system and be employed to analyze the genomic data transmitted to and entered into the system. Particularly, the genomic app store enables customers that desire to develop genetic tests, e.g., like a NICU test, and once developed may be uploaded on to the system, e.g., genetic marketplace, for purchase and running as a platform thereon, so that anyone running the newly developed system platform, can deploy the uploaded tests via the web portal. More particularly, a user can browse the web portal "app" store, find a desired test, e.g., the NICU test, download it, and/or configure the system to implement it, such as on their uploadable genetic data. The online "cohort" marketplace, therefore, presents a rapid and efficient way to deploy new genetic analytic applications, which applications allow for identical results to be obtained from any of the present system platforms that runs the downloaded application. More particularly, the online market place provides a mechanism for anyone to work with the system to develop genetic analysis applications that remote users can download and configure for use in accordance with the present workflow models.

Another aspect of the cohort marketplace disclosed herein is that it allows for the secure sharing of data. For instance, the transmittal and storage of genomic data should be highly protected. However, often such genetic data is large and difficult to transfer in a secure and protected manner, such as where the subject's identity is restricted. Accordingly, the present genetics market place allows cohort participants to share genetic data without having to identify the subject. In such a market place, cohort participants can share questions and processes so as to advance their research in a protected and secure environment, without risking the identity of their respective subject's genomes. Additionally, a user can enlist the help of other researchers in the analysis of their sample sets without identifying to whom those genomes belong.

For instance, a user can identify subjects having a specific genotype and/or phenotype, such as stage 3 breast cancer, and/or having been treated with a particular drug. A cohort can be formed to see how these drugs affect cancerous cell growth on a genetic level. Therefore, these characteristics, amongst others, may form a cohort selection criteria that will allow other researchers, e.g., remotely located, to perform standard genetic analyses on the genetic data, using uniform analytic procedures, on subjects they have access to that fit within the cohort criteria. In this manner, a given researcher need not be responsible for identifying and securing all members of a sample set, e.g., subjects fitting within the criteria, to substantiate his or her scientific inquiry.

Particularly, Researcher A may set up a research cohort within the marketplace, and identify the appropriate selection criteria for subjects, the genomic test(s) to be run, and the parameters by which the test is to be run. Researchers B and C, located remotely from Researcher A, may then sign up for the cohort, identify and select subjects matching the criteria, and then run the specified tests on their subjects, using the uniform procedures disclosed herein, so as to help Researcher A achieve or better accomplish his or her research goals in an expeditious manner. This is beneficial because only a portion of genetic data is being transmitted, subject identity is protected, and as the data is being analyzed using the same genetic analysis system employing the same parameters, the results data will be the same regardless of where and on what machine the test(s) are run. Consequently, the cohort market place allows users to form and build cohorts simply by posting the selection criteria and run parameters on the dashboard. Compensation rates may also be posted and payments rendered by employing a suitably configured commerce, e.g., monetary exchange, program.

Anyone that accepts participation in the cohort can then download the criteria and data file(s) and/or use genetic data of subjects they have already generated and/or stored in performing the requested analyses. For instance, each cohort participant will have, or be able to generate, a database of BCL and/or FASTQ files that are stored in their individual servers. These genetic files will have been derived from subjects who happen to meet the selection criteria. Specifically, this stored genetic and/or other data of the subject may be scanned so as to determine suitability for inclusion within the cohort selection criteria. Such data may have been generated for a number of purposes, but regardless of the reasons for the generation, once generated it may be selected and subjected to the requested pipeline analyses and used for inclusion within the cohort.

Accordingly, in various embodiments, the cohort system may be a forum for connecting researchers, so as to allow them to pool their resources and data, e.g., genetic sequence data. For example, engaging a cohort would allow a first researcher to introduce a project requiring genetic data analyses requiring the mining and/or examination of a number of genomes from various subjects, such as with respect to mapping, aligning, variant calling, and/or the like. Therefore, instead of having to gather subjects and collect sample sets individually, the cohort initiator can advertise the need for a prescribed analyses procedure to be run on sample sets previously or to be collected by others, and as such a collective approach to generating sample sets and analyzing the same is provided for by the cohort organization herein. Particularly, the cohort initiator can set up the cohort selection, create a configuration file to be shared with the potential cohort participants, create the workflow parameters, e.g., within a workflow folder, and can thereby automate data generation and analyses, e.g., via the workflow management system. The system may also enable the commercial aspect of the transaction, e.g., the payment processing for compensating the cohort participants for their provision of genetic data sets that may be analyzed, such as with respect to mapping, aligning, variant calling, and/or with respect to tertiary analyses.

In various embodiments, the cohort structured analyses may be directed to primary processing, e.g., of either DNA or RNA, such as with respect to image processing and/or base quality score recalibration, methylation analysis, and the like; and/or may be directed to the performance of secondary analysis, such as with respect to mapping, aligning, sorting, variant calling, and the like; and/or may be directed to tertiary analysis, such as with respect to array, genomic, epigenomic, metagenomic, genotyping, variants, and/or other forms of tertiary analyses. Additionally, it is to be understood that although many of the pipelines and analyses performed thereby may involve primary and/or secondary processing, various analysis platforms herein may not be directed to primary or secondary processing. For instance, in certain instances, an analysis platform may be exclusively directed to performing tertiary analysis, such as on genetic data, or other forms of genomics and/or bioinformatics analyses.

For example, in particular embodiments, with respect to the particular analytical procedures to be run, the analyses to be performed may include one or more of mapping, aligning, sorting, variant calling, and the like, so as to produce results data that may be subjected to one or more other secondary and/or tertiary analyses procedures, depending on the specific pipelines selected to be run. The workflow may be simple or it may be complex, e.g., it may require the performance of one pipeline module, e.g., mapping, or multiple modules, such as mapping, aligning, sorting, variant calling, and/or others, but an important parameter is that the workflow should be identical for each person that takes part of the cohort. Particularly, a unique feature of the system is that the requester establishing the cohort sets forth the control parameters so as to ensure that the analysis to be performed are performed in the same manner, regardless of where those procedures are performed and on what machines.

Consequently, when setting up the cohort the requester will upload both selection criteria along with a configuration file. Other cohort participants will then view the selection criteria to determine if they have data sets of genetic information falling within the set forth criteria, and if so will perform the requested analysis on the data, based on the settings of the configuration file. Researches may sign up to be selected as a cohort participant, and if subscription is great a lottery or competition can be held to select the participants. In various instances, a bidding system could be initiated. The results data generated by the cohort participants may be processed onsite or on the cloud, and as long as the configuration file is followed, the processing of the data will be the same. Particularly, the configuration file sets forth how the BioIT analytics device is to be configured, and once the device is set up in accordance with the prescribed configuration, a device associated with the system will perform the requested genetic analyses in the same manner regardless of where located, e.g., locally or remotely. The results data may then be uploaded onto the cohort market place, and payment tendered and received in view of the received results data.

For instance, the analysis of the genetic data may be performed locally, and the results uploaded onto the cloud, or the genetic data itself may be uploaded and the analyses run on the cloud, e.g., a server or server network, such as quantum processing platform, associated with the cloud. In various instances, it may be useful to only upload the results data, so as to better protect the subjects' identities. Particularly, by uploading only results data, not only is security protected, but large amounts of data need not be transferred, thereby enhancing system efficiency.

More particularly, in various instances, a compressed file containing results data from one or more of the pipelines may be uploaded, and in some instances, only a file containing a description of variations need be uploaded. In some instances, only an answer need be given, such as a text answer, e.g., a "yes" or "no" answer. Such answers are preferable as they do not set forth the identity of the subject. However, if the analyses need to be performed online, e.g., in the cloud, selected BCL and/or FASTQ files may be uploaded, the analyses performed, and the results data may then be pushed back to the initial submitter, who can then upload the results data at the cohort interface. The original raw data may then be deleted from the online memory. In this and other such manners, the cohort requester will not have access to the identities of the subjects.

Compression, such as that employed in "just in time analysis" (JIT), is particularly useful in enhancing cohort efficiency. For instance, using typical procedures, the movement of data into and out of the cohort system is very expensive. Accordingly, although in various configurations, raw and/or uncompressed data uploaded to the system may be stored there, in particular instances, the data can be compressed prior to being uploaded, the data may then be processed within the system, and the results can then be compressed prior to being transmitted out of the system, such as where the compression is effectuated in accordance with a JIT protocol. In this instance, storage of such data, such as in a compressed form is less expensive, and therefore the cohort system is very cost efficient.

Additionally, in various instances, a plurality of cohorts may be provided within an online marketplace, and given the compression processes herein described, data may be transmitted from one cohort to another, so as to allow researches of various different cohorts to share data between them, which without the compression methods disclosed herein could be prohibitively costly. Particularly, without the speed and efficiency of JIT compression data once transmitted into the cloud, would typically stay in the cloud, albeit it would be accessible therein for review and manipulation. However, JIT allows data to be quickly transmitted to and from the cloud for both local and/or cloud based processing. Further, as can be seen with respect to FIGS. 41B and 43, in particular instances, the system 1 may be configured for subjecting the generated and/or secondarily processed data to further processing, e.g., via a local 100 and/or a remote 300 computing resource, such as by running it through one or more tertiary processing pipelines, such as one or more of a micro-array analysis pipeline, a genome, e.g., whole genome analysis pipeline, genotyping analysis pipeline, exome analysis pipeline, epigenome analysis pipeline, metagenome analysis pipeline, microbiome analysis pipeline, genotyping analysis pipeline, including joint genotyping, variants analyses pipeline, including structural variants pipelines, somatic variants pipelines, and GATK and/or MuTect2 pipelines, as well as RNA sequencing pipelines, and/or other tertiary processing pipeline. The results data from such processing may then be compressed and/or stored remotely 400 and/or be transferred so as to be stored locally 200.

Particularly, one or more, e.g., all, of these functions, may be performed locally, e.g., on site 10, on a local cloud 30, or via controlled access through the hybrid cloud 50. In such an instance, a developer environment is created that allows a user to control the functionality of the system 1 to meet his or her individual needs and/or to allow access thereto for others seeking the same or similar results. Consequently, the various components, processes, procedures, tools, tiers, and hierarchies of the system may be configurable such as via a GUI interface that allows the user to select which components of the system to be run, on which data, at what time, and in what order in accordance with the user determined desires and protocols, so as to generate relevant data and connections between data that may be securely communicated throughout the system whether locally or remotely. As indicated, these components can be made to communicate seamlessly together, e.g., regardless of location and/or how connected, such as by being in a tightly coupled configuration and/or a seamless cloud based coupling, and/or by being configurable, e.g., via a JIT protocol, so as to run the same or similar processes in the same or similar manner, such as by employing corresponding API interfaces dispersed throughout the system, the employment of which allows the various users to configure the various components to run the various procedures in like manner.

For instance, an API may be defined in a header file with respect to the processes to be run by each particular component of the system 1, wherein the header describes the functionality and determines how to call a function, such as the parameters that are passed, the inputs received and outputs transmitted, and the manner in which this occurs, what comes in and how, what goes out and how, and what gets returned, and in what manner. For example, in various embodiments, one or more of the components and/or elements thereof, which may form one or more pipelines of one or more tiers of the system may be configurable such as by instructions entered by a user and/or one or more second and/or third party applications. These instructions may be communicated to the system via the corresponding APIs which communicate with one or more of the various drivers of the system, instructing the driver(s) as to which parts of the system, e.g., which modules and/or which processes thereof are to be activated, when, and in what order, given a preselected parameter configuration, which may be determined by a user selectable interface, e.g., GUI.

Particularly, the one or more DMA drivers of the system 1 may be configured to run in corresponding fashion, such as at the kernel level of each component and the system 1 as a whole. In such an instance, one or more of the provided kernel's may have their own very low level, basic API that provides access to the hardware and functions of the various components of the system 1 so as to access applicable registers and modules so as to configure and direct the processes and the manners in which they are run on the system 1. Specifically, on top of this layer, a virtual layer of service functions may be built so as to form the building blocks that are used for a multiplicity of functions that send files down to the kernel(s) and get results back, encodes, encrypts, and/or transmits the relevant data and further performs more higher level functions thereon. On top of that layer an additional layer may be built that uses those service functions, which may be an API level that a user may interface with, which may be adapted to function primarily for configuration of the system 1 as a whole or its component parts, downloading files, and uploading results, which files and/or results may be transmitted throughout the system either locally or globally. Additional APIs may be configured and included as set forth in more detail above with respect to the secure storage of data.

Such configuring of the various APIs, memories, and/or firmware of the system may include communicating with registers and also performing function calls. For example, as described herein above, one or more function calls necessary and/or useful to perform the steps, e.g., sequentially, to execute a mapping and/or aligning and/or sorting and/or variant call, or other secondary and/or tertiary functions as herein described may be implemented in accordance with the hardware operations and/or related algorithms so as to generate the necessary processes and perform the required steps.

Specifically, because in certain embodiments one or more of these operations may be based on one or more structures, the various structures needed for implementing these operations may need to be constructed. There will therefore be a function call that performs this function, which function call will cause the requisite structure to be built for the performance of the operation, and because of this a call will accept a file name of where the structure parameter files are stored and will then generate one or more data files that contain and/or configure the requisite structure. Another function call may be to load the structure that was generated via the respective algorithm and transfer that down to the memory on the chip and/or system 1, and/or put it at the right spot where the hardware is expecting them to be. Of course, various data will need to be downloaded onto the chip and/or otherwise be transferred to the system generator, as well for the performance of the various other selected functions of the system 1, and the configuration manager can perform these functions, such as by loading everything that needs to be there in order for the modules of pipelines of the tiers of the platforms of the chip and/or system as a whole to perform their functions, into a memory on, attached, or otherwise associated with the chip and/or system.

Additionally, the system may be configured to allow various components of the system to communicate with one another, such as to allow one or more chips of the system 1 to interface with the circuit board of the sequencer 121, the computing resource 100/300, transformer 151, analyzer 152, interpreter 310, collaborator 320, or other system component, when included therewith, so as to receive the FASTQ and/or other generated and/or processed genetic sequencing files directly from the sequencer or other processing component such as immediately once they have been generated and/or processed and then transfers that information to the configuration manager which then directs that information to the appropriate memory banks in the hardware and/or software that makes that information available to the pertinent modules of the hardware, software, and/or system as a whole so that they can perform their designated functions on that information so as to call bases, map, align, sort, etc. the sample DNA/RNA with respect to the reference genome, and or to run associated secondary and/or tertiary processing operations thereon.

Accordingly, in various embodiments, a client level interface (CLI) may be included wherein the CLI may allow the user to call one or more of these functions directly. In various embodiments, the CLI may be a software application, e.g., having a GUI, which is adapted to configure the accessibility and/or use of the hardware and/or various other software applications of the system. The CLI, therefore, may be a program that accepts instructions, e.g., arguments, and makes functionality available simply by calling an application program. As indicated above, the CLI can be command line based or GUI (graphical user interface) based. The line based commands happen at a level below the GUI, where the GUI includes a windows based file manager with click on function boxes that delineate which modules, which pipelines, which tiers, of which platforms will be used and the parameters of their use. For example, in operation, if instructed, the CLI will locate the reference, will determine if a hash table and/or index needs to be generated, or if already generated locate where it is stored, and direct the uploading of the generated hash table and/or index, etc. These types of instructions may appear as user options at the GUI that the user can select the associated chip(s)/system 1 to perform.

Furthermore, a library may be included wherein the library may include pre-existing, editable, configuration files, such as files orientated to the typical user selected functioning of the hardware and/or associated software, such as with respect to a portion or whole genome and/or protein analysis, for instance, for various analyses, such as personal medical histories and ancestry analysis, or disease diagnostics, or drug discovery, therapeutics, and/or one or more of the other analytics, etc. These types of parameters may be preset, such as for performing such analyses, and may be stored in the library. For example, if the platform herein described is employed such as for NIPT, NICU, Cancer, LDT, AgBio, and related research on a collective level, the preset parameters may be configured differently than if the platform were directed simply to researching genomic and/ or genealogy based research, such as on an individual level.

More particularly, for specific diagnosis of an individual, accuracy may be an important factor. Therefore, the parameters of the system may be set to ensure increased accuracy albeit in exchange for possibly a decrease in speed. However, for other genomics applications, speed may be the key determinant and therefore the parameters of the system may be set to maximize speed, which however may sacrifice some accuracy. Accordingly, in various embodiments, often used parameter settings for performing different tasks can be preset into the library to facilitate ease of use. Such parameter settings may also include the necessary software applications and/or hardware configurations employed in running the system 1. For instance, the library may contain the code that executes the API, and may further include sample files, scripts, and any other ancillary information necessary for running the system 1. Hence, the library may be configured for compiling software for running the API as well as various of the executables.

Additionally, as can be seen with respect to FIGS. 42C and 43, the system may be configured such that one or more of the system components may be performed remotely, such as where the system component is adapted to run one or more comparative functions on the data, such as an interpretive function 310 and/or collaborative function 320. For instance, where an interpretive protocol is employed on the data, the interpretive protocol 312 may be configured to analyze and draw conclusions about the data and/or determine various relationships with respect thereto, one or more other analytical protocols may also be performed and include annotating the data 311, performing a diagnostic 313 on the data, and/or analyzes the data, so as to determine the presence or absence of one or more biomarkers 314. As indicated, one or more of these functions may be directed by the WMS, and/or performed by the A/I module disclosed herein.

Additionally, where a collaborative protocol is performed, the system 1 may be configured for providing an electronic forum where data sharing 321 may occur, which data sharing protocol may include user selectable security 324 and/or privacy 322 settings that allow the data to be encrypted and/or password protected, so that the identity and sources of the data may be hidden from a user of the system 1. In particular instances, the system 1 may be configured so as to allow a 3rd party analyzer 121 to run virtual simulations on the data. Further, one generated, the interpreted data and/or the data subjected to one or more collaborative analyses may be stored either remotely 400 or locally 200 so as to be made available to the remote 300 or local 100 computing resources, such as for further processing and/or analysis.

Figure 44:
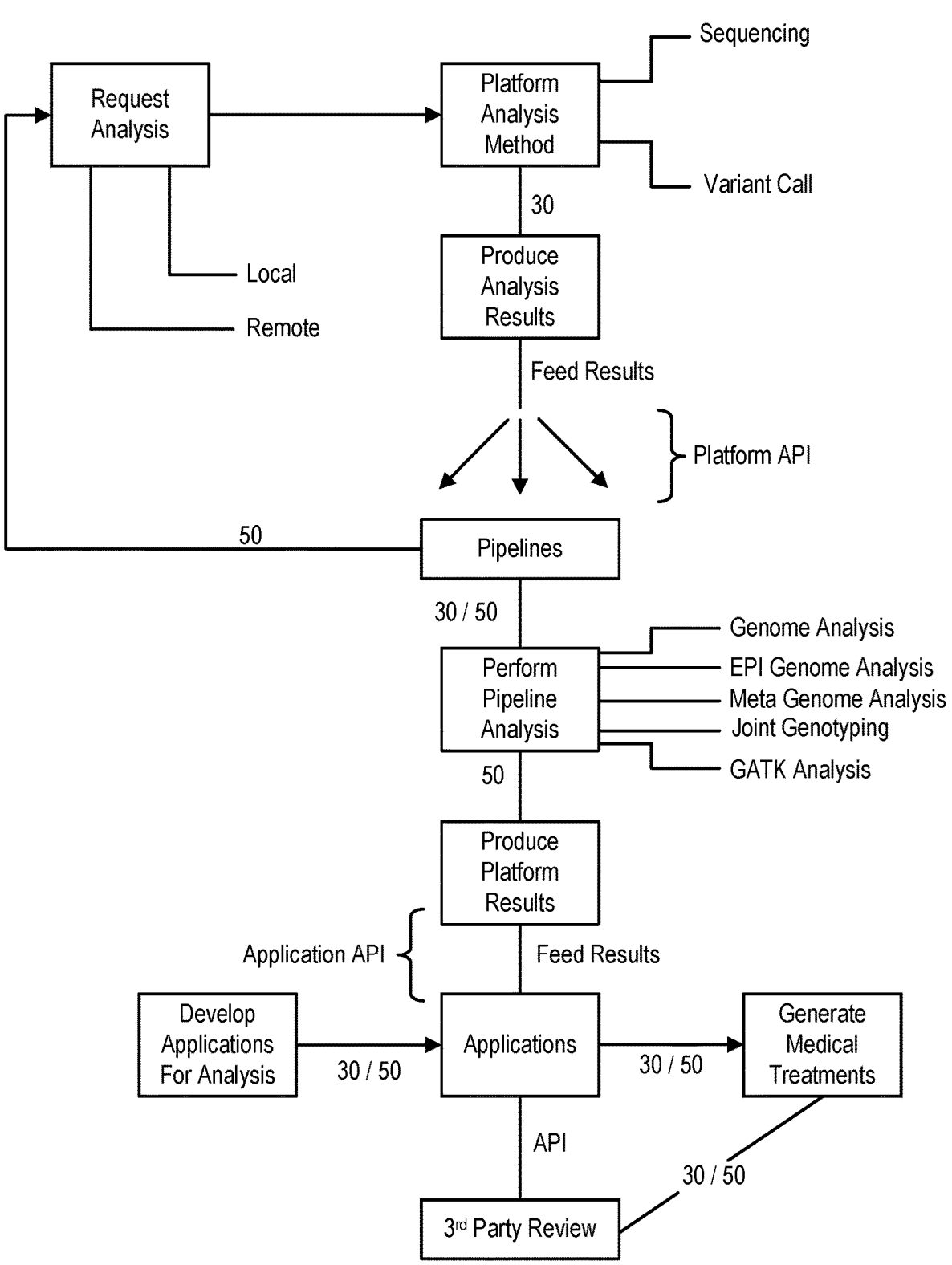
FIG. 44 depicts a flow diagram for an analysis pipeline of the disclosure.

In another aspect, as can be seen with respect to FIG. 44, a method for using the system to generate one or more data files upon which one or more secondary and/or tertiary processing protocols may be run is provided. For instance, the method may include providing a genomic infrastructure such as for one or more of onsite, cloud-based, and/or hybrid genomic and/or bioinformatics generation and/or processing and/or analysis.

In such an instance, the genomic infrastructure may include a bioinformatics processing platform having one or more memories that are configured to store one or more configurable processing structures for configuring the system so as to be able to perform one or more analytical processing functions on data, such as data including a genomic sequence of interest or processed result data pertaining thereto. The memory may include the genomic sequence of interest to be processed, e.g., once generated and/or acquired, one or more genetic reference sequences, and/or may additionally include an index of the one or more genetic reference sequences and/or a list of splice junctions pertaining thereto. The system may also include an input having a platform application programming interface (API) for selecting from a list of options one or more of the configurable processing structures, such as for configuring the system, such as by selecting which processing functions of the system will be run on the data, e.g., the pre- or processed genomic sequences of interest. A graphical user interface (GUI) may also be present, such as operably associated with the API, so as to present a menu by which a user can select which of the available options he or she desires to be run on the data.

Hence, in these and/or other such instances, the hybrid cloud 50 may be configured for allowing seamless and protected transmission of data throughout the components of the system, such as where the hybrid cloud 50 is adapted to allow the various users of the system to configure its component parts and/or the system itself, e.g., via the WMS, so as to meet the research, diagnostic, therapeutic and/or prophylactic discovery and/or development needs of the user. Particularly, the hybrid cloud 50 and/or the various components of the system 1 may be operably connected with compatible and/or corresponding API interfaces that are adapted to allow a user to remotely configure the various components of the system 1 so as to deploy the resources desired in the manner desired, and further to do so either locally, remotely, or a combination of the same, such as based on the demands of the system and the particulars of the analyses being performed, all the while being enabled to communicate in a secured, encryptable environment.

As described above, the system may be implemented on one or more integrated circuits that may be formed of one or more sets of configurable, e.g., preconfigured and/or hard-wired, digital logic circuits that may be interconnected by a plurality of physical electrical interconnects. In such an instance, the integrated circuit may have an input, such as a memory interface, for receiving one or a plurality of the configurable structure protocols, e.g., from the memory, and may further be adapted for implementing the one or more structures on the integrated circuit in accordance with the configurable processing structure protocols. The memory interface of the input may also be configured for receiving the genomic sequence data, which may be in the form of a plurality of reads of genomic data. The interface may also be adapted for accessing the one or more genetic reference sequences and the index(es).

In various instances, the digital logic circuits may be arranged as a set of processing engines that are each formed of a subset of the digital logic circuits. The digital logic circuits and/or processing engines may be configured so as to perform one or more pre-configurable steps of a primary, secondary, and/or tertiary processing protocol so as to generate the plurality of reads of genomic sequence data, and/or for processing the plurality of reads of genomic data, such as according to the genetic reference sequence(s) or other genetic sequence derived information. The integrated circuit may further have an output so as to output result data from the primary, secondary, and/or tertiary processing, such as according to the platform application programming interface (API).

Particularly, in various embodiments, the digital logic circuits and/or the sets of processing engines may form a plurality of genomic processing pipelines, such as where each pipeline may have an input that is defined according to the platform application programming interface so as to receive the result data from the primary and/or secondary processing by the bioinformatics processing platform, and for performing one or more analytic processes thereon so as to produce result data. Additionally, the plurality of genomic processing pipelines may have a common pipeline API that defines a secondary and/or tertiary processing operation to be run on the result data from the primary and/or secondary processed data, such as where each of the plurality of genomic processing pipelines is configured to perform a subset of the secondary and/or tertiary processing operations and to output result data of the secondary and/or tertiary processing according to the pipeline API.

In such instances, a plurality of the genomic analysis applications may be stored in the memory and/or an associated searchable application repository, such as where each of the plurality of genomic analysis applications are accessible via an electronic medium by a computer such as for execution by a computer processor, so as to perform a targeted analysis of the genomic pre- or post-processed data from the result data of the primary, secondary, and/or tertiary processing, such as by one or more of the plurality of genomic processing pipelines. In particular instances, each of the plurality of genomic analysis applications may be defined by the API and may be configured for receiving the result data of the primary, secondary, and/or tertiary processing, and/or for performing the target analysis of the pre- or post-processed genomic data, and for outputting the result data from the targeted analysis to one of one or more genomic databases.

The method may additionally include, selecting, e.g., from the menu of the GUI, one or more genomic processing pipelines from a plurality of the available genomic processing pipelines of the system; selecting one or more genomic analysis applications from the plurality of genomic analysis applications that are stored in an application repository; and executing, using a computer processor, the one or more selected genomic analysis applications to perform a targeted analysis of genomic data from the result data of the primary, secondary, and/or tertiary processing.

Additionally, in various embodiments, all of mapping, aligning, and sorting, and variant calling may take place on the chip, and local realignment, duplicate marking, base quality score recalibration may, and/or one or more of the tertiary processing protocols and/or pipelines, in various embodiments, also may take place on the chip or in software, and in various instances, various compression protocols, such as SAM and/or BAM and/or CRAM, may also take place on the chip. However, once the primary, secondary, and/or tertiary processed data has been produced, it may be compressed, such as prior to being transmitted, such as by being sent across the system, being sent up to the cloud, such as for the performance of the variant calling module, a secondary, tertiary, and/or other processing platform, such as including an interpretive and/or collaborative analysis protocol. This might be useful especially given the fact that variant calling, including the tertiary processing thereof, can be a moving target, e.g., there is not one standardized agreed upon algorithm that the industry uses.

Hence, different algorithms can be employed, such as by remote users, so as to achieve a different type of result, as desired, and as such having a cloud based module for the performance of this function may be useful for allowing the flexibility to select which algorithm is useful at any particular given moment, and also as for serial and/or parallel processing. Accordingly, any one of the modules disclosed herein can be implemented as either hardware, e.g., on the chip, or software, e.g., on the cloud, but in certain embodiments, all of the modules may be configured so that their function may be performed on the chip, or all of the modules may be configured so that their function may be performed remotely, such as on the cloud, or there will be a mixture of modules wherein some are positioned on one or more chips and some are positioned on the cloud. Further, as indicated, in various embodiments, the chip(s) itself may be configured so as to function in conjunction with, and in some embodiments, in immediate operation with a genetic sequencer, such as an NGS and/or sequencer on a chip.

Figure 45:
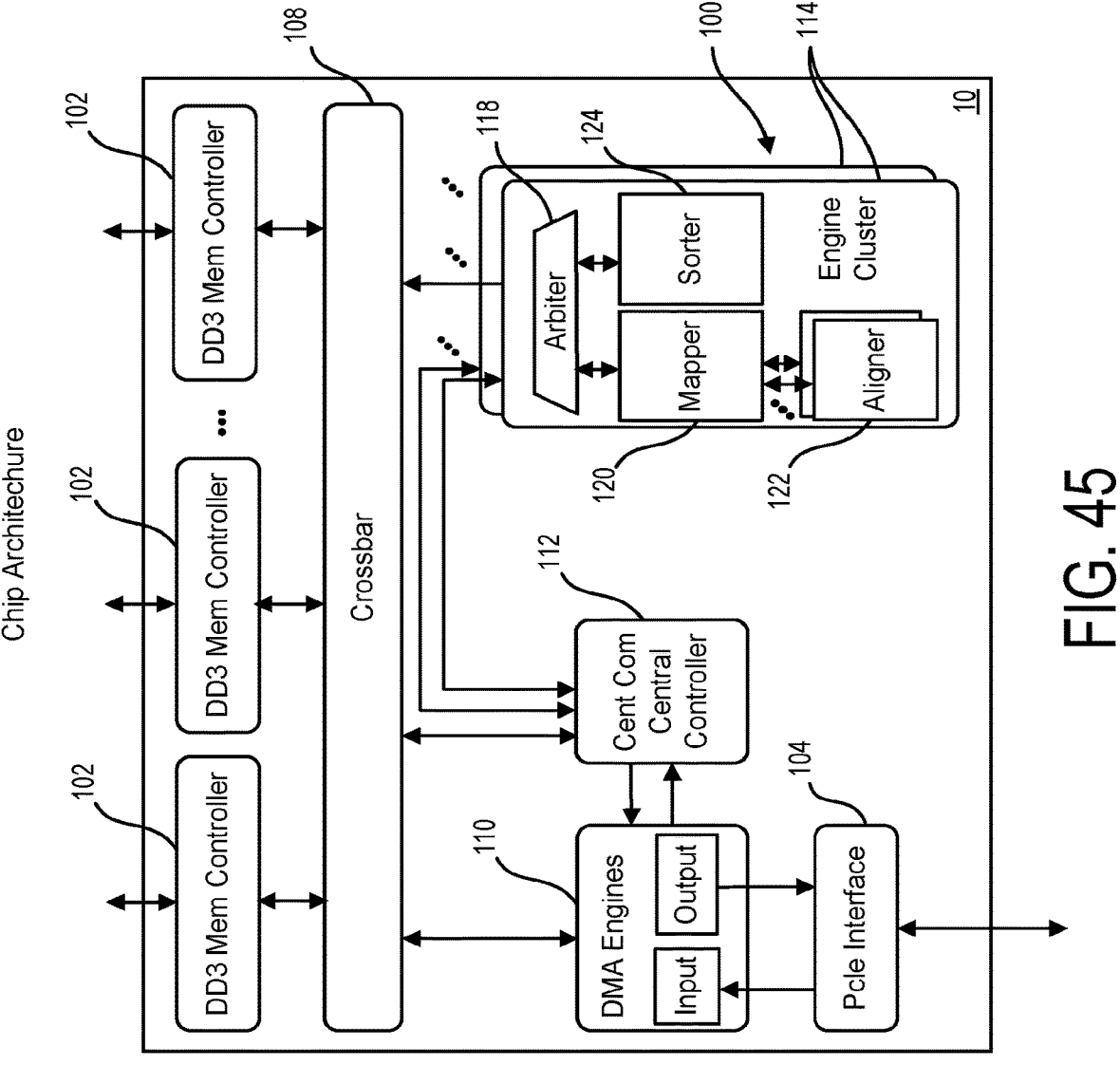
FIG. 45 is a block diagram of a hardware processor architecture in accordance with an implementation of the disclosure.

More specifically, in various embodiments, an apparatus of the disclosure may be a chip, such as a chip that is configured for processing genomics data, such as by employing a pipeline of data analysis modules. Accordingly, as can be seen with respect to FIG. 45, a genomics pipeline processor chip 100 is provided along with associated hardware of a genomics pipeline processor system 10. The chip 100 has one or more connections to external memory 102 (at "DDR3 Mem Controller"), and a connection 104 (e.g., PCIe or QPI Interface) to the outside world, such as a host computer 1000, for example. A crossbar 108 (e.g., switch) provides access to the memory interfaces to various requestors. DMA engines 110 transfer data at high speeds between the host and the processor chip's 100 external memories 102 (via the crossbar 108), and/or between the host and a central controller 112. The central controller 112 controls chip operations, especially coordinating the efforts of multiple processing engines 13. The processing engines are formed of a set of hardwired digital logic circuits that are interconnected by physical electrical interconnects, and are organized into engine clusters 11/114. In some implementations, the engines 13 in one cluster 11/114 share one crossbar port, via an arbiter 115. The central controller 112 has connections to each of the engine clusters. Each engine cluster 11/114 has a number of processing engines 13 for processing genomic data, including a mapper 120 (or mapping module), an aligner 122 (or aligning module), and a sorter 124 (or sorting module), one or more processing engines for the performance of other functions, such as variant calling, may also be provided. Hence, an engine cluster 11/114 can include other engines or modules, such as a variant caller module, as well.

In accordance with one data flow model consistent with implementations described herein, the host CPU 1000 sends commands and data via the DMA engines 110 to the central controller 112, which load-balances the data to the processing engines 13. The processing engines return processed data to the central controller 112, which streams it back to the host via the DMA engines 110. This data flow model is suited for mapping and alignment and variant calling. As indicated, in various instances, communication with the host CPU may be through a relatively loose or tight coupling, such as a low latency, high bandwidth interconnect, such as a QPI, such as to maintain cache coherency between associated memory elements of the two or more devices.

For instance, in various instances, due to various power and/or space constraints, such as when performing big data analytics, such as mapping/aligning/variant calling in a hybrid software/hardware accelerated environment, as described herein, where data needs to be moved both rapidly and seamlessly between system devices, a cache coherent tight coupling interface may be useful for performing such data transmissions throughout the system to and from the coupled devices, such as to and from the sequencer, DSP (digital signal processor), CPU and/or GPU or CPU/GPU hybrid, accelerated integrated circuit, e.g., FPGA, ASIC (on network card), as well as other Smart Network Accelerators in a rapid, cache-coherent manner. In such instances, a suitable cache coherent, tight-coupling interconnect may be one or more of a single interconnect technology specification that is configured to ensure that processing, such as between a multiplicity of processing platforms, using different instruction set architectures (ISA), can coherently share data between the different platforms and/or with one or more associated accelerators, e.g., such as a hardwired FPGA implemented accelerator, so as to enable efficient heterogeneous computing, and thereby significantly improve the computing efficiency of the system, which in various instances may be configured as a cloud-based server system. Hence, in certain instances, a high bandwidth, low latency, cache coherent interconnect protocol, such as a QPI, Coherent Processor Accelerator Interface (CAPI), NVLink/GPU, or other suitable interconnect protocol may be employed so as to expedite various data transmissions between the various components of the system, such as pertaining to the mapping, aligning, and/or variant calling compute functions that may involve the use of acceleration engines the functioning of which requires the need to access, process, and move data seamlessly among various system components irrespective of where the various data to be processed resides in the system. And, where such data is retained within an associated memory device, such as a RAM or DRAM, the transmission activities may further involve expedited and coherent search and in-memory database processing.

Particularly, in particular embodiments, such heterogeneous computing may involve a multiplicity of processing and/or acceleration architectures that may be interconnected in a reduced instruct set computing format. In such an instance, such an interconnect device may be a coherent connect interconnect six (CCVI) device, which is configured to allow all computing componentry within the system to address, read, and/or write to one or more associated memories in a single, consistent, and coherent manner. More particularly, a CCVI interconnect may be employed so as to connect various of the devices of the system, such as the CPU and/or GPU or CPU/GPU hybrid, FPGA, and/or associated memories, etc. one with the other, such as in a high bandwidth manner that is configured to increase transfer rates between the various components while evidencing extremely reduced latency rates. Specifically, a CCVI interconnect may be employed and configured so as to allow components of the system to access and process data irrespective of where the data resides, and without the need for complex programing environments that would otherwise need to be implemented to make the data coherent. Other such interconnects that may be employed so as to speed up, e.g., decrease, processing time and increase accuracy include QPI, CAPI, NVLink, or other interconnect that may be configured to interconnect the various components of the system and/or to ride on top of an associated PCI-express peripheral interconnect.

Hence, in accordance with an alternative data flow model consistent with implementations described herein, the host CPU 1000 streams data into the external memory 1014, either directly via DMA engines 110 and the crossbar 108, or via the central controller 112. The host CPU 1000 sends commands to the central controller 112, which sends commands to the processing engines 13, which instruct the processing engines as to what data to process. Because of the tight coupling, the processing engines 13 access input data directly from the external memory 1014 or a cache associated therewith, process it, and write results back to the external memory 1014, such as over the tightly coupled interconnect 3, reporting status to the central controller 112. The central controller 112 either streams the result data back to the host 1000 from the external memory 1014, or notifies the host to fetch the result data itself via the DMA engines 110.

Figure 46:
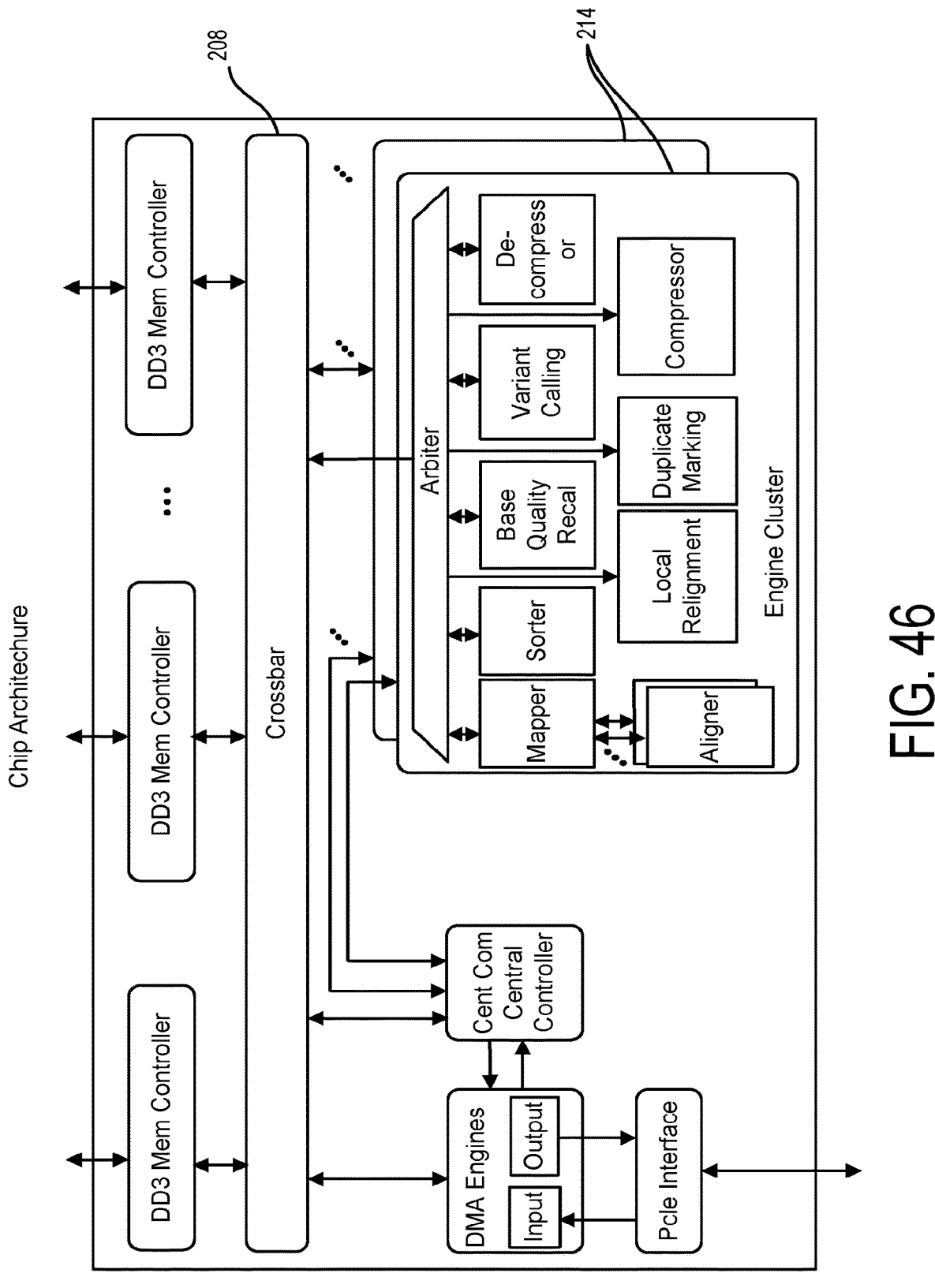
FIG. 46 is a block diagram of a hardware processor architecture in accordance with another implementation.

FIG. 46 illustrates a genomics pipeline processor and system 20, showing a full complement of processing engines 13 inside an engine cluster 11/214. The pipeline processor system 20 may include one or more engine clusters 11/214. In some implementations, the pipeline processor system 20 includes four or more engine clusters 11/214. The processing engines 13 or processing engine types can include, without limitation, a mapper, an aligner, a sorter, a local realigner, a base quality recalibrater, a duplicate marker, a variant caller, a compressor and/or a decompressor. In some implementations, each engine cluster 11/214 has one of each processing engine type. Accordingly, all processing engines 13 of the same type can access the crossbar 208 simultaneously, through different crossbar ports, because they are each in a different engine cluster 11/214. Not every processing engine type needs to be formed in every engine cluster 11/214. Processing engine types that require massive parallel processing or memory bandwidth, such as the mapper (and attached aligner(s)) and sorter, may appear in every engine cluster of the pipeline processor system 20. Other engine types may appear in only one or some of the engine clusters 214, as needed to satisfy their performance requirements or the performance requirements of the pipeline processor system 20.

Figure 47:
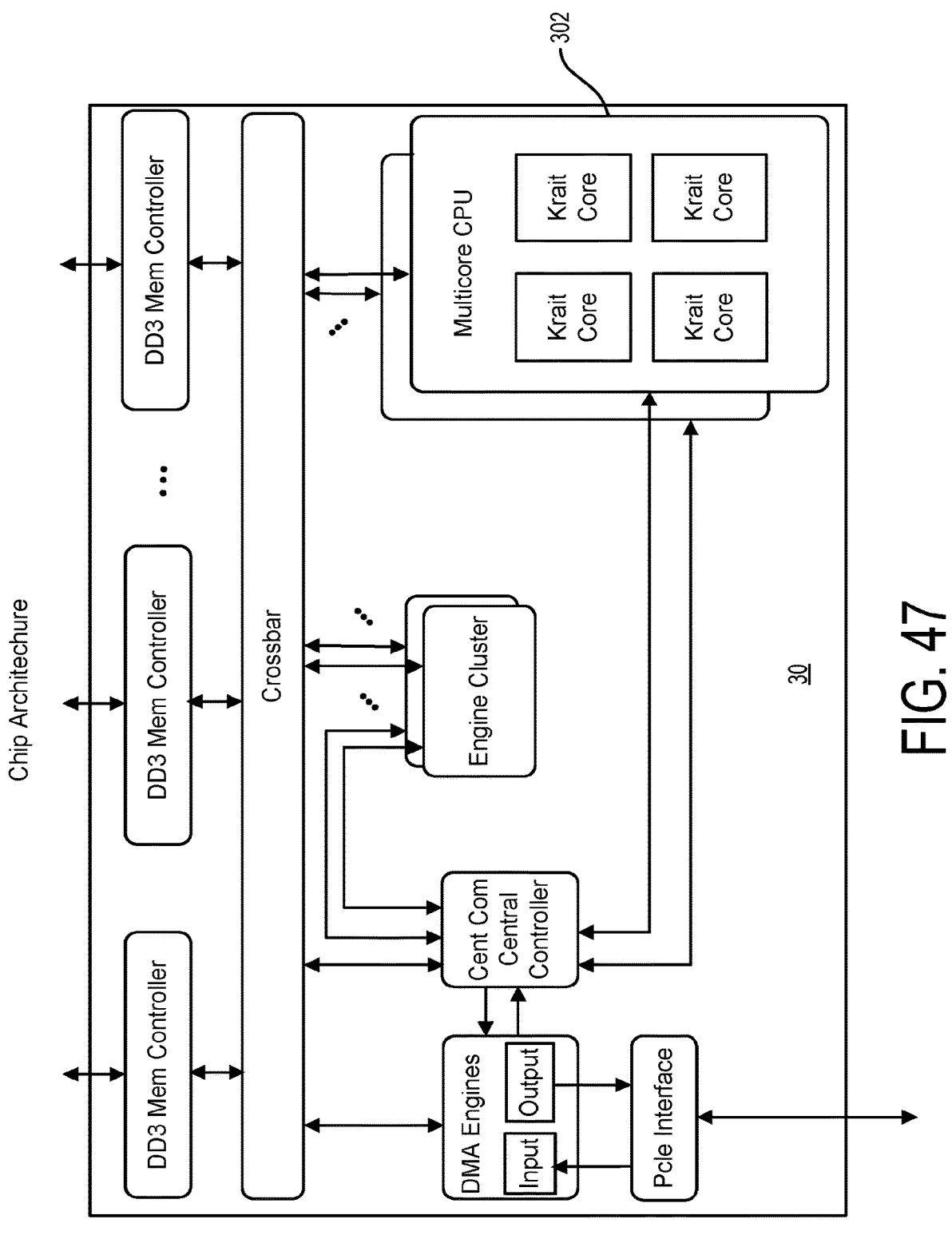
FIG. 47 is a block diagram of a hardware processor architecture in accordance with yet another implementation.

FIG. 47 illustrates a genomics pipeline processor system 30, showing, in addition to the engine clusters 11 described above, one or more embedded central processing units (CPUs) 302. Examples of such embedded CPUs include Snapdragons® or standard ARM® cores, or in other instances may be an FPGA. These CPUs execute fully programmable bio-IT algorithms, such as advanced variant calling, such as the building of a DBG or the performance of an HMM. Such processing is accelerated by computing functions in the various engine clusters 11, which can be called by the CPU cores 302 as needed. Furthermore, even engine-centric processing, such as mapping and alignment, can be managed by the CPU cores 302, giving them heightened programmability.

Figure 48:
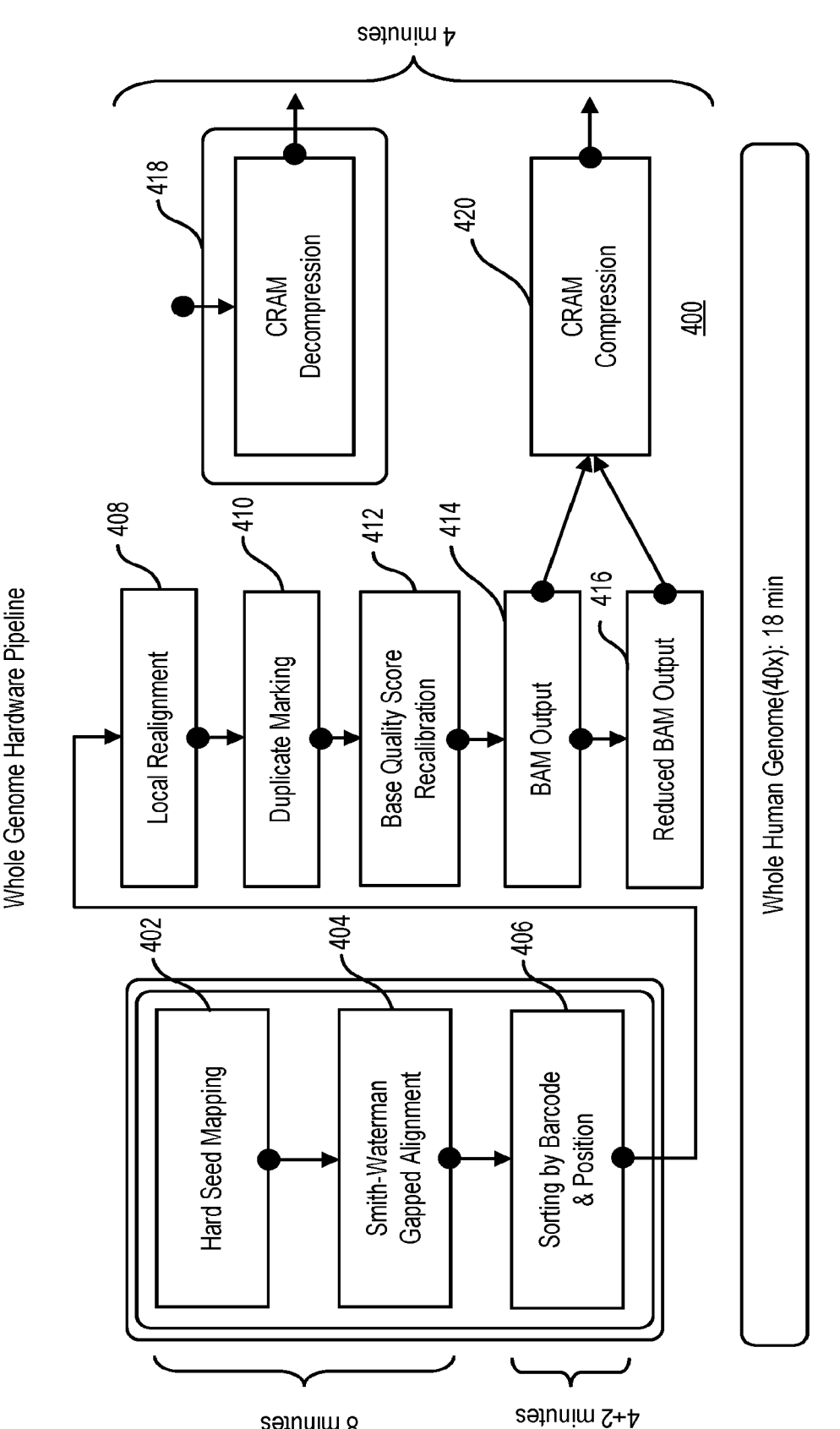
FIG. 48 illustrates a genetic sequence analysis pipeline.

FIG. 48 illustrates a processing flow for a genomics pipeline processor system and method. In some preferred implementations, there are three passes over the data. The first pass includes mapping 402 and alignment 404, with the full set of reads streamed through the engines 13. The second pass includes sorting 406, where one large block to be sorted (e.g., a substantial portion or all reads previously mapped to a single chromosome) is loaded into memory, sorted by the processing engines, and returned to the host. The third pass includes downstream stages (local realignment 408, duplicate marking 410, base quality score recalibration (BQSR) 412, SAM output 414, reduced BAM output 416, and/or CRAM compression 418). The steps and functions of the third pass may be done in any combination or subcombination, and in any order, in a single pass.

Hence, in this manner data is passed relatively seamlessly from the one or more processing engines, to the host CPU, such as in accordance with one or more of the methodologies described herein. Hence, a virtual pipeline architecture, such as described above, is used to stream reads from the host into circular buffers in memory, through one processing engine after another in sequence, and back out to the host. In some implementations, CRAM decompression can be a separate streaming function. In some implementations, the SAM output 414, reduced BAM output 416, and/or CRAM compression 418 can be replaced with variant calling, compression and decompression.

Figure 49:
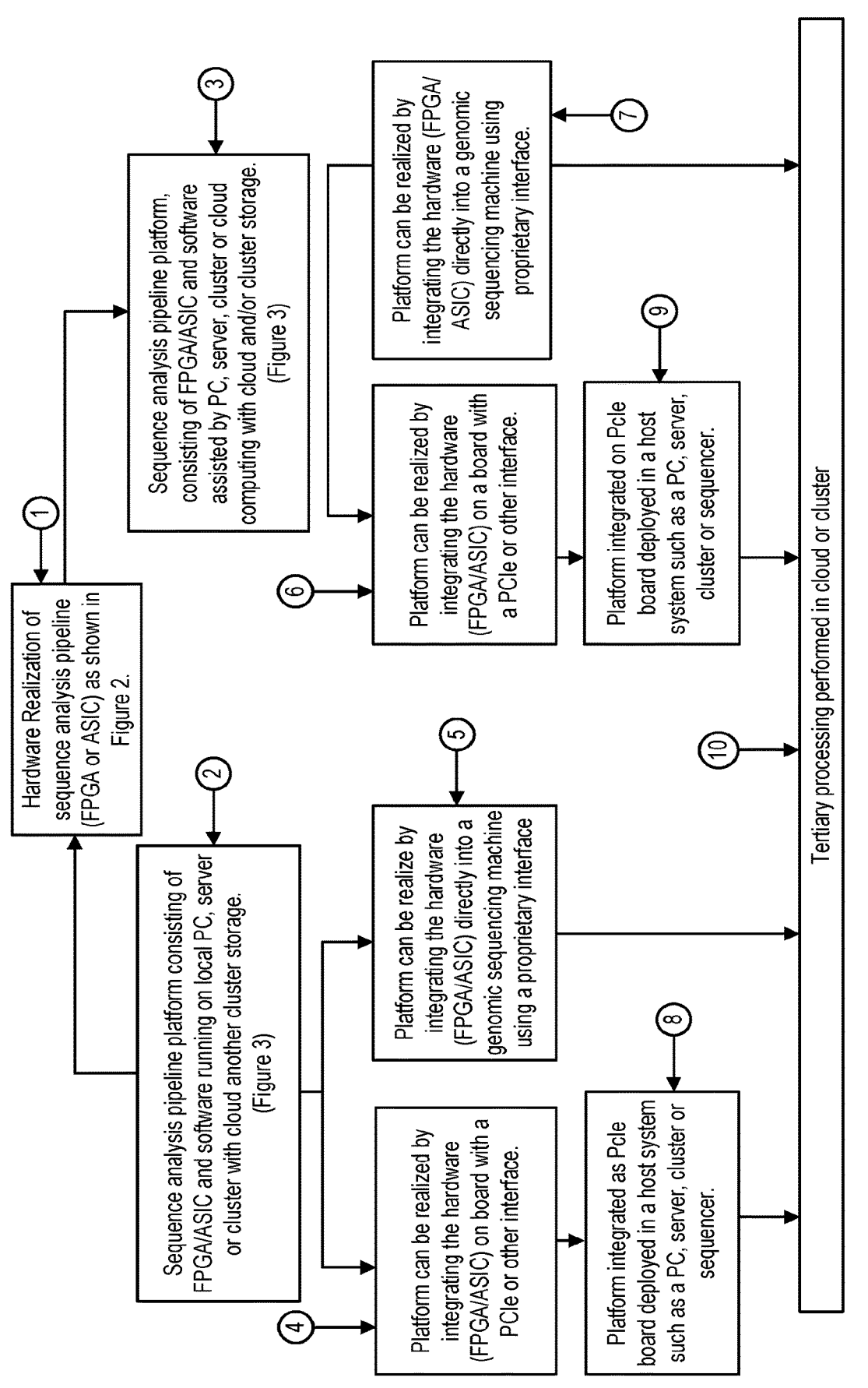
FIG. 49 illustrates processing steps using a genetic sequence analysis hardware platform.

In various instances, a hardware implementation of a sequence analysis pipeline is described. This can be done in a number of different ways such as an FPGA or ASIC or structured ASIC implementation. The functional blocks that are implemented by the FPGA or ASIC or structured ASIC are set forth in FIG. 49. Accordingly, the system includes a number of blocks or modules to do sequence analysis. The input to the hardware realization can be a FASTQ file, but is not limited to this format. In addition to the FASTQ file, the input to the FPGA or ASIC or structured ASIC consists of side information, such as Flow Space Information from technology such as from the NGS. The blocks or modules may include the following blocks: Error Control, Mapping, Alignment, Sorting, Local Realignment, Duplicate Marking, Base Quality Recalibration, BAM and Side Information reduction and/or variant calling.

These blocks or modules can be present inside, or implemented by, the hardware, but some of these blocks may be omitted or other blocks added to achieve the purpose of realizing a sequence analysis pipeline. Blocks 2 and 3 describe two alternatives of the sequence analysis pipeline platform. The sequence analysis pipeline platform comprising an FPGA or ASIC or structured ASIC and software assisted by a host (e.g., PC, server, cluster or cloud computing) with cloud and/or cluster storage. Blocks 4-7 describe different interfaces that the sequence analysis pipeline can have. In Blocks 4 and 6 the interface can be a PCIe and/or QPI/CAPI/CCVI/NVLink interface, but is not limited to a PCIe, QPI, or other interface. In Blocks 5 and 7 the hardware (FPGA or ASIC or structured ASIC) can be directly integrated into a sequencing machine. Blocks 8 and 9 describe the integration of the hardware sequence analysis pipeline integrated into a host system such as a PC, server cluster or sequencer. Surrounding the hardware FPGA or ASIC or structured ASIC are a plurality of DDR3 memory elements and a PCIe/QPI/CAPI/CCVI/NVLink interface. The board with the FPGA/ASIC/sASIC connects to a host computer, consisting of a host CPU and/or GPU, that could be either a low power CPU such as an ARM®, Snapdragon®, or any other processor. Block 10 illustrates a hardware sequence analysis pipeline API that can be accessed by third party applications to perform tertiary analysis.

Figure 50A:
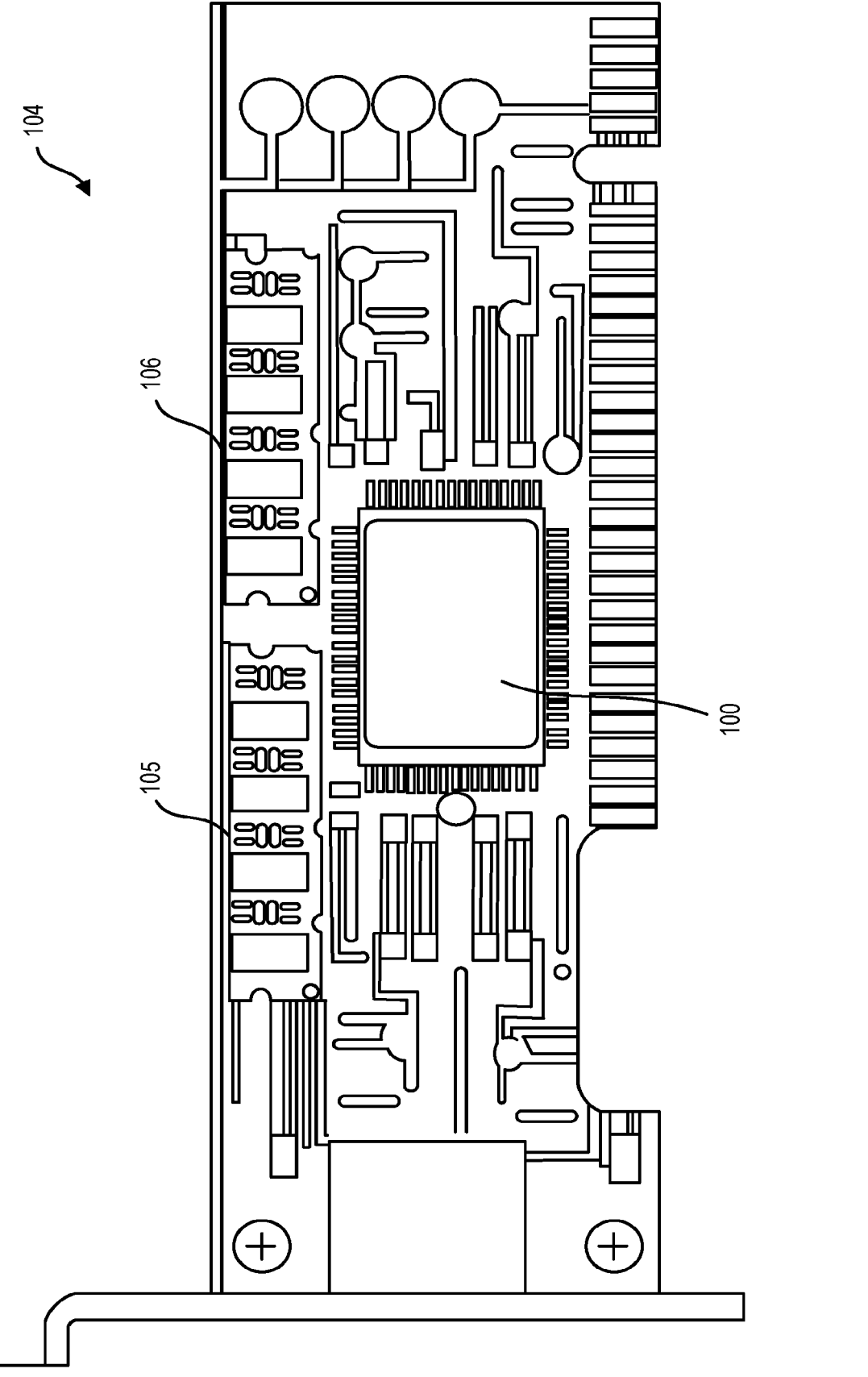
FIG. 50A illustrates an apparatus in accordance with an implementation of the disclosure.
Figure 50B:
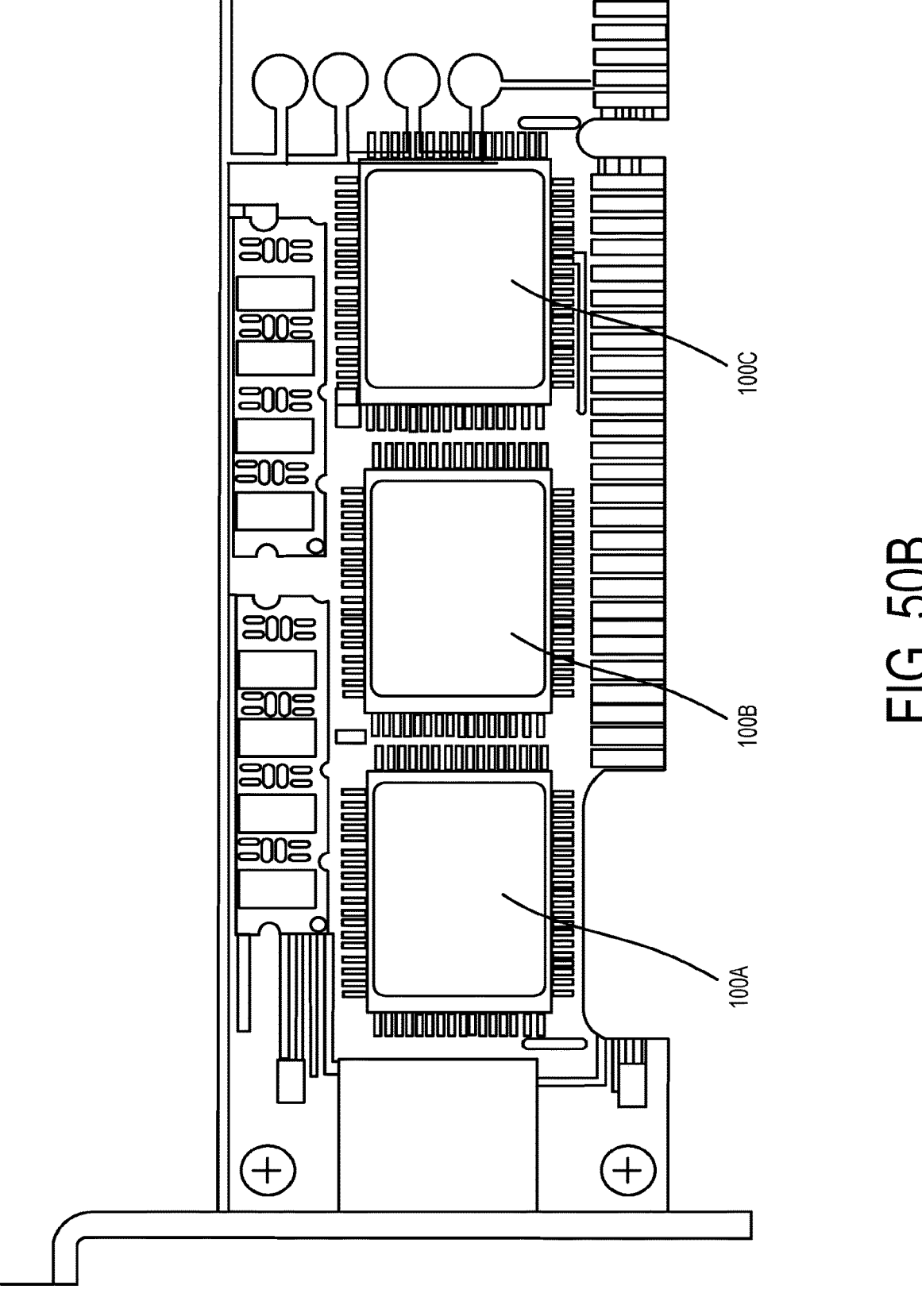
FIG. 50B illustrates another apparatus in accordance with an alternative implementation of the disclosure.

FIGS. 50A and 50B depict an expansion card 104 having a processing chip 100, e.g., an FPGA, of the disclosure, as well as one or more associated elements 105 for coupling the FPGA 100 with the host CPU/GPU, such as for the transferring of data, such as data to be processed and result data, back and forth from the CPU/GPU to the FPGA 100. FIG. 50B depicts the expansion card of FIG. 50A having a plurality, e.g., 3, slots containing a plurality, e.g., 3, processing chips of the disclosure.

Specifically, as depicted in FIGS. 50A and 50B, in various embodiments, an apparatus of the disclosure may include a computing architecture, such as embedded in a silicon field gate programmable array (FPGA) or application specific integrated circuit (ASIC) 100. The FPGA 100 can be integrated into a printed circuit board (PCB) 104, such as a Peripheral Component Interface—Express (PCIe) card, which can be plugged into a computing platform. In various instances, as shown in FIG. 50A, the PCIe card 104 may include a single FPGA 100, which FPGA may be surrounded by local memories 105, however, in various embodiments, as depicted in FIG. 50B, the PCIe card 104 may include a plurality of FPGAs 100A, 100B and 100C. In various instances, the PCI card may also include a PCIe bus. This PCIe card 104 can be added to a computing platform to execute algorithms on extremely large data sets. In an alternative embodiment, as noted above with respect to FIG. 34, in various embodiments, the FPGA may be adapted so as to be directly associated with the CPU/GPU, such as via an interloper, and tightly coupled therewith, such as via a QPI, CAPI, CCVI interface. Accordingly, in various instances, the overall work flow of genomic sequencing involving the FPGA may include the following: Sample preparation, Alignment (including mapping and alignment), Variant analysis, Biological Interpretation, and/or Specific Applications.

Hence, in various embodiments, an apparatus of the disclosure may include a computing architecture that achieves the high performance execution of algorithms, such as mapping and alignment algorithms, that operate on extremely large data sets, such as where the data sets exhibit poor locality of reference (LOR). These algorithms are designed to reconstruct a whole genome from millions of short read sequences, from modern so-called next generation sequencers, require multi-gigabyte data structures that are randomly accessed. Once reconstruction is achieved, as described herein above, further algorithms with similar characteristics are used to compare one genome to libraries of others, do gene function analysis, etc.

There are two other typical architectures that in general may be constructed for the performance of one or more of the operations herein described in detail, such as including purpose multicore CPUs and general purpose Graphic Processing Units (GPGPUs). In such an instance, each CPU/GPU in a multicore system may have a classical cache based architecture, wherein instructions and data are fetched from a level 1 cache (L1 cache) that is small but has extremely fast access. Multiple L1 caches may be connected to a larger but slower shared L2 cache. The L2 cache may be connected to a large but slower DRAM (Dynamic Random Access Memory) system memory, or may be connected to an even larger but slower L3 cache which may then connected to DRAM. An advantage of this arrangement may be that applications in which programs and data exhibit locality of reference behave nearly as if they are executing on a computer with a single memory as large as the DRAM but as fast as the L1 cache. Because full custom, highly optimized CPUs operate at very high clock rates, e.g., 2 to 4 GHz, this architecture may be essential to achieving good performance. Additionally, as discussed in detail with respect to FIG. 33, in various embodiments the CPU may be tightly coupled to an FPGA, such as an FPGA configured for running one or more functions related to the various operations described herein, such as via a high bandwidth, low latency interconnect such as a QPI, CCVI, CAPI so as to further enhance performance as well as the speed and coherency of the data transferred throughout the system. In such an instance, cache coherency may be maintained between the two devices, as noted above.

Further, GPGPUs may be employed to extend this architecture, such as by implementing very large numbers of small CPUs, each with their own small L1 cache, wherein each CPU executes the same instructions on different subsets of the data. This is a so called SIMD (Single Instruction stream, Multiple Data stream) architecture. Economy may be gained by sharing the instruction fetch and decode logic across a large number of CPUs. Each cache has access to multiple large external DRAMs via an interconnection network. Assuming the computation to be performed is highly parallelizable, GPGPUs have a significant advantage over general purpose CPUs due to having large numbers of computing resources. Nevertheless, they still have a caching architecture and their performance is hurt by applications that do not have a high enough degree of locality of reference. That leads to a high cache miss rate and processors that are idle while waiting for data to arrive from the external DRAM.

For instance, in various instances, Dynamic RAMs may be used for system memory because they are more economical than Static RAMs (SRAM). The rule of thumb used to be that DRAMs had 4× the capacity for the same cost as SRAMs. However, due to declining demand for SRAMs in favor of DRAMs, which difference has increased considerably due to the economies of scale that favor DRAMs that are in high demand. Independent of cost, DRAMs are 4× as dense as SRAMs laid out in the same silicon area because they only require one transistor and capacitor per bit compared to 4 transistors per bit to implement the SRAM's flip-flop. The DRAM represents a single bit of information as the presence or absence of charge on a capacitor.

A problem with this arrangement is that the charge decays over time, so it has to be refreshed periodically. The need to do this has led to architectures that organize the memory into independent blocks and access mechanisms that deliver multiple words of memory per request. This compensates for times when a given block is unavailable while being refreshed. The idea is to move a lot of data while a given block is available. This is in contrast to SRAMs in which any location in memory is available in a single access in a constant amount of time. This characteristic allows memory accesses to be single word oriented rather than block oriented. DRAMs work well in a caching architecture because each cache miss leads to a block of memory being read in from the DRAM. The theory of locality of reference is that if just accessed word N, then probably going to access words N+1, N+2, N+3 and so on, soon.

Figure 51:
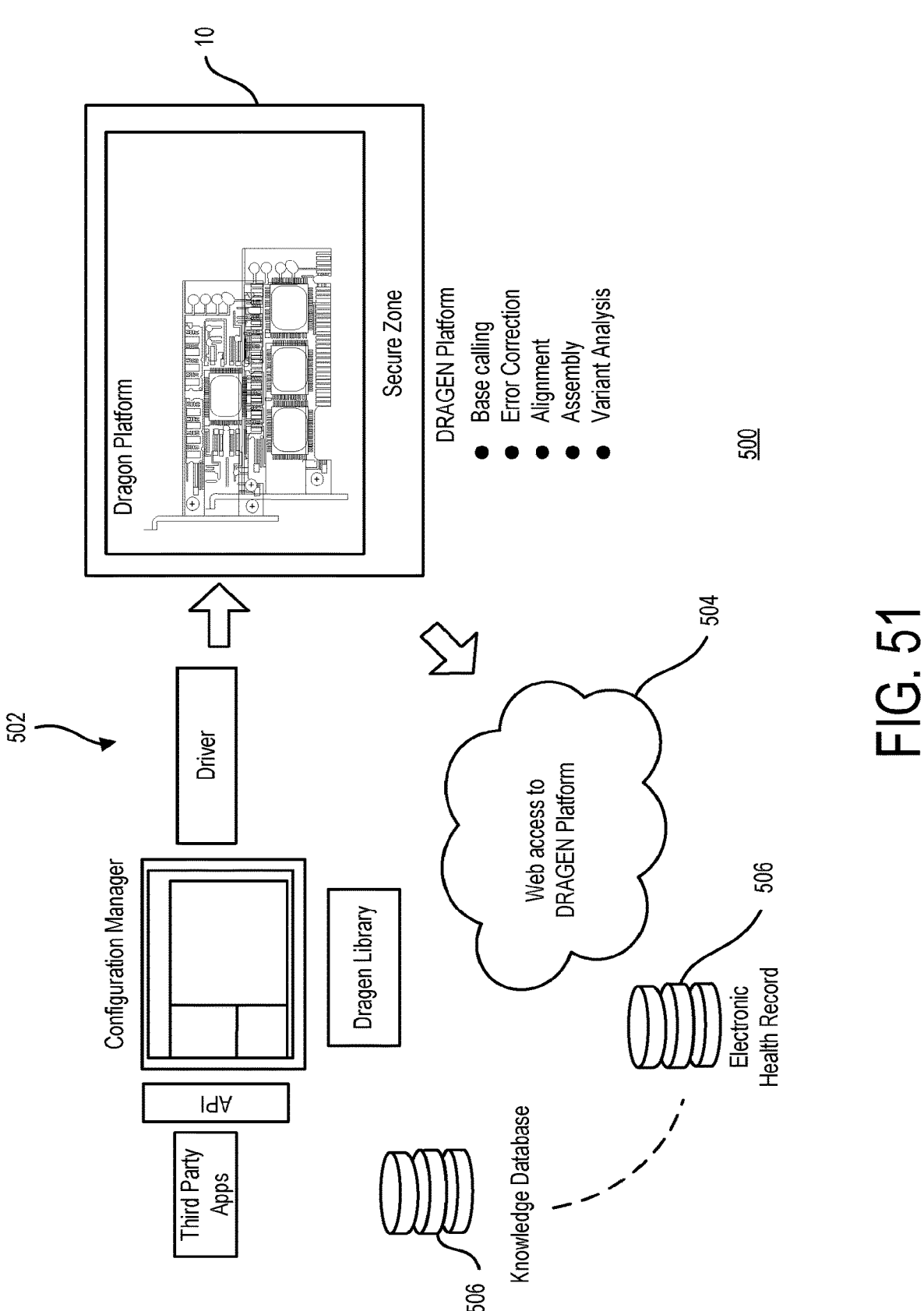
FIG. 51 illustrates a genomics processing system in accordance with an implementation.

FIG. 51 provides an exemplary implementation of a system 500 of the disclosure, including one or more of the expansions cards of FIG. 50, such as for bioinformatics processing 10. The system includes a Bio IT processing chip 100 that is configured for performing one or more functions in a processing pipeline, such as base calling, error correction, mapping, alignment, sorting, assembly, variant calling, and the like as described herein.

The system 500 further includes a configuration manager that is adapted for configuring the onboard functioning of the one or more processors 100. Specifically, in various embodiments, the configuration manager is adapted to communicate instructions to the internal controller of the FPGA, e.g., firmware, such as by a suitably configured driver over a loose or tightly coupled interconnect, so as to configure the one or more processing functions of the system 500. For instance, the configuration manager may be adapted to configure the internal processing clusters 11 and/or engines 13 associated therewith so as to perform one or more desired operations, such as mapping, aligning, sorting, variant calling, and the like, in accordance with the instructions received. In such a manner only the clusters 11 containing the processing engines 13 for performing the requested processing operations on the data provided from the host system 1000 to the chip 100 may be engaged to process the data in accordance with the received instructions.

Additionally, in various embodiments, the configuration manager may further be adapted so as to itself be adapted, e.g., remotely, by a third party user, such as over an API connection, as described in greater detail herein above, such as by a user interface (GUI) presented by an App of the system 500. Additionally, the configuration manager may be connected to one or more external memories, such as a memory forming or otherwise containing a database, such as a data base including one or more reference or individually sequenced genomes and/or an index thereof, and/or one or more previously mapped, aligned, and/or sorted genomes or portions thereof. In various instances, the database may further include one or more genetic profiles characterizing a diseased state such as for the performance of one or more tertiary processing protocols, such as upon newly mapped, aligned genetic sequences or a VCF pertaining thereto.

The system 500 may also include a web-based access so as to allow remote communications such as via the internet so as to form a cloud or at least a hybrid cloud 504 communications platform. In such a manner as this, the processed information generated from the Bio IT processor, e.g., results data, may be encrypted and stored as an electronic health record, such as in an external, e.g., remote, database. In various instances, the EMR database may be searchable, such as with respect to the genetic information stored therein, so as to perform one or more statistical analyses on the data, such as to determine diseased states or trends or for the purposes of analyzing the effectiveness of one or more prophylactics or treatments pertaining thereto. Such information along with the EMR data may then be further processed and/or stored in a further database 508 in a manner so as to insure the confidentiality of the source of the genetic information.

More particularly, FIG. 51 illustrates a system 500 for executing a sequence analysis pipeline on genetic sequence data. The system 500 includes a configuration manager 502 that includes a computing system. The computing system of the configuration manager 502 can include a personal computer or other computer workstation, or can be implemented by a suite of networked computers. The configuration manager 502 can further include one or more third party applications connected with the computing system by one or more APIs, which, with one or more proprietary applications, generate a configuration for processing genomics data from a sequencer or other genomics data source. The configuration manager 502 further includes drivers that load the configuration to the genomics pipeline processor system 10. The genomics pipeline processor system 10 can output result data to, or be accessed via, the Web 504 or other network, for storage of the result data in an electronic health record 506 or other knowledge database 508.

As discussed in several places herein above, the chip implementing the genomics pipeline processor can be connected or integrated in a sequencer. The chip can also be connected or integrated, e.g., directly via an interloper, or indirectly, e.g., on an expansion card such as via a PCIe, and the expansion card can by connected or integrated in a sequencer. In other implementations, the chip can be connected or integrated in a server computer that is connected to a sequencer, to transfer genomic reads from the sequencer to the server. In yet other implementations, the chip can be connected or integrated in a server in a cloud computing cluster of computers and servers. A system can include one or more sequencers connected (e.g. via Ethernet) to a server containing the chip, where genomic reads are generated by the multiple sequencers, transmitted to the server, and then mapped and aligned in the chip.

For instance, in general next generation DNA sequencer (NGS) data pipelines, the primary analysis stage processing is generally specific to a given sequencing technology. This primary analysis stage functions to translate physical signals detected inside the sequencer into "reads" of nucleotide sequences with associated quality (confidence) scores, e.g. FASTQ format files, or other formats containing sequence and usually quality information. Primary analysis, as mentioned above, is often quite specific in nature to the sequencing technology employed. In various sequencers, nucleotides are detected by sensing changes in fluorescence and/or electrical charges, electrical currents, or radiated light. Some primary analysis pipelines often include: Signal processing to amplify, filter, separate, and measure sensor output; Data reduction, such as by quantization, decimation, averaging, transformation, etc.; Image processing or numerical processing to identify and enhance meaningful signals, and associate them with specific reads and nucleotides (e.g. image offset calculation, cluster identification); Algorithmic processing and heuristics to compensate for sequencing technology artifacts (e.g. phasing estimates, cross-talk matrices); Bayesian probability calculations; Hidden Markov models; Base calling (selecting the most likely nucleotide at each position in the sequence); Base call quality (confidence) estimation, and the like. As discussed herein above, one or more of these steps may be benefitted by implementing one or more of the necessary processing functions in hardware, such as implemented by an integrated circuit, e.g., an FPGA. Further, after such a format is achieved, secondary analysis proceeds, as described herein, to determine the content of the sequenced sample DNA (or RNA etc.), such as by mapping and aligning reads to a reference genome, sorting, duplicate marking, base quality score recalibration, local re-alignment, and variant calling. Tertiary analysis may then follow, to extract medical or research implications from the determined DNA content.

Accordingly, given the sequential nature of the above processing functions, it may be advantageous to integrate primary, secondary, and/or tertiary processing acceleration in a single integrated circuit, or multiple integrated circuits positioned on a single expansion card. This may be beneficial because sequencers produce data that typically requires both primary and secondary analysis so as to be useful and may further be used in various tertiary processing protocols, and integrating them in a single device is most efficient in terms of cost, space, power, and resource sharing. Hence, in one particular aspect, the disclosure is directed to a system, such as to a system for executing a sequence analysis pipeline on genetic sequence data. In various instances, the system may include an electronic data source, such as a data source that provides digital signals, for instance, digital signals representing a plurality of reads of genomic data, where each of the plurality of reads of genomic data include a sequence of nucleotides. The system may include one or more of a memory, such as a memory storing one or more genetic reference sequences and/or an index of the one or more genetic reference sequences; and/or the system may include a chip, such as an ASIC, FPGA, or sASIC.

One or more aspects or features of the subject matter described herein can be realized in digital electronic circuitry, integrated circuitry, specially designed application specific integrated circuits (ASICs), field programmable gate arrays (FPGAs), or structured ASIC computer hardware, firmware, software, and/or combinations thereof.

These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

Additionally, due to the immense growth in data production and acquisition in the $21^{st}$ Century, a need has developed for increased processing power that is capable of handling the ever-growing computationally intense analyses upon which modern development is founded. Supercomputers have been introduced, and have been useful for advancing technological development over a wide range of platforms. However, although supercomputing is useful, it has proven to be insufficient for some of the very complex computing problems many of today's technology companies face. Particularly, since the sequencing of the human genome, the technological advancement in the biological arts has been exponential. Nevertheless, in view of the high rate and increased complexity of the raw data produced every day, there has evolved a problematic bottleneck in the processing and analysis of the data generated. Quantum computers have been developed therefor to help resolve this bottleneck. Quantum computing represents a new frontline in computing, providing an entirely new approach to solving the world's most challenging computational needs.

Quantum computing has been known since 1982. For instance, in the International Journal of Theoretical Physics, Richard Feynman theorized a system for performing quantum computing. Specifically, Feynman proposed a quantum system that could be configured for use in simulating other quantum systems in such a manner that the conventional functions of computer processing can be performed more quickly and efficiently. See Feynman, 1982, International Journal of Theoretical Physics 21, pp. 467-488, which is hereby incorporated by reference in its entirety. Particularly, a quantum computer system can be designed so as to exhibit exponential time-savings in complex computations. Such controllable quantum systems are commonly known as quantum computers, and have been successfully developed into general purpose processing computers that not only can be used to simulate quantum systems, but can also be adapted for running specialized quantum algorithms. More particularly, complex problems can be modeled in the form of an equation, such as a Hamiltonian, which may be represented in the quantum system in a manner that the behavior of the system provides information regarding the solution to the equation. See Deutsch, 1985, Proceedings of the Royal Society of London A 400, pp. 97-117, which is hereby incorporated by reference in its entirety. In such instances, solving a model for the behavior of the quantum system may be configured so as to involve solving a differential equation related to the wave-mechanical description of a particle, e.g., Hamiltonian, of the quantum system.

In essence, quantum computing is a computational system that uses quantum-mechanical phenomena, e.g., superposition and/or entanglement, to perform various calculations on large amounts of data extremely fast. As such, quantum computers are a vast improvement over conventional digital logic computers. Specifically, conventional digital logic circuits function by using binary digital logic gates that are formed through the hardwiring of electronic circuitry on a conductive substrate. In a digital logic circuit an "on/off" state of a transistor serves as a basic unit of information, e.g., a bit. Particularly, a common digital computer processor employs binary digits, e.g., bits, in an "on" or "off" state, e.g., as a 0 or 1, to encode data. Quantum computation, on the other hand, employs an information device that uses superpositions of entangled states, called quantum bits or qubits, to encode data.

The basis for performing such quantum computations is an information device, e.g., a unit, which forms the quantum bit. The qubit is analogous to the digital "bit" in traditional digital computers, except that the qubit has far more computational potential than a digital bit. Particularly, as described in greater detail herein, instead of only encoding one of two discrete states, like a "0" and a "1," as found in a digital bit, a qubit can also be placed in a superposition of "0" and "1." Specifically, the qubit can exist in both the "0" and "1" state at the same time. Consequently, the qubit can perform a quantum computation on both states simultaneously. In general, N qubits can be in a superposition of $2^n$ states. Quantum algorithms, therefore, can make use of this superposition property to speed up certain computations.

A qubit, therefore, is analogous to a bit in a traditional digital computer, and is a type of information device that exhibits coherence. Particularly, a quantum computing device is built up from a plurality of information device, e.g., qubit, building blocks. For instance, the computing power of a quantum computer increases as the information devices that form its building blocks are coupled, e.g., entangled, together in a controllable manner. In such an instance, the quantum state of one information device affects the quantum state of each of the other information devices to which it is coupled.

Accordingly, like the bit in classic digital computing, the qubit in quantum computing serves as the basic unit for the encoding of information, such as quantum information. Similar to a bit, the qubit encodes data in a two-state system, which in this instance is a quantum-mechanical system. Specifically, for the qubit, the two quantum states involve entanglement, such as involving the polarization of a single photon. Hence, where in a classical system, a bit has to be in one state or the other, in a quantum computing platform, the qubit may be in a superposition of both states at the same time, which property is fundamental to quantum processing. Consequently, the distinguishing feature between the qubit and the classical bit is that multiple qubits exhibit quantum entanglement. Such entanglement is a nonlocal property that allows a set of qubits to express higher correlation than is possible in a classical system.

In order to function, such information devices, e.g., quantum bits, must fulfill several requirements. First, the information device must be reducible to a quantum two-level system. This means that the information device must have two distinguishable quantum states that may be used for performing computations. Second, the information devices must be capable of producing quantum effects like entanglement and superposition. Additionally, in certain instances, the information device may be configured for storing information, e.g., quantum information, such as in a coherent form. In such instances, the coherent device may have a quantum state that persists without significant degradation for a long period of time, such as on the order of microseconds or more.

Particularly, quantum entanglement is the physical phenomenon that occurs when a pair or a group of particles are generated or otherwise configured to interact in a manner that the quantum state of one particle cannot be described independently of another, despite the space that separates them. Consequently, instead of describing the state of one particle in isolation of the others, a quantum state must be described for the system as a whole. In such instances, the measurements of various physical properties, such as position, momentum, spin, and/or polarization, performed on entangled particles are correlated. For example, if a pair of particles are generated in such a way that their total spin is known to be zero, and one particle is found to have clockwise spin on a certain axis, the spin of the other particle, measured on the same axis, will be found to be counterclockwise, as to be expected due to their entanglement.

Hence, one particle of an entangled pair simply "knows" what measurement has been performed on the other, and with what outcome, even though there is no known means for such information to have been communicated between the particles, which at the time of measurement may be separated by arbitrarily large distances. Because of this relationship, unlike classical bits that can only have one value at a time, entanglement allows multiple states to be acted on simultaneously. It is these unique entangled relationships and quantum states that have been capitalized upon for the development of quantum computing.

Accordingly, there are various kinds of physical operations employing pure qubit states that can be performed. For instance, a quantum logic gate can be formed and configured to operate on the basic qubit, where the qubit undergoes a unitary transformation, such as where the unitary transformations corresponds to rotations, or other quantum phenomena, of the qubit. In fact, any two-level system can be used as a qubit, such as photons, electrons, nuclear spins, coherent light states, optical lattices, Josephson junctions, quantum dots, and the like. Specifically, a quantum gate is the basis for a quantum circuit operating on a small number of qubits. For instance, a quantum circuit is comprised of quantum gates that act on fixed numbers of qubits, such as two or three, or more. Qubits, therefore, are the building blocks of quantum circuits, like classical logic gates are for conventional digital circuits. Specifically, a quantum circuit is a model for quantum computation where the computation is a sequence of quantum gates that are reversible transformations on a quantum mechanical analog of an n-bit register. Such analogous structures are referred to as n-qubit registers. Hence, unlike classical logic gates Quantum logic gates are always reversible.

Particularly, as described herein, a digital logic gate is a physical, wired device that may be implemented using one or more diodes or transistors that act as electronic switches for performing logical operations, e.g., Boolean functions, on one or more binary inputs, so as to produce a single binary output. With amplification, logic gates can be cascaded in the same way that Boolean functions can be composed, allowing the construction of a physical model of all of Boolean logic, and therefore, all of the algorithms and mathematics that can be described with Boolean logic can be performed by digital logic gates. In a like manner a cascade of quantum logic gates can be formed for the performance of Boolean logic operations.

Quantum gates are usually represented as matrices. In various implementations, a quantum gate acts on k qubits that may be represented by a $2k \times 2k$ unitary matrix. In such instances, the number of qubits in the input and output of the gate should be equal, and the action of the gate on a specific quantum state is found by multiplying the vector that represents the state by the matrix representing the gate. Hence, given this configuration quantum computational operations may be executed on a very small number of quantum bits. For instance, there are quantum algorithms that are configured for running much more complex computations faster than any possible probabilistic classical algorithm. Particularly, a quantum algorithm is an algorithm that runs on a quantum circuit model of computation.

Where a classical algorithm is a finite sequence of step-by-step instructions or procedures that may be performed by digital logic circuits of a classic computer; a quantum algorithm is a step-by-step procedure, where each of the steps can be performed on a quantum computer. However, even though quantum algorithms exist, such as Shor's, Grovar's, and Simon's algorithms, all classical algorithms can also be performed on a quantum computer with the correct configurations. Quantum algorithms are usually used for those algorithms that are inherently quantum, e.g., such as involving superposition or quantum entanglement. Quantum algorithms may be stated in various models of quantum computation, such as the Hamiltonian oracle model.

Accordingly, as a classical computer has a memory made up of bits, where each bit is represented by either a "1" or a"0"; a quantum computer supports a sequence of qubits where a single qubit can represent a one, a zero, or any quantum superposition of those two qubit states. Consequently, a pair of qubits can be in any quantum superposition of 4 states, and three qubits can be in any superposition of 8 states. In general, a quantum computer with n qubits can be in an arbitrary superposition of up to $2^n$ different states simultaneously, which compares to a normal computer that can only be in one of these $2^n$ states at any one time. Therefore, qubits can hold exponentially more information than their classical counterparts. In action, a quantum computer operates by setting the qubits in a drift that solves the problem by manipulating those qubits with a fixed sequence of quantum logic gates. It is this sequence of quantum logic gates that forms the operations of quantum algorithms. The calculation ends with a measurement, collapsing the system of qubits into one of the $2^n$ pure states, where each qubit is "0" or "1", thereby decomposing into a classical state. Hence, traditional algorithms may also be performed on a quantum computing platform, where the outcome is typically n classical bits of information.

In standard notation, the basic states of a qubit are referred to as the "0" and "1" states. However, during quantum computation, the state of a qubit, in general, may be a superposition of the basic or basis states such that the qubit has a nonzero probability of occupying the "0" basis state and a simultaneous nonzero probability of occupying the "1" basis state. Accordingly, the quantum nature of the qubit is largely derived from its ability to exist in a coherent superposition of basis states, and for the state of the qubit to have a phase. A qubit will retain this ability to exist as a coherent superposition of basis states as long as the qubit is sufficiently isolated from sources of decoherence.

Consequently, to complete a computation using a qubit, the state of the qubit is measured. As indicated above, when a measurement of the qubit is done, the quantum nature of the qubit may be temporarily lost and the superposition of the basis states may collapse to either the "0" basis state or the "1" basis state. Thus, in such a manner as this, the qubit regains its similarity to a conventional digital "bit". However, the actual state of the qubit after it has collapsed will depend on the various probability states present immediately prior to the measurement operation. Thus, qubits may be employed to form quantum circuits, which themselves may be configured to form a quantum computer.

There are several general approaches to the design and operation of a quantum computer. One approach that has been put forth is that of a circuit model for quantum computing. Circuit model quantum computing requires long quantum coherence, so the type of information device used in quantum computers that support such an approach may be the qubit, which by definition has long coherence times. Accordingly, the circuit model for quantum computing is based upon the premise that qubits can be formed of and be acted on by logical gates, much like bits, and can be programmed using quantum logic in order to perform calculations, such as Boolean computations. Research has been done to develop qubits that can be programmed to perform quantum logic functions in this manner. For example, see Shor, 2001, arXiv.org:quant-ph/0005003, which is hereby incorporated by reference in its entirety. Likewise, a computer processor may take the form of a quantum processor such as a superconducting quantum processor.

A superconducting quantum processor may include a number of qubits and associated local bias devices, for instance, two, three, or more superconducting qubits. Accordingly, although in various embodiments, a computer processor may be configured as a non-traditional superconducting processor, in other embodiments, it the computer processor may be configured as a superconducting processor. For instance, in some embodiments, a non-traditional superconducting processor may be configured so as to not focus on quantum effects such as superposition, entanglement, and/or quantum tunneling, but may rather operate by emphasizing different principles, such as those principles that govern the operation of classical computer processors. In other embodiments, the computer processor may be configured as a traditional superconducting processor such as by being adapted to process through various quantum effects, such as superposition, entanglement, and/or quantum tunneling.

Accordingly, in various instances, there may be certain advantages to the implementation of such superconducting processors. Particularly, due to their natural physical properties, superconducting processors in general may be capable of higher switching speeds and shorter computation times than non-superconducting processors, and therefore it may be more practical to solve certain problems on superconducting processors. Further, detail and embodiments of exemplary quantum processors that may be used in conjunction with the present devices, systems, and the methods of their use are described in U.S. Ser. Nos. 11/317,838; 12/013,192; 12/575,345; 12/266,378; 13/678,266; and Ser. No. 14/255,561; as well as the various divisionals, continuations, and/or continuation in parts thereof; including U.S. Pat. Nos. 7,533,068; 7,969,805; 9,026,574; 9,355,365; 9,405,876; and all of their foreign counterparts, which are hereby incorporated by reference in their entireties.

Further, in addition to the above quantum devices and systems, methods for their use in solving complex computational problems are also presented. For instance, the quantum devices and systems herein disclosed may be employed for controlling the quantum state of one or more information devices and/or systems, in a coherent manner, so as to perform one or more steps in a bioinformatics and/or genomics processing pipeline, such as for the performance of one or more operations in an image processing, base calling, mapping, aligning, sorting, variant calling, and/or other genomics and/or bioinformatics pipeline. In particular embodiments, the one or more operations may include performing a burrow-wheelers, smith-waterman, and/or an HMM operation.

Particularly, solving complex genomics and/or bioinformatics computational problems using a quantum computing device may include generating one or more qubits and using the same to form a quantum logic circuit representation of the computational problem, encoding the logic circuit representation as a discrete optimization problem, and solving the discrete optimization problem using the quantum processor. The representation may be an arithmetic and/or geometric problem for solution by an addition, subtraction, multiplication, and/or divide circuit. The discrete optimization problem may be composed of a set of miniature optimization problems, where each miniature optimization problem encodes a respective logic gate from the logic circuit representation. For instance, a mathematical circuit may employ binary representations of factors, and these binary representations may be decomposed to reduce the total number of variables required to represent the mathematical circuit. Accordingly, in accordance with the teachings herein, a computer processor may take the form of a digital and/or an analog processor, for instance, a quantum processor such as a superconducting quantum processor. A superconducting quantum processor may include a number of qubits and associated local bias devices, for instance two or more superconducting qubits, which may be formed into one or more quantum logic circuit representations.

More particularly, in various embodiments, a superconducting integrated circuit may be provided. Specifically, in particular embodiments, such a superconducting integrated circuit may include a first superconducting current path that is disposed in a metal, e.g., first, metal layer. A dielectric, e.g., first dielectric, layer may also be included, such as where at least a portion of the dielectric layer is associated within and/or carried on the first metal layer. A second superconducting current path may also be included and disposed in a second metal layer, such as metal layer that is carried on or otherwise associated with the first dielectric layer. In such an embodiment, at least a portion of the second superconducting current path may overlay at least a portion of the first superconducting current path. Likewise, a second dielectric layer may also be included, such as where at least a portion of the second dielectric layer is associated with or carried on the second metal layer. Additionally, a third superconducting current path may be included and disposed in a third metal layer that may be associated with or carried on the second dielectric layer, such as where at least a portion of the third superconducting current path may overlay at least a portion of one or both of the first and second superconducting current paths. One or more additional metal layers, dielectric layers, and/or current paths may also be included and configured accordingly.

Further, a first superconducting connection may be positioned between the first superconducting current path and the third superconducting current path, such as where the first superconducting connection extends through both the first dielectric layer and the second dielectric layer. A second superconducting connection may also be included and positioned between the first superconducting current path and the third superconducting current path, such as where the second superconducting connection may extend through both the first dielectric layer and the second dielectric layer. Additionally, at least a portion of the second superconducting current path may be encircled by an outer superconducting current path that may be formed by at least a portion of one or more of the first superconducting current path, at least a portion of the second superconducting current path, and/or the first and second superconducting connections. Accordingly, in such instances, the second superconducting current path may be configured to couple, e.g., inductively couple, a signal to the outer superconducting current path.

In some embodiments, a mutual inductance between the second superconducting current path and the outer superconducting current path may be sub-linearly proportional to a thickness of the first dielectric layer and a thickness of the second dielectric layer. The first and the second superconducting connections may also each include at least one respective superconducting via. Further, in various embodiments, the second superconducting current path may be a portion of an input signal line and one or both the first and the third superconducting current paths may be coupled to a superconducting programmable device. In other embodiments, the second superconducting current path may be a portion of a superconducting programmable device and both the first and the third superconducting current paths may be coupled to an input signal line. In particular embodiments, the superconducting programmable device may be a superconducting qubit, which may then be coupled, e.g., quantumly coupled, to one or more other qubits so as to from a quantum circuit, such as of a quantum processing device.

Accordingly, provided herein are devices, systems, and methods for solving computational problems, especially problems related to resolving the genomics and/or bioinformatics bottleneck described herein above. In various embodiments, these devices, systems and methods introduce a technique whereby a logic circuit representation of a computational problem may be solved directly and/or may be encoded as a discrete optimization problem, and the discrete optimization problem may then be solved using a computer processor, such as a quantum processor. For instance, in particular embodiments, solving such discrete optimization problems may include executing the logic circuit to solve the original computational problem.

Hence, the devices, systems, and methods described herein may be implemented using any form of computer processor such as including traditional logic circuits and/or logic circuit representations, such as configured for use as a quantum processor and/or in super conducting processing. Particularly, various steps in performing an image processing, base calling, mapping, aligning, and/or variant calling bioinformatics pipeline may be encoded as discrete optimization problems and as such may be particularly well-suited to be solved using the quantum processors, disclosed herein. In other instances, such computations may be resolved more generally by a computer processor that harnesses quantum effects to achieve such computation; and/or in other instances, such computations may be performed using a dedicated integrated circuit, such as an FPGA, ASIC, or structured ASIC, as described herein in detail. In some embodiments, the discrete optimization problem is cast as a problem by configuring the logic circuits, qubits, and/or couplers in a quantum processor. In some embodiments, the quantum processor may be specifically adapted to facilitate solving such discrete optimization problems.

As disclosed throughout this specification and the appended claims, reference is often made to a "logic circuit representation", e.g., of a computational problem. Depending on the context, a logic circuit may incorporate a set of logical inputs, a set of logical outputs, and a set of logic gates (e.g., NAND gates, XOR gates, and the like) that transform the logical inputs to the logical outputs through a set of intermediate logical inputs and intermediate logical outputs. A complete logic circuit may include a representation of the input(s) to the computational problem, a representation of the output(s) of the computational problem, and a representation of the sequence of intermediate steps in between the input(s) and the output(s).

Thus, for various purposes of the present devices, systems, and methods, the computational problem may be defined by its input(s), its output(s), and the intermediate steps that transform the input(s) to the output(s) and a "logic circuit representation" may include all of these elements. Those of skill in the art will appreciate that the encoding of a "logic circuit representation" of a computational problem as a discrete optimization problem, and the subsequent mapping of the discrete optimization problem to a quantum processor, may result in any number of layers involving any number of qubits per layer. Furthermore, such a mapping may implement any scheme of inter-qubit coupling to enable any scheme of inter-layer coupling (e.g., coupling between the qubits of different layers) and intra-layer coupling (e.g., coupling between the qubits within a particular layer).

Accordingly, as indicated, in some embodiments, the structure of a logic circuit may be stratified into layers. For example, the logical input(s) may represent a first layer, each sequential logical (or arithmetic) operation may represent a respective additional layer, and the logical output(s) may represent another layer. And as previously described, a logical operation may be executed by a single logic gate or by a combination of logic gates, depending on the specific logical operation being executed. Thus, a "layer" in a logic circuit may include a single logic gate or a combination of logic gates depending on the particular logic circuit being implemented.

Consequently, in various embodiments such as where the structure of a logic circuit stratifies into layers (for example, with the logical input(s) representing a first layer, each sequential logical operation representing a respective additional layer, and the logical output(s) representing another layer), each layer may be embodied by a respective set of qubits in the quantum and/or superconducting processor. For example, in one embodiment of a quantum processor, one or more, e.g., each, row of qubits may be programmed to represent a respective layer of a quantum logic circuit. That is, particular qubits may be programmed to represent the inputs to a logic circuit, other qubits may be programmed to represent a first logical operation (executed by either one or a plurality of logic gates), and further qubits may be programmed to represent a second logical operation (similarly executed by either one or a plurality of logic gates), and yet further qubits may be programmed to represent the outputs of the logic circuit.

Additionally, with various sets of qubits representing various layers of the problem, it can be advantageous to enable independent dynamic control of each respective set. Further, in various embodiments, various serial logic circuits may be mapped to the quantum processor, and the respective qubits mapped to facilitate the functional interactions for quantum processing in a manner suitable to enable independent control thereof. From the above, those of skill in the art will appreciate how a similar objective function may be defined for any logic gate. Thus, in some embodiments, the problem representing a logic circuit may essentially be comprised of a plurality of miniature optimization problems, where each gate in the logic circuit corresponds to a particular miniature optimization problem.

Hence, exemplary logic circuit representations may be generated using systems and methods that are known in the art. In one example, a logic circuit representation of the computational problem, e.g., the genomics and/or bioinformatics problem, may be generated and/or encoded using a classical digital computer processor and/or a quantum and/or superconducting processor as described herein. Accordingly, a logic circuit representation of the computational problem may be stored in at least one computer- or processor-readable storage medium, such as a computer-readable non-transitory storage medium or memory (e.g., volatile or non-volatile). Therefore, as discussed herein, the logic circuit representation of the computational problem may be encoded as a discrete optimization problem, or a set of optimization objectives, and in various embodiments, such as where a classical digital computer processing paradigm is configured to solve the problem, the system may be configured so that bit strings that satisfy the logic circuit have energy of zero and all other bit strings have energy greater than zero, where the discrete optimization problem may be solved in such a manner as to establish a solution to the original computational problem.

Further, in other embodiments, the discrete optimization problem may be solved using a computer processor, such as a quantum processor. In such an instance, solving the discrete optimization problem may then involve, for example, evolving the quantum processor to the configuration that minimizes the energy of the system in order to establish a bit string that satisfies the optimization objective(s). Accordingly, in some embodiments, the act of solving a discrete optimization problem may include three acts. First, the discrete optimization problem may be mapped to a computer processor. In some embodiments, the computer processor may include a quantum and/or super conducting processor and mapping the discrete optimization problem to the computer processor may include programming the elements (e.g., qubits and couplers) of the quantum and/or superconducting processor. Mapping the discrete optimization problem to the computer processor may include the discrete optimization problem in at least one computer or processor-readable storage medium, such as a computer-readable non-transitory storage medium or memory (e.g., volatile or non-volatile).

Accordingly, in view of the above, in various instances, a device, system, and method for executing a sequence analysis pipeline, such as on genomics material, is provided. For instance, the genomics material may include a plurality of reads of genomic data, such as in an image file, BCL, FASTQ file, and the like. In various embodiments, the device and/or system may be employed for executing a sequence analysis on genomic data, e.g., reads of genomic data, such as by using an index of one or more genetic reference sequences, e.g., stored in a memory, for example, where each read of genomic data and each reference sequence represents a sequence of nucleotides.

Particularly, in various embodiments, the device may be a quantum computing device, such as formed of a set of quantum logic circuits, e.g., hardwired quantum logic circuits, for instance, where the logic circuits are interconnected with one another. In various instances, the quantum logic circuits may be interconnected by one or more superconducting connections.

Additionally, one or more of the superconducting connections may include a memory interface, such as for accessing the memory. Together the logic circuits and interconnects may be configured to process information represented as a quantum state that is itself represented as a set of one or more qubits. More particularly, the set of hardwired quantum logic circuits may be arranged as a set of processing engines, such as where each processing engine may be formed of a subset of the hardwired quantum logic circuits, and may be configured to perform one or more steps in the sequence analysis pipeline on the reads of genomic data.

For instance, the set of processing engines may be configured so as to include an image processing, base calling, mapping, aligning, sorting, variant calling, and/or other genomics and/or bioinformatics processing module. For example, in various embodiments, a mapping module, such as in a first hardwired configuration, may be included. Additionally, in further embodiments, an alignment module, such as in a second hardwired configuration, may be included. Further, a sorting module, such as in a third hardwired configuration, may be included. And, in additional embodiments, a variant calling module, such as in a fourth hardwired configuration, may be included. Further still, in various embodiments, an image processing and/or base calling module may be included in further hardwired configurations, such as where one or more of these hardwired configurations may include hardwired quantum logic circuits may be arranged as a set of processing engines.

More particularly, in particular instances, a quantum computing device and/or system may include a mapping module, where the mapping module comprises a set of quantum logic circuits that are arranged as a set of processing engines, one or more of which are configured for performing one or more steps of a mapping procedure. For instance, one or more quantum processing engines may be configured to receive a read of genomic data, such as via one or more of a plurality of superconducting connections. Further, the one or more quantum processing engines may be configured to extract a portion of the read to generate a seed, such as where the seed may represent a subset of the sequence of nucleotides represented by the read. Additionally, one or more of the quantum processing engines may be configured to calculate a first address within the index based on the seed, and access the address in the index in the memory, so as to receive a record from the address, such as where the record represents position information in the genetic reference sequence. Furthermore, the one or more quantum processing engines may be configured to determine, e.g., based on the record, one or more matching positions from the read to the genetic reference sequence; and output at least one of the matching positions to the memory via the memory interface.

Further still, the mapping module may include a set of quantum logic circuits that are arranged as a set of processing engines configured for calculating a second address within the index, e.g., based on both of the record and of a second subset of the sequence of nucleotides that is not contained in the first subset of the sequence of nucleotides. The processing engine(s) may then access the second address in the index in the memory so as to receive a second record from the second address, such as where the second record, or a subsequent record, includes position information in the genetic reference sequence. The processing engine may further be configured for determining, based on the position information, the one or more matching positions from the read to the genetic reference sequence.

Additionally, in various instances, a quantum computing device and/or system may include an alignment module, where the alignment module comprises a set of quantum logic circuits that are arranged as a set of processing engines, one or more of which are configured for performing one or more steps of an alignment procedure. For instance, one or more quantum processing engines may be configured to receive a plurality of mapped positions for the read from the memory, and to access the memory to retrieve a segment of the genetic reference sequence corresponding to each of the mapped positions. The one or more processing engines formed as an alignment module may further be configured to calculate an alignment of the read to each retrieved segment of the genetic reference sequence so as to generate a score for each alignment. Further, once one or more scores have been generated at least one best-scoring alignment of the read may be selected. In particular instances, the quantum computing device may include a set of quantum logic circuits that are arranged as a set of processing engines that are configured for performing a gapped or gapless alignment, such as a Smith Waterman alignment.

Further, in certain instances, a quantum computing device and/or system may include a variant calling module, where the variant calling module comprises a set of quantum logic circuits that are arranged as a set of processing engines, one or more of which are configured for performing one or more steps of a variant calling procedure. For instance, the quantum computing variant calling module may include a set of quantum logic circuits that are adapted for executing an analysis on a plurality of reads of genomic data, such as using one or more candidate haplotypes, e.g., stored in a memory, where each read of genomic data and each candidate haplotype represent a sequence of nucleotides.

Specifically, the set of quantum logic circuits may be formed as one or more quantum processing engines that are configured to receive one or more of the reads of genomic data and generate and/or receive the one or more candidate haplotypes, e.g., from the memory, such as via one or more of a plurality of superconducting connections. Further, the one or more quantum processing engines may be configured to receive one or more of the reads of genomic data and the one or more candidate haplotypes from the memory, as well as to compare nucleotides in each of the one or more reads to the one or more candidate haplotypes, so as to determine a probability of each candidate haplotype representing a correct variant call. Additionally, one or more of the quantum processing engines may be configured to generate an output based on the determined probability.

Additionally, in various instances, the set of quantum logic circuits may be formed as one or more quantum processing engines that are configured to determine a probability of observing each read of the plurality of reads based on at least one candidate haplotype being a true sequence of nucleotides, e.g., of a source organism of the plurality of reads. In particular instances, with respect to determining probability, the one or more quantum processing engines may be configured for executing a Hidden Markov Model. More particularly, in additional embodiments, the one or more quantum processing engines may be configured for merging the plurality of reads into one or more contiguous nucleotide sequences, and/or for generating the one or more candidate haplotypes from the one or more contiguous nucleotide sequences. For instance, in various embodiments, the merging of the plurality of reads includes the one or more quantum processing engines constructing a De Bruijn graph.

Accordingly, in light of the above, a system for performing various computations in solving problems related to genomics and/or bioinformatics processing is provided. For instance, the system may include one or more of an onsite automated sequencer, e.g., NGS, and/or a processing server either or both of which may include one or more CPUs, GPUs, and/or other integrated circuits, such as including an FPGA, ASIC, and/or structured ASIC that are configured as herein described for performing one or more steps in a sequence analysis pipeline. Particularly, the Next Gen Sequencer may be configured for sequencing a plurality of nucleic acid sequences so as to generate one or more image, BCL, and/or FASTQ files representing the sequenced nucleic acid sequences, which nucleic acid sequences may be a DNA and/or an RNA sequence. These sequence files may be processed by the sequencer itself or by an associated server unit, such as where the sequencer and/or the associated server includes an integrated circuit, such as an FPGA or ASIC, configured as herein described for performing one or more steps in a secondary sequence analysis pipeline.

However, in various instances, such as where the automated sequencer and/or an associated server is not configured for performing a secondary sequence analysis on the data generated from the sequencer, the generated data may be transmitted to a remote server that is configured for performing a secondary and/or tertiary sequence analysis on the data, such as via a cloud mediated interface. In such an instance, the cloud accessible server may be configured for receiving the generated sequence data, such as in image, BCL, and/or in FASTQ form, and may further be configured for performing a primary, e.g., image processing, and/or a secondary and/or tertiary processing analysis, such as a sequence analysis pipeline, on the received data. For instance, the cloud accessible server may be one or more servers including a CPU and/or a GPU one or both of which may be associated with an integrated circuit, such as an FPGA or ASIC, as herein described. Particularly, in certain instances, the cloud accessible server may be a quantum computing server, as herein described.

Specifically, the cloud accessible server may be configured for performing a primary, secondary, and/or tertiary genomics and/or bioinformatics analysis on the received data, which analyses may include performing one or more steps in one or more of an image processing, base calling, mapping, aligning, sorting, and/or variant calling protocols. In certain instances, some of the steps may be performed by one processing platform, such as a CPU or GPU, and others may be performed by another processing platform, such as an associated, e.g., tightly coupled, integrated circuit, such as an FPGA or ASIC, that is specifically configured for performing various of the steps in the sequence analysis pipeline. In such instances, where data and the results of analysis are to be transferred from one platform to another, the system and its components may be configured for compressing the data prior to transfer, and decompressing the data once transferred, and as such the system components may be configured for generating one or more of a SAM, BAM, or CRAM files, such as for transfer. Additionally, in various embodiments, the cloud accessible server may be a quantum computing platform that is configured herein to perform one or more steps in the sequence analysis pipeline, as described herein, and may include the performance of one or more secondary and/or tertiary processing steps in accordance with one or more of the methods disclosed herein.

Further, with respect to quantum computing, detail and embodiments of exemplary quantum processors and the methods of their use that may be employed in conjunction with the present devices, systems, and methods are described in U.S. Pat. Nos. 7,135,701; 7,533,068; 7,969,805; 8,560,282; 8,700,689; 8,738,105; 9,026,574; 9,355,365; 9,405,876; as well as the various counterparts thereto, which are hereby incorporated by reference in their entireties.

Additionally, with respect to the artificial intelligence module set forth above, in one aspect, a cloud accessible artificial intelligence module is provided, and is configured for being communicably and operably coupled to one or more of the other components of the BioIT pipeline disclosed herein. For instance, the A/I module may work closely with the WMS so as to efficiently direct and/or control the various processes of the system disclosed herein. Accordingly, in various embodiments, an A/I module is provided, wherein the A/I module is configured for acting as an interface between the genomic world and the clinical world.

For instance, in various instances, the BioIT system may be configured for receiving clinical data. In such an instance, the workflow manager system may be configured for receiving and analyzing the clinical data, and other such data, and implementing one or more correlations and/or further analyses thereon. For example, in various embodiments, the methods and/or systems herein disclosed herein may be adapted for correlating genomic data with clinical data, which data may include one or more personal health records (PHR) and/or electronic medical records (EMR).

Specifically, as described herein above, in particular instances, the mapper, aligner, and variant caller of the system are configured for receiving genetic sequence data, such as in a FASTQ and/or BCL file format, and processing the received genetic data, which processed data may then be stored and/or otherwise made accessible to the tertiary processing module, such as for further processing. In certain embodiments, the system may be configured for generating or receiving genetic sequence data. In various instances, as indicated, the genetic sequence data may be obtained directly by sequencing the entire genome of an individual, or a portion thereof, such as by manual or automated, e.g., NextGen, DNA/RNA sequencing so as to determine the sequence of nucleotide bases in the genetic sample from the individual.

In particular embodiments, the source of genetic data may be derived and/or received from public or private databases, such as from academic and/or commercial diagnostic laboratories. Such sequenced genetic sequence data can be provided as electronic text files, html files, xml files and various other regular databases formats, as discussed herein above. For instance, the genetic sequence data may be received as a BCL and/or a FASTQ file. Once the subject's genetic, e.g., nucleotide, sequences are obtained, they may be subjected to various different bioinformatics techniques, such as where these nucleotide sequences may then be assembled together to generate a mapped and aligned genomic sequence of the subject.

Specifically, the subject's genetic sequence may be mapped and aligned to genomic positions relative to a static or dynamic reference genome, in accordance with the methods disclosed herein above, so as to generate a mapped and aligned genomic sequence data. In various instances, this genomic data not only includes the mapped and aligned nucleotide sequence of the individual, but may also include epigenetic information, such as DNA methylation patterns, histone deacetylation patterns, and the like. This mapped and aligned sequence may then be compared to one or more static and/or dynamic reference genomic sequences to determine how the genomic sequence of the individual varies from that of the reference.

More specifically, the subject's DNA may be subjected to one or more variant calling protocols. For instance, variant calling, as described above, is a method of identifying factual differences between sequence reads of test samples and a reference sequence. Variant calling may be used to identify somatic variants with a high degree of confidence. For example, variant calling may be employed to determine a subject's Single Nucleotide Polymorphisms ("SNP"). An SNP is DNA sequence variation occurring when a single nucleotide in the genome differs between members of a species (or between paired chromosomes in an individual).

Additionally, in accordance with the methods disclosed herein above, the variants in the individual's sampled sequence may be determined so as to provide the system with the individual's variant information, and then such data may be employed in comparison to a their EMR/PHR to determine a correlation between a disease phenotype and their genetic profile. Particularly, the individual's genomic data may be analyzed, e.g., visualized, and annotated such as with respect to chromosomal or genomic annotations, which may reference one or more alleles. For instance, a chromosome is a strand of DNA that is encoded with genes, and an allele may be any two or more alternative forms of the same gene that have the same relative position on homologous chromosomes.

DNA is deoxyribonucleic acid, which contains the genetic code. It consists of two nucleotide chains in a double helix and joined by hydrogen bonds between complimentary bases of adenine and thymine, and cystosine and guanine. A subject's genome is the full set of chromosomes, which includes the genetic material of an organism, and includes genes and non-coding sequences of DNA/RNA. The exome is part of the genome formed by exons, the sequences which when transcribed remain within the mature RNA after the introns are removed by RNA splicing. Likewise, a nucleic acid library is a plurality of polynucleotide molecules that are prepared, assemble and/or modified for a specific process.

In various instances, genomic annotative information may be received from a third party, such as the University of California of Santa Cruz browser and the Ensemble Genome Browser, which display various annotations for a specific region of the genome. Specifically, Ensemble is a joint project between the European Molecular Biology Laboratory, the European Bioinformatics Institute and the Wellcome Trust Sanger Institute. Such genomic data may be in the form of individual samples containing genetic, e.g., chromosomal, information.

In various embodiments, the genomic data may include one or more measurements, such as a measurement of at least one event, e.g., an aberration, such as at a particular location on the chromosome and/or related to the genome generally. Examples of such measurements may include the expression of a gene, an exon at a particular location, the number of copies of a portion of the genome that have been gained or lost, the extent of methylation of the genome at a particular location, the affinity of certain promoters to bind to a particular area on the genome, etc. In some cases, the frequency of the event may be calculated, such as based on a frequency of the occurrence of the event in the selected sample.

Particularly, in certain instances, it may be desirable to calculate the frequency of the aberration, such as the frequency of a gain or loss of chromosomal copies, such as when compared to a reference sample in a selected population of samples. In other circumstances, it may be desirable to review an annotation or flag, demarcating specific information related to a particular chromosomal region, intron, exon, gene, or the like. Such information might include items such as what genes are present in a location and if there are known copy number polymorphisms in that area (e.g., including a list of such polymorphisms). Other items might include information pertaining to the presence of microRNAs and potential Single Nucleotide Polymorphism (SNP)s in the area, etc.

The individual's variant information, e.g., variant calls, may then be subjected to further processing and used in accordance with the methods herein to determine or predict the occurrence of a diseased state in the individual. For instance, in one aspect of the disclosure, the system may further be configured for correlating the received and/or generated genomic data with clinical data, which data may include one or more personal health records (PHR) and/or electronic medical records (EMR). For example, the clinical data with which to form such a correlation may be from a wide array of sources, and may refer to a variety of traits, such as one or more phenotypic traits.

Specifically, phenotypic traits refer to the composite of an organism's observable characteristics, which includes but is not limited to its morphology, development, biochemical or physiological properties, phenology, behavior, products of behavior, and likewise. Phenotypic traits may also include observable disease traits, such as various cancers, heart disease, Age-related Macular Degeneration, and the like. A phenotype results from the expression of an organism's genes as well as the influence of environmental factors.

Accordingly, in various instances, presented herein is a method for correlating genomic data, e.g., variant call data, with clinical data, EMR/PHR. For example, the method may include identifying one or more sources of genome data for a subject, e.g., one or more genome files, generating and/or receiving the genomic data, e.g., a BAM, SAM, and/or CRAM file, and generating an index file for each genome file. In various instances, each genome file may be identified with a unique DID. Once the index file is generated it may be encrypted and/or transmitted to a central depository, e.g., utilizing a processor at a source site for the source. Additionally, the method may include identifying electronic medical record (EMR) and/or personal health record (PHR) data for each source of genome data, and once identified, the method may include correlating each genome file with a corresponding EMR/PHR data. In various instances, the method may include the connecting with a database, such as an outside repository, and/or searching and receiving genomic and/or clinical data, which when collected may be correlated with one another.

Further presented herein is a system for performing the searching, identifying, and correlating, such as for correlating genomic data with clinical data. Accordingly, in various embodiments, components of the system may include one or more of a server, including a processor, a database, a central depository and/or repository site, one or more sources for genome and/or EMR/PHR data, a search browser, and the like. For instance, one or more central repository sites may be included, such as where the repository is associated with a database, such as a database that includes one or more genomic, clinical, and/or index files. Each of the plurality of index files represents encrypted genome files, e.g., encrypted genome, EMR, PHR files, such as where the encrypted files are associated with a unique DID, such as where each EMR/PHR file matches a genome file having the same unique DID. Such encryption and the system set up is important for maintaining privacy. The browser may be configured for searching the plurality of files, such as via use of the one or more index files.

The files, e.g., records and/or index files, may be transmitted from each source of generation to a repository using any suitable transference protocol, and may be searchable at a chromosome level, exome level, gene level, allele panel, at an individual SNP, or any relevant level. The server may be a plurality of servers, such as a server at the central repository of the clinical data, and/or a server at the central repository of the genomic data, and/or a server at a third site such as a brokering server at a brokerage site. In various embodiments, each genomic file, and each clinical file, and/or each index file may be stored as part of a plurality of searchable files, in accordance with respective unique DID identifiers, such as where each EMR/PHR and/or genome data has a unique DID.

The method therefore includes identifying electronic medical record (EMR) and/or personal health record (PHR) data at each respective source. Each EMR/PHR data matches a genome file of the plurality of genome files. The EMR/PHR data of a subject may include general health records, medical procedure records, allergies, illnesses, and the like of the subject. The EMR/PHR/genomic data may be encrypted and/or indexed and stored remotely or locally. For instance, the remote storage site may be a warehouse, for storing enormous data, or may be a local storage database, not requiring large storage resources. In various instances, the centralized brokerage server need only maintain a plurality of index files that can be easily searched. Further, the processing of the genomic/EMR/PHR data may be performed at the site or storage and/or data generation.

Hence, the method may also include searching the plurality of searchable files, e.g., using a browser, such as a browser associated with the brokering server, and/or matching each genome file with a corresponding EMR/PHR data. It is to be noted that the owner of an encrypted file controls access to the file, and all files and their access may be tracked throughout the system, such as by the DID. For instance, the genomic data generated herein may include variant call data, such as a subjects VCF files, which files may be indexed and stored as one or more index files, such as an encrypted index file. A DID is a De-identified Identifier, e.g., a unique ID token may be any suitable source of encrypting data so as to include no readily accessible identifying information like a patient's email, phone number, date-of-birth, zip, etc. The DID number may be provided to each index file to maintain privacy and anonymity.

For instance, the encryption algorithm may be utilized to generate the DID for the index file, and may be the same algorithm used for encrypting the EMR/PHR data, and therefore the files can be matched based on the DID number. Accordingly, in certain embodiments, a system for genomic visualization with privacy control is provided. The system may include one or more central depository sites, one or more sources of genomic data, one or more sources of EMR/PHR data, one or more search entities, so as to allow system users and/or data owners of the genomic data and EMR data to access the system, search the data, and to retrieve correlated records thereof.

In one instance, the central depository site may function as a brokerage of data between sources that have generated genomic data and/or EMR/PHR data, and/or multiple searchers that utilize the information for academic, commercial, and other purposes. The search entities may be researchers like universities, biotechnology companies, hospitals, and the like, wherein the owner may have control access to the unencrypted data, and may track the data as it is distributed to search entities. Hence, in particular instances, the method may include correlating genomic data, generated at one site, with clinical data, e.g., EMR/PHR data, generated at another site.

The method, therefore, may include identifying and/or activating one or more sources of genomic data generation, which may include, receiving a genetic sample, sequencing and/or processing the same so as to produce genomic data, such as in the form of one or more variant call files. Once the genomic files are generated, the may be encrypted, indexed, stored (locally), and/or transferred, e.g., for remote storage, such as one or more files. In such an instance, each of the plurality of genome files may be given and be identified with a unique DID. Likewise, one or more sources for electronic medical records (EMR) and/or personal health records (PHR) data may be identified and/or activated, such as for the generation and/or retrieval of clinical data. Each EMR/PHR data may also be given a unique DID in such a manner that each EMR/PHR data matches a corresponding genome file. Hence, in a manner such as this, each genome file may be correlated with a corresponding associated EMR/PHR data. A system administrator, a clinician, the owner of an encrypted file, and/or someone with the appropriate authority may set the access rights so as to control access to the encrypted files, and the system may track the access of the encrypted files.

Accordingly, as disclosed herein, the BioIT system may not only be configured for receiving clinical data, but in various instances, the system may further be configured for correlating the genomic data, e.g., generated by the system, with the clinical data received and/or generated by the system. For instance, the workflow manager system may be configured for implementing one or more deterministic rule systems, so as to derive results data pursuant to its analysis of the genomic and/or clinical data. For example, in certain embodiments, the various databases of the system may be configured so as to have a relational architecture These constructions may be represented by one or more table structures. A series of tables, for instance, may then be employed by which correlations may be made by the WMS in an iterative fashion. For example, in various use models a first correlation may be made with respect to a subject's name with a medical condition. Another table may then be employed to correlate the subject's medical condition with their medicine. Likewise, a further table may be used to correlate the progress of the medicine with respect to the alleviation of symptoms and/or the disease itself. A key may be used to correlate the tables, which key may be accessed in response to question prompt or command. The key may be any common identifier, such as a name, a number, e.g., a social security number, tax identification number, employee number, a phone number, and the like, by which one or more of the tables may be accessed, correlated, and/or a question answered. Without the key, it becomes more difficult to build correlations between the information in one table with that of another.

Accordingly, a data structure for answering a query is presented wherein the data architecture may be structured and searched in response to the query. In a typical architecture the database may be a relational database, such as a Structured Query Language (SQL) database, which may be implemented via a relational database management system (WMS). For example, in one implementation, the SQL database may be a document based database, such as where one or more tables, e.g., look up tables (LUT), form a structure wherein data may be stored, searched, relations determined, and queries answered.

Particularly, in various embodiments, a documents or table based database may be presented, searched, and used to determine relationships from which answers to one or more queries may be determined. For instance, typically, SQL databases have a relational architecture. These constructions may be represented by a table structure. A series of tables, for instance, may then be employed by which correlations may be made in an iterative fashion. For example, with respect to the genomics analyses discussed herein, a first correlation may be made with respect to a subject's DID and with respect to their clinical profile, e.g., medical condition, as set forth in their EMR/PHR. Another table may then be employed to correlate the subject's medical condition (EMR/PHR) with their genomic profile and/or a medicine to be prescribed.

Likewise, a further table may be used to correlate the progress of the medicine with respect to the alleviation of symptoms and/or the disease itself, and/or the genetic response thereto. The subject's DID may serve as a key that may be used to correlate the tables, which key may be accessed in response to question prompt or command. Specifically, the key may be the subject's DID, or may be any common identifier, such as a name, a number, e.g., a social security number, tax identification number, employee number, a phone number, and the like, by which one or more of the tables may be accessed, correlated, and/or a question answered. A further data architecture that may be used to structure a database is a data tree, where various data elements may be stored in a compressed, but correlated fashion, and/or in a hash table, as described herein above. However, in various embodiments, these data structures may be less than ideal.

Accordingly, in other instances, a graph based architecture may be structured and used to determine the results for one or more queries. Particularly, a knowledge graph architecture may be employed to structure the database, so as to enhance the performance of computational analyses executed using that database. Particularly, the sophisticated algorithms disclosed herein, are adapted for structuring the infrastructure of a relational database so as to enable more efficient and accurate searching such as via performing graph based analyses, as well as for performing table or tree based analyses.

Consequently, in one aspect, a device, system, and methods of using the same to build a searchable, relational data structure, such as described herein, are provided. Specifically, in one instance, the machines and methods disclosed herein may be employed so as to generate and/or otherwise collect data, such as results data pertaining to secondary and/or tertiary processing. More Specifically, in a first instance, the machines and methods disclosed herein may be employed to generate one or more of BCL, FASTQ, BAM, CRAM, SAM, and/or VCF data, and in a second instance, the machines and methods disclosed herein may be used to generate a searchable data structure for storing that data in a relational architecture. In various instances, additional data may be generated or otherwise be transmitted into the system, such as via a suitably configured API, which data may also be configured for being stored in the relational data structure, such as other genomics, genetic, and/or other clinical data.

For instance, in another aspect of the disclosure, the system may include an artificial intelligence (A/I) module that may be configured to provide a more comprehensive analysis on generated and/or provided data. For example, the A/I module may be configured so as to implement one or more machine learning protocols on the data of the system that are devised to teach the AI module to make correlations between the genetic and/or genomic data, e.g., generated by the system, and a clinical deposition of one or more subjects, such as in view of EMR and other clinically relevant data input into the system.

Specifically, the A/I module may be configured for receiving one or more inputs and may be adapted for building and structuring a database. For instance, in a first step, data may be collected, cleaned, and then be prepared for analysis. In various embodiments, the data may be labeled and/or categorized, such as with respect to metadata. For example, a skimmer may be implemented for the purposes of structuring the database, such as for providing a relational structure to the database. And once the database is structured, it may then be populated with data, in accordance with determined or inferred relationships.

In certain instances, a machine learning protocol, as disclosed herein, may be employed so as to determine relationships between data points entered into the database. Such relationships may be determined based on known facts, and as such the learning may be supervised learning, e.g., such as where the data entered into the database is categorized in accordance with one or more categories and/or labels. Particularly, known factors may be used to label, categorize, and store data, which may be informed by the query being sought to be answered. Hence, knowing factors by which to label and categorize the data being stored makes building the storage architecture more efficient.

In other instances, the learning may be inferred, such as in an unsupervised learning. For instance, in certain instances, the data to be stored may not be known, relationships between the data may not have been determined, and the query to be answered may also not be identified. In such instances, the data to be stored is unsupervised, and as such, patterns in data to be stored and their relationships, such as commonalities between data points, may be determined, and once determined such patterns may then be used in forming the architecture that structures the data storage.

For example, in various embodiments, the A/I module may include programing directed at training the system to more rapidly, e.g., instantly, recognize how an output was achieved based on the type and characteristics of the input received. The system therefore is configured for learning from the inputs it receives, and the results it outputs, so as to be able to draw correlations more rapidly and accurately based on the initial input of data received.

Typically, the input data may be of two general types. In a first instance, the data may be of a type where the output, e.g., the answer, is known. This type of data is may be input into the system and used for training purposes. The second type of data may be data where the answer is unknown, and therefore, must be determined. This data may be any form of data, but in various instances, may be genomic data, upon which analysis is to be made; or it may be clinical data to which clinically relevant results are to be determined. This data may be used to enhance the A/I module's ability to learn from the first type of input data, so as to better predict the outcome for the second kind of input data. Specifically, based on historical evidence, the A/I module may be configured to learn to predict outcomes based on previously observed data.

More specifically, a clinical genomics platform is presented herein, wherein the clinical genomics platform is configured to correlate clinical outcomes of diseases with genomics data. In such an instance, the clinical profiles of subjects may be input into the system and may be assessed along with their determined genomic profile. Particularly, in combining these two datasets, the A/I module is configured for determining the various interrelationships between them. Accordingly, at the heart of the A/I platform is a graph database, which is configured for receiving data from a plurality of different sources, such as from sources of genomic information, clinical information, and any type of other data useful in accordance with the systems and methods disclosed herein. As described above, such data may be generated and/or received by the system, such as from a clinical data storage facility storing electronic medical records, a clinic, a medical health care facility, a biomonitor and/or biological tracking device, such as from a Fitbit, or other such tracker, and/or the like.

As indicated, the system may be configured for employing the received data in one or more learning protocols, such as for machine learning. For instance, machine learning takes place by training the system to instantly recognize how an output was achieved based on the type and characteristics of the input received. Accordingly, the present system is configured for learning from the inputs it receives and the results it outputs, so as to learn to draw correlations more rapidly and accurately based on the initial input of data received. The system, therefore, receives a first set of data wherein the outcome is known, and this data is employed by the system to generate one or more rules by which a result may be obtained, and once obtained compared to the known outcome. Consequently, the system is configured to train itself to better recognize correlations between data points within the database more accurately, e.g., with less false positives, and more efficiently, and to make predictive outcomes. In such a manner the machine learning algorithm may learn behaviors, determine accuracy, and may be used by the artificial intelligence module to analyze further sample sets with respect to answering one or more search queries, such as a query requiring the A/I module to infer correlations between nodes or datasets. Hence, once the A/I machine learns the behavior, the learned behavior may then be applied to a second type of data, such as an inference engine, that is used to answer one or more unknown variables.

The more the machine learns from the first type of input data, the better the inference engine becomes at predicting the outcome for the second kind of input data. More specifically, based on historical evidence, the artificial intelligence module may be configured to learn to predict outcomes based on previously observed data. With respect to the genomics and/or clinical data of the system, the present clinical genomics platform is configured to correlate clinical outcomes of diseases with genomics data. In such an instance, the clinical profiles of subjects are assessed along with their determined genomic profile. However, in order to combine these two, their interrelationships are determined.

Accordingly, in a first step, a graph database or knowledge graph may be constructed. For example, in this instance, the knowledge graph may be composed of three typical elements, which basically include a subject, a predicate, and an object, these may form nodes, and the relationship between the nodes must be determined. Any particular data point may be selected as a node, and nodes may vary based on the queries being performed. There are several different types of relationships that can be determined. For instance, relationships may be determined based on their effects, e.g., they are effect based; or they may be determined based on inferences, e.g., relationships that are unknown but determinable. Particularly, each effect and/or relationship may be characterized by different properties, which properties may be used to generate weights, probabilities, make assumptions, and the like. Such properties may be used to populate the knowledge graph with data points that may form the nodes of the graph. More particularly, to better determine causal and/or predictable outcomes the various different relationships may be weighted, such as based on the degree of certainty, number of commonalities, number of instances sharing the node, number of common relationships, and the like. In various embodiments, a schema may be formed, such as where the schema is an architecture that is used to give structure to the graph. Hence, the construction and implementation of a dynamic knowledge graph is at the heart of the clinical genomics processing platform.

For example, with respect to constructing the knowledge graph, any particular data point may form a node. For instance, on one side of the graph a disease condition may form a node, and on the other side of the graph a genotype, e.g., a sequence of variances, may form a node. In between these two nodes may be a third node, e.g., a series of third nodes, such as one or more symptoms, one or more medications, one or more allergies, one or more other conditions or phenotypic traits, e.g., blood pressure, cholesterol, etc. Additionally, in between these nodes are the relationships that may be determined.

Specifically, when building the knowledge graph, clinical data input into the system, such as from a medical records facility, e.g., electronic medical records, family history of medical conditions, etc. that may be encrypted and securely transferred electronically. Likewise, genomic data from the subject may be sequenced and generated in accordance with the secondary processing steps set forth herein. Further, once these two nodes have been established one or more third nodes may be input into the system, from the presence of which the relationship(s) between the two original nodes may be determined.

For instance, in one example, a first node may be represented by the medical records of a person or a population of people, and a second node may be represented by a disease characteristic. In such an instance, one or more third nodes may be input to the system and generated within the graph, such as where the third node may be a medication; a physical, biological, mental, condition and/or characteristic; an allergy; geographical region; diet, a food item and/or ingredient; an environmental condition; a geographical condition; powerlines, cellular towers; and/or the like. A series of relationships may then be determined by analyzing various points of connection between these three items. Particularly, in a particular instance, one node may represent a patient suffering from a disease condition, a second node may be the patient's genomic data, and among the third nodes may be the patient's genomic variations, e.g., the subject's mutations, chromosome by chromosome, their medication, physiological conditions, and the like. Likewise, this process may be repeated for multiple subjects having the same diagnosis and/or condition. Hence, in a manner such as this the correlation between the clinical and genomics worlds may be determined.

Accordingly, a step in building a clinical genomics graph is to define the anchor nodes, these represent the two bounding elements between which all the various commonalities are defined and explored. Hence, a further step is to define all the possible known correspondences between the two anchor nodes, which may be represented in the graph as a third node. These known correspondences may be built around detailing the effects caused by and/or the characteristics of one node or the other. These may form the known and/or observable relationships between the nodes. From these known relationships, a second type of relationship may be explored and/or determined which relationships may be built on inferences. Further, to better determine causal and/or predictable outcomes the various different relationships may be weighted, such as based on the degree of certainty, number of commonalities, number of instances sharing the node, number of common relationships, and the like.

Hence, the construction and implementation of a dynamic knowledge graph is at the heart of the clinical genomics processing platform. As indicated, the various processing platforms of the global system may be coupled together, so as to seamlessly transfer data between its various components. For instance, as indicated, the mapping, aligning, and/or variant calling pipelines may be configured for transmitting its data, e.g., results data, to the artificial intelligence module. Particularly, the A/I module may be configured for receiving inputs of data from one or more of the secondary processing platform components, and/or one or more of the other component of the system. More particularly, the A/I module is configured for receiving mapping, aligned, and/or variant called data from the mapper, aligner, and/or variant calling processing engines, and for taking that data and using it to generate one or more nodes within the knowledge graph. Further, as indicated, the A/I module may be configured for receiving input data from one or more other sources, such as from a medical office, a health care service provider, a research lab, a records storage facility, and the like, such as where the records include data pertaining to the physical, mental, and/or emotional well-being of one or more subjects, and for taking that data and using it to generate one or more nodes within the knowledge graph.

Additionally, once the knowledge graph architecture has been constructed, it can continually be updated and grown by adding more and more pertinent data into the knowledge structure, building more and more potential nodes and/or relationships. In such an instance, the bounding nodes may be of any combination of nodes, and as such, in certain instances, may be user selectable. For instance, in various embodiments, the system may be configured for being accessible by a third party. In such an instance, the user may access the A/I module, e.g., via a suitably configured user interface, upload pertinent information into the system and/or determine the relevant nodes by which to bound an inquiry, e.g., by clicking on or drag and dropping them, and may formulate a relevant question to be answered by the A/I module. Accordingly, the user may review and/or select the bounding nodes, and then allow the system to generate an appropriate knowledge map employing the selected nodes, and determine the relationships between the nodes, from which relationships various inquiries may be queried and answered, or at least be inferred, e.g., by the A/I system.

For example, in one use model, a user may be a physician who desires to know how a certain drug dosage is affecting a patient with respect to a given disease. Consequently, the physician may upload the patient's EMR, the disease condition, and the drug dosage, and with this data the A/I module may generate a suitable knowledge graph (and/or add to an already existing knowledge graph), from which knowledge graph the bounding nodes may be selected and relationships determined. Further, in various instances, the user may upload the patient's genetic data, which data may be subjected to secondary processing, and the results thereof, e.g., mapped, aligned, and/or variant call result data, and uploaded into the A/I module. In such an instance, the disease and/or EMR and/or family medical history data may be correlated with the genomic data from which data various relationships may be determined, inferences assessed, and predictions made.

Specifically, the physician may perform one or more clinically relevant tests on the subject, enter the data into the patient's Electronic Medical Records, and upload the subject's EMR, the disease condition, and the drug dosage into the system, e.g., the A/I module thereof, such as in a burst or streaming fashion. With this data the A/I module may generate a suitable knowledge graph (and/or add to an already existing knowledge graph), from which knowledge graph the bounding nodes may be selected and relationships determined. A workflow for a drug dosage calculation may be worked up, e.g., previously embedded within the system or entered into the system, a query may then be run, and a predictive model may be initiated on the data to determine one or more relevant query results that are particular to the individual's personal characteristics with respect to the generated work up.

Particularly, since everyone's metabolism is generally different from one another, the dosage of a drug required to reach maximum efficacy within a given time period will differ for each individual. Accordingly, the present system may be configurable so as to account for the personal characteristics of an individual, both genetically, e.g., from the genomic analyses performed by the system disclosed herein, and/or phenotypically, e.g., from the clinical data uploaded into the system by the physician, which characteristic data may then be employed by the A/I module so as to determine one or more correlations and/or perform one or more calculations with respect thereto and thereby derive and report on an accurate dosage of one or more drugs that may then be appropriately administered to the subject for the treatment and/or prevention of a condition.

Additionally, a subject's genetic profile may also be accounted for. For instance, the physician, or the system itself, may upload a subject's genetic data, e.g., DNA and/or RNA, which data may be subjected to secondary processing, and the results thereof, e.g., mapped, aligned, and/or variant call results data, may be uploaded into the A/I module. In such an instance, the patient's clinical data, e.g., disease and/or EMR and/or family medical history data, may also be uploaded into the system and may be populated into a knowledge graph of the system, whereby various nodes may be identified and/or correlated with the genomic data from which correlations various relationships may be determined, inferences assessed, calculations performed, and predictions made and/or reported.

And, because of the rapidity by which the present system and its methods are able to transmit and generate results data, the system may be readily adapted for providing point of care devices and services. Specifically, a subject's DNA/RNA may be obtained, entered into the system and/or otherwise be sequenced and be uploaded into the BioIT platform disclosed herein. This VCF data may be entered into the system, and consequently be used to form one or more nodes of the system, such as where each node is composed of one or more properties, e.g., all of the determined genetic and/or chromosomal properties may be uploaded into the system. In such a manner, this data, as well as any other relevant data, e.g., the patient's EMR data, along with all properties relevant to a particular query to be analyzed, may be uploaded into the system and be used to form a constellation of nodes, which nodes may be employed to determine various relationships pertinent to the subject, such as by querying the system and allowing it to generate the appropriate connections from which an answer may be inferred.

Additionally, the system may be configured for receiving a plurality of genomic profiles form one or more subjects, which may or may not be related to one another. The subject's VCFs may be received or generated by the system, e.g., all of the determined chromosomal properties may be uploaded, for instance, as a constellation of nodes, which nodes may be used to determine various relationships pertinent to none or more of the subjects, such as by querying the system and allowing it to generate the appropriate connections from which an answer may be inferred. More specifically, one or more subject's phenotypical characteristics, e.g., the human phenotype ontology, may be uploaded into the system, so as to generate a further constellation of nodes. For instance, when the genomic and/or medical histories of two people are entered into the system, any relationships between them may be determined by the A/I module, such as with respect to common genotypes, phenotypes, conditions, environments, geographies, allergies, ethnic-cultural backgrounds, medications, and the like.

Particularly, such data, e.g., one or more subjects VCF and/or EMR(PHR) data, may compose the various inputs into the system. More particularly, a subject's entire VCF, e.g., their entire characteristics of genetic variance, along with its attendant properties, may be uploaded into the system, and may be used to form nodes that populate a knowledge graph. Likewise, the patient's relevant portions of their EMR/PHR, and/or other relevant clinical data, may be entered into the system, along with their attendant properties, and may be used to further populate the knowledge graph. Once populated in a manner such as this, one or more queries may be run against the data so as to isolate various sub-profiles that may then be mined for relevant relationships and/or correlations.

More specifically, one or more subject's phenotypical characteristics, e.g., the human phenotype ontology: "HPO", may be uploaded into the system, so as to generate a further constellation of nodes. For instance, when the genomic and/or medical histories and/or HPO, of two or more people are entered into the system, any relationships between them may be determined by the A/I module, such as with respect to genotypes, phenotypes, conditions, environments, geographies, allergies, ethnic-cultural backgrounds, medications, and the like that are common between them. Relationships between two or more characteristics in a subject, or between subjects, may then be determined.

For example, in such a manner as this, a subject's phenotypic characteristics may be correlated with their genotypic make up, such as by correlating the patient's clinical, e.g., phenotypic data, with their genetic, e.g., variance, data. This may be done for a single subject or multiple subjects, e.g., forming a population of subjects. More particularly, in one use model, a relationship between two properties, e.g., property A: a subject's systolic, and property B, the subject's diastolic blood pressure, may be determined by the system.

Specifically, a series of historic readings for each property, e.g., systolic and diastolic readings, may be entered into the system, e.g., 1,000 readings of each, whereby the machine learning platform of the system may analyze the readings, and/or determine one or more correlations and/or relationships between the two properties, such that if a given property A, e.g., systolic, input is entered into the system, the predicted property B, e.g., diastolic, output may be inferred, taking the predictive weights between the two into account. In such an instance, when evaluating the inputs with reference to properties A and B, a relationship between the two may be determined by the artificial intelligence processor, such that if given a new input for property A, the determined relationship may then be used to predict what the outcome of property B will be, given that the two properties are in fact mathematically related.

This machine learned relationship may, therefore, be employed to determine when the two properties are in alignment with one another, e.g., everything is functioning as it should, and, may further be used to determine when things are not functioning in alignment, such as when the predicted outcome is not observed, and thus, is indicative of their being a problematic state. It is to be noted that although the preceding example was given with respect to blood pressure, within a single subject, the same will apply to any to given nodes that are in a mathematical relationship to one another, such as with respect to a multiplicity of subjects and/or a variety of conditions.

In certain instances, however, the relationship between two or more properties are not linear, but rather may be more complex. For instance, in certain embodiments, the artificial intelligence module may be configured to model more complex processing of relationships in a manner similar to a neural network, such as in a deep learning protocol. Accordingly, although in some instances, the relationships may be configured in a linear array, such as to form a direct linkage between the properties, in other instances, the relationships may be layered one on top of the other so as to form a stacked, e.g., neural, network of information.

Hence, in particular instances, the relationships may be formed in a multiplicity of stages and/or levels, where one level of information is connected to the next level of information, such as in a deep learning protocol. Additionally, the relationships between the various properties from one level to another may be strengthened, and therefore given greater weight, or weakened, and consequently given less weight, by the machine learning protocol engaged. Accordingly, as information is processed and allocated across the properties in the different levels of the system, at each stage, a variety of different points are being given greater and greater weights, such that when given a particular input, the A/I module may more efficiently predict a given outcome more accurately based on the various different levels of weighted historical information.

For example, the A/I system may be adapted so as to process information in a layered or multi-staged fashion, such as for the purpose of deep learning. Accordingly, the system may be configured to evaluate data in stages. Specifically, the A/I module may be adapted such that as it examines various data, such as when performing a learning protocol, stage by stage, each connection between data gets weighted by the system, e.g., based on historical evidence and/or characteristics of relationships. The more stages of learning that are initiated within the system the better the weighting between junctions will be, and the deeper the learning. Further, uploading data in stages allows for a greater convergence of data within the system. Particularly, various feature extraction paradigms may also be employed so as to better organize, weight, and analyze the most salient features of the data to be uploaded. Additionally, in order to better correlate the data, one or more users may input and/or modulate basic weighting functions, while the system itself may employ a more advanced weighting function based on active learning protocols.

Particularly, a deep learning protocol may be employed in training and implementing a search function of the disclosure as discussed herein. More particularly, deep learning is a paradigm where increased levels of datasets are employed in generating an answer to a query. If there is only one stage of learning involved, when answering a query, the network architecture may be configured as a neural network. However, if the determination implements a multi-stage learning process, when deriving an answer to a query, the architecture may be configured as a deep learning network.

The more stages there are, where each stage includes a weight, the deeper the learning will be. However, with each stage added, the computing power required to make the data converge becomes greater and greater. Specifically, with each additional data set being processed, another node is generated, which increases the level of future processing power. With respect to the present disclosure, when running a deep learning protocol, the process first implements a feature extraction protocol, where salient features are extracted and considered in comparison with similar features stored in a database of previously extracted features, such as where each feature represents a characteristic that may be categorized into one or more labels, which labels may be used to recognize patterns whereby the machine can therefore be trained to recognize the reoccurrence of those patterns in other representations, and thereby draw conclusory predictions based on those recognized patterns.

Accordingly, in order to do machine learning there needs to be a library of functions. This is useful, for instance, where an anchor characterization may be identified, such as of an image or video, and subsequent analysis or distribution does not involve analysis or distribution of the entire subsequent characterizations, but rather, only data pertaining to any differences or divergence from the anchor. This is termed feature extraction, the preferential analysis of the anchor characterization, or in some instances, only the deltas. Accordingly, in various instances, methods disclosed herein are directed to using labels, e.g., pointers, to categorize and structure a database, such as for use in the artificial intelligence module to analyze data therein. In such machine learning the data may be first cleaned and prepared for feature extraction, e.g., of genetic and/or clinical and/or other significant data. Specifically, such features for extraction may include BCL or FASTQ files, BAM, CRAM, SAM files, as well as other features that can be employed in accelerating processing of both genomic and phenotypic data so as to more efficiently and accurately determine correlations between genetic identity with phenotypic outcome.

Splice junctions may also be employed as a feature for extraction: for instance, differentiation in splicing regulates the way DNA is transcribed and how the proteins are configured and function. Particularly, the percentage of splicing may be determinative of disease characterization. More particularly, up to 60% of genetic disease caused by mutation may be related to a defect in the splicing process. Additionally, nearly $\frac{1}{3}$ of disease causing mutation alter a splice cite thereby leading to abnormal exome skipping. Nearly 45% of disease associated variants are in introns, and most of them are believed to model a splicing pattern consisting of a deviation in alternative splicing patterns. The percentage of splicing may also be measured and may be considered as one of its features, such as for alternative splicing. Such variations may be extracted from the BAM/VCF files, and can thereby generate a splice junction library, which may be captured with respect to an individual, a group of individuals, a population, and may be based on one feature, a plurality of features, etc. thereby building a library of features as data is coming into the system. And once the data is in the system must train the machine to build the graph assembly so s to generate potential levels of correspondences.

As indicated, the A/I system may be configured for answering a query, such as from a third party, such as a physician or medical researcher. Accordingly, when performing a search function of the A/I repository or database, the database may be configured as a relational database, wherein the architecture of that database is such that it is structured as a table, or the architecture may be configured such that data is stored therein in a graph form, such as a knowledge graph, as described above.

Additionally, when performing a search of the database, the search may be an effect based or an inference based search query. An effect based search is typically one where the outcome is known and/or expected, whereas in an inference based search, the outcome is not known. Although table based searching is useful, it is based on known relationships that are categorized by tables, which may be searched by using the known key. Such searching is generally effect based searching, where the answer is known, and the relationship with its query simply needs to be identified, e.g., via the use of the key. Inference based searching, on the other hand, is where the relationship between two data points is unknown, but to be determined based on the building of a knowledge graph and the learnings of the system with respect to other relationships and the rules of those relationships, allow for new relationships to be discovered and otherwise unknown outcomes to be determined.

As such, it is the generation and implementation of the knowledge graph that is at the heart of the present search function in an inference based learning schema upon which the machine learning and artificial intelligence engines, as herein described, are primarily built. Hence, as data flows into the database, it is formulated into one or more of these, or another, such structure, and the data, e.g., where its relationship to other data is known, may then be employed to train the search function of the system to determine data points and/or relationships between data points where the relationship was not heretofore previously known, that is a key is not required to determine the presence of the relationship.

Specifically, once the known relationships have been determined, through a training process, the newly trained system, and the rules developed, may then be employed to infer other relationships, heretofore unknown, between the data points with a probability establishing the prediction that the inferred relationship is in fact an actual relationship. Accordingly, as set forth above, the system herein disclosed may be employed to receive data from different sources, such as clinical data on one hand, for instance, one or more electronic medical/health records of one or more subjects, and genomic data, such as derived from the secondary processes disclosed herein, on the other hand, thereby correlating the clinical and genomic worlds. In such a manner, the EMRs of a subject may be entered into the system as one set of data points, and likewise the subject's genomic data may also be entered into the system as well, and this data may be employed to build a knowledge graph whereby the various relationships, known and inferred, may be determined. This may be done for one or a plurality of subjects, where the relationships and the learnings therefrom may be used to determine known outcomes, such as for training the system, and once suitably trained the system may then employ these learnings in determining heretofore unknown relationships so as to infer outcomes therefrom.

Hence, known facts and relationships may be used to train the A/I engine, which once trained may determine rules by which unknown relationships may be determined and outcomes based on those relationships may be inferred and/or otherwise determined, such as by a suitably configured inference engine of the system. More particularly, a subject's medical information and/or health records may be entered as data into the system, as described above, and may be used to generate a knowledge graph. As this data has been determined by medical examination, this data is known, and therefore fact-based data. Such data, for instance, may be entered into the system, such as through a graphical user interface presented on a client computer of the system positioned within a doctor's office, or the like.

In such a manner, one or more medical records, e.g., clinical data, from one or more subject's may be entered into the system such as by a remote interface. The clinical data may be any data of clinical significance, such as medical or health data, disease related data, medication or prescription data, dental history, allergy data, and the like. The data may also include the donor's characteristic data, such as the donors gender, age, weight, other physical characteristic data, and the like. The data, e.g., donor data, may be encrypted and associated with a de-identified identifier (DID), so as to keep the donor's personal identification information secrete.

Likewise, as discussed herein above, the donor's genetic data may also be uploaded into or generated by the system, and may then be correlated with their genomic data, such as genomic data generated by the system, in accordance with the methods disclosed herein. The genomic data may include their variant call files, e.g., mutation data, as well as other related genomic information, as disclosed herein. Further, in various embodiments, the donor data may be from a plurality of donors, such as from a groups or groups, a community or communities, from a population or populations, and the like. In various instances, the system may be configured such that this data may be uploaded into the system automatically, from one or more sources.

Accordingly, the A/I system server, e.g., inference engine implementation, may be positioned remotely from the location from where the clinical and/or genomic data is uploaded into the system, but may be accessed locally or remotely as described herein in accordance with the hybrid cloud configurations. This data serves many purposes, one such purpose being the training of the A/I engine, and/or its use in one or more predictive models. In such training, known relationships and outcomes can be treated as if they are unknown, and consequently the machine may be made to determine the relationships and predict the outcomes anew, which training may continue until the system has learned to predict the right outcome.

Particularly, this training, e.g., two class-model training may be used for a sub-portion of the data, e.g., 50%, the training portion, and the other data may be used to test the learnings from the training portion to predict the known outcomes, with respect to the other 50% of the data. Hence, the first portion of the data may be employed to develop a training model, and the second portion of the data may be used to test the training models to enhance the accuracy of a predictive model, which once sufficiently trained may be employed to make other inferences and thereby predict other outcomes.

For example, once trained, the inference engine may be employed to search the database in response to a user enter query and based on the known and/or inferred relationship between the various data of the system an answer to that query may be inferred and an outcome predicted, e.g., a given request may be input into the system, and an answer may then be generated by the system based on the relationships between the data. One, two, three, or more inputs may be entered into the system, in addition to a query, and an output may be determined and returned by the system. For instance, a subject's, e.g., donors, mutational profile may be correlated with their clinical data, and be uploaded into a database of potentially correlated data from other subject's, whereby the system may perform a comparison between the clinical and/or genomic data of one or more subjects, such as for use in training and/or the development of predictive models. Specifically, as indicted above, the data entered into the system may be used to train the system, and once trained the system may be employed to make one or more correlations or predictions, therewith, such as in response to a query.

Accordingly, in various instances, the system may include an inference engine, such as configured as a neural network, that is adapted for receiving a plurality of inputs, performing an analysis of the data, and generate one or more correlations between the various data points. In particular instances, the system is configured for allowing the inference engine to be accessed remotely, such as via a cloud based interface accessed through a client computer. Once accessed, information pertaining to a particular subject may be uploaded onto the system, or if already uploaded may be accessed, such as by their DID.

For instance, once uploaded, the system may feed the subject's data into a knowledge graph of the system with respect to a given population of interest. Specifically, the system may receive the subject's data, and based on an initial analysis of the data may tag and store the data in relation to one or more populations to which the data may be fit. Such groupings may be made based on a number of characteristics, including age, weight, gender, medical conditions, prescribed medicines or treatments, genetic and/or clinical profile (EMR/PHR), demographics (national origin, ethnic/religious background, sexual orientation, etc.) and the like, which data may be uploaded into the system, and may serve as nodes for generating the knowledge graph, in relation to others in the defined population of interest, where each node may be defined by a number of properties. Once the pertinent group has been defined and the relevant properties characterized within the knowledge graph, the inference engine may then be employed so as to determine both known and inferred correlations between the various data points and/or their characteristics. Such inferences may be performed automatically, or in response to an entered query.

Particularly, in one use model, a physician may access the inference engine via a graphical user interface of a computer at his office, he may upload subject information, which information may be encrypted and transmitted to a central repository, e.g., server system, which may receive the encoded data, de-encrypt it, and use the data to build a knowledge graph, by pulling up data from other subject's that have correspondingly related characteristics so as to generate the nodes of the graph. The physician may then enter a query by which to initiate a search of the data base, and the inference engine in response to the query can then define the relationships between relevant nodes, and form those known relationships either return an answer, or generate, e.g., infer, further heretofore unknown relationships by which an answer may be determined and returned to the physician along with a predictive quality score, e.g., confidence score, as to how accurate the returned answer is expected to be. Based on the confidence score and/or other pertinent factors the rules that the inference engine uses to define the various relationships between particular nodes in the knowledge graph may be adjusted to be stricter or more lenient as to what data points and which relationships will be considered as valid when making a given predictive model, e.g., which nodes may be considered as objects, which may be considered as subjects and predicates, and which may be correlated as objects.

Hence, in a manner such as this, once a subject's genetic and/or genomic profile is known, this data may be used in relation to their clinical profile, e.g., EMR/PHR, so as to determine the effectiveness a particular medication prescription, as to medicine to be administered and/or dosage, and the like, or other treatment regimen will have on this particular subject, such as based on their genetic profile, which may further be determined in relationship to other known or unknown subjects having similar genetic profiles, medical records, or other similar conditions. The system is particularly useful when there are strong genetic relationships between individuals forming corresponding nodes, such as between family members, and/or who may or may not be suffering from the same or similar medical conditions and/or may be on the same or similar treatment regimes. Such relationships strengthen the relationships between the nodes, and the number of relationships between two nodes may also be used to strengthen the confidence when making a prediction between an inferred relationship between given nodes.

Consequently, once the various relationships have been defined and weighted, a predictive query, such as in the form of an "If"/"Then" statement may be made, such as where the physician enters a query into the system, and the inference engine determines the "then" portion of the statement by employing a predictive model to generate a resultant outcome, such as based on a probability outlook. As noted above, in a manner such as this, the physician does not need to have access to identifying information for any other subject save the one they are currently representing. Hence, the physician may enter their subject's conditions and/or present characteristics, and a proposed treatment plan, and the inference engine may then use that data to build a knowledge graph whereby the system may then return a proposed outlook for the subject with relation to the treatment plan, and/or may suggest alternative or supplemental treatments that may be useful to implement in substitution or in addition to the originally proposed treatment plan.

Particularly, the present system in this manner will be useful in determining what medications or other treatments to prescribe, the dosage, the periodicity, and other clinically relevant parameters for a subject, such as by taking into account one or more of their genetic, genomic, clinical, and other such data in relationship to one or more other data points. More particularly, the system may be configured for not only determining based on a subject's genetic makeup and other associated data, for instance, their mutational profile, what diseases they may be particularly susceptible for, but what treatments, e.g., drug prescriptions and usage, may be of benefit to the subject, e.g., given their present conditions.

In various instances, certain aspects of the artificial intelligence module may be accelerated, such as by being implemented in hardware, such as by a suitably configured integrated circuit, such as by an FPGA, ASIC, Structured ASIC, and the like. For instance, in certain embodiments, the A/I system may be configured to model a neural network, including a deep learning neural network, which may be formed of layers and layers or processing engines, where the more layers provided the deeper the learning configuration, and where each processing engine is trained in accordance with the methods disclosed herein to perform predictive analyses, which based on the number of layers may allow for exponential analyses to be performed.

Accordingly, to provide for interaction with a user, one or more aspects or features of the subject matter described herein can be implemented on a computer having a display device, such as for example a cathode ray tube (CRT), a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track-pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method for constructing and using a chimeric reference standard specific to an individual subject for improving accuracy of analysis of a plurality of portions of a genome of the subject, the method comprising:

comparing a first portion of the genome of the subject to each reference standard of a plurality of reference standards stored in a database, wherein the genome of the subject is based on a biological sample obtained from the subject;

selecting a portion of a first reference standard that satisfies a predetermined matching threshold to a first portion of the genome of the subject based on the comparison of the first portion to the plurality of reference standards;

comparing a second portion of the genome of the subject to each reference standard of the plurality of reference standards;

selecting a portion of a second reference standard that satisfies a predetermined matching threshold to the second portion of the genome of the subject based on the comparison of the second portion to the plurality of references standards;

creating a chimeric reference standard, whereby the creating comprises inserting the selected portions of the first reference standard and the second reference standard into respective portions of a hash table maintained in one or more memory devices; and using the hash table and the genome of the subject in order to perform one or more of a mapping, aligning, and/or variant calling procedure.

2. The method of claim 1, wherein the first reference standard is a linear reference standard, and wherein the second reference standard is a cultural reference standard.

3. The method of claim 1, wherein the first reference standard is a linear reference standard, and wherein the second reference standard is a different linear reference standard.

4. The method of claim 1, wherein the first reference standard is cultural reference standard, and wherein the second reference standard is a different cultural reference standard.

5. The method of claim 1, wherein at least one of the first reference standard and the second reference standard is a previously generated chimeric reference standard.

6. A non-transitory computer-readable medium storing software comprising instructions executable by one or more computers which, upon such execution, cause the one or more computers to perform operations for constructing and using a chimeric reference standard specific to an individual subject for improving accuracy of analysis of a plurality of portions of a genome of the subject, the operations comprising:

comparing a first portion of the genome of the subject to each reference standard of a plurality of reference standards stored in a database, wherein said genome is based on a biological sample obtained from said subject;

selecting a portion of a first reference standard that satisfies a predetermined matching threshold to a first portion of the genome of the subject based on the comparison of the first portion to the plurality of reference standards;

comparing a second portion of the genome of the subject to each reference standard of the plurality of reference standards;

selecting a portion of a second reference standard that satisfies a predetermined matching threshold to the second portion of the genome of the subject based on the comparison of the second portion to the plurality of references standards;

creating a chimeric reference standard, whereby the creating comprises inserting the selected portions of the first reference standard and the second reference standard into respective portions of a hash table maintained in one or more memory devices; and using the hash table and the genome of the subject in order to perform one or more of a mapping, aligning, and/or variant calling procedure.

7. The computer-readable medium of claim 6, wherein the first reference standard is a linear reference standard, and wherein the second reference standard is a cultural reference standard.

8. The computer-readable medium of claim 6, wherein the first reference standard is a linear reference standard, and wherein the second reference standard is a different linear reference standard.

9. The computer-readable medium of claim 6, wherein the first reference standard is cultural reference standard, and wherein the second reference standard is a different cultural reference standard.

10. The computer-readable medium of claim 6, wherein at least one of the first reference standard and the second reference standard is a previously generated chimeric reference standard.

11. A system for constructing and using a chimeric reference standard specific to an individual for improving accuracy of nucleic acid sequence analysis of nucleic acid sequences from the subject, the system comprising:

one or more computers and one or more storage devices storing instructions that are operable, when executed by the one or more computers, to cause the one or more computers to perform operations, the operations comprising:

comparing a first portion of a genome of the subject to each reference standard of a plurality of reference standards stored in a database, wherein the genome of the subject is based on a biological sample obtained from the subject;

selecting a portion of a first reference standard that satisfies a predetermined matching threshold to a first portion of the genome of the subject based on the comparison of the first portion to the plurality of reference standards;

comparing a second portion of the genome of the subject to each reference standard of the plurality of reference standards;

selecting a portion of a second reference standard that satisfies a predetermined matching threshold to the second portion of the genome of the subject based on the comparison of the second portion to the plurality of references standards;

creating a chimeric reference standard, whereby the creating comprises inserting the selected portions of the first reference standard and the second reference standard into respective portions of a hash table maintained in one or more memory devices; and using the hash table and the genome of the subject in order to perform one or more of a mapping, aligning, and/or variant calling procedure.

12. The system of claim 11, wherein the first reference standard is a linear reference standard, and wherein the second reference standard is a cultural reference standard.

13. The system of claim 11, wherein the first reference standard is a linear reference standard, and wherein the second reference standard is a different linear reference standard.

14. The system of claim 11, wherein the first reference standard is cultural reference standard, and wherein the second reference standard is a different cultural reference standard.

15. The system of claim 11, wherein at least one of the first reference standard and the second reference standard is a previously generated chimeric reference standard.

* * * * *